US009956047B2

(12) United States Patent
Bojarski et al.

(10) Patent No.: US 9,956,047 B2
(45) Date of Patent: May 1, 2018

(54) PATIENT-ADAPTED AND IMPROVED ARTICULAR IMPLANTS, DESIGNS AND RELATED GUIDE TOOLS

(71) Applicant: ConforMIS, Inc., Bedford, MA (US)

(72) Inventors: Raymond A. Bojarski, Attleboro, MA (US); Nam T. Chao, Marlborough, MA (US); John Slamin, Wrentham, MA (US); Philipp Lang, Lexington, MA (US); Wolfgang Fitz, Sherborn, MA (US); Daniel Steines, Lexington, MA (US)

(73) Assignee: ConforMIS, Inc., Billerica, MA (US)

( * ) Notice: Subject to any disclaimer, the term of this patent is extended or adjusted under 35 U.S.C. 154(b) by 0 days. days.

(21) Appl. No.: 15/137,607

(22) Filed: Apr. 25, 2016

(65) Prior Publication Data

US 2016/0310282 A1   Oct. 27, 2016

Related U.S. Application Data

(63) Continuation of application No. 13/938,081, filed on Jul. 9, 2013, now Pat. No. 9,320,620, which is a
(Continued)

(51) Int. Cl.
*A61F 2/38* (2006.01)
*A61F 2/30* (2006.01)
(Continued)

(52) U.S. Cl.
CPC ............ *A61B 34/10* (2016.02); *A61B 17/155* (2013.01); *A61B 17/157* (2013.01);
(Continued)

(58) Field of Classification Search
CPC .... A61F 2/30942; A61F 2/5046; A61F 2/389; A61F 2/3886; A61F 2/3859; A61F 2/30;
(Continued)

(56) References Cited

U.S. PATENT DOCUMENTS

| 3,816,855 | A | 6/1974 | Saleh ................................. 3/1 |
| 3,982,281 | A | 9/1976 | Giliberty ......................... 3/1.913 |

(Continued)

FOREIGN PATENT DOCUMENTS

| CN | 1780594 A | 5/2006 | .............. A61F 2/30 |
| CN | 100502808 C | 6/2009 | .............. A61F 2/30 |

(Continued)

OTHER PUBLICATIONS

Overhoff et al., "Total Knee Arthroplasty: Coordinate System Definition and Planning Based on 3-D Ultrasound Image Volumes," CARS, pp. 283-288, 2001.
(Continued)

*Primary Examiner* — Pedro Philogene
(74) *Attorney, Agent, or Firm* — Sunstein Kann Murphy & Timbers LLP

(57) ABSTRACT

Methods and devices are disclosed relating improved articular models, implant components, and related guide tools and procedures. In addition, methods and devices are disclosed relating articular models, implant components, and/or related guide tools and procedures that include one or more features derived from patient-data, for example, images of the patient's joint. The data can be used to create a model for analyzing a patient's joint and to devise and evaluate a course of corrective action. The data also can be used to create patient-adapted implant components and related tools and procedures.

17 Claims, 199 Drawing Sheets

Related U.S. Application Data continuation of application No. 13/294,564, filed on Nov. 11, 2011, now Pat. No. 8,906,107, which is a continuation of application No. 12/660,529, filed on Feb. 25, 2010, now Pat. No. 8,480,754, and a continuation-in-part of application No. 12/712,072, filed on Feb. 24, 2010, now Pat. No. 8,234,097.

(60) Provisional application No. 61/155,362, filed on Feb. 25, 2009, provisional application No. 61/269,405, filed on Jun. 24, 2009, provisional application No. 61/273,216, filed on Jul. 31, 2009, provisional application No. 61/275,174, filed on Aug. 26, 2009, provisional application No. 61/280,493, filed on Nov. 4, 2009, provisional application No. 61/284,458, filed on Dec. 18, 2009, provisional application No. 61/155,359, filed on Feb. 25, 2009, provisional application No. 61/220,726, filed on Jun. 26, 2009, provisional application No. 61/208,440, filed on Feb. 24, 2009, provisional application No. 61/208,444, filed on Feb. 24, 2009.

(51) Int. Cl.
| | | |
|---|---|---|
| *A61B 34/10* | (2016.01) | |
| *A61F 2/50* | (2006.01) | |
| *A61B 17/15* | (2006.01) | |
| *B33Y 80/00* | (2015.01) | |
| *A61B 17/17* | (2006.01) | |

(52) U.S. Cl.
CPC ......... *A61F 2/30942* (2013.01); *A61F 2/384* (2013.01); *A61F 2/389* (2013.01); *A61F 2/3859* (2013.01); *A61F 2/5046* (2013.01); *A61B 17/1764* (2013.01); *A61B 2034/107* (2016.02); *A61B 2034/108* (2016.02); *A61F 2/3886* (2013.01); *A61F 2002/30324* (2013.01); *A61F 2002/30327* (2013.01); *A61F 2002/30952* (2013.01); *A61F 2002/3895* (2013.01); *B33Y 80/00* (2014.12)

(58) Field of Classification Search
CPC ......... A61F 2/38; A61F 2/461; A61F 2/3877; A61F 2/4405; A61F 2/442; A61F 2002/30324; A61F 2002/30327; A61F 2002/30952; A61F 2002/30604; A61F 2002/30616; A61F 2002/3895; A61F 2002/30387; A61F 2002/30433; A61F 2002/3863; A61F 2250/0036; A61F 2250/0039; A61B 17/1764; A61B 17/155; A61B 17/157; A61B 34/10; Y10T 29/49
USPC ...... 623/22.11, 19.11, 17.11; 606/79, 87–89, 606/86 R
See application file for complete search history.

(56) References Cited

U.S. PATENT DOCUMENTS

| | | | |
|---|---|---|---|
| 4,178,641 A | 12/1979 | Grundei et al. ............. 3/1.911 |
| 4,309,778 A | 1/1982 | Buechel et al. ............. 3/1.911 |
| 4,637,382 A | 1/1987 | Walker | |
| 4,662,889 A | 5/1987 | Zichner et al. .............. 623/20 |
| 4,704,686 A | 11/1987 | Aldinger ................. 364/468 |
| 4,714,472 A | 12/1987 | Averill et al. .................. 623/20 |
| 4,822,365 A | 4/1989 | Walker et al. ................. 623/20 |
| 4,936,853 A | 6/1990 | Fabian et al. ................. 623/20 |
| 4,936,862 A | 6/1990 | Walker et al. ................. 623/23 |
| 5,274,565 A | 12/1993 | Reuben ................. 364/474.24 |
| 5,507,820 A | 4/1996 | Pappas .................... 623/20 |
| 5,681,354 A | 10/1997 | Eckhoff ..................... 623/20 |
| 5,728,162 A | 3/1998 | Eckhoff ..................... 623/20 |
| 5,768,134 A | 6/1998 | Swaelens et al. ........ 364/468.28 |
| 5,769,092 A | 6/1998 | Williamson, Jr. ............ 128/898 |
| 5,824,102 A | 10/1998 | Buscayret ................ 623/20 |
| 5,871,018 A | 2/1999 | Delp et al. ................. 128/898 |
| 5,871,542 A | 2/1999 | Goodfellow et al. | |
| 6,013,103 A | 1/2000 | Kaufman et al. ............. 623/20 |
| 6,120,543 A | 9/2000 | Kubein-Meesenburg et al. .......................... 623/20 |
| 6,152,960 A | 11/2000 | Pappas .................... 623/20.31 |
| 6,165,221 A | 12/2000 | Schmotzer ............... 623/20.11 |
| 6,190,415 B1 | 2/2001 | Cooke et al. | |
| 6,325,828 B1 | 12/2001 | Dennis et al. ............ 623/20.14 |
| 6,402,786 B1 | 6/2002 | Insall et al. ............... 623/20.35 |
| 6,893,467 B1 | 5/2005 | Bercovy ................... 623/20.14 |
| 6,902,582 B2 | 6/2005 | Kubein-Meesenburg et al. .......................... 623/20.31 |
| 7,048,741 B2 | 5/2006 | Swanson ..................... 606/88 |
| 7,060,101 B2 | 6/2006 | O'Connor et al. ......... 623/20.32 |
| 7,105,026 B2 | 9/2006 | Johnson et al. ........... 623/20.14 |
| 7,172,596 B2 | 2/2007 | Coon et al. ................. 606/87 |
| 7,264,635 B2 | 9/2007 | Suguro et al. ............. 623/20.14 |
| 7,678,152 B2 | 3/2010 | Suguro et al. ............. 623/20.27 |
| 7,799,077 B2 | 9/2010 | Lang et al. ............... 623/14.12 |
| 8,192,498 B2 | 6/2012 | Wagner et al. ............ 623/20.21 |
| 8,211,181 B2 | 7/2012 | Walker ....................... 623/20.21 |
| 8,221,430 B2 | 7/2012 | Park et al. .................. 606/88 |
| 8,236,061 B2 | 8/2012 | Heldreth et al. ............ 623/20.31 |
| 8,311,306 B2 | 11/2012 | Pavlovskaia et al. | |
| 8,317,797 B2* | 11/2012 | Rasmussen .......... A61B 17/025 606/105 |
| 8,352,056 B2 | 1/2013 | Lee et al. ..................... 700/97 |
| 8,473,305 B2 | 6/2013 | Belcher et al. ................. 705/2 |
| 8,486,150 B2 | 7/2013 | White et al. .............. 623/20.21 |
| 8,521,492 B2 | 8/2013 | Otto et al. ..................... 703/6 |
| 8,532,807 B2 | 9/2013 | Metzger ....................... 700/98 |
| 8,545,569 B2 | 10/2013 | Fitz et al. ................... 623/20.14 |
| 8,771,365 B2 | 7/2014 | Bojarski et al. ........... 623/20.32 |
| 8,882,847 B2 | 11/2014 | Burdulis, Jr. et al. ..... 623/20.32 |
| 8,906,107 B2 | 12/2014 | Bojarski et al. ........... 623/20.35 |
| 8,932,363 B2 | 1/2015 | Tsougarakis et al. ..... 623/20.14 |
| 8,974,539 B2 | 3/2015 | Bojarski et al. ........... 623/20.35 |
| 9,320,620 B2 | 4/2016 | Bojarski et al. ............... 606/79 |
| 9,387,079 B2 | 7/2016 | Bojarski et al. | |
| 9,603,711 B2 | 3/2017 | Bojarski et al. | |
| 2001/0051831 A1 | 12/2001 | Subba Rao et al. ........ 623/22.42 |
| 2002/0087274 A1 | 7/2002 | Alexander et al. ............ 702/19 |
| 2004/0006394 A1 | 1/2004 | Lipman et al. ............ 623/20.29 |
| 2004/0098132 A1 | 5/2004 | Andriacchi et al. ....... 623/20.35 |
| 2004/0133276 A1 | 7/2004 | Lang et al. ................ 623/14.12 |
| 2004/0204766 A1 | 10/2004 | Siebel ....................... 623/20.31 |
| 2005/0154471 A1 | 7/2005 | Aram et al. ............... 623/20.15 |
| 2005/0197814 A1 | 9/2005 | Aram et al. .................. 703/11 |
| 2006/0004460 A1* | 1/2006 | Engh ................... A61F 2/30724 623/20.21 |
| 2006/0058884 A1* | 3/2006 | Aram ................. A61B 17/1764 623/20.15 |
| 2006/0235537 A1 | 10/2006 | Kuczynski et al. ......... 623/20.3 |
| 2007/0038223 A1 | 2/2007 | Marquart et al. ............ 606/86 |
| 2007/0100462 A1 | 5/2007 | Lang et al. ............... 623/20.29 |
| 2007/0173858 A1* | 7/2007 | Engh ........................ A61F 2/38 606/99 |
| 2007/0255288 A1 | 11/2007 | Mahfouz et al. ............. 606/102 |
| 2007/0282451 A1 | 12/2007 | Metzger et al. ........... 623/20.28 |
| 2008/0009950 A1 | 1/2008 | Richardson ............... 623/20.29 |
| 2008/0051910 A1 | 2/2008 | Kammerzell et al. | |
| 2008/0058945 A1 | 3/2008 | Hajaj et al. ............... 623/20.14 |
| 2008/0119940 A1 | 5/2008 | Otto et al. ................. 623/20.31 |
| 2008/0133020 A1 | 6/2008 | Blackwell et al. ........ 623/20.34 |
| 2008/0140212 A1* | 6/2008 | Metzger ................ A61F 2/3886 623/20.31 |
| 2008/0195216 A1 | 8/2008 | Philipp ..................... 623/18.11 |
| 2008/0215059 A1 | 9/2008 | Carignan et al. ............. 606/96 |
| 2008/0255445 A1 | 10/2008 | Neubauer et al. ............ 600/416 |
| 2008/0269596 A1 | 10/2008 | Revie et al. ................. 600/424 |
| 2009/0062925 A1 | 3/2009 | Samuelson ................ 623/23.12 |
| 2009/0149977 A1 | 6/2009 | Schendel ...................... 700/98 |
| 2009/0226068 A1 | 9/2009 | Fitz et al. ..................... 382/131 |
| 2009/0228113 A1 | 9/2009 | Lang et al. ............... 623/20.32 |

(56) References Cited

U.S. PATENT DOCUMENTS

| | | | |
|---|---|---|---|
| 2009/0270868 A1 | 10/2009 | Park et al. | 606/87 |
| 2009/0276045 A1 | 11/2009 | Lang | 623/14.12 |
| 2010/0042105 A1 | 2/2010 | Park et al. | 606/87 |
| 2010/0274534 A1 | 10/2010 | Steines et al. | 703/1 |
| 2010/0305575 A1 | 12/2010 | Wilkinson et al. | 606/88 |
| 2011/0022179 A1 | 1/2011 | Andriacchi et al. | 623/20.18 |
| 2011/0029091 A1 | 2/2011 | Bojarski et al. | 623/20.32 |
| 2011/0046735 A1 | 2/2011 | Metzger et al. | 623/14.12 |
| 2011/0071645 A1 | 3/2011 | Bojarski et al. | 623/20.35 |
| 2011/0071802 A1 | 3/2011 | Bojarski et al. | 703/1 |
| 2011/0087332 A1 | 4/2011 | Bojarski et al. | 623/20.32 |
| 2011/0087465 A1 | 4/2011 | Mahfouz | 703/1 |
| 2011/0093108 A1 | 4/2011 | Ashby et al. | 700/103 |
| 2011/0160867 A1 | 6/2011 | Meridew et al. | 623/20.36 |
| 2011/0264097 A1 | 10/2011 | Hodorek et al. | 606/88 |
| 2011/0288669 A1 | 11/2011 | Sanford et al. | 700/103 |
| 2011/0305379 A1 | 12/2011 | Mahfouz | 382/131 |
| 2012/0022659 A1 | 1/2012 | Wentorf | 623/20.32 |
| 2012/0066892 A1 | 3/2012 | Lang et al. | 29/592 |
| 2012/0265496 A1 | 10/2012 | Mahfouz | |
| 2012/0310246 A1 | 12/2012 | Belcher et al. | 606/80 |
| 2012/0310362 A1 | 12/2012 | Li et al. | |
| 2013/0144570 A1 | 6/2013 | Axelson, Jr. et al. | 703/1 |
| 2013/0158671 A1 | 6/2013 | Uthgenannt et al. | 623/20.35 |
| 2013/0289570 A1 | 10/2013 | Chao | 606/88 |
| 2014/0136154 A1 | 5/2014 | Bojarski et al. | 703/1 |
| 2014/0188240 A1 | 7/2014 | Lang et al. | |
| 2014/0194996 A1 | 7/2014 | Bojarski et al. | 623/20.35 |
| 2014/0257508 A1 | 9/2014 | Bojarski et al. | |
| 2015/0032217 A1 | 1/2015 | Bojarski et al. | 623/20.32 |
| 2015/0081029 A1 | 3/2015 | Bojarski et al. | 623/20.32 |
| 2016/0038293 A1 | 2/2016 | Slamin et al. | |
| 2016/0317312 A1 | 11/2016 | Bojarski et al. | |
| 2016/0324581 A1 | 11/2016 | Bojarski et al. | |
| 2016/0331467 A1 | 11/2016 | Slamin et al. | |

FOREIGN PATENT DOCUMENTS

| | | | | |
|---|---|---|---|---|
| EP | 0093869 A1 | 3/1983 | | A61F 1/00 |
| EP | 0600806 B1 | 6/1994 | | A61F 2/38 |
| EP | 2173260 B1 | 4/2010 | | A61F 17/15 |
| JP | 56-83343 A | 7/1981 | | A61F 1/03 |
| WO | WO 00/13616 | 3/2000 | | A61F 2/38 |
| WO | WO 00/76428 A1 | 12/2000 | | A61F 2/38 |
| WO | WO 02/096268 A2 | 12/2002 | | |
| WO | WO 2004/043305 A1 | 5/2004 | | A61F 2/30 |
| WO | WO 2005/002473 A1 | 1/2005 | | A61F 2/38 |
| WO | WO 2006/092600 A1 | 9/2006 | | A61F 19/00 |
| WO | WO 2007/092841 A2 | 8/2007 | | A61F 17/15 |
| WO | WO 2009/105495 A1 | 8/2009 | | A61F 2/38 |
| WO | WO 2010/099359 A1 | 9/2010 | | A61F 2/00 |
| WO | WO 10/151564 | 12/2010 | | A61F 2/38 |
| WO | WO 2010/140036 A1 | 12/2010 | | A61F 2/38 |
| WO | WO 2011/094540 A2 | 8/2011 | | A61F 2/38 |
| WO | WO-2012112694 A2 | 8/2012 | | |
| WO | WO-2012112701 A2 | 8/2012 | | |
| WO | WO-2012112702 A2 | 8/2012 | | |
| WO | WO-2013056036 A1 | 4/2013 | | |
| WO | WO 13/152341 | 10/2013 | | A61F 2/38 |
| WO | WO-2014145281 A1 | 9/2014 | | |

OTHER PUBLICATIONS

International Searching Authority, International Search Report—International Application No. PCT/US2012/025274 dated Oct. 25, 2012, together with the Written Opinion of the International Searching Authority, 12 pages.

International Searching Authority, International Search Report—International Application No. PCT/US12/59936 dated Jan. 9, 2013, together with the Written Opinion of the International Searching Authority, 11 pages.

International Searching Authority, International Search Report—International Application No. PCT/US2013/035536 dated Jul. 18, 2013, together with the Written Opinion of the International Searching Authority, 9 pages.

International Searching Authority, International Search Report—International Application No. PCT/US2014/030015 dated Aug. 27, 2014, together with the Written Opinion of the International Searching Authority, 9 pages.

Chinese Patent Office, Search Report dated May 12, 2015, 3 pages.

European Patent Office, Extended European Search Report—Application No. 12840579.2-1654 dated Apr. 14, 2015, 6 pages.

European Patent Office, Partial Supplementary European Search Report—Application No. 13771863.1-1654, dated Apr. 26, 2016, 7 pages.

International Searching Authority, International Search Report—International Application No. PCT/US2012/025277 dated Oct. 25, 2012, together with the Written Opinion of the International Searching Authority, 12 pages.

European Patent Office, Extended European Search Report—Application No. 14763622.9-1654 dated Oct. 26, 2016, 8 pages.

Sunstein Kann Murphy & Timbers LLP, Request for Continued Examination and Response dated Feb. 22, 2017, pertaining to U.S. Appl. No. 14/389,987, 12 pages.

United States Patent & Trademark Office, Office Action dated Oct. 26, 2016, pertaining to U.S. Appl. No. 13/872,017, 9 pages.

Sunstein Kann Murphy & Timbers LLP, Request for Continued Examination and Response dated Feb. 27, 2017, pertaining to U.S. Appl. No. 13/872,017, 17 pages.

United States Patent & Trademark Office, Office Action dated Mar. 10, 2017, pertaining to U.S. Appl. No. 13/872,017. 7 pages.

United States Patent & Trademark Office, Office Action dated Aug. 10, 2016, pertaining to U.S. Appl. No. 15/144,356 1 pages.

Sunstein Kann Murphy & Timbers LLP, Response to Office Action dated Aug. 10, 2016, pertaining to U.S. Appl. No. 15/144,365, 11 pages.

United States Patent & Trademark Office, Office Action dated Dec. 22, 2016, pertaining to U.S. Appl. No. 15/144,356, 12 pages.

Sunstein Kann Murphy & Timbers LLP, Request for Continued Examination and Response dated Mar. 20, 2017, pertaining to U.S. Appl. No. 15/144,356. 13 pages.

United States Patent & Trademark Office, Office Action dated May 2, 2017, pertaining to U.S. Appl. No. 15/144,356, 10 pages.

United States Patent & Trademark Office, Office Action dated Sep. 29, 2016, pertaining to U.S. Appl. No. 15/144,415, 9 pages.

Sunstein Kann Murphy & Timbers LLP, Office Action dated Mar. 7, 2017, pertaining to U.S. Appl. No. 15/144,415, 13 pages.

United States Patent & Trademark Office, Office Action dated Mar. 7, 2017, pertaining to U.S. Appl. No. 15/144,415, 8 pages.

Amendment to Office Action dated May 2, 2017, pertaining to U.S. Appl. No. 15/144,356, 12 pages.

Seedhom et al. "Dimensions of the Knee. Radiographic and Autopsy Study of Sizes Required by a Knee Prosthesis", Ann. Rheum Dis, pp. 54-58, 1972.

Erkman et al. "A Study of Knee Geometry Applied to the Design of Condylar Prostheses", Biomedical Engineering, pp. 14-17, Jan. 1974.

Fehring et al. "Differences Between the Sexes in the Anatomy of the Anterior Condyle of the Knee", Journal of Bone & Joint Surgery, pp. 2335-2341, 2009.

Mensch et al. "Knee Morphology as a Guide to Knee Replacement", Clinical Orthopaedics and Related Research, pp. 231-241, 1975.

Office Action dated Jun. 15, 2017, pertaining to U.S. Appl. No. 14/389,987, 10 pages.

Office Action dated Jun. 21, 2017, pertaining to U.S. Appl. No. 15/144,415, 11 pages.

RCE, Amendment and Interview Summary dated Aug. 29, 2017, pertaining to U.S. Appl. No. 13/294,617, 13 pages.

Response to Office Action dated Mar. 7, 2017, pertaining to U.S. Appl. No. 15/144,415, 13 pages.

Amendment to Office Action dated Jun. 21, 2017, pertaining to U.S. Appl. No. 15/144,415, 13 pages.

Amendment to Office Action dated Sep. 20, 2016, pertaining to U.S. Appl. No. 14/315,714, 12 pages.

Notice of Allowance dated Oct. 18, 2016, pertaining to U.S. Appl. No. 12/799,641, 8 pages.

(56) References Cited

OTHER PUBLICATIONS

Notice of Allowance dated Oct. 30, 2017, pertaining to U.S. Appl. No. 15/144,415, 5 pages.
Notice of Allowance dated Sep. 21, 2017, pertaining to U.S. Appl. No. 13/294,617, 5 pages.
Office Action dated Aug. 17, 2015, pertaining to U.S. Appl. No. 14/315,714, 8 pages.
Office Action dated Feb. 28, 2017, pertaining to U.S. Appl. No. 14/315,714, 8 pages.
Office Action dated Jul. 19, 2017, pertaining to U.S. Appl. No. 14/315,714, 12 pages.
Office Action dated Mar. 29, 2016, pertaining to U.S. Appl. No. 14/315,714, 7 pages.
Office Action dated Sep. 20, 2016, pertaining to U.S. Appl. No. 14/315,714, 7 pages.
Office Action dated Sep. 26, 2017, pertaining to U.S. Appl. No. 15/144,356, 11 pages.
RCE and Response dated Jun. 28, 2017, pertaining to U.S. Appl. No. 14/315,714, 16 pages.
Request for Continued Examination and Response dated Apr. 20, 2016, pertaining to U.S. Appl. No. 12/799,641, 11 pages.
Request for Continued Examination and Response filed Aug. 3, 2016, pertaining to U.S. Appl. No. 14/315,714, 18 pages.
Response to Notice of Non-Compliant Amendment dated Mar. 29, 2017, pertaining to U.S. Appl. No. 14/389,987, 6 pages.
Response to Office Action dated Aug. 17, 2015, pertaining to U.S. Appl. No. 14/315,714, 10 pages.

\* cited by examiner

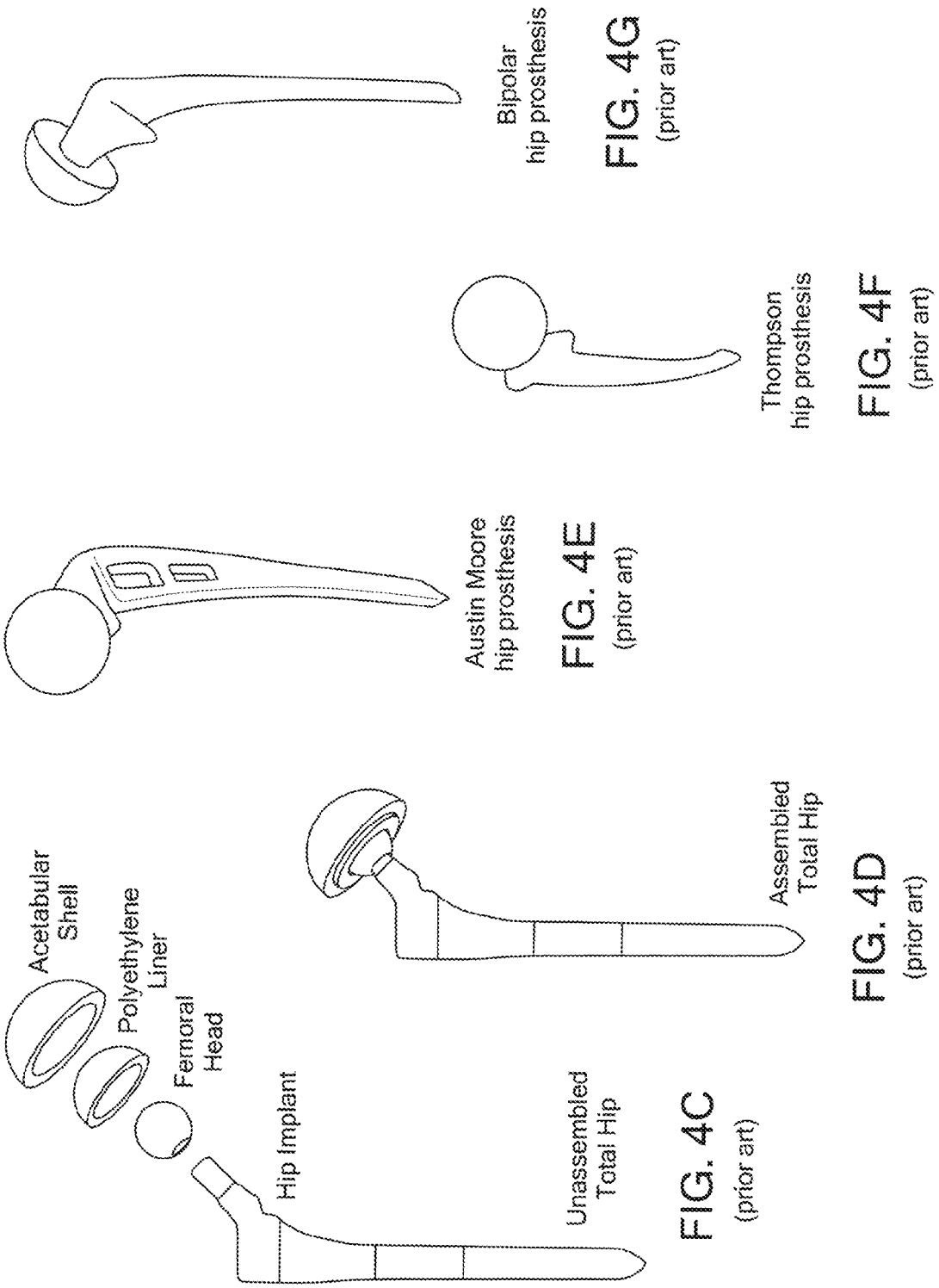

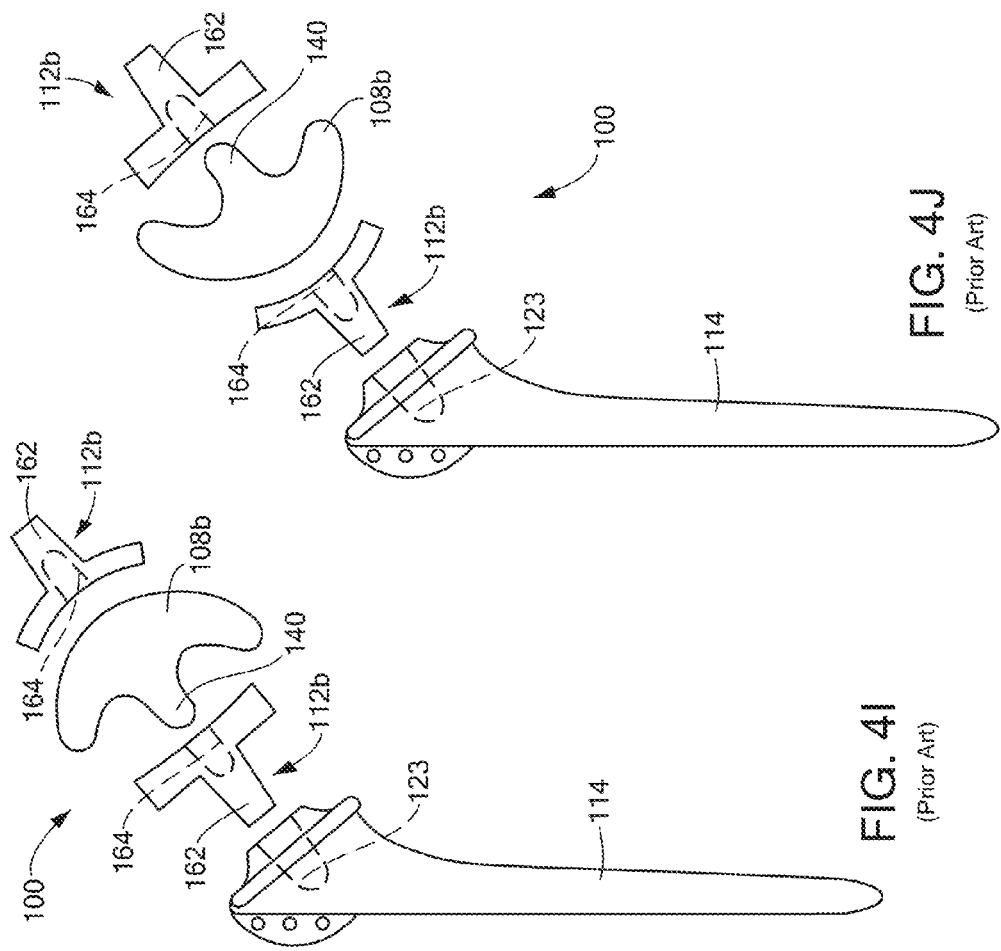
FIG. 4J (Prior Art)
FIG. 4I (Prior Art)
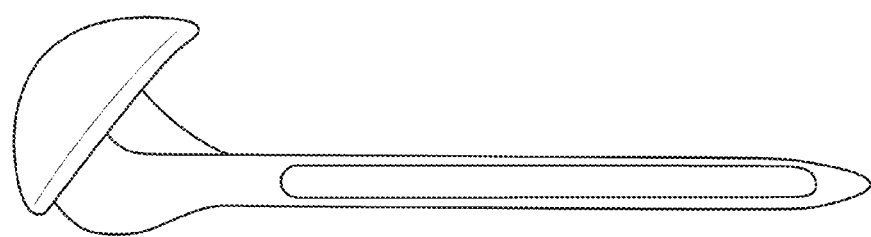
FIG. 4H (Prior Art)

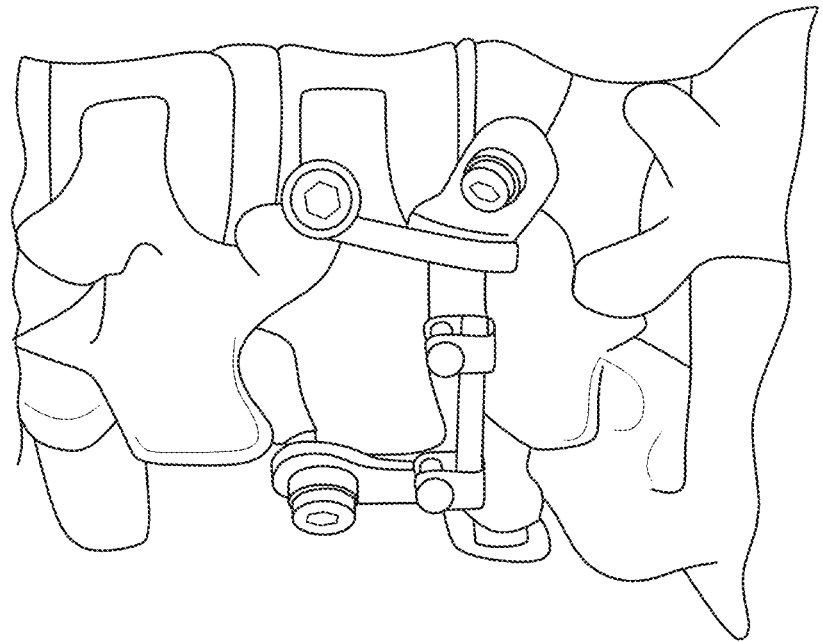
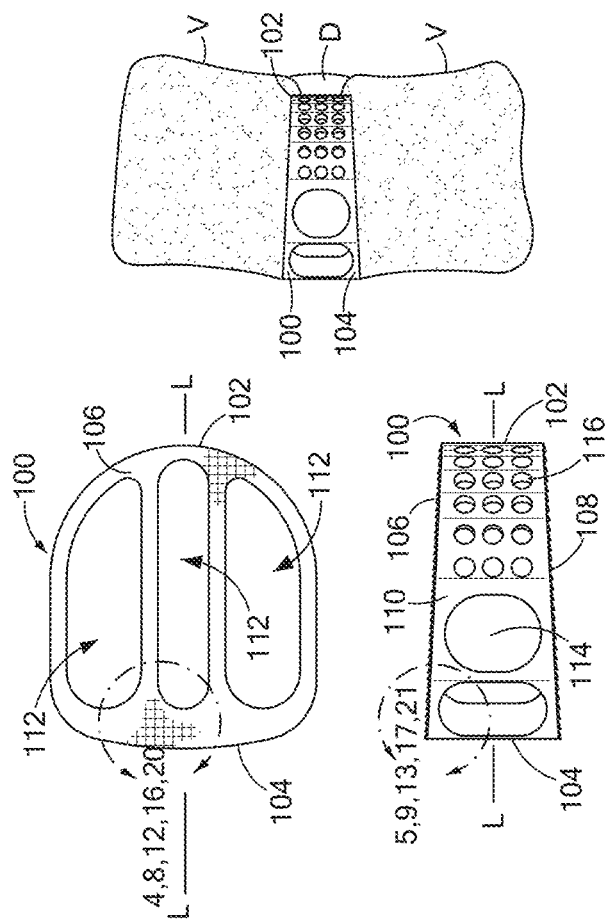
FIG. 4K (prior art)
FIG. 4L (prior art)
FIG. 4M (prior art)

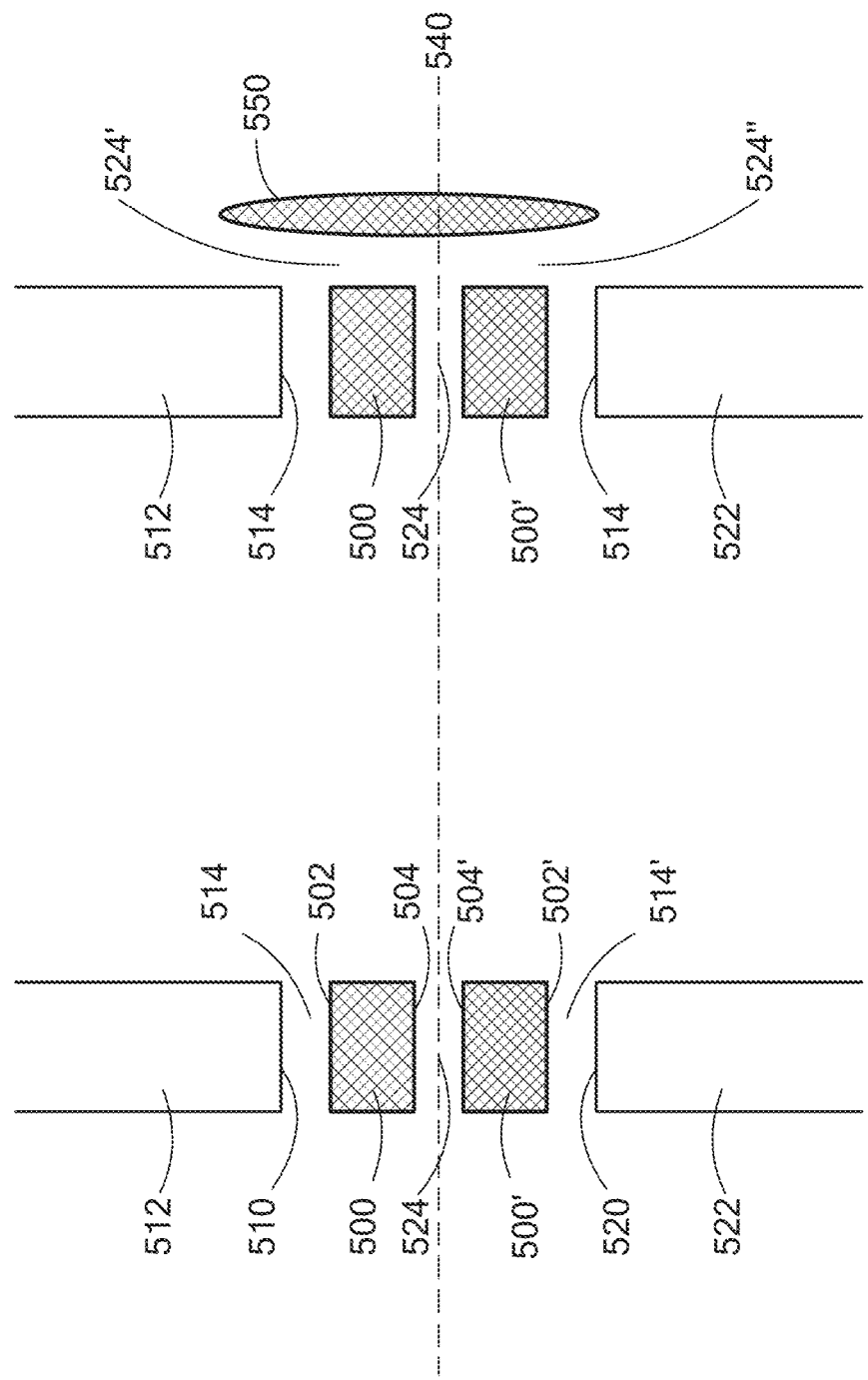

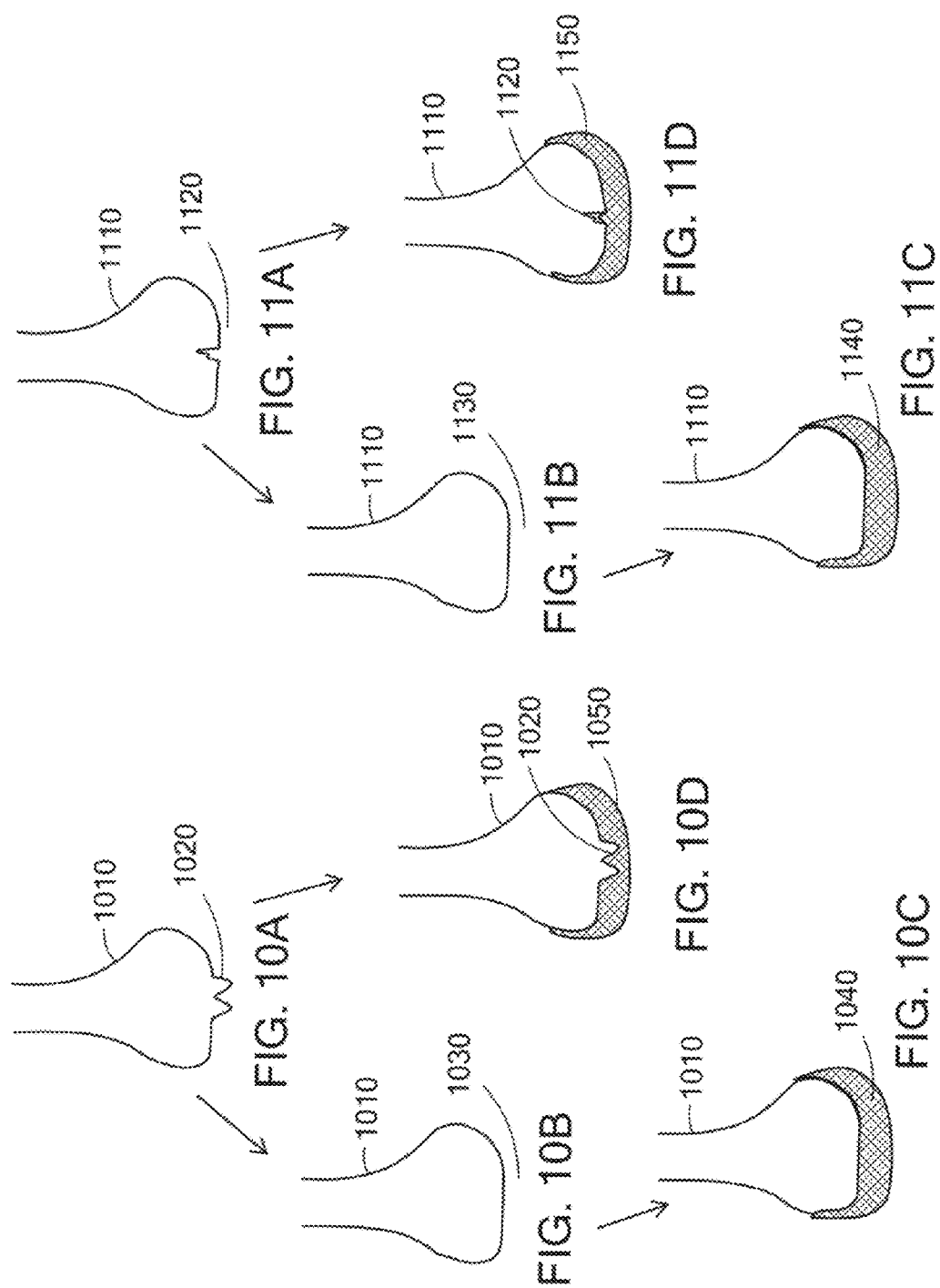

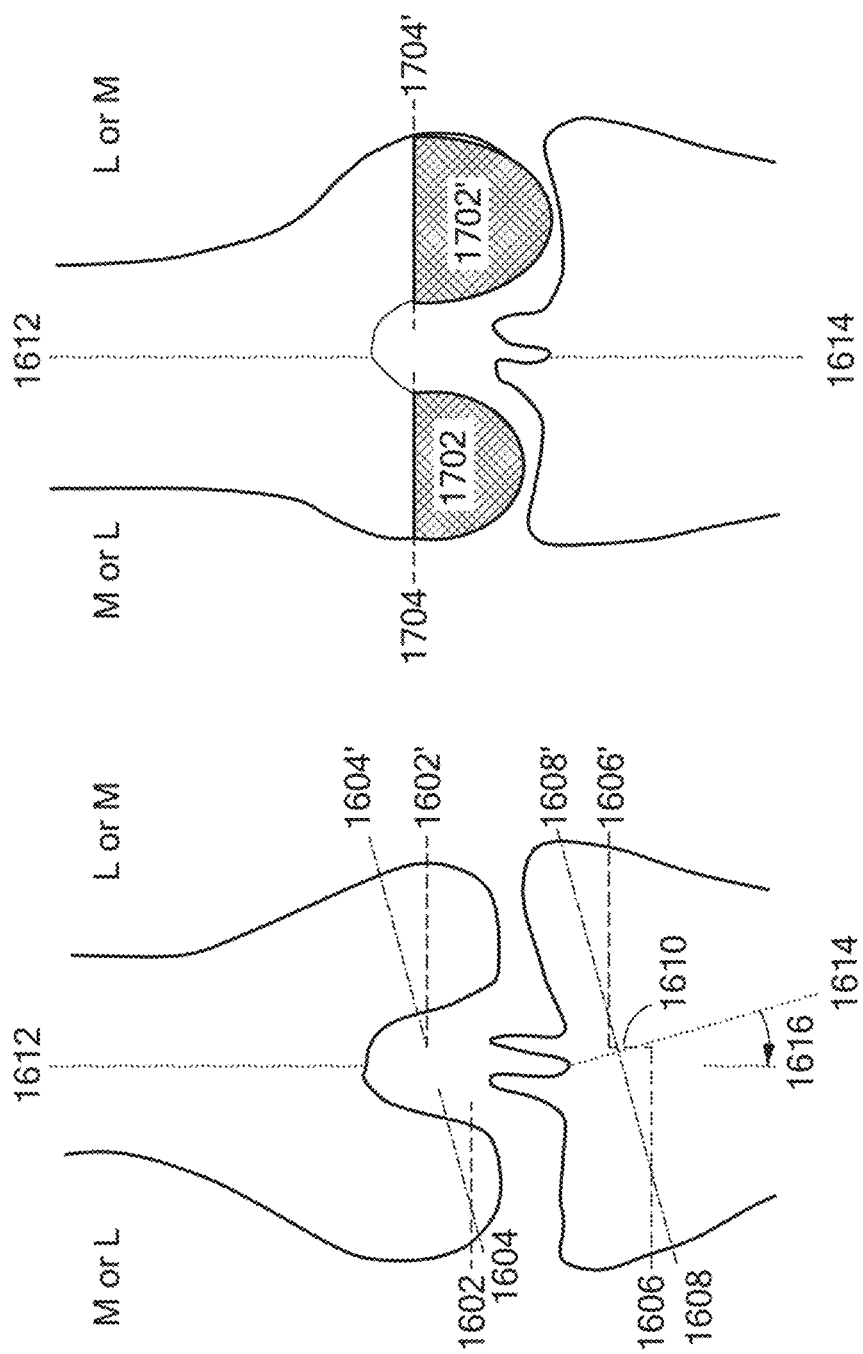

- Wide trochlea thickness
- Shallow trochlea depth

- Small trochlea thickness
- Deep trochlea depth

- Measure of condyle length
- Each condyle assessed independantly
- One or more measures can apply per condyle

- Measure of condyle width
- Each condyle assessed independantly
- One or more measures per condyle ~ "Normal" femur / tibia width ratio

- Various M-L measures
- See and compare these and tibial trays in FIGS. 63A-64F

- Wide femur
- Narrow tibia
- Note change in tibial insert aspects

- Narrow femur
- Wide tibia

- Deep trochlea
- Note change in tibial insert aspects

FEA analysis

Side view of implant

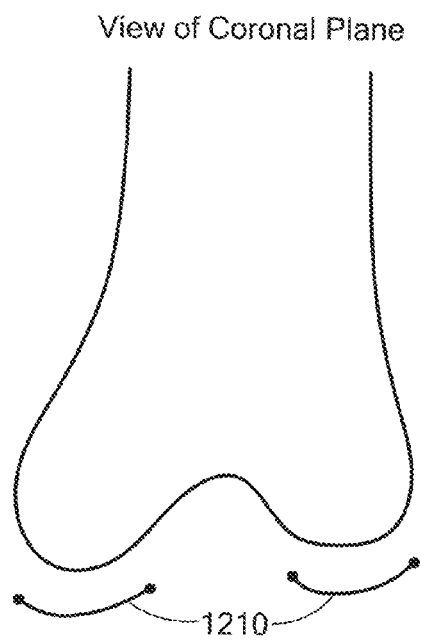
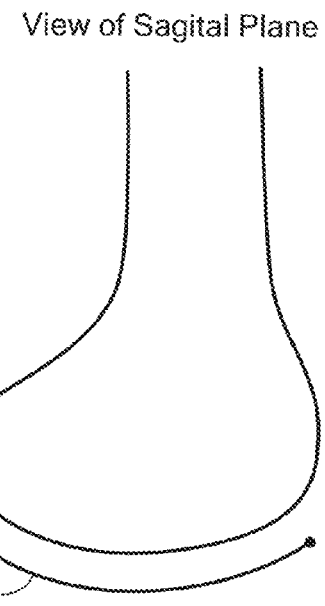
FIG. 32A          FIG. 32B
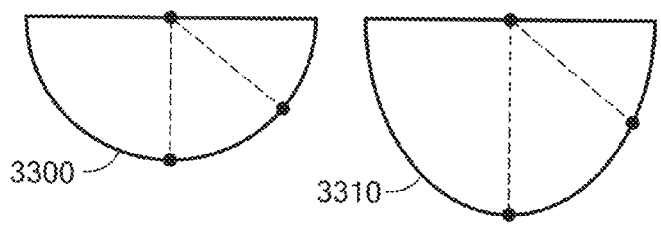
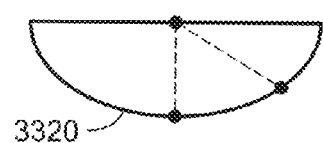
FIG. 33A     FIG. 33B     FIG. 33C
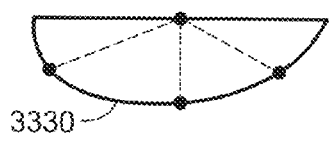
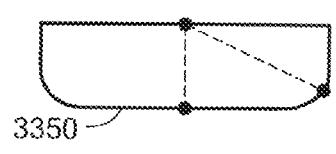
FIG. 33D     FIG. 33E     FIG. 33F

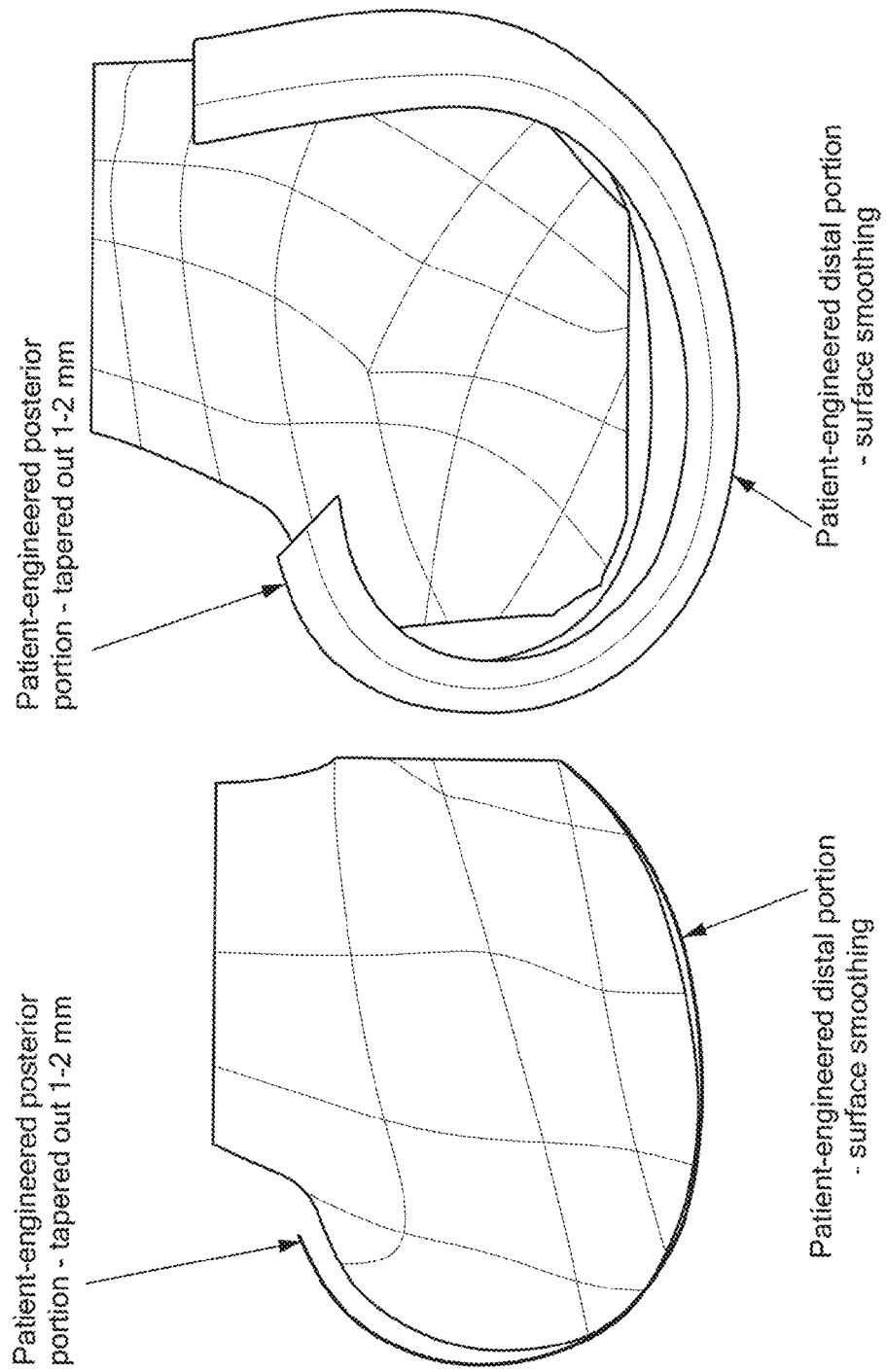

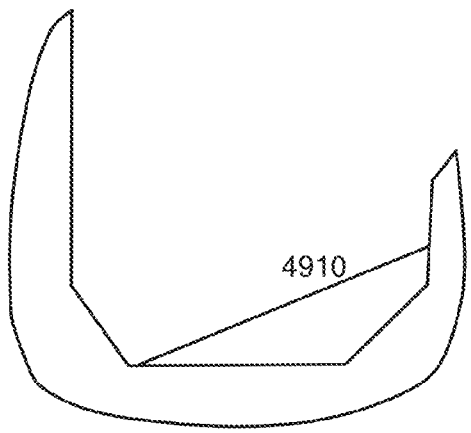
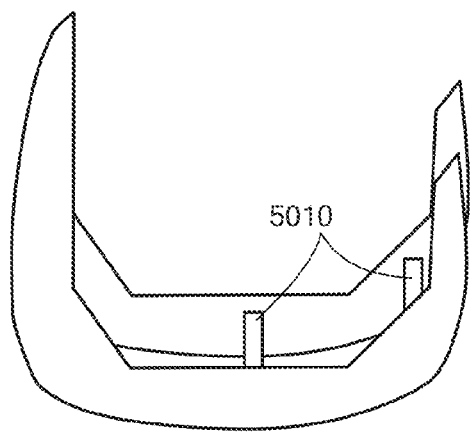
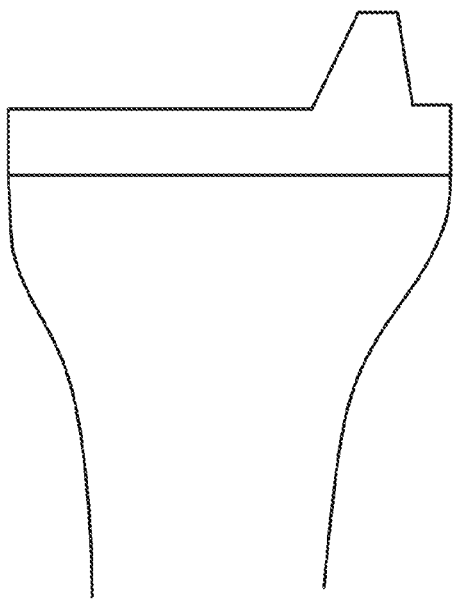
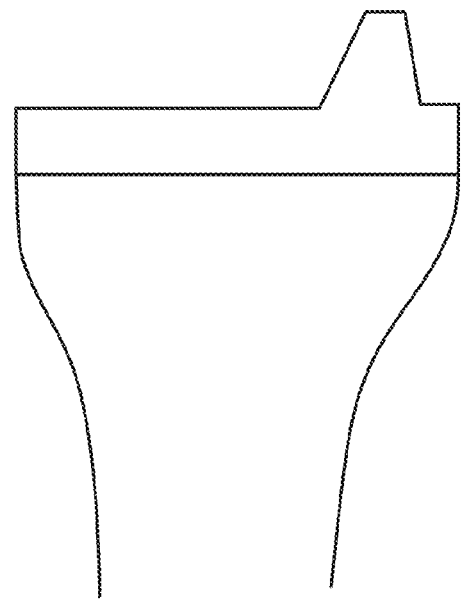
FIG. 50A  FIG. 50B

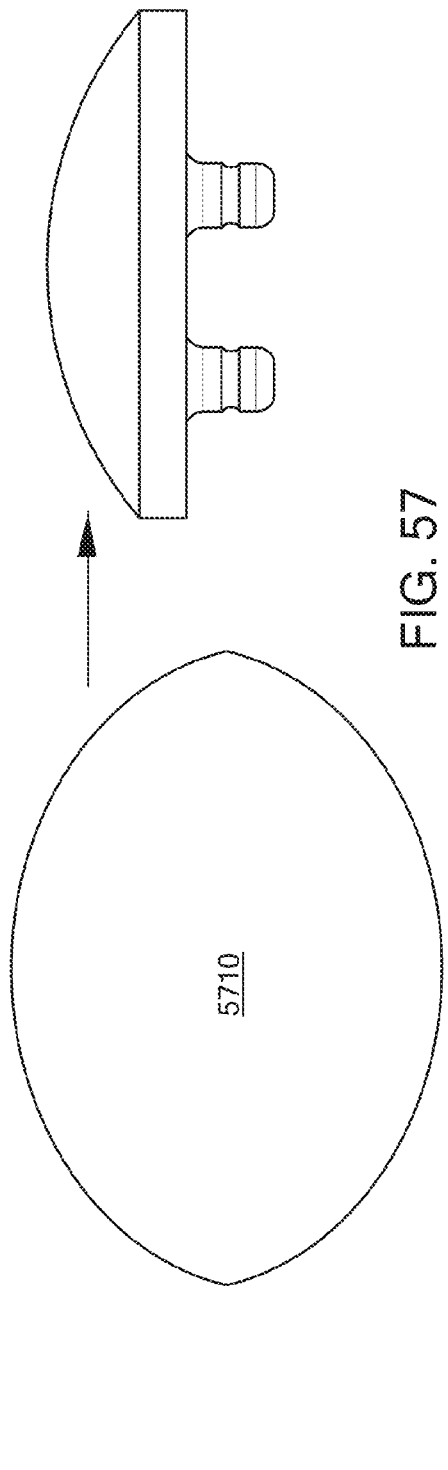
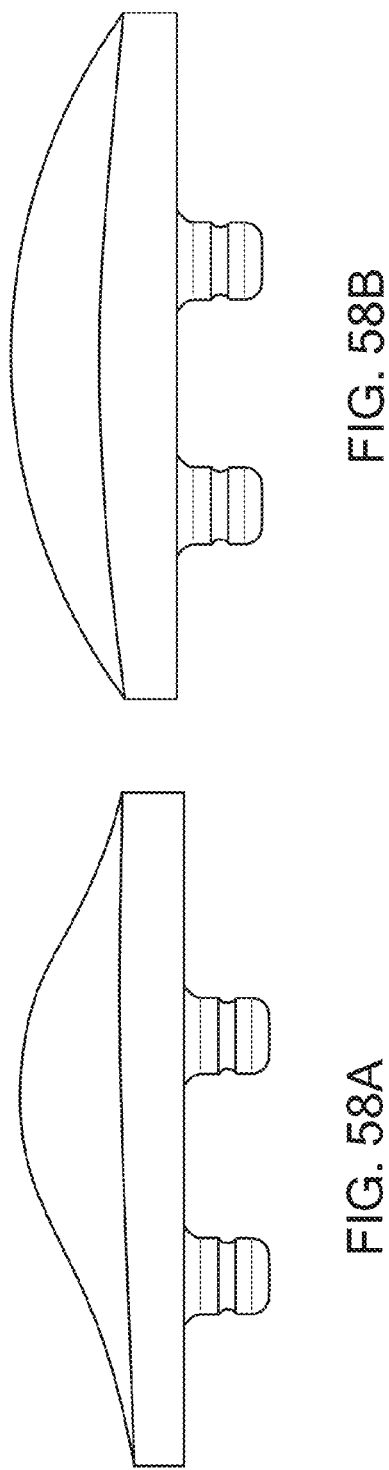

| Size (mm) | Height | Edge Thk. |
|---|---|---|
| 27 x 32 | 8mm | 3.1mm |
| 30 x 35 | 8 | 2.0 |
| 33 x 38 | 10 | 2.7 |
| 36 x 41 | 10 | 1.3 |

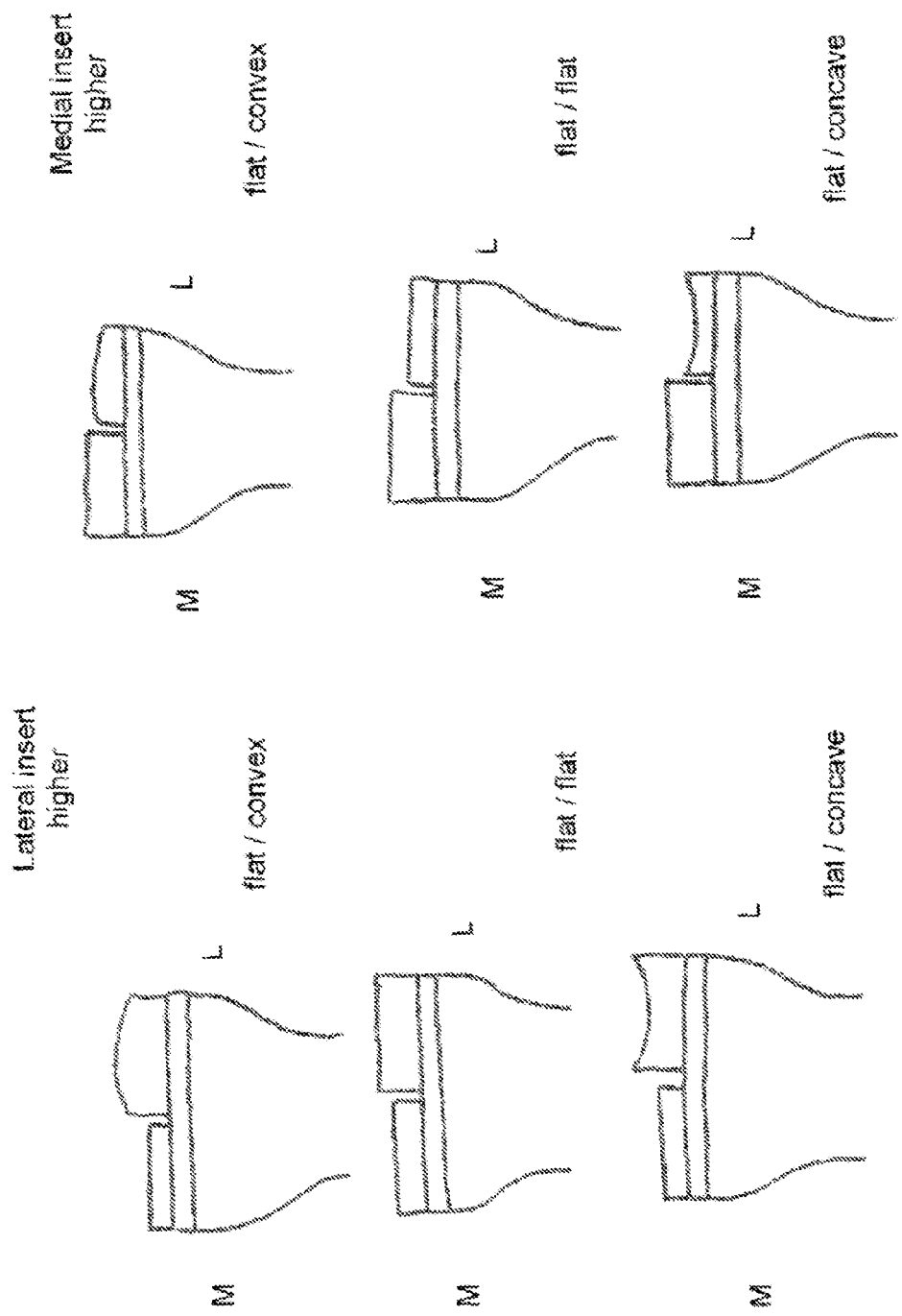

Stippled line = outline of tibial implant avoiding interference with PCL
PCL attachment

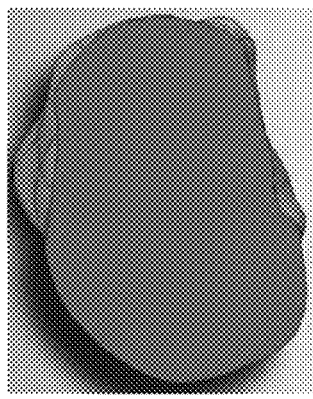
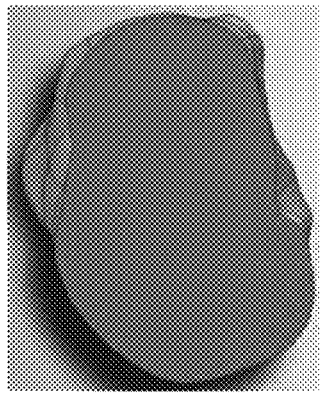
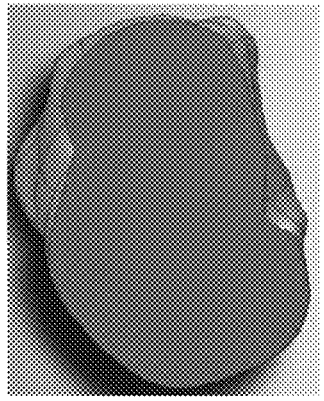
FIG. 65

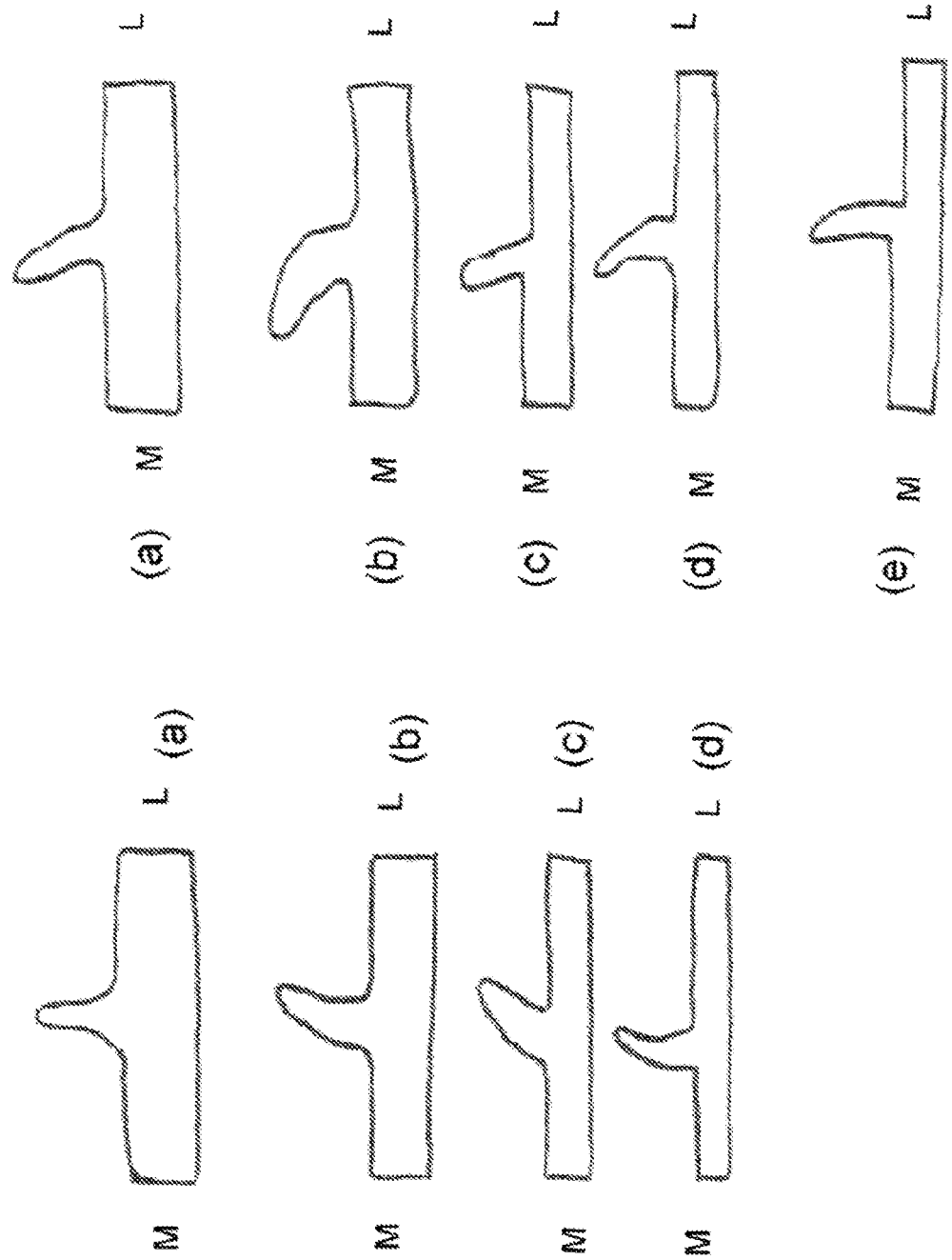

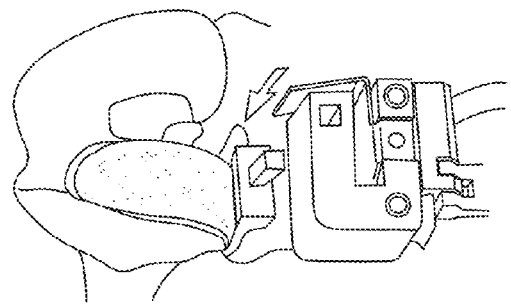
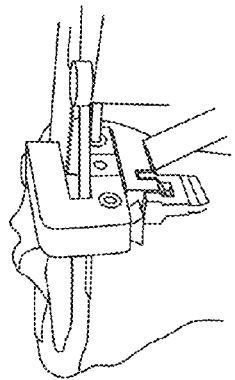
FIG. 73E
FIG. 73F
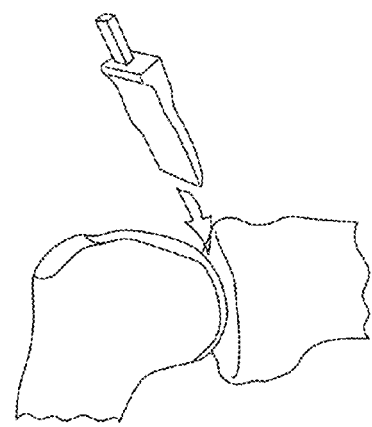
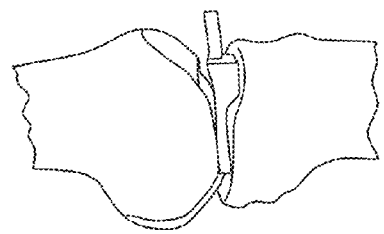
FIG. 73C
FIG. 73D
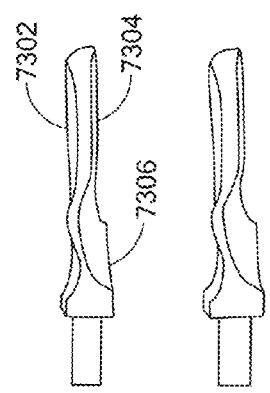
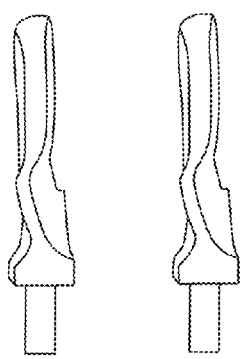
FIG. 73A
FIG. 73B

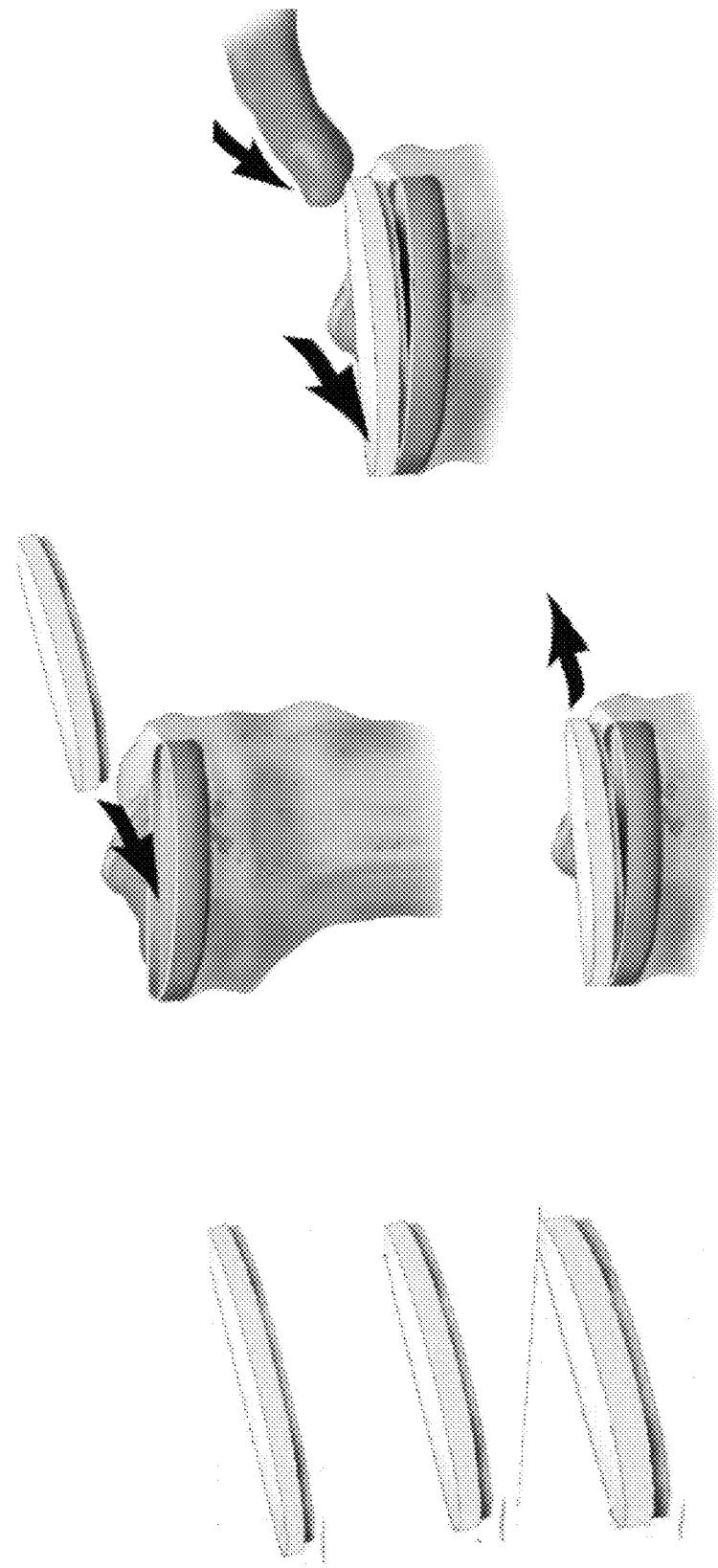

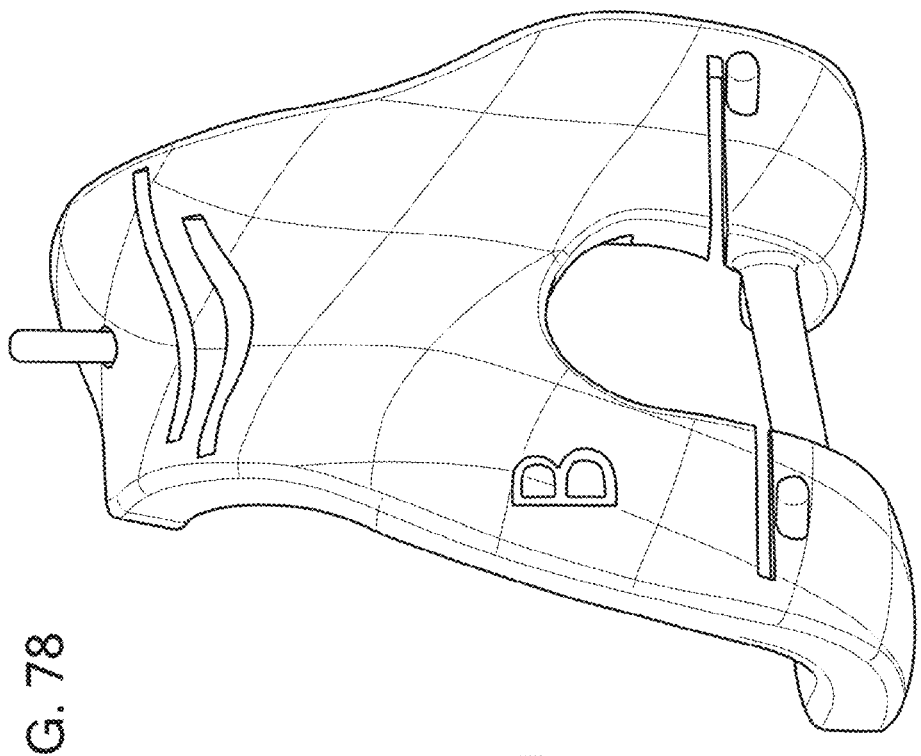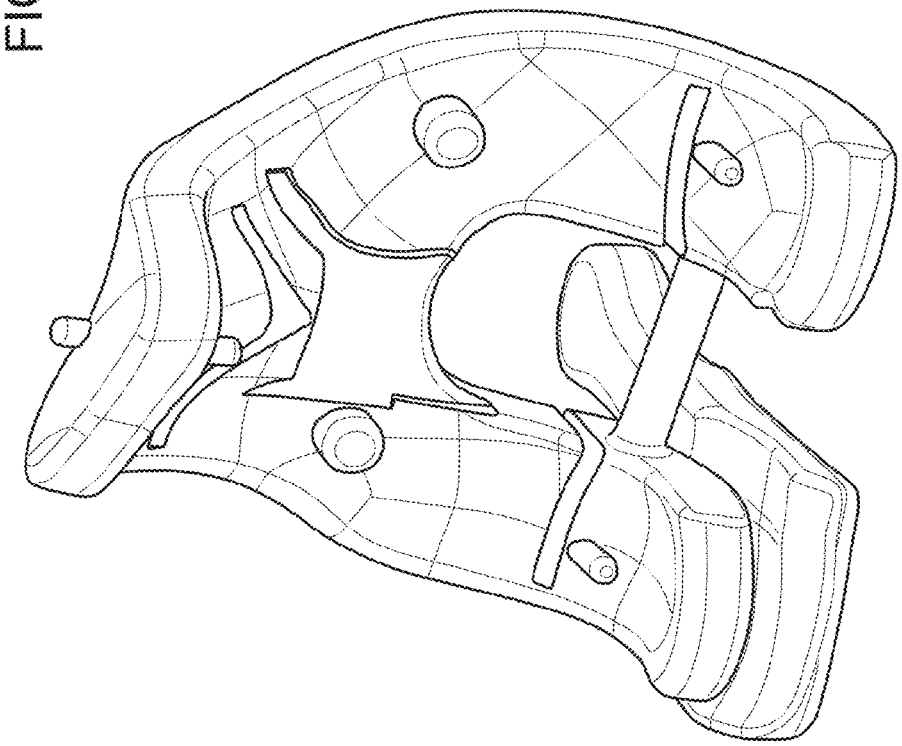
FIG. 78

Tibial Guide designed to seat on cartilage proximally on the tibia and conform to the bone surface anteriorly.
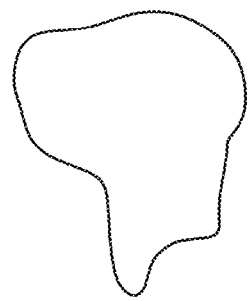
- 2mm one cut
- 5° AP Slope
- Perp. Mechanical Axis
- Assumption of 2mm cartilage thickness
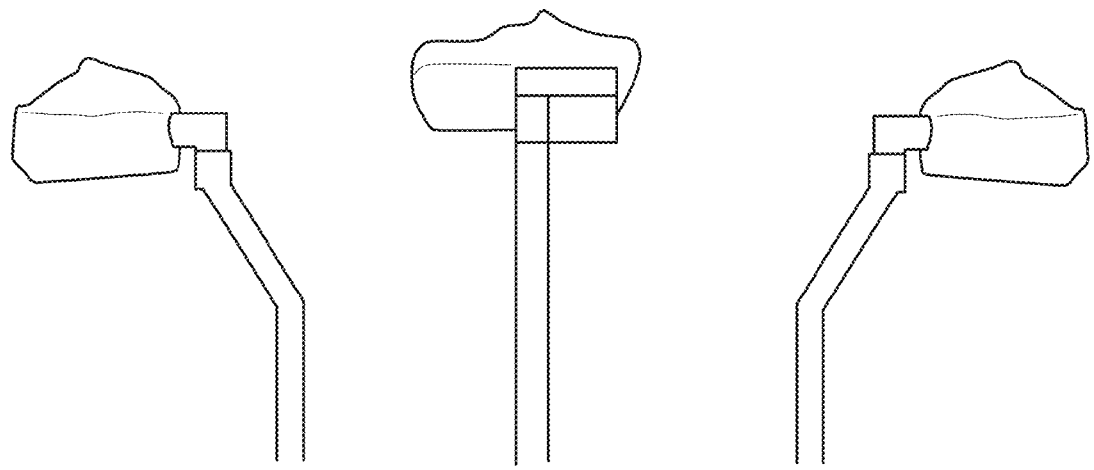
FIG. 84A

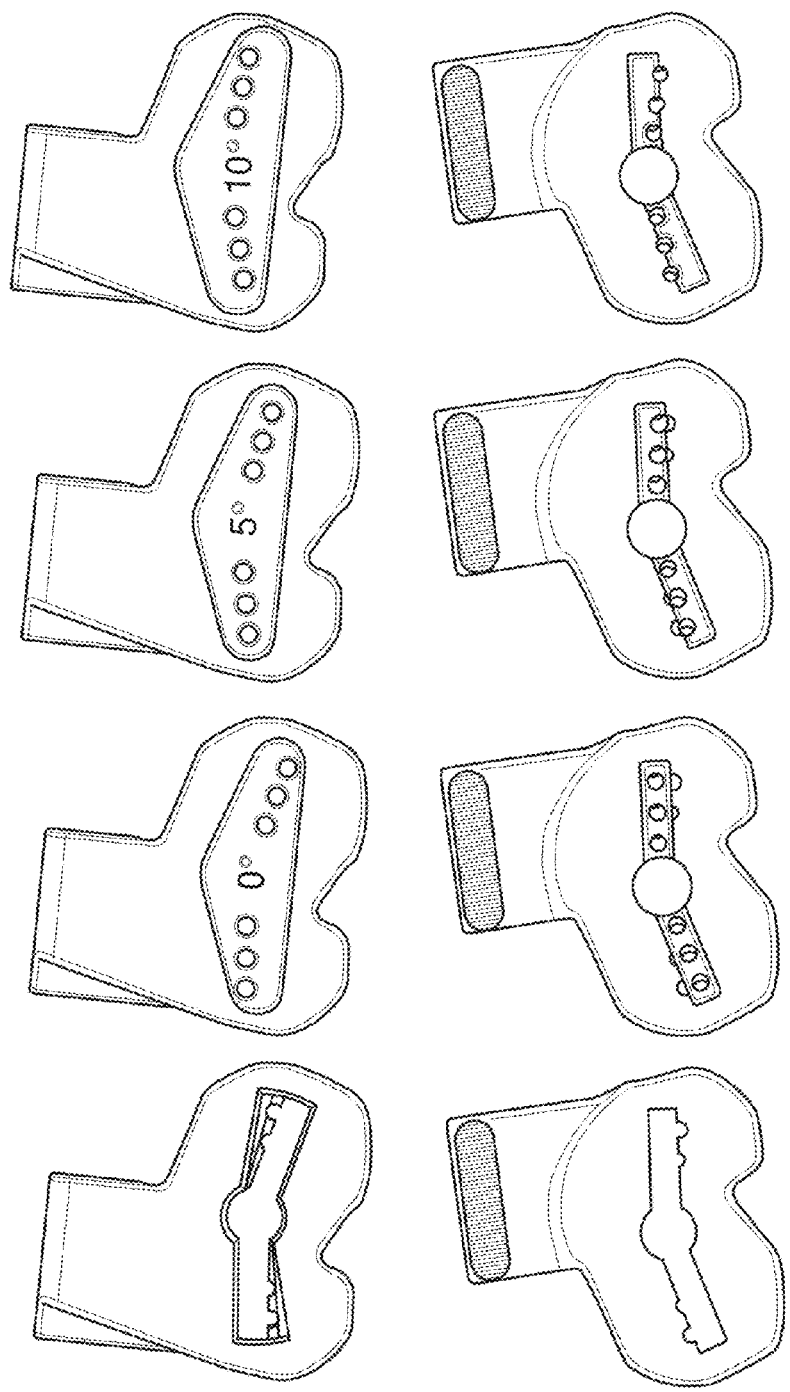

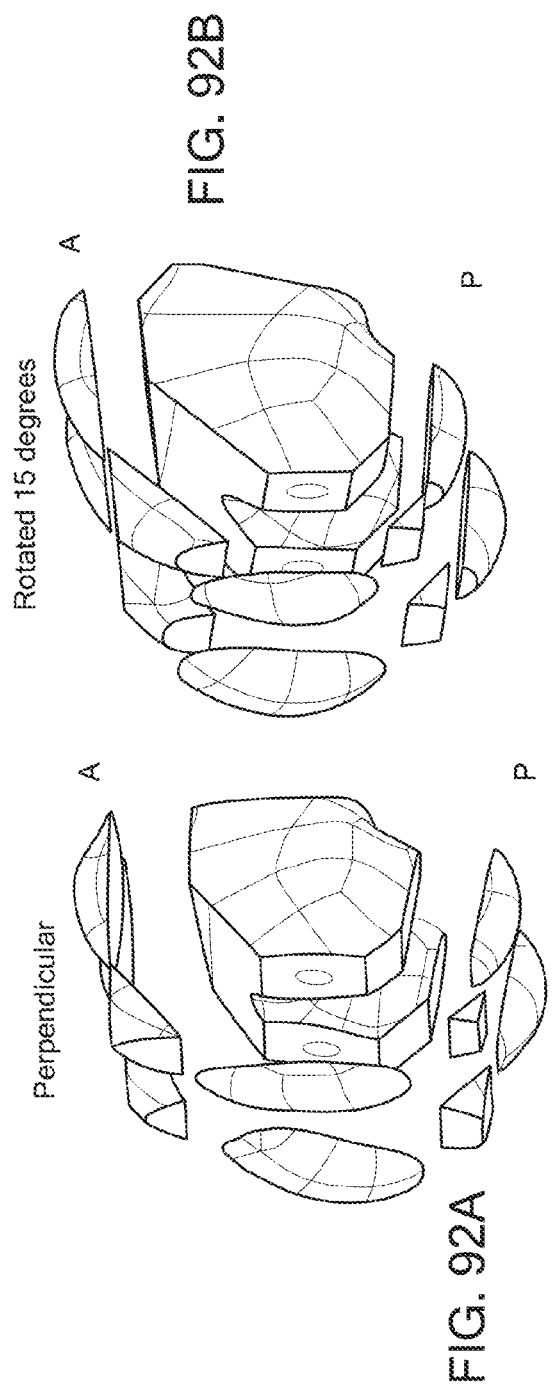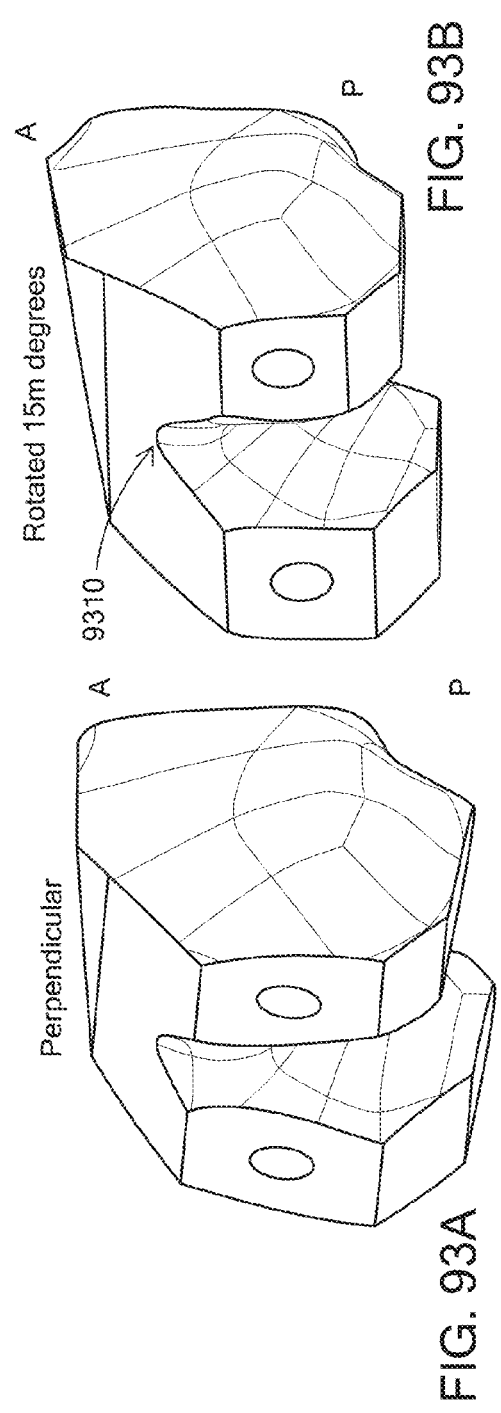

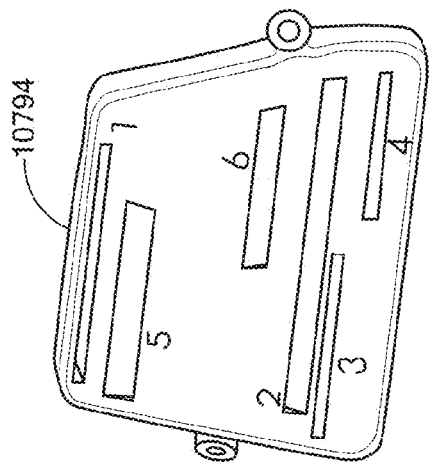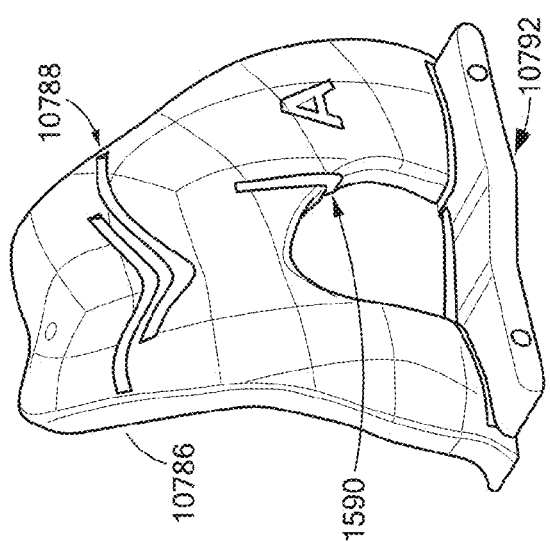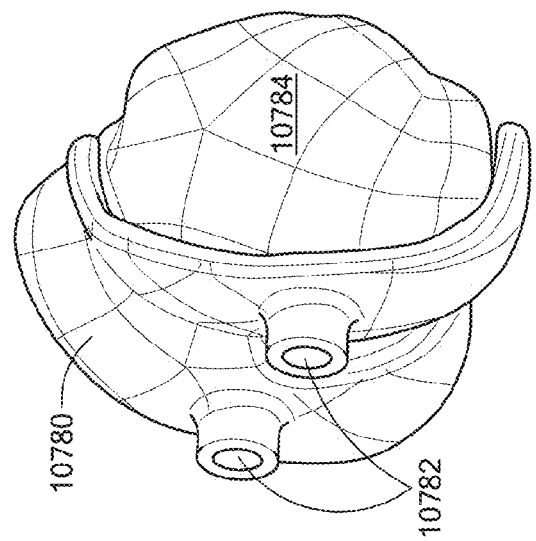

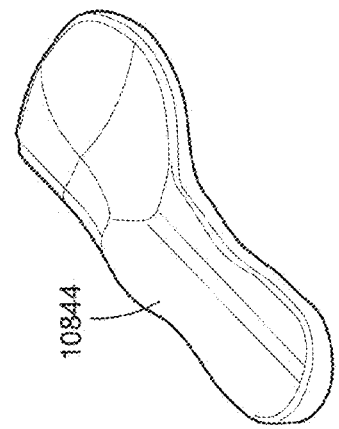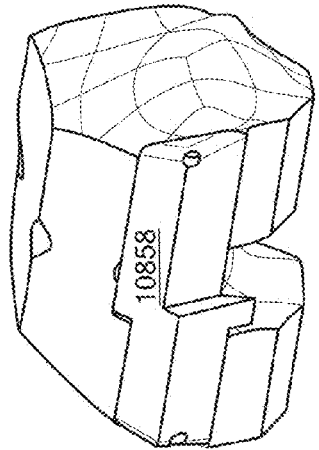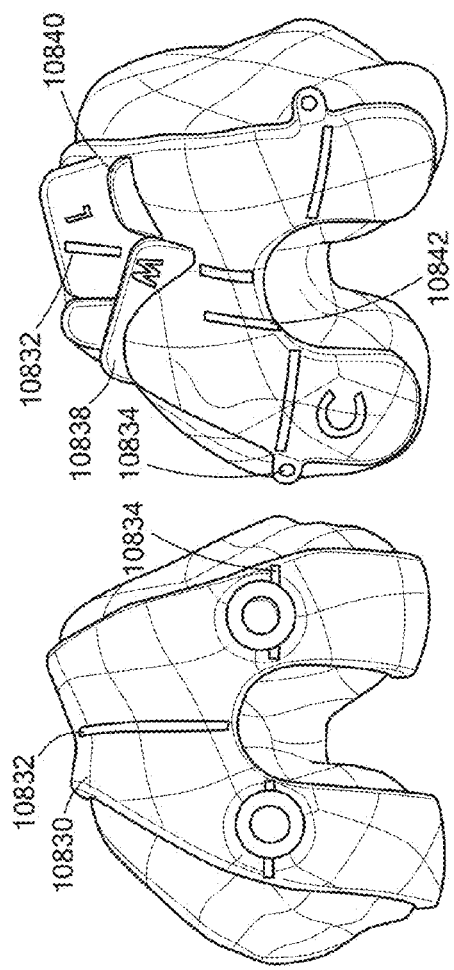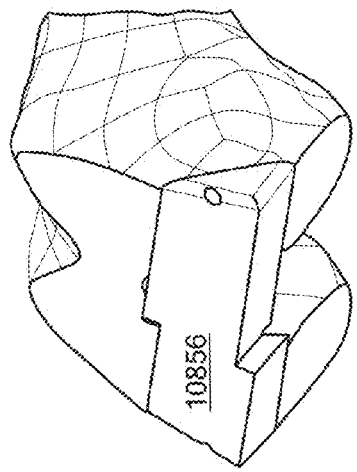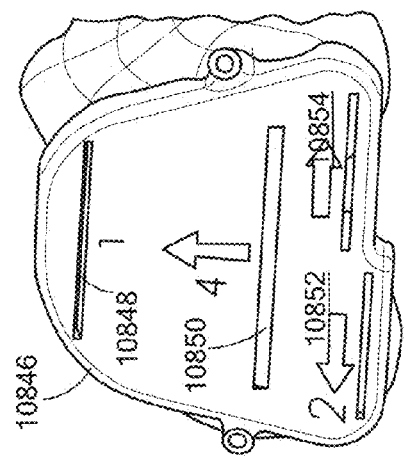

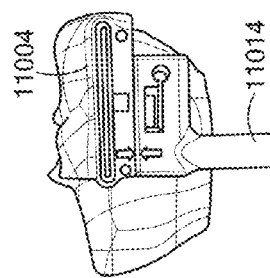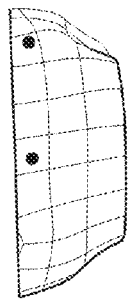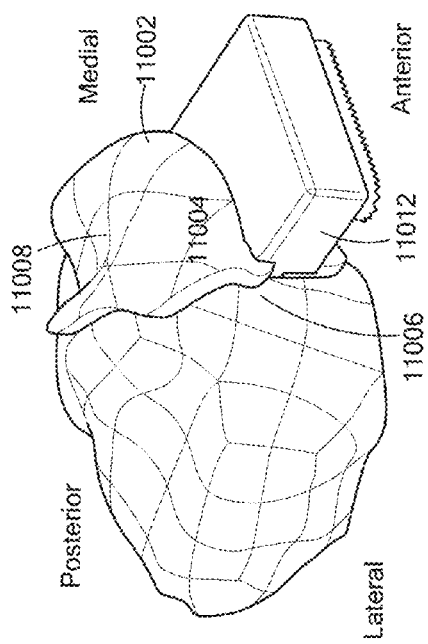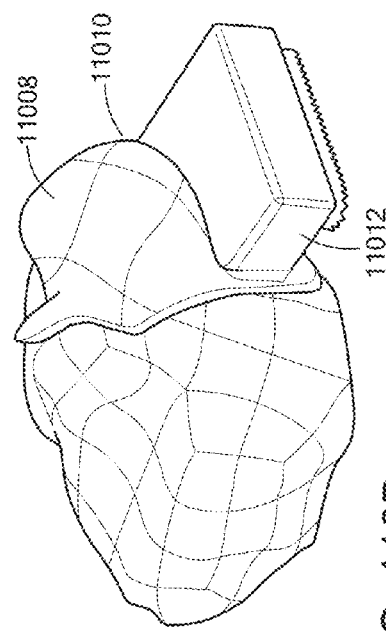
FIG. 110C
FIG. 110D
FIG. 110A
FIG. 110B

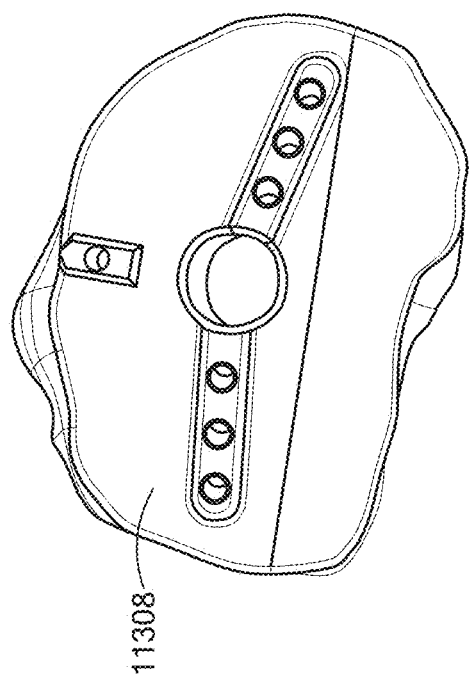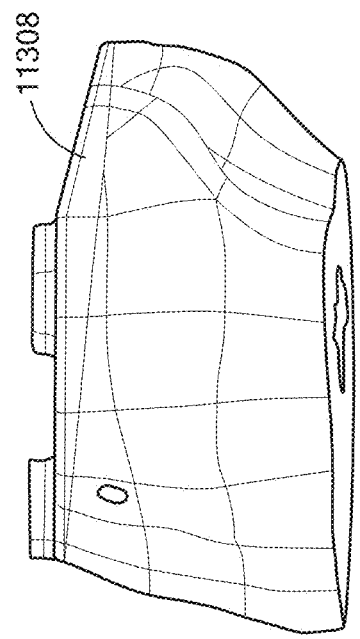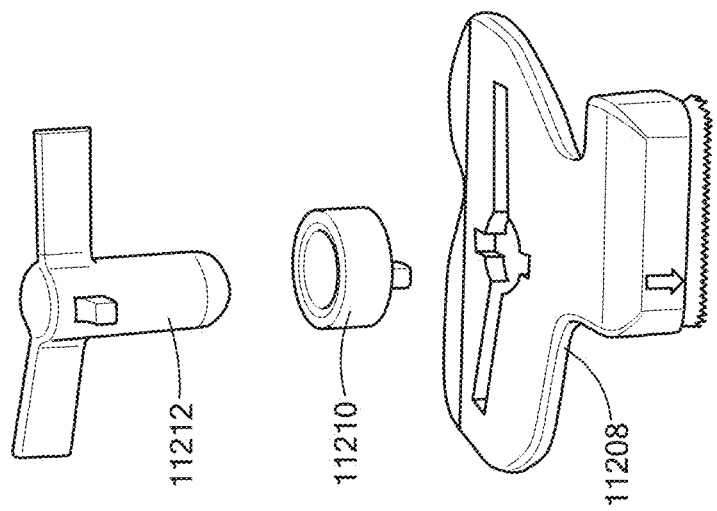
FIG. 113A
FIG. 113B
FIG. 112

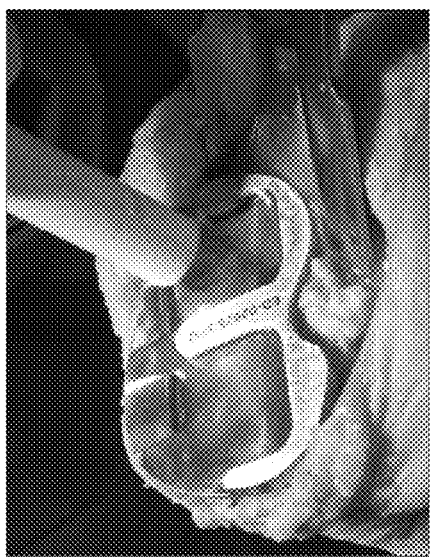
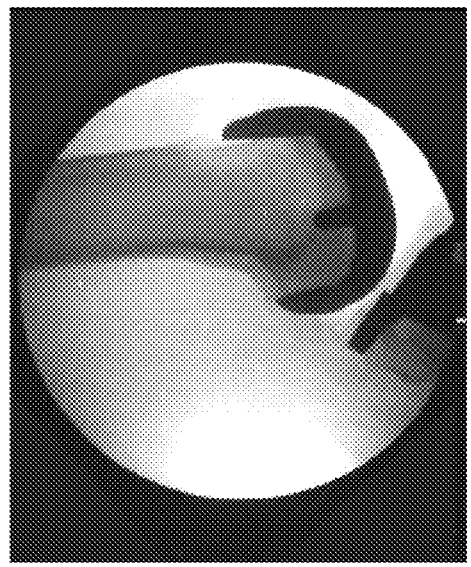
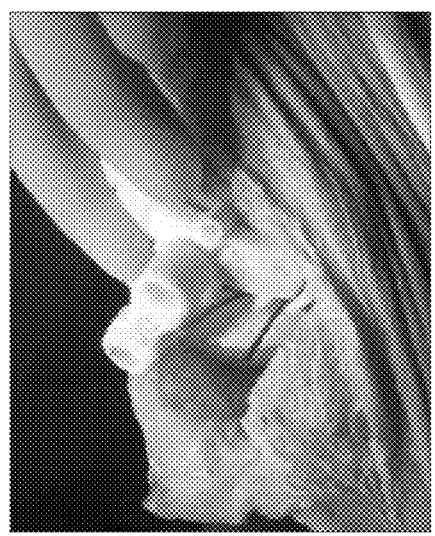
FIG. 117A
FIG. 117B
FIG. 117C
FIG. 117D

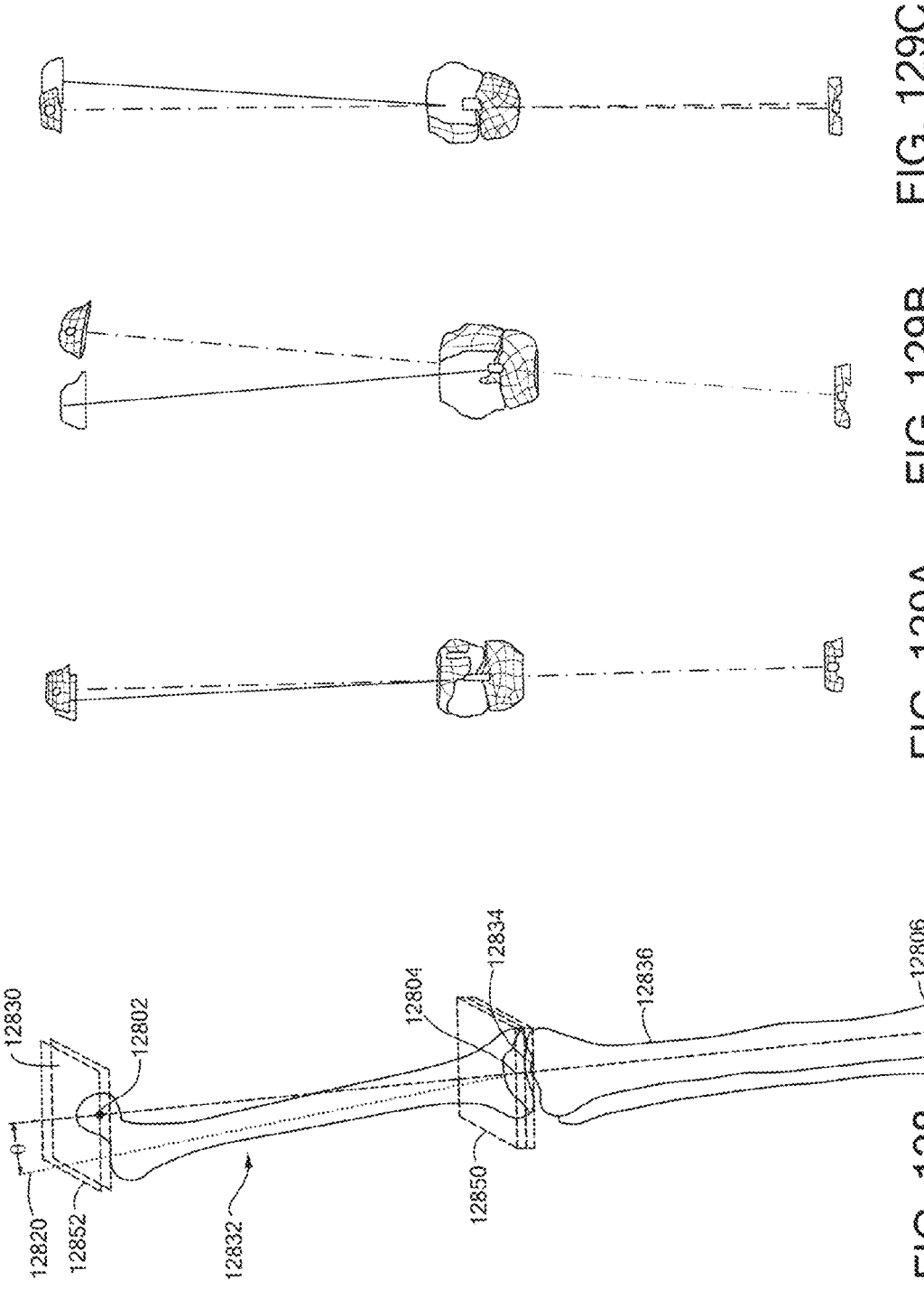

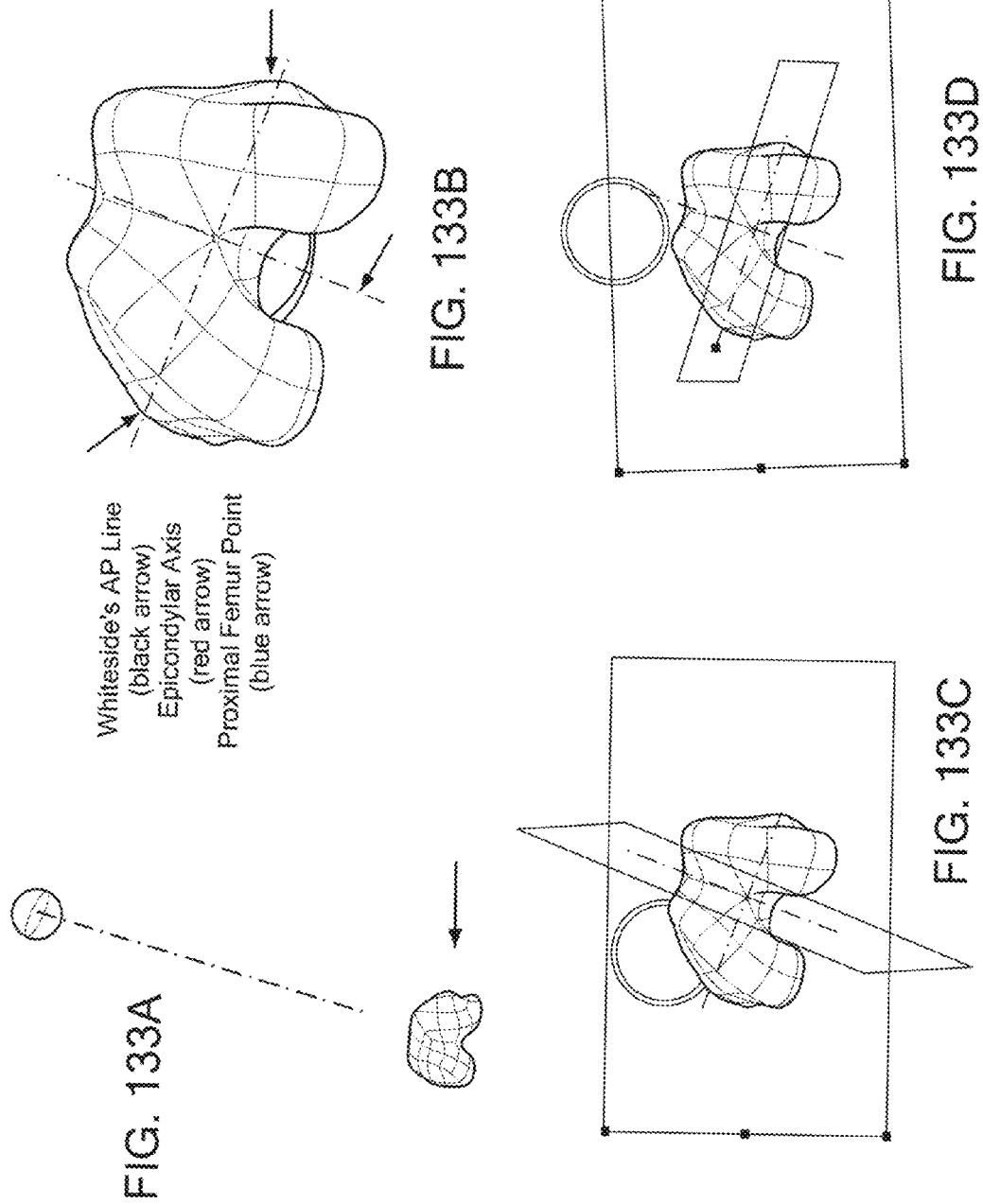

 
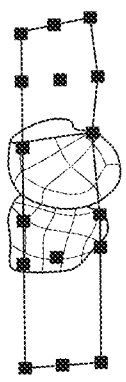 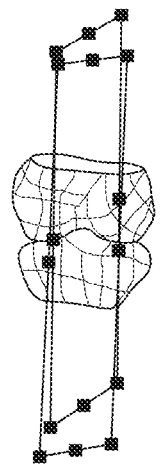
 
FIG. 134A    FIG. 134B

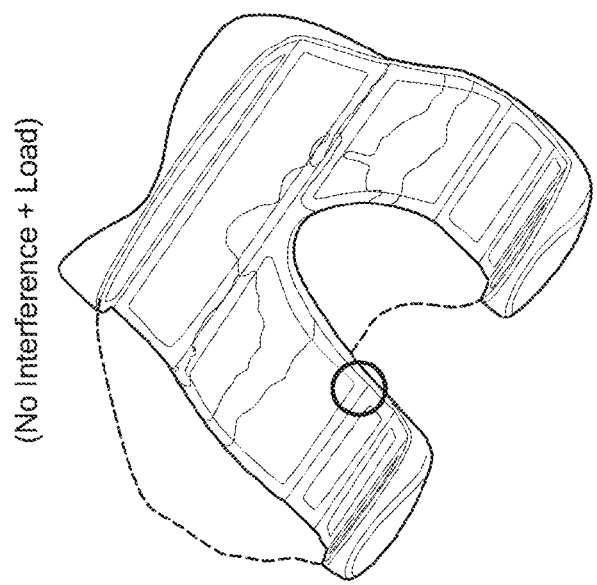
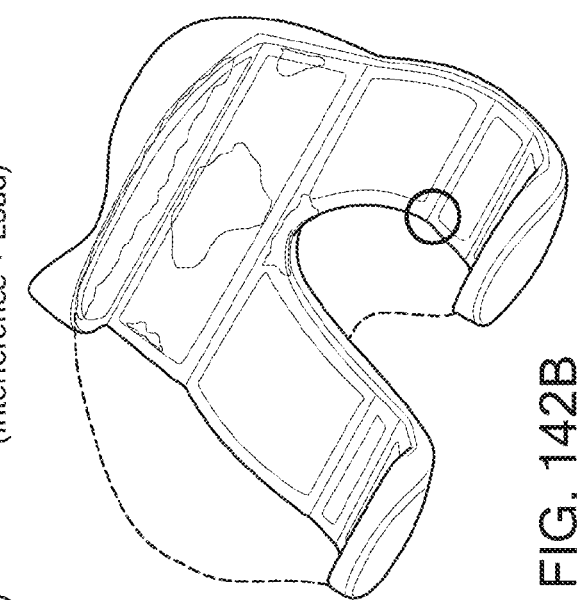
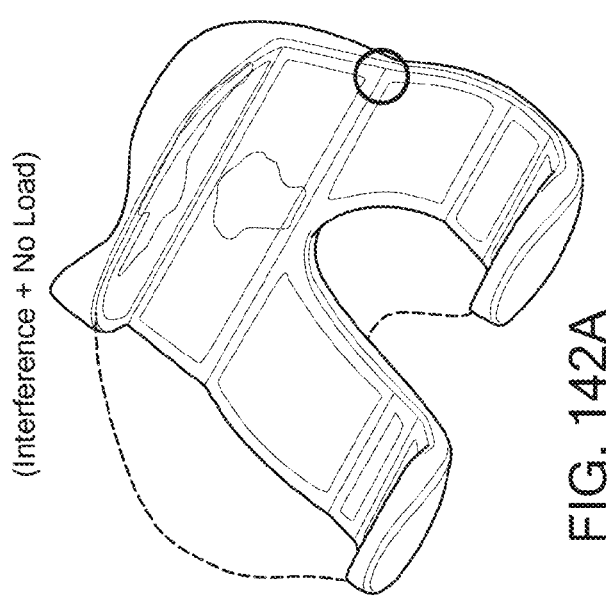
FIG. 142C (No Interference + Load)
FIG. 142B (Interference + Load)
FIG. 142A (Interference + No Load)

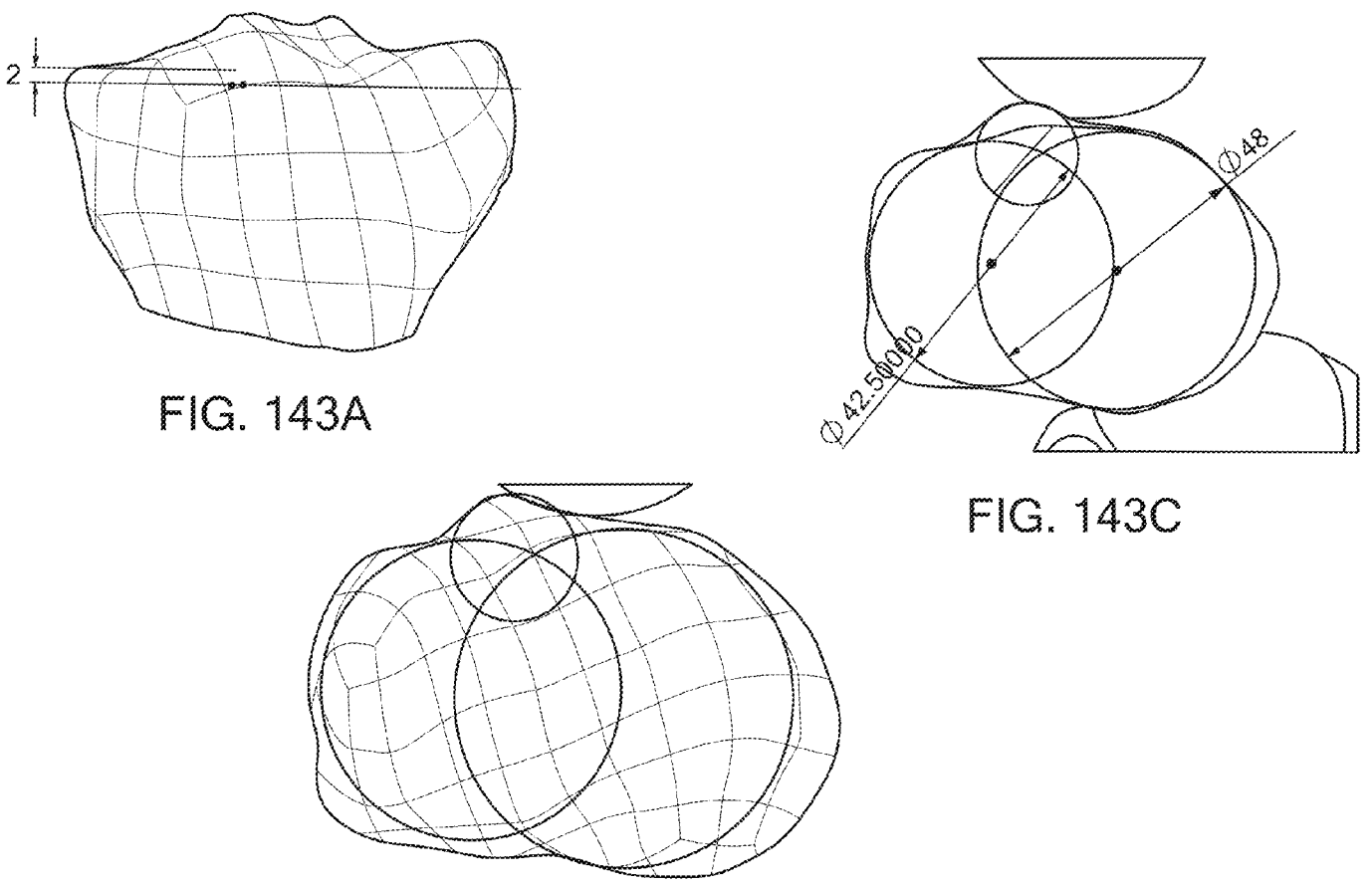

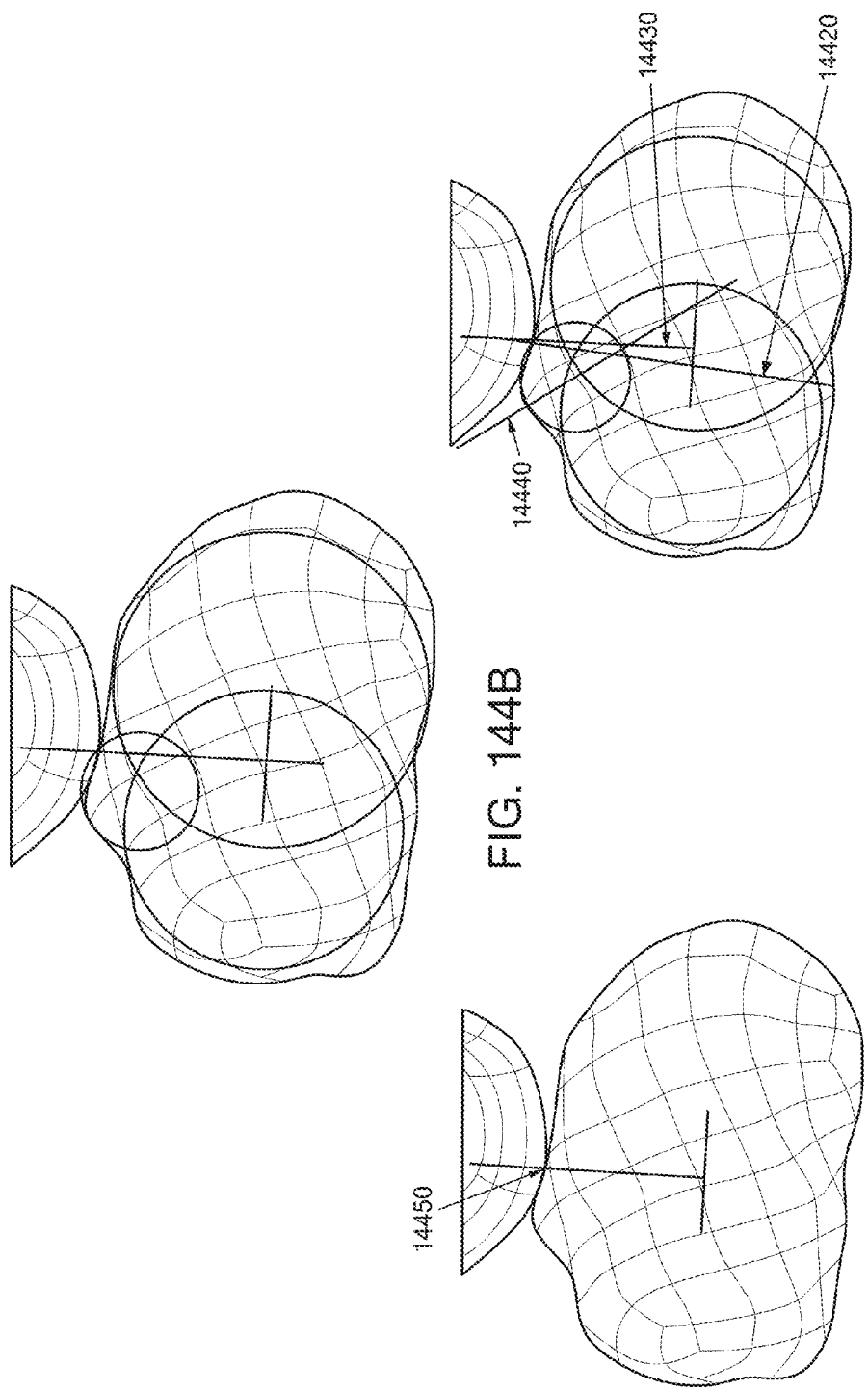

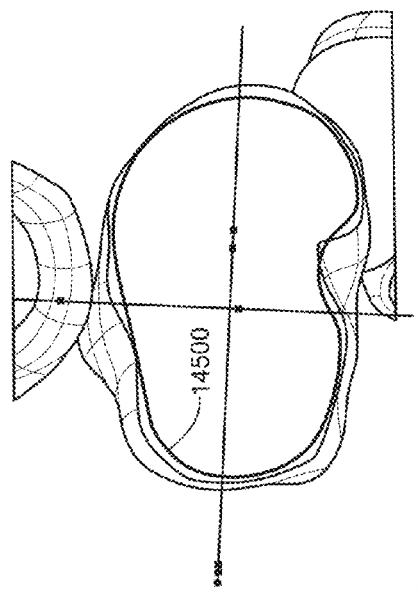
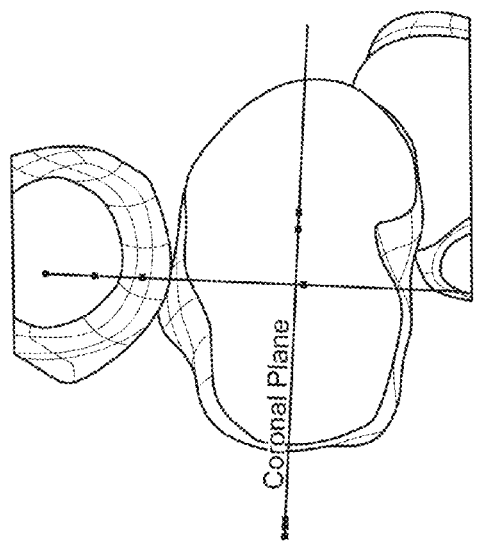
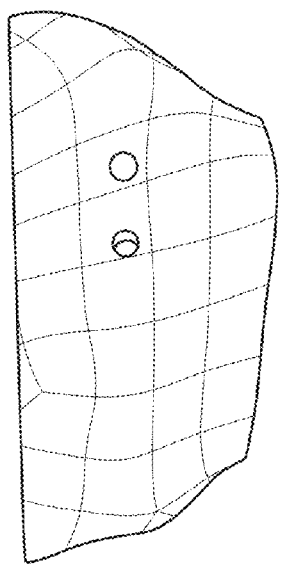
FIG. 145C
FIG. 145B
FIG. 145A

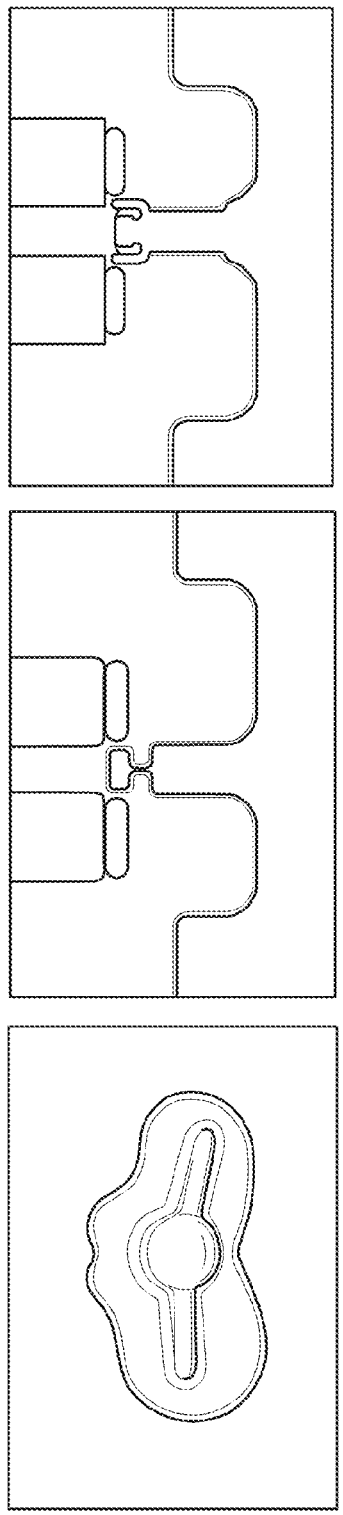
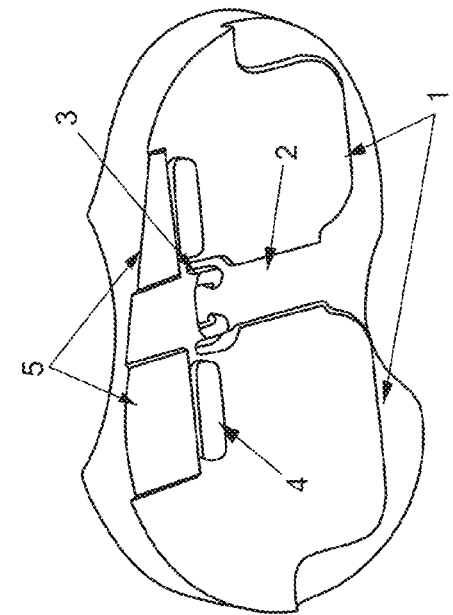
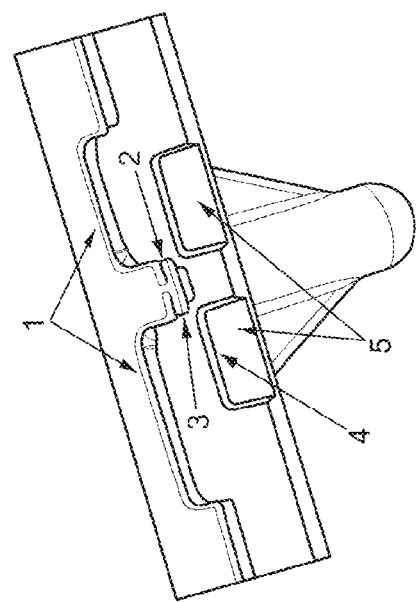
FIG. 157A  FIG. 157B  FIG. 157C  FIG. 157D  FIG. 157E 1 piece insert 2 piece insert 1 piece insert 2 piece insert 1 piece insert 2 piece insert

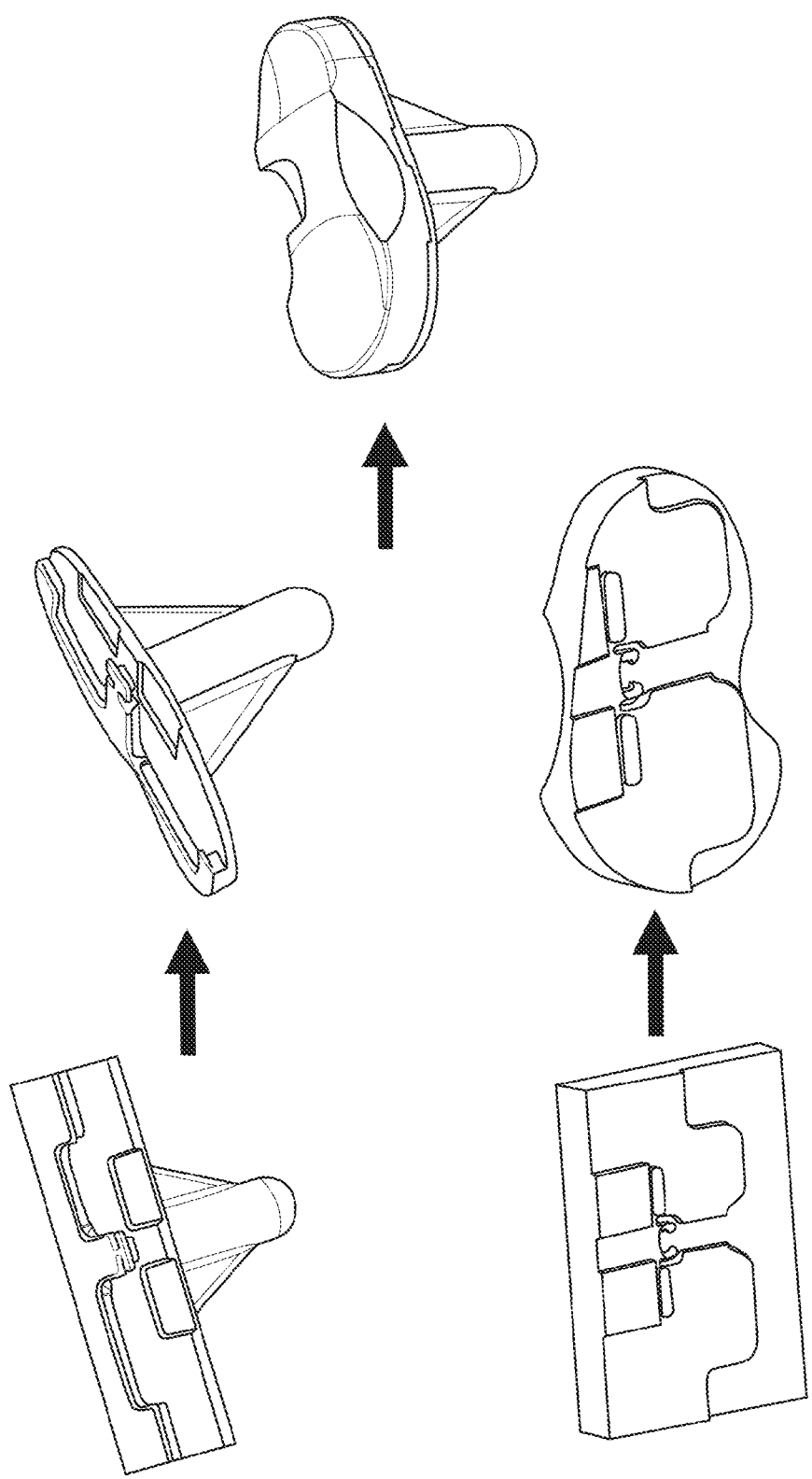

Tibial Rotation Continues

TABLE I Data on Rotational Angle θ

| Tibial Anteroposterior Axis | Angle θ° | | |
|---|---|---|---|
| | All Knees (N = 53) | Male Patients (N = 11) | Female Patients (N = 42) |
| 1 | 16.5 +/- 7.4 (1.0 to 32.0) | 16.0 +/- 7.3 (6.1 to 26.0) | 16.7 +/- 7.5 (1.0 to 32.0) |
| 2 | 8.0 +/- 7.6 (-10.0 to 24.0) | 7.4 +/- 7.5 (-4.5 to 18.0) | 8.2 +/- 7.5 (-10.0 to 24.0) |
| 3 | 3.6 +/- 6.8 (-16.0 to 16.0) | 3.3 +/- 7.3 (-8.0 to 14.0) | 3.7 +/- 6.7 (-16.0 to 18.0) |
| 4 | 19.7 +/- 6.4 (7.0 to 33.0) | 20.5 +/- 5.9 (12.0 to 30.5) | 19.5 +/- 6.5 (7.0 to 33.0) |
| 5 | 5.9 +/- 6.6 (-7.0 to 20.0) | 5.8 +/- 5.2 (-2.0 to 16.0) | 6.0 +/- 6.9 (-7.0 to 20.0) |

*The values are given as the mean and the standard deviation, with the range in parentheses. A positive value of the angle indicates external rotation of the anteroposterior axis of the distal end of the tibia.

TABLE II Predicted Postoperative Tibial Coronal Alignement

| Tibial Anteroposterior Axis | Angle θ for All Knees (N - 53) | |
|---|---|---|
| | 7° Slope | 0° Slope |
| 1 | 4.3 +/- 1.9 (0.2 to 8.2) | 2.3 +/- 1.0 (0.1 to 4.6) |
| 2 | 2.1 +/- 2.0 (-2.6 to 6.3) | 1.1 +/- 1.1 (-1.4 to 3.5) |
| 3 | 1.0 +/- 1.8 (-4.1 to 4.3) | 0.5 +/- 1.0 (-2.2 to 2.4) |
| 4 | 5.1 +/- 1.6 (1.7 to 8.2) | 2.8 +/- 0.9 (0.9 to 4.7) |
| 5 | 1.5 +/- 1.7 (-1.7 to 5.2) | 0.9 +/- 0.9 (-0.9 to 2.5) |

*The values are given as the man and the standard deviation, with the range in parentheses. A positive value indicates varus alignment.

(Mizu-uchi et al, Effect of Ankle Rotation on Cutting of the Tibia in TKA, JBJ S 2006; Vol 88; Pages 2632-2636)

FIG. 161C

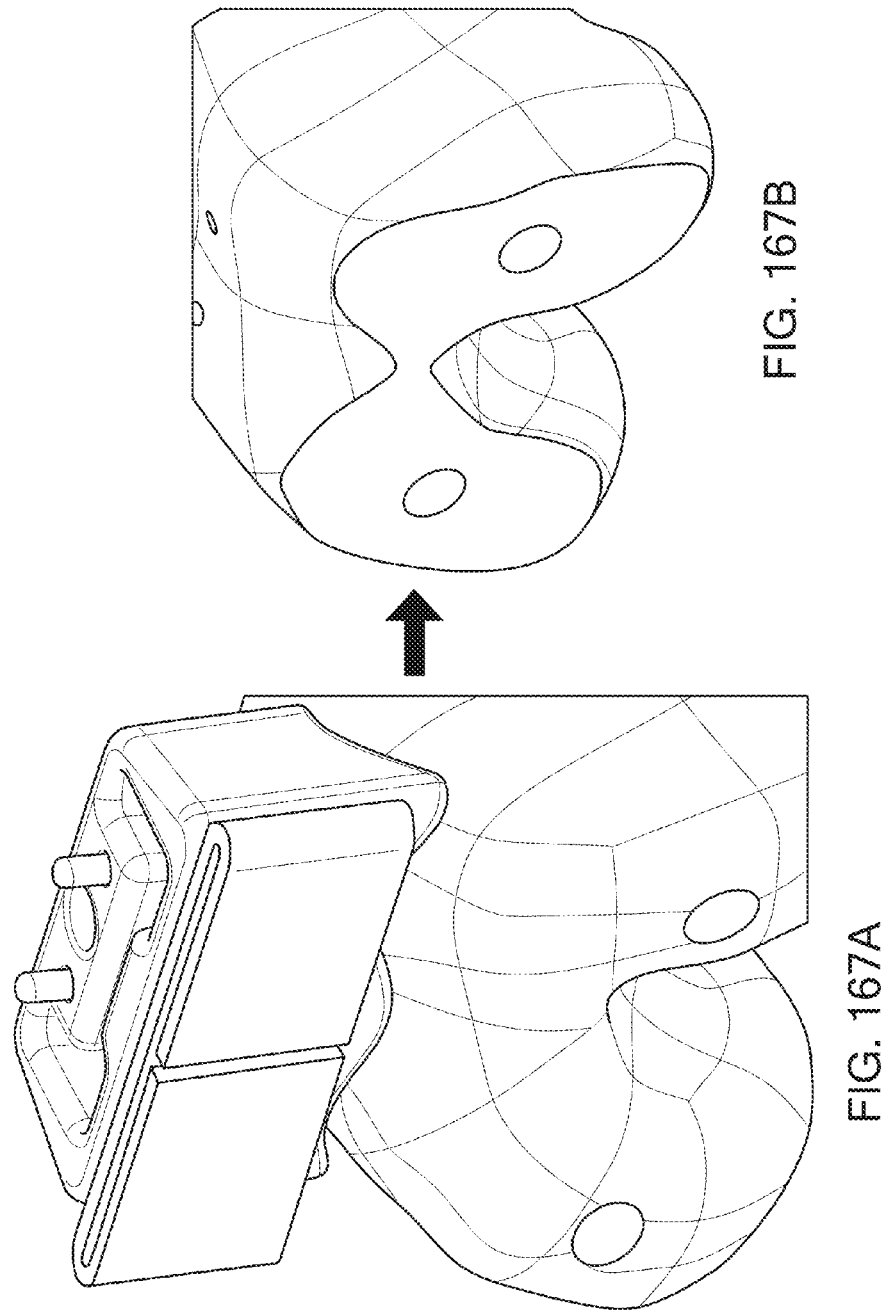

PATIENT-ADAPTED AND IMPROVED ARTICULAR IMPLANTS, DESIGNS AND RELATED GUIDE TOOLS

RELATED APPLICATIONS

This application is a continuation of U.S. Ser. No. 13/938,081, filed Jul. 9, 2013, entitled "Patient-Adapted and Improved Articular Implants, Designs and Related Guide Tools," which in turn is a continuation of U.S. Ser. No. 13/294,564, filed Nov. 11, 2011, entitled "Patient-Adapted and Improved Orthopedic Implants, Designs and Related Guide Tools," which in turn is a continuation of U.S. Ser. No. 12/660,529, filed Feb. 25, 2010, entitled "Patient-Adapted and Improved Articular Implants, Designs and Related Guide Tools," which in turn claims the benefit of: U.S. Ser. No. 61/155,362, entitled "Patient-Specific Orthopedic Implants And Models," filed Feb. 25, 2009; U.S. Ser. No. 61/269,405, entitled "Patient-Specific Orthopedic Implants And Models," filed Jun. 24, 2009; U.S. Ser. No. 61/273,216, entitled "Patient-Specific Orthopedic Implants And Models," filed Jul. 31, 2009; U.S. Ser. No. 61/275,174, entitled "Patient-Specific Orthopedic Implants And Models," filed Aug. 26, 2009; U.S. Ser. No. 61/280,493, entitled "Patient-Adapted and Improved Orthopedic Implants, Designs and Related Tools," filed Nov. 4, 2009; U.S. Ser. No. 61/284,458, entitled "Patient-Adapted And Improved Orthopedic Implants, Designs And Related Tools," filed Dec. 18, 2009; U.S. Ser. No. 61/155,359, entitled "Patient Selectable Joint Arthroplasty Devices and Surgical Tools," filed Feb. 25, 2009; and U.S Ser. No. 61/220,726, entitled "Patient-Specific Orthopedic Implants And Models," filed Jun. 26, 2009.

U.S. Ser. No. 12/660,529 is also a continuation-in-part of U.S. Ser. No. 12/712,072, entitled "Automated Systems For Manufacturing Patient-Specific Orthopedic Implants And Instrumentation" filed Feb. 24, 2010, which claims the benefit of U.S. Ser. No. 61/208,440, entitled "Automated Systems for Manufacturing Patient-Specific Orthopedic Implants and Instrumentation" filed Feb. 24, 2009, and U.S. Ser. No. 61/208,444, entitled "Automated Systems for Manufacturing Patient-Specific Orthopedic Implants and Instrumentation" filed Feb. 24, 2009.

Each of the above-described applications is hereby incorporated herein by reference in its entirety.

TECHNICAL FIELD

The invention relates to improved and/or patient-adapted (e.g., patient-specific and/or patient-engineered) orthopedic implants and guide tools, as well as related methods, designs and models.

BACKGROUND

Generally, a diseased, injured or defective joint, such as, for example, a joint exhibiting osteoarthritis, has been repaired using standard off-the-shelf implants and other surgical devices. Specific off-the-shelf implant designs have been altered over the years to address particular issues. For example, several existing designs include implant components having rotating parts to enhance joint motion. Ries et al. describes design changes to the distal or posterior condyles of a femoral implant component to enhance axial rotation of the implant component during flexion. See U.S. Pat. Nos. 5,549,688 and 5,824,105. Andriacchi et al. describes a design change to the heights of the posterior condyles to enhance high flexion motion. See U.S. Pat. No. 6,770,099. However, in altering a design to address a particular issue, historical design changes frequently have created one or more additional issues for future designs to address. Collectively, many of these issues have arisen from one or more differences between a patient's existing or healthy joint anatomy and the corresponding features of an implant component.

Historically, joint implants have employed a one-size-fits-all (or a few-sizes-fit-all) approach to implant design that has resulted in significant differences between a patient's existing or healthy biological structures and the resulting implant component features in the patient's joint. Accordingly, advanced implant designs and related devices and methods that address the needs of individual patient's are needed.

SUMMARY

The embodiments described herein include advancements in or arise out of the area of patient-adapted articular implants that are tailored to address the needs of individual, single patients. Such patient-adapted articular implants offer advantages over the traditional one-size-fits-all approach, or a few-sizes-fit-all approach. The advantages include, for example, better fit, more natural movement of the joint, reduction in the amount of bone removed during surgery and a less invasive procedure. Such patient-adapted articular implants can be created from images of the patient's joint. Based on the images, patient-adapted implant components can be selected and/or designed to include features (e.g., surface contours, curvatures, widths, lengths, thicknesses, and other features) that match existing features in the single, individual patient's joint as well as features that approximate an ideal and/or healthy feature that may not exist in the patient prior to a procedure. Moreover, by altering the design approach to address several design implant issues, several non-traditional design approaches have been identified that offer improvements over traditional implant designs.

Patient-adapted features can include patient-specific and/or patient-engineered. Patient-specific (or patient-matched) implant component or guide tool features can include features adapted to match one or more of the patient's biological features, for example, one or more biological/anatomical structures, alignments, kinematics, and/or soft tissue impingements. Patient-engineered (or patient-derived) features of an implant component can be designed and/or manufactured (e.g., preoperatively designed and manufactured) based on patient-specific data to substantially enhance or improve one or more of the patient's anatomical and/or biological features.

The patient-adapted (e.g., patient-specific and/or patient-engineered) implant components and guide tools described herein can be selected (e.g., from a library), designed (e.g., preoperatively designed including, optionally, manufacturing the components or tools), and/or selected and designed (e.g., by selecting a blank component or tool having certain blank features and then altering the blank features to be patient-adapted). Moreover, related methods, such as designs and strategies for resectioning a patient's biological structure also can be selected and/or designed. For example, an implant component bone-facing surface and a resectioning strategy for the corresponding bone-facing surface can be selected and/or designed together so that an implant component's bone-facing surface matches the resected surface. In addition, one or more guide tools optionally can be selected and/or designed to facilitate the resection cuts that are predetermined in accordance with resectioning strategy and implant component selection and/or design.

In certain embodiments, patient-adapted features of an implant component, guide tool or related method can be achieved by analyzing imaging test data and selecting and/or designing (e.g., preoperatively selecting from a library and/or designing) an implant component, a guide tool, and/or a procedure having a feature that is matched and/or optimized for the particular patient's biology. The imaging test data can include data from the patient's joint, for example, data generated from an image of the joint such as x-ray imaging, cone beam CT, digital tomosynthesis, and ultrasound, a MRI or CT scan or a PET or SPECT scan, is processed to generate a varied or corrected version of the joint or of portions of the joint or of surfaces within the joint. Certain embodiments provide method and devices to create a desired model of a joint or of portions or surfaces of a joint based on data derived from the existing joint. For example, the data can also be used to create a model that can be used to analyze the patient's joint and to devise and evaluate a course of corrective action. The data and/or model also can be used to design an implant component having one or more patient-specific features, such as a surface or curvature.

In one aspect, embodiments described herein provide a pre-primary articular implant component that includes (a) an outer, joint-facing surface and an inner, bone-facing surface. The outer, joint-facing surface can include a bearing surface. The inner joint facing surface can include one or more patient-engineered bone cuts selected and/or designed from patient-specific data. In certain embodiments, the patient-engineered bone cuts can be selected and/or designed from patient-specific data to minimize the amount of bone resected in one or more corresponding predetermined resection cuts. In certain embodiments, the patient-engineered bone cuts substantially negatively-match one or more predetermined resection cuts. The predetermined resection cuts can be made at a first depth that allows, in a subsequent procedure, removal of additional bone to a second depth required for a traditional primary implant component. In addition, the pre-primary articular implant component can be a knee joint implant component, a hip joint implant component, a shoulder joint implant component, or a spinal implant component. For example, the pre-primary articular implant component can be a knee joint implant component, such as a femoral implant component. Moreover, the pre-primary articular implant component can include six or more (e.g., six, seven, eight, nine, ten, eleven, twelve, thirteen, or more) patient-engineered bone cuts on its bone facing surface.

In certain embodiments, the pre-primary articular implant component can include an implant component thickness in one or more regions that is selected and/or designed from patient-specific data to minimize the amount of bone resected. The one or more regions comprises the implant component thickness perpendicular to a planar bone cut and between the planar bone cut and the joint-surface of the implant component.

In another aspect, embodiments described herein provide methods for minimizing resected bone from, and/or methods for making an articular implant for, a single patient in need of an articular implant replacement procedure. These methods can include (a) identifying unwanted tissue from one or more images of the patient's joint; (b) identifying a combination of resection cuts and implant component features that remove the unwanted tissue and also provide maximum bone preservation; and (c) selecting and/or designing for the patient a combination of resection cuts and implant component features that provide removal of the unwanted tissue and maximum bone preservation. In certain embodiments, the unwanted tissue is diseased tissue or deformed tissue.

In certain embodiments, step (c) can include designing for the single patient a combination of resection cuts and implant component features that provide removal of the unwanted tissue and maximum bone preservation. Designing can include manufacturing. Moreover, the implant component features in step (c) can include one or more of the features selected from the group consisting of implant thickness, bone cut number, bone cut angles, and/or bone cut orientations.

In certain embodiments, a measure of bone preservation can include total volume of bone resected, volume of bone resected from one or more resection cuts, volume of bone resected to fit one or more implant component bone cuts, average thickness of bone resected, average thickness of bone resected from one or more resection cuts, average thickness of bone resected to fit one or more implant component bone cuts, maximum thickness of bone resected, maximum thickness of bone resected from one or more resection cuts, maximum thickness of bone resected to fit one or more implant component bone cuts.

In certain embodiments, a minimum implant component also can be established. For example, step (a) also can include identifying a minimum implant component thickness for the single patient. Step (b) also can include identifying a combination of resection cuts and/or implant component features that provide a minimum implant thickness determined for the single patient. Step (c) also can include selecting and/or designing the combination of resection cuts and/or implant component features that provides at least a minimum implant thickness for the single patient. The minimum implant component thickness is based on one or more of femur and/or condyle size or patient weight.

The articular implant component can be a knee joint implant component, a hip joint implant component, a shoulder joint implant component, or a spinal implant component. For example, the pre-primary articular implant component can be a knee joint implant component, such as a femoral implant component.

In another aspect, embodiments described herein provide a femoral implant component that includes (a) a joint-facing surface comprising a bearing surface portion, and (b) a bone-facing surface comprising six or more bone cuts.

In another aspect, embodiments described herein provide a femoral implant component that includes (a) a joint-facing surface comprising a bearing surface portion, and (b) a bone-facing surface comprising a distal bone cut having two or more planar facets or portions that are non-coplanar with each other. In certain embodiments, the two or more facets or portions are non-parallel with each other. The first of the two or more facets or portions can be on a lateral condyle bone-facing surface and the second can be on a medial condyle bone-facing surface.

In another aspect, embodiments described herein provide a femoral implant component that includes (a) a joint-facing surface comprising a bearing surface portion, and (b) a bone-facing surface comprising an anterior bone cut having two or more planar facets or portions that are non-coplanar with each other. In certain embodiments, the two or more planar facets or portions are non-parallel with each other.

In another aspect, embodiments described herein provide a femoral implant component that includes (a) a joint-facing surface comprising a bearing surface portion, and (b) a bone-facing surface comprising a posterior bone cut having two or more facets or portions that are non-parallel with each other. In certain embodiments, the first of the two or more facets or portions can be on a lateral condyle bone-facing surface and the second can be on a medial condyle bone-facing surface.

In another aspect, embodiments described herein provide a femoral implant component that includes (a) a joint-facing surface comprising a bearing surface portion, and (b) a bone-facing surface comprising an anterior chamfer bone cut having two or more planar facets or portions that are non-coplanar with each other. In certain embodiments, the two or more planar facets or portions are non-parallel with each other. The first of the two or more facets or portions can be on a lateral condyle bone-facing surface and the second can be on a medial condyle bone-facing surface.

In another aspect, embodiments described herein provide a femoral implant component that includes (a) a joint-facing surface comprising a bearing surface portion, and (b) a bone-facing surface comprising a posterior chamfer bone cut having two or more facets or portions that are non-parallel with each other. In certain embodiments, the first of the two or more facets or portions can be on a lateral condyle bone-facing surface and the second can be on a medial condyle bone-facing surface.

In another aspect, embodiments described herein provide a femoral implant component that includes (a) a joint-facing surface comprising lateral and medial condylar surface portions, and (b) a bone-facing surface comprising an anterior bone cut, wherein the distance between the anterior bone cut and the lateral condylar surface portion is different from the distance between the anterior bone cut and the medial condylar surface portion. In certain embodiments, the two or more facets or portions are substantially non-parallel.

In another aspect, embodiments described herein provide a femoral implant component that includes (a) a lateral and medial condylar portions, and (b) a bone-facing surface comprising a distal bone cut facet that is asymmetric about its center line in a sagittal plane. In certain embodiments, the asymmetric distal bone cut facet lies on the bone-facing surface of the lateral condyle. In certain embodiments, the the asymmetric distal bone cut facet lies on the bone-facing surface of the medial condyle.

In another aspect, embodiments described herein provide a femoral implant component that includes a femoral implant component having a bone-facing surface comprising one or more bone cuts, wherein at least one of the one or more bone cuts comprises two planar bone cut facets separated by at least one step cut. In certain embodiments, the step cut is substantially perpendicular to at least one of the bone cut facets. In certain embodiments, the step cut can rise or fall at about 30 degrees or more from at least one of the bone cut facet planes.

In another aspect, embodiments described herein provide implant components having an inner, bone-facing surface designed to negatively-match a bone surface that was cut, for example based on pre-determined geometries or based on patient-specific geometries. In certain embodiments, an outer joint-facing surface includes at least in a portion that substantially negatively-matches a feature of the patient's anatomy and/or an opposing outer joint-facing surface of a second implant component. In certain embodiments, by creating negatively-matching component surfaces at a joint interface, the opposing surfaces may not have an anatomic or near-anatomic shape, but instead may be negatively-matching or near-negatively-matching to each other. This can have various advantages, such as reducing implant and joint wear and providing more predictable joint movement.

In another aspect, some embodiments provide implant components having one or more patient-specific curvatures or radii of curvature in one dimension, and one or more standard or engineered curvatures or radii of curvature in a second dimension.

In another aspect, some embodiments provide methods of designing, selecting, manufacturing, and implanting the patient-adapted implant components.

It is to be understood that the features of the various embodiments described herein are not mutually exclusive and may exist in various combinations and permutations.

BRIEF DESCRIPTION OF THE DRAWINGS

The foregoing and other objects, aspects, features, and advantages of embodiments will become more apparent and may be better understood by referring to the following description, taken in conjunction with the accompanying drawings, in which:

FIGS. 4A-4M illustrate exemplary traditional implants including traditional knee-joint implants (FIGS. 4A and 4B), traditional hip-joint implants (FIGS. 4C-4G), traditional shoulder-joint implants (FIGS. 4H-4J), and traditional spinal implants (FIGS. 4K-4M);

FIGS. 5A-5C schematically represent three illustrative embodiments of implants and/or implant components;

FIG. 10A is a drawing of a cross-sectional view of an end of a femur with an osteophyte; FIG. 10B is a drawing of the end of the femur of FIG. 10A with the osteophyte virtually removed; FIG. 10C is a drawing of the end of the femur of FIG. 10B with the osteophyte virtually removed and showing a cross-sectional view of an implant designed to the shape of the femur with the osteophyte removed; FIG. 10D is a drawing of the end of the femur of FIG. 10A and shows a cross-sectional view of an implant designed to the shape of the femur with the osteophyte intact;

FIG. 11A is a drawing of a cross-sectional view of an end of a femur with a subchondral void in the bone; FIG. 11B is a drawing of the end of the femur of FIG. 11A with the void virtually removed; FIG. 11C is a drawing of the end of the femur of FIG. 11B with the void virtually removed and showing a cross-sectional view of an implant designed to the shape of the femur with the void removed; FIG. 11D is a drawing of the end of the femur of FIG. 11A and showing a cross-sectional view of an implant designed to the shape of the femur with the void intact;

FIG. 16 illustrates a coronal plane of the knee with exemplary resection cuts that can be used to correct lower limb alignment in a knee replacement;

FIG. 17 depicts a coronal plane of the knee shown with femoral implant medial and lateral condyles having different thicknesses to help to correct limb alignment;

FIGS. 32A and 32B show the load bearing surfaces of a femoral implant component in a coronal view (FIG. 32A) and in a sagittal view (FIG. 32B);

FIGS. 33A through 33F illustrate exemplary types of curvatures for one or more condylar coronal or sagittal curvatures;

FIGS. 34A and 34B illustrate a design for a femoral implant component having a J-curve that is patient-specific in part and patient-engineered in part.

FIGS. 50A and 50B illustrate a femoral implant component comprising and intercondylar box (FIG. 50A) or intercondylar bars (FIG. 50B) and an engaging tibial implant component;

FIG. 57 illustrates a prolate-shaped patella implant component;

FIGS. 58A-58D show various aspects of embodiments of patella implant components;

FIGS. 63A through 63J show exemplary combinations of tibial tray designs;

FIG. 65 shows proximal tibial resection cut depths of 2 mm, 3 mm and 4 mm;

FIG. 70A illustrates a tibial cut with an AP slope of 7° and having a J-Curve of the patient's natural J-Curve; FIG. 70B illustrates a tibial cut with an AP slope of 7° and having a J-Curve tilted 7° posteriorly to achieve a thicker poly anteriorly;

FIGS. 71A and 71B depict exemplary cross-sections of tibial implant components having a post (or keel or projection) projecting from the bone-facing surface of the implant component;

FIG. 73A depicts a medial balancer chip insert from top view to show the superior surface of the chip; FIG. 73B depicts a side view of a set of four medial balancer chip inserts; FIG. 73C depicts a medial balancing chip being inserted in flexion between the femur and tibia; FIG. 73D depicts the medial balancing chip insert in place while the knee is brought into extension; FIG. 73E depicts a cutting guide attached to the medial balancing chip; FIG. 73F shows that the inferior surface of the medial balancing chip can act as cutting guide surface for resectioning the medial portion of the tibia;

FIG. 75A depicts a set of three medial tibial component insert trials having incrementally increasing thicknesses; FIG. 75B depicts the process of placing and adding various tibial component insert trials; FIG. 75C depicts the process of placing the selected tibial component insert;

FIG. 78 shows a guide tool for making distal and posterior resection cuts to the distal femur;

FIG. 84A shows a tibial guide tool for making a resection cut.

FIGS. 85A through 85D show exemplary tools for intraoperatively preparing a rotated tibial implant component;

FIGS. 92A and 92B illustrate five femoral resection cuts for the two designs shown in FIGS. 91A and 91B, respectively;

FIGS. 93A and 93B illustrate the completed cut femur models for each of two cut designs;

in FIG. 102B, a femur having five optimized resection cuts for matching to an optimized five-bone-cut implant component; in FIG. 102C, a femur having five, not flexed resection cuts for matching to an optimized five-bone-cut implant component; and in FIG. 102D, a femur having five, flexed resection cuts for matching to an optimized five-bone-cut, flexed implant component;

FIGS. 107A, 107B, and 107C illustrate a set of three guide tools, which collectively supplied all of the guide slots and holes to perform each of several predetermined femoral resection cuts and peg hole placements;

FIGS. 108A through 108F illustrate a different set of femoral guide tools to perform each of several predetermined femoral resection cuts and peg hole placements;

FIG. 110A illustrates a cutting guide tool for accurately resectioning the proximal tibia; FIG. 110B illustrates an alternate tibial cutting guide tool; FIG. 110C illustrates a tibial alignment guide tool and down rod for confirming prior the alignment of the cutting guide tool; FIG. 110D illustrates a resected tibia marked with a pen or other instrument to establish landmarks for placement of subsequent tools;

FIG. 112 illustrates a tibial keel prep guide tool for establishing the keel slot in the patient's resected proximal tibial surface;

FIGS. 113A and 113B illustrates an alternative tibial keel prep guide tool;

FIGS. 115A and 115B illustrate a tibial implant component comprising a tibial tray (FIG. 115A) and a set of tibial inserts (FIG. 115B);

Figure 116B:
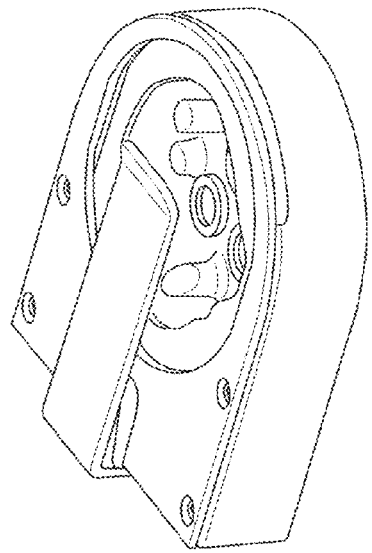
Figure 116D:
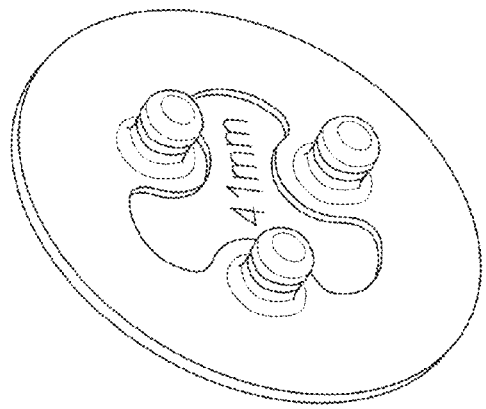
Figure 116A:
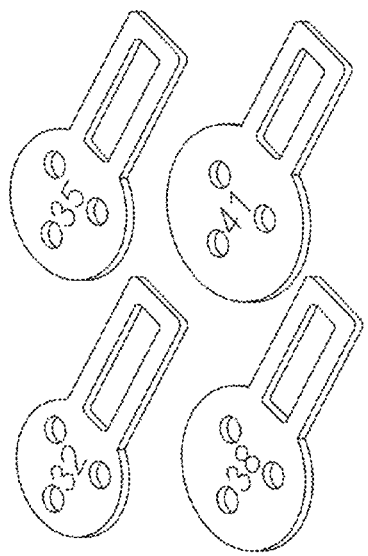
Figure 116C:
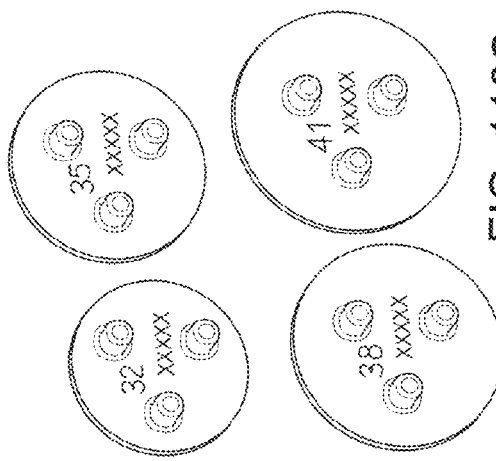
Figure 118A:
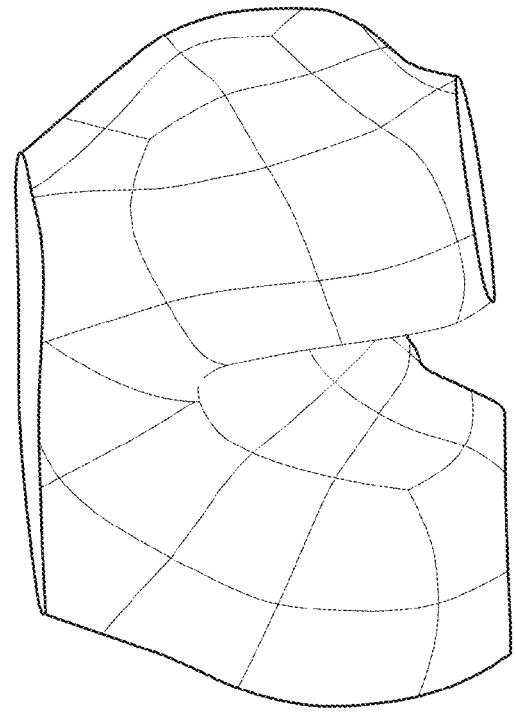
Figure 118B:
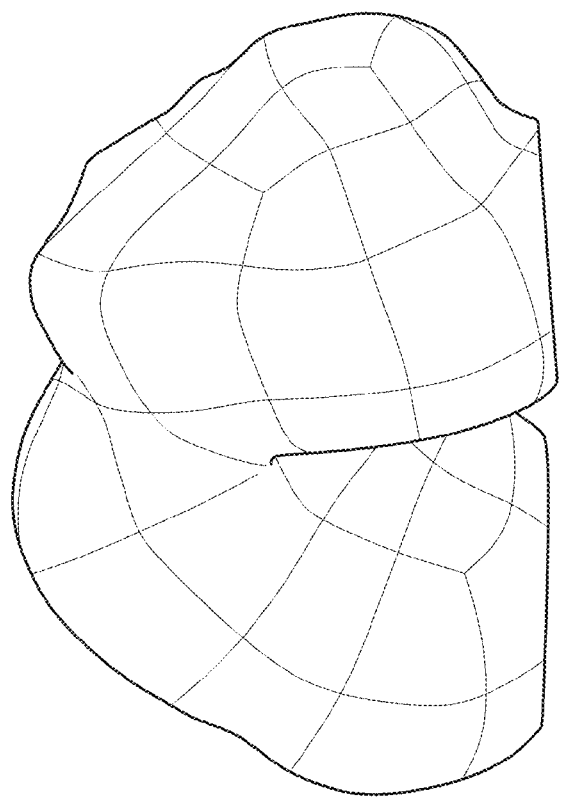
Figure 119B:
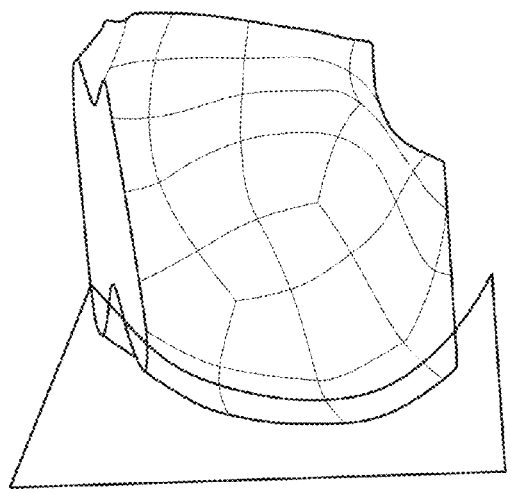
Figure 119A:
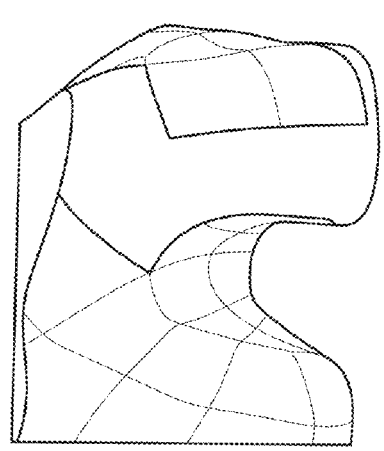
Figure 119C:
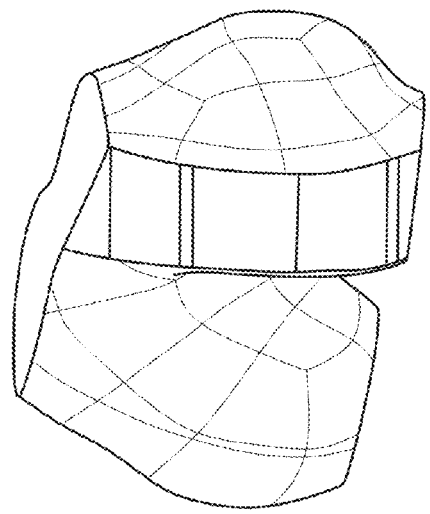
Figure 120B:
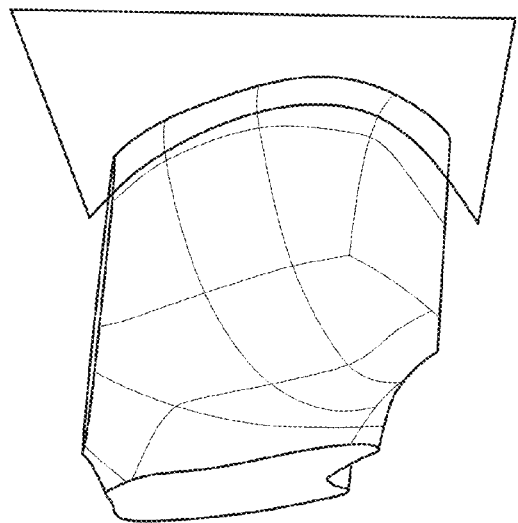
Figure 120C:
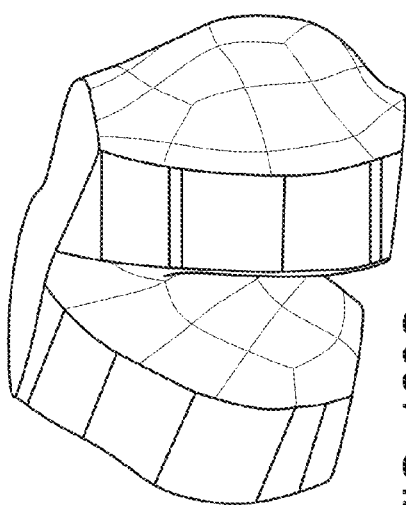
Figure 120A:
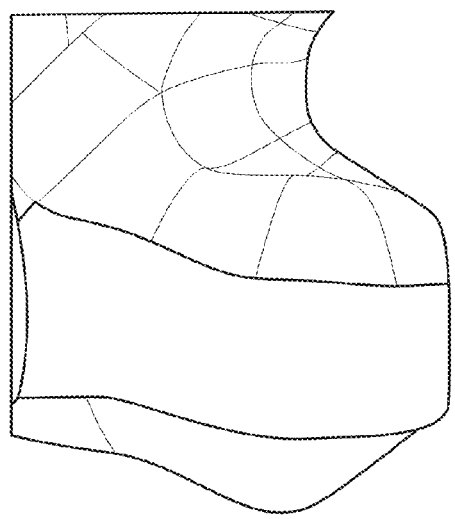
Figure 121A:
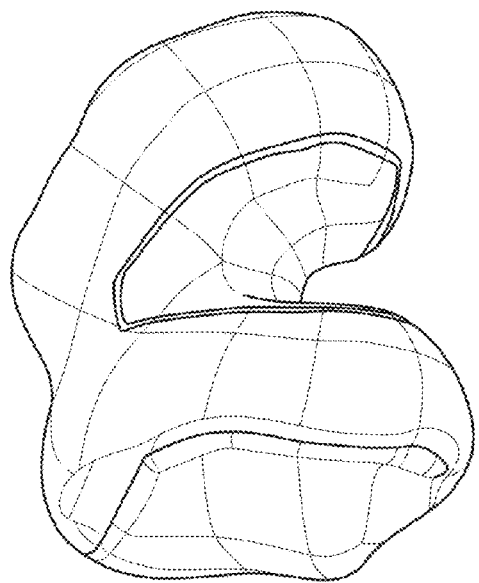
Figure 121B:
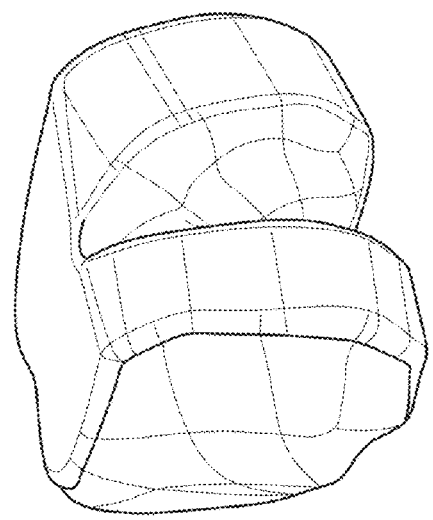
Figure 121C:
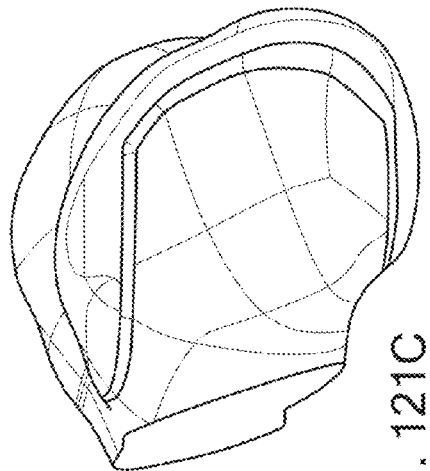
Figure 122A:
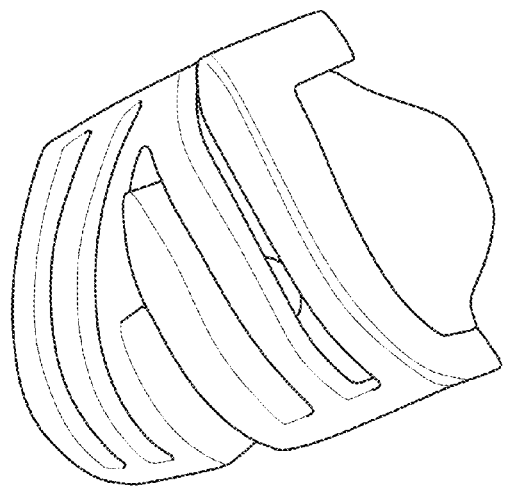
Figure 122B:
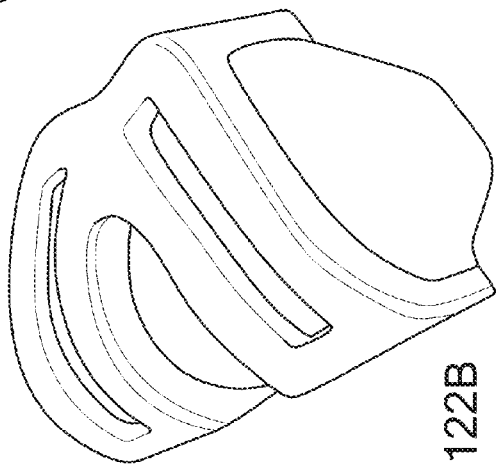
Figure 122C:
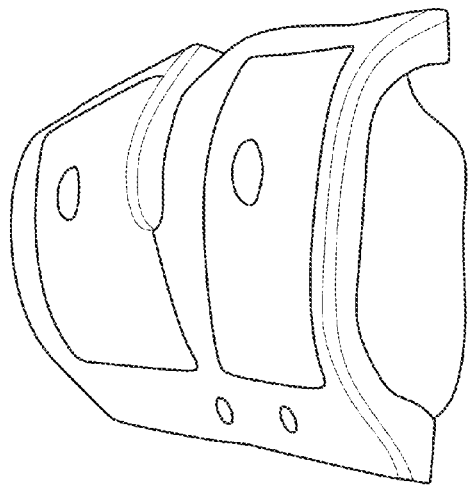
Figure 123B:
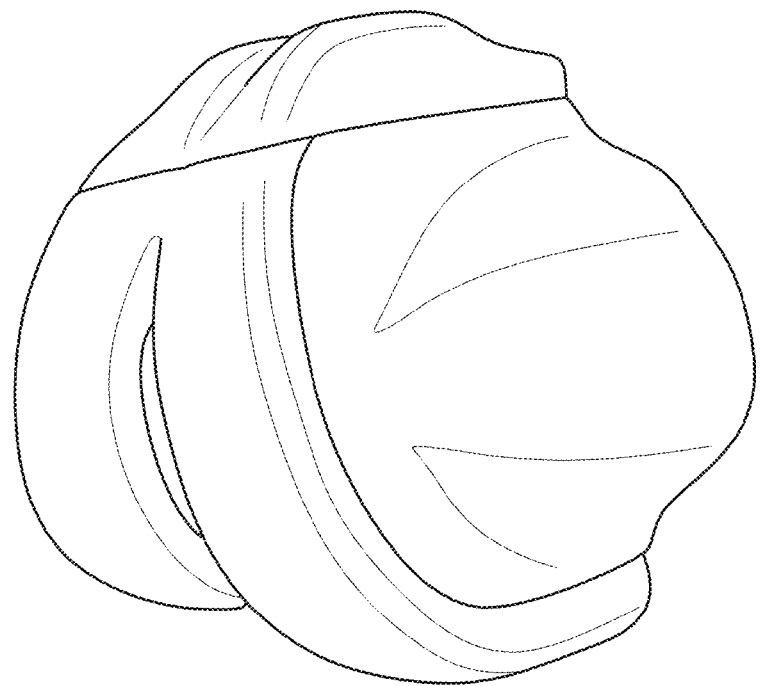
Figure 123A:
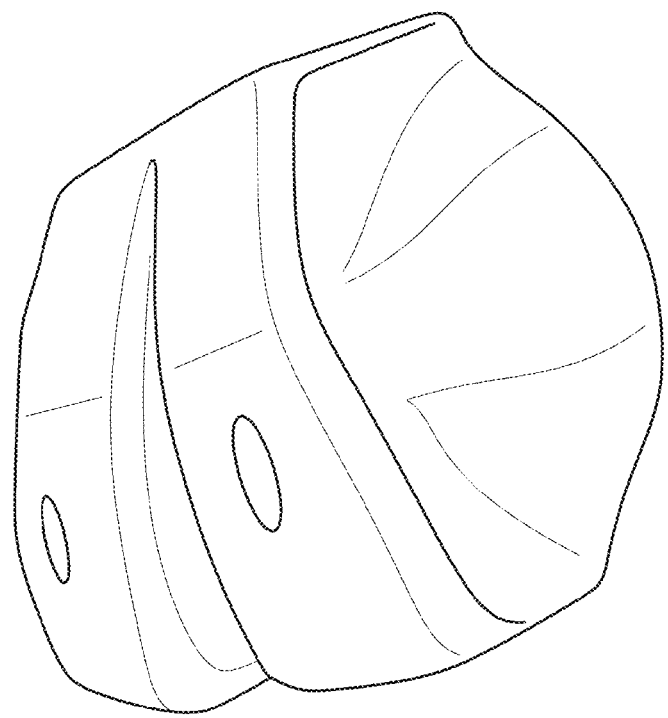
Figure 124B:
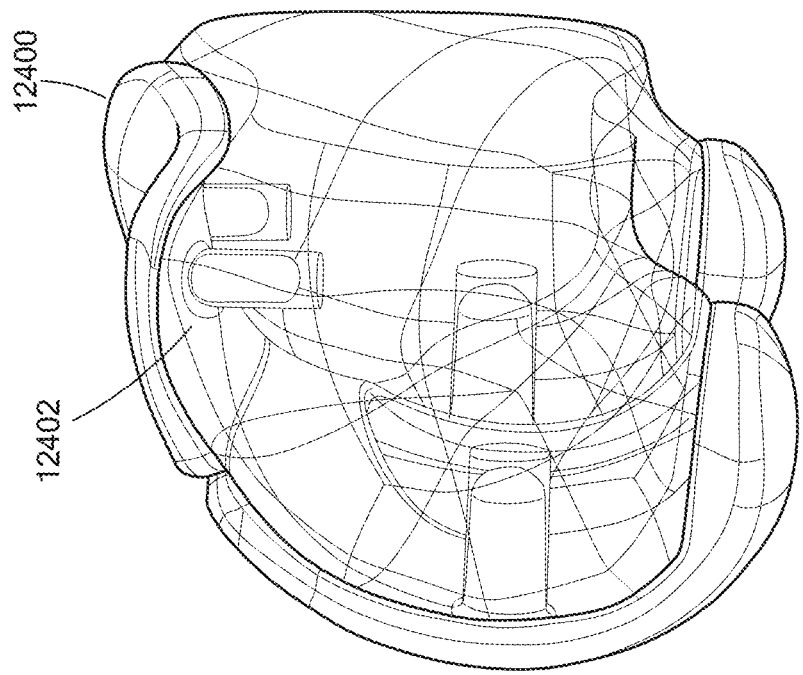
Figure 124A:
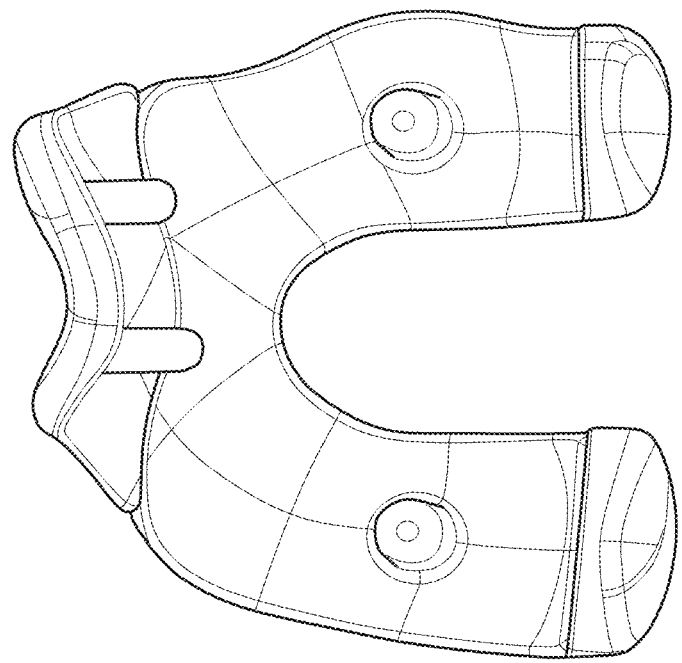
Figure 125A:
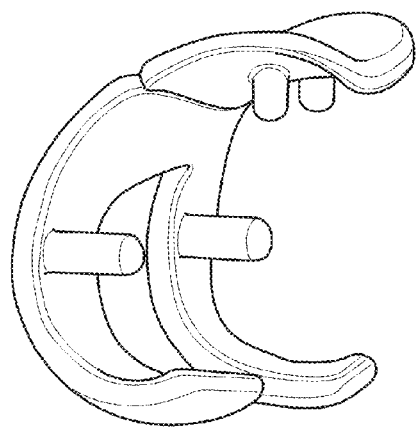
Figure 125B:
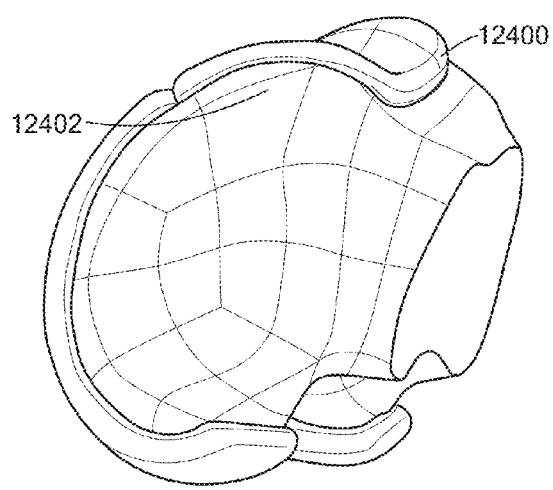
Figure 125C:
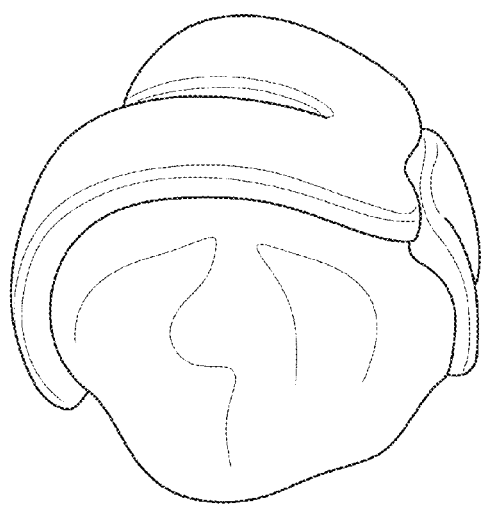
Figure 126A:
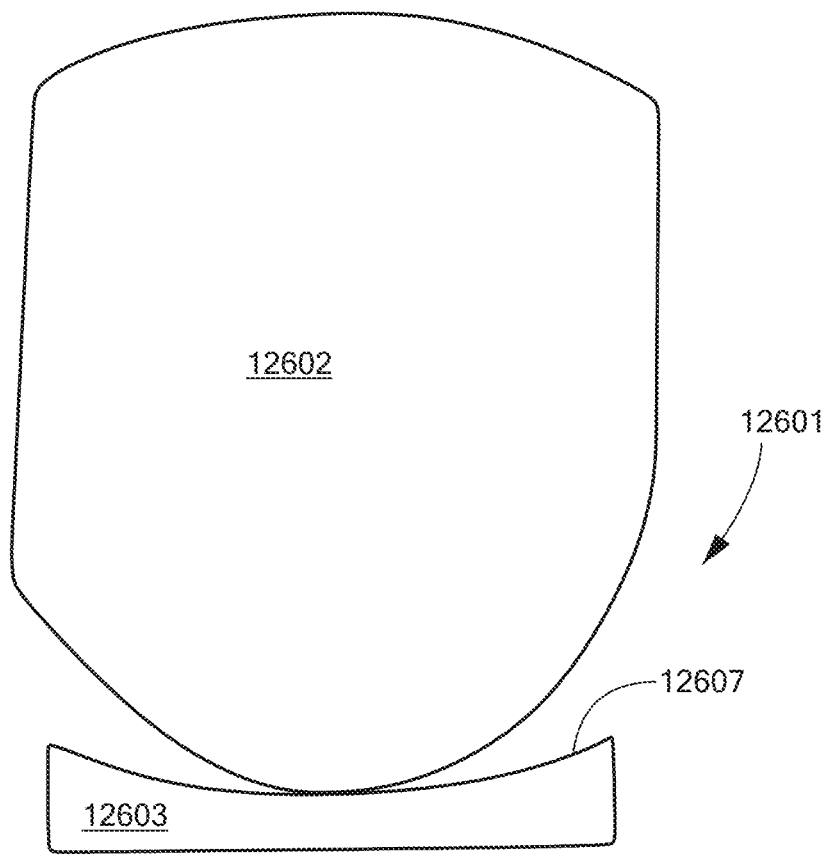
Figure 126B:
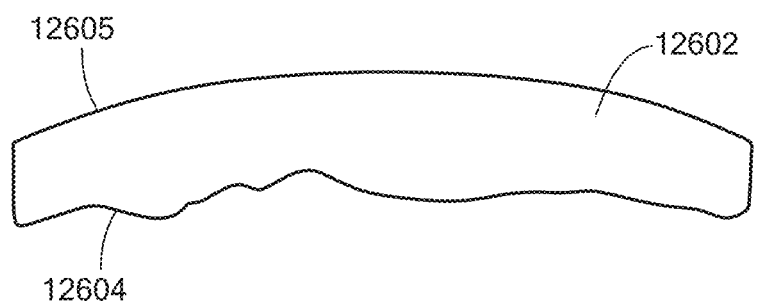
Figure 126E:
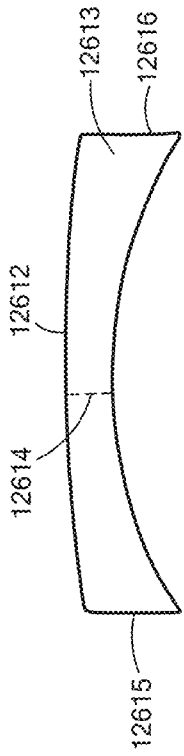
Figure 136C:
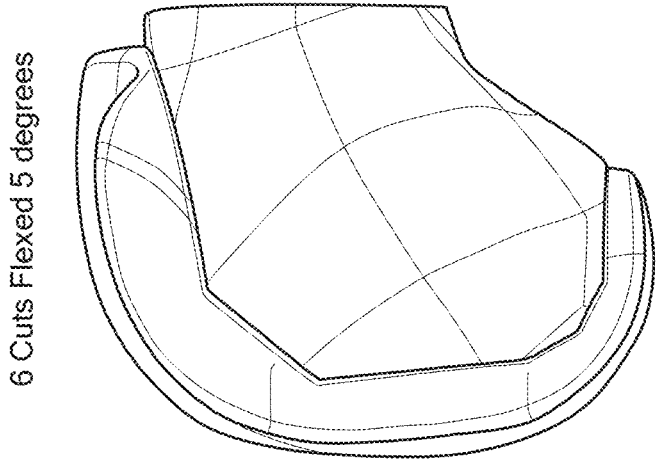
Figure 136B:
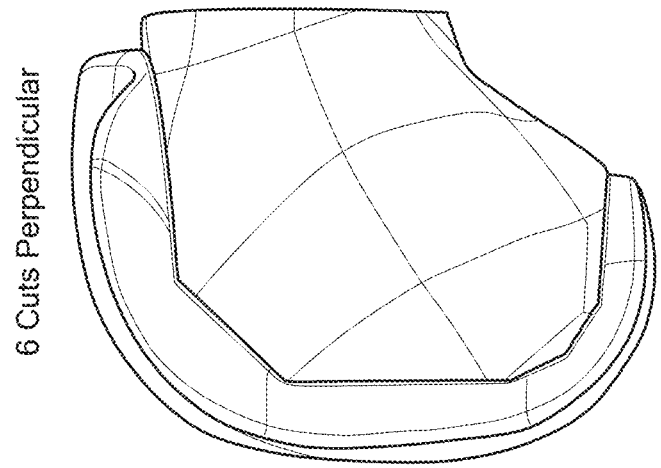
Figure 136A:
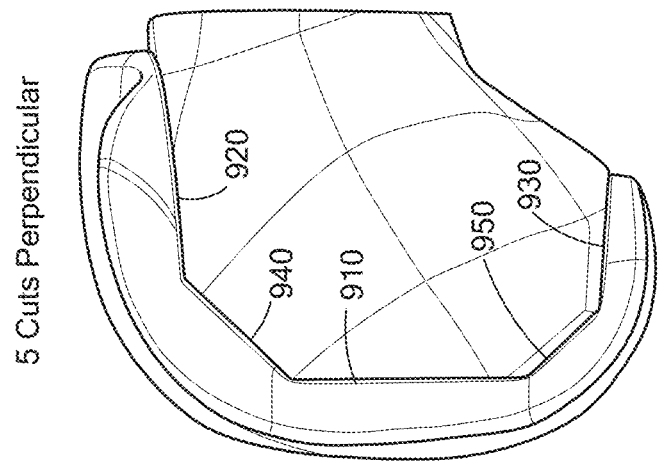
Figure 137C:
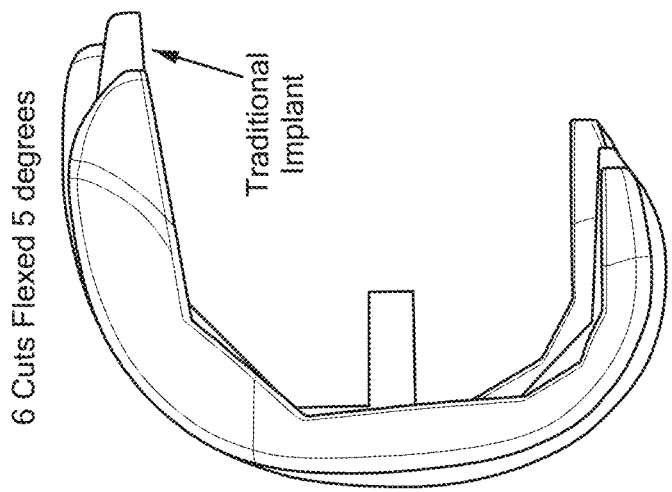
Figure 137B:
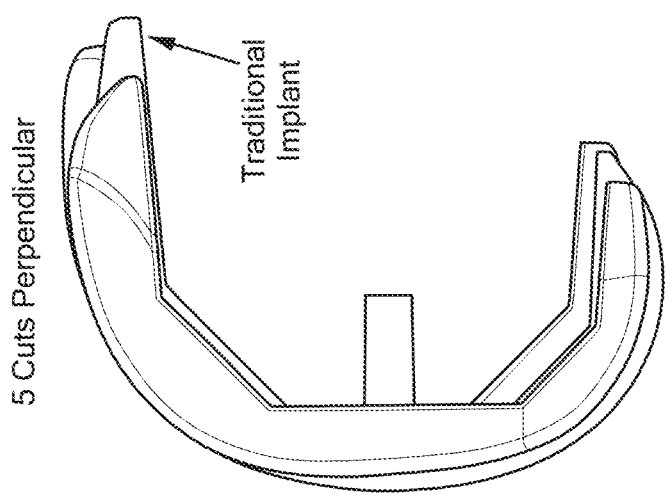
Figure 137A:
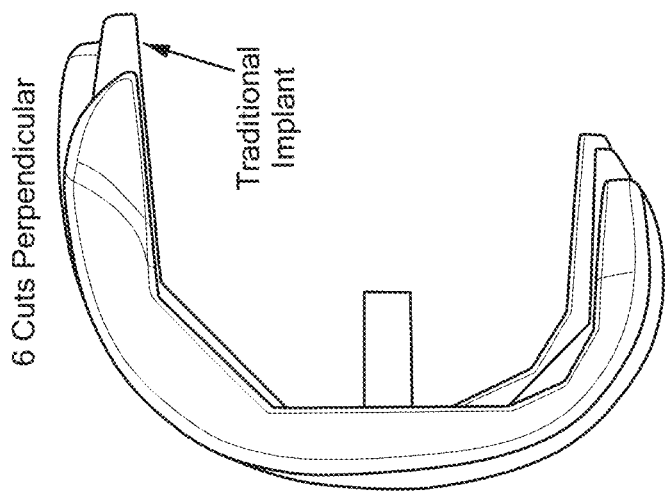
Figure 139:
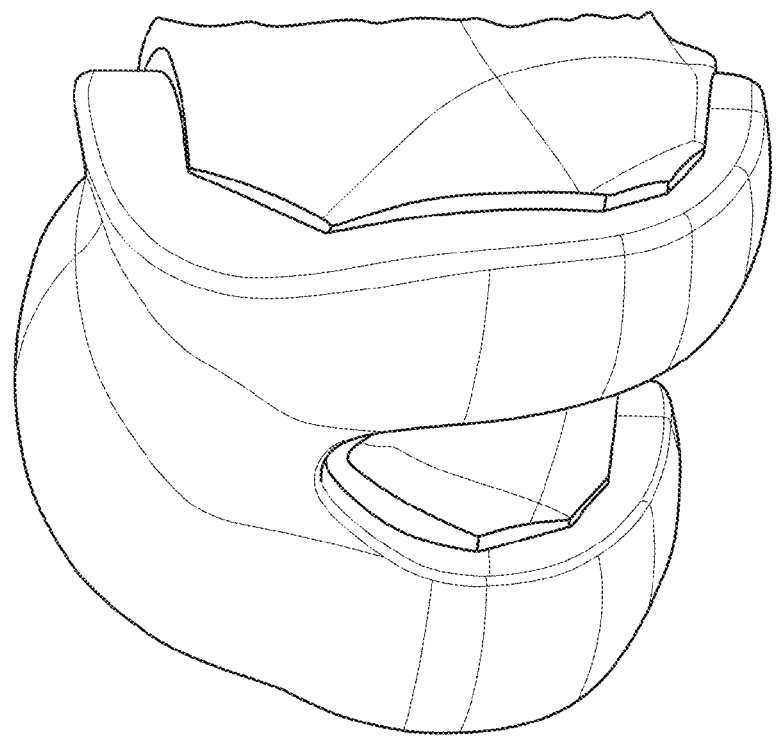
Figure 138:
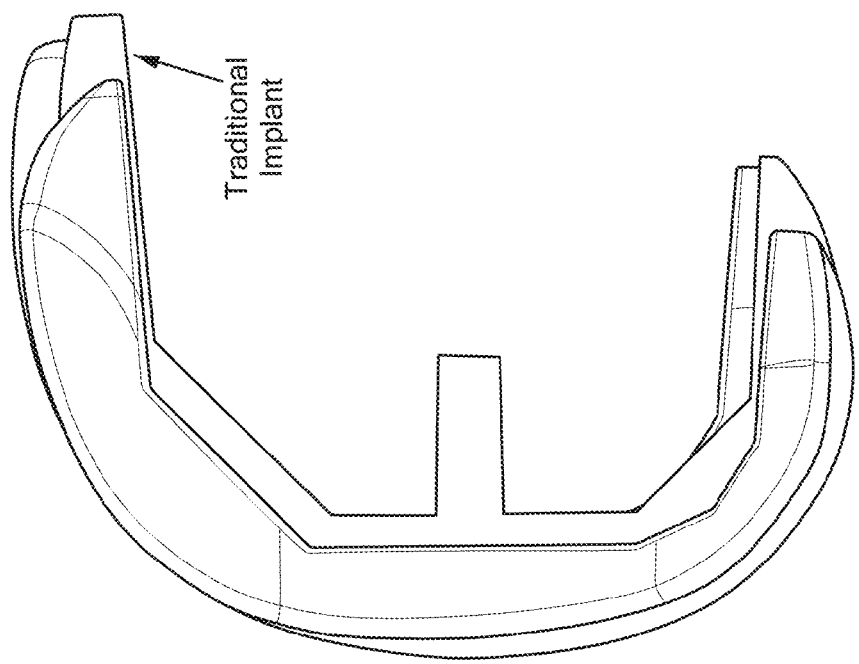
Figure 140:
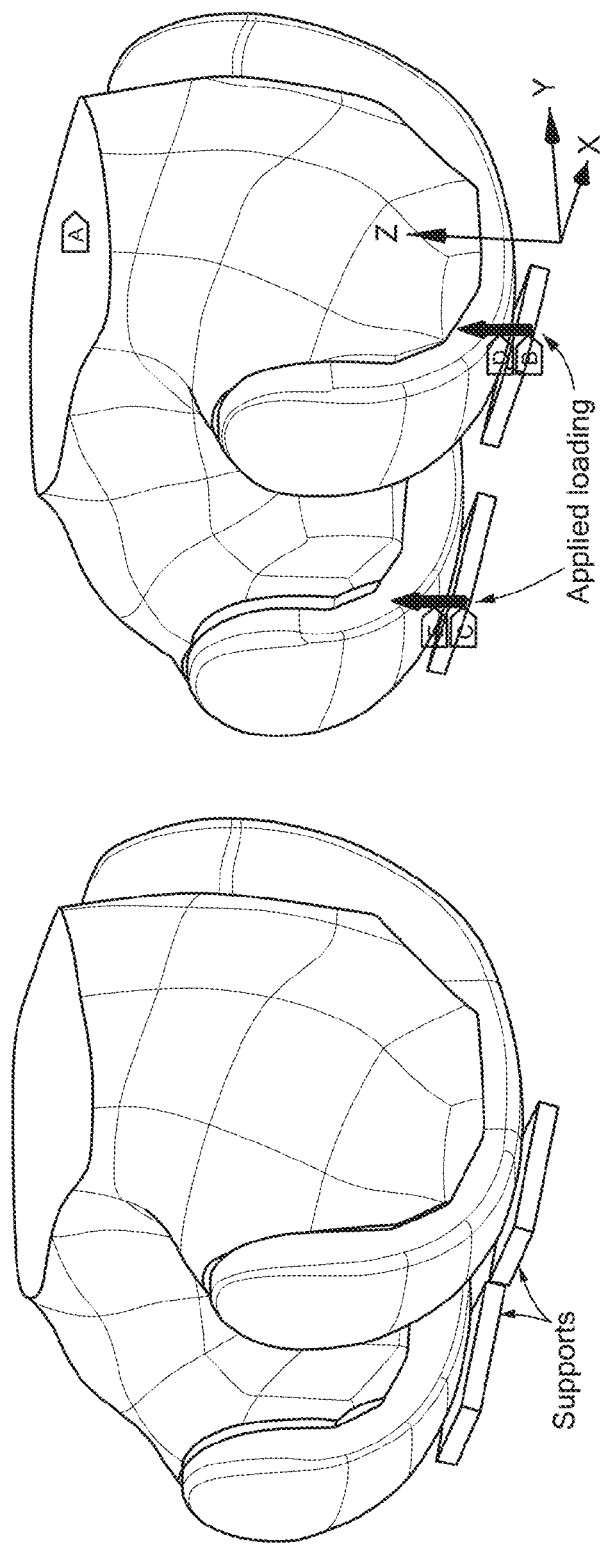
Figure 158A:
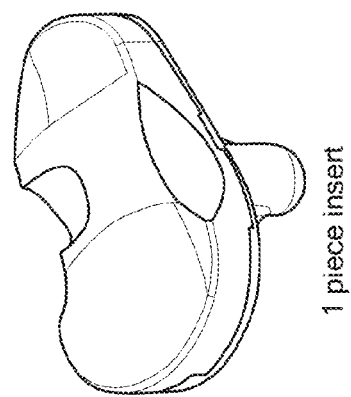
Figure 159A:
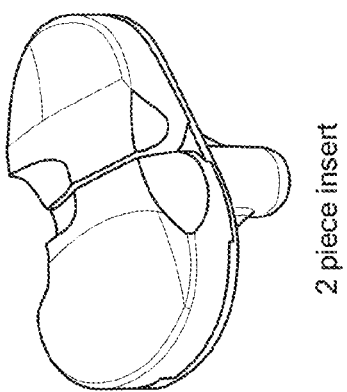
Figure 158B:
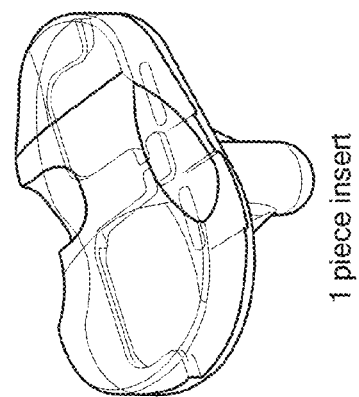
Figure 159B:
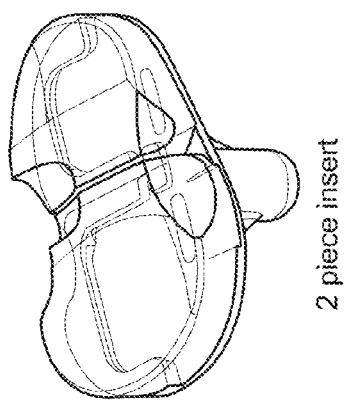
Figure 158C:
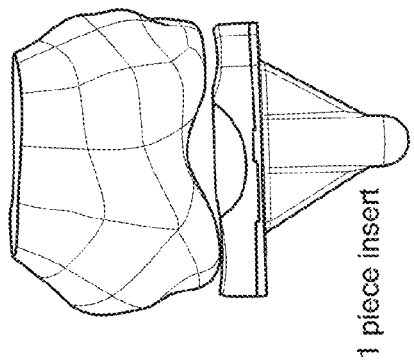
Figure 159C:
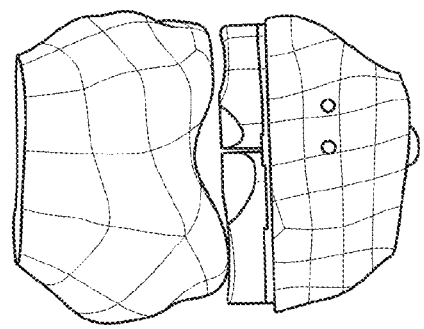
Figure 161A:
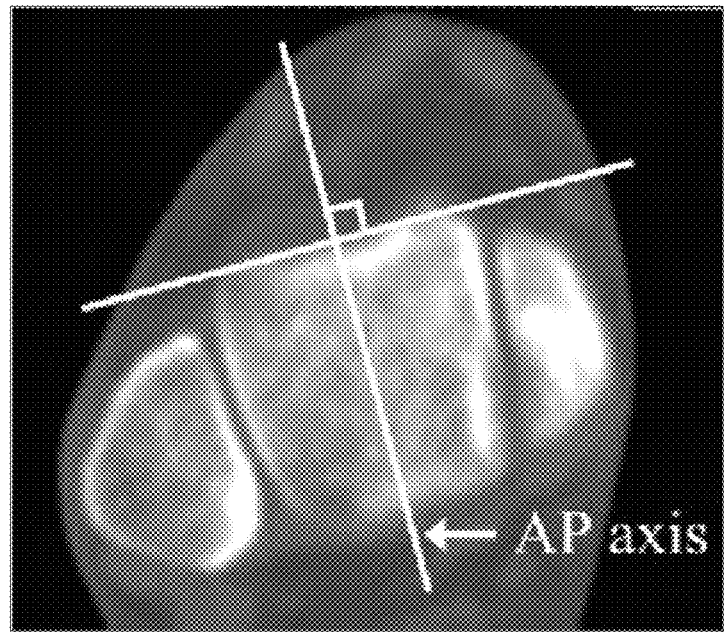
Figure 161B:
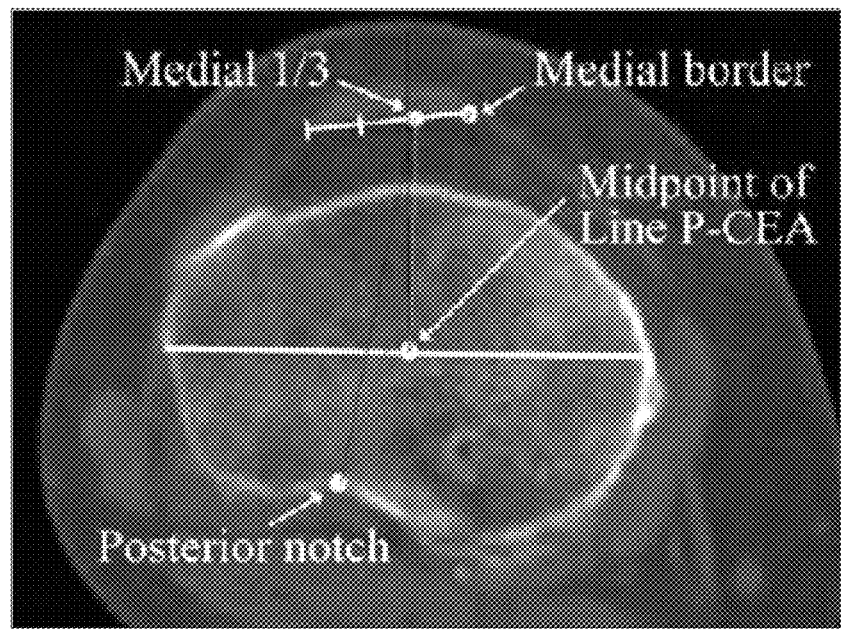
Figure 162:
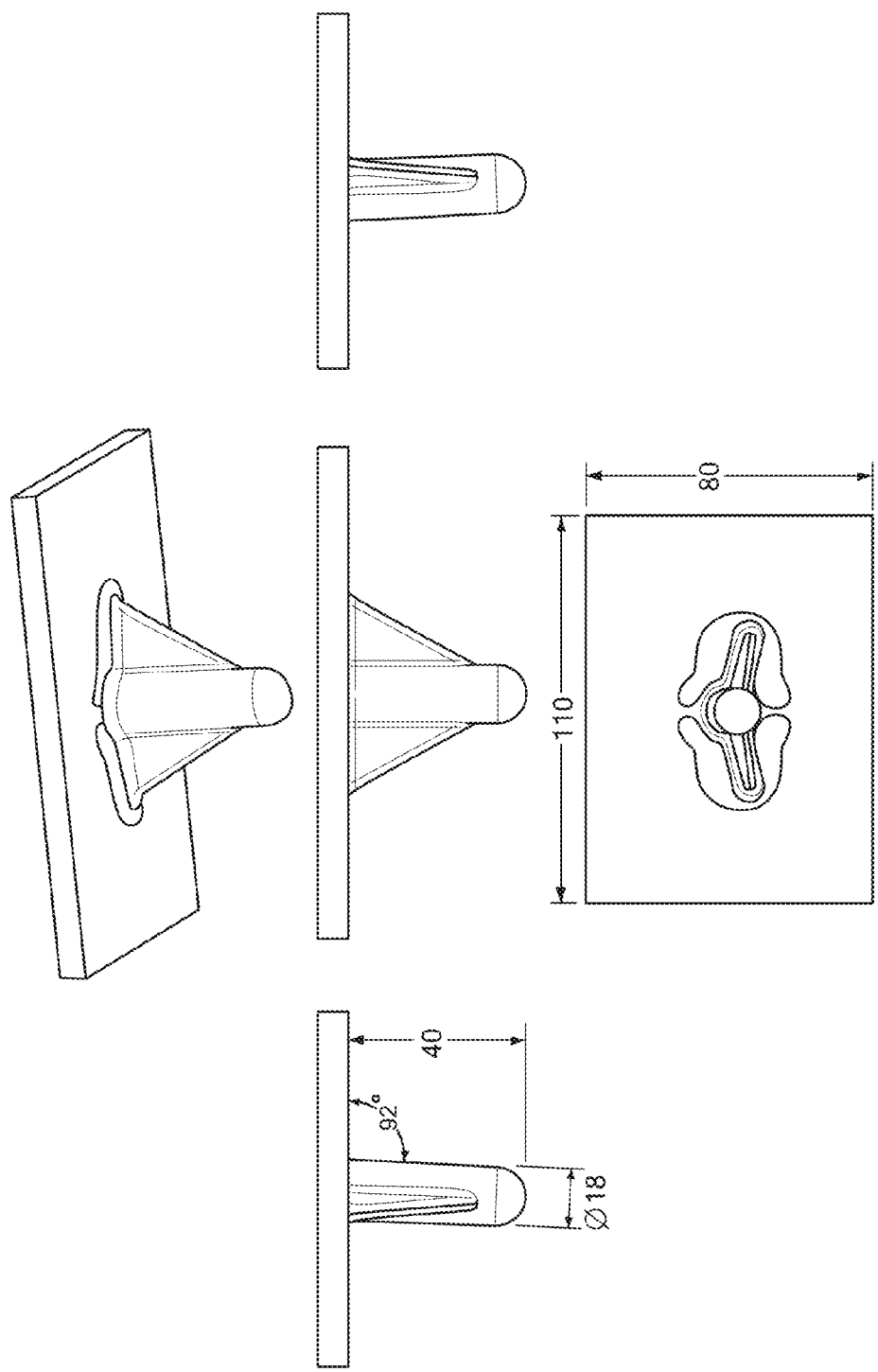
Figure 164A:
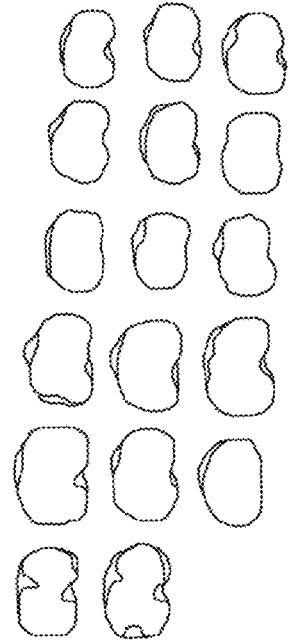
Figure 164B:
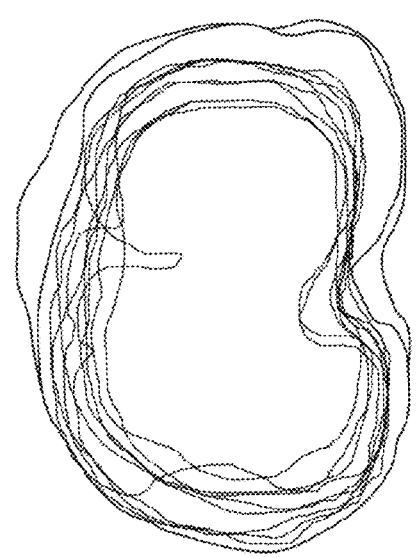
Figure 163A:
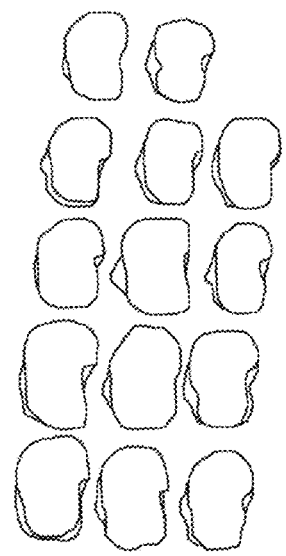
Figure 163B:
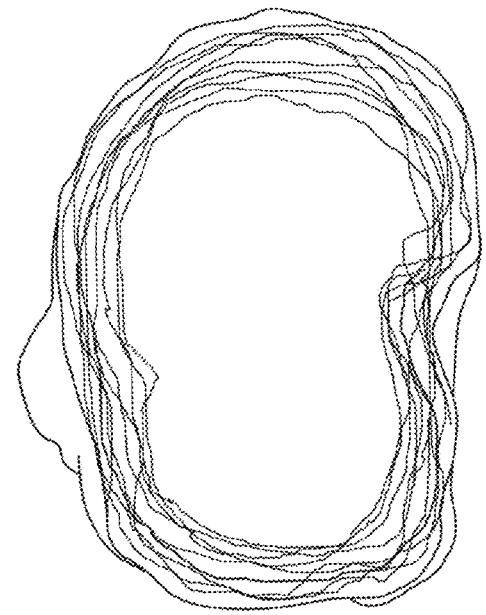
Figure 165B:
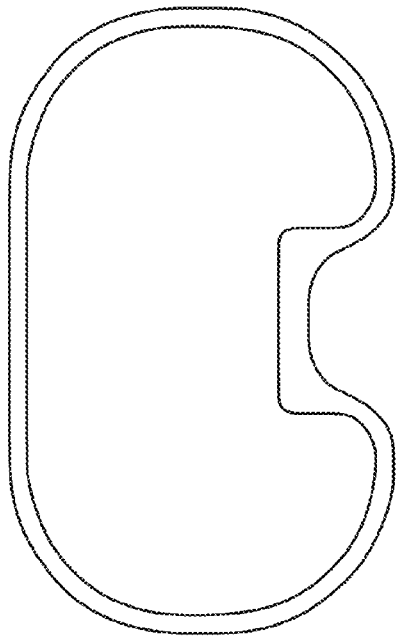
Figure 165D:
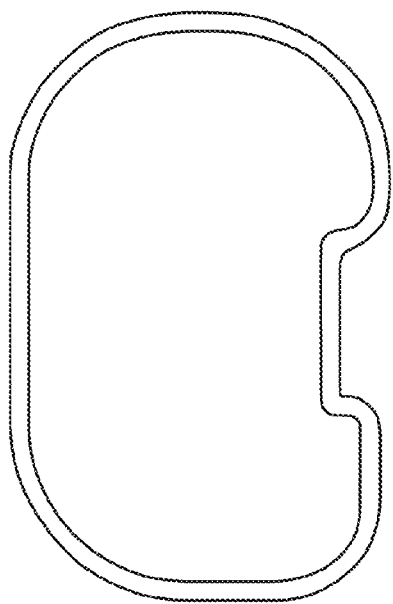
Figure 165A:
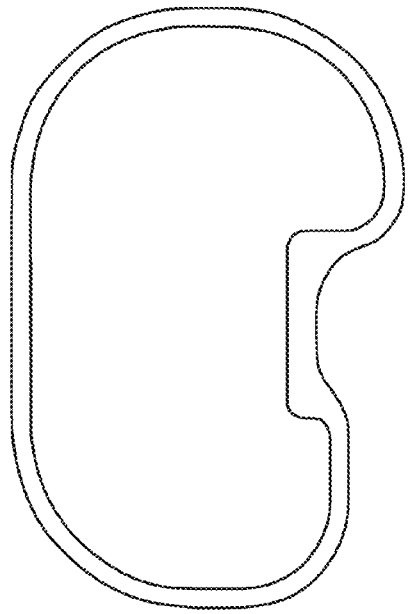
Figure 165C:
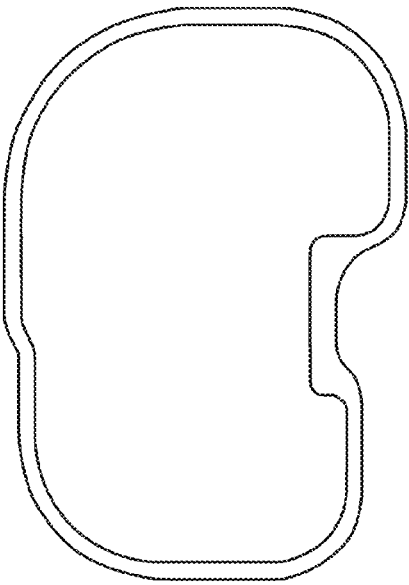
Figures 166A, 166B:
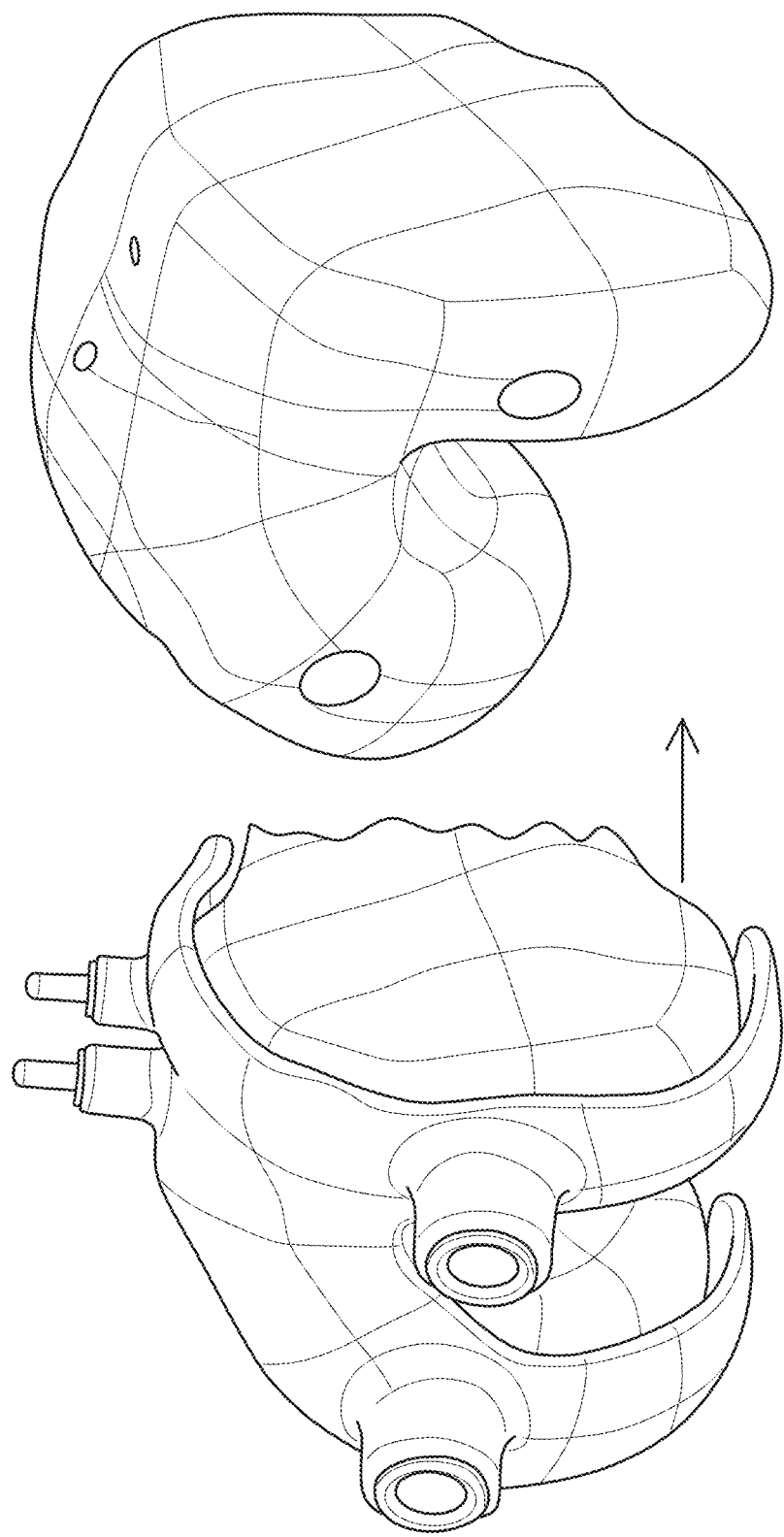
Figure 168B:
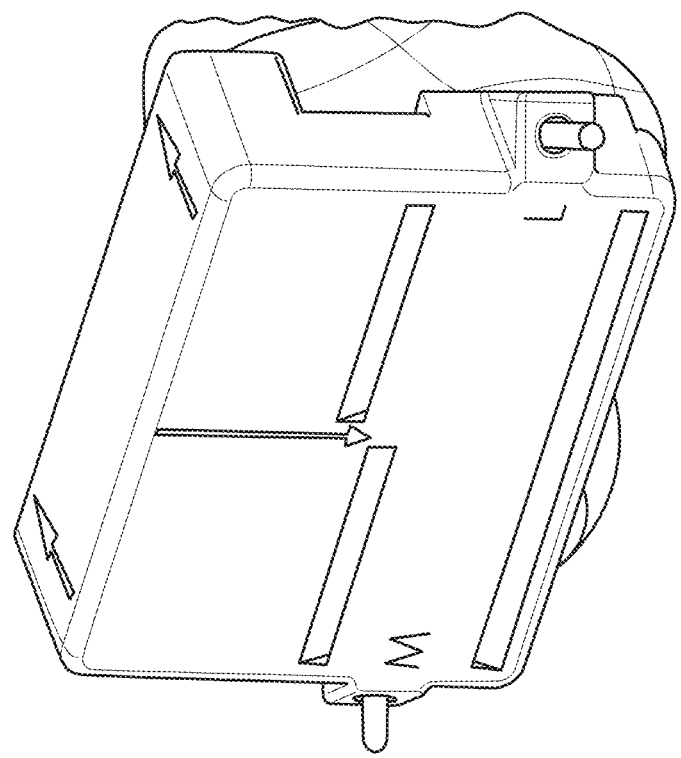
Figure 168A:
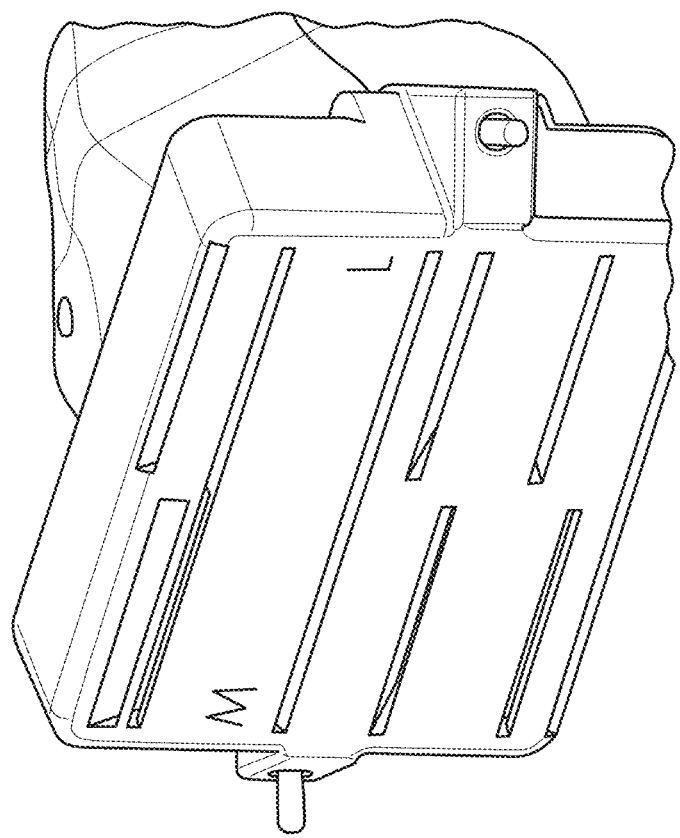
Figure 169A:
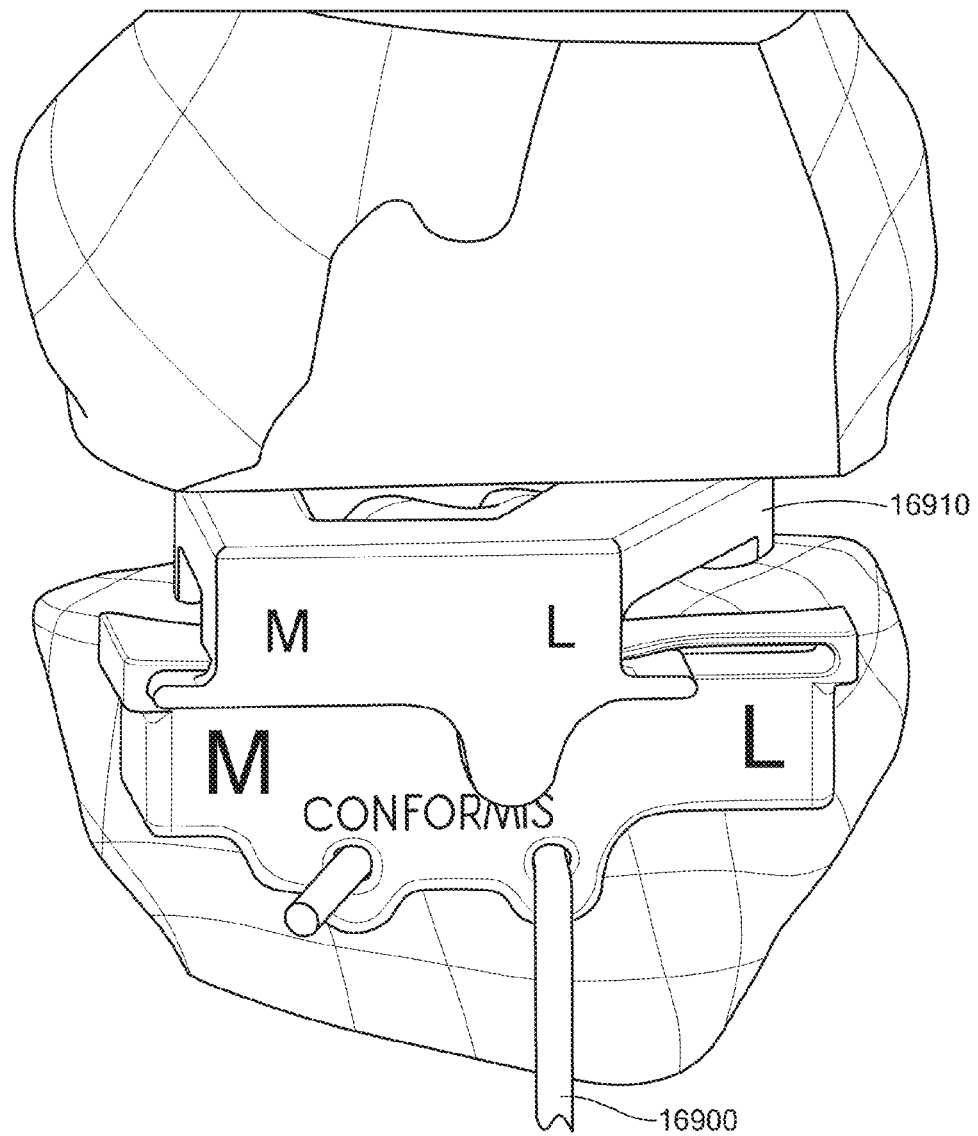
Figure 169B:
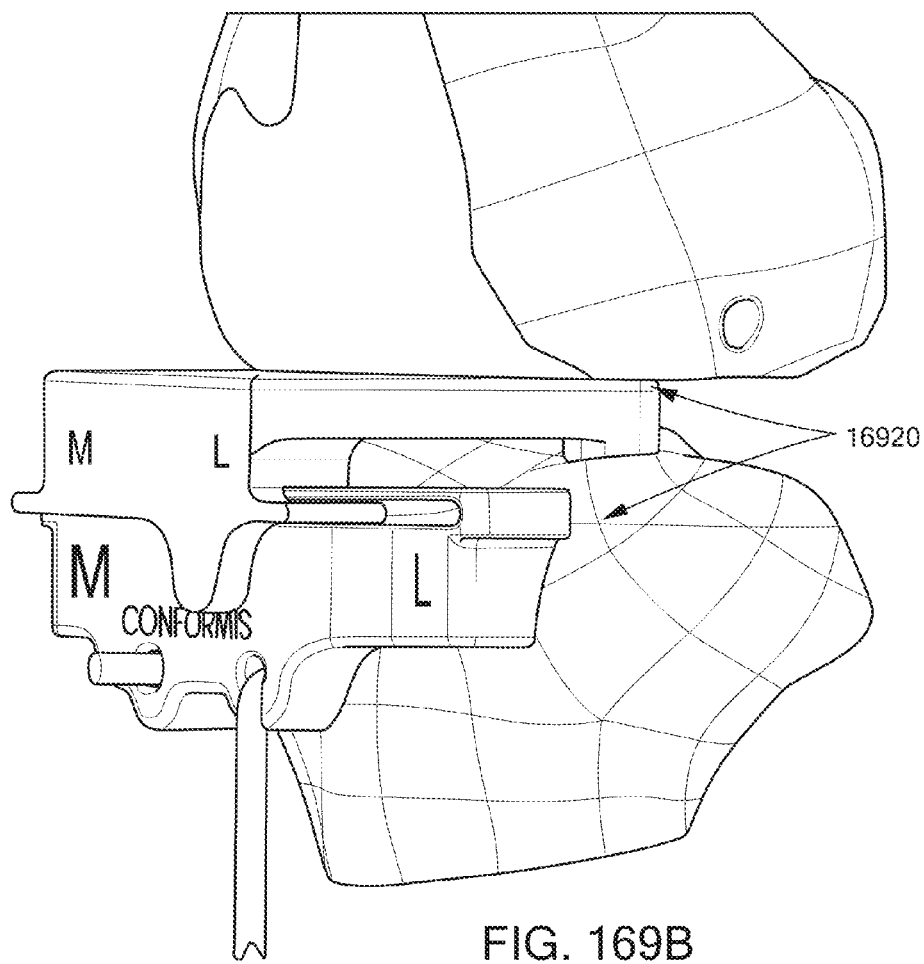
Figure 170:
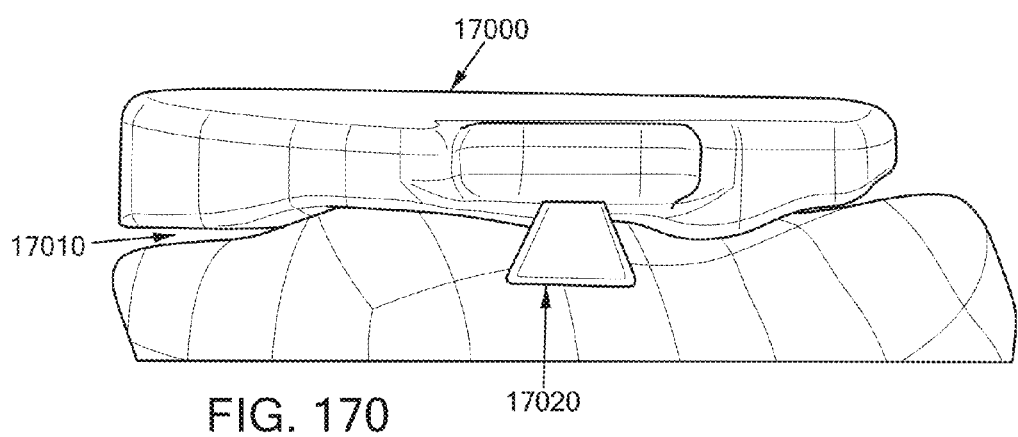
Figure 171B:
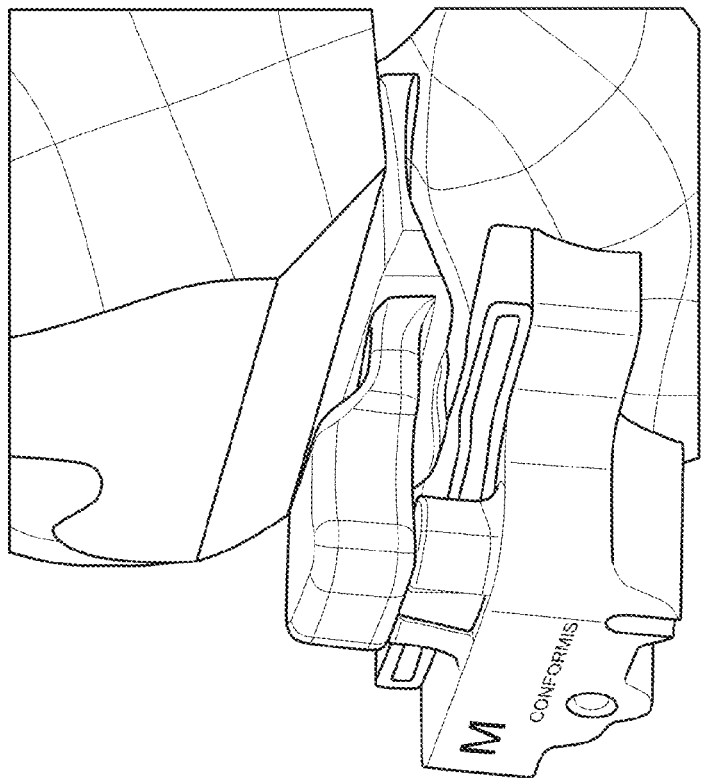
Figure 171A:
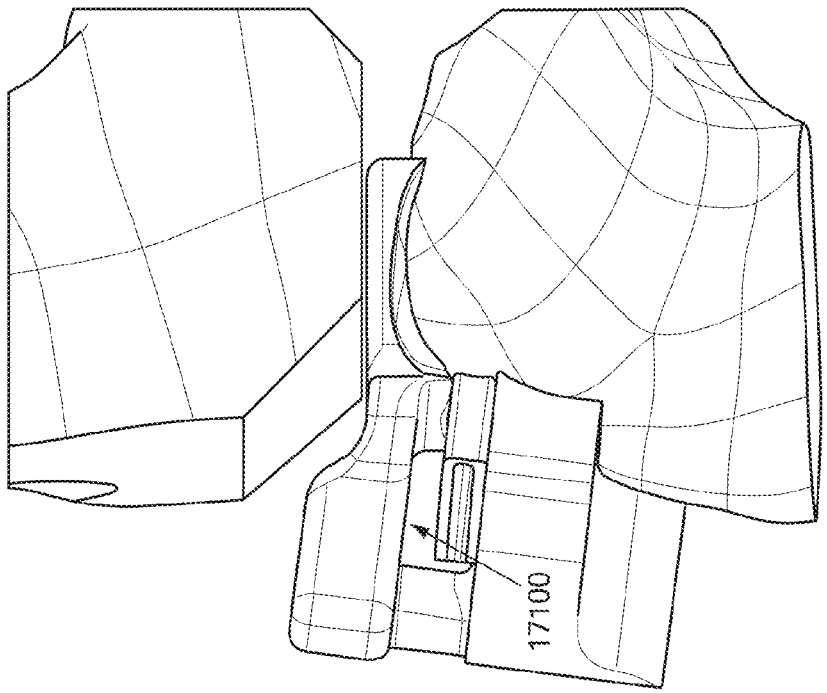
Figure 173:
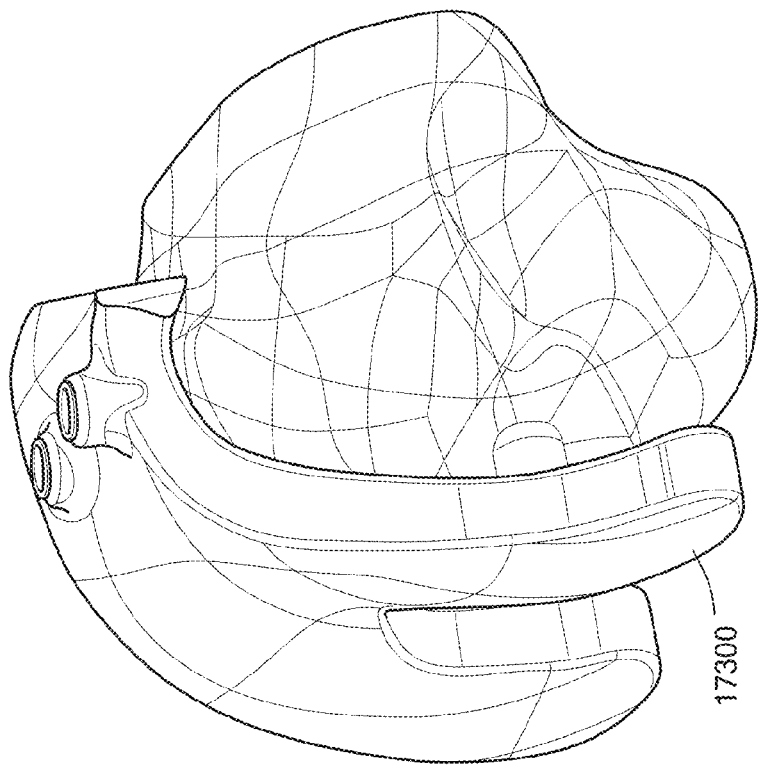
Figure 172:
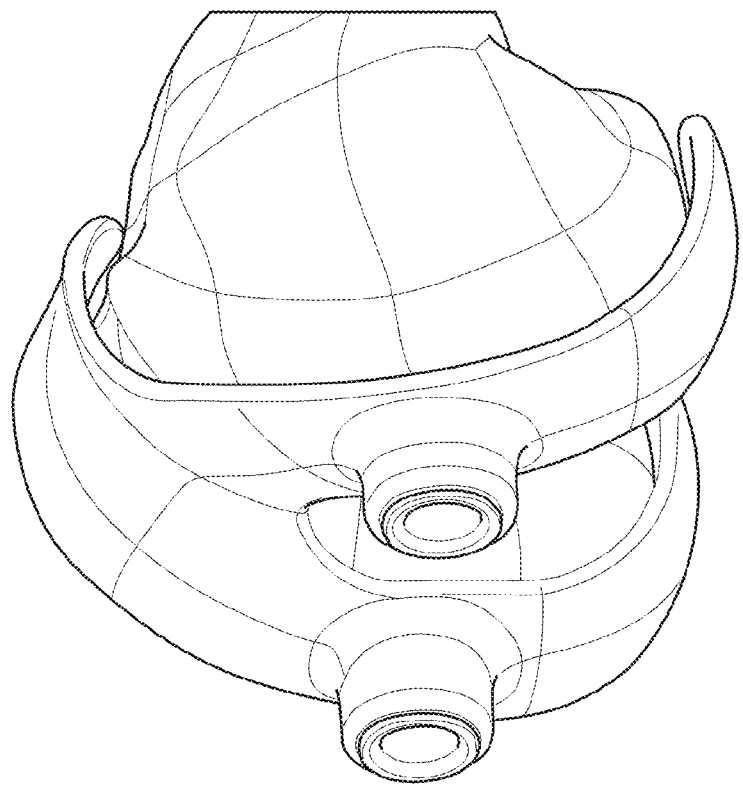
Figure 174:
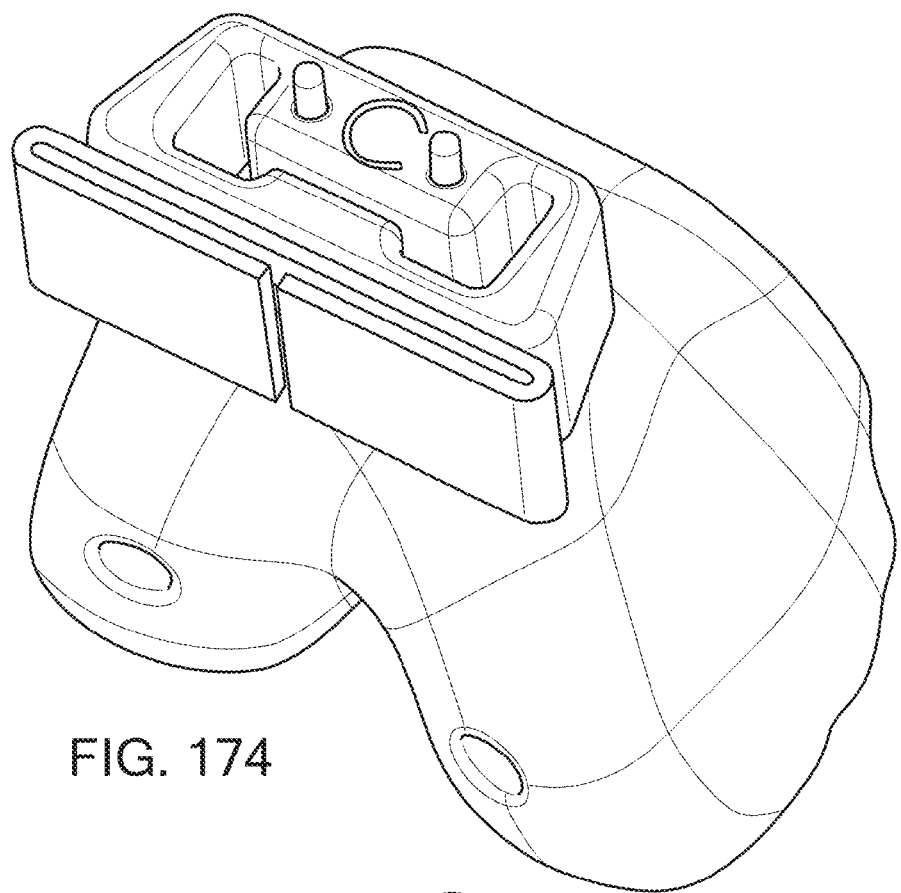
Figure 175:
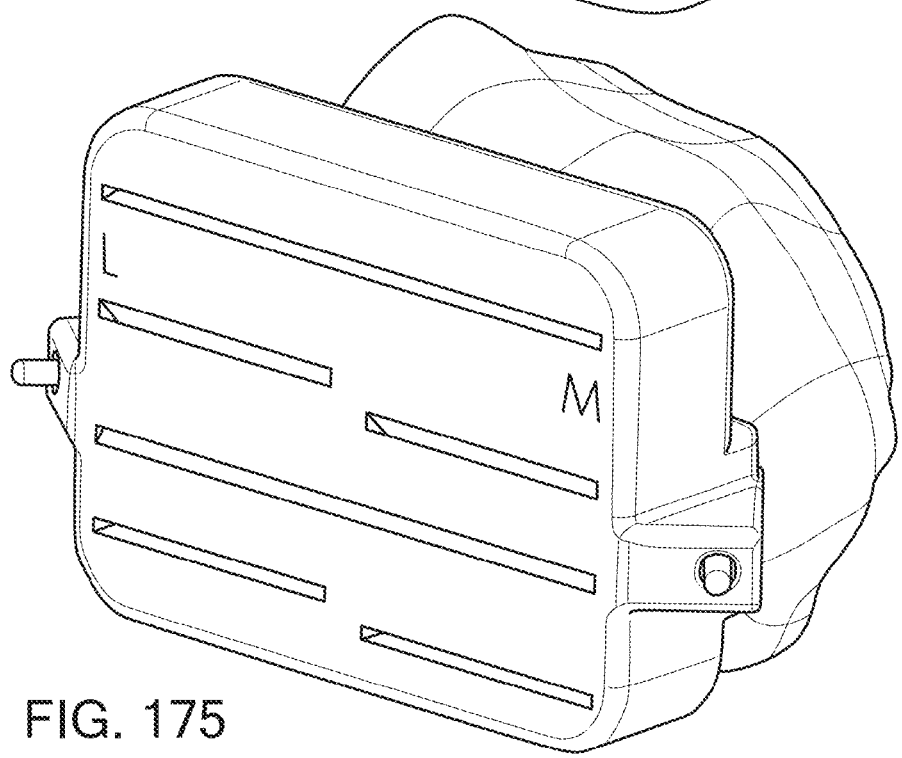

FIG. 116A illustrates a set of patella sizers; FIG. 116B illustrates a patellar cutting tool to cut the patella to a predetermined depth of resection; FIG. 116C illustrates implant trials; FIG. 116D illustrates a patellar implant;

FIGS. 117A through 117D show exemplary steps in a surgical implantation procedure;

FIGS. 118A and 118B illustrate a patient-specific femoral model and posterior and anterior resection cut lines for a patient-specific implant component having a curvilinear cut;

FIG. 119A to FIG. 119C illustrate steps for performing a curvilinear resection cut between planar anterior and posterior cuts on a medial condyle;

FIGS. 120A to 120C illustrate steps for performing a curvilinear resection cut between planar anterior and posterior cuts on a lateral condyle;

FIG. 121A illustrate a model of a femur having predetermined resection cuts including a curvilinear cut; FIGS. 121B and 121C illustrate the corresponding patient-specific implant component for the resection cuts depicted in FIG. 121A;

FIG. 122A shows a model of a bone along with a jig that allows preparation of predetermined resection holes and, optionally, resection cuts surfaces to match predetermined resection cuts specific to a patient's particular anatomy; FIGS. 122B and 122C show an alternative set of jigs that can be used with a router-type saw;

FIG. 123A shows a model of the prepared bone following jig-guided bone cuts; FIG. 123B shows the model of FIG. 123A with a two-piece patient-specific implant component designed with an inner bone-facing surface that substantially negatively-matches the patient's resected bone surface, including curvilinear bone and resection cuts;

FIGS. 124A and 124B illustrate a femoral implant component designed with two pieces with one piece having on its inner, bone-facing surface a single, posterior cut;

FIGS. 125A and 125B illustrate a femoral implant component design having two pieces; FIG. 125C shows an example of the two-piece implant component positioned on a model of the femur;

This example illustrates exemplary implant components having enhanced articular surfaces (i.e., joint-facing surfaces). FIG. 126A is a front schematic view of engaging portions of a single compartment (e.g., a single condyle) of a knee implant; FIG. 126B is a cross-sectional schematic view in the coronal plane of the femoral component of FIG. 126A; FIGS. 126C to 126F show cross-sectional schematic views in the coronal plane of respective alternate embodiments of the femoral component;

FIGS. 127A to 127F illustrate an exemplary design of a knee implant, including a femoral component and a patella component;

FIG. 128 illustrates the mechanical axis of a patient's lower extremity defined by the center of hip, the center of the knee, and the center of the ankle;

FIGS. 129A to 129C each illustrate a model showing the existing misalignment of a patient's lower extremity and the virtual alignment determined using the model;

FIGS. 130A to 130D illustrate virtual alignment steps relating to determining a patient's tibial mechanical axis;

FIGS. 131A to 131F illustrate virtual alignment steps relating to determining the coronal and sagittal planes of a patient's tibial mechanical axis;

FIGS. 132A to 132D illustrate virtual alignment steps relating to determining a patient's femoral mechanical axis;

FIGS. 133A to 133D illustrate virtual alignment steps relating to determining the coronal and sagittal planes of a patient's femoral mechanical axis;

FIGS. 134A and 134B illustrate virtual alignment steps for aligning a patient's femoral and tibial mechanical axes in coronal and sagittal planes;

FIGS. 135A to 135G illustrate comparisons between the patient's before and after virtual alignment;

FIGS. 136A to 136C illustrate three femoral implant components that were analyzed by FEA, including, respectively, a component with six bone cuts and a perpendicular distal bone cut ("Perp 6-Cuts"), a component with five bone cuts and a perpendicular distal bone cut ("Perp 5-Cuts"), and a component with six bone cuts and flexed bone cuts ("Flexed 6-Cuts");

FIGS. 137A to 137C each illustrate a traditional implant component overlaid with each of the three tested implant components;

FIG. 138 illustrate a traditional component overlaid with the 6-Cuts implant component in an overlaid position that respects the actual implant placements based on movement of the joint-line;

FIG. 139 illustrate the joint-facing surface of the 6-Cuts implant component positioned on a femur having six corresponding resection cuts;

FIG. 140 shows exemplary set-up information for FEA testing on knee implant components;

FIGS. 141A to 141H illustrate various aspects of the FEA testing of three femoral implant components;

FIGS. 142A, 142B, and 142C illustrate the FEA-identified high stress locations for the implant components, which was the same for all three models tested;

FIG. 143A illustrates a tibial proximal resection cut that can be selected and/or designed to be a certain distance below a particular location on the patient's tibial plateau; FIG. 143B illustrates anatomic sketches (e.g., using a CAD program to manipulate a model of the patient's biological structure) overlaid with the patient's tibial plateau; FIG. 143C illustrates sketched overlays used to identify the centers of tubercles and the centers of one or both of the lateral and medial plateaus;

FIGS. 144A to 144C illustrate one or more axes that can be derived from anatomic sketches;

FIG. 145A depicts a proximal tibial resection made at 2 mm below the lowest point of the patient's medial tibial plateau with a an A-P slope cut that matched the A-P slope; FIGS. 145B and 145C illustrate an implant selected and/or designed to have 90% coverage of the patient's cut tibial surface;

FIGS. 146A to 156C describe exemplary steps for performing resection cuts to the tibia using the anatomical references identified above;

FIGS. 157A to 157E illustrate various aspects of an embodiment of a tibial implant component, including a view of the tibial tray bottom (FIG. 157A), a view of the tibial tray top (FIG. 157B), a view of the tibial insert bottom (FIG. 157C), a top-front (i.e., proximal-anterior) perspective view of the tibial tray (FIG. 157D), and a bottom front (i.e., distal anterior) perspective view of the tibial insert (FIG. 157E);

FIGS. 158A to 158C show aspects of an embodiment of a tibial implant component that includes a tibial tray and a one-piece insert;

FIGS. 159A to 159C show aspects of an embodiment of a tibial implant component that includes a tibial tray and a one-piece insert;

FIGS. 160A to 160C show exemplary steps for altering a blank tibial tray and a blank tibial insert to each include a patient-adapted profile, for example, to substantially match the profile of the patient's resected tibial surface;

FIGS. 161A to 161C show exemplary strategies for establishing proper tibial rotation for a patient;

FIG. 162 illustrates exemplary stem design options for a tibial tray;

FIGS. 163A and 163B show an approach in certain embodiments for identifying a tibial implant perimeter profile based on the depth and angle of the proximal tibial resection, which can applied in the selection and/or design of the tibial tray perimeter profile and/or the tibial insert perimeter profile;

FIGS. 164A and 164B show the same approach as described for FIGS. 163A and 163B, but applied to a different patient having a smaller tibia (e.g., smaller diameter and perimeter length);

FIGS. 165A to 165D show four different exemplary tibial implant profiles, for example, having different medial and lateral condyle perimeter shapes;

FIGS. 166A and 166B illustrate a first femur jig used to establish peg holes and pin placements for a subsequent jig used for a distal cut;

FIGS. 167A and 167B illustrate a distal femoral resection cut performed with a second femur jig;

FIG. 168A illustrates an anterior cut, posterior cut, and chamfer cut performed with a third femur jig; FIG. 168B illustrate an additional femoral jig for making additional resection cuts;

FIGS. 169A and 169B illustrate and exemplary tibial jig;

FIG. 170 illustrates and exemplary balancing chip;

FIGS. 171A and 171B illustrate an exemplary balancing chip attached to a tibial jig;

FIG. 172 illustrates a first jig used to establish placement and alignment of femoral implant peg holes;

FIG. 173 illustrates a second jig used to establish placement pins for the distal cut jig;

FIG. 174 illustrates a distal cut jig positioned based on the placement established by the previous jig; and FIG. 175 illustrates remaining resection cuts performed with a chamfer cut jig.

Additional figure descriptions are included in the text below. Unless otherwise denoted in the description for each figure, "M" and "L" in certain figures indicate medial and lateral sides of the view; "A" and "P" in certain figures indicate anterior and posterior sides of the view, and "S" and "I" in certain figures indicate superior and inferior sides of the view.

DETAILED DESCRIPTION

1. Introduction

When a surgeon uses a traditional off-the-shelf implant to replace a patient's joint, for example, a knee joint, hip joint, or shoulder joint, certain features of the implant typically do not match the particular patient's biological features. These mismatches can cause various complications during and after surgery. For example, surgeons may need to extend the surgery time and apply estimates and rules of thumb during surgery to address the mismatches. For the patient, complications associated with these mismatches can include pain, discomfort, soft tissue impingement, and an unnatural feeling of the joint during motion, e.g., so-called mid-flexion instability, as well as an altered range of movement and an increased likelihood of implant failure. In order to fit a traditional implant component to a patient's articular bone, surgeons typically remove substantially more of the patient's bone than is necessary to merely clear diseased bone from the site. This removal of substantial portions of the patient's bone frequently diminishes the patient's bone stock to the point that only one subsequent revision implant is possible.

Certain embodiments of the implants, guide tools, and related methods of designing (e.g., designing and making), and using the implants and guide tools described herein can be applied to any joint including, without limitation, a spine, spinal articulations, an intervertebral disk, a facet joint, a shoulder, an elbow, a wrist, a hand, a finger, a hip, a knee, an ankle, a foot, or a toe joint. Furthermore, various embodiments described herein can apply to methods and procedures, and the design of methods and procedures, for resectioning the patient's anatomy in order to implant the implant components described herein and/or to using the guide tools described herein.

1.1 Patient-Adapted Features

Certain embodiments relate to patient-adapted implants, guide tools, and related methods. Patient-adapted features of an implant component, guide tool or related implantation method can be achieved by analyzing imaging test data and selecting and/or designing (e.g., preoperatively selecting from a library and/or preoperatively designing) an implant component, a guide tool, and/or a procedure having a feature that is matched and/or optimized for the particular patient's anatomy and/or biology. Accordingly, the patient-adapted implant components, guide tools, and/or methods include one or more patient-adapted features. Patient-adapted features can include patient-specific features and/or patient-engineered features.

Certain embodiments relate to patient-specific implants, guide tools, and related methods. For example, some embodiments relate to articular implant components having one or more patient-specific features adapted to match one or more of the patient's biological features, such as one or more of biological/anatomical structures, alignments, kinematics, and/or soft tissue impingements. Accordingly, the one or more patient-specific features of an implant component can include, but are not limited to, one or more implant component surfaces, such as surface contours or angles, and one or more implant component dimensions such as thickness, width, depth, or length. The patient-specific feature(s) of an implant component can be designed based on patient-specific data to substantially match one or more of the patient's biological features (i.e., anatomical and/or biological features). In various embodiments described herein, the act of designing an implant component can include manufacturing the implant component having the related design features. For example, designing an implant component can include preoperatively establishing a design of one or more features of an implant component, for example, using a CAD computer program on a computer system specialized operated for such use and having one or more user interfaces, and instructing the transfer of that design data, for example, from a CAD computer program or computer system to a CAM (computer-aided manufacturing) computer program or computer system. Optionally, in certain embodiments, designing the implant can further include instructing the initiation of manufacturing the physical implant and/or manufacturing the implant.

Alternatively, patient-specific feature(s) of an implant component or guide tool can be achieved by analyzing imaging test data and selecting (e.g., preoperatively selecting from a library of implant components) the implant component that best fits one or more pre-determined patient-specific parameters that are derived from the imaging test.

Moreover, an implant component or guide tool can include a patient-specific feature that is both selected and designed. For example, an implant component initially can be selected (e.g., preoperatively selected from a library of implants) to have a feature with a standard or blank dimension, or with a larger or smaller dimension than the predetermined patient-specific dimension. Then, the implant component can be machined (if selected from an actual library of implant components) or manufactured (if selected from a virtual library of implant components) so that the standard dimension or blank dimension or larger-dimensioned or smaller-dimensioned implant feature is altered to have the patient-specific dimension.

In addition or alternatively, certain embodiments relate to patient-engineered implants, guide tools, and related methods. Some embodiments relate to articular implant components having one or more patient-engineered features optimized from patient-specific data to meet one or more parameters to enhance one or more of the patient's biological features, such as one or more biological/anatomical structures, alignments, kinematics, and/or soft tissue impingements. Accordingly, the one or more patient-engineered features of an implant component can include, but are not limited to, one or more implant component surfaces, such as surface contours, angles or bone cuts, and dimensions such as thickness, width, depth, or length of one or more aspects of the implant component. The patient-engineered feature(s) of an implant component can be designed and/or manufactured (e.g., preoperatively designed and manufactured) based on patient-specific data to substantially enhance or improve one or more of the patient's anatomical and/or biological features. Methods for preparing certain patient-engineered features are described, for example, in U.S. Ser. No. 12/712,072, entitled "Automated Systems For Manufacturing Patient-Specific Orthopedic Implants And Instrumentation" filed Feb. 24, 2010, which is incorporated herein by reference.

As with the patient-specific feature(s) of an implant component or guide tool, the patient-engineered features of an implant component or guide tool can be designed (e.g., preoperatively designed and manufactured) or they can be selected, for example, by selecting an implant component that best meets the one or more predetermined parameters that enhance one or more features of the patient's biology.

Moreover, an implant component or guide tool can include a patient-engineered feature that is both selected and designed. For example, an implant component initially can be selected (e.g., preoperatively selected from a library of implants) to have a feature with a larger or smaller dimension than the desired patient-engineered dimension. Then, the implant component can be machined (if selected from an actual library of implant components) or manufactured (if selected from a virtual library of implant components) so that the larger-dimensioned or smaller-dimensioned implant feature is altered to have the desired patient-engineered dimension.

1.2 Combinations of Patient-Adapted and Standard Features

A single implant component, guide tool, and/or related method can include one or more patient-specific features, one or more patient-engineered features, and/or one or more standard (e.g., off-the-shelf features). The standard, off-the-shelf features can be selected to best fit with one or more of the patient-specific and/or patient-engineered features. For example, in a knee joint, a metal backed tibial component can include a standard locking mechanism and a patient-adapted (i.e., patient-specific or patient-engineered) perimeter of the tibial component. A patient-specific perimeter of the tibial component can be achieved, for example, by cutting the perimeter of a selected tibial component to match the patient's cortical bone perimeter in one or more dimensions of one more sections. Similarly, a polyethylene insert can be chosen that includes a standard locking mechanism, while the perimeter is adapted for better support to the patient's tibial bone perimeter or the perimeter of the metal backing.

In certain aspects, an implant, guide tool, and/or related method can include one or more patient-adapted features and one or more standard features. For example, the joint-facing surface of an implant component can include a patient-specific feature (e.g., curvature) in the axis or axes of motion and one or more standard features in other axes. Using a curvature in the direction of motion that is matched to the patient's curvature (patient-specific) or that is optimized based on the patient's curvature (patient-engineered) can help to maintain and/or improve the biomechanical aspects of the patient's joint.

As one illustrative example, in certain embodiments, the joint-facing surface of a condylar portion of a femoral implant component and/or a corresponding groove in the bearing surface of a tibial implant component can include a patient-specific sagittal curvature (e.g., having one or more patient-specific radii of curvature) and a standard coronal curvature or radii of curvature. Coronal radii of curvature also can be patient-derived, but an average or an optimum can be derived across the articular surface that is constant along the extent of the articular surface in the coronal plane. The patient-specific sagittal curvature or radii of curvature can be designed from patient-specific data to match an existing feature of the patient's biology or it can be patient-engineered from patient-specific data to improve an existing feature of the patient's biology.

In certain embodiments, implant components and/or related methods described herein can include a combination of patient-specific and patient-engineered features. For example, patient-specific data collected preoperatively can be used to engineer one or more optimized surgical cuts to the patient's bone and to design or select a corresponding implant component having or more bone-facing surfaces or facets (i.e., "bone cuts") that specifically match one or more of the patient's resected bone surfaces. The surgical cuts to the patient's bone can be optimized (i.e., patient-engineered) to enhance one or more parameters, such as: (1) deformity correction and limb alignment (2) maximizing preservation of bone, cartilage, or ligaments, (3) maximizing preservation and/or optimization of other features of the patient's anatomy, such as trochlea and trochlear shape, (4) restoration and/or optimization of joint kinematics or biomechanics, (5) restoration or optimization of joint-line location and/or joint gap width, (6) and/or addressing one or more other parameters. Based on the optimized surgical cuts and, optionally, on other desired features of the implant component, the implant component's bone-facing surface can be designed or selected to, at least in part, negatively-match the shape of the patient's resected bone surface.

Optionally, the implant component can include other patient-adapted features. For example, the joint-facing surface can be designed to, at least in part, substantially negatively-match an opposing surface at the joint cavity (e.g., the surface of the patient's biological structure, native or resected, or the surface of an opposing implant component. In certain embodiments, the joint-facing surface of the implant component can include patient-adapted features such as a patient-specific sagittal curvature and a patient-engineered coronal curvature, or a patient-specific sagittal curvature and a patient-specific coronal curvature. These curvatures can be patient-specific in at least a portion or the entire joint-facing surface of the implant. Alternatively or in addition, one or more of these curvatures can be patient-adapted in one condyle, but not patient-adapted in the other condyle. Moreover, the shape (e.g., curvature) of a first condyle can be used, for example, to generate a shape (e.g., curvature) for the second condyle.

1.3 Implant Systems

An implant (i.e., an implant system) can include one or more implant components, which, as described above, can each include one or more patient-specific features, one or more patient-engineered features, and one or more standard (e.g., off-the-shelf) features. Moreover, an implant system can include one or more patient-adapted (e.g., patient-specific and/or patient-engineered) implant components and one or more standard implant components.

For example, a knee implant can include a femoral implant component having one or more patient-adapted and standard features, and an off-the-shelf tibial implant component having only standard features. In this example, the entire tibial implant component can be off-the-shelf. Alternatively, a metal-backed implant component (or portion of an implant component) can be patient-specific, e.g., matched in the A-P dimension or the M-L dimension to the patient's tibial cortical bone, while the corresponding plastic insert implant component (or corresponding portion of the implant component) can include a standard off-the-shelf configuration.

Figure 1A:
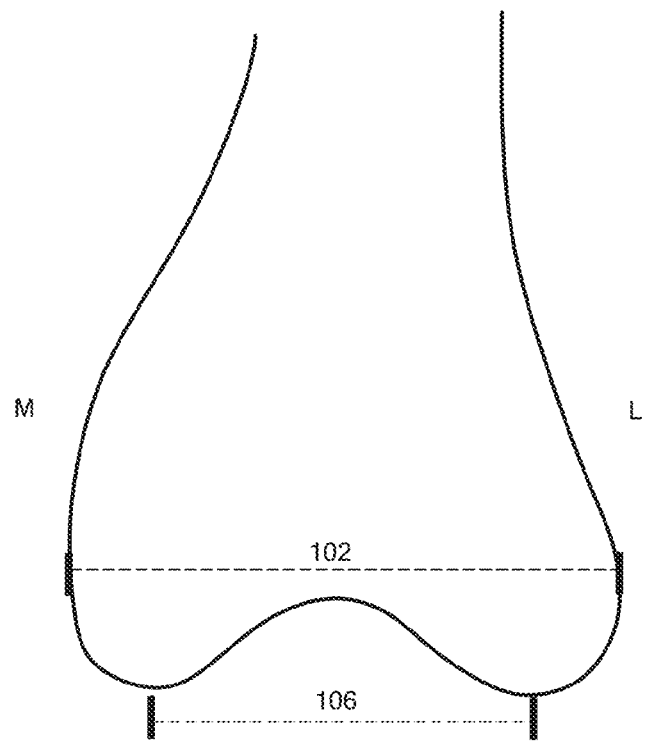
FIGS. 1A and 1B show schematic representations in a coronal plane of a patient's distal femur (FIG. 1A) and a femoral implant component (FIG. 1B)
Figure 1B:
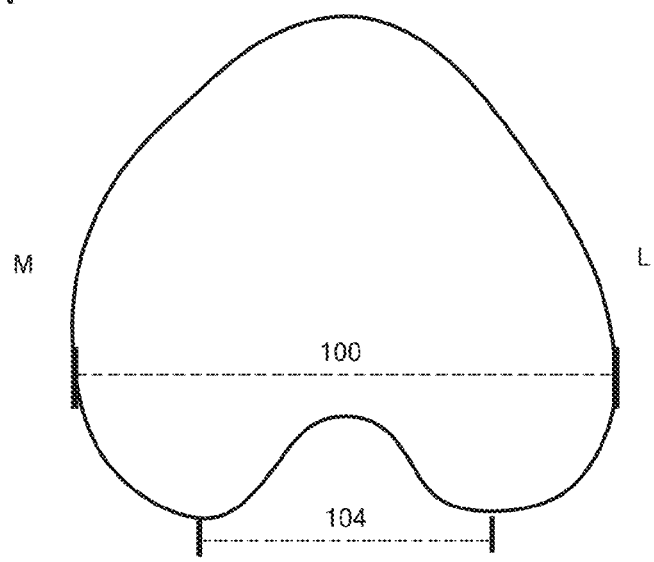

Off-the-shelf configuration can mean that the tibial insert has fixed, standard dimensions to fit, for example, into a standard tibial tray. Off-the-shelf configuration also can mean that the tibial insert has a fixed, standard dimension or distance between two tibial dishes or curvatures to accommodate the femoral bearing surface. The latter configuration is particularly applicable in an implant system that uses a femoral implant component that is patient-specifically matched in the M-L dimension to the distal femur of the patient's bone, but uses a standardized intercondylar notch width on the femoral component to achieve optimal mating with a corresponding tibial insert. For example, FIGS. 1A and 1B show schematic representations in a coronal plane of a patient's distal femur (FIG. 1A) and a femoral implant component (FIG. 1B). As shown in the figures, the implant component M-L dimension 100 (e.g. epicondylar M-L dimension) patient-specifically matches the corresponding M-L dimension of the patient's femur 102. However, the intercondylar M-L dimension (i.e., notch width) of the implant component, 104, can be standard, which in this figure is shorter than the patient's intercondylar M-L dimension 106. In this way, the epicondylar M-L dimension of the implant component is patient-specific, while the intercondylar M-L dimension (i.e., notch width) is designed to be a standard length, for example, so that is can properly engage during joint motion a tibial insert having a standard distance between its dishes or curvatures that engage the condyles of the femoral implant component.

1.4 Improved Implants, Guide Tools and Related Methods

Certain embodiments are directed to implants, guide tools, and/or related methods that can be used to provide to a patient a pre-primary procedure and/or a pre-primary implant such that a subsequent, replacement implant can be performed with a second (and, optionally, a third, and optionally, a fourth) patient-adapted pre-primary implant or with a traditional primary implant. In certain embodiments, the pre-primary implant procedure can include 3, 4, 5, 6, 7, or more resection or surgical cuts to the patient's bone and the pre-primary implant can include on its corresponding bone-facing surface a matching number and orientation of bone-cut facets or surfaces.

In one illustrative embodiment, a first pre-primary joint-replacement procedure includes a patient-adapted implant component, guide tool, and/or related method. The patient-adapted implant component, guide tool, and/or related method can be preoperatively selected and/or designed from patient-specific data, such as one or more images of the patient's joint, to include one or more features that are patient-specific or patient-engineered. The features (e.g., dimensions, shape, surface contours) of the first pre-primary implant and, optionally, patient-specific data (e.g., features of the patient's resected bone surfaces and features of the patient's contralateral joint) can be stored in a database. When the first pre-primary implant fails, for example, due to bone loss or osteolysis or aseptic loosening at a later point in time (e.g., 15 years after the original implantation) a second implant can be implanted. For the second implant procedure, the amount of diseased bone can be assessed. If the amount of diseased bone to be resected is minimal, the patient-specific data can be used to select and/or design a second pre-primary procedure and/or a pre-primary implant. If the amount of diseased bone to be resected is substantial, a traditional primary procedure and a traditional implant can be employed.

Alternatively, certain embodiments are directed to implants, guide tools, and/or related methods that can be used to provide to a patient a primary procedure and/or a primary implant such that a subsequent replacement implant can be used as part of a traditional revision procedure. Certain embodiments are directed to implants, guide tools, and/or related methods that can be used to provide a patient-adapted revision implant. For example, following a traditional implant, a subsequent revision can include a patient-adapted procedure and/or a patient-adapted implant component as described herein.

Figure 2:
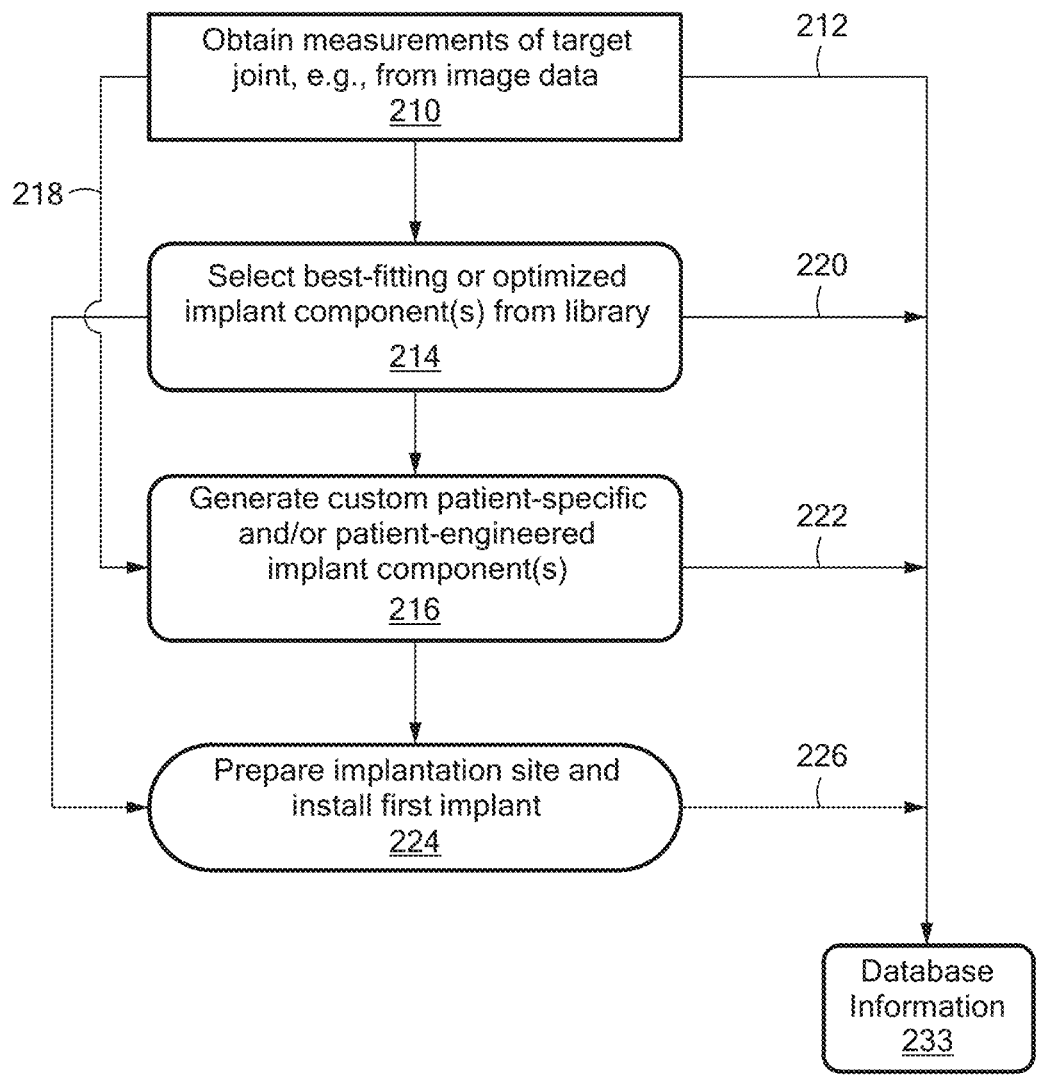
FIG. 2 is a flow chart illustrating a process that includes selecting and/or designing an initial patient-adapted implant.

FIG. 2 is a flow chart illustrating a process that includes selecting and/or designing a first patient-adapted implant, for example, a pre-primary implant. First, using the techniques described herein or those suitable and known in the art, measurements of the target joint are obtained 210. This step can be repeated multiple times, as desired. Optionally, a virtual model of the joint can be generated, for example, to determine proper joint alignment and the corresponding resection cuts and implant component features based on the determined proper alignment. This information can be collected and stored 212 in a database 213. Once measurements of the target joint are obtained and analyzed to determine resection cuts and patient-adapted implant features, the patient-adapted implant components can be selected 214 (e.g., selected from a virtual library and optionally manufactured without further design alteration 215, or selected from a physical library of implant components). Alternatively, or in addition, one or more implant components with best-fitting and/or optimized features can be selected 214 (e.g., from a library) and then further designed (e.g., designed and manufactured) 216. Alternatively or in addition, one or more implant components with best-fitting and/or optimized features can be designed (e.g., designed and manufactured) 218, 216 without an initial selection from a library. Using a virtual model to assess the selected or designed implant component(s), this process also can be repeated as desired (e.g., before one or more physical components are selected and/or generated). The information regarding the selected and/or designed implant component(s) can be collected and stored 220, 222 in a database 213. Once a desired first patient-adapted implant component or set of implant components is obtained, a surgeon can prepare the implantation site and install the first implant 224. The information regarding preparation of the implantation site and implant installation can be collected and stored 226 in a database 213. In this way, the information associated with the first pre-primary implant component is available for use by a surgeon for subsequent implantation of a second pre-primary or a primary implant.

Figure 3:
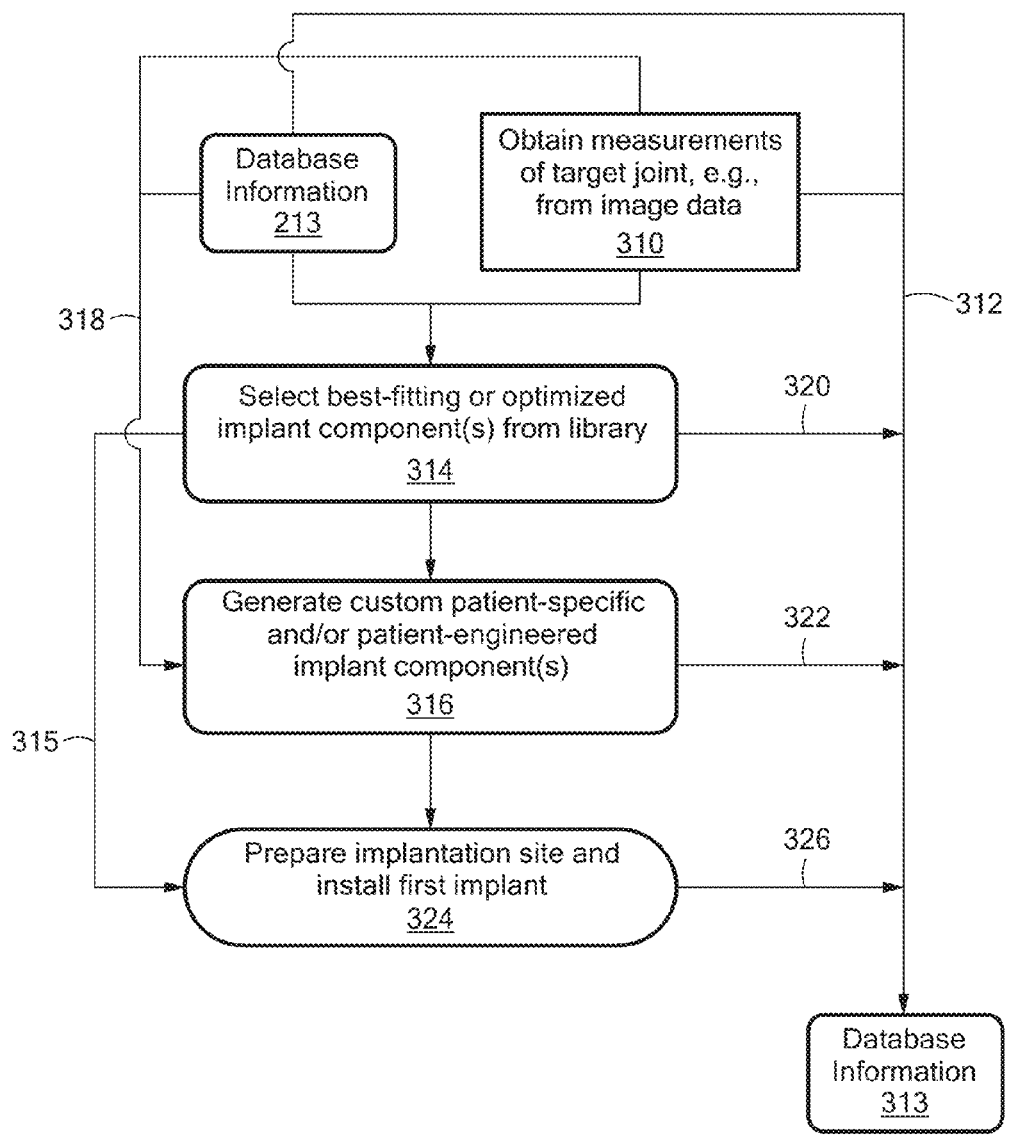
FIG. 3 is a flow chart illustrating a process that includes selecting and/or designing a second patient-adapted implant.

FIG. 3 is a flow chart illustrating a process that includes selecting and/or designing a second implant. In certain embodiments, the second implant can be a traditional primary implant. Alternatively, the second implant can be a patient-adapted implant, which optionally can be used as second pre-primary implant that allows for a subsequent (i.e., third) primary implant using a traditional implant.

The steps described in FIG. 3 are similar to those described above for a first pre-primary implant (see FIG. 2); however, in the second implant process, the database information 213 collected and stored in the first implant process can be used as part of the process for the second implant. In addition to the database information from the first implant process 213, additional measurements of the target joint optionally can be obtained 310 and used together with the database information 213 from the first implant process as a basis for selecting and/or designing a second implant. This step can be repeated multiple times, as desired. Optionally, a virtual model of the joint can be generated (with our without a model of the first implant), for example, to determine proper joint alignment, corresponding resection cuts and, optionally, patient-adapted implant component features based on the determined proper alignment. This information can be collected and stored 312 as new or additional database information 313. Once the database information from the first implant process and optionally new measurements of the target joint and first implant are obtained and analyzed, the implant component(s) for the second implant can be selected 314 (e.g., selected from a virtual library and optionally manufactured without further design alteration 315, or selected from a physical library of implant components, or selected from among traditional implant components). Alternatively or in addition, one or more implant components with best-fitting and/or optimized features can be selected 314 (e.g., from a library) and then further designed (e.g., designed and manufactured) 316. Alternatively or in addition, one or more implant components with best-fitting and/or optimized features can be designed (e.g., designed and manufactured) 038 without an initial selection from a library. Using a virtual model to assess the selected or designed implant component, this process also can be repeated as desired (e.g., before one or more physical components are selected and/or generated). The information regarding the selected and/or designed implant components for the second implant can be collected and stored 320, 322 in a database 313. Once a desired implant component or set of implant components is obtained for the second implant, a surgeon can prepare the implantation site, including removing the first implant, and install the second implant 324. The information regarding preparation of the implantation site and second implant installation can be collected and stored 326 in a database 313.

The second implant can have standard attachment mechanisms, e.g., a stem and or pegs or other attachment means known in the art. Alternatively, the attachment mechanisms can be patient-specific by deriving shape information on the residual bone, e.g., of a femur and acetabulum or of a femur and a tibia or of a humerus and a glenoid, using image data, e.g., CT or MRI data. One or more dimensions or shapes or joint-facing surfaces of the second implant can be adapted to include, at least in part, information reflective of the corresponding dimension(s) or shape(s) or joint-facing surface(s) of the first implant. In this manner, a better functional result can be achieved with the revision implant by maintaining patient-specific shapes and/or geometry in the revision implant by accessing data in the patient database.

Accordingly, certain embodiments described herein are directed to implants, implant components, guide tools, and related methods that address many of the problems associated with traditional implants, such as mismatches between an implant component and a patient's biological features (e.g., a feature of a biological structure, a distance or space between two biological structures, and/or a feature associated with anatomical function) and substantial bone removal that limits subsequent revisions following a traditional primary implant.

2. Exemplary Implant Systems and Patient-Adapted Features

Figure 4B:
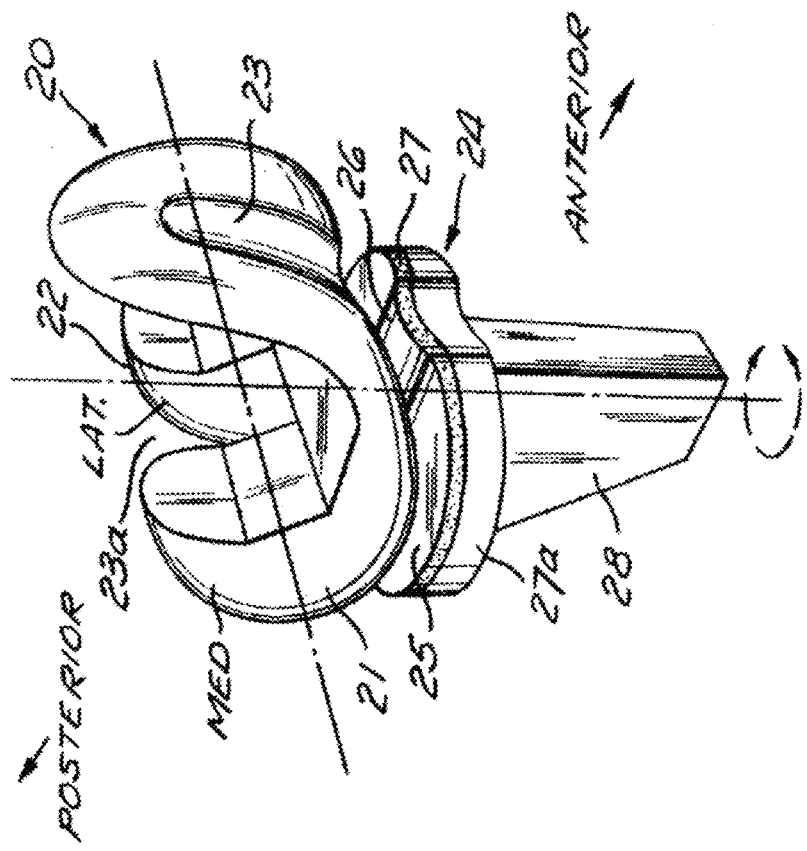
Figure 4A:
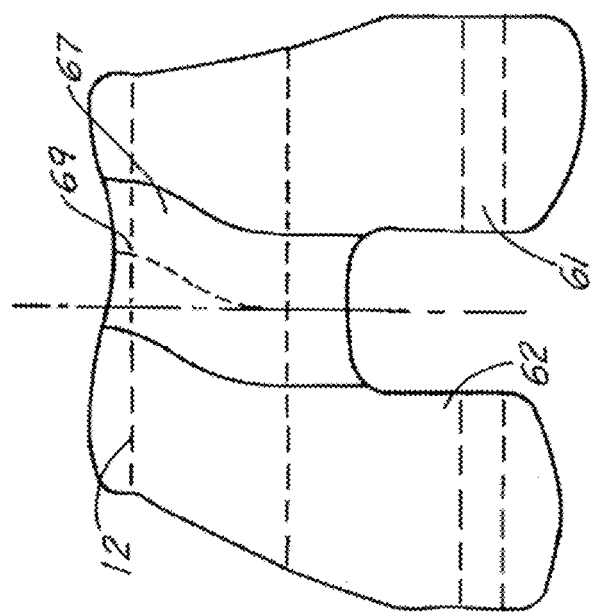

The concepts described herein can be embodied in various types of articular implants including, but not limited to, knee-joint implants, hip-joint implants, shoulder-joint implants, and spinal implants (e.g., intervertebral implants and facet joint implants), as well as related surgical tools (e.g., guide tools) and methods. Exemplary traditional implants are illustrated in FIGS. 4A-4M. In particular, FIGS. 4A and 4B illustrate exemplary traditional knee-joint implants as described, for example, in U.S. Pat. Nos. 5,824,105 and 5,133,758, respectively; FIGS. 4C-4G illustrate traditional hip-joint implants, including Austin Moore-type, Thompson-type, and Bipolar hip-type prostheses; FIGS. 4H-4J illustrate traditional shoulder-joint implants as described, for example, in U.S. Pat. No. 7,175,663; and FIGS. 4K-4M illustrate traditional spinal implants, as described, for example, in U.S. Pat. No. 7,166,129 and at the web site, www.facetsolutions.com/AFRSproduct.html.

In certain embodiments described herein, an implant or implant system can include one, two, three, four or more components having one or more patient-specific features that substantially match one or more of the patient's biological features, for example, one or more dimensions and/or measurements of an anatomical/biological structure, such as bone, cartilage, tendon, or muscle; a distance or space between two or more aspects of a biological structure and/or between two or more different biological structures; and a biomechanical or kinematic quality or measurement of the patient's biology. In addition or alternatively, an implant component can include one or more features that are engineered to optimize or enhance one or more of the patient's biological features, for example, (1) deformity correction and limb alignment (2) preserving bone, cartilage, and/or ligaments, (3) preserving and/or optimizing other features of the patient's anatomy, such as trochlea and trochlear shape, (4) restoring and/or optimizing joint kinematics or biomechanics, and/or (5) restoring and/or optimizing joint-line location and/or joint gap width. In addition, an implant component can be designed and/or manufactured to include one or more standard (i.e., non-patient-adapted) features.

Exemplary patient-adapted (i.e., patient-specific and/or patient-engineered) features of the implant components described herein are identified in Table 1. One or more of these implant component features can be selected and/or designed based on patient-specific data, such as image data.

TABLE 1

Exemplary implant features that can be patient-adapted based on patient-specific measurements

| Category | Exemplary feature |
|---|---|
| Implant or implant or component (applies knee, shoulder, hip, ankle, or other implant or implant component) | One or more portions of, or all of, an external implant component curvature |
| | One or more portions of, or all of, an internal implant dimension |
| | One or more portions of, or all of, an internal or external implant angle |
| | Portions or all of one or more of the ML, AP, SI dimension of the internal and external component and component |

TABLE 1-continued

Exemplary implant features that can be patient-adapted
based on patient-specific measurements

| Category | Exemplary feature |
|---|---|
| | features |
| | An outer locking mechanism dimension between a plastic or non-metallic insert and a metal backing component in one or more dimensions |
| | Component height |
| | Component profile |
| | Component 2D or 3D shape |
| | Component volume |
| | Composite implant height |
| | Insert width |
| | Insert shape |
| | Insert length |
| | Insert height |
| | Insert profile |
| | Insert curvature |
| | Insert angle |
| | Distance between two curvatures or concavities |
| | Polyethylene or plastic width |
| | Polyethylene or plastic shape |
| | Polyethylene or plastic length |
| | Polyethylene or plastic height |
| | Polyethylene or plastic profile |
| | Polyethylene or plastic curvature |
| | Polyethylene or plastic angle |
| | Component stem width |
| | Component stem shape |
| | Component stem length |
| | Component stem height |
| | Component stem profile |
| | Component stem curvature |
| | Component stem position |
| | Component stem thickness |
| | Component stem angle |
| | Component peg width |
| | Component peg shape |
| | Component peg length |
| | Component peg height |
| | Component peg profile |
| | Component peg curvature |
| | Component peg position |
| | Component peg thickness |
| | Component peg angle |
| | Slope of an implant surface |
| | Number of sections, facets, or cuts on an implant surface |
| Femoral implant or implant component | Condylar distance of a femoral component, e.g., between femoral condyles |
| | A condylar coronal radius of a femoral component |
| | A condylar sagittal radius of a femoral component |
| Tibial implant or implant component | Slope of an implant surface |
| | Condylar distance, e.g., between tibial joint-facing surface concavities that engage femoral condyles |
| | Coronal curvature (e.g., one or more radii of curvature in the coronal plane) of one or both joint-facing surface concavities that engage each femoral condyle |
| | Sagittal curvature (e.g., one or more radii of curvature in the sagittal plane) of one or both joint-facing surface concavities that engage each femoral condyle |

The patient-adapted features described in Table 1 also can be applied to patient-adapted guide tools described herein.

The patient-adapted implant components and guide tools described herein can include any number of patient-specific features, patient-engineered features, and/or standard features. Illustrative combinations of patient-specific, patient-engineered, and standard features of an implant component are provided in Table 2. Specifically, the table illustrates an implant or implant component having at least thirteen different features. Each feature can be patient-specific (P), patient-engineered (PE), or standard (St). As shown, there are 105 unique combinations in which each of thirteen is either patient-specific, patient-engineered, or standard features.

TABLE 2

Exemplary combinations of patient-specific (P), patient-engineered (PE), and standard (St) features[1] in an implant

| Implant system number | Implant feature number[2] | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| 1 | P | P | P | P | P | P | P | P | P | P | P | P | P |
| 2 | PE | PE | PE | PE | PE | PE | PE | PE | PE | PE | PE | PE | PE |
| 3 | St | St | St | St | St | St | St | St | St | St | St | St | St |
| 4 | P | St | St | St | St | St | St | St | St | St | St | St | St |
| 5 | P | P | St | St | St | St | St | St | St | St | St | St | St |
| 6 | P | P | P | St | St | St | St | St | St | St | St | St | St |
| 7 | P | P | P | P | St | St | St | St | St | St | St | St | St |
| 8 | P | P | P | P | P | St | St | St | St | St | St | St | St |
| 9 | P | P | P | P | P | P | St | St | St | St | St | St | St |
| 10 | P | P | P | P | P | P | P | St | St | St | St | St | St |
| 11 | P | P | P | P | P | P | P | P | St | St | St | St | St |
| 12 | P | P | P | P | P | P | P | P | P | St | St | St | St |
| 13 | P | P | P | P | P | P | P | P | P | P | St | St | St |
| 14 | P | P | P | P | P | P | P | P | P | P | P | St | St |
| 15 | P | P | P | P | P | P | P | P | P | P | P | P | St |
| 16 | P | PE | PE | PE | PE | PE | PE | PE | PE | PE | PE | PE | PE |
| 17 | P | P | PE | PE | PE | PE | PE | PE | PE | PE | PE | PE | PE |
| 18 | P | P | P | PE | PE | PE | PE | PE | PE | PE | PE | PE | PE |
| 19 | P | P | P | P | PE | PE | PE | PE | PE | PE | PE | PE | PE |
| 20 | P | P | P | P | P | PE | PE | PE | PE | PE | PE | PE | PE |
| 21 | P | P | P | P | P | P | PE | PE | PE | PE | PE | PE | PE |
| 22 | P | P | P | P | P | P | P | PE | PE | PE | PE | PE | PE |
| 23 | P | P | P | P | P | P | P | P | PE | PE | PE | PE | PE |
| 24 | P | P | P | P | P | P | P | P | P | PE | PE | PE | PE |
| 25 | P | P | P | P | P | P | P | P | P | P | PE | PE | PE |
| 26 | P | P | P | P | P | P | P | P | P | P | P | PE | PE |
| 27 | P | P | P | P | P | P | P | P | P | P | P | P | PE |
| 28 | PE | St | St | St | St | St | St | St | St | St | St | St | St |
| 29 | PE | PE | St | St | St | St | St | St | St | St | St | St | St |
| 30 | PE | PE | PE | St | St | St | St | St | St | St | St | St | St |
| 31 | PE | PE | PE | PE | St | St | St | St | St | St | St | St | St |
| 32 | PE | PE | PE | PE | PE | St | St | St | St | St | St | St | St |
| 33 | PE | PE | PE | PE | PE | PE | St | St | St | St | St | St | St |
| 34 | PE | PE | PE | PE | PE | PE | PE | St | St | St | St | St | St |
| 35 | PE | PE | PE | PE | PE | PE | PE | PE | St | St | St | St | St |
| 36 | PE | PE | PE | PE | PE | PE | PE | PE | PE | St | St | St | St |
| 37 | PE | PE | PE | PE | PE | PE | PE | PE | PE | PE | St | St | St |
| 38 | PE | PE | PE | PE | PE | PE | PE | PE | PE | PE | PE | St | St |
| 39 | PE | PE | PE | PE | PE | PE | PE | PE | PE | PE | PE | PE | St |
| 40 | P | PE | St | St | St | St | St | St | St | St | St | St | St |
| 41 | P | PE | PE | St | St | St | St | St | St | St | St | St | St |
| 42 | P | PE | PE | PE | St | St | St | St | St | St | St | St | St |
| 43 | P | PE | PE | PE | PE | St | St | St | St | St | St | St | St |
| 44 | P | PE | PE | PE | PE | PE | St | St | St | St | St | St | St |
| 45 | P | PE | PE | PE | PE | PE | PE | St | St | St | St | St | St |
| 46 | P | PE | PE | PE | PE | PE | PE | PE | St | St | St | St | St |
| 47 | P | PE | PE | PE | PE | PE | PE | PE | PE | St | St | St | St |
| 48 | P | PE | PE | PE | PE | PE | PE | PE | PE | PE | St | St | St |
| 49 | P | PE | PE | PE | PE | PE | PE | PE | PE | PE | PE | St | St |
| 50 | P | PE | PE | PE | PE | PE | PE | PE | PE | PE | PE | PE | St |
| 51 | P | P | PE | St | St | St | St | St | St | St | St | St | St |
| 52 | P | P | PE | PE | St | St | St | St | St | St | St | St | St |
| 53 | P | P | PE | PE | PE | St | St | St | St | St | St | St | St |
| 54 | P | P | PE | PE | PE | PE | St | St | St | St | St | St | St |
| 55 | P | P | PE | PE | PE | PE | PE | St | St | St | St | St | St |
| 56 | P | P | PE | PE | PE | PE | PE | PE | St | St | St | St | St |
| 57 | P | P | PE | PE | PE | PE | PE | PE | PE | St | St | St | St |
| 58 | P | P | PE | PE | PE | PE | PE | PE | PE | PE | St | St | St |
| 59 | P | P | PE | PE | PE | PE | PE | PE | PE | PE | PE | St | St |
| 60 | P | P | PE | PE | PE | PE | PE | PE | PE | PE | PE | PE | St |
| 61 | P | P | P | PE | St | St | St | St | St | St | St | St | St |
| 62 | P | P | P | PE | PE | St | St | St | St | St | St | St | St |
| 63 | P | P | P | PE | PE | PE | St | St | St | St | St | St | St |
| 64 | P | P | P | PE | PE | PE | PE | St | St | St | St | St | St |
| 65 | P | P | P | PE | PE | PE | PE | PE | St | St | St | St | St |
| 66 | P | P | P | PE | PE | PE | PE | PE | PE | St | St | St | St |
| 67 | P | P | P | PE | PE | PE | PE | PE | PE | PE | St | St | St |
| 68 | P | P | P | PE | PE | PE | PE | PE | PE | PE | PE | St | St |
| 69 | P | P | P | PE | PE | PE | PE | PE | PE | PE | PE | PE | St |
| 70 | P | P | P | P | PE | St | St | St | St | St | St | St | St |
| 71 | P | P | P | P | PE | PE | St | St | St | St | St | St | St |
| 72 | P | P | P | P | PE | PE | PE | St | St | St | St | St | St |
| 73 | P | P | P | P | PE | PE | PE | PE | St | St | St | St | St |
| 74 | P | P | P | P | PE | PE | PE | PE | PE | St | St | St | St |
| 75 | P | P | P | P | PE | PE | PE | PE | PE | PE | St | St | St |
| 76 | P | P | P | P | PE | PE | PE | PE | PE | PE | PE | St | St |
| 77 | P | P | P | P | PE | PE | PE | PE | PE | PE | PE | PE | St |
| 78 | P | P | P | P | P | PE | St | St | St | St | St | St | St |
| 79 | P | P | P | P | P | PE | PE | St | St | St | St | St | St |
| 80 | P | P | P | P | P | PE | PE | PE | St | St | St | St | St |
| 81 | P | P | P | P | P | PE | PE | PE | St | St | St | St | St |
| 82 | P | P | P | P | P | PE | PE | PE | PE | St | St | St | St |
| 83 | P | P | P | P | P | PE | PE | PE | PE | PE | St | St | St |
| 84 | P | P | P | P | P | PE | PE | PE | PE | PE | PE | St | St |
| 85 | P | P | P | P | P | P | PE | St | St | St | St | St | St |
| 86 | P | P | P | P | P | P | PE | St | St | St | St | St | St |
| 87 | P | P | P | P | P | P | PE | PE | St | St | St | St | St |
| 88 | P | P | P | P | P | P | PE | PE | PE | St | St | St | St |
| 89 | P | P | P | P | P | P | PE | PE | PE | PE | St | St | St |
| 90 | P | P | P | P | P | P | PE | PE | PE | PE | PE | St | St |
| 91 | P | P | P | P | P | P | P | PE | St | St | St | St | St |
| 92 | P | P | P | P | P | P | P | PE | PE | St | St | St | St |
| 93 | P | P | P | P | P | P | P | PE | PE | PE | St | St | St |
| 94 | P | P | P | P | P | P | P | PE | PE | PE | PE | St | St |
| 95 | P | P | P | P | P | P | P | PE | PE | PE | PE | PE | St |
| 96 | P | P | P | P | P | P | P | P | PE | St | St | St | St |
| 97 | P | P | P | P | P | P | P | P | PE | PE | St | St | St |
| 98 | P | P | P | P | P | P | P | P | PE | PE | PE | St | St |
| 99 | P | P | P | P | P | P | P | P | PE | PE | PE | PE | St |
| 100 | P | P | P | P | P | P | P | P | PE | St | St | St | St |
| 101 | P | P | P | P | P | P | P | P | PE | PE | St | St | St |
| 102 | P | P | P | P | P | P | P | P | PE | PE | PE | St | St |
| 103 | P | P | P | P | P | P | P | P | P | PE | St | St | St |
| 104 | P | P | P | P | P | P | P | P | P | PE | PE | St | St |
| 105 | P | P | P | P | P | P | P | P | P | P | PE | St | St |

[1] S = standard, off-the-shelf, P = patient-specific, PE = patient-engineered (e.g., constant coronal curvature, derived from the patient's coronal curvatures along articular surface)
[2] Each of the thirteen numbered implant features represents a different exemplary implant feature, for example, for a knee implant the thirteen features can include: (1) femoral implant component M-L dimension, (2) femoral implant component A-P dimension, (3) femoral implant component bone cut, (4) femoral implant component sagittal curvature, (5) femoral implant component coronal curvature, (6) femoral implant component inter-condylar distance, (7) femoral implant component notch location/geometry, (8) tibial implant component M-L dimension, (9) tibial implant component A-P dimension, (10) tibial implant component insert inter-condylar distance, (11) tibial implant component insert lock, (12) tibial implant component metal backing lock, and (13) tibial implant component metal backing perimeter.

The term "implant component" as used herein can include: (i) one of two or more devices that work together in an implant or implant system, or (ii) a complete implant or implant system, for example, in embodiments in which an implant is a single, unitary device. The term "match" as used herein is envisioned to include one or both of a negative-match, as a convex surface fits a concave surface, and a positive-match, as one surface is identical to another surface.

Figure 5A:
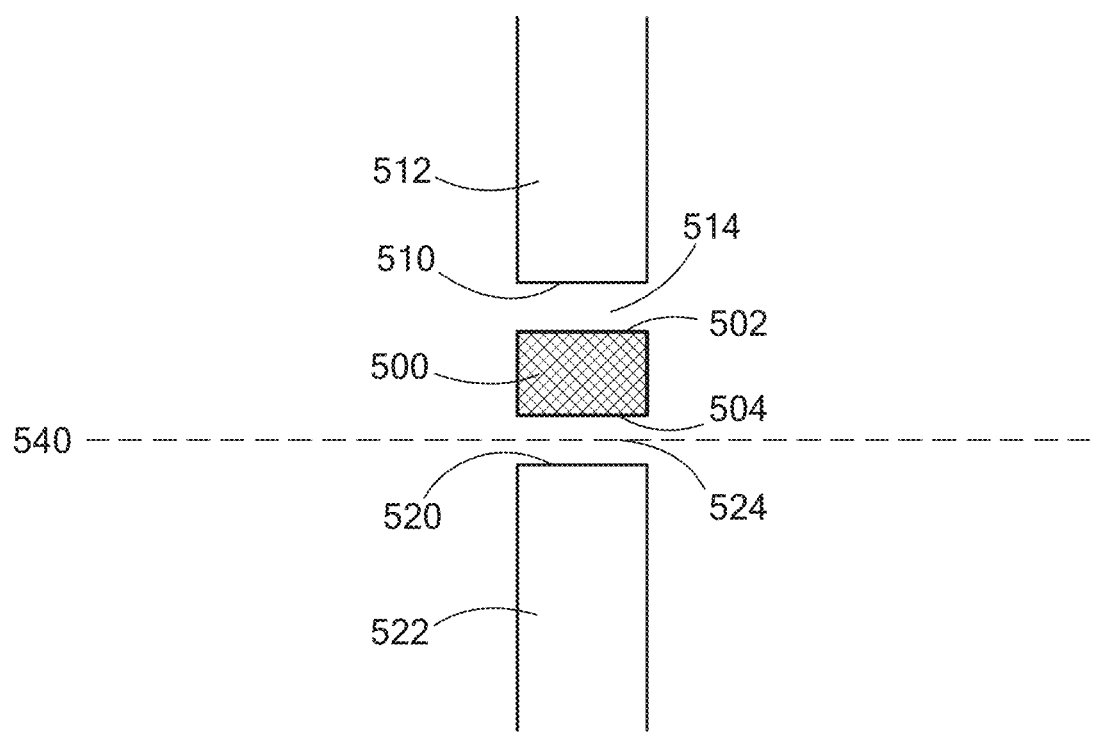

Three illustrative embodiments of implants and/or implant components are schematically represented in FIGS. 5A-5C. In FIG. 5A, the illustrative implant component 500 includes an inner, bone-facing surface 502 and an outer, joint-facing surface 504. The inner bone-facing surface 502 engages a first articular surface 510 of a first biological structure 512, such as bone or cartilage, at a first interface 514. The articular surface 510 can be a native surface, a resected surface, or a combination of the two. The outer, joint-facing surface 504 opposes a second articular surface 520 of a second biological structure 522 at a joint interface 524. The dashed line across each figure illustrates a patient's joint-line. In certain embodiments, one or more features of the implant component, for example, an M-L, A-P, or S-I dimension, a feature of the inner, bone-facing surface 502, and/or a feature of the outer, joint-facing surface 504, are patient-adapted (i.e., include one or more patient-specific and/or patient-engineered features).

The illustrative embodiment shown in FIG. 5B includes two implant components 500, 500'. Each implant component 500, 500' includes an inner, bone-facing surface 502, 502' and an outer, joint-facing surface 504, 504'. The first inner, bone-facing surface 502 engages a first articular surface 510 of a first biological structure 512 (e.g., bone or cartilage) at a first interface 514. The first articular surface 510 can be a native surface, a cut surface, or a combination of the two. The second bone-facing surface 502' engages a second articular surface 520 of a second biological structure 522 at a second interface 514'. The second articular surface 520 can be a native surface, a resected surface, or a combination of the two. In addition, an outer, joint-facing surface 504 on the first component 500 opposes a second, outer joint-facing surface 504' on the second component 500' at the joint interface 524. In certain embodiments, one or more features of the implant component, for example, one or both of the inner, bone-facing surfaces 502, 502' and/or one or both of the outer, joint-facing surfaces 504, 504', are patient-adapted (i.e., include one or more patient-specific and/or patient-engineered features).

The illustrative embodiment represented in FIG. 5C includes the two implant components 500, 500', the two biological structures 512, 522, the two interfaces 514, 514', and the joint interface 524, as well as the corresponding surfaces, as described for the embodiment illustrated in FIG. 5B. However, FIG. 5C also includes structure 550, which can be an implant component in certain embodiments or a biological structure in certain embodiments. Accordingly, the presence of a third structural 550 surface in the joint creates a second joint interface 524', and possibly a third 524", in addition to joint interface 524. Alternatively or in addition to the patient-adapted features described above for components 500 and 500', the components 500, 500' can include one or more features, such as surface features at the additional joint interface(s) 524, 524", as well as other dimensions (e.g., height, width, depth, contours, and other dimensions) that are patient-adapted, in whole or in part. Moreover, structure 550, when it is an implant component, also can have one or more patient-adapted features, such as one or more patient-adapted surfaces and dimensions.

Traditional implants and implant components can have surfaces and dimensions that are a poor match to a particular patient's biological feature(s). The patient-adapted implants, guide tools, and related methods described herein improve upon these deficiencies. The following two subsections describe two particular improvements, with respect to the bone-facing surface and the joint-facing surface of an implant component; however, the principles described herein are applicable to any aspect of an implant component.

2.1 Bone-Facing Surface of an Implant Component

In certain embodiments, the bone-facing surface of an implant can be designed to substantially negatively-match one more bone surfaces. For example, in certain embodiments at least a portion of the bone-facing surface of a patient-adapted implant component can be designed to substantially negatively-match the shape of subchondral bone, cortical bone, endosteal bone, and/or bone marrow. A portion of the implant also can be designed for resurfacing, for example, by negatively-matching portions of a bone-facing surface of the implant component to the subchondral bone or cartilage. Accordingly, in certain embodiments, the bone-facing surface of an implant component can include one or more portions designed to engage resurfaced bone, for example, by having a surface that negatively-matches uncut subchondral bone or cartilage, and one or more portions designed to engage cut bone, for example, by having a surface that negatively-matches a cut subchondral bone.

In certain embodiments, the bone-facing surface of an implant component includes multiple surfaces, also referred to herein as bone cuts. One or more of the bone cuts on the bone-facing surface of the implant component can be selected and/or designed to substantially negatively-match one or more surfaces of the patient's bone. The surface(s) of the patient's bone can include bone, cartilage, or other biological surfaces. For example, in certain embodiments, one or more of the bone cuts on the bone-facing surface of the implant component can be designed to substantially negatively-match (e.g., the number, depth, and/or angles of cut) one or more resected surfaces of the patient's bone. The bone-facing surface of the implant component can include any number of bone cuts, for example, two, three, four, less than five, five, more than five, six, seven, eight, nine or more bone cuts. In certain embodiments, the bone cuts of the implant component and/or the resection cuts to the patient's bone can include one or more facets on corresponding portions of an implant component. For example, the facets can be separated by a space or by a step cut connecting two corresponding facets that reside on parallel or non-parallel planes. These bone-facing surface features can be applied to various joint implants, including knee, hip, spine, and shoulder joint implants.

Figure 6A:
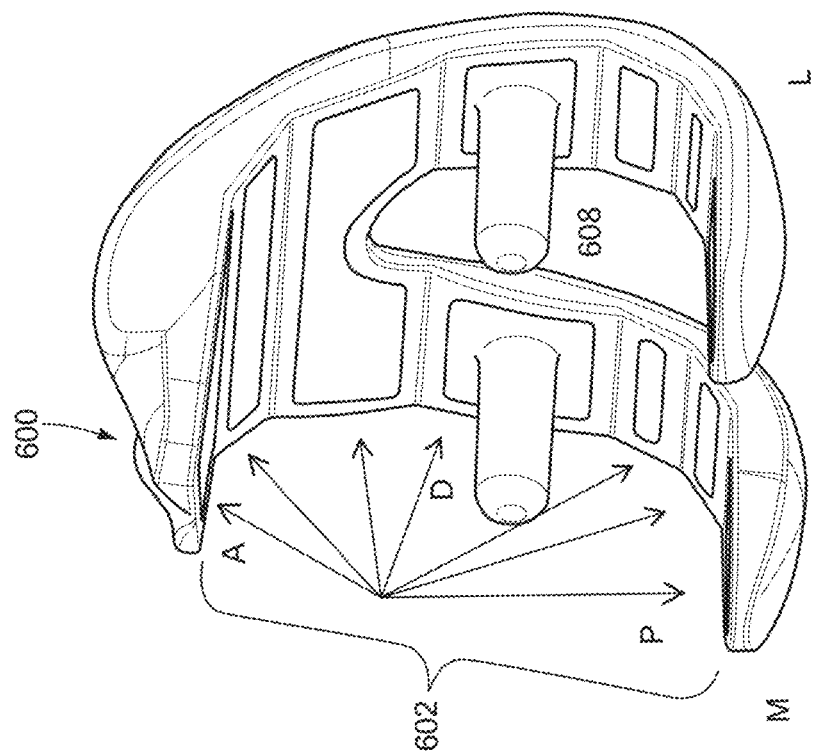
FIGS. 6A-6C depict designs of implant components that have six bone cuts (FIG. 6A), seven bone cuts (FIG. 6B), and three bone cuts with one being a curvilinear bone cut (FIG. 6C)
Figure 6B:
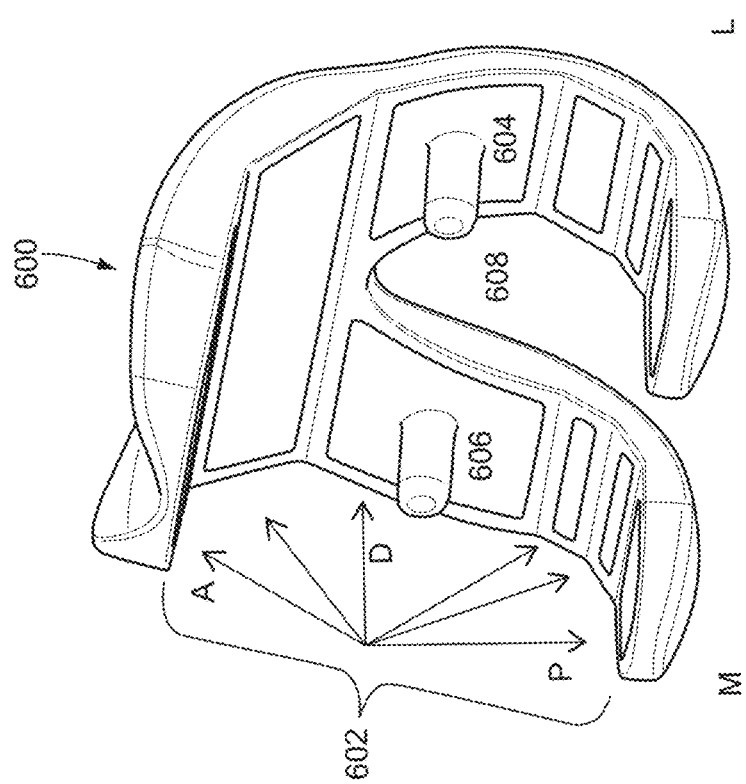

FIG. 6A illustrates an exemplary femoral implant component 600 having six bone cuts. FIG. 6B illustrates a femoral implant component 600 having seven bone cuts. In FIG. 6A and FIG. 6B, the six or seven respective bone cuts are identified by arrows on the inner, bone-facing surface 602 of the implant component 600. The bone cuts can include, for example, an anterior bone cut A, a distal bone cut D, and a posterior bone cut P, as well as one or more anterior chamfer bone cuts between the anterior bone cut A and distal bone cut D, and/or one or more posterior chamfer bone cuts between the distal posterior bone cut P and the distal bone cut D. The implant component depicted in FIG. 6A includes one anterior chamfer bone cut and two posterior chamfer bone cuts, in addition to anterior, posterior and distal bone cuts. The implant component depicted in FIG. 6B includes two anterior chamfer bone cuts and two posterior chamfer bone cuts, in addition to anterior, posterior and distal bone cuts.

Any one or more bone cuts can include one or more facets. For example, the implant components exemplified in FIG. 6A and FIG. 6B depict corresponding condylar facets for each of the distal bone cut, posterior bone cut, first posterior chamfer bone cut and second posterior chamfer bone cut. In FIG. 6A, distal bone cut facets on lateral and medial condyles are identified by 604 and 606, respectively. Facets of a bone cut can be separated by a space between corresponding regions of an implant component, as exemplified by the condylar facets separated by the intercondylar space 608 in FIG. 6A and FIG. 6B. Alternatively or in addition, facets of a bone cut can be separated by a step cut, for example, a vertical or angled cut connecting two non-coplanar or non facets of a bone cut. As shown by the implant components exemplified in each of FIG. 6A and FIG. 6B, each bone cut and/or bone cut facet can be substantially planar. Two substantially planar facets of the same bone cut can be non-coplanar (i.e., not lying in the same cut plane) and/or non-parallel (i.e., not lying in the same cut plane and not lying in a substantially parallel cut plane).

Figure 6C:
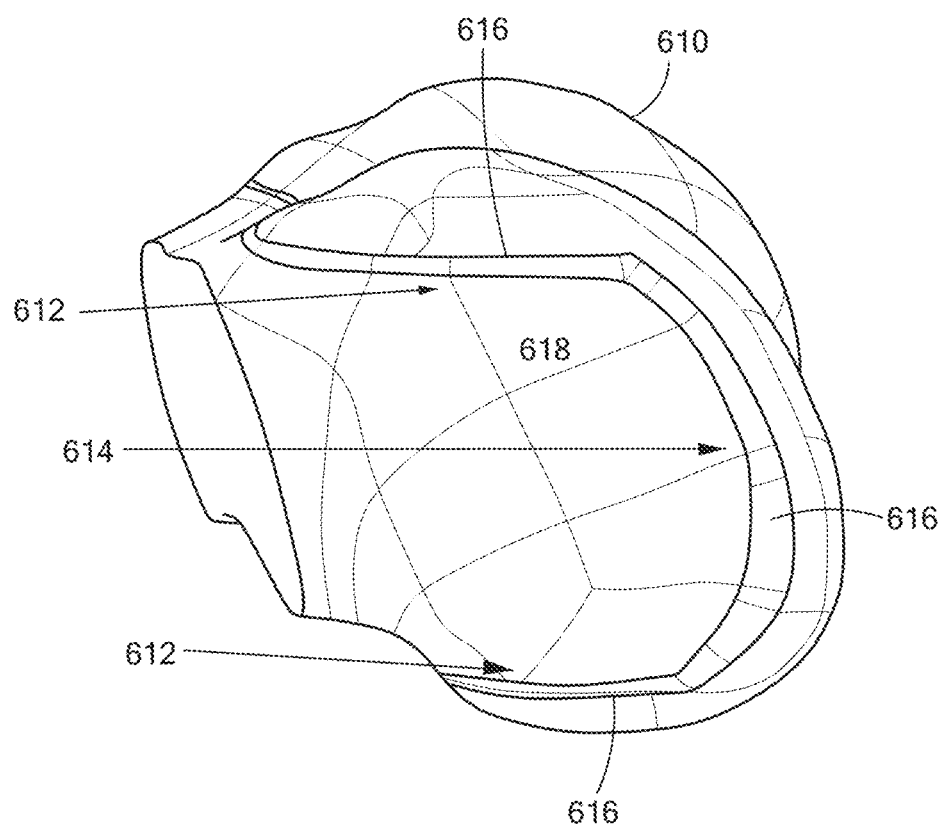

In certain embodiments, one or more bone cut facets, bone cuts, and/or the entire bone-facing surface of an implant can be non-planar, for example, substantially curvilinear. FIG. 6C illustrates a femoral implant component 610 having two planar bone cuts 612 and one curvilinear bone cut 614. In the figure, the femoral implant component 610 is shown attached to resected surfaces 616 of a femur 618.

In certain embodiments, corresponding sections of an implant component can include different thicknesses (i.e., distance between the component's bone-facing surface and joint-facing surface), surface features, bone cut features, section volumes, and/or other features. For example, as shown in FIG. 6A, the corresponding distal lateral and medial sections of the implant, identified by 604 and 606 on their respective bone cut facets, include different thicknesses, section volumes, bone cut angles, and bone cut surface areas. As this example illustrates, one or more of the thicknesses, section volumes, bone cut angles, bone cut surface areas, bone cut curvatures, numbers of bone cuts, peg placements, peg angles, and other features may vary between two or more sections (e.g., corresponding sections on lateral and medial condyles) of an implant component. Alternatively or in addition, one, more, or all of these features can be the same in corresponding sections of an implant component. An implant design that allows for independent features on different sections of an implant allows various options for achieving one or more goals, including, for example, (1) deformity correction and limb alignment (2) preserving bone, cartilage, and/or ligaments, (3) preserving and/or optimizing other features of the patient's anatomy, such as trochlea and trochlear shape, (4) restoring and/or optimizing joint kinematics or biomechanics, and/or (5) restoring and/or optimizing joint-line location and/or joint gap width.

In certain embodiments, it can be advantageous to maintain certain features across different portions of an implant component, while varying certain other features. For example, two or more corresponding sections of an implant component can include the same implant thickness(es). As a specific example, with a femoral implant component, corresponding medial and lateral sections of the implant's condyles (e.g., distal medial and lateral condyle and/or posterior medial and lateral condyles) can be designed to include the same thickness or at least a threshold thickness, particularly the bone cut intersections. Alternatively or in addition, every section on the medial and lateral condyles can be designed to include the same thickness or at least a threshold thickness. This approach is particularly useful when the corresponding implant sections are exposed to similar stress forces and therefore require similar minimum thicknesses in response to those stresses. Alternatively or in addition, an implant design can include a rule, such that a quantifiable feature of one section is always greater than, greater than or equal to, less than, or less than or equal to the same feature of another section of the implant component. For example, in certain embodiments, an implant design can include a lateral distal and/or posterior condylar portion that is thicker than or equal in thickness to the corresponding medial distal and/or posterior condylar portion. Similarly, in certain embodiments, an implant design can include a lateral distal posterior condyle height that is higher than or equal to the corresponding medial posterior condyle height.

In certain embodiments, one or more of an implant component's bone cut or bone cut facet features (e.g., thickness, section volume, cut angle, surface area, and/or other features) can be patient-adapted. For example, as described more fully below, patient-specific data, such as imaging data of a patient's joint, can be used to select and/or design an implant component (and, optionally, a corresponding surgical procedure and/or surgical tool) that matches a patient's anatomy and/or optimizes a parameter of that patient's anatomy. Alternatively or in addition, one or more aspects of an implant component, for example, one or more bone cuts, can be selected and/or designed to match predetermined resection cuts. Predetermined as used herein includes, for example, preoperatively determined (e.g., preoperatively selected and/or designed). For example, predetermined resection cuts can include resection cuts determined preoperatively, optionally as part of the selection and/or design of one or more implant components and/or one or more guide tools. Similarly, a surgical guide tool can be selected and/or designed to guide the predetermined resection cuts. For example, the resection cuts and matching component bone cuts (and, optionally, a guide tool) can be selected and/or designed, for example, to remove diseased or malformed tissue and/or to optimize a desired anatomical and/or kinematic parameter, such as maximizing bone preservation, correcting a joint and/or alignment deformity, enhancing joint kinematics, enhancing or preserving joint-line location, and/or other parameter(s) described herein.

2.2 Joint-Facing Surface of an Implant Component

In various embodiments described herein, the outer, joint-facing surface of an implant component includes one or more patient-adapted (e.g., patient-specific and/or patient-engineered features). For example, in certain embodiments, the joint-facing surface of an implant component can be designed to match the shape of the patient's biological structure. The joint-facing surface can include, for example, the bearing surface portion of the implant component that engages an opposing biological structure or implant component in the joint to facilitate typical movement of the joint. The patient's biological structure can include, for example, cartilage, bone, and/or one or more other biological structures.

For example, in certain embodiments, the joint-facing surface of an implant component is designed to match the shape of the patient's articular cartilage. For example, the joint-facing surface can substantially positively-match one or more features of the patient's existing cartilage surface and/or healthy cartilage surface and/or a calculated cartilage surface, on the articular surface that the component replaces. Alternatively, it can substantially negatively-match one or more features of the patient's existing cartilage surface and/or healthy cartilage surface and/or a calculated cartilage surface, on the opposing articular surface in the joint. As described below, corrections can be performed to the shape of diseased cartilage by designing surgical steps (and, optionally, patient-adapted surgical tools) to re-establish a normal or near normal cartilage shape that can then be incorporated into the shape of the joint-facing surface of the component. These corrections can be implemented and, optionally, tested in virtual two-dimensional and three-dimensional models. The corrections and testing can include kinematic analysis and/or surgical steps.

In certain embodiments, the joint-facing surface of an implant component can be designed to positively-match the shape of subchondral bone. For example, the joint-facing surface of an implant component can substantially positively-match one or more features of the patient's existing subchondral bone surface and/or healthy subchondral bone surface and/or a calculated subchondral bone surface, on the articular surface that the component attaches to on its bone-facing surface. Alternatively, it can substantially negatively-match one or more features of the patient's existing subchondral bone surface and/or healthy subchondral bone surface and/or a calculated subchondral bone surface, on the opposing articular surface in the joint. Corrections can be performed to the shape of subchondral bone to re-establish a normal or near normal articular shape that can be incorporated into the shape of the component's joint-facing surface. A standard thickness can be added to the joint-facing surface, for example, to reflect an average cartilage thickness. Alternatively, a variable thickness can be applied to the component. The variable thickness can be selected to reflect a patient's actual or healthy cartilage thickness, for example, as measured in the individual patient or selected from a standard reference database.

In certain embodiments, the joint-facing surface of an implant component can include one or more standard features. The standard shape of the joint-facing surface of the component can reflect, at least in part, the shape of typical healthy subchondral bone or cartilage. For example, the joint-facing surface of an implant component can include a curvature having standard radii or curvature of in one or more directions. Alternatively or in addition, an implant component can have a standard thickness or a standard minimum thickness in select areas. Standard thickness(es) can be added to one or more sections of the joint-facing surface of the component or, alternatively, a variable thickness can be applied to the implant component.

Certain embodiments, such as those illustrated by FIGS. 5B and 5C, include, in addition to a first implant component, a second implant component having an opposing joint-facing surface. The second implant component's bone-facing surface and/or joint-facing surface can be designed as described above. Moreover, in certain embodiments, the joint-facing surface of the second component can be designed, at least in part, to match (e.g., substantially negatively-match) the joint-facing surface of the first component. Designing the joint-facing surface of the second component to complement the joint-facing surface of the first component can help reduce implant wear and optimize kinematics. Thus, in certain embodiments, the joint-facing surfaces of the first and second implant components can include features that do not match the patient's existing anatomy, but instead negatively-match or nearly negatively-match the joint-facing surface of the opposing implant component.

However, when a first implant component's joint-facing surface includes a feature adapted to a patient's biological feature, a second implant component having a feature designed to match that feature of the first implant component also is adapted to the patient's same biological feature. By way of illustration, when a joint-facing surface of a first component is adapted to a portion of the patient's cartilage shape, the opposing joint-facing surface of the second component designed to match that feature of the first implant component also is adapted to the patient's cartilage shape. When the joint-facing surface of the first component is adapted to a portion of a patient's subchondral bone shape, the opposing joint-facing surface of the second component designed to match that feature of the first implant component also is adapted to the patient's subchondral bone shape. When the joint-facing surface of the first component is adapted to a portion of a patient's cortical bone, the joint-facing surface of the second component designed to match that feature of the first implant component also is adapted to the patient's cortical bone shape. When the joint-facing surface of the first component is adapted to a portion of a patient's endosteal bone shape, the opposing joint-facing surface of the second component designed to match that feature of the first implant component also is adapted to the patient's endosteal bone shape. When the joint-facing surface of the first component is adapted to a portion of a patient's bone marrow shape, the opposing joint-facing surface of the second component designed to match that feature of the first implant component also is adapted to the patient's bone marrow shape.

The opposing joint-facing surface of a second component can substantially negatively-match the joint-facing surface of the first component in one plane or dimension, in two planes or dimensions, in three planes or dimensions, or in several planes or dimensions. For example, the opposing joint-facing surface of the second component can substantially negatively-match the joint-facing surface of the first component in the coronal plane only, in the sagittal plane only, or in both the coronal and sagittal planes.

In creating a substantially negatively-matching contour on an opposing joint-facing surface of a second component, geometric considerations can improve wear between the first and second components. For example, the radii of a concave curvature on the opposing joint-facing surface of the second component can be selected to match or to be slightly larger in one or more dimensions than the radii of a convex curvature on the joint-facing surface of the first component. Similarly, the radii of a convex curvature on the opposing joint-facing surface of the second component can be selected to match or to be slightly smaller in one or more dimensions than the radii of a concave curvature on the joint-facing surface of the first component. In this way, contact surface area can be maximized between articulating convex and concave curvatures on the respective surfaces of first and second implant components.

The bone-facing surface of the second component can be designed to negatively-match, at least in part, the shape of articular cartilage, subchondral bone, cortical bone, endosteal bone or bone marrow (e.g., surface contour, angle, or perimeter shape of a resected or native biological structure). It can have any of the features described above for the bone-facing surface of the first component, such as having one or more patient-adapted bone cuts to match one or more predetermined resection cuts.

Many combinations of first component and second component bone-facing surfaces and joint-facing surfaces are possible. Table 3 provides illustrative combinations that may be employed.

TABLE 3

Illustrative Combinations of Implant Components

| $1^{st}$ component bone-facing surface | $1^{st}$ component joint-facing surface | $1^{st}$ component bone cut(s) | $2^{nd}$ component joint facing surface | $2^{nd}$ component bone facing surface | $2^{nd}$ component bone cuts |
|---|---|---|---|---|---|
| Example: Femur | Example: Femur | Example: Femur | Example: Tibia | Example: Tibia | Example: Tibia |

TABLE 3-continued

Illustrative Combinations of Implant Components

| 1st component bone-facing surface | 1st component joint-facing surface | 1st component bone cut(s) | 2nd component joint facing surface | 2nd component bone facing surface | 2nd component bone cuts |
|---|---|---|---|---|---|
| At least one bone cut | Cartilage | Yes | Negative-match of 1st component joint-facing (opposing cartilage) | At least one bone cut | Yes |
| At least one bone cut | Cartilage | Yes | Negative-match of 1st component joint-facing (opposing cartilage) | Subchondral bone | Optional |
| At least one bone cut | Cartilage | Yes | Negative-match of 1st component joint-facing (opposing cartilage) | Cartilage (same side, e.g. tibia) | Optional |
| At least one bone cut | Subchondral bone | Yes | Negative-match of 1st component joint-facing (opposing subchondral bone) | At least one bone cut | Yes |
| At least one bone cut | Subchondral bone | Yes | Negative-match of 1st component joint-facing (opposing subchondral bone) | Subchondral bone | Optional |
| At least one bone cut | Subchondral bone | Yes | Negative-match of 1st component joint-facing (opposing subchondral bone) | Cartilage (same side, e.g. tibia) | Optional |
| Subchondral bone | Cartilage | Optional | Negative-match of 1st component joint-facing (opposing cartilage) | At least one bone cut | Yes |
| Subchondral bone | Cartilage | Optional | Negative-match of 1st component joint-facing (opposing cartilage) | Subchondral bone | Optional |
| Subchondral bone | Cartilage | Optional | Negative-match of 1st component joint-facing (opposing cartilage) | Cartilage (same side, e.g. tibia) | Optional |
| Subchondral bone | Subchondral bone | Optional | Negative-match of 1st component joint-facing (opposing subchondral bone) | At least one bone cut | Yes |
| Subchondral bone | Subchondral bone | Optional | Negative-match of 1st component joint-facing (opposing subchondral bone) | Subchondral bone | Optional |
| Subchondral bone | Subchondral bone | Optional | Negative-match of 1st component joint-facing (opposing subchondral bone) | Cartilage (same side, e.g. tibia) | Optional |
| Subchondral bone | Standard/ Model | Optional | Negative-match of 1st component joint-facing standard | At least one bone cut | Yes |
| Subchondral bone | Standard/ Model | Optional | Negative-match of 1st component joint-facing standard | Subchondral bone | Optional |
| Subchondral bone | Standard/ Model | Optional | Negative-match of 1st component joint-facing standard | Cartilage (same side, e.g. tibia) | Optional |
| Subchondral bone | Subchondral bone | Optional | Non-matching standard surface | At least one bone cut | Yes |
| Subchondral bone | Cartilage | Optional | Non-matching standard surface | At least one bone cut | Yes |

2.3 Multi-Component Implants and Implant Systems

Figure 7A:
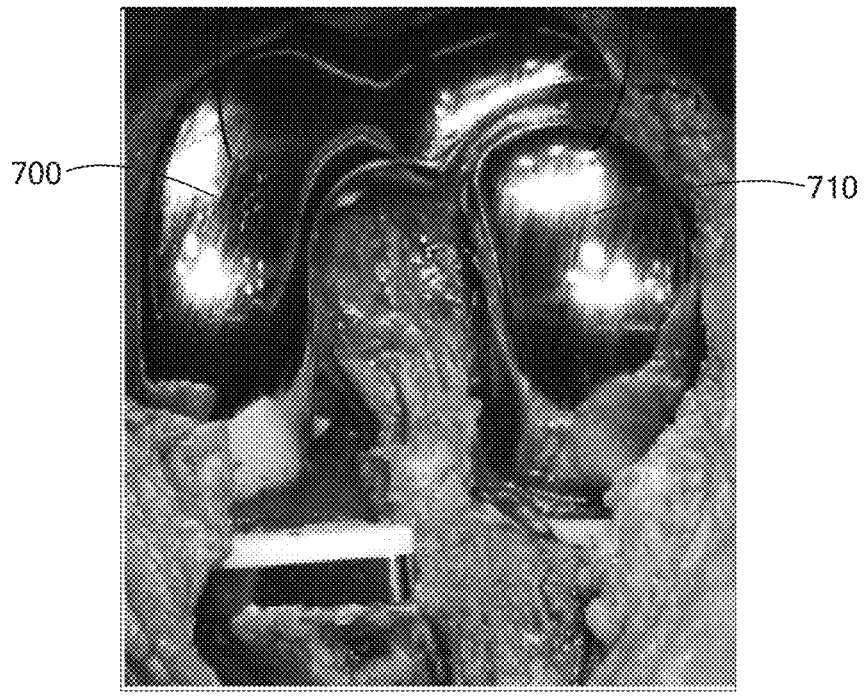
FIG. 7A is a photograph showing an exemplary knee replacement using a patient-specific bicompartmental device and a patient-specific unicompartmental device.
Figures 7B, 7C:
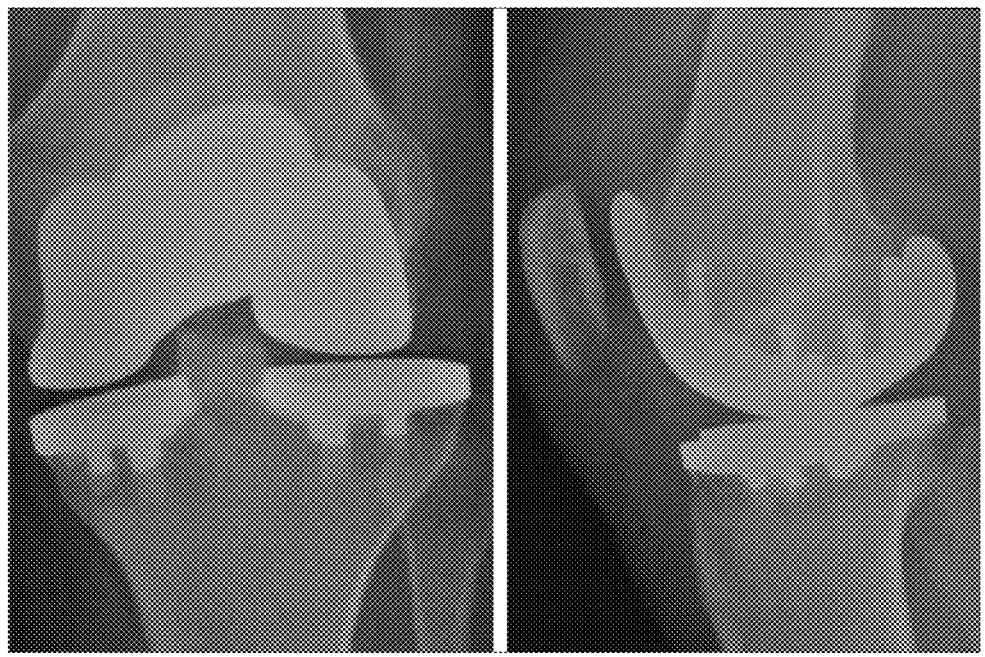
FIGS. 7B and 7C are x-ray images showing the device of FIG. 7A in the coronal plane and in the sagittal plane, respectively.

The implants and implant systems described herein include any number of patient-adapted implant components and any number of non-patient-adapted implant components. An illustrative implant or implant system is depicted in FIGS. 7A-7C. Specifically, FIG. 7A shows a photograph of a patient-adapted knee replacement implant system that includes a patient-specific bicompartmental implant component 700 and patient-specific unicompartmental implant component 710. Both components are patient-specific on both their bone-facing surfaces and on their joint-facing surfaces. FIGS. 7B and 7C show x-ray images showing the implant of FIG. 7A in the coronal plane (FIG. 7B) and the sagittal plane (FIG. 7C).

In certain embodiments, the implants and implant systems described herein can include a combination of implant components, such as a traditional unicompartmental device with a patient-specific bicompartmental device or a combination of a patient-specific unicompartmental device with standard bicompartmental device. Such implant combinations allow for a flexible design of an implant or implant system that includes both standard and patient-specific features and components. This flexibility and level of patient-specificity allows for various engineered optimizations, such as retention of alignments, maximization of bone preservation, and/or restoration of normal or near-normal patient kinematics.

In certain embodiments, an implant component is designed and installed as one or more pieces. For example, FIGS. 8A-8E illustrates a femoral implant component that can be installed in two pieces.

Embodiments described herein can be applied to partial or total joint replacement systems. Bone cuts or changes to an implant component dimension described herein can be applied to a portion of the dimension, or to the entire dimension.

3. Collecting and Modeling Patient-Specific Data

As mentioned above, certain embodiments include implant components designed and made using patient-specific data that is collected preoperatively. The patient-specific data can include points, surfaces, and/or landmarks, collectively referred to herein as "reference points." In certain embodiments, the reference points can be selected and used to derive a varied or altered surface, such as, without limitation, an ideal surface or structure. For example, the reference points can be used to create a model of the patient's relevant biological feature(s) and/or one or more patient-adapted surgical steps, tools, and implant components. For example the reference points can be used to design a patient-adapted implant component having at least one patient-specific or patient-engineered feature, such as a surface, dimension, or other feature.

Sets of reference points can be grouped to form reference structures used to create a model of a joint and/or an implant design. Designed implant surfaces can be derived from single reference points, triangles, polygons, or more complex surfaces, such as parametric or subdivision surfaces, or models of joint material, such as, for example, articular cartilage, subchondral bone, cortical bone, endosteal bone or bone marrow. Various reference points and reference structures can be selected and manipulated to derive a varied or altered surface, such as, without limitation, an ideal surface or structure.

The reference points can be located on or in the joint that will receive the patient-specific implant. For example, the reference points can include weight-bearing surfaces or locations in or on the joint, a cortex in the joint, and/or an endosteal surface of the joint. The reference points also can include surfaces or locations outside of but related to the joint. Specifically, reference points can include surfaces or locations functionally related to the joint. For example, in embodiments directed to the knee joint, reference points can include one or more locations ranging from the hip down to the ankle or foot. The reference points also can include surfaces or locations homologous to the joint receiving the implant. For example, in embodiments directed to a knee, a hip, or a shoulder joint, reference points can include one or more surfaces or locations from the contralateral knee, hip, or shoulder joint.

3.1 Measuring Biological Features

Reference points and/or data for obtaining measurements of a patient's joint, for example, relative-position measurements, length or distance measurements, curvature measurements, surface contour measurements, thickness measurements (in one location or across a surface), volume measurements (filled or empty volume), density measurements, and other measurements, can be obtained using any suitable technique. For example, one dimensional, two-dimensional, and/or three-dimensional measurements can be obtained using data collected from mechanical means, laser devices, electromagnetic or optical tracking systems, molds, materials applied to the articular surface that harden as a negative match of the surface contour, and/or one or more imaging techniques described above and/or known in the art. Data and measurements can be obtained non-invasively and/or preoperatively. Alternatively, measurements can be obtained intraoperatively, for example, using a probe or other surgical device during surgery.

In certain embodiments, an imaging data collected from the patient, for example, imaging data from one or more of x-ray imaging, digital tomosynthesis, cone beam CT, non-spiral or spiral CT, non-isotropic or isotropic MRI, SPECT, PET, ultrasound, laser imaging, photo-acoustic imaging, is used to qualitatively and/or quantitatively measure one or more of a patient's biological features, one or more of normal cartilage, diseased cartilage, a cartilage defect, an area of denuded cartilage, subchondral bone, cortical bone, endosteal bone, bone marrow, a ligament, a ligament attachment or origin, menisci, labrum, a joint capsule, articular structures, and/or voids or spaces between or within any of these structures. The qualitatively and/or quantitatively measured biological features can include, but are not limited to, one or more of length, width, height, depth and/or thickness; curvature, for example, curvature in two dimensions (e.g., curvature in or projected onto a plane), curvature in three dimensions, and/or a radius or radii of curvature; shape, for example, two-dimensional shape or three-dimensional shape; area, for example, surface area and/or surface contour; perimeter shape; and/or volume of, for example, the patient's cartilage, bone (subchondral bone, cortical bone, endosteal bone, and/or other bone), ligament, and/or voids or spaces between them.

In certain embodiments, measurements of biological features can include any one or more of the illustrative measurements identified in Table 4.

TABLE 4

Exemplary patient-specific measurements of biological features that can be used in the creation of a model and/or in the selection and/or design of an implant component

| Anatomical feature | Exemplary measurement |
| --- | --- |
| Joint-line, joint gap | Location relative to proximal reference point |
|  | Location relative to distal reference point |
|  | Angle |
|  | Gap distance between opposing surfaces in one or more locations |
|  | Location, angle, and/or distance relative to contralateral joint |

TABLE 4-continued

Exemplary patient-specific measurements of biological features that can be used in the creation of a model and/or in the selection and/or design of an implant component

| Anatomical feature | Exemplary measurement |
| --- | --- |
| Soft tissue tension and/or balance | Joint gap distance |
| | Joint gap differential, e.g., medial to lateral |
| Medullary cavity | Shape in one or more dimensions |
| | Shape in one or more locations |
| | Diameter of cavity |
| | Volume of cavity |
| Subchondral bone | Shape in one or more dimensions |
| | Shape in one or more locations |
| | Thickness in one or more dimensions |
| | Thickness in one or more locations |
| | Angle, e.g., resection cut angle |
| Cortical bone | Shape in one or more dimensions |
| | Shape in one or more locations |
| | Thickness in one or more dimensions |
| | Thickness in one or more locations |
| | Angle, e.g., resection cut angle |
| Endosteal bone | Shape in one or more dimensions |
| | Shape in one or more locations |
| | Thickness in one or more dimensions |
| | Thickness in one or more locations |
| | Angle, e.g., resection cut angle |
| Cartilage | Shape in one or more dimensions |
| | Shape in one or more locations |
| | Thickness in one or more dimensions |
| | Thickness in one or more locations |
| | Angle, e.g., resection cut angle |
| Intercondylar notch | Shape in one or more dimensions |
| | Location |
| | Height in one or more locations |
| | Width in one or more locations |
| | Depth in one or more locations |
| | Angle, e.g., resection cut angle |
| Medial condyle | 2D and/or 3D shape of a portion or all |
| | Height in one or more locations |
| | Length in one or more locations |
| | Width in one or more locations |
| | Depth in one or more locations |
| | Thickness in one or more locations |
| | Curvature in one or more locations |
| | Slope in one or more locations and/or directions |
| | Angle, e.g., resection cut angle |
| Lateral condyle | 2D and/or 3D shape of a portion or all |
| | Height in one or more locations |
| | Length in one or more locations |
| | Width in one or more locations |
| | Depth in one or more locations |
| | Thickness in one or more locations |
| | Curvature in one or more locations |
| | Slope in one or more locations and/or directions |
| | Angle, e.g., resection cut angle |
| Trochlea | 2D and/or 3D shape of a portion or all |
| | Height in one or more locations |
| | Length in one or more locations |
| | Width in one or more locations |
| | Depth in one or more locations |
| | Thickness in one or more locations |
| | Curvature in one or more locations |
| | Slope in one or more locations and/or directions |
| | Angle, e.g., resection cut angle |
| Medial trochlea | 2D and/or 3D shape of a portion or all |
| | Height in one or more locations |
| | Length in one or more locations |
| | Width in one or more locations |
| | Depth in one or more locations |
| | Thickness in one or more locations |
| | Curvature in one or more locations |
| | Slope in one or more locations and/or directions |
| | Angle, e.g., resection cut angle |
| Central trochlea | 2D and/or 3D shape of a portion or all |
| | Height in one or more locations |
| | Length in one or more locations |
| | Width in one or more locations |
| | Depth in one or more locations |
| | Thickness in one or more locations |

TABLE 4-continued

Exemplary patient-specific measurements of biological features
that can be used in the creation of a model and/or in the selection
and/or design of an implant component

| Anatomical feature | Exemplary measurement |
|---|---|
| Lateral trochlea | Curvature in one or more locations<br>Slope in one or more locations and/or directions<br>Angle, e.g., resection cut angle<br>2D and/or 3D shape of a portion or all<br>Height in one or more locations<br>Length in one or more locations<br>Width in one or more locations<br>Depth in one or more locations<br>Thickness in one or more locations<br>Curvature in one or more locations<br>Slope in one or more locations and/or directions<br>Angle, e.g., resection cut angle |
| Entire tibia | 2D and/or 3D shape of a portion or all<br>Height in one or more locations<br>Length in one or more locations<br>Width in one or more locations<br>Depth in one or more locations<br>Thickness in one or more locations<br>Curvature in one or more locations<br>Slope in one or more locations and/or directions<br>Angle, e.g., resection cut angle<br>Axes, e.g., A-P and/or M-L axes<br>Osteophytes<br>Plateau slope(s), e.g., relative slopes medial and lateral<br>Plateau heights(s), e.g., relative heights medial and lateral<br>Bearing surface radii, e.g., e.g., relative radii medial and lateral<br>Perimeter profile |
| Medial tibia | 2D and/or 3D shape of a portion or all<br>Height in one or more locations<br>Length in one or more locations<br>Width in one or more locations<br>Depth in one or more locations<br>Thickness or height in one or more locations<br>Curvature in one or more locations<br>Slope in one or more locations and/or directions<br>Angle, e.g., resection cut angle<br>Perimeter profile |
| Lateral tibia | 2D and/or 3D shape of a portion or all<br>Height in one or more locations<br>Length in one or more locations<br>Width in one or more locations<br>Depth in one or more locations<br>Thickness/height in one or more locations<br>Curvature in one or more locations<br>Slope in one or more locations and/or directions<br>Angle, e.g., resection cut angle<br>Perimeter profile |
| Entire patella | 2D and/or 3D shape of a portion or all<br>Height in one or more locations<br>Length in one or more locations<br>Width in one or more locations<br>Depth in one or more locations<br>Thickness in one or more locations<br>Curvature in one or more locations<br>Slope in one or more locations and/or directions<br>Perimeter profile<br>Angle, e.g., resection cut angle |
| Medial patella | 2D and/or 3D shape of a portion or all<br>Height in one or more locations<br>Length in one or more locations<br>Width in one or more locations<br>Depth in one or more locations<br>Thickness in one or more locations<br>Curvature in one or more locations<br>Slope in one or more locations and/or directions<br>Angle, e.g., resection cut angle |
| Central patella | 2D and/or 3D shape of a portion or all<br>Height in one or more locations<br>Length in one or more locations<br>Width in one or more locations<br>Depth in one or more locations<br>Thickness in one or more locations<br>Curvature in one or more locations |

TABLE 4-continued

Exemplary patient-specific measurements of biological features that can be used in the creation of a model and/or in the selection and/or design of an implant component

| Anatomical feature | Exemplary measurement |
|---|---|
| Lateral patella | Slope in one or more locations and/or directions<br>Angle, e.g., resection cut angle<br>2D and/or 3D shape of a portion or all<br>Height in one or more locations<br>Length in one or more locations<br>Width in one or more locations<br>Depth in one or more locations<br>Thickness in one or more locations<br>Curvature in one or more locations |
| Femoral head | Slope in one or more locations and/or directions<br>Angle, e.g., resection cut angle<br>2D and/or 3D shape of a portion or all<br>Height in one or more locations<br>Length in one or more locations<br>Width in one or more locations<br>Depth in one or more locations<br>Thickness in one or more locations<br>Curvature in one or more locations |
| Acetabulum | Slope in one or more locations and/or directions<br>Angle, e.g., resection cut angle<br>2D and/or 3D shape of a portion or all<br>Height in one or more locations<br>Length in one or more locations<br>Width in one or more locations<br>Depth in one or more locations<br>Thickness in one or more locations<br>Curvature in one or more locations |
| Glenoid | Slope in one or more locations and/or directions<br>Angle, e.g., resection cut angle<br>2D and/or 3D shape of a portion or all<br>Height in one or more locations<br>Length in one or more locations<br>Width in one or more locations<br>Depth in one or more locations<br>Thickness in one or more locations<br>Curvature in one or more locations |
| Humeral head | Slope in one or more locations and/or directions<br>Angle, e.g., resection cut angle<br>2D and/or 3D shape of a portion or all<br>Height in one or more locations<br>Length in one or more locations<br>Width in one or more locations<br>Depth in one or more locations<br>Thickness in one or more locations<br>Curvature in one or more locations |
| Ankle joint | Slope in one or more locations and/or directions<br>Angle, e.g., resection cut angle<br>2D and/or 3D shape of a portion or all<br>Height in one or more locations<br>Length in one or more locations<br>Width in one or more locations<br>Depth in one or more locations<br>Thickness in one or more locations<br>Curvature in one or more locations |
| Elbow | Slope in one or more locations and/or directions<br>Angle, e.g., resection cut angle<br>2D and/or 3D shape of a portion or all<br>Height in one or more locations<br>Length in one or more locations<br>Width in one or more locations<br>Depth in one or more locations<br>Thickness in one or more locations<br>Curvature in one or more locations |
| Wrist | Slope in one or more locations and/or directions<br>Angle, e.g., resection cut angle<br>2D and/or 3D shape of a portion or all<br>Height in one or more locations<br>Length in one or more locations<br>Width in one or more locations<br>Depth in one or more locations<br>Thickness in one or more locations<br>Curvature in one or more locations<br>Slope in one or more locations and/or directions<br>Angle, e.g., resection cut angle |

TABLE 4-continued

Exemplary patient-specific measurements of biological features that can be used in the creation of a model and/or in the selection and/or design of an implant component

| Anatomical feature | Exemplary measurement |
|---|---|
| Hand | 2D and/or 3D shape of a portion or all |
| | Height in one or more locations |
| | Length in one or more locations |
| | Width in one or more locations |
| | Depth in one or more locations |
| | Thickness in one or more locations |
| | Curvature in one or more locations |
| | Slope in one or more locations and/or directions |
| | Angle, e.g., resection cut angle |
| Finger | 2D and/or 3D shape of a portion or all |
| | Height in one or more locations |
| | Length in one or more locations |
| | Width in one or more locations |
| | Depth in one or more locations |
| | Thickness in one or more locations |
| | Curvature in one or more locations |
| | Slope in one or more locations and/or directions |
| | Angle |
| Spine | 2D and/or 3D shape of a portion or all |
| | Height in one or more locations |
| | Length in one or more locations |
| | Width in one or more locations |
| | Depth in one or more locations |
| | Thickness in one or more locations |
| | Curvature in one or more locations |
| | Slope in one or more locations and/or directions |
| | Angle, e.g., resection cut angle |
| Spinal facet joint | 2D and/or 3D shape of a portion or all |
| | Height in one or more locations |
| | Length in one or more locations |
| | Width in one or more locations |
| | Depth in one or more locations |
| | Thickness in one or more locations |
| | Curvature in one or more locations |
| | Slope in one or more locations and/or directions |
| | Angle, e.g., resection cut angle |

Depending on the clinical application, a single or any combination or all of the measurements described in Table 4 and/or known in the art can be used. Additional patient-specific measurements and information that be used in the evaluation can include, for example, joint kinematic measurements, bone density measurements, bone porosity measurements, identification of damaged or deformed tissues or structures, and patient information, such as patient age, weight, gender, ethnicity, activity level, and overall health status.

The patient-specific measurements selected for the evaluation then can be used to select (e.g., from a library), to design, or to select and design an implant component having one or more measurements corresponding to or derived from the one or more of the assessed patient-specific measurements. For example, the implant component can include one or more patient-specific measurements and/or one or more patient-engineered measurements. Optionally, one or more patient-specific models, one or more patient-adapted surgical steps, and/or one or more patient-adapted surgical guide tools also can be selected and/or designed to include one or more measurements corresponding to or derived from the one or more of these patient-specific measurements.

3.2 Generating a Model of a Joint

In certain embodiments, one or more models of at least a portion of a patient's joint can be generated. Specifically, the patient-specific data and/or measurements described above can be used to generate a model that includes at least a portion of the patient's joint. Optionally, one or more patient-engineered resection cuts, one or more drill holes, one or more patient-adapted guide tools, and/or one or more patient-adapted implant components can be included in a model. In certain embodiments, a model of at least part of a patient's joint can be used to directly generate a patient-engineered resection cut strategy, a patient-adapted guide tool design, and/or a patient-adapted implant component design for a surgical procedure (i.e., without the model itself including one or more resection cuts, one or more drill holes, one or more guide tools, and/or one or more implant components). In certain embodiments, the model that includes at least a portion of the patient's joint also can include or display, as part of the model, one or more resection cuts, one or more drill holes, (e.g., on a model of the patient's femur), one or more guide tools, and/or one or more implant components that have been designed for the particular patient using the model. Moreover, one or more resection cuts, one or more drill holes, one or more guide tools, and/or one or more implant components can be modeled and selected and/or designed separate from a model of a particular patient's biological feature.

Figure 9:
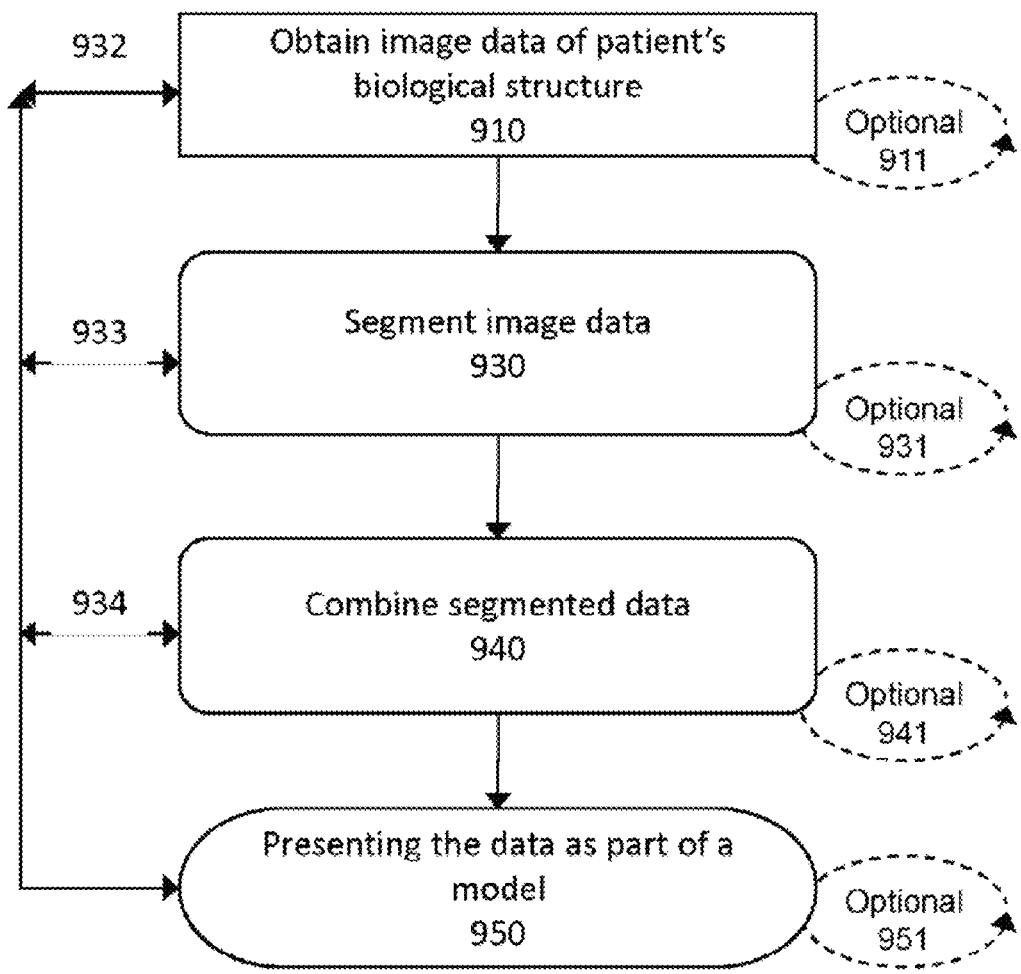
FIG. 9 is a flow chart illustrating a process for generating a model of a patient's joint (and/or a resection cut, guide tool, and/or implant component)

Various methods can be used to generate a model. As illustrated in FIG. 9A, in certain embodiments the method of generating a model of a patient's joint (and/or a resection cut, drill hole, guide tool, and/or implant component) can include one or more of the steps of obtaining image data of a patient's biological structure 910; segmenting the image data 930; combining the segmented data 940; and presenting the data as part of a model 950.

Image data can be obtained 910 from near or within the patient's biological structure of interest. For example, pixel or voxel data from one or more radiographic or tomographic images of a patient's joint can be obtained, for example, using computed or magnetic resonance tomography. In this or a subsequent step, one or more of the pixels or voxels can be converted into one or a set of values. For example, a single pixel/voxel or a group of pixel/voxels can be converted to coordinate values, e.g., a point in a 2D or 3D coordinate system. The set of values also can include a value corresponding to the pixel/voxel intensity or relative grayscale color. Moreover, the set of values can include information about neighboring pixels or voxels, for example, information corresponding to relative intensity or grayscale color and or information corresponding to relative position.

Then, the image data can be segmented 930 to identify those data corresponding to a particular biological feature of interest. Optionally, the segmented data can be combined. For example, in a single image segmented and selected reference points (e.g., derived from pixels or voxels) and/or other data can be combined to create a line representing the surface outline of a biological structure. Moreover, the segmented and selected data from multiple images can be combined to create a 3D representation of the biological structure. Alternatively, the images can be combined to form a 3D data set, from which the 3D representation of the biological structure can be derived directly using a 3D segmentation technique, for example an active surface or active shape model algorithm or other model based or surface fitting algorithm.

Optionally, the 3D representation of the biological structure can be generated or manipulated, for example, smoothed or corrected, for example, by employing a 3D polygon surface, a subdivision surface or parametric surface, for example, a non-uniform rational B-spline (NURBS) surface. For a description of various parametric surface representations see, for example Foley, J. D. et al., Computer Graphics: Principles and Practice in C; Addison-Wesley, 2nd edition, 1995). Various methods are available for creating a parametric surface. For example, the 3D representation can be converted directly into a parametric surface, for example, by connecting data points to create a surface of polygons and applying rules for polygon curvatures, surface curvatures, and other features. Alternatively, a parametric surface can be best-fit to the 3D representation, for example, using publicly available software such as Geomagic® software (Research Triangle Park, N.C.).

Then, the data can be presented as part of a model 950, for example, a patient-specific virtual model that includes the biological feature of interest. Optionally, the data associated with one or more biological features can be transferred to one or more resection cuts, drill holes, guide tools, and/or implant components, which also can be included as part of the same model or in a different model. The virtual model(s) can be used to generate one or more patient-adapted guide tools and/or implant components for surgical use, for example, using computer-aided design (CAD) software and/or one or more of the several manufacturing techniques described below, optionally in conjunction with computer-aided manufacturing (CAM) software.

As will be appreciated by those of skill in the art, one or more of these steps 910, 930, 940, 950 can be repeated 911, 931, 941, 951 as often as desired to achieve the desired result. Moreover, the steps can be repeated reiteratively 932, 933, 934. Moreover, the practitioner can proceed directly 933 from the step of segmenting image data 930 to presenting the data as part of a model 950. Data, models and/or any related guide tools or implant components can be collected in one or more libraries for subsequent use for the same patient or for a different patient (e.g., a different patient with similar data).

3.3 Modeling and Addressing Joint Defects

In certain embodiments, the reference points and/or measurements described above can be processed using mathematical functions to derive virtual, corrected features, which may represent a restored, ideal or desired feature from which a patient-adapted implant component can be designed. For example, one or more features, such as surfaces or dimensions of a biological structure can be modeled, altered, added to, changed, deformed, eliminated, corrected and/or otherwise manipulated (collectively referred to herein as "variation" of an existing surface or structure within the joint).

Variation of the joint or portions of the joint can include, without limitation, variation of one or more external surfaces, internal surfaces, joint-facing surfaces, uncut surfaces, cut surfaces, altered surfaces, and/or partial surfaces as well as osteophytes, subchondral cysts, geodes or areas of eburnation, joint flattening, contour irregularity, and loss of normal shape. The surface or structure can be or reflect any surface or structure in the joint, including, without limitation, bone surfaces, ridges, plateaus, cartilage surfaces, ligament surfaces, or other surfaces or structures. The surface or structure derived can be an approximation of a healthy joint surface or structure or can be another variation. The surface or structure can be made to include pathological alterations of the joint. The surface or structure also can be made whereby the pathological joint changes are virtually removed in whole or in part.

Once one or more reference points, measurements, structures, surfaces, models, or combinations thereof have been selected or derived, the resultant shape can be varied, deformed or corrected. In certain embodiments, the variation can be used to select and/or design an implant component having an ideal or optimized feature or shape, e.g., corresponding to the deformed or corrected joint feature or shape. For example, in one application of this embodiment, the ideal or optimized implant shape reflects the shape of the patient's joint before he or she developed arthritis.

Alternatively or in addition, the variation can be used to select and/or design a patient-adapted surgical procedure to address the deformity or abnormality. For example, the variation can include surgical alterations to the joint, such as virtual resection cuts, virtua; drill holes, virtual removal of osteophytes, and/or virtual building of structural support in the joint deemed necessary or beneficial to a desired final outcome for a patient.

Corrections can be used to address osteophytes, subchondral voids, and other patient-specific defects or abnormalities. In the case of osteophytes, a design for the bone-facing surface of an implant component or guide tool can be selected and/or designed after the osteophyte has been virtually removed. Alternatively, the osteophyte can be integrated into the shape of the bone-facing surface of the implant component or guide tool. FIGS. 10A-10D are exemplary drawings of an end of a femur 1010 having an osteophyte 1020. In the selection and/or design of an implant component for a particular patient, an image or model of the patient's bone that includes the osteophyte can be transformed such that the osteophyte 1020 is virtually removed, as shown in FIG. 10B at removed osteophyte 1030, to produce, as shown in FIG. 10C, an implant component 1040 based on a smooth surface at the end of femur 1010. Alternatively, as shown in FIG. 10D, an implant component 1050 can be selected and/or designed to conform to the shape of the osteophyte 1020. In the case of building additional or improved structure, additional features of the implant component then can be derived after bone-facing surface correction is modeled. Optionally, a surgical strategy and/or one or more guide tools can be selected and/or designed to reflect the correction and correspond to the implant component.

Similarly, to address a subchondral void, a selection and/or design for the bone-facing surface of an implant component can be derived after the void has been virtually removed (e.g., filled). Alternatively, the subchondral void can be integrated into the shape of the bone-facing surface of the implant component. FIGS. 11A-11D are exemplary drawings of an end of a femur 1110 having a subchondral void 1120. During development of an implant, an image or model of the patient's bone that includes the void can be transformed such that the void 1120 is virtually removed, as shown in FIG. 11B at removed void 1130, to produce, as shown in FIG. 11C, an implant component 1140 based on a smooth surface at the end of femur 1110. Alternatively, implant 1110 can be selected and/or designed to conform to the shape of void 1120, as shown in FIG. 11D. Note that, while virtually conforming to void 1120, implant 1150 may not practically be able to be inserted into the void. Therefore, in an certain embodiments, the implant may only partially protrude into a void in the bone. Optionally, a surgical strategy and/or one or more guide tools can be selected and/or designed to reflect the correction and correspond to the implant component.

In addition to osteophytes and subchondral voids, the methods, surgical strategies, guide tools, and implant components described herein can be used to address various other patient-specific joint defects or phenomena. In certain embodiments, correction can include the virtual removal of tissue, for example, to address an articular defect, to remove subchondral cysts, and/or to remove diseased or damaged tissue (e.g., cartilage, bone, or other types of tissue), such as osteochondritic tissue, necrotic tissue, and/or torn tissue. In such embodiments, the correction can include the virtual removal of the tissue (e.g., the tissue corresponding to the defect, cyst, disease, or damage) and the bone-facing surface of the implant component can be derived after the tissue has been virtually removed. In certain embodiments, the implant component can be selected and/or designed to include a thickness or other features that substantially matches the removed tissue and/or optimizes one or more parameters of the joint. Optionally, a surgical strategy and/or one or more guide tools can be selected and/or designed to reflect the correction and correspond to the implant component.

In certain embodiments, a correction can include the virtual addition of tissue or material, for example, to address an articular defect, loss of ligament stability, and/or a bone stock deficiency, such as a flattened articular surface that should be round. In certain embodiments, the additional material may be virtually added (and optionally then added in surgery) using filler materials such as bone cement, bone graft material, and/or other bone fillers. Alternatively or in addition, the additional material may be virtually added as part of the implant component, for example, by using a bone-facing surface and/or component thickness that match the correction or by otherwise integrating the correction into the shape of the implant component. Then, the joint-facing and/or other features of the implant can be derived. This correction can be designed to re-establish a near normal shape for the patient. Alternatively, the correction can be designed to establish a standardized shape or surface for the patient.

In certain embodiments, the patient's abnormal or flattened articular surface can be integrated into the shape of the implant component, for example, the bone-facing surface of the implant component can be designed to substantially negatively-match the abnormal or flattened surface, at least in part, and the thickness of the implant can be designed to establish the patient's healthy or an optimum position of the patient's structure in the joint. Moreover, the joint-facing surface of the implant component also can be designed to re-establish a near normal anatomic shape reflecting, for example, at least in part the shape of normal cartilage or subchondral bone. Alternatively, it can be designed to establish a standardized shape.

In certain embodiments, models can be generated to show defects of interest in a patient's joint. For example, a model or set of models of a patient's joint can be generated showing defects of interest and, optionally, another model or set of models can be generated showing no defects (e.g., as defect and reference, or before and after models). Alternatively, or in addition, the same or additional models can be generated with and/or without resection cuts, guide tools, and/or implant components positioned in the model. Moreover, the same or additional models can be generated to show defects of interest that interfere with one or more resection cuts, guide tools, and/or implant components. Such models, showing defects of interest, resection cuts, guide tools, implant components, and/or interfering defects of interest, can be particularly useful as a reference or guide to a surgeon or clinician prior to and/or during surgery, for example, in identifying proper placement of a guide tool or implant component at one or more steps in a surgery, and/or in identifying features of a patient's anatomy that he or she may want to alter during one or more steps in a surgery. Accordingly, such models that provide, for example, patient-specific renderings of implant assemblies and defects of interest (e.g., osteophyte structures) together with bone models, are useful in aiding surgeons and clinicians in surgery planning and/or during surgery.

In certain embodiments, a model or set of models of a patient's biological structure are obtained and/or generated to show one or more defects of interest, one or more resection cuts, one or more guide tools, one or more implant components, and/or a combination of any of these. For models that include defects of interest, the defects can be categorized and differentiated into various groups and displayed on the model or set of models in any way that conveys the appropriate information to a surgeon or clinician. For example, two or more defects can be differentiated into categories based on defect type, defect location, severity of the defect, potential interference with a guide tool or implant component, and/or any one or more other useful categories.

Figure 12A:
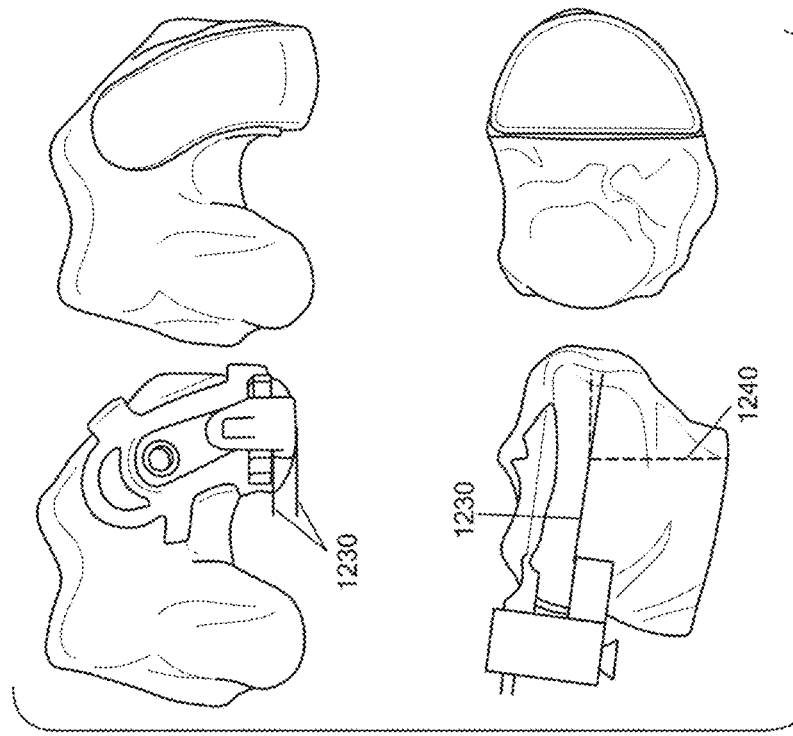
FIGS. 12A and 12B illustrate models for one particular patient receiving a single compartment knee implant and in need of osteophyte removal prior to placement of the implant components.
Figure 12B:
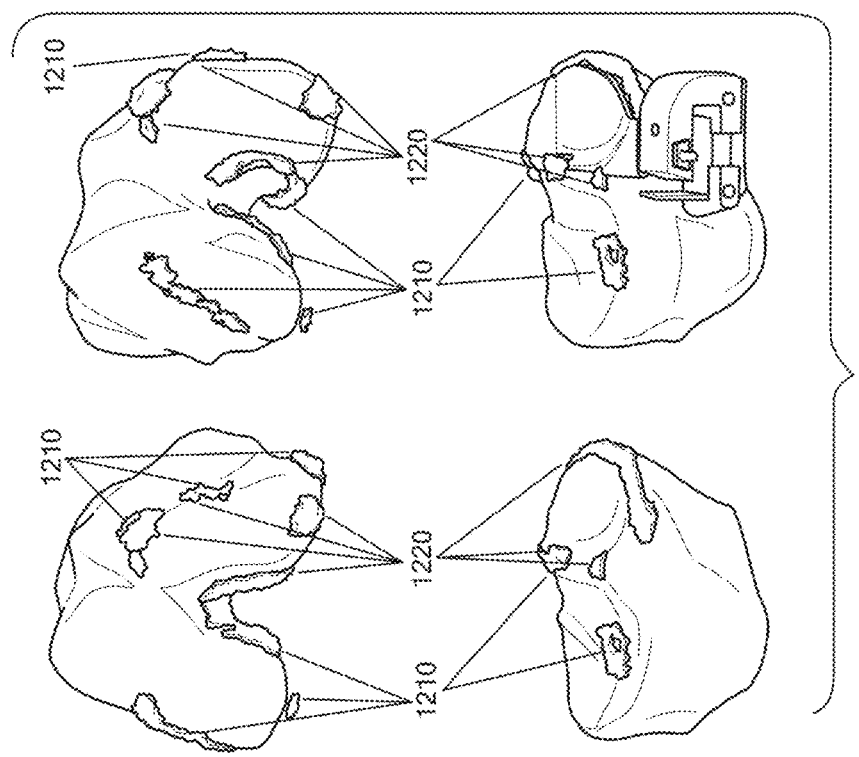

In certain embodiments, one or more additional models or set of models of the patient's biological structure also can be generated and conveyed to the surgeon or clinician to show an additional presence, or absence, of one or more defects of interest, one or more resection cuts, one or more guide tools, and/or one or more implant components, or any combination of these. FIGS. 12A and 12B illustrate models for one particular patient receiving a single compartment knee implant having both femoral and tibial implant components. In a first set of models, illustrated in FIG. 12A, the top panel shows two perspectives of a patient's distal femur and the bottom panel shows two images of the patient's proximal tibia, without (left image) and with (right image) a patient-adapted guide tool. In both the top and bottom panels, defects, osteophytes in this example, are categorized and differentiated into two colors, beige and red. The light-colored osteophytes 1210 depict osteophytes that do not interfere with placement of the guide tools or implant components. The dark-colored osteophytes 1220 depict osteophytes that will interfere with placement of a guide tool or an implant component. Accordingly, the categorization of the osteophytes serve as a guide or reference to the surgeon or clinician in determining which osteophytes should be removed prior to placement of the guide tools or implant components.

In a second set of models, illustrated in FIG. 12B, the top panel shows two images of a patient's distal femur with a patient-adapted guide tool (left image) and with a patient-adapted unicompartmental femoral implant component (right image). The bottom panel shows two images of the patient's proximal tibia, with a patient-adapted guide tool (left image) and with a patient-adapted unicompartmental tibial implant component (right image). The images in this figure show no osteophytes. Instead, these images show how each guide tool and implant component engages the patient's biological structure. In addition, the images showing the guide tools also show corresponding resection planes 1230 and the patient's tibial mechanical axis 1240. Accordingly, these images can serve as a guide or reference to the surgeon or clinician in planning and/or determining the surgical placement of the guide tools, implant components, and related resection cuts.

Figure 13B:
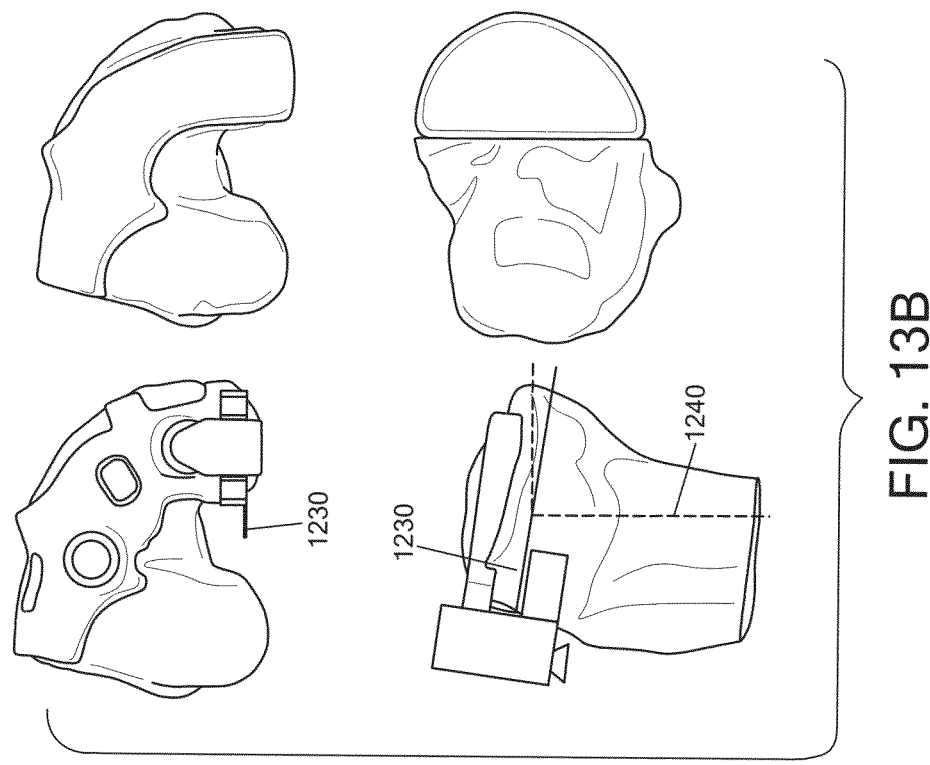
FIGS. 13A and 13B illustrate models for one particular patient receiving a bicompartmental knee implant and in need of osteophyte removal prior to placement of the implant components.
Figure 13A:
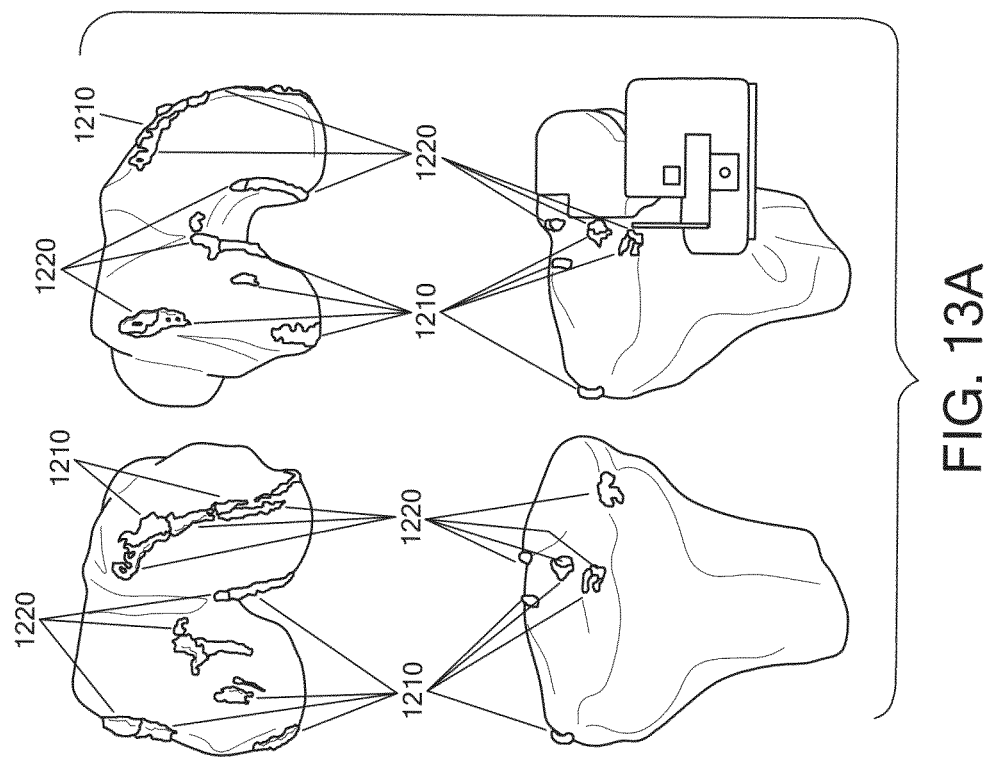

FIGS. 13A and 13B illustrate models for a different patient receiving a bicompartmental knee implant having both femoral and tibial implant components. The features in FIGS. 13A and 13B are similar to those described above for FIGS. 12A and 12B. In comparing the models for the two different individuals, it is clear that the individual receiving the unicompartmental knee implant (FIGS. 12A and 12B) has substantially more osteophyte coverage than the individual receiving the bicompartmental knee implant (FIGS. 13A and 13B).

Figure 14:
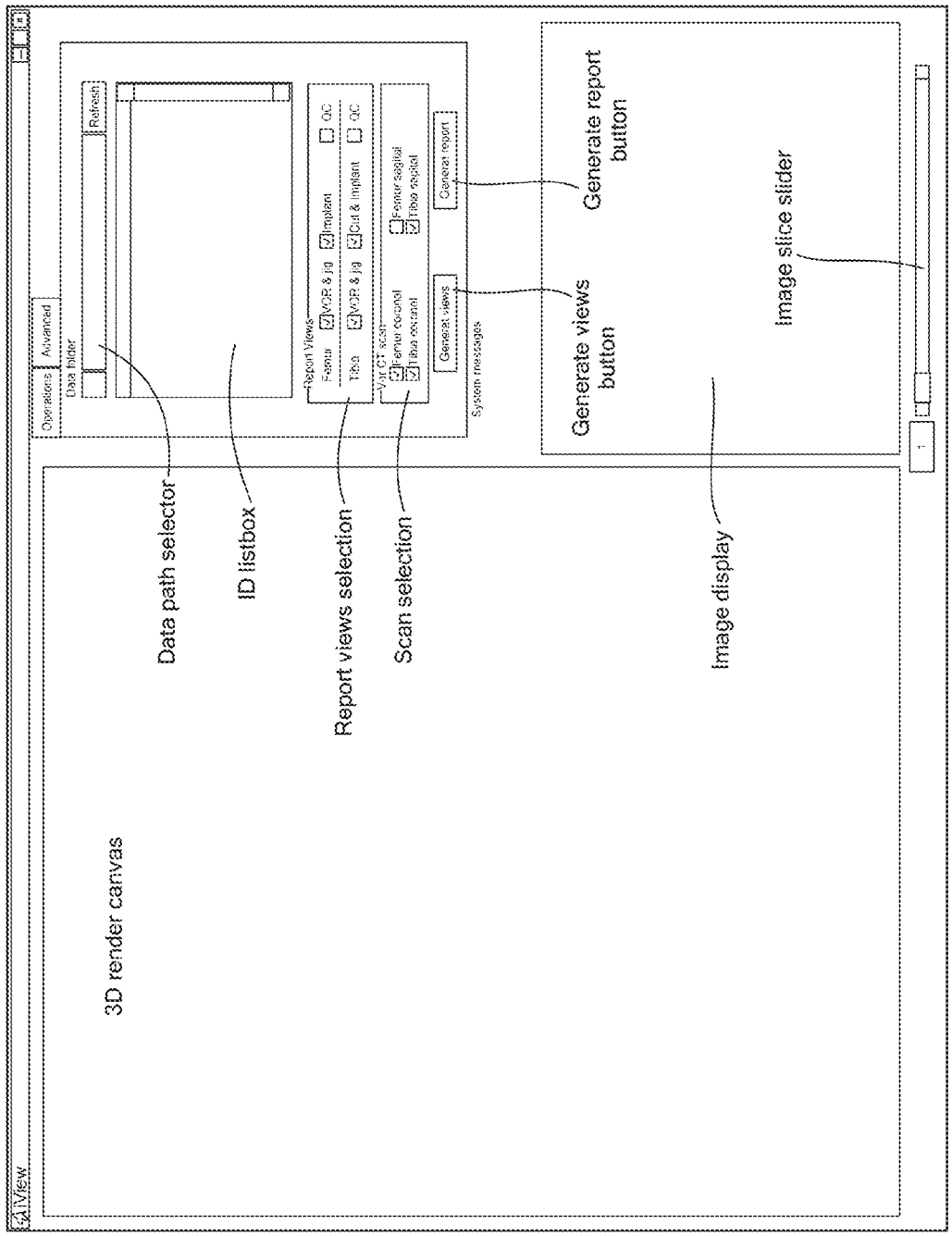
FIG. 14 displays an image of user interface for a computer software program for generating models of patient-specific renderings of implant assembly and defects (e.g., osteophyte structures), together with bone models.

Computer software programs to generate models of patient-specific renderings of implant assembly and defects (e.g., osteophyte structures), together with bone models, to aid in surgery planning can be developed using various publicly available programming environments and languages, for example, Matlab 7.3 and Matlab Compiler 4.5, C++ or Java. In certain embodiments, the computer software program can have a user interface that includes one or more of the components identified in FIG. 14. Alternatively, one or more off-the-shelf applications can be used to generate the models, such as SolidWorks, Rhinoceros, 3D Slicer or Amira.

Figure 15:
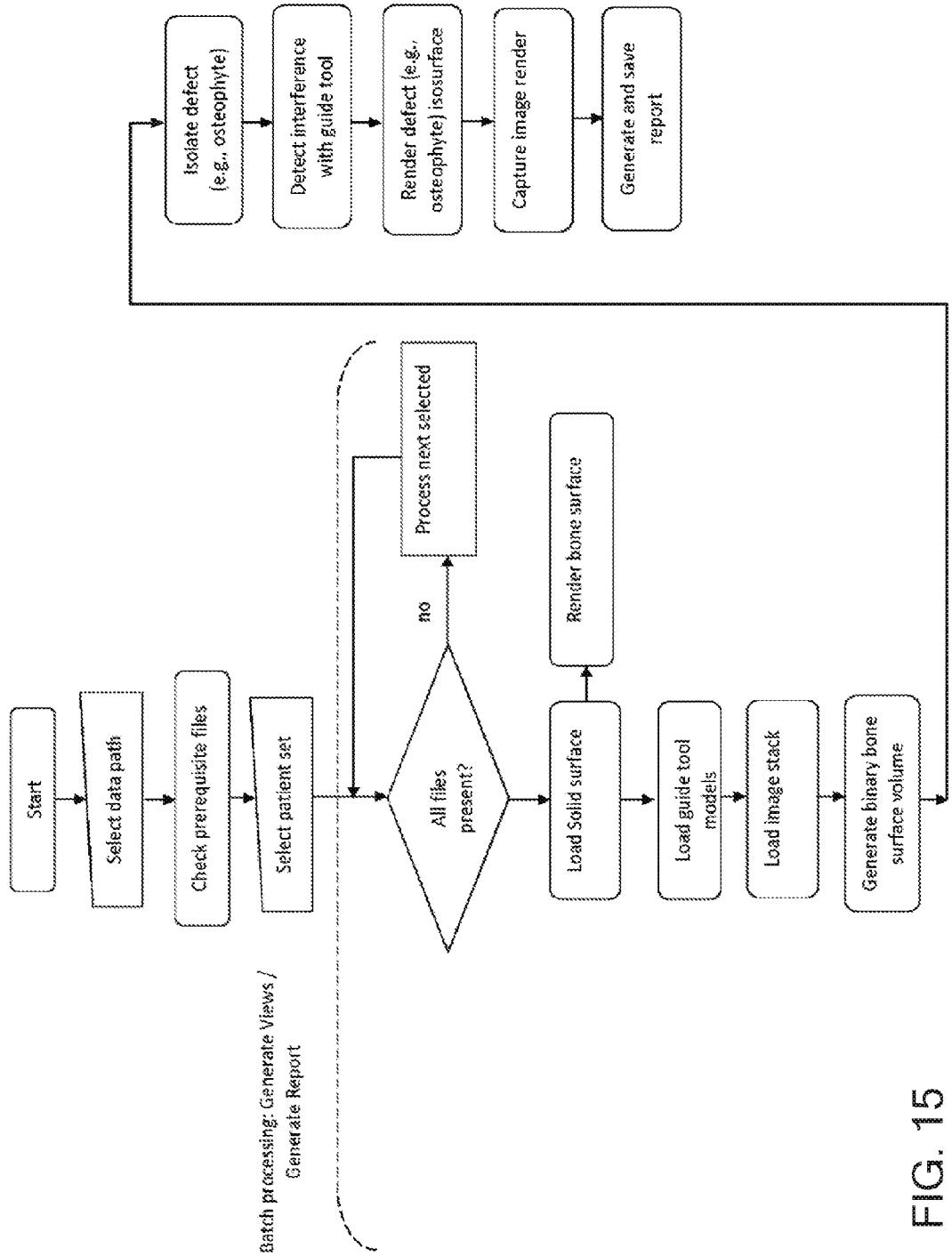
FIG. 15 shows an illustrative flow chart of the high level processes of an exemplary computer software program for generating models of patient-specific renderings of implant assembly and defects (e.g., osteophyte structures), together with bone models.

An illustrative flow chart of the high level processes of an exemplary computer software program is shown in FIG. 15. Briefly, a data path associated with one or more patient folders that include data files, for example, patient-specific CT images, solid models, and segmentation images, is selected. The data files associated with the data path can be checked, for example, using file filters, to confirm that all data files are present. For example, in generating models for a knee implant, a data path can confirm the presence of one, several, or all coronal CT data files, sagittal CT data files, a femoral solid model data file, a tibial solid model data file, a femoral guide tool model, a tibial guide tool model, a femoral coronal segmentation model, a femoral sagittal segmentation model, a tibial coronal segmentation model, and a tibial sagittal segmentation model. If the filter check identifies a missing file, the user can be notified. In certain instances, for example, if a tibial or femoral guide tool model file is unavailable, the user may elect to continue the process without certain steps, for example, without guide tool—defect (e.g., osteophyte) interference analysis.

Next, a patient-specific bone-surface model is obtained and/or rendered. The bone surface model provides basic patient-specific features of the patient's biological structure and serves as a reference for comparison against a model or value that includes the defect(s) of interest. As an illustrative example, previously generated patient-specific files, for example, STL files exported from "SOLID" IGES files in SolidWorks, can be loaded, for example, as triangulation points with sequence indices and normal vectors. The triangles then can be rendered (e.g., using Matlab TRISURF function) to supply or generate the bone-surface model. The bone surface model can include corrections of defects, such as osteophytes removed from the bone. In a similar fashion, one or more guide tool models can be obtained and/or rendered.

Next, a patient-specific model or values of the patient's biological feature that include the defect of interest can be obtained and/or rendered. For example, patient-specific defects, such as osteophytes, can be identified from analysis of the patient's segmentation images and corresponding CT scan images. The transformation matrix of scanner coordinate space to image matrix space can be calculated from image slice positions (e.g., the first and last image slice positions). Then, patient-specific segmentation images for the corresponding scan direction can be assessed, along with CT image slices that correspond to the loaded segmentation images. Images can be processed slice by slice and, using selected threshold values (e.g., intensity thresholds, Hounsfield unit thresholds, or neighboring pixel/voxel value thresholds), pixels and/or voxels corresponding to the defects of interest (e.g., osteophytes) can be identified. The identified voxels can provide a binary bone surface volume that includes the defects of interest as part of the surface of the patient's biological structure. Various masks can be employed to mask out features that are not of interest, for example, an adjacent biological surface. In some instances, masking can generate apparent unattached portions of an osteophyte defect, for example, when a mask covers a portion of an osteophyte extension.

Next, the defects of interest are isolated by comparing the model that does not include the defects of interest (e.g., bone-surface model) with the model or value that does include the defects of interest (e.g., the binary bone surface volume). For example, the triangulation points of the bone surface model can be transformed onto an image volume space to obtain a binary representation of the model. This volume binary can be dilated and thinned to obtain a binary bone model. The binary bone model then can serve as a mask to the binary bone surface volume to identify defect volume separate from the binary bone surface volume. For example, for osteophyte detection, the osteophyte volume (e.g., osteophyte binary volume), as well as the osteophyte position and attachment surface area, can be distinguished from the patient's biological structure using this comparative analysis. Various thresholds and filters can be applied to remove noise and/or enhance defect detection in this step. For example, structures that have less than a minimum voxel volume (e.g., less than 100 voxels) can be removed. Alternatively, or in addition, rules can be added to "reattach" any portion of an osteophyte defect that appears unattached, e.g., due to a masking step.

In an alternative approach, surface data can be used instead of voxel or volume data when comparing the bone surface model with corrected defects and the patient's actual bone surface. The bone surface model, for example, can be loaded as a mesh surface (e.g. in an STL file) or a parametric surface (e.g. in an IGES file) without conversion to volumetric voxel data. The patient's natural bone surface can be derived from the medical image data (e.g. CT data) using, for example, a marching cubes or isosurface algorithm, resulting in a second surface data set. The bone surface model and the natural bone surface can be compared, for example, by calculating intersection between the two surfaces.

Next, optionally, the models can be used to detect interference between any defect volume and the placement of one or more guide tools and/or implant components. For example, guide tool model triangulation points can be transformed onto an image volume space to obtain a binary representation of the guide tool. The binary structure then can be manipulated (e.g., dilated and eroded using voxel balls having pre-set diameters) to obtain a solid field mask. The solid field mask can be compared against the defect volume, for example, the osteophyte binary volume, to identify interfering defect volume, for example, interfering osteophyte binary volume. In this way, interfering defect volume and non-interfering defect volume can be determined (e.g., using Matlab ISOSURFACE function), for example, using representative colors or some other distinguishing features in a model. See, e.g., FIGS. 12A and 13A. The resulting model image can be rendered on a virtual rendering canvas (e.g., using Matlab GETFRAME function) and saved onto a computer-readable medium.

Finally, optionally, as exemplified by FIGS. 12A-B and 13A-B, one or more combinations of model features can be combined into one or models or sets of models that convey desired information to the surgeon or clinician. For example, patient-specific bone models can be combined with any number of defects or defect types, any number of resection cuts, any number of drill holes, any number of axes, any number of guide tools, and/or any number of implant components to convey as much information as desired to the surgeon or clinician. The patient-specific bone model can model any biological structure, for example, any one or more (or portion of) a femoral head and/or an acetabulum; a distal femur, one or both femoral condyle(s), and/or a tibial plateau; a trochlea and/or a patella; a glenoid and/or a humeral head; a talar dome and/or a tibial plafond; a distal humerus, a radial head, and/or an ulna; and a radius and/or a scaphoid. Defects that can be combined with a patient-specific bone model can include, for example, osteophytes, voids, subchondral cysts, articular shape defects (e.g., rounded or flattened articular surfaces or surface portions), varus or valgus deformities, or any other deformities known to those in the art.

The models can include virtual corrections reflecting a surgical plan, such as one or more of removed osteophytes, cut planes, drill holes, realignments of mechanical or anatomical axes. The models can include comparison views demonstrating the anatomical situation before and after applying the planned correction. The individual steps of the surgical plan can also be illustrated in a series of step-by-step images wherein each image shows a different step of the surgical procedure.

The models can be presented to the surgeon as a printed or digital set of images. In another embodiment, the models are transmitted to the surgeon as a digital file, which the surgeon can display on a local computer. The digital file can contain image renderings of the models. Alternatively, the models can be displayed in an animation or video. The models can also be presented as a 3D model that is interactively rendered on the surgeon's computer. The models can, for example, be rotated to be viewed from different angles. Different components of the models, such as bone surfaces, defects, resection cuts, axes, guide tools or implants, can be turned on and off collectively or individually to illustrate or simulate the individual patient's surgical plan. The 3D model can be transmitted to the surgeon in a variety of formats, for example in Adobe 3D PDF or as a SolidWorks eDrawing.

3.4 Modeling Proper Limb Alignment

Proper joint and limb function depend on correct limb alignment. For example, in repairing a knee joint with one or more knee implant components, optimal functioning of the new knee depends on the correct alignment of the anatomical and/or mechanical axes of the lower extremity. Accordingly, an important consideration in designing and/or replacing a natural joint with one or more implant components is proper limb alignment or, when the malfunctioning joint contributes to a misalignment, proper realignment of the limb.

Certain embodiments described herein include collecting and using data from imaging tests to virtually determine in one or more planes one or more of an anatomic axis and a mechanical axis and the related misalignment of a patient's limb. The misalignment of a limb joint relative to the axis can identify the degree of deformity, for example, varus or valgus deformity in the coronal plane or genu antecurvatum or recurvatum deformity in the sagittal plane. Then, one or more of the patient-specific implant components and/or the implant procedure steps, such as bone resection, can be designed to help correct the misalignment.

The imaging tests that can be used to virtually determine a patient's axis and misalignment can include one or more of such as x-ray imaging, digital tomosynthesis, cone beam CT, non-spiral or spiral CT, non-isotropic or isotropic MM, SPECT, PET, ultrasound, laser imaging, and photoacoustic imaging, including studies utilizing contrast agents. Data from these tests can be used to determine anatomic reference points or limb alignment, including alignment angles within the same and between different joints or to simulate normal limb alignment. Any anatomic features related to the misalignment can be selected and imaged. For example, in certain embodiments, such as for a knee or hip implant, the imaging test can include data from at least one of, or several of, a hip joint, knee joint and ankle joint. The imaging test can be obtained in lying, prone, supine or standing position. The imaging test can include only the target joint, or both the target joint and also selected data through one or more adjoining joints.

Using the image data, one or more mechanical or anatomical axes, angles, planes or combinations thereof can be determined. In certain embodiments, such axes, angles, and/or planes can include, or be derived from, one or more of a Whiteside's line, Blumensaat's line, transepicondylar line, femoral shaft axis, femoral neck axis, acetabular angle, lines tangent to the superior and inferior acetabular margin, lines tangent to the anterior or posterior acetabular margin, femoral shaft axis, tibial shaft axis, transmalleolar axis, posterior condylar line, tangent(s) to the trochlea of the knee joint, tangents to the medial or lateral patellar facet, lines tangent or perpendicular to the medial and lateral posterior condyles, lines tangent or perpendicular to a central weight-bearing zone of the medial and lateral femoral condyles, lines transecting the medial and lateral posterior condyles, for example through their respective centerpoints, lines tangent or perpendicular to the tibial tuberosity, lines vertical or at an angle to any of the aforementioned lines, and/or lines tangent to or intersecting the cortical bone of any bone adjacent to or enclosed in a joint. Moreover, estimating a mechanical axis, an angle, or plane also can be performed using image data obtained through two or more joints, such as the knee and ankle joint, for example, by using the femoral shaft axis and a centerpoint or other point in the ankle, such as a point between the malleoli.

As one example, if surgery of the knee or hip is contemplated, the imaging test can include acquiring data through at least one of, or several of, a hip joint, knee joint or ankle joint. As another example, if surgery of the knee joint is contemplated, a mechanical axis can be determined. For example, the centerpoint of the hip knee and ankle can be determined. By connecting the centerpoint of the hip with that of the ankle, a mechanical axis can be determined in the coronal plane. The position of the knee relative to said mechanical axis can be a reflection of the degree of varus or valgus deformity. The same determinations can be made in the sagittal plane, for example to determine the degree of genu antecurvatum or recurvatum. Similarly, any of these determinations can be made in any other desired planes, in two or three dimensions.

Exemplary methods for virtually aligning a patient's lower extremity are described below in Example 9. In particular, Example 9 illustrates methods for determining a patient's tibial mechanical axis, femoral mechanical axis, and the sagittal and coronal planes for each axis. However, any current and future method for determining limb alignment and simulating normal knee alignment can be used.

Once the proper alignment of the patient's extremity has been determined virtually, one or more surgical steps (e.g., resection cuts), surgical tools (e.g., tools to guide the resection cuts), and/or implant components (e.g., components having variable thicknesses to address misalignment).

3.5 Modeling Articular Cartilage

Cartilage loss in one compartment can lead to progressive joint deformity. For example, cartilage loss in a medial compartment of the knee can lead to varus deformity. In certain embodiments, cartilage loss can be estimated in the affected compartments. The estimation of cartilage loss can be done using an ultrasound MRI or CT scan or other imaging modality, optionally with intravenous or intra-articular contrast. The estimation of cartilage loss can be as simple as measuring or estimating the amount of joint space loss seen on x-rays. For the latter, typically standing x-rays are preferred. If cartilage loss is measured from x-rays using joint space loss, cartilage loss on one or two opposing articular surfaces can be estimated by, for example, dividing the measured or estimated joint space loss by two to reflect the cartilage loss on one articular surface. Other ratios or calculations are applicable depending on the joint or the location within the joint. Subsequently, a normal cartilage thickness can be virtually established on one or more articular surfaces by simulating normal cartilage thickness. In this manner, a normal or near normal cartilage surface can be derived. Normal cartilage thickness can be virtually simulated using a computer, for example, based on computer models, for example using the thickness of adjacent normal cartilage, cartilage in a contralateral joint, or other anatomic information including subchondral bone shape or other articular geometries. Cartilage models and estimates of cartilage thickness can also be derived from anatomic reference databases that can be matched, for example, to a patient's weight, sex, height, race, gender, or articular geometry(ies).

In certain embodiments, a patient's limb alignment can be virtually corrected by realigning the knee after establishing a normal cartilage thickness or shape in the affected compartment by moving the joint bodies, for example, femur and tibia, so that the opposing cartilage surfaces including any augmented or derived or virtual cartilage surface touch each other, typically in the preferred contact areas. These contact areas can be simulated for various degrees of flexion or extension.

4. Parameters for Selecting and/or Designing a Patient-Adapted Implant

The patient-adapted implants (e.g., implants having one or more patient-specific and/or patient-engineered features) of certain embodiments can be designed based on patient-specific data to optimize one or more parameters including, but not limited to: (1) deformity correction and limb alignment (2) maximum preservation of bone, cartilage, or ligaments, (3) preservation and/or optimization of features of the patient's biology, such as trochlea and trochlear shape, (4) restoration and/or optimization of joint kinematics, and (5) restoration or optimization of joint-line location and/or joint gap width. Various features of an implant component that can be designed or engineered based on the patient-specific data to help meet any number of user-defined thresholds for these parameters. The features of an implant that can be designed and/or engineered patient-specifically can include, but are not limited to, (a) implant shape, external and internal, (b) implant size, (c) and implant thickness.

There are several advantages that a patient-specific implant designed and/or engineered to meet or improve one of more of these parameters can have over a traditional implant. These advantages can include, for example: improved mechanical stability of the extremity; opportunity for a pre-primary or additional revision implant; improved fit with existing or modified biological features; improved motion and kinematics, and other advantages.

4.1 Deformity Correction and Optimizing Limb Alignment

Information regarding the misalignment and the proper mechanical alignment of a patient's limb, for example, as illustrated in Example 9, can be used to preoperatively design and/or select one or more features of a joint implant and/or implant procedure. For example, based on the difference between the patient's misalignment and the proper mechanical axis, a knee implant and implant procedure can be designed and/or selected preoperatively to include implant and/or resection dimensions that substantially realign the patient's limb to correct or improve a patient's alignment deformity. In addition, the process can include selecting and/or designing one or more surgical tools (e.g., guide tools or cutting jigs) to direct the clinician in resectioning the patient's bone in accordance with the preoperatively designed and/or selected resection dimensions.

In certain embodiments, the degree of deformity correction that is necessary to establish a desired limb alignment is calculated based on information from the alignment of a virtual model of a patient's limb. The virtual model can be generated from patient-specific data, such 2D and/or 3D imaging data of the patient's limb. The deformity correction can correct varus or valgus alignment or antecurvatum or recurvatum alignment. In a preferred embodiment, the desired deformity correction returns the leg to normal alignment, for example, a zero degree biomechanical axis in the coronal plane and absence of genu antecurvatum and recurvatum in the sagittal plane.

The preoperatively designed and/or selected implant or implant component, resection dimension(s), and/or cutting jig(s) can be employed to correct a patient's alignment deformity in a single plane, for example, in the coronal plane or in the sagittal plane, in multiple planes, for example, in the coronal and sagittal planes, and/or in three dimensions. For example, Example 9 describes a virtual model of a patient's misaligned lower limb and virtually corrected limb. In particular, the patient's lower limb is misaligned in the coronal plane, for example, a valgus or varus deformity. The deformity correction can be achieved by designing and/or selecting one or more of a resection dimension, an implant component thickness, and an implant component surface curvature that adjusts the mechanical axis or axes into alignment in one or more planes. For example, a lower limb misalignment can be corrected in a knee replacement by designing or selecting one or more of a femoral resection dimension, a femoral implant component thickness, a femoral implant component surface curvature, a tibial resection dimension, a tibial implant component thickness, a tibial implant component insert thickness, and a tibial implant component surface curvature to adjust the femoral mechanical axis and tibial mechanical axis into alignment in the coronal plane.

FIG. 16 illustrates a coronal plane of the knee with exemplary resection cuts that can be used to correct lower limb alignment in a knee replacement. As shown in the figure, the selected and/or designed resection cuts can include different cuts on different portions of a patient's biological structure. For example, resection cut facets on medial and lateral femoral condyles can be non-coplanar and parallel 1602, 1602', angled 1604, 1604', or non-coplanar and non-parallel, for example, cuts 1602 and 1604' or cuts 1602' and 1604. Similar, resection cut facets on medial and lateral portions of the tibia can be non-coplanar and parallel 1606, 1606', angled and parallel 1608, 1608', or non-coplanar and non-parallel, for example, cuts 1606 and 1608' or cuts 1606' and 1608. Non-coplanar facets of resection cuts can include a step-cut 1610 to connect the non-coplanar resection facet surfaces. Selected and/or designed resection dimensions can be achieved using one or more selected and/or designed guide tools (e.g., cutting jigs) that guide resectioning (e.g., guide cutting tools) of the patient's biological structure to yield the predetermined resection surface dimensions (e.g., resection surface(s), angles, and/or orientation(s)). In certain embodiments, the bone-facing surfaces of the implant components can be designed to include one or more features (e.g., bone cut surface areas, perimeters, angles, and/or orientations) that substantially match one or more of the resection cut or cut facets that were predetermined to enhance the patient's alignment. As shown in FIG. 16, certain combinations of resection cuts can aid in bringing the femoral mechanical axis 1612 and tibial mechanical axis 1614 into alignment 1616.

Alternatively, or in addition, certain implant features, such as different implant thicknesses and/or surface curvatures across two different sides of the plane in which the mechanical axes 1612, 1614 are misaligned also can aid correcting limb alignment. For example, FIG. 17 depicts a coronal plane of the knee shown with femoral implant medial and lateral condyles 1702, 1702' having different thicknesses to help to correct limb alignment. These features can be used in combination with any of the resection cut 1704, 1704' described above and/or in combination with different thicknesses on the corresponding portions of the tibial component. As described more fully below, independent tibial implant components and/or independent tibial inserts on medial and lateral sides of the tibial implant component can be used enhance alignment at a patient's knee joint. An implant component can include constant yet different thicknesses in two or more portions of the implant (e.g., a constant medial condyle thickness different from a constant lateral condyle thickness), a gradually increasing thickness across the implant or a portion of the implant, or a combination of constant and gradually increasing thicknesses.

Figure 18:
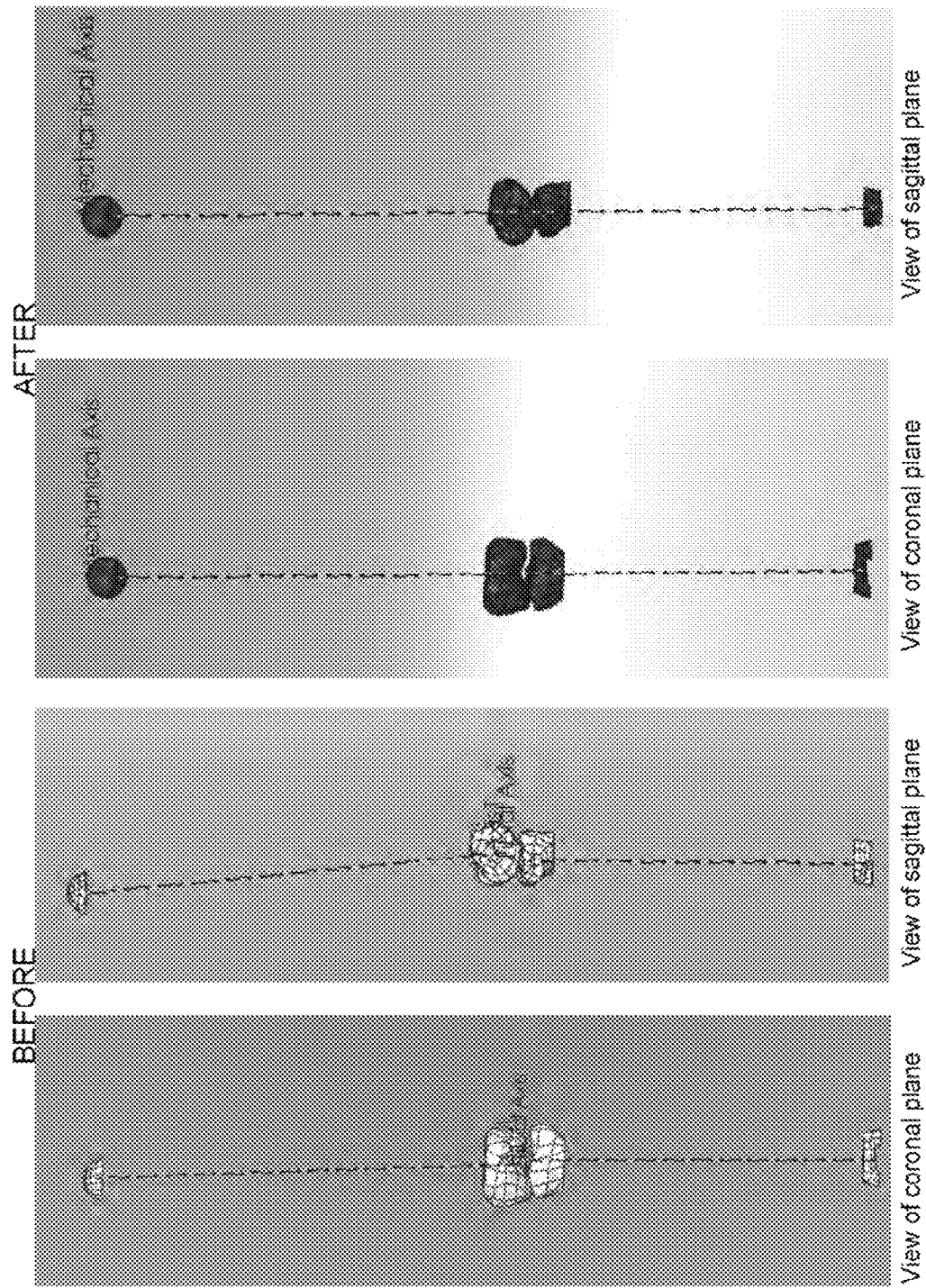
FIG. 18 illustrates a virtual model of a patient's limb that is misaligned in the sagittal plane, for example, a genu antecurvatum deformity, and the virtually corrected limb.

FIG. 18 illustrates a virtual model of a patient's limb that is misaligned in the sagittal plane, for example, a genu antecurvatum deformity, and the virtually corrected limb. The deformity correction can be achieved using a similar design approach as described above for a coronal plane deformity. However, the selection and/or design of one or more femoral resection dimensions, femoral implant component thicknesses, femoral implant component surface curvatures, tibial resection dimensions, tibial implant component thicknesses, tibial implant component insert thicknesses, and/or tibial implant component surface curvatures can be used to adjust the femoral mechanical axis and tibial mechanical axis into alignment in the sagittal plane (e.g., by altering corresponding features across the sagittal plane, for example, by altering anterior features relative to corresponding posterior features). Alignment deformities in both the coronal and sagittal planes, or in multiple planes about the mechanical axes, can be addressed by designing and/or selecting one or more resection dimensions, one or more implant component thicknesses, and/or one or more implant component surface curvatures.

Figures 19A, 19B:
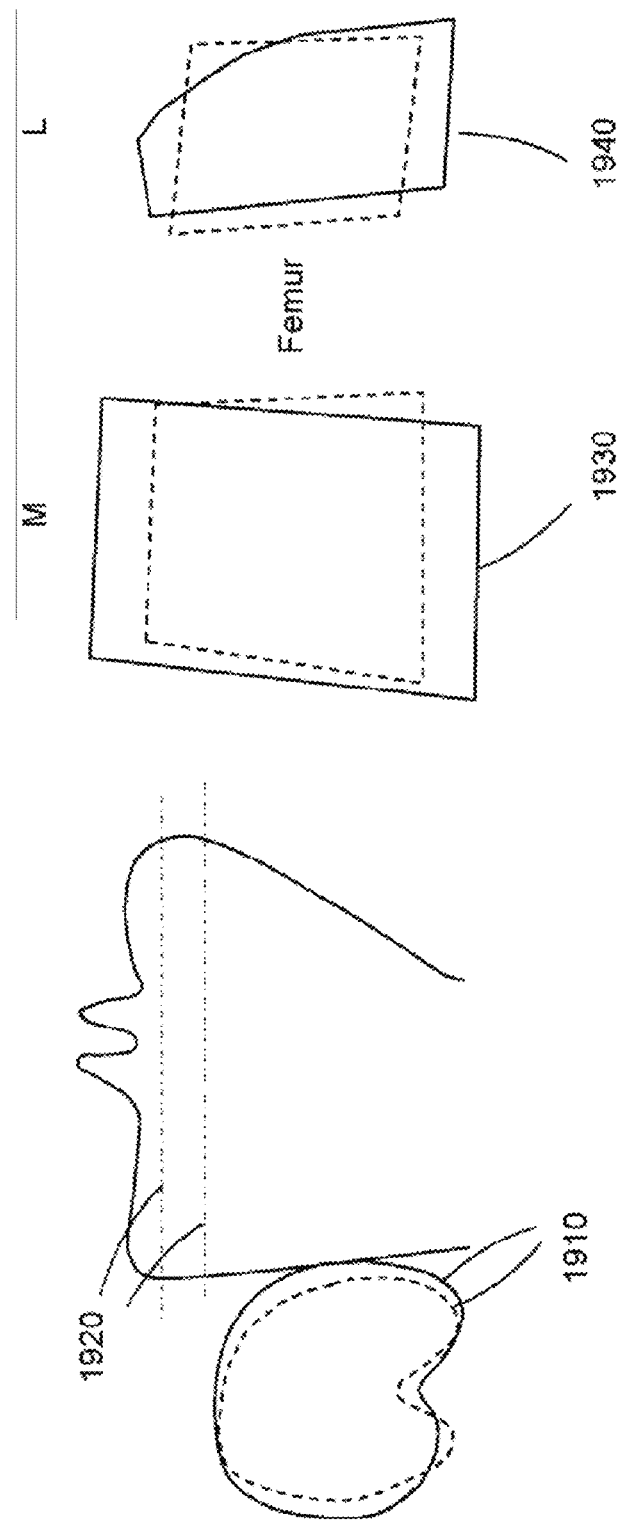
FIG. 19A illustrates perimeters and areas of two bone surface areas for two different bone resection cut depths.
FIG. 19B is a distal view of the femur in which two different resection cuts are applied.

In certain embodiments, an implant component that is preoperatively designed and/or selected to correct a patient's alignment also can be designed or selected to include additional patient-specific or patient-engineered features. For example, the bone-facing surface of an implant or implant component can be designed and/or selected to substantially negatively-match the resected bone surface. As depicted in FIG. 19A, the perimeters and areas 1910 of two bone surface areas is different for two different bone resection cut depths 1920. Similarly, FIG. 19B depicts a distal view of the femur in which two different resection cuts are applied. As shown, the resected perimeters and surface areas for two distal facet resection depths are different for each of the medial condyle distal cut facet 1930 and the lateral condyle distal cut facet 1940.

If resection dimensions are angled, for example, in the coronal plane and/or in the sagittal plane, various features of the implant component, for example, the component bone-facing surface, can be designed and/or selected based on an angled orientation into the joint rather than on a perpendicular orientation For example, the perimeter of tibial implant or implant component that substantially positively-matches the perimeter of the patient's cut tibial bone has a different shape depending on the angle of the cut. Similarly, with a femoral implant component, the depth or angle of the distal condyle resection on the medial and/or lateral condyle can be designed and/or selected to correct a patient alignment deformity. However, in so doing, one or more of the implant or implant component condyle width, length, curvature, and angle of impact against the tibia can be altered. Accordingly in certain embodiments, one or more implant or implant component features, such as implant perimeter, condyle length, condyle width, curvature, and angle is designed and/or selected relative to the a sloping and/or non-coplanar resection cut.

4.2 Preserving Bone, Cartilage or Ligament

Traditional orthopedic implants incorporate bone cuts. These bone cuts achieve two objectives: they establish a shape of the bone that is adapted to the implant and they help achieve a normal or near normal axis alignment. For example, bone cuts can be used with a knee implant to correct an underlying varus of valgus deformity and to shape the articular surface of the bone to fit a standard, bone-facing surface of a traditional implant component. With a traditional implant, multiple bone cuts are placed. However, since traditional implants are manufactured off-the-shelf without use of patient-specific information, these bone cuts are pre-set for a given implant without taking into consideration the unique shape of the patient. Thus, by cutting the patient's bone to fit the traditional implant, more bone is discarded than is necessary with an implant designed to address the particularly patient's structures and deficiencies.

In certain embodiments, resection cuts are optimized to preserve the maximum amount of bone for each individual patient, based on a series of two-dimensional images or a three-dimensional representation of the patient's articular anatomy and geometry and the desired limb alignment and/or desired deformity correction. Resection cuts on two opposing articular surfaces can be optimized to achieve the minimum amount of bone resected from one or both articular surfaces.

By adapting resection cuts in the series of two-dimensional images or the three-dimensional representation on two opposing articular surfaces such as, for example, a femoral head and an acetabulum, one or both femoral condyle(s) and a tibial plateau, a trochlea and a patella, a glenoid and a humeral head, a talar dome and a tibial plafond, a distal humerus and a radial head and/or an ulna, or a radius and a scaphoid, certain embodiments allow for patient individualized, bone-preserving implant designs that can assist with proper ligament balancing and that can help avoid "overstuffing" of the joint, while achieving optimal bone preservation on one or more articular surfaces in each patient.

Figure 20:
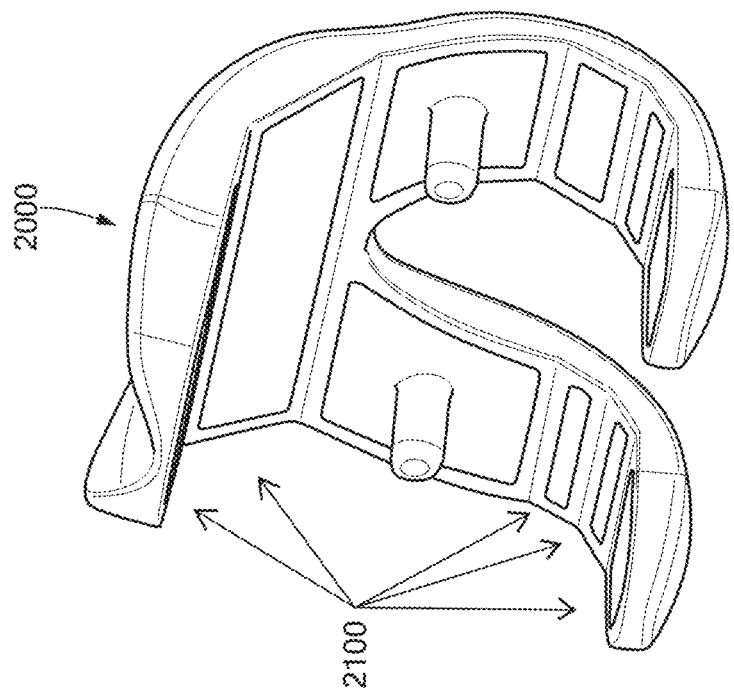
FIG. 20 depicts a femoral implant component having six bone cuts with the intersect of bone cuts on the inner, bone-facing surface of the implant highlighted.

The resection cuts also can be designed to meet or exceed a certain minimum material thickness, for example, the minimum amount of thickness required to ensure biomechanical stability and durability of the implant. In certain embodiments, the limiting minimum implant thickness can be defined at the intersection of two adjoining bone cuts on the inner, bone-facing surface of an implant component. For example, in the femoral implant component 2000 shown in FIG. 20, the minimum thickness of the implant component appears at one or more intersections 2100. In certain embodiments of a femoral implant component, the minimum implant thickness can be less than 10 mm, less than 9 mm, less than 8 mm, less than 7 mm, and/or less than 6 mm.

These optimizations can be performed for one, two, or three opposing articular surfaces, for example, in a knee they can be performed on a tibia, a femur and a patella.

In a knee, different resection cuts can be planned for a medial and lateral femoral condyle. In certain embodiments, a single bone cut can be optimized in a patient to maximize bone preservation in that select area, for example, a posterior condyle. Alternatively, multiple or all resection cuts can be optimized. Since a patient's medial and lateral femoral condyles typically have different geometries, including, for example, width, length and radii of curvature in multiple planes, for example, the coronal and the sagittal plane, then one or more resection cuts can be optimized in the femur individually for each condyle, resulting in resection cuts placed at a different depths, angles, and/or orientations in one condyle relative to the other condyle. For example, a horizontal cut in a medial condyle may be anatomically placed more inferior relative to the limb than a horizontal cut in a lateral condyle. The distance of the horizontal cut from the subchondral bone may be the same in each condyle or it can be different in each condyle. Chamfer cuts in the medial and lateral condyle may be placed in different planes rather than the same plane in order to optimize bone preservation. Moreover, chamfer cuts in the medial and lateral condyle may be placed at a different angle in order to maximize bone preservation. Posterior cuts may be placed in a different plane, parallel or non-parallel, in a medial and a lateral femoral condyle in order to maximize bone preservation. A medial condyle may include more bone cut facets than a lateral condyle in order to enhance bone preservation or vice versa.

In certain embodiments, a measure of bone preservation can include total volume of bone resected, volume of bone resected from one or more resection cuts, volume of bone resected to fit one or more implant component bone cuts, average thickness of bone resected, average thickness of bone resected from one or more resection cuts, average thickness of bone resected to fit one or more implant component bone cuts, maximum thickness of bone resected, maximum thickness of bone resected from one or more resection cuts, maximum thickness of bone resected to fit one or more implant component bone cuts.

Certain embodiments of femoral implant components described herein include more than five bone cuts, for example, six, seven, eight, nine or more bone cuts on the inner, bone-facing surface of the implant component. These bone cuts can be standard, in whole or in part, or patient-adapted, in whole or in part. Alternatively, certain embodiments include five bone cuts that are patient-adapted based on one or more images of the patient's knee. A femoral implant component with greater than five bone cuts of and/or with patient-adapted bone cuts can allow for enhanced bone preservation over a traditional femoral implant with five standard bone cuts and therefore can perform as a pre-primary implant.

Figure 21:
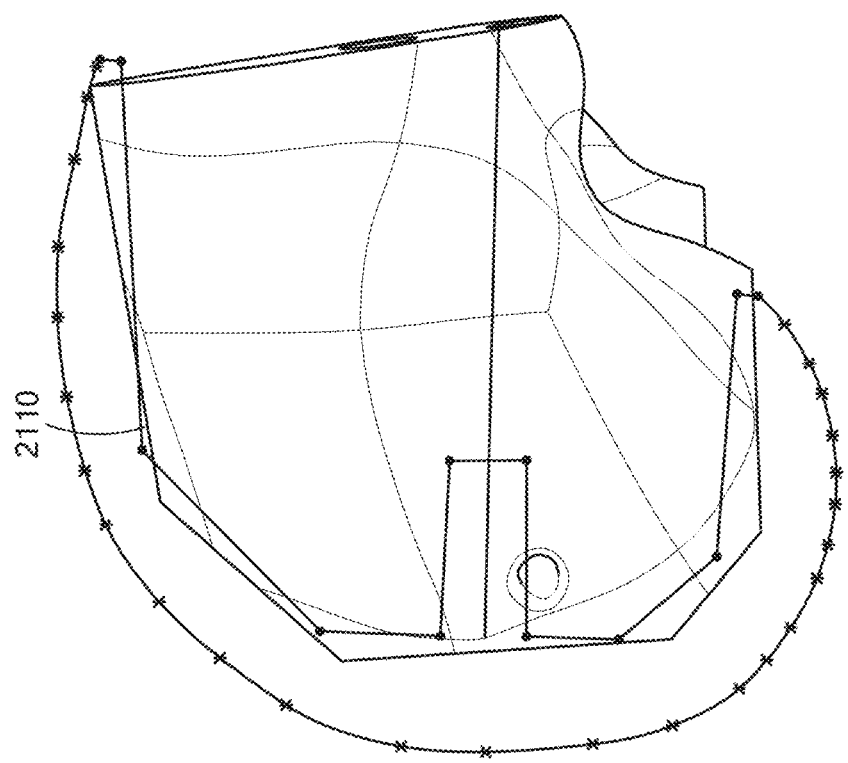
FIG. 21 illustrates a computer model of a distal femur having optimized bone cuts for a pre-primary implant overlaid with a traditional primary implant (shown in outline)

A patient-specific implant having bone cuts that are non-parallel to the cuts of a subsequent primary can result in the primary implant having small gaps between the bone and the inner, bone-facing surface of the primary implant. These small gaps can result misalignment intersects between the pre-primary implant and the subsequent primary implant. For example, as shown in FIG. 21, the bone cuts (shown in red) for a pre-primary implant component having a 5-flex cut can retain bone as compared to a traditional primary implant (shown in outline), but a small gap 2110 also can be created by the pre-primary cut. Any such small gaps 2120 can be filled with bone cement when fitting a subsequent primary implant.

In addition to optimizing bone preservation, another factor in determining the depth, number, and/or orientation of resection cuts and/or implant component bone cuts is desired implant thickness. A minimum implant thickness can be included as part of the resection cut and/or bone cut design to ensure a threshold strength for the implant in the face of the stresses and forces associated with joint motion, such as standing, walking, and running. Table 5 shows the results of a finite element analysis (FEA) assessment for femoral implant components of various sizes and with various bone cut numbers and orientations. The maximum principal stress observed in FEA analysis can be used to establish an acceptable minimum implant thickness for an implant component having a particular size and, optionally, for a particular patient (e.g., having a particular weight, age, activity level, etc). Before, during, and/or after establishing a minimum implant component thickness, the optimum depth of the resection cuts and the optimum number and orientation of the resection cuts and bone cuts, for example, for maximum bone preservation, can designed.

In certain embodiments, an implant component design or selection can depend, at least in part, on a threshold minimum implant component thickness. In turn, the threshold minimum implant component thickness can depend, at least in part, on patient-specific data, such as condylar width, femoral transepicondylar axis length, and/or the patient's specific weight. In this way, the threshold implant thickness, and/or any implant component feature, can be adapted to a particular patient based on a combination of patient-specific geometric data and on patient-specific anthropometric data. This approach can apply to any implant component feature for any joint, for example, the knee, the hip, or the shoulder.

TABLE 5

Finite Element Analysis for Various Implant Designs

| Implant Description | Distal Condyle Geomery | Relative Size | Scan # | Maximum Principal Stress, mPa |
|---|---|---|---|---|
| 6-Cut, non-flexed | coplanar | Sigma #1.5 | 3017 | 161 |
| 5-Cut, non-flexed | coplanar | Sigma #1.5 | 3017 | 201 |
| 6-Cut, flexed 5 degrees | coplanar | Sigma #1.5 | 3017 | 229 |
| 6-Cut, non-flexed | coplanar | Sigma #3 | 2825 | 221 |
| 5-Cut, non-flexed | coplanar | Sigma #3 | 2825 | 211 |
| 6-Cut, flexed 5 degrees | coplanar | Sigma #3 | 2825 | 198 |
| 5-Cut, non-flexed | coplanar | Sigma #7 | 1180 | 292 |
| 6-Cut, non-flexed | coplanar | Sigma #7 | 1180 | 221 |
| 6-Cut, flexed 5 degrees | coplanar | Sigma #7 | 1180 | 214 |
| 7-Cut non-flexed | coplanar | Sigma #7 | 1180 | 203 |
| 6-Cut, non-flexed | non-coplanar, w/step | Sigma #7 | 1180 | 173 |
| 7-cut, flexed 5 degrees | non-coplanar, w/out step | Sigma #7 | 1180 | 202 |

A weighting optionally can be applied to each bone with regard to the degree of bone preservation achieved. For example, if the maximum of bone preservation is desired on a tibia or a sub-segment of a tibia, femoral bone cuts can be adapted and moved accordingly to ensure proper implant alignment and ligament balancing. Conversely, if maximum bone preservation is desired on a femoral condyle, a tibial bone cut can be adjusted accordingly. If maximum bone preservation is desired on a patella, a resection cut on the opposing trochlea can be adjusted accordingly to ensure maximal patellar bone preservation without inducing any extension deficits. If maximum bone preservation is desired on a trochlea, a resection cut on the opposing patella can be adjusted accordingly to ensure maximal patellar bone preservation without inducing any extension deficits. Any combination is possible and different weightings can be applied. The weightings can be applied using mathematical models or, for example, data derived from patient reference databases.

Implant design and modeling also can be used to achieve ligament sparing, for example, with regard to the PCL and/or the ACL. An imaging test can be utilized to identify, for example, the origin and/or the insertion of the PCL and the ACL on the femur and tibia. The origin and the insertion can be identified by visualizing, for example, the ligaments directly, as is possible with MRI or spiral CT arthrography, or by visualizing bony landmarks known to be the origin or insertion of the ligament such as the medial and lateral tibial spines.

An implant system can then be selected or designed based on the image data so that, for example, the femoral component preserves the ACL and/or PCL origin, and the tibial component preserves the ACL and/or PCL attachment. The implant can be selected or designed so that bone cuts adjacent to the ACL or PCL attachment or origin do not weaken the bone to induce a potential fracture.

For ACL preservation, the implant can have two unicompartmental tibial components that can be selected or designed and placed using the image data. Alternatively, the implant can have an anterior bridge component. The width of the anterior bridge in AP dimension, its thickness in the superoinferior dimension or its length in mediolateral dimension can be selected or designed using the imaging data and, specifically, the known insertion of the ACL and/or PCL.

Figure 22B:
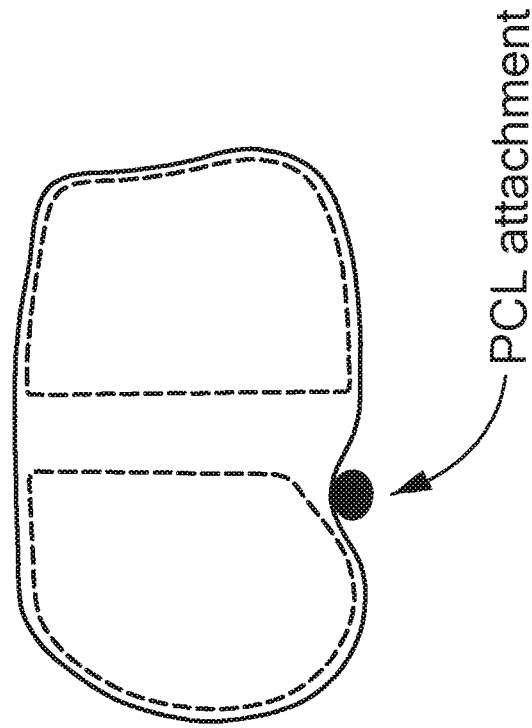
FIGS. 22A and 22B depict the posterior margin of an implant component selected and/or designed using the imaging data or shapes derived from the imaging data so that the implant component will not interfere with and stay clear of the patient's PCL.
Figure 22A:
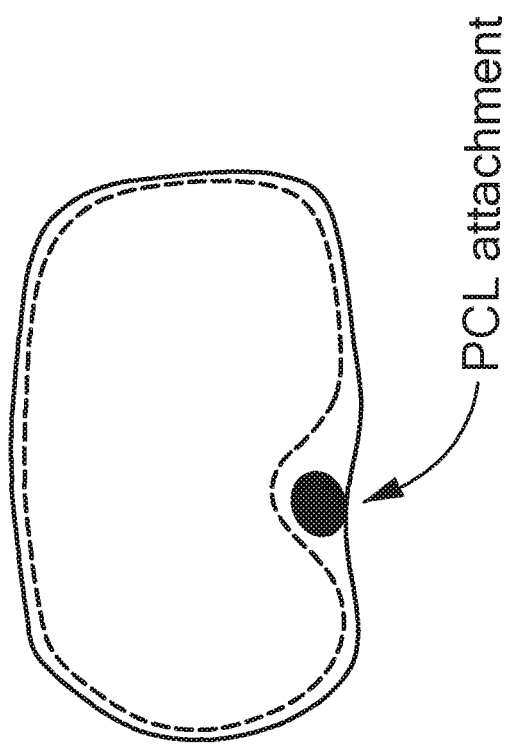

As can be seen in FIGS. 22A and 22B, the posterior margin of an implant component, e.g. a polyethylene- or metal-backed tray with polyethylene inserts, can be selected and/or designed using the imaging data or shapes derived from the imaging data so that the implant component will not interfere with and stay clear of the PCL. This can be achieved, for example, by including concavities in the outline of the implant that are specifically designed or selected or adapted to avoid the ligament insertion.

Any implant component can be selected and/or adapted in shape so that it stays clear of important ligament structures. Imaging data can help identify or derive shape or location information on such ligamentous structures. For example, the lateral femoral condyle of a unicompartmental, bicompartmental or total knee system can include a concavity or divet to avoid the popliteus tendon. In a shoulder, the glenoid component can include a shape or concavity or divet to avoid a subscapularis tendon or a biceps tendon. In a hip, the femoral component can be selected or designed to avoid an iliopsoas or adductor tendons.

4.3 Establishing Normal or Near-Normal Joint Kinematics

In certain embodiments, bone cuts and implant shape including at least one of a bone-facing or a joint-facing surface of the implant can be designed or selected to achieve normal joint kinematics.

In certain embodiments, a computer program simulating biomotion of one or more joints, such as, for example, a knee joint, or a knee and ankle joint, or a hip, knee and/or ankle joint can be utilized. In certain embodiments, patient-specific imaging data can be fed into this computer program. For example, a series of two-dimensional images of a patient's knee joint or a three-dimensional representation of a patient's knee joint can be entered into the program. Additionally, two-dimensional images or a three-dimensional representation of the patient's ankle joint and/or hip joint may be added.

Alternatively, patient-specific kinematic data, for example obtained in a gait lab, can be fed into the computer program. Alternatively, patient-specific navigation data, for example generated using a surgical navigation system, image guided or non-image guided can be fed into the computer program. This kinematic or navigation data can, for example, be generated by applying optical or RF markers to the limb and by registering the markers and then measuring limb movements, for example, flexion, extension, abduction, adduction, rotation, and other limb movements.

Optionally, other data including anthropometric data may be added for each patient. These data can include but are not limited to the patient's age, gender, weight, height, size, body mass index, and race. Desired limb alignment and/or deformity correction can be added into the model. The position of bone cuts on one or more articular surfaces as well as the intended location of implant bearing surfaces on one or more articular surfaces can be entered into the model.

A patient-specific biomotion model can be derived that includes combinations of parameters listed above. The biomotion model can simulate various activities of daily life including normal gait, stair climbing, descending stairs, running, kneeling, squatting, sitting and any other physical activity. The biomotion model can start out with standardized activities, typically derived from reference databases. These reference databases can be, for example, generated using biomotion measurements using force plates and motion trackers using radiofrequency or optical markers and video equipment.

The biomotion model can then be individualized with use of patient-specific information including at least one of, but not limited to the patient's age, gender, weight, height, body mass index, and race, the desired limb alignment or deformity correction, and the patient's imaging data, for example, a series of two-dimensional images or a three-dimensional representation of the joint for which surgery is contemplated.

An implant shape including associated bone cuts generated in the preceding optimizations, for example, limb alignment, deformity correction, bone preservation on one or more articular surfaces, can be introduced into the model. Table 6 includes an exemplary list of parameters that can be measured in a patient-specific biomotion model.

TABLE 6

Parameters measured in a patient-specific biomotion model for various implants

| Joint implant | Measured Parameter |
| --- | --- |
| knee | Medial femoral rollback during flexion |
| knee | Lateral femoral rollback during flexion |
| knee | Patellar position, medial, lateral, superior, inferior for different flexion and extension angles |
| knee | Internal and external rotation of one or more femoral condyles |
| knee | Internal and external rotation of the tibia |
| knee | Flexion and extension angles of one or more articular surfaces |
| knee | Anterior slide and posterior slide of at least one of the medial and lateral femoral condyles during flexion or extension |
| knee | Medial and lateral laxity throughout the range of motion |
| knee | Contact pressure or forces on at least one or more articular surfaces, e.g. a femoral condyle and a tibial plateau, a trochlea and a patella |
| knee | Contact area on at least one or more articular surfaces, e.g. a femoral condyle and a tibial plateau, a trochlea and a patella |
| knee | Forces between the bone-facing surface of the implant, an optional cement interface and the adjacent bone or bone marrow, measured at least one or multiple bone cut or bone-facing surface of the implant on at least one or multiple articular surfaces or implant components. |
| knee | Ligament location, e.g. ACL, PCL, MCL, LCL, retinacula, joint capsule, estimated or derived, for example using an imaging test. |
| knee | Ligament tension, strain, shear force, estimated failure forces, loads for example for different angles of flexion, extension, rotation, abduction, adduction, with the different positions or movements optionally simulated in a virtual environment. |
| knee | Potential implant impingement on other articular structures, e.g. in high flexion, high extension, internal or external rotation, abduction or adduction or any combinations thereof or other angles/positions/movements. |
| Hip, shoulder or other joint | Internal and external rotation of one or more articular surfaces |
| Hip, shoulder or other joint | Flexion and extension angles of one or more articular surfaces |
| Hip, shoulder or other joint | Anterior slide and posterior slide of at least one or more articular surfaces during flexion or extension, abduction or adduction, elevation, internal or external rotation |
| Hip, shoulder or other joint | Joint laxity throughout the range of motion |
| Hip, shoulder or other joint | Contact pressure or forces on at least one or more articular surfaces, e.g. an acetabulum and a femoral head, a glenoid and a humeral head |
| Hip, shoulder or other joint | Forces between the bone-facing surface of the implant, an optional cement interface and the adjacent bone or bone marrow, measured at least one or multiple bone cut or bone-facing surface of the implant on at least one or multiple articular surfaces or implant components. |
| Hip, shoulder or other joint | Ligament location, e.g. transverse ligament, glenohumeral ligaments, retinacula, joint capsule, estimated or derived, for example using an imaging test. |
| Hip, shoulder or other joint | Ligament tension, strain, shear force, estimated failure forces, loads for example for different angles of flexion, extension, rotation, abduction, adduction, with the different positions or movements optionally simulated in a virtual environment. |

TABLE 6-continued

Parameters measured in a patient-specific biomotion model for various implants

| Joint implant | Measured Parameter |
|---|---|
| Hip, shoulder or other joint | Potential implant impingement on other articular structures, e.g. in high flexion, high extension, internal or external rotation, abduction or adduction or elevation or any combinations thereof or other angles/positions/movements. |

The above list is not meant to be exhaustive, but only exemplary. Any other biomechanical parameter known in the art can be included in the analysis.

The resultant biomotion data can be used to further optimize the implant design with the objective to establish normal or near normal kinematics. The implant optimizations can include one or multiple implant components. Implant optimizations based on patient-specific data including image based biomotion data include, but are not limited to:

Changes to external, joint-facing implant shape in coronal plane
Changes to external, joint-facing implant shape in sagittal plane
Changes to external, joint-facing implant shape in axial plane
Changes to external, joint-facing implant shape in multiple planes or three dimensions
Changes to internal, bone-facing implant shape in coronal plane
Changes to internal, bone-facing implant shape in sagittal plane
Changes to internal, bone-facing implant shape in axial plane
Changes to internal, bone-facing implant shape in multiple planes or three dimensions
Changes to one or more bone cuts, for example with regard to depth of cut, orientation of cut Any single one or combinations of the above or all of the above on at least one articular surface or implant component or multiple articular surfaces or implant components.

When changes are made on multiple articular surfaces or implant components, these can be made in reference to or linked to each other. For example, in the knee, a change made to a femoral bone cut based on patient-specific biomotion data can be referenced to or linked with a concomitant change to a bone cut on an opposing tibial surface, for example, if less femoral bone is resected, the computer program may elect to resect more tibial bone.

Similarly, if a femoral implant shape is changed, for example on an external surface, this can be accompanied by a change in the tibial component shape. This is, for example, particularly applicable when at least portions of the tibial bearing surface negatively-match the femoral joint-facing surface.

Similarly, if the footprint of a femoral implant is broadened, this can be accompanied by a widening of the bearing surface of a tibial component. Similarly, if a tibial implant shape is changed, for example on an external surface, this can be accompanied by a change in the femoral component shape. This is, for example, particularly applicable when at least portions of the femoral bearing surface negatively-match the tibial joint-facing surface.

Similarly, if a patellar component radius is widened, this can be accompanied by a widening of an opposing trochlear bearing surface radius, or vice-versa.

These linked changes also can apply for hip and/or shoulder implants. For example, in a hip, if a femoral implant shape is changed, for example on an external surface, this can be accompanied by a change in an acetabular component shape. This is, for example, particularly applicable when at least portions of the acetabular bearing surface negatively-match the femoral joint-facing surface. In a shoulder, if a glenoid implant shape is changed, for example on an external surface, this can be accompanied by a change in a humeral component shape. This is, for example, particularly applicable when at least portions of the humeral bearing surface negatively-match the glenoid joint-facing surface, or vice-versa.

Any combination is possible as it pertains to the shape, orientation, and size of implant components on two or more opposing surfaces.

By optimizing implant shape in this manner, it is possible to establish normal or near normal kinematics. Moreover, it is possible to avoid implant related complications, including but not limited to anterior notching, notch impingement, posterior femoral component impingement in high flexion, and other complications associated with existing implant designs. For example, certain designs of the femoral components of traditional knee implants have attempted to address limitations associated with traditional knee implants in high flexion by altering the thickness of the distal and/or posterior condyles of the femoral implant component or by altering the height of the posterior condyles of the femoral implant component. Since such traditional implants follow a one-size-fits-all approach, they are limited to altering only one or two aspects of an implant design. However, with the design approaches described herein, various features of an implant component can be designed for an individual to address multiple issues, including issues associated with high flexion motion. For example, designs as described herein can alter an implant component's bone-facing surface (for example, number, angle, and orientation of bone cuts), joint-facing surface (for example, surface contour and curvatures) and other features (for example, implant height, width, and other features) to address issues with high flexion together with other issues.

Biomotion models for a particular patient can be supplemented with patient-specific finite element modeling or other biomechanical models known in the art. Resultant forces in the knee joint can be calculated for each component for each specific patient. The implant can be engineered to the patient's load and force demands. For instance, a 1251*b*. patient may not need a tibial plateau as thick as a patient with 280 lbs. Similarly, the polyethylene can be adjusted in shape, thickness and material properties for each patient. For example, a 3 mm polyethylene insert can be used in a light patient with low force and a heavier or more active patient may need an 8 mm polymer insert or similar device.

4.4 Restoration or Optimization of Joint-Line Location and Joint Gap Width

Traditional implants frequently can alter the location of a patient's existing or natural joint-line. For example, with a traditional implant a patient's joint-line can be offset proximally or distally as compared to the corresponding joint-line on the corresponding limb. This can cause mechanical asymmetry between the limbs and result in uneven movement or mechanical instability when the limbs are used together. An offset joint-line with a traditional implant also can cause the patient's body to appear symmetrical.

Figures 23A, 23B:
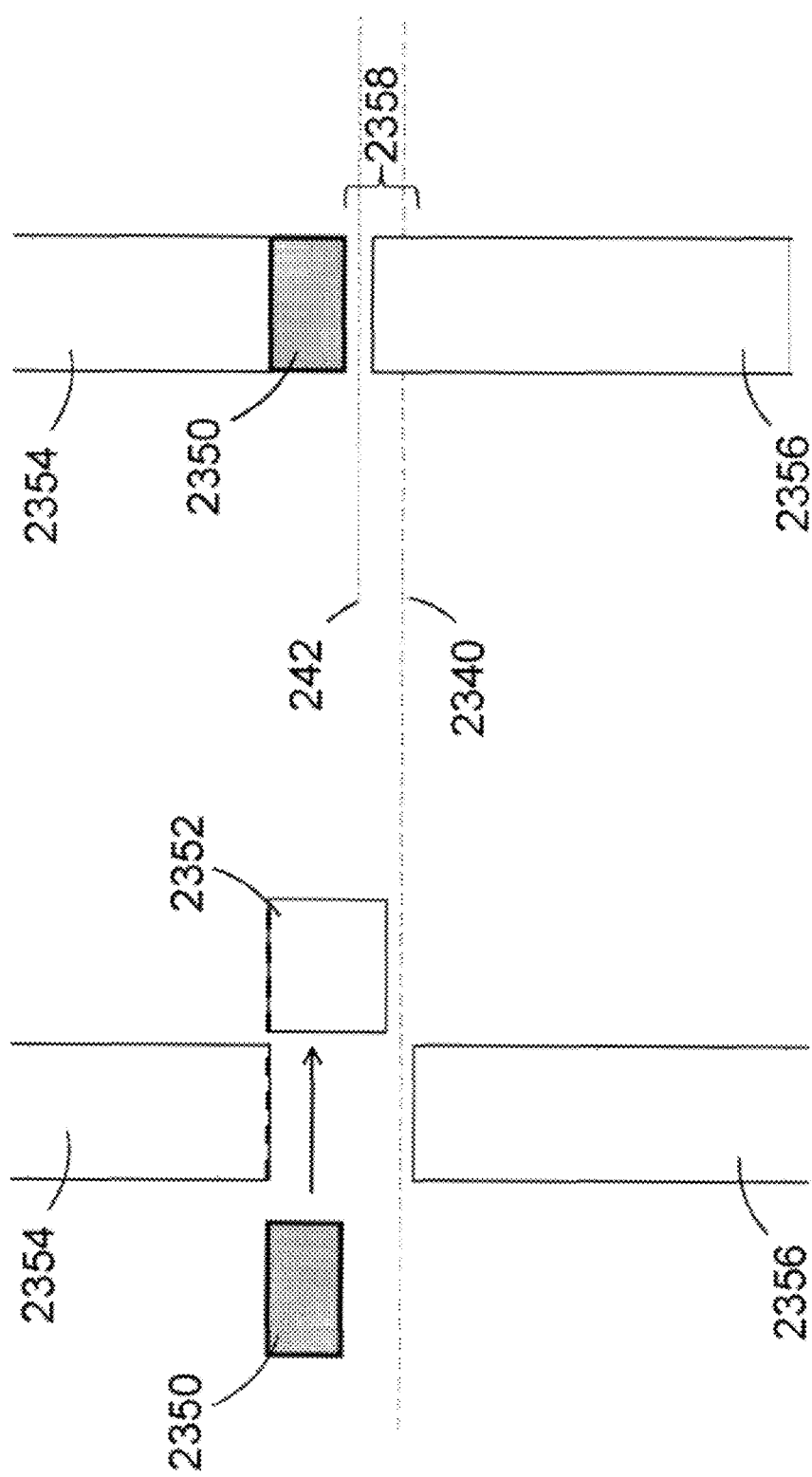
FIGS. 23A and 23B schematically show a traditional implant component that dislocates the joint-line.

Traditional implants frequently alter the location of a patient's existing or natural joint-line because they have a standard thickness that is thicker or thinner than the bone and/or cartilage that they are replacing. For example, a schematic of a traditional implant component is shown in FIGS. 23A and 23B. In the figure, the dashed line represents the patient's existing or natural joint-line 2340 and the dotted line represents the offset joint-line 2342 following insertion of the traditional implant component 2350. As shown in FIG. 23A, the traditional implant component 2350 with a standard thickness replaces a resected piece 2352 of a first biological structure 2354 at an articulation between the first biological structure 2354 and a second biological structure 2356. The resected piece 2352 of the biological structure can include, for example, bone and/or cartilage, and the biological structure 2354 can include bone and/or cartilage. In the figure, the standard thickness of the traditional implant component 2350 differs from the thickness of the resected piece 2352. Therefore, as shown in FIG. 23B, the replacement of the resected piece 2352 with the traditional implant component 2350 creates a wider joint gap 2358 and/or an offset joint-line. Surgeons can address the widened joint gap 2358 by pulling the second biological structure 2356 toward the first biological structure 2354 and tightening the ligaments associated with the joint. However, while this alteration restores some of the mechanical instability created by a widened joint gap, it also exacerbates the displacement of the joint-line.

Certain embodiments are directed to implant components, and related designs and methods, having one or more features that are engineered from patient-specific data to restore or optimize the particular patient's joint-line location. In addition or alternatively, certain patient-specific implant components, and related designs and methods, can have one or more features that are engineered from patient-specific data to restore or optimize the particular patient's joint gap width.

Figure 23C:
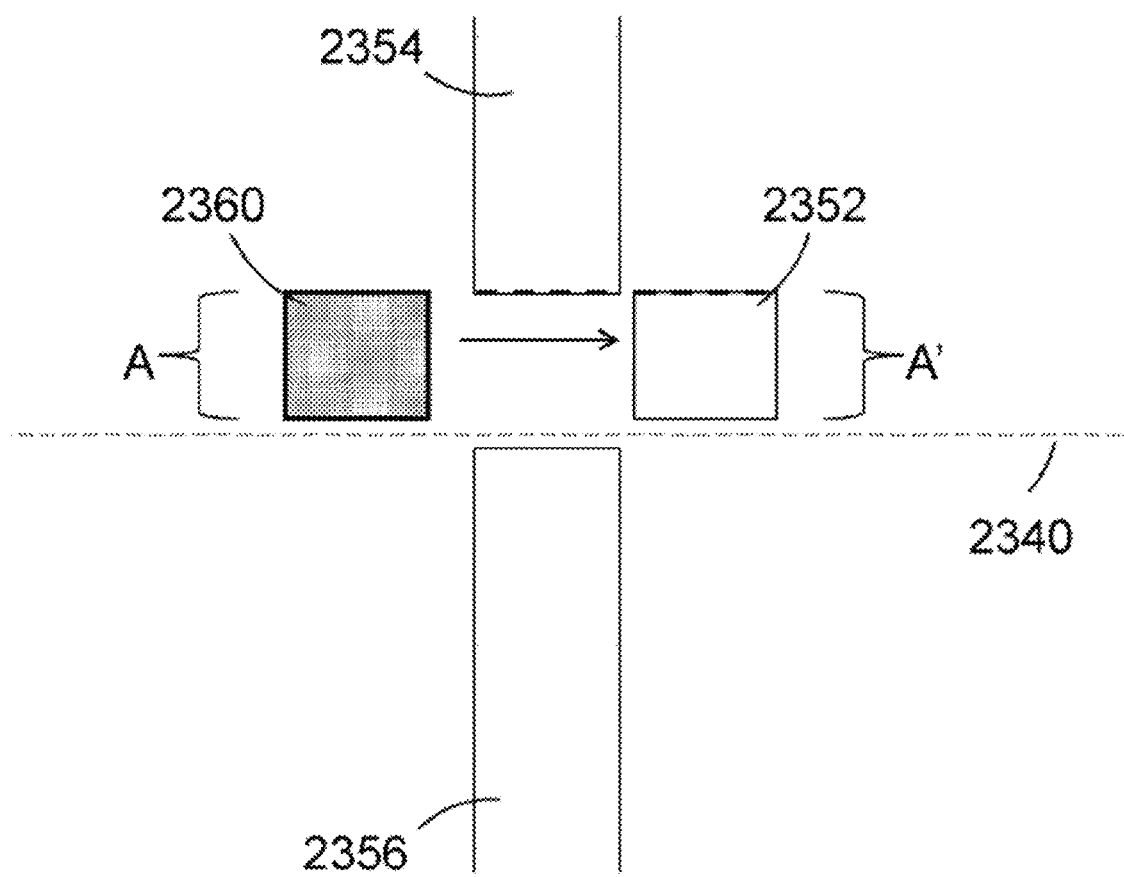
FIG. 23C schematically shows a patient-specific implant component in which the existing or natural joint-line is retained.

In certain embodiments, an implant component can be designed based on patient-specific data to include a thickness profile between its joint-facing surface and its bone-facing surface to restore and/or optimize the particular patient's joint-line location. For example, as schematically depicted in FIG. 23C, the thickness profile (shown as A) of the patient-specific implant component 2360 can be designed to, at least in part, substantially positively-match the distance from the patient's existing or natural joint-line 2340 to the articular surface of the biological structure 2354 that the implant 2360 engages. In the schematic depicted in the figure, the patient joint gap width also is retained.

The matching thickness profile can be designed based on one or more of the following considerations: the thickness (shown as A' in FIG. 23C) of a resected piece of biological structure that the implant replaces; the thickness of absent or decayed biological structure that the implant replaces; the relative compressibility of the implant material(s) and the biological material(s) that the implant replaces; and the thickness of the saw blade(s) used for resectioning and/or material lost in removing a resected piece.

For embodiments directed to an implant component thickness that is engineered based on patient-specific data to optimize joint-line location (and/or other parameters such as preserving bone), the minimum acceptable thickness of the implant can be a significant consideration. Minimal acceptable thickness can be determined based on any criteria, such as a minimum mechanical strength, for example, as determined by FEA. Accordingly, in certain embodiments, an implant or implant design includes an implant component having a minimal thickness profile. For example, in certain embodiments a pre-primary or primary femoral implant component can include a thickness between the joint-facing surface and the bone-facing surface of the implant component that is less than 5 mm, less than 4 mm, less than 3 mm, and/or less than 2 mm.

In certain embodiments, the implant component thickness can range from about 2 mm to about 3 mm. Therefore, for patients that require only minimal bone resectioning of no more than 2-3 mm depth from the joint-line, an implant component designed with a thickness to substantially positively-match the 2-3 mm bone resectioning can maintain the joint-line location. Moreover, a subsequent traditional primary implant, for example, of 5 mm or greater thickness can be applied later with an additional cut depth of 3-2 mm or greater (for a total 5 mm cut depth). This can allow for maintenance of the joint-line with the subsequent, traditional primary as well.

Figure 24:
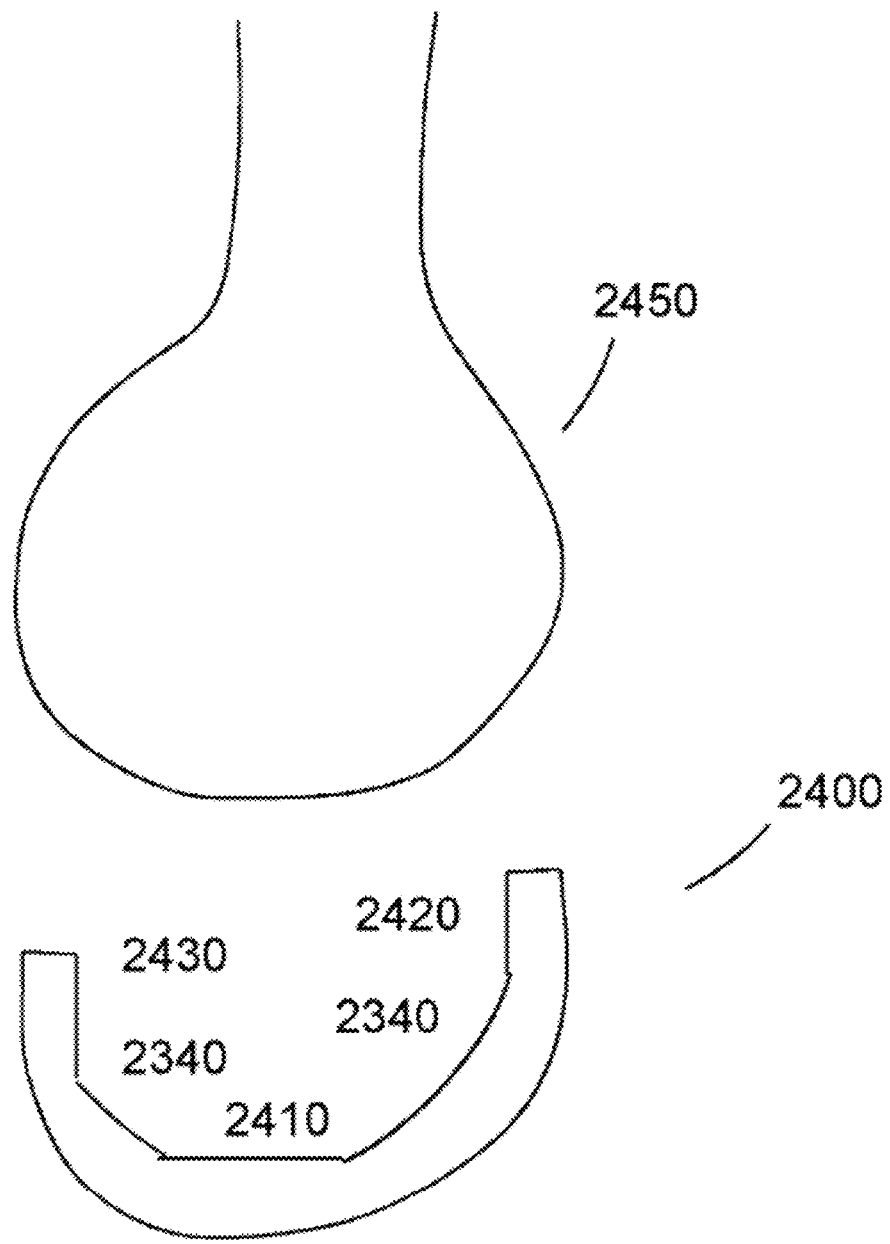
FIG. 24 depicts an implant or implant design that includes a straight distal cut, a straight anterior cut, a straight posterior cut, and curvilinear chamfer cuts.

Certain embodiments directed to implants or implant designs optimized to achieve minimal implant thickness can include a higher number of bone cuts, for example, six, seven, eight, nine or more bone cuts, on the inner, bone-facing surface of the implant. The bone cuts can be oriented in various dimensions, for example, in a flexed-orientation. Moreover, certain embodiments can include on the inner, bone-facing surface any combination of straight cuts and curvilinear cuts. One or more curvilinear cuts can be designed to substantially positively-match the patient's uncut articular surface, such as a subchondral bone surface exposed by resurfacing. Alternatively, one or more curvilinear cuts can be designed to substantially positively-match a cut surface of the patient's bone, for example, a cut curvilinear surface. Example 5 describes an example of an implant and implant design that includes a straight anterior cut, a straight posterior cut, and a curvilinear cut in between. Moreover, as depicted in FIG. 24, an implant 2400 can include a planar distal cut 2410, a straight anterior cut 2420, a straight posterior cut 2430, and curvilinear chamfer cuts 2440 in between to substantially negatively-match corresponding resected surface(s) of the femur 2450. Example 6 describes an example of an implant or implant design that includes on the inner, bone-facing surface one or no straight cuts and portions that substantially positively-match an uncut articular bone surface.

The inner, bone-facing surface of the implant component can be designed to substantially negatively-match the cut bone surface, both curved and straight portions. The curved cuts to the bone can be performed with a router saw, as described in Example 5. Any number of the cuts can have a depth of 2-3 mm, and the implant component thickness can be designed to positively-match the cut depth across a portion of the implant or across the entire implant.

By positively-matching the implant component thickness profile with the cut depth profile, and by negatively-matching the component bone-facing surface with the resected articular surface of the biological structure, certain features of the component joint-facing surface can positively-match the corresponding biological features that it replaces. For example, if the component bone-facing surface and thickness match the corresponding features of the biological structure, the component joint-facing curvature, such as a j-curve, also can match the corresponding surface curvature of the patient's biological structure.

Figure 25:
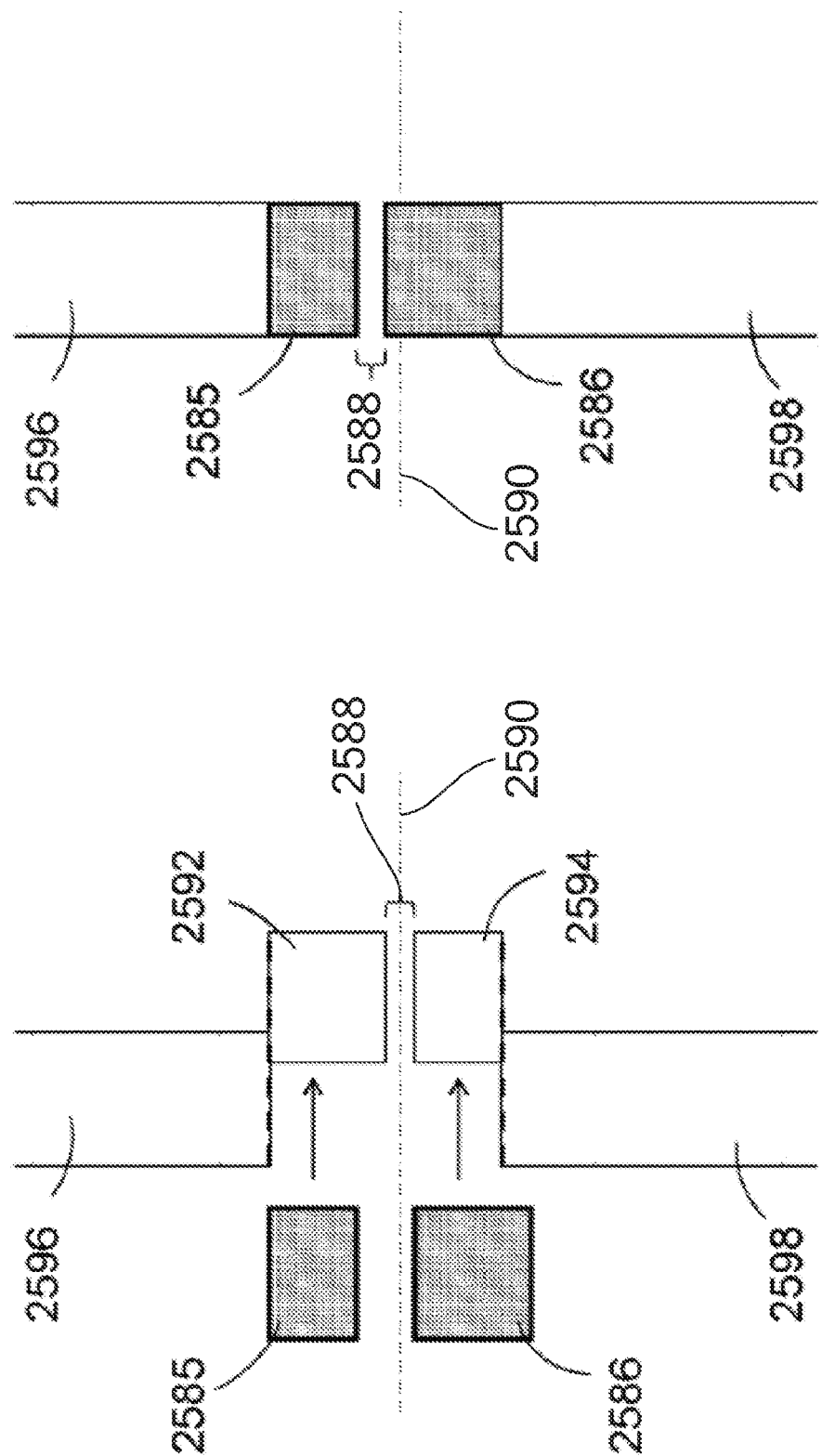
FIGS. 25A and 25B schematically show a patient-specific implant component designed to substantially positively-match the patient's existing or natural joint gap.

In certain embodiments, one or more implant components can be designed based on patient-specific data to include a thickness profile that retains, restores, and/or optimizes the particular patient's joint gap width. For example, as schematically depicted in FIGS. 25A and 25B, the patient-specific implant components 2585, 2586 can be designed to, at least in part, substantially positively-match the patient's existing or natural joint gap 2588. In the figure, the dashed line represents the patient's existing or natural joint-line 2590. The patient-specific implant components 2585, 2586 do not have thicknesses that match the corresponding resected pieces 2592, 2594 of biological structures 2596, 2598. However, as shown in FIG. 25B, the implant components 2585, 2586 are designed to retain the patient's specific gap width 2588.

If the thickness of an implant component is greater than the depth of the corresponding bone cut, then the thicker implant component can shift the joint-line down. However, as shown in FIGS. 25A and 25B, the joint gap width can be retained by designing a second implant component to offset the greater thickness of the first implant component. For example, in total knee replacements that include both a femoral implant component and a tibial implant component, if the femoral implant component is thicker than the depth of the corresponding bone cut, more tibial bone can be cut and/or a thinner tibial implant can be used.

One or more components of a tibial implant can be designed thinner to retain, restore, and/or optimize a patient's joint-line and/or joint gap width. For example, one or both of a tibial tray and a tibial tray insert (e.g., a poly insert) can be designed and/or selected (e.g., preoperatively selected) to be thinner in one or more locations in order to address joint-line and/or joint-gap issues for a particular patient. In certain embodiments, a tibial bone cut and/or the thickness of a corresponding portion of a tibial implant component may be less than about 6 mm, less than about 5 mm, less than about 4 mm, less than about 3 mm, and/or less than about 2 mm.

In certain embodiments, one or more implant components can designed based on patient-specific data to include a thickness profile that retains or alters a particular patient's joint gap width to retain or correct another patient-specific feature. For example, the patient-specific data can include data regarding the length of the patient's corresponding limbs (e.g., left and right limbs) and the implant component(s) can be designed to, at least in part, alter the length of one limb to better match the length of the corresponding limb.

5. Selecting and/or Designing an Implant Component and, Optionally, Related Surgical Steps and Guide Tools Any combination of one or more of the above-identified parameters and/or one or more additional parameters can be used in the design and/or selection of a patient-adapted (e.g., patient-specific and/or patient-engineered) implant component and, in certain embodiments, in the design and/or selection of corresponding patient-adapted resection cuts and/or patient-adapted guide tools. In particular assessments, a patient's biological features and feature measurements are used to select and/or design one or more implant component features and feature measurements, resection cut features and feature measurements, and/or guide tool features and feature measurements.

In certain embodiments, the assessment process includes selecting and/or designing one or more features and/or feature measurements of an implant component and, optionally, of a corresponding resection cut strategy and/or guide tool that is adapted (e.g., patient-adapted based on one or more of a particular patient's biological features and/or feature measurements) to achieve or address, at least in part, one or more of the following parameters for the particular patient: (1) correction of a joint deformity; (2) correction of a limb alignment deformity; (3) preservation of bone, cartilage, and/or ligaments at the joint; (4) preservation, restoration, or enhancement of one or more features of the patient's biology, for example, trochlea and trochlear shape; (5) preservation, restoration, or enhancement of joint kinematics, including, for example, ligament function and implant impingement; (6) preservation, restoration, or enhancement of the patient's joint-line location and/or joint gap width; and (7) preservation, restoration, or enhancement of other target features.

Correcting a joint deformity and/or a limb alignment deformity can include, for example, generating a virtual model of the patient's joint, limb, and/or other relevant biological structure(s); virtually correcting the deformity and/or aligning the limb; and selecting and/or designing one or more surgical steps (e.g., one or more resection cuts), one or more guide tools, and/or one or more implant components to physically perform and/or accommodate the correction.

Preserving, restoring, or enhancing bone, cartilage, and/or ligaments can include, for example, identifying diseased tissue from one or more images of the patient's joint, identifying a minimum implant thickness for the patient (based on, for example, femur and/or condyle size and patient weight); virtually assessing combinations of resection cuts and implant component features, such as variable implant thickness, bone cut numbers, bone cut angles, and/or bone cut orientations; identifying a combination of resection cuts and/or implant component features that, for example, remove diseased tissue and also provide maximum bone preservation (i.e., minimum amount of resected bone) and at least the minimum implant thickness for the particular patient; and selecting and/or designing one or more surgical steps (e.g., one or more resection cuts), one or more guide tools, and/or one or more implant components to provide the resection cuts and/or implant component features that provide removal of the diseased tissue, maximum bone preservation, and at least the minimum implant thickness for the particular patient.

Preserving or restoring one or more features of a patient's biology can include, for example, selecting and/or designing one or more surgical steps (e.g., one or more resection cuts), one or more guide tools, and/or one or more implant components so that one or more of the patient's postoperative implant features substantially match the patient's preoperative biological features or the patient's healthy biological features (e.g., as identified from a previous image of the patient's joint when it was healthy or from an image the patient's contralateral healthy joint).

Enhancing one or more features of a patient's biology can include, for example, selecting and/or designing one or more surgical steps (e.g., one or more resection cuts), one or more guide tools, and/or one or more implant components so that the implant component, once implanted, includes features that approximate one or more features of a healthy biological feature for the particular patient.

Preservation or restoration of the patient's joint kinematics can include, for example, selecting and/or designing one or more surgical steps (e.g., one or more resection cuts), one or more guide tools, and/or one or more implant components so that the patient's post-operative joint kinematics substantially match the patient's pre-operative joint kinematics and/or substantially match the patient's healthy joint kinematics (e.g., as identified from previous images of the patient's joint when it was healthy or from an image the patient's contralateral healthy joint).

Enhancing the patient's joint kinematics can include, for example, selecting and/or designing one or more surgical steps (e.g., one or more resection cuts), one or more guide tools, and/or one or more implant components that provide healthy joint kinematics estimated for the particular patient and/or that provide proper joint kinematics to the patient. Optimization of joint kinematics also can include optimizing ligament loading or ligament function during motion.

Preservation or restoration of the patient's joint-line location and/or joint gap width can include, for example, selecting and/or designing one or more surgical steps (e.g., one or more resection cuts), one or more guide tools, and/or one or more implant components so that the patient's joint-line and or joint-gap width substantially match the patient's existing joint-line and or joint-gap width or the patient's healthy joint-line and/or joint-gap width (e.g., as identified from previous images of the patient's joint when it was healthy or from an image the patient's contralateral healthy joint).

Enhancing the patient's joint-line location and/or joint gap width can include, for example, selecting and/or designing one or more surgical steps (e.g., one or more resection cuts), one or more guide tools, and/or one or more implant components that provide a healthy joint-line location and/or joint gap width and/or estimated for the particular patient and/or that provide proper kinematics to the patient.

5.1 Using Parameters to Assess and Select and/or Design an Implant Component

Assessment of the above-identified parameters, optionally with one or more additional parameters, can be conducted using various formats. For example, the assessment of one or more parameters can be performed in series, in parallel, or in a combination of serial and parallel steps, optionally with a software-directed computer. For example, one or more selected implant component features and feature measurements, optionally with one or more selected resection cut features and feature measurements and one or more selected guide tool features and feature measurements can be altered and assessed in series, in parallel, or in a combination format, to assess the fit between selected parameter thresholds and the selected features and feature measurements. Any one or more of the parameters and features and/or feature measurements can be the first to be selected and/or designed. Alternatively, one or more, or all, of the parameters and/or features can be assessed simultaneously.

The assessment process can be iterative in nature. For example, one or more first parameters can be assessed and the related implant component and/or resection cut features and feature measurements tentatively or conditionally can be determined. Next, one or more second parameters can be assessed and, optionally, one or more features and/or feature measurements determined. Then, the tentative or conditional features and/or feature measurements for the first assessed parameter(s) optionally can be altered based on the assessment and optional determinations for the second assessed parameters. The assessment process can be fully automated or it can be partially automated allowing for user interaction. User interaction can be particularly useful for quality assurance purposes.

In the assessment, different weighting can be applied to any of the parameters or parameter thresholds, for example, based on the patient's age, the surgeon's preference or the patient's preference. Feedback mechanisms can be used to show the user or the software the effect that certain feature and/or feature measurement changes can have on desired changes to parameters values, e.g., relative to selected parameter thresholds. For example, a feedback mechanism can be used to determine the effect that changes in features intended to maximize bone preservation (e.g., implant component thickness(es), bone cut number, cut angles, cut orientations, and related resection cut number, angles, and orientations) have on other parameters such as limb alignment, deformity correction, and/or joint kinematic parameters, for example, relative to selected parameter thresholds. Accordingly, implant component features and/or feature measurements (and, optionally, resection cut and guide tool features and/or feature measurements) can be modeled virtually and modified reiteratively to achieve an optimum solution for a particular patient.

Figure 26:
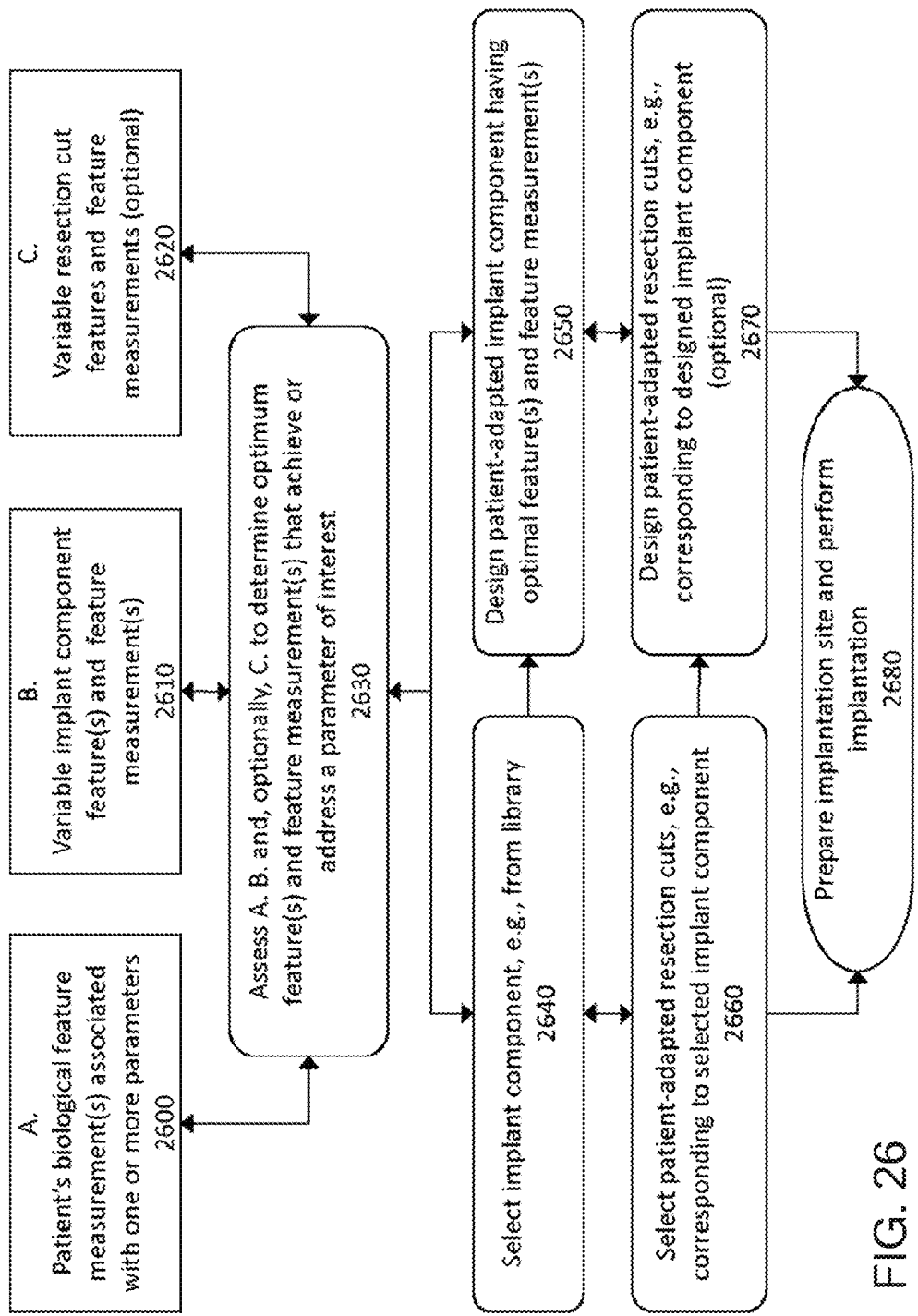
FIG. 26 is a flow chart illustrating the process of assessing and selecting and/or designing one or more implant component features and/or feature measurements, and, optionally assessing and selecting and/or designing one or more resection cut features and feature measurements, for a particular patient.

FIG. 26 is a flow chart illustrating the process of assessing and selecting and/or designing one or more implant component features and/or feature measurements, and, optionally assessing and selecting and/or designing one or more resection cut features and feature measurements, for a particular patient. Using the techniques described herein or those suitable and known in the art, one or more of the patient's biological features and/or feature measurements are obtained 2600. In addition, one or more variable implant component features and/or feature measurements are obtained 2610. Optionally, one or more variable resection cut features and/or feature measurements are obtained 2620. Moreover, one or more variable guide tool features and/or feature measurements also can optionally be obtained. Each one of these step can be repeated multiple times, as desired.

The obtained patient's biological features and feature measurements, implant component features and feature measurements, and, optionally, resection cut and/or guide tool features and/or feature measurements then can be assessed to determine the optimum implant component features and/or feature measurements, and optionally, resection cut and/or guide tool features and/or feature measurements, that achieve one or more target or threshold values for parameters of interest 2630 (e.g., by maintaining or restoring a patient's healthy joint feature). As noted, parameters of interest can include, for example, one or more of (1) joint deformity correction; (2) limb alignment correction; (3) bone, cartilage, and/or ligaments preservation at the joint; (4) preservation, restoration, or enhancement of one or more features of the patient's biology, for example, trochlea and trochlear shape; (5) preservation, restoration, or enhancement of joint kinematics, including, for example, ligament function and implant impingement; (6) preservation, restoration, or enhancement of the patient's joint-line location and/or joint gap width; and (7) preservation, restoration, or enhancement of other target features. This step can be repeated as desired. For example, the assessment step 2630 can be reiteratively repeated after obtaining various feature and feature measurement information 2600, 2610, 2620.

Once the one or more optimum implant component features and/or feature measurements are determined, the implant component(s) can be selected 2640, designed 2650, or selected and designed 2640, 2650. For example, an implant component having some optimum features and/or feature measurements can be designed using one or more CAD software programs or other specialized software to optimize additional features or feature measurements of the implant component. One or more manufacturing techniques described herein or known in the art can be used in the design step to produce the additional optimized features and/or feature measurements. This process can be repeated as desired.

Optionally, one or more resection cut features and/or feature measurements can be selected 2660, designed 2670, or selected and further designed 2660, 2670. For example, a resection cut strategy selected to have some optimum features and/or feature measurements can be designed further using one or more CAD software programs or other specialized software to optimize additional features or measurements of the resection cuts, for example, so that the resected surfaces substantially match optimized bone-facing surfaces of the selected and designed implant component. This process can be repeated as desired.

Moreover, optionally, one or more guide tool features and/or feature measurements can be selected, designed, or selected and further designed. For example, a guide tool having some optimum features and/or feature measurements can be designed further using one or more CAD software programs or other specialized software to optimize additional features or feature measurements of the guide tool. One or more manufacturing techniques described herein or known in the art can be used in the design step to produce the additional, optimized features and/or feature measurements, for example, to facilitate one or more resection cuts that, optionally, substantially match one or more optimized bone-facing surfaces of a selected and designed implant component. This process can be repeated as desired.

As will be appreciated by those of skill in the art, the process of selecting and/or designing an implant component feature and/or feature measurement, resection cut feature and/or feature measurement, and/or guide tool feature and/or feature measurement can be tested against the information obtained regarding the patient's biological features, for example, from one or more MRI or CT or x-ray images from the patient, to ensure that the features and/or feature measurements are optimum with respect to the selected parameter targets or thresholds. Testing can be accomplished by, for example, superimposing the implant image over the image for the patient's joint. Once optimum features and/or feature measurements for the implant component, and optionally for the resection cuts and/or guide tools, have been selected and/or designed, the implant site can be prepared, for example by removing cartilage and/or resectioning bone from the joint surface, and the implant component can be implanted into the joint 2680.

The joint implant component bone-facing surface, and optionally the resection cuts and guide tools, can be selected and/or designed to include one or more features that achieve an anatomic or near anatomic fit with the existing surface or with a resected surface of the joint. Moreover, the joint implant component joint-facing surface, and optionally the resection cuts and guide tools, can be selected and/or designed, for example, to replicate the patient's existing joint anatomy, to replicate the patient's healthy joint anatomy, to enhance the patient's joint anatomy, and/or to optimize fit with an opposing implant component. Accordingly, both the existing surface of the joint and the desired resulting surface of the joint can be assessed. This technique can be particularly useful for implants that are not anchored into the bone.

As will be appreciated by those of skill in the art, the physician, or other person can obtain a measurement of a biological feature (e.g., a target joint) 2600 and then directly select 2640, design, 2650, or select and design 2640, 2650 a joint implant component having desired patient-adapted features and/or feature measurements. Designing can include, for example, design and manufacturing.

5.2 Setting and Weighing Parameters

As described herein, certain embodiments can apply modeling, for example, virtual modeling and/or mathematical modeling, to identify optimum implant component features and measurements, and optionally resection features and measurements, to achieve or advance one or more parameter targets or thresholds. For example, a model of patient's joint or limb can be used to identify, select, and/or design one or more optimum features and/or feature measurements relative to selected parameters for an implant component and, optionally, for corresponding resection cuts and/or guide tools. In certain embodiments, a physician, clinician, or other user can select one or more parameters, parameter thresholds or targets, and/or relative weightings for the parameters included in the model. Alternatively or in addition, clinical data, for example obtained from clinical trials, or intraoperative data, can be included in selecting parameter targets or thresholds, and/or in determining optimum features and/or feature measurements for an implant component, resection cut, and/or guide tool.

Certain embodiments described herein include generating and/or using a model, for example, a virtual model, of the patient's joint that includes selected parameters and/or parameter measurements and virtually selecting and/or designing one or more implant components, and optionally resection cuts and/or guide tools to fit the virtual model in accordance with the selected parameters and/or parameter measurements. This approach allows for iterative selection and/or design improvement and can include steps to virtually assess fit relative to the selected parameters and/or parameter measurements, such as (1) correction of a joint deformity; (2) correction of a limb alignment deformity; (3) preservation of bone, cartilage, and/or ligaments at the joint; (4) preservation, restoration, or enhancement of one or more features of the patient's biology, for example, trochlea and trochlear shape; (5) preservation, restoration, or enhancement of joint kinematics, including, for example, ligament function and implant impingement; (6) preservation, restoration, or enhancement of the patient's joint-line location and/or joint gap width; and (7) preservation, restoration, or enhancement of other target features.

One or more parametric thresholds and/or weightings can be applied for the selection and/or designing process. Different parameters can have the same weighting or they can have different weightings. A parameter can include one or more thresholds for selecting one or more implants. The thresholds can include one or more minimum threshold values (e.g., with different weightings), for example, 80%, greater than 80%, 85%, greater than 85%, 90%, greater than 90%, 95%, greater than 95%, 97%, greater than 97%, 98%, greater than 98%, 99%, greater than 99%, 100%, and/or greater than 100% a target value, such as minimum implant coverage of a certain surface on the patient's anatomical structure. Alternatively or in addition, the thresholds can include one or more maximum threshold values (e.g., with different weightings), such as 105%, less than 105%, 103%, less than 103%, 102%, less than 102%, 101%, less than 101%, 100%, and/or less than 100% a target value, such as maximum implant coverage of a certain surface on the patient's anatomical structure.

One or more parameter thresholds can be absolute, for example, by selecting and/or designing for only implants that meet the threshold, for example, a threshold for a particular patient of 95% mediolateral femoral condyle coverage all around the condyle(s). An example of a selection and/or design process having multiple absolute thresholds is a process that selects and/or designs femoral implant components that must meet both a minimum threshold for a particular patient of 95% mediolateral femoral condyle coverage in the central weight-bearing region, and a minimum threshold of greater than 80% mediolateral femoral condyle coverage outside the weight-bearing area.

Alternatively or in addition, one or more parameter thresholds can be contingent on one or more other factors. In particular, a selection and/or designing process can successively search a library for implants based on contingent thresholds. For example, femoral implant components meeting a minimum threshold of 99% mediolateral femoral condyle coverage initially can be selected. If no implant meets the threshold, or if some implants meet the threshold but do not meet other parameter thresholds, then a second selection round can include implants meeting a minimum threshold of 98% mediolateral femoral condyle coverage. The process can continue to use additional, contingent thresholds until an implant with the selected parameter thresholds is identified.

Different thresholds can be defined in different anatomic regions and for different parameters. For example, in certain embodiments of a knee implant design, the amount of mediolateral tibial implant component coverage can be set at 90%, while the amount of anteroposterior tibial implant component coverage can be set at 85%. In another illustrative example, the congruency in intercondylar notch shape can be set at 80% required, while the required mediolateral condylar coverage can be set at 95%.

5.3 Computer-Aided Optimization

Any of the methods described herein can be performed, at least in part, using a computer-readable medium having instructions stored thereon, which, when executed by one or more processors, causes the one or more processors to perform one or more operations corresponding to one or more steps in the method. Any of the methods can include the steps of receiving input from a device or user and producing an output for a user, for example, a physician, clinician, technician, or other user. Executed instructions on the computer-readable medium (i.e., a software program) can be used, for example, to receive as input patient-specific information (e.g., images of a patient's biological structure) and provide as output a virtual model of the patient's biological structure. Similarly, executed instructions on a computer-readable medium can be used to receive as input patient-specific information and user-selected and/or weighted parameters and then provide as output to a user values or ranges of values for those parameters and/or for resection cut features, guide tool features, and/or implant component features. For example, in certain embodiments, patient-specific information can be input into a computer software program for selecting and/or designing one or more resection cuts, guide tools, and/or implant components, and one or more of the following parameters can be optimization in the design process: (1) correction of joint deformity; (2) correction of a limb alignment deformity; (3) preservation of bone, cartilage, and/or ligaments at the joint; (4) preservation, restoration, or enhancement of one or more features of the patient's biology, for example, trochlea and trochlear shape; (5) preservation, restoration, enhancement of joint kinematics, including, for example, ligament function and implant impingement; (6) preservation, restoration, or enhancement of the patient's joint-line location and/or joint gap width; and (7) preservation, restoration, or enhancement of other target features.

Optimization of multiple parameters may result in conflicting constraints; for example, optimizing one parameter may cause an undesired deviation to one or more other parameters. In cases where not all constraints can be achieved at the same time, parameters can be assigned a priority or weight in the software program. The priority or weighting can be automated (e.g., part of the computer program) and/or it can be selected by a user depending on the user's desired design goals, for example, minimization of bone loss, or retention of existing joint-line to preserve kinematics, or combination to accommodate both parameters in overall design. As an illustrative example, in certain embodiments, selection and/or design of a knee implant can include obtaining patient-specific information (e.g., from radiographic images or CT images) of a patient's knee and inputting that information into the computer program to model features such as minimum thickness of femoral component (to minimize resected bone on femur), tibial resection cut height (to minimize resected bone on tibia), and joint-line position (preferably to preserve for natural kinematics). These features can be modeled and analyzed relative to a weighting of parameters such as preserving bone and preserving joint kinematics. As output, one or more resection cut features, guide tool features, and/or implant component features that optimize the identified parameters relative to the selective weightings can be provided.

In any automated process or process step performed by the computer system, constraints pertaining to a specific implant model, to a group of patients or to the individual patient may be taken into account. For example, the maximum implant thickness or allowable positions of implant anchors can depend on the type of implant. The minimum allowable implant thickness can depend on the patient's bone quality.

Any one or more steps of the assessment, selection, and/or design may be partially or fully automated, for example, using a computer-run software program and/or one or more robots. For example, processing of the patient data, the assessment of biological features and/or feature measurements, the assessment of implant component features and/or feature measurements, the optional assessment of resection cut and/or guide tool features and/or feature measurements, the selection and/or design of one or more features of a patient-adapted implant component, and/or the implantation procedure(s) may be partially or wholly automated. For example, patient data, with optional user-defined parameters, may be inputted or transferred by a user and/or by electronic transfer into a software-directed computer system that can identify variable implant component features and/or feature measurements and perform operations to generate one or more virtual models and/or implant design specifications, for example, in accordance with one or more target or threshold parameters. Implant selection and/or design data, with optional user-defined parameters, may be inputted or transferred by a user and/or by electronic transfer into a software-directed computer system that performs a series of operations to transform the data and optional parameters into one or more implant manufacturing specifications. Implant design data or implant manufacturing data, optionally with user-defined parameters, may be inputted or transferred by a user and/or by electronic transfer into a software-directed computer system that directs one or more manufacturing instruments to produce one or more implant components from a starting material, such as a raw material or starting blank material. Implant design data, implant manufacturing data, or implant data, optionally with user-defined parameters, may be inputted or transferred by a user and/or by electronic transfer into a software-directed computer system that performs a series of operations to transform the data and optional parameters into one or more surgical procedure specifications or instructions. Implant design data, implant manufacturing data, implant data, or surgical procedure data, optionally with user-defined parameters, may be inputted or transferred by a user and/or by electronic transfer into a software-directed computer system that directs one or more automated surgical instruments, for example, a robot, to perform one or more surgical steps. In certain embodiments, one or more of these actions can be performed as steps in a single process by one or more software-directed computer systems.

In certain embodiments, the implant component includes one or more bone cuts on its bone-facing surface. Features of these bone cuts, and optionally features of corresponding resection cuts, can be optimized by a computer system based on patient-specific data. For example, the bone cut number and one or more bone cut planes, angles, or depths, as well as the corresponding resection cut number and one or more resection cut planes, angles, or depths, can be optimized, for example, to preserve the maximum amount of bone for each individual patient based on a series of two-dimensional images or a three-dimensional representation of the articular anatomy and geometry and/or on a target limb alignment and/or deformity correction. Optionally, one or more of the bone cut features and/or resection cut features can be adjusted by the operator.

The computer system also can construct the implant surfaces. Surfaces may be composed of different elements. In certain embodiments, elements of the surfaces can conform to the patient's anatomy. In these situations, the computer system can build a surface using the patient's anatomical model, for example by constructing a surface that is identical with or mostly parallel to the patient's anatomical surface. In certain embodiments, the computer system can use geometric elements such as arcs or planes to construct a surface. Transitions between surfaces can be smoothed using tapers or fillets. Additionally, the computer system may take into account constraints such as a minimum or maximum threshold thickness or length or curvature of parts or features of the implant component when constructing the surfaces.

In another embodiment, the computer system can automatically or semi-automatically add other features to the implant design. For example, the computer system can add pegs or anchors or other attachment mechanisms. The system can place the features using anatomical landmarks. Constraints can be used to restrict the placement of the features. Examples of constraints for placement of pegs are the distance between pegs and from the pegs to the edge of the implant, the height of the pegs that results from their position on the implant, and forcing the pegs to be located on the center line. Optionally, the system can allow the user to fine-tune the peg placement, with or without enforcing the constraints.

5.4 Selecting and/or Designing an Implant Component

Using patient-specific features and feature measurements, and selected parameters and parameter thresholds, an implant component, resection cut strategy, and/or guide tool can be selected (e.g., from a library) and/or designed (e.g. virtually designed and manufactured) to have one or more patient-adapted features. In certain embodiments, one or more features of an implant component (and, optionally, one or more features of a resection cut strategy and/or guide tool) are selected for a particular patient based on patient-specific data and desired parameter targets or thresholds. For example, an implant component or implant component features can be selected from a virtual library of implant components and/or component features to include one or more patient-specific features and/or optimized features for a particular patient. Alternatively or in addition, an implant component can be selected from an actual library of implant components to include one or more patient-specific features and/or optimized features for the particular patient.

In certain embodiments, one or more features of an implant component (and, optionally, one or more features of a resection cut strategy and/or guide tool) can be designed (e.g., designed and manufactured) to include one or more patient-specific features and/or optimized features for a particular patient. In certain embodiments, one or more features of an implant component (and, optionally, one or more features of a resection cut strategy and/or guide tool) can be both selected and designed (e.g., designed and manufactured) to include one or more patient-specific features and/or optimized features for the particular patient. For example, an implant component having features that achieve certain parameter thresholds but having other features that do not achieve other parameter thresholds (e.g., a blank feature or a smaller or larger feature) can be selected, for example, from a library of implant components. The selected component then can be further designed (e.g. virtually designed and machined) to alter the blank or smaller or larger feature to be achieve the selected parameter, for example, a patient-specific or patient-engineered feature or feature measurement.

An implant component can include one or more selected features and one or more designed features. Alternatively or in addition, an implant component can include one or more features that are selected and designed or altered to be patient-specific or patient-engineered. Moreover, an implant component can include any number of selected and/or designed features derived from any number of patient-specific measurements, including one or more of the exemplary measurements described above in Table 4. Depending on the clinical application a single or any combination or all of the measurements described in Table 4 and/or known in the art can be used. Additional patient-specific measurements and information that be used in the evaluation can include, for example, joint kinematic measurements, bone density measurements, bone porosity measurements, identification of damaged or deformed tissues or structures, and patient information, such as patient age, weight, gender, ethnicity, activity level, and overall health status.

The patient-specific measurements selected for the evaluation can be used to select and/or design any selected implant features, including one or more of the exemplary features described in Table 1. The features can be selected and/or designed to be either patient-specific and/or patient-engineered.

For example, one or more of an M-L measurement, an A-P measurement, and an S-I measurement of a patient's joint can be obtained from the subject preoperatively, for example, from one or more images of the subject's joint. Then, based on the one or more measurements, an implant or implant component for the subject's joint can be selected and/or designed preoperatively to include an M-L, A-P, and/or S-I measurement that is selected from a library to match the patient's M-L, A-P, and/or S-I measurement.

The process can include generating and/or using a model, for example, a virtual model, of the patient's joint that includes the selected measurements and virtually fitting one or more selected and/or designed implants into the virtual model. This approach allows for iterative selection and/or design improvement and can include steps to virtually assess the fit, such as virtual kinematics assessment.

In another embodiment, the process of selecting an implant component also includes selecting one or more component features that optimizes fit with another implant component. In particular, for an implant that includes a first implant component and a second implant component that engage, for example, at a joint interface, selection of the second implant component can include selecting a component having a surface that provides best fit to the engaging surface of the first implant component. For example, for a knee implant that includes a femoral implant component and a tibial implant component, one or both of components can be selected based, at least in part, on the fit of the outer, joint-facing surface with the outer-joint-facing surface of the other component. The fit assessment can include, for example, selecting one or both of the medial and lateral tibial grooves on the tibial component and/or one or both of the medial and lateral condyles on the femoral component that substantially negatively-matches the fit or optimizes engagement in one or more dimensions, for example, in the coronal and/or sagittal dimensions. For example, a surface shape of a non-metallic component that best matches the dimensions and shape of an opposing metallic or ceramic or other hard material suitable for an implant component. By performing this component matching, component wear can be reduced.

For example, if a metal backed tibial component is used with a polyethylene insert or if an all polyethylene tibial component is used, the polyethylene will typically have one or two curved portions typically designed to mate with the femoral component in a low friction form. This mating can be optimized by selecting a polyethylene insert that is optimized or achieves an optimal fit with regard to one or more of: depth of the concavity, width of the concavity, length of the concavity, radius or radii of curvature of the concavity, and/or distance between two (e.g., medial and lateral) concavities. For example, the distance between a medial tibial concavity and a lateral tibial concavity can be selected so that it matches or approximates the distance between a medial and a lateral implant condyle component.

Not only the distance between two concavities, but also the radius/radii of curvature can be selected or designed so that it best matches the radius/radii of curvature on the femoral component. A medial and a lateral femoral condyle and opposite tibial component(s) can have a single radius of curvature in one or more dimensions, e.g., a coronal plane. They can also have multiple radii of curvature. The radius or radii of curvature on the medial condyle and/or lateral tibial component can be different from that/those on a lateral condyle and/or lateral tibial component.

Similar matching of polyethylene or other plastic shape to opposing metal or ceramic component shape can be performed in the shoulder, e.g. with a glenoid component, or in a hip, e.g. with an acetabular cup, or in an ankle, e.g. with a talar component.

Figure 27:
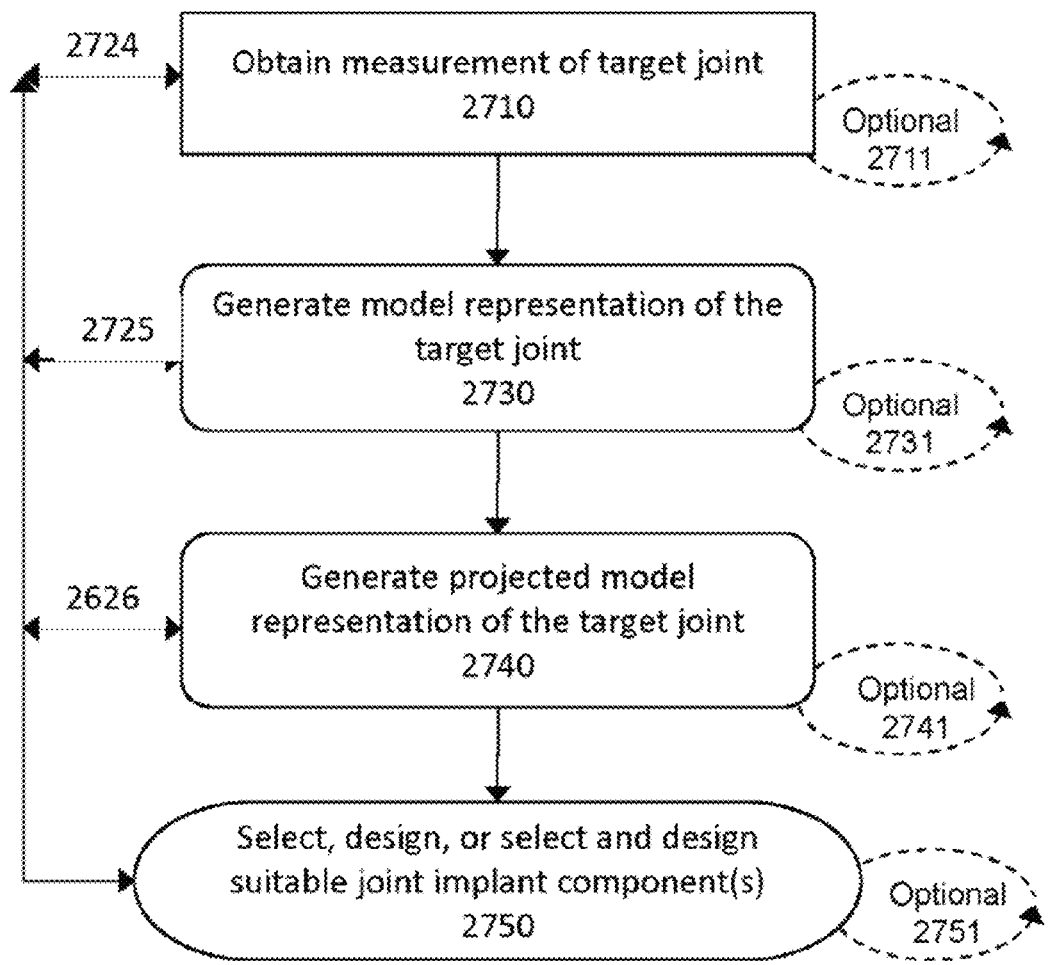
FIG. 27 is an illustrative flow chart showing exemplary steps taken by a practitioner in assessing a joint and selecting and/or designing a suitable replacement implant component.
Figure 28B:
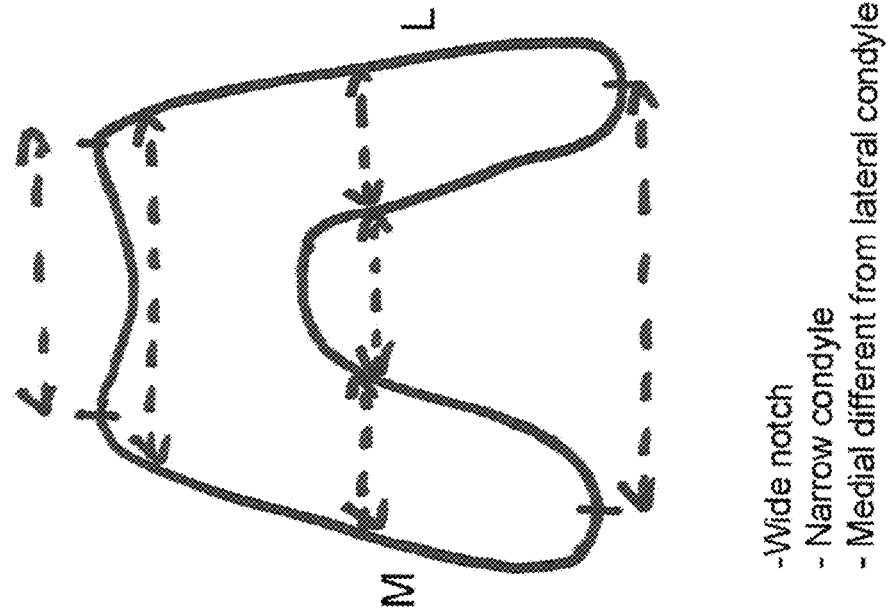
FIGS. 28A through 28K show implant components with exemplary features that can be selected and/or designed, e.g., derived from patient-specific and adapted to a particular patient, as well as be included in a library.
Figure 28A:
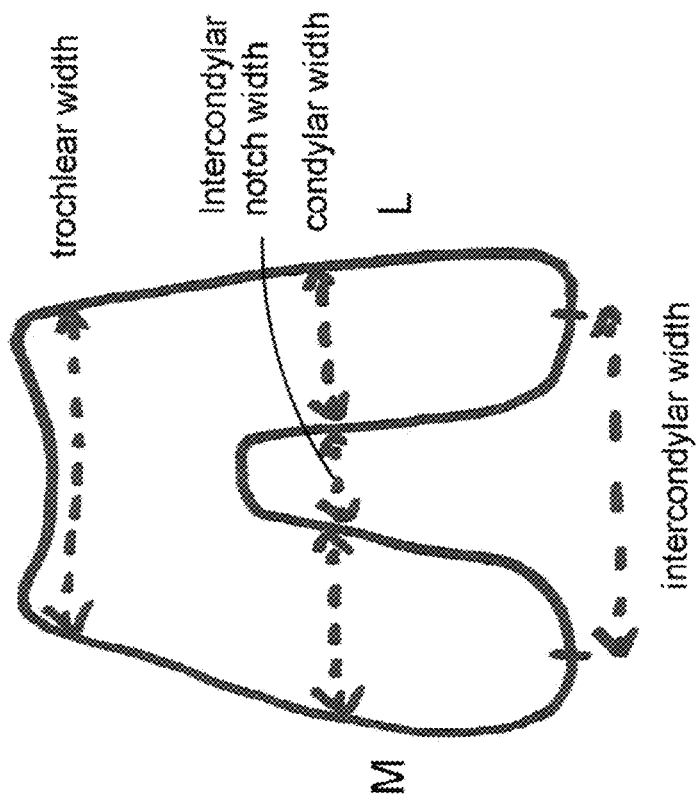
Figure 28D:
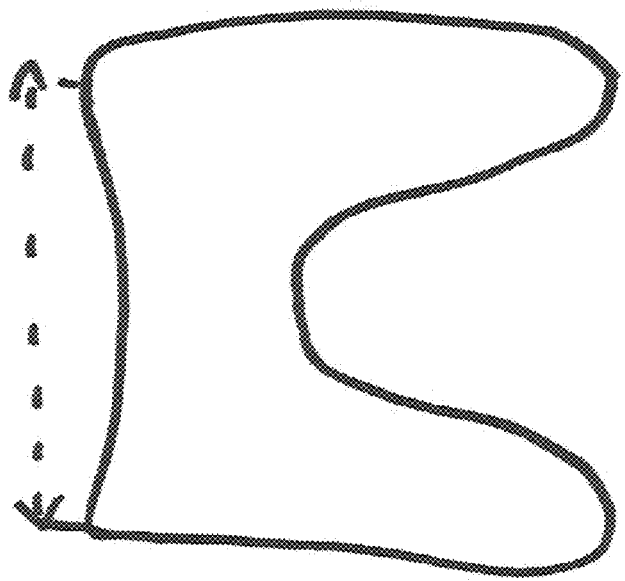
Figure 28C:
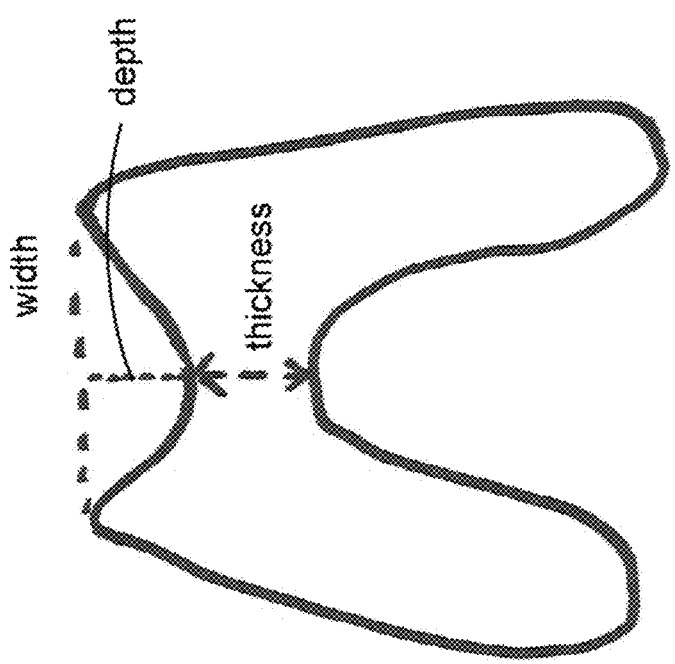
Figure 28F:
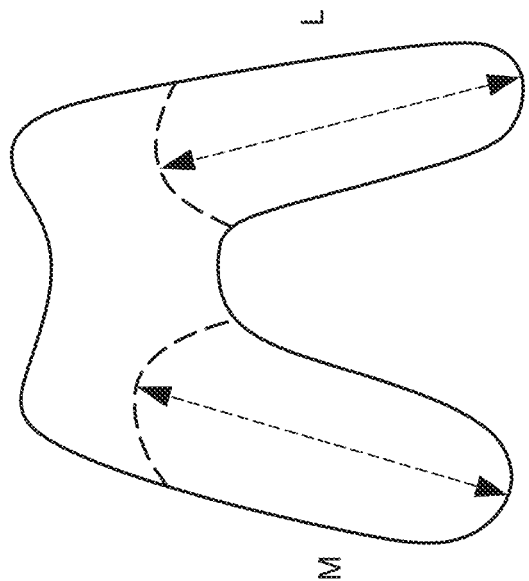
Figure 28E:
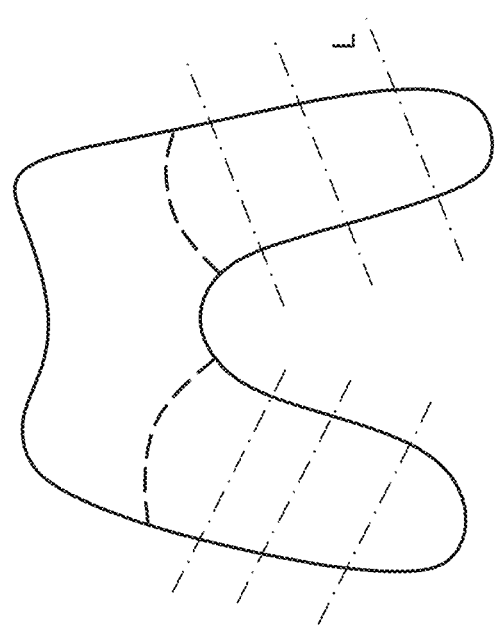
Figure 28H:
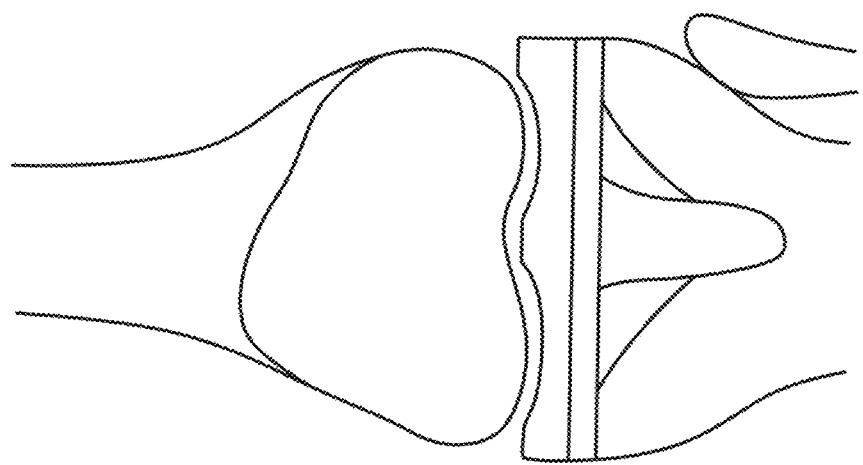
Figure 28G:
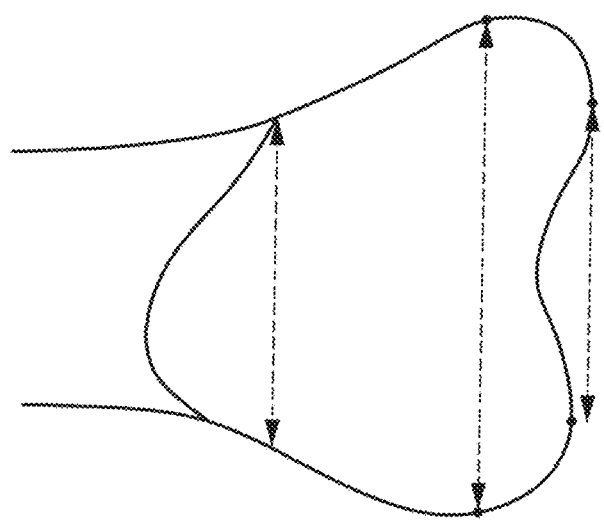
Figure 28J:
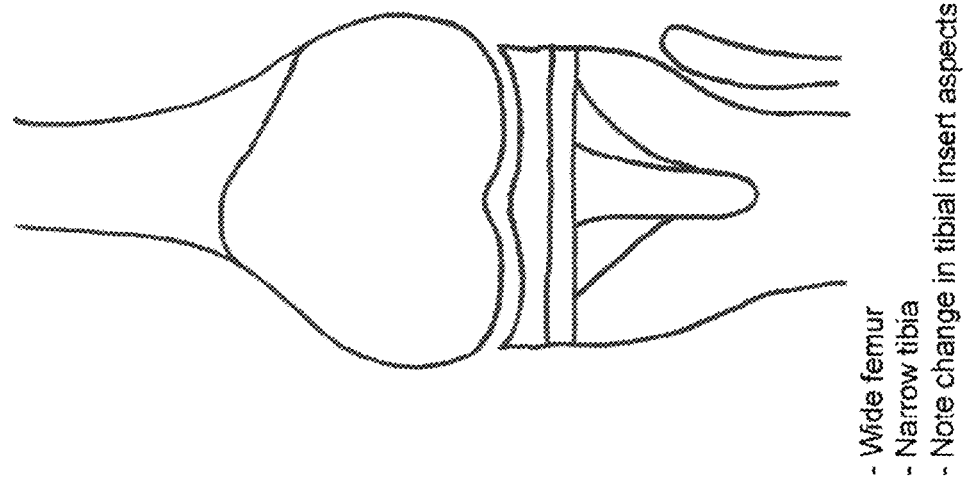
Figure 28I:
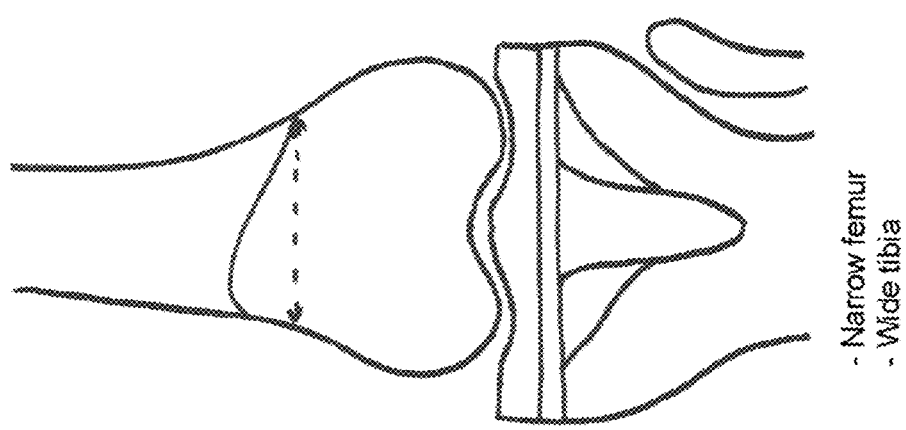

FIG. 27 is an illustrative flow chart showing exemplary steps taken by a practitioner in assessing a joint and selecting and/or designing a suitable replacement implant component. First, a practitioner obtains a measurement of a target joint 2710. The step of obtaining a measurement can be accomplished, for example, based on an image of the joint. This step can be repeated 2711 as necessary to obtain a plurality of measurements, for example, from one or more images of the patient's joint, in order to further refine the joint assessment process. Once the practitioner has obtained the necessary measurements, the information can be used to generate a model representation of the target joint being assessed 2730. This model representation can be in the form of a topographical map or image. The model representation of the joint can be in one, two, or three dimensions. It can include a virtual model and/or a physical model. More than one model can be created 2731, if desired. Either the original model, or a subsequently created model, or both can be used.

After the model representation of the joint is generated 2730, the practitioner optionally can generate a projected model representation of the target joint in a corrected condition 2740, e.g., based on a previous image of the patient's joint when it was healthy, based on an image of the patient's contralateral healthy joint, based on a projected image of a surface that negatively-matches the opposing surface, or a combination thereof. This step can be repeated 2741, as necessary or as desired. Using the difference between the topographical condition of the joint and the projected image of the joint, the practitioner can then select a joint implant 2750 that is suitable to achieve the corrected joint anatomy. As will be appreciated by those of skill in the art, the selection and/or design process 2750 can be repeated 2751 as often as desired to achieve the desired result. Additionally, it is contemplated that a practitioner can obtain a measurement of a target joint 2710 by obtaining, for example, an x-ray, and then selects a suitable joint replacement implant 2750.

One or more of these steps can be repeated reiteratively 2724, 2725, 2726. Moreover, the practitioner can proceed directly from the step of generating a model representation of the target joint 2730 to the step of selecting a suitable joint implant component 2750. Additionally, following selection and/or design of the suitable joint implant component 2750, the steps of obtaining measurement of a target joint 2710, generating model representation of target joint 2730 and generating projected model 40, can be repeated in series or parallel as shown by the flow 2724, 2725, 2726.

5.5 Libraries

As described herein, implants of various sizes, shapes, curvatures and thicknesses with various types and locations and orientations and number of bone cuts can be selected and/or designed and manufactured. The implant designs and/or implant components can be selected from, catalogued in, and/or stored in a library. The library can be a virtual library of implants, or components, or component features that can be combined and/or altered to create a final implant. The library can include a catalogue of physical implant components. In certain embodiments, physical implant components can be identified and selected using the library. The library can include previously-generated implant components having one or more patient-adapted features, and/or components with standard or blank features that can be altered to be patient-adapted. Accordingly, implants and/or implant features can be selected from the library.

FIGS. 28A to 28K show implant components with exemplary features that can be included in a library and selected based on patient-specific data to be patient-specific and/or patient engineered.

A virtual or physical implant component can be selected from the library based on similarity to prior or baseline parameter optimizations, such as one or more of (1) deformity correction and limb alignment (2) maximum preservation of bone, cartilage, or ligaments, (3) preservation and/or optimization of other features of the patient's biology, such as trochlea and trochlear shape, (4) restoration and/or optimization of joint kinematics, and (5) restoration or optimization of joint-line location and/or joint gap width. Accordingly, one or more implant component features, such as (a) component shape, external and/or internal, (b) component size, and/or (c) component thickness, can be determined precisely and/or determined within a range from the library selection. Then, the selected implant component can be designed or engineered further to include one or more patient-specific features. For example, a joint can be assessed in a particular subject and a pre-existing implant design having the closest shape and size and performance characteristics can be selected from the library for further manipulation (e.g., shaping) and manufacturing prior to implantation. For a library including physical implant components, the selected physical component can be altered to include a patient-specific feature by adding material (e.g., laser sintering) and/or subtracting material (e.g., machining).

Accordingly, in certain embodiments an implant can include one or more features designed patient-specifically and one or more features selected from one or more library sources. For example, in designing an implant for a total knee replacement comprising a femoral component and a tibial component, one component can include one or more patient-specific features and the other component can be selected from a library. Table 7 includes an exemplary list of possible combinations.

TABLE 7

Illustrative Combinations of Patient-Specific and Library-Derived Components

| Implant component(s) | Implant component(s) having a patient-specific feature | Implant component(s) having a library derived feature |
|---|---|---|
| Femoral, Tibial | Femoral and Tibial | Femoral and Tibial |
| Femoral, Tibial | Femoral | Femoral and Tibial |
| Femoral, Tibial | Tibial | Femoral and Tibial |
| Femoral, Tibial | Femoral and Tibial | Femoral |
| Femoral, Tibial | Femoral and Tibial | Tibial |
| Femoral, Tibial | Femoral and Tibial | none |

In certain embodiments, a library can be generated to include images from a particular patient at one or more ages prior to the time that the patient needs a joint implant. For example, a method can include identifying patients eliciting one or more risk factors for a joint problem, such as low bone mineral density score, and collecting one or more images of the patient's joints into a library. In certain embodiments, all patients below a certain age, for example, all patients below 40 years of age can be scanned to collect one or more images of the patient's joint. The images and data collected from the patient can be banked or stored in a patient-specific database. For example, the articular shape of the patient's joint or joints can be stored in an electronic database until the time when the patient needs an implant. Then, the images and data in the patient-specific database can be accessed and a patient-specific and/or patient-engineered partial or total joint replacement implant using the patient's originally anatomy, not affected by arthritic deformity yet, can be generated. This process results is a more functional and more anatomic implant.

5.6 Generating an Articular Repair System

The articular repair systems (e.g., resection cut strategy, guide tools, and implant components) described herein can be formed or selected to achieve various parameters including a near anatomic fit or match with the surrounding or adjacent cartilage, subchondral bone, menisci and/or other tissue. The shape of the repair system can be based on the analysis of an electronic image (e.g., MRI, CT, digital tomosynthesis, optical coherence tomography or the like). If the articular repair system is intended to replace an area of diseased cartilage or lost cartilage, the near anatomic fit can be achieved using a method that provides a virtual reconstruction of the shape of healthy cartilage in an electronic image.

In one embodiments, a near normal cartilage surface at the position of the cartilage defect can be reconstructed by interpolating the healthy cartilage surface across the cartilage defect or area of diseased cartilage. This can, for example, be achieved by describing the healthy cartilage by means of a parametric surface (e.g. a B-spline surface), for which the control points are placed such that the parametric surface follows the contour of the healthy cartilage and bridges the cartilage defect or area of diseased cartilage. The continuity properties of the parametric surface will provide a smooth integration of the part that bridges the cartilage defect or area of diseased cartilage with the contour of the surrounding healthy cartilage. The part of the parametric surface over the area of the cartilage defect or area of diseased cartilage can be used to determine the shape or part of the shape of the articular repair system to match with the surrounding cartilage.

In another embodiment, a near normal cartilage surface at the position of the cartilage defect or area of diseased cartilage can be reconstructed using morphological image processing. In a first step, the cartilage can be extracted from the electronic image using manual, semi-automated and/or automated segmentation techniques (e.g., manual tracing, region growing, live wire, model-based segmentation), resulting in a binary image. Defects in the cartilage appear as indentations that can be filled with a morphological closing operation performed in 2-D or 3-D with an appropriately selected structuring element. The closing operation is typically defined as a dilation followed by an erosion. A dilation operator sets the current pixel in the output image to 1 if at least one pixel of the structuring element lies inside a region in the source image. An erosion operator sets the current pixel in the output image to 1 if the whole structuring element lies inside a region in the source image. The filling of the cartilage defect or area of diseased cartilage creates a new surface over the area of the cartilage defect or area of diseased cartilage that can be used to determine the shape or part of the shape of the articular repair system to match with the surrounding cartilage or subchondral bone.

As described above, the articular repair system can be formed or selected from a library or database of systems of various sizes, including various medio-lateral (ML) antero-posterior (AP) and supero-inferior (SI) dimensions, curvatures and thicknesses, so that it achieves a near anatomic fit or match with the surrounding or adjacent cartilage, cortical bone, trabecular bone, subchondral bone, as well as cut bone, before or after preparing an implantation site. These systems can be pre-made or made to order for an individual patient. In order to control the fit or match of the articular repair system with the surrounding or adjacent cartilage, cortical bone, trabecular bone, subchondral bone, as well as cut bone before or after preparing an implantation site or menisci and other tissues preoperatively, a software program can be used that projects the articular repair system over the anatomic position where it will be implanted. Suitable software is commercially available and/or readily modified or designed by a skilled programmer.

In yet another embodiment, the articular surface repair system can be projected over the implantation site prior to, during or after planning or simulating the surgery virtually using one or more 3-D images. The cartilage, cortical bone, trabecular bone, subchondral bone, as well as cut bone, before or after preparing an implantation site and other anatomic structures are extracted from a 3-D electronic image such as an MRI or a CT using manual, semi-automated and/or automated segmentation techniques. In select embodiments, segmentation is not necessary and data are directly displayed using the grayscale image information.

Optionally, a 3-D representation of the cartilage, cortical bone, trabecular bone, subchondral bone, as well as cut bone, before or after preparing an implantation site and other anatomic structures as well as the articular repair system is generated, for example using a polygon or non-uniform rational B-spline (NURBS) surface or other parametric surface representation. For a description of various parametric surface representations see, for example Foley, J. D. et al., Computer Graphics: Principles and Practice in C; Addison-Wesley, 2nd edition, 1995).

The 3D representations of the cartilage, cortical bone, trabecular bone, subchondral bone, as well as cut bone, before or after preparing an implantation site and other anatomic structures and the articular repair system can be merged into a common coordinate system. The articular repair system can then be placed at the desired implantation site. The representations of the cartilage, cortical bone, trabecular bone, subchondral bone, as well as cut bone, before or after preparing an implantation site, menisci and other anatomic structures and the articular repair system are rendered into a 3-D image, for example application programming interfaces (APIs) OpenGL® (standard library of advanced 3-D graphics functions developed by SG), Inc.; available as part of the drivers for PC-based video cards, for example from www.nvidia.com for NVIDIA video cards or www.3dlabs.com for 3Dlabs products, or as part of the system software for Unix workstations) or DirectX® (multimedia API for Microsoft Windows® based PC systems; available from www.microsoft.com). The 3-D image can be rendered showing the cartilage, cortical bone, trabecular bone, subchondral bone, as well as cut bone, before or after preparing an implantation site, menisci or other anatomic objects, and the articular repair system from varying angles, e.g., by rotating or moving them interactively or non-interactively, in real-time or non-real-time.

The software can be designed so that the articular repair system, including surgical tools and instruments with the best fit relative to the cartilage, cortical bone, trabecular bone, subchondral bone, as well as cut bone, before or after preparing an implantation site is automatically selected, for example using some of the techniques described above. Alternatively, the operator can select an articular repair system, including surgical tools and instruments and project it or drag it onto the implantation site using suitable tools and techniques. The operator can move and rotate the articular repair system in three dimensions relative to the implantation site, cut or uncut, and can perform a visual inspection of the fit between the articular repair system and the implantation site, cut or uncut. The visual inspection can be computer assisted. The procedure can be repeated until a satisfactory fit has been achieved. The procedure can be performed manually by the operator; or it can be computer assisted in whole or part. For example, the software can select a first trial implant that the operator can test. The operator can evaluate the fit. The software can be designed and used to highlight areas of poor alignment between the implant and the surrounding cartilage or subchondral bone or menisci or other tissues. Based on this information, the software or the operator can then select another implant and test its alignment. One of skill in the art will readily be able to select, modify and/or create suitable computer programs for the purposes described herein.

In another embodiment, the implantation site can be visualized using one or more cross-sectional 2D images. Typically, a series of 2D cross-sectional images will be used. The 2D images can be generated with imaging tests such as CT, MRI, digital tomosynthesis, ultrasound, or optical coherence tomography using methods and tools known to those of skill in the art. The articular repair system can then be superimposed onto one or more of these 2-D images. The 2-D cross-sectional images can be reconstructed in other planes, e.g., from sagittal to coronal, etc. Isotropic data sets (e.g., data sets where the slice thickness is the same or nearly the same as the in-plane resolution) or near isotropic data sets can also be used. Multiple planes can be displayed simultaneously, for example using a split screen display. The operator can also scroll through the 2D images in any desired orientation in real-time or near-real-time; the operator can rotate the imaged tissue volume while doing this. The articular repair system can be displayed in cross-section utilizing different display planes, e.g., sagittal, coronal or axial, typically matching those of the 2-D images demonstrating the cartilage, cortical bone, trabecular bone, subchondral bone, as well as cut bone, before or after preparing an implantation site, menisci or other tissue. Alternatively or in addition, a three-dimensional display can be used for the articular repair system. The 2D electronic image and the 2D or 3-D representation of the articular repair system can be merged into a common coordinate system. The articular repair system can then be placed at the desired implantation site. The series of 2D cross-sections of the anatomic structures, the implantation site and the articular repair system can be displayed interactively (e.g., the operator can scroll through a series of slices) or noninteractively (e.g., as an animation that moves through the series of slices), in real-time or non-real-time.

In another embodiment, the fit between the implant and the implantation site is evaluated. The implant can be available in a range of different dimensions, sizes, shapes and thicknesses. Different dimensions, sizes, shapes and thicknesses can be available for a medial condyle, a lateral condyle, a trochlea, a medial tibia, a lateral tibia, the entire tibia, a medial patella, a lateral patella an entire patella, a medial trochlea, a central trochlea, a lateral trochlea, a portion of a femoral head, an entire femoral head, a portion of an acetabulum, an entire acetabulum, a portion of a glenoid, an entire glenoid, a portion of a humeral head, an entire humeral head, a portion of an ankle joint an entire ankle joint, a portion or an entire elbow, wrist, hand, finger, spine, facet joint.

In certain embodiment, a combination of parameters can be selected. For example, one or more of an M-L measurement, an A-P measurement, and an S-I measurement of a patient's joint can be obtained from the subject preoperatively, for example, from one or more images of the subject's joint. Then, based on the one or measurements, an implant or implant component for the subject's joint can be designed or selected preoperatively.

6. Designing and/or Selecting a Femoral Implant Component

The following subsections describe aspects of certain embodiments of models, implant designs, implants, and implant components related to a knee replacement. While the sections particularly describe embodiments of total knee implants, it is understood that the teachings are applicable to other embodiments including, but not limited to, unicompartmental knee implants, bicompartmental knee implants, and other articular implants such as shoulder implants, hip implants, and spinal facet implants.

6.1 Femoral Implant Component

Figure 29:
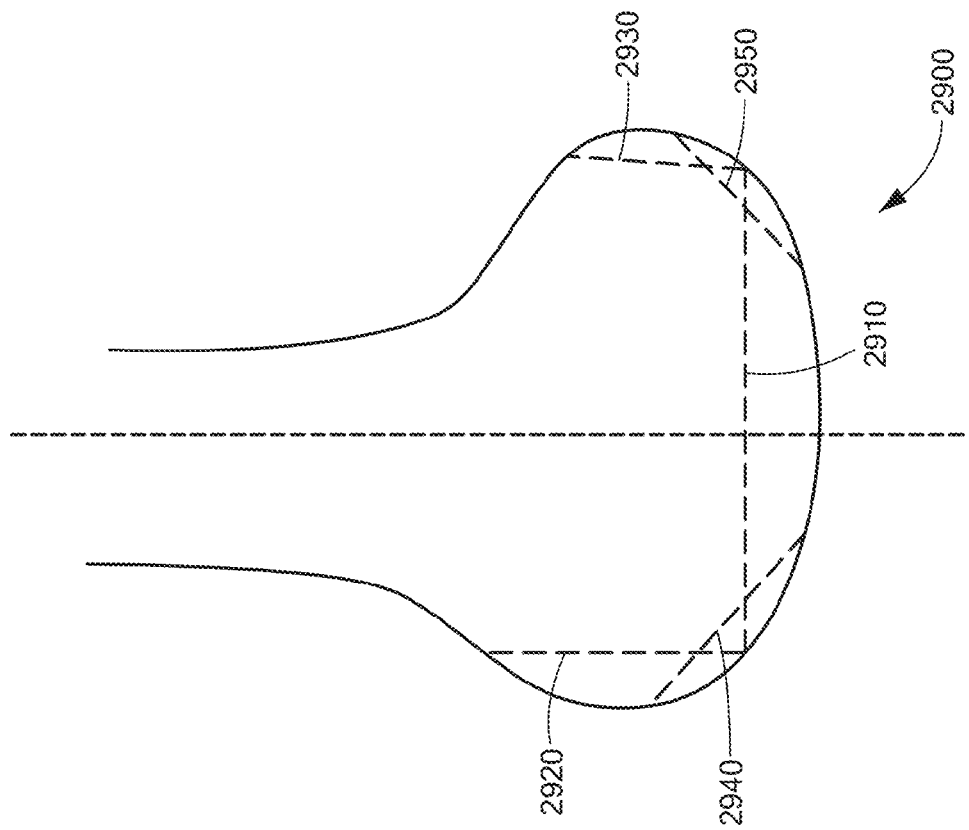
FIG. 29 shows a coronal view of a patient's femoral bone and, in dashed lines, standard bone cuts performed with a traditional total knee implant.
Figure 28K:
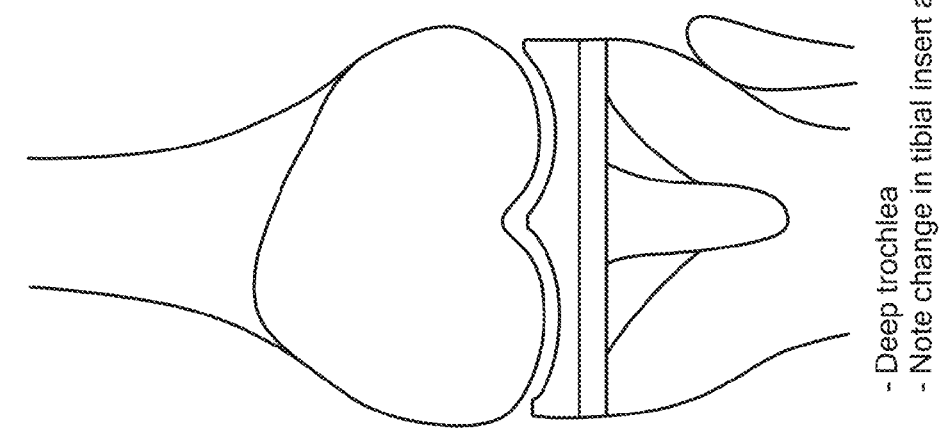

A traditional femoral implant component used in a primary total knee arthroplasty ("TKA") includes: an outer, joint-facing surface (i.e., inferior surface) having a standard topography; an inner, bone-facing surface (i.e., superior surface) that includes five standard bone cuts; and a standard implant thickness between the joint-facing surface and the bone-facing surface. FIG. 29 shows a coronal view of a patient's femoral bone 2900 and (in dashed lines) the five standard resection cuts used to remove portions of the subject's distal femur in order to fit the traditional femoral implant component. As shown by the dashed lines in the figure, a traditional resection performed in a TKA includes a horizontal resection cut 2910, an anterior resection cut 2920, a posterior resection cut 2930, an anterior chamfer resection cut 2940, and a posterior chamfer resection cut 2950. The anterior and posterior resection cuts 2920, 2930 typically are placed in a substantially coronal plane. With a traditional implant, the five standard resection cuts are performed so that the patient's distal femur approximately negatively-matches the standard five bone cuts on the inner, bone-facing surface of the traditional femoral implant component. In other words, the patient's bone is resected to fit the shape of the traditional femoral implant component.

Dissimilarly, in various embodiments described herein, one or more features of an implant component and/or implant procedure are designed and/or selected to provide a patient-adapted implant component. For example, in certain embodiments, one or more features of an implant component and/or implant procedure are designed and/or selected preoperatively, based on patient-specific data, to substantially match (e.g., substantially negatively-match and/or substantially positively-match) one or more of the patient's biological structures or a predetermined percentage thereof. For example, in certain embodiments, a femoral implant component can include an outer, joint-facing surface (i.e., inferior surface) having a sagittal or j-curve on one or both condyles that, at least in part, positively-matches the corresponding bone or cartilage curvature on the patient's uncut femur. This patient-specific implant component feature can be preoperatively selected and/or designed based on the patient's joint dimensions as seen, for example, on a series of two-dimensional images or a three-dimensional representation generated, for example, from a CT scan or MRI scan.

Alternatively or in addition, one or more features of an implant component and/or implant procedure can be preoperatively derived from patient-specific data to provide a patient-engineered feature, for example, to optimize one or more parameters, such as one or more of the parameters described above. For example, in certain embodiments, a bone preserving femoral implant component can include an inner, bone-facing surface (i.e., superior surface) having one or bone cuts that, at least in part, are patient-derived, optionally together with matching patient-derived resection cuts, to minimize the amount of resected bone (and maximize the amount of retained bone), for example, on the patient's femur. This patient-engineered implant component feature can be preoperatively selected and/or designed based on the patient's joint dimensions as seen, for example, on a series of two-dimensional images or a three-dimensional representation generated, for example, from a CT scan or MRI scan.

In certain embodiments, the size of an implant component can be designed and/or selected to substantially match the size of a patient's corresponding biological structure or a predetermined percentage thereof. For example, the ML and/or AP and/or proximal-distal dimensions of one or more sections of a femoral implant component can be preoperatively designed and/or selected to substantially match the corresponding dimension(s) of a patient's distal femur as determined, for example, from one or more images of the patient's joint. In certain embodiments, the size of the femoral implant component can be designed and/or selected based on one or more patient-specific dimensions, such as the length of the patient's epicondylar axis, which can be determined from preoperatively collected patient data, such as image data.

Figures 30A, 30B:
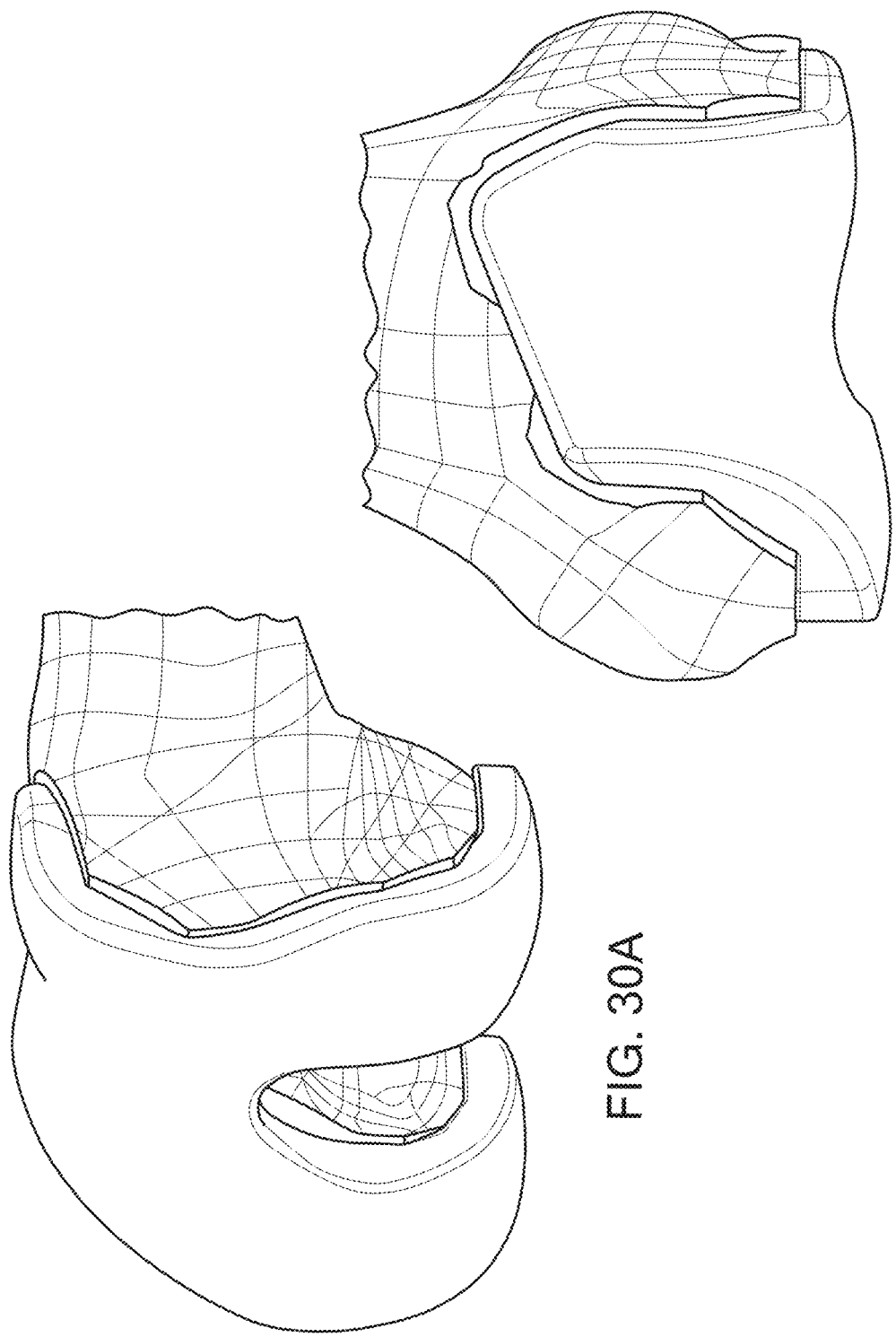
FIGS. 30A and 30B show the surface area of all or part of the bone-facing surface of the implant component substantially matching the corresponding resected surface area of a patient's femur.

In certain embodiments, an area measurement on the implant component can be designed and/or selected preoperatively to match, in whole or in part, a corresponding area measurement on the patient's femur or a predetermined percentage thereof. For example, as shown in FIGS. 30A and 30B, the surface area of all or part of the bone-facing surface of the implant component can be designed and/or selected from patient-specific data, in conjunction with a preoperatively designed resection strategy, to substantially match the corresponding resected surface area of the patient's femur. As shown in the figures, the surface area of the implant component is a close fit to the resected surface area. In certain embodiments, the implant component substantially covers the resected surface area, for example, by covering up to 100% and at least 90%, greater than 90%, at least 95%, greater than 95%, at least 97%, greater than 97%, at least 98%, greater than 98%, at least 99%, and/or greater than 99% of the resected surface area of the patient's distal femur.

In certain embodiments, the thickness of one or portions of an implant component can be designed and/or selected to match the corresponding dimension of the patient's biological structure. For example, the implant component thickness can be designed and/or selected to substantially match in one or more sections the thickness of the patient's cartilage, the thickness of the patient's resected bone, the total thickness of the patient's cartilage and resected bone, or an optimized thickness based on one or more of the parameters described above. In certain embodiments, the additive thickness of two or more implant components, for example, femoral and tibial implant components, can be designed and/or selected together to substantially match in one or more sections the patient's joint-gap distance, for example, the distance between the patient's femoral and tibial bone surfaces, uncut or resected.

As will be appreciated by those of skill in the art, the thickness of any implant component described herein can vary between different locations across its surface depending upon the patient's anatomy and/or the depth of the damage to the cartilage and/or bone to be corrected at any particular location on the patient's articular surface.

In certain embodiments, the implant component design and/or selection can include a thickness, a minimum implant thickness, and/or a maximum implant thickness that is engineered from patient-specific data to provide to the patient an optimized implant fit with respect to one or more parameters. Moreover, the additive thickness of two or more implant components can be engineered from patient-specific data to optimize the implant thickness for meeting one or more of the parameters described above. For example, the femoral and/or tibial implant thicknesses can be engineered from patient-specific data to optimize or correct the patient's joint-gap distance. The patient-specific data that may be used to engineer a minimum implant thickness can include, for example, one or more of patient height, patient weight, patient age, patient activity level, patient joint-size (e.g., epicondylar distance or condylar width), and other patient-specific data.

Figure 31B:
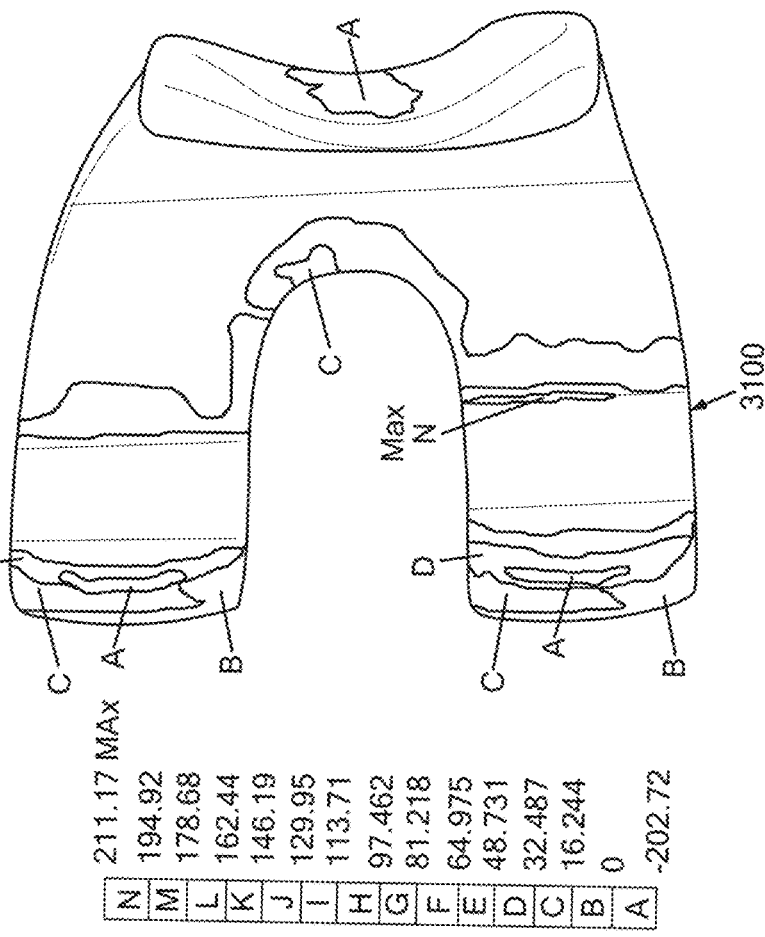
FIG. 31B illustrates an FEA analysis of the same implant component.
Figure 31A:
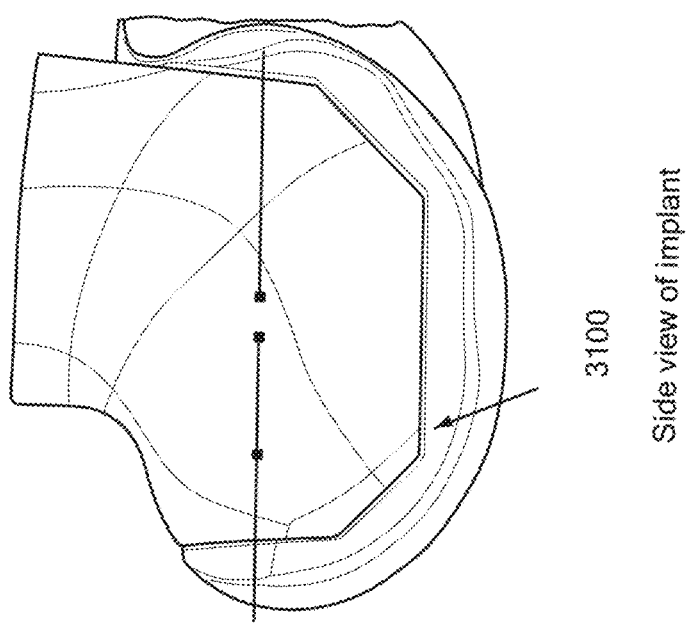
FIG. 31A shows a femoral implant component with the thinnest part of the implant component appearing at the intersection of the implant component's distal bone cut and a posterior chamfer bone cut.

In preferred embodiments, the minimum implant component thickness can be engineered based on, or together with, other patient-engineered dimensions or features of the implant component, for example, one or more of implant component size, implant component condyle width, and one or more implant component surface curvatures. For example, as shown in FIG. 31A, the thinnest part of a femoral implant component frequently appears at the intersection of the implant component's distal bone cut and a posterior bone cut 3100. This portion of an implant component also frequently shows the highest stress load, as exemplified by the FEA analysis results shown in FIG. 31B. Accordingly, the minimum implant component thickness for this or any portion of the implant component can be engineered based on one or more factors related to stress load, for example: the size of the patient; the size of the patient's femur; the size of the patient's condyle; the size of the patient-engineered implant component; the size of the implant component condyle; and the implant component's joint-facing surface curvature in the region that is opposite the intersection of the distal bone cut and posterior bone cut. In this way, a patient-specific minimum implant thickness can be engineered from patient-specific data, such as image data, and designed into the patient-adapted implant. This allows for minimal bone to be resected in the implant procedure and thereby can help to maximize bone preservation for any particular patient. Preservation of bone can allow for a subsequent knee implant to be a primary knee implant procedure, rather than a revision procedure.

In addition or alternatively, the implant component can be designed to include a standard minimum thickness and/or a standard maximum thickness in one or more locations. For example, in certain embodiments, the implant component can include a minimum implant thickness of 9 mm, less than 9 mm, 8 mm, less than 8 mm, 7 mm, less than 7 mm, 6 mm, less than 6 mm, 5 mm, and/or less than 5 mm.

In certain embodiments, both medial and lateral condyles include the same minimum implant thickness.

In certain embodiments, the joint-facing surface of a femoral implant component includes one or more patient-specific dimensions that positively or negatively-match the patient's biological structure or that are engineered from patient-specific data to provide to the patient an optimized implant fit with respect to one or more parameters, for example, as described above. For example, a femoral implant component can be designed and/or selected to include a joint-facing surface that substantially positively-matches one or more dimensions of the patient's femoral joint-facing surface, for example, as determined by preoperatively collected data, such as image data. The patient's femoral joint-facing surface that is included in the image data can include, for example, one or more of the cartilage surface and the bone surface of the patient's femur.

The joint-facing surface of a femoral implant component includes bearing surfaces that contact one or more opposing surfaces during proper joint function. In a total knee implant, the bearing surfaces include one or more portions of the medial and lateral condyles of the femoral component and also the corresponding surfaces on the tibial component. Bearing surfaces also can include the trochlear area of a femoral implant component and the corresponding surface of a patella or patella implant component. In certain embodiments, the femoral implant component can be designed and/or selected to include a joint-facing surface that substantially negatively-matches one or more dimensions of an opposing surface, such as a tibial surface or a patellar surface, of the patient's biological structure or of another implant component, such as a tibial implant component or a patellar implant component.

The primary load bearing surfaces of the femoral implant component include the joint-facing surfaces of the medial and lateral femoral condyles. In particular, these condylar surfaces engage the tibia or a tibial implant component during knee joint motion. Accordingly, the design of these condyles can affect various parameters; for example, as described above, such as kinematics and implant wear, particularly the proper motion of the implant at the joint.

In certain embodiments, one or more dimensions or features of one or both implant component condyles is designed and/or selected preoperatively to be patient-specific (e.g., to substantially match the patient's condyle or condyles in one or more dimensions or features). In addition or alternatively, one or more dimensions or features of one or both implant component condyles can be designed and/or selected preoperatively to be patient-engineered (e.g., engineered from patient-specific data to provide to the patient and optimized fit). The patient-specific data used to design and/or select the patient-adapted (e.g., patient-specific or patient-engineered) dimensions or features can include one or more images of, at least in part, one or both of the patient's femoral condyles. Accordingly, the manufactured femoral implant component generated from this design and/or selection includes a condyle having one or more patient-adapted dimensions or features.

The one or more patient-adapted dimensions or features of one or both condyles can include, for example, width in one or more locations, height in one or more locations, intercondylar distance in one or more locations, and one or more curvatures of at least a portion of the joint-facing surface of the condyle. The curvatures can include, for example, one or more of a sagittal curvature on the medial condyle, a coronal curvature on the lateral condyle, a sagittal curvature on the lateral condyle and a coronal curvature on the lateral condyle. The dimensions or features on the medial and lateral condyles of the implant component can be designed and/or selected independently of the corresponding dimensions on the other condyle, provided that patient-specific data (e.g., image data) is available for the appropriate condyle.

Any implant component dimensions or features that are not patient-adapted can have a standard dimension or feature. In addition, an implant design can include applying a standard dimension or feature if patient-specific data exceeds or fails to meet a certain threshold value. For example, in certain embodiments, intercondylar distance can be patient-specific; however, if the patient-specific data shows that the patient's intercondylar distance does not exceed a minimum intercondylar distance, such as 40 mm, a standard intercondylar distance of 40 mm can be included in the femoral implant component.

In certain embodiments, one or more of the condylar width, area, and height of an implant component can be designed and/or selected preoperatively to be patient-adapted in one or more locations along one or both condyles.

For example, the width of one or both implant component condyles can be designed and/or selected from patient-specific data to substantially match the corresponding width of the patient's resected condyle surface. Similarly, the two-dimensional area of a portion of the bone-facing surface of one or both implant component condyles can be designed and/or selected from patient-specific data to substantially match the corresponding area of the patient's resected condyle. In this way, the implant component can include one or both condyles that, at least in part, substantially covers the width and/or area of resected bone surface on the condyle, for example, by covering up to 100% and at least 90%; greater than 90%; at least 95%; greater than 95%; at least 97%; greater than 97%; at least 98%; greater than 98%; at least 99%; and/or greater than 99% of the width and/or area of the patient's resected condyle surface.

In addition or alternatively, the height of a portion of one or both implant component condyles can be designed and/or selected from patient-specific data to substantially match the corresponding height of the patient's condyle, for example, the height of the corresponding resected portion of the patients' condyle.

In certain embodiments, one or both of the intercondylar distance and the intercondylar angle of the implant component can be designed and/or selected preoperatively to be patient-specific in one or more locations. For example, the distance and/or angle between the implant component condyles can be designed and/or selected from patient-specific data to substantially match the corresponding distance and/or angle of the patient's condyles at one or more locations.

The intercondylar distance can be measured from any point on the medial condyle to any point on the lateral condyle. For example, the intercondylar distance can be measured as the distance between the outside edges of the condyles (e.g., from the medial edge of the medial condyle to lateral edge of the lateral condyle), as the distance between the inside edges of the condyles (e.g., from the lateral edge of the medial condyle to the medial edge of the lateral condyle), or as the distance from the sagittal crest of the medial condyle (i.e., the J-curve of the medial condyle) to the sagittal crest of the lateral condyle (i.e., the J-curve of the lateral condyle).

The intercondylar angle can be measured as the angle between a line on the medial condyle and a line on the lateral condyle. For example, the intercondylar angle can be measured as the angle between a tangent line to any point on the medial condyle and a tangent line to any point on the lateral condyle. One or each tangent line can be defined by a point on the outside edge of a respective condyle, by a point on the inside edge of a respective condyle, or by a point on the J-curve of a respective condyle. Alternatively, one or both lines used to measure the angle can be defined by any two or more points on the same condyle, rather than as a tangent line. In particular, in certain embodiments, the implant component includes a patient-adapted (e.g., patient-specific or patient-adapted) intercondylar angle at the trochlear notch.

In certain embodiments, the joint-facing surface of a femoral implant component can be designed and/or selected to include one or more of a patient-specific curvature, at least in part, a patient-engineered curvature, at least in part, and a standard curvature, at least in part. Various exemplary combinations of implant components having patient-adapted (e.g., patient-specific or patient-engineered) and standard coronal and sagittal condylar curvatures are shown in Table 8.

TABLE 8

Exemplary combinations of patient-adapted and standard condylar curvatures for a femoral implant component

| Group description | Medial condyle coronal curvature | Medial condyle sagittal curvature | Lateral condyle coronal curvature | Lateral condyle sagittal curvature |
|---|---|---|---|---|
| All standard curvatures | standard | standard | standard | standard |
| 1 patient-adapted curvature, at least in part | patient-adapted | standard | standard | standard |
| | standard | patient-adapted | standard | standard |
| | standard | standard | patient-adapted | standard |
| | standard | standard | standard | patient-adapted |
| 2 patient-adapted curvatures, at least in part | patient-adapted | patient-adapted | standard | standard |
| | patient-adapted | standard | patient-adapted | standard |
| | patient-adapted | standard | standard | patient-adapted |
| | standard | patient-adapted | patient-adapted | standard |
| | standard | patient-adapted | standard | patient-adapted |
| | standard | patient-adapted | standard | patient-adapted |
| | standard | standard | patient-adapted | patient-adapted |
| 3 patient-adapted curvatures, at least in part | patient-adapted | patient-adapted | patient-adapted | standard |
| | patient-adapted | patient-adapted | standard | patient-adapted |
| | patient-adapted | standard | patient-adapted | patient-adapted |
| | standard | patient-adapted | patient-adapted | patient-adapted |
| 4 patient-adapted curvatures, at least in part | patient-adapted | patient-adapted | patient-adapted | patient-adapted |

In certain embodiments, the joint-facing surface of the femoral implant component can be designed and/or selected to include a patient-specific curvature, at least in part. For example, any one or more of a coronal curvature of the medial condyle, a sagittal curvature of the medial condyle, a coronal curvature of the lateral condyle, and a sagittal curvature of the lateral condyle can be designed and/or selected preoperatively to substantially match the patient's corresponding curvature, e.g., subchondral bone or cartilage, at least in part, or can be derived from the patient's corresponding curvature, e.g. of subchondral bone or cartilage, at least in part.

In certain embodiments, the load-bearing portion of one or both implant condyles that contacts the tibial plateau during a normal range of motion (e.g., from the distal portion to the posterior portion of the implant component's joint-facing condyle surfaces) can be designed and/or selected to include one or more patient-specific curvatures. FIGS. 32A and 32B show exemplary load bearing surfaces of a femur in coronal view (FIG. 32A) and in sagittal view (FIG. 32B). As indicated by the figures, the load bearing surface on each of the medial and lateral condyles includes a coronal curvature 3210 and a sagittal curvature 3220. Non-patient-specific curvatures can include standard curvatures (e.g., selected from a family of standard curvatures, for example, a family of 3, 4, 5, 6, 7, or more standard curvatures) and/or engineered curvatures (e.g., engineered from patient-specific data to optimize one or more parameters, for example, as described above). For example, a femoral implant component can include a medial condyle having a patient-specific sagittal curvature, at least in part, and a standard coronal curvature; and a lateral condyle having standard coronal and sagittal curvatures.

In certain embodiments, the joint-facing surface of a femoral implant component can be designed and/or selected to include, at least in part, a patient-engineered curvature. For example, the joint-facing surface can be designed and/or selected to include a patient-engineered curvature, at least in part, for any one or more of a medial condyle coronal curvature, a medial condyle sagittal curvature, a lateral condyle coronal curvature, and a lateral condyle sagittal curvature. In certain embodiments, one or more load-bearing portions of the condylar sagittal and/or coronal curvature is designed and/or selected to be patient-engineered. Non-patient-engineered curvatures can include standard curvatures and/or patient-specific curvatures.

In certain embodiments, an implant component curvature can be preoperatively engineered based on patient-specific data to correct or optimize the patient's condyle curvature. The procedure can use a model or a mathematical formula to engineer a corrected or optimized condyle curvature and/or shape. The model or mathematical formula can be based on one or more patient-specific dimensions. For example, in certain embodiments, the implant component can include one or more curvatures that have been smoothed to address minor imperfections in the patient's corresponding curvature. In certain embodiments, one condyle can be engineered to have a curvature relative to the corresponding curvature in the patient's other condyle. For example, an implant component can be engineered to have a lateral sagittal J-curve engineered based on the patient's medial sagittal J-curve. The lateral J-curve can be engineered to have one or more radii of curvature that are shorter, for example, 5%, 10%, 15%, 20%, 10-15%, and/or 0-20% shorter, than the corresponding radii of curvature of the patient's medial J-curve. In certain embodiments, the implant component can be designed to have a lateral J-curve shape that substantially positively-matches the patient's medial J-curve shape.

In patients in need of knee replacement, the lateral condyle is sometimes deformed or hypoplastic, which can contribute to a valgus deformity. In fact, hypoplastic lateral condyles may be present in 20% of patients that require knee replacement. An implant that is engineered from patient-specific data to address this deformity, by correcting or optimizing the lateral condyle, can include one or more expanded curvatures in one or more locations on the lateral condyle, relative to the patient's corresponding uncut medial or lateral condyle. Accordingly, the implant is engineered to include additional material on the outer, joint-facing surface of the implant component's lateral condyle. The expanded curvature(s) and/or material on the outside of the condyle can be used to design a material savings on the inside of the corresponding section of the implant component, for example, by maintaining a minimum material/implant thickness from the outside (joint-facing surface) to the inside (bone-facing surface) of the implant component. In this way, by adding material to the external contour of the implant component and maintaining a minimum material thickness of the implant component, bone preservation can be maximized. Specifically, with more material on the joint-facing surface of the implant and less material on the inner, bone-facing surface of the implant, the resection cuts are made closer to the surface of the bone. Accordingly, this approach uses the patient-adapted design of the implant component to both correct a condyle shape abnormality, such as a lateral condyle abnormality, such as hypoplasia, and to maximize bone preservation.

In certain embodiments, one or more curvatures on one or both condyles can be engineered from patient-specific data, for example, in order to optimize joint kinematics. For example, the medial condyle in the trochlear region of the implant component can be engineered to be 5 mm lateral relative to the patient's condyle, which can help lateralize the patella.

Different curvatures can be selected on the medial condyle and the lateral condyle of an implant component. Moreover, one or more curvatures of one condyle can be patient-specific, in whole or in part, while one or more curvatures on the same condyle or on the other condyle can be patient-engineered, in whole or in part, or standard, in whole or in part.

The one or more patient-adapted (i.e., patient-specific or patient-engineered) curvatures and standard curvatures on the joint-facing surface of a femoral implant component can be combined in a condyle to take on any overall shape. FIGS. 33A through 33F illustrate exemplary types of curvatures 3300, 3310, 3320, 3330, 3340 for one or more condylar coronal or sagittal curvatures. An implant component condyle can include a surface curvature corresponding to a section of any one or more geometric shapes, such as a circle, a parabola, a hyperbola, an ellipsoid, and any other geometric shape, optionally standard or patient-adapted or patient-derived. The curvature also can include, in part, a substantially straight line portion, as illustrated by the curvature 3350 in FIG. 33F. Different portions of a condyle, such as the anterior portion, the distal portion, the posterior portion, the load-bearing portion, and/or the non-load-bearing portion, each can include a different curvature than one or more other portions, in a sagittal plane or in a coronal plane or in an axial plane in a trochlea, for example. For example, in certain embodiments the load bearing-portion of the medial condyle can include a different curvature than the non-load-bearing portions of the same condyle and optionally, than any or all sections of the lateral condyle. Similarly, in certain embodiments the load bearing-portion of the lateral condyle can include a different curvature than the non-load-bearing portions of the same condyle and optionally, than any or all sections of the medial condyle. These curvature features also can apply to the curved portion on one or both of the lateral and medial surfaces of the proximal tibia that engage the lateral and medial femoral condyles during normal motion.

The curvature 3300 in FIG. 33A corresponds to a section of a circle, and, accordingly, can be defined by a single radius of curvature across its entire curvature. Two exemplary radii of curvature are shown as dotted lines in FIG. 33A. However, the curvatures 3310, 3320, 3330, 3340 in FIGS. 33B through 33E each correspond to a section of a non-circular geometric shape and therefore each include radii having different lengths across their curvatures. Moreover, the straight line portion of the curvature 3350 illustrated in FIG. 33F includes no radius of curvature. Accordingly, as exemplified by the circular curvature 3300 shown in FIG. 33A, a curvature or a portion of a curvature of an implant component, for example, a condylar coronal or sagittal curvature on the joint-facing surface of a femoral implant component can include a single radius of curvature. Alternatively or in addition, as exemplified by the non-circular curvatures 3310, 3320, 3330, 3340 shown in FIGS. 33B through 33F, a curvature or a portion of a curvature of an implant component, for example, a condylar coronal or sagittal curvature on the joint-facing surface of a femoral implant component, can include multiple radii of curvature and, optionally, no radii of curvature (e.g., for a straight line portion of a curvature).

Moreover, in certain embodiments, a curvature or a portion of a curvature of an implant component, for example, a condylar coronal or sagittal curvature on the joint-facing surface of a femoral implant, component can include a combination of patient-specific radii of curvature, patient-engineered radii of curvature, and/or standard radii of curvature. In other words, a curvature can include a portion that is patient-specific, a portion that is patient-engineered, and/or a portion that is standard. These can be present in the same plane or dimension, e.g., a sagittal dimension, a coronal dimension or an axial dimension, or these can be present in different dimensions. For example, at least a portion of a sagittal curvature of the implant can be patient-specific or patient-engineered, while at least a portion of a coronal curvature can be standard or constant patient-engineered. For example, FIGS. 34A and 34B illustrate a design for a femoral implant component having a J-curve that is patient-specific in part and patient-engineered in part. Specifically, as shown in the figure, the J-curve is designed to be patient-specific except for a distal portion and a posterior portion of the curvature. In the distal portion, the J-curve is smoothed relative to the patient's J-curve. In the posterior portion, the J-curve is tapered out 1-2 mm relative to the patient's J-curve.

Figure 35B:
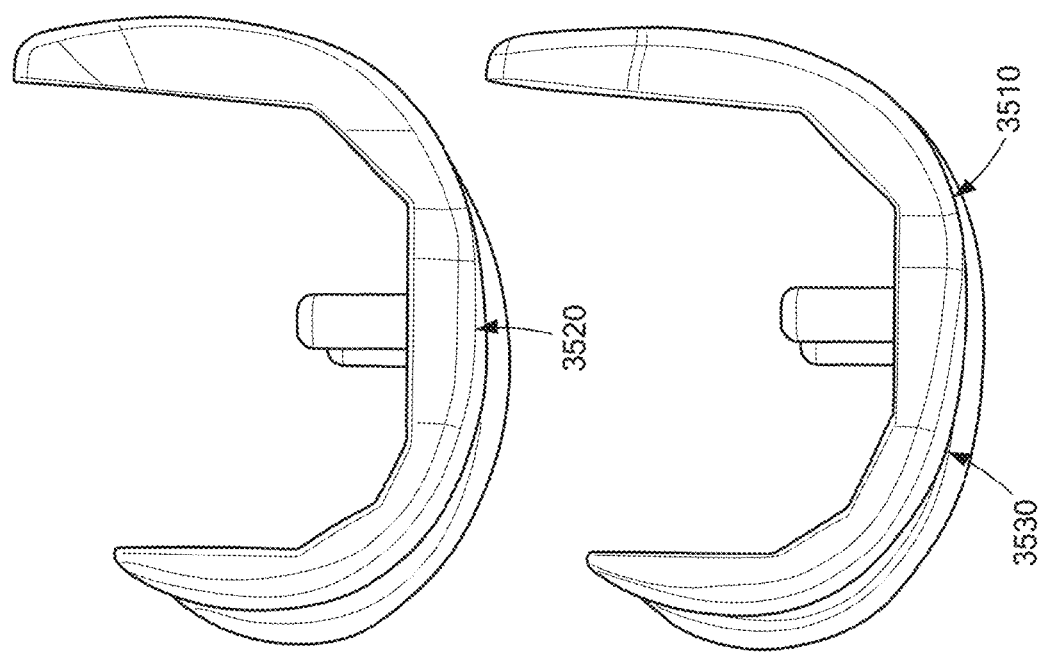
FIGS. 35A and 35B illustrate two femoral implant components, one having a J-curve that is substantially patient-specific and one having a J-curve that is partially patient-specific and partially patient-engineered.
Figure 35A:
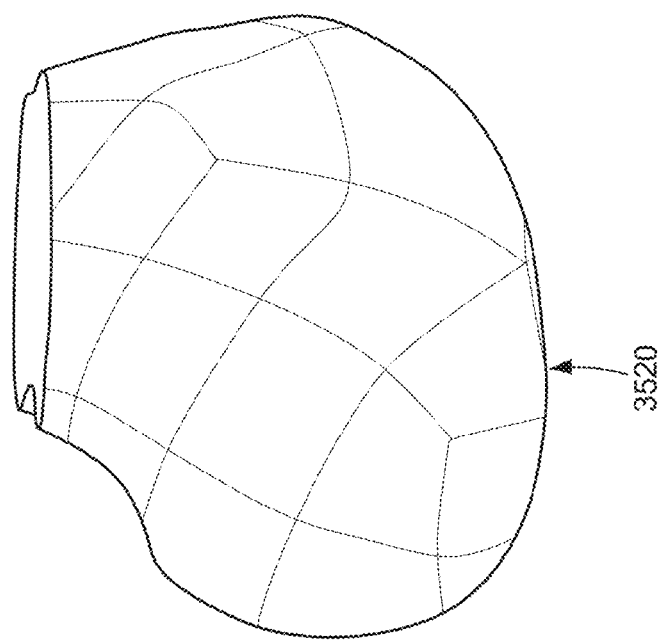

FIGS. 35A and 35B illustrate two femoral implant components, one having a J-curve that is substantially patient-specific and one having a J-curve that is partially patient-specific and partially patient-engineered. Specifically, both implant components shown on the right side of the figure were designed based on patient-specific data. However, the top implant component includes a J-curve that, at least in its load-bearing portion, substantially positively-matches the patient's J-curve. The bottom implant component includes a J-curve that was engineered in region 3510 to diverge from the patient-specific J-curve. These engineered alterations from a patient's existing J-curve can be employed for example, to match or approximate the height of the patient's existing or missing cartilage, to correct an abnormality in the patient's existing J-curve (e.g., arthritic flattening of the condyle, subchondral cysts, or osteophyte formation), to match one or more features of a corresponding implant component (e.g., a tibial implant component), and/or to optimize the patient's biomechanics or one or more other parameters determined by a clinician or operator to be important.

One or more radii of a condylar curvature of a femoral implant component can be engineered from patient-data to optimize or correct any one or more parameters, for example, any one or more parameters described above. For example, with reference to FIGS. 35A and 35B, the distal load-bearing portion of the J-curve frequently has the flattest surface 3520. In certain embodiments, this portion of the J-curve can be engineered to shift the flattest portion anteriorly or posteriorly to correct or optimize the patient's biomechanics, joint alignment, implant load pattern, and/or implant wear pattern. In FIGS. 35A and 35B, the flattest portion 3520 of the J-curve in the top implant component appears at the distal portion of the implant. However, the bottom implant is engineered to include the flattest portion 3530 of the J-curve further posterior to the distal position. In certain embodiments, an implant component's entire condylar sagittal curvature can be flexed (e.g., rotated anteriorly or posteriorly, for example, about the femoral mechanical axis or the sagittal axis) in an implant relative to the patient's corresponding curvature, in order to correct or optimize the patient's biomechanics and/or alignment.

Figure 36:
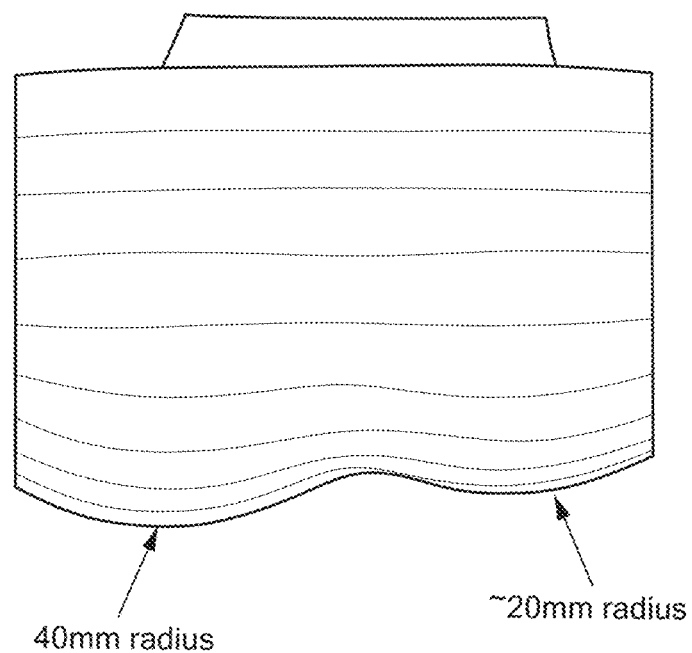
FIG. 36 illustrates the use of a coronal curvature having a longer radius of curvature versus a coronal curvature having shorter radius of curvature.

In certain preferred embodiments, the femoral implant component is preoperatively designed and/or selected to include one or both condylar, bearing surfaces having a sagittal curvature (e.g., a J-curve) that, at least in part, substantially positively-matches or is derived from the corresponding sagittal curvature of the patient's condyle, e.g. portions of cartilage or subchondral bone or combinations thereof, as determined from patient-specific data including, for example, image data. In addition, the coronal curvature of the implant component can include a standard curvature, for example, selected by choosing from among a family of 5, 6, 7, 8, 9, or 10 implants or implant blanks the one that includes a coronal curvature that is most similar to the patient's coronal curvature in one or more locations on the curvature. Alternatively, an implant component condyle curvature can be selected by choosing from among a family of implants or implant blanks the one that, as compared to the patient's curvature, includes longer and/or shorter radii of curvature at a load-bearing portion of the curvature, in order to achieve a less constraining or a more constraining biomechanical situation during knee motion. FIG. 36 illustrates the use of a coronal curvature having a longer radius of curvature (e.g., 40 mm radius of curvature) versus a coronal curvature having shorter radius of curvature (e.g., 20 mm radius of curvature).

The radii of curvature of a human femoral condyle coronal curvature typically range from 20 to 30 mm. In certain embodiments, one or both femoral implant component condyles and/or the corresponding curvature of the bearing surface on the tibial implant component, include a coronal curvature that matches a particular patient's coronal curvature. In certain embodiments, one or both femoral implant component condyles and/or the corresponding curvature of the bearing surface on the tibial implant component, include a standard coronal curvature within the range of typical human coronal curvatures, for example, from about 20 mm to about 30 mm. In certain embodiments, one or both femoral implant component condyles and/or the corresponding curvature of the bearing surface on the tibial implant component, include a standard coronal curvature outside of the range of typical human coronal curvatures, for example, less than 20 mm, about 15 mm, less than 15 mm, greater than 30 mm, 35 mm, greater than 35 mm, between about 30 mm and about 40 mm, 40 mm, and/or greater than 40 mm. The tibial implant component can be designed to match or reflect at least one of a sagittal femoral curvature or a coronal femoral curvature. The corresponding radii on the tibial implant component can be applied or derived from the femur in a ratio, e.g., 1:1, 1:2, 1:3, 1:4, 1:5, 1:8, 1:10, 1:15, 1:20, in at least one of a sagittal dimension or a coronal dimension, or combinations thereof, medially only, laterally only, or both. For example, in certain embodiments, at least a portion of the femoral implant's coronal curvature (e.g., the center portion of the condyle) and/or the corresponding portion of the tibial implant component curvature can correspond to a section of a circle having a radius of curvature less than 20 mm, less than 15 mm, 15 mm, greater than 30 mm, 35 mm, greater than 35 mm, 40 mm, and/or greater than 40 mm.

Figure 37:
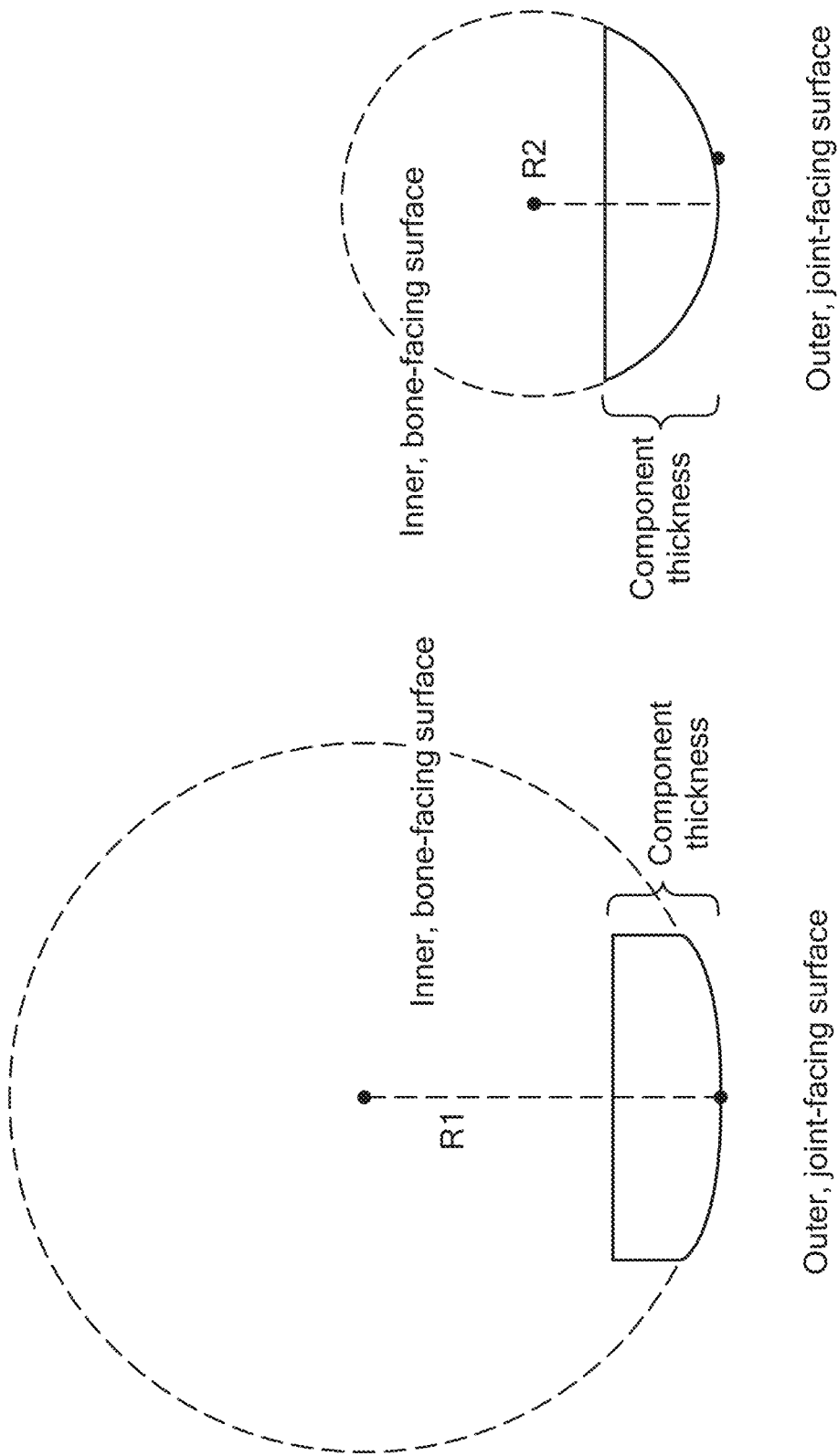
FIGS. 37A and 37B show cross-sections from a coronal view of two femoral condyle sections of a femoral component.

Using longer radii of curvature (e.g., greater than 30 mm, 35 mm, greater than 35 mm, 40 mm, and/or 40 mm) for a femoral implant's condylar coronal curvature can provide certain advantages. For example, FIGS. 37A and 37B show coronal cross-sections of two femoral implant component condyles. As shown, each condyle includes an outer, joint-facing surface coronal curvature having a constant radius of curvature, at least in part (depicted as radius R1 and radius R2, respectively). In addition, as shown, the two condyles have the same maximum component thickness (with the condyle in FIG. 37A having a longer radius of curvature than the condyle in FIG. 37B). As can be seen from a comparison of figures, where the width and maximum component thickness are the same for the two components, the component with the longer radius of curvature allows for more material at the edge of the component, and therefore can be less likely to fail in this area of the femoral implant component. In certain embodiments, the one or more condylar curvatures, e.g., one or more coronal curvatures and/or sagittal curvatures, and/or component width, can be engineered from patient-specific data to be as close to the patient-specific curvature and/or width as possible after a threshold minimum thickness and/or minimum edge thickness or minimum chamfer cut thickness is achieved. For example, a threshold minimum thickness and/or minimum edge thickness and/or minimum chamfer cut thickness can be set initially (e.g., predetermined). Material properties of the implant component and/or loading conditions or biomechanical modeling including finite element modeling can assist in determining the threshold minimum thickness and/or minimum edge thickness. Subsequently, one or more patient-specific curvatures or widths or shapes are derived, for example by determining the curvature or width or shape of subchondral bone or cartilage. These curvatures can be used to derive a shape or curvature or width of one or more bearing surfaces of the implant component, e.g., in a coronal plane, sagittal plane or axial plane. The shape or curvature or width of the one or more bearing surfaces of the implant component then can be altered in order to achieve the predetermined minimum thickness or minimum edge thickness or minimum chamfer cut thickness criterion. This alteration can be performed using computerized methods as well as manual, e.g., operator selected, methods.

Similarly, a maximum thickness, and/or maximum edge thickness and/or maximum chamfer cut thickness and/or maximum bone-cut thickness can be predetermined. The shape or curvature or width of the one or more bearing surfaces of the implant then can be altered in order to achieve the predetermined maximum thickness and/or maximum edge thickness and/or maximum chamfer cut thickness and/or maximum bone cut thickness criterion. By optimizing against a maximum bone-cut thickness, the implant can be selected or designed so that it is sufficiently bone preserving to be a pre-primary implant, e.g., where, for example, a distal bone cut is distal to the bone cut with a standard of the shelf femoral component implant, thereby enabling later revision to a standard total knee system.

Various dimensions and features of a patient's condyles, such as width, area, height, intercondylar distance, intercondylar angle, and surface contour and curvatures, e.g., of the patient's cartilage or subchondral bone or combinations thereof, including normal or diseased cartilage, can be determined from one or more images of the patient's knee joint. In certain embodiments, a dimension or feature of the patient's condyles can be assessed to include cartilage on the patient's distal femur. In certain embodiments, a dimension or feature can be assessed based on the patient's bone, for example, subchondral bone, on the patient's distal femur. If subchondral bone is used to assess the patient's condylar curvature, optionally a standard cartilage thickness (e.g., 2 mm), or an approximate cartilage thickness derived from patient-specific data (e.g., age, joint-size, contralateral joint measurements, and/or other data), can be used as part of the preoperative implant design, for example, to correct or address for joint-line movement associated with lost cartilage. Alternatively, the cartilage thickness can be measured directly in or more regions.

Figure 38:
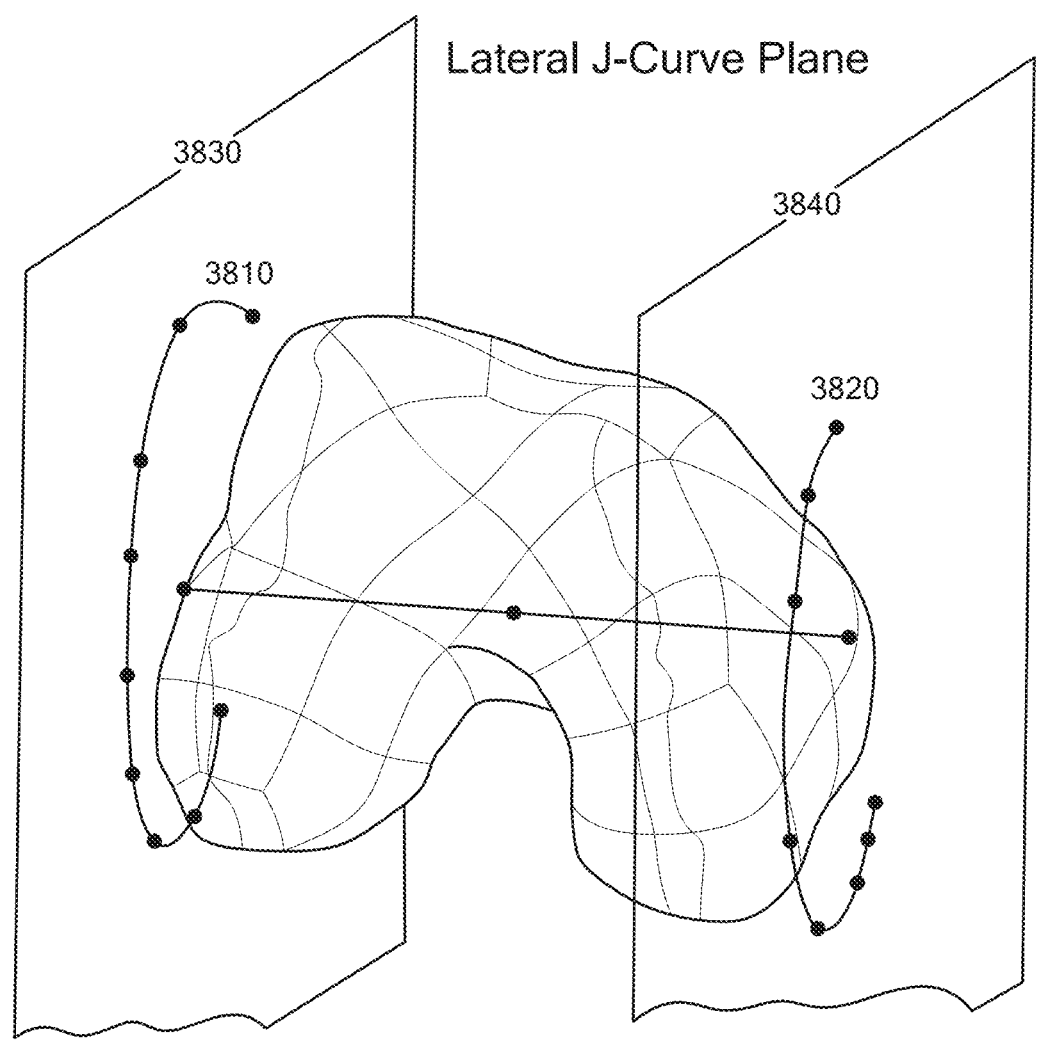
FIG. 38 illustrates a patient's J-curve can be determined independently for lateral and medial condyles.

The sagittal and/or coronal curvatures of a patient's condyle can be determined from image data by assessing the surface of the condyle in a substantially sagittal or coronal plane. Alternatively or in addition, the curvature(s) also can be assessed in an axial plane, for example for a patella, a trochlea, a glenoid, or an acetabulum. For example, as shown in FIG. 38, a patient's J-curve can be determined independently for lateral and medial condyles. Then, one or both of the patient's lateral and medial condylar J-curves can be applied to one or more sections of a femoral implant component's medial and/or lateral J-curves. For example, the distal point of the lateral condyle through a range of motion 3810 and the distal point of the medial condyle through a range of motion 3820 can independently be applied, respectively, to a lateral sagittal plane 3830 defined by the patient's epicondylar axis and to a medial sagittal plane 3840 defined by the patient's epicondylar axis to yield independent lateral and medial J-curves that are applied to the patient-specific implant component. In certain embodiments, as shown in FIG. 38, a model of a patient's femur can be generated from images of the patient's femur. The images can include, for example, x-ray, cone beam CT, digital tomosynthesis, ultrasound, laser imaging, MRI, CT, PET, SPECT, and/or other images and combinations thereof. In certain embodiments, as shown in FIG. 38, the patient's J-curve can be transferred onto a single plane (e.g., a substantially sagittal plane) and then that planar curvature, or a portion thereof, can be transferred into the design of the femoral implant component as a single planar curvature. In certain embodiments, the patient's J-curve can lie in more than one plane and more than one plane can be used to transfer and apply the J-curve to the implant component, for example, such that the J-curve lies in one plane for a portion and then angles away from that plane for a portion. Moreover, in certain embodiments, one or both of the implant component's condylar J-curves or portions thereof can match the patient's J-curve planar orientation. For example, corresponding medial and lateral planes that include portions of the patient's medial and lateral J-curves, respectively, can be non-parallel to each other (e.g., angled toward each other anteriorly) or otherwise angled relative to an anatomical feature (e.g., the epicondylar axis, femoral mechanical axis, trochlear J-curve, and/or some other feature). The corresponding J-curve portions of the femoral implant component and, optionally, the tibial implant component can be designed to match this planar orientation. For example, the J-curve or portions thereof (e.g., the distal and/or posterior load-bearing portions) can match the patient's J-curve in a sagittal direction or in both a sagittal and coronal direction.

In one embodiment, the medial or lateral femoral condyle can have a constant coronal curvature, which can be standard or patient-derived or selected. The constant coronal curvature can be the same on the medial and the lateral condyle or it can be different. The constant coronal curvature can be combined with a patient-specific or patient-derived, at least in part, sagittal curvature on one or both condyles.

In a different embodiment, the same condyle can have two areas with different constant coronal curvatures. For example, the central, distal load bearing portion of one or both femoral condyles can have a different constant coronal curvature than the high posterior portion of one or both condyles. The use of two different constant coronal curvatures in these different areas of the condyle can, for example, be advantageous in select high-flexion designs whereby one or more constant coronal curvatures are adapted or selected to maximize tibiofemoral contact area and minimize tibiofemoral contact stress and resultant wear for one or more flexion angles. More than two constant coronal curvatures are possible on a condyle. The transition between a first area of constant coronal curvature and a second and, optionally, third or fourth, area of constant coronal curvature can be selected or designed to coincide with certain anatomic features, e.g. a sulcus line. The transition between a first area of constant coronal curvature and a second and, optionally, third or fourth, area of constant coronal curvature can be selected or designed to include one or two or multiple coronal radii that allow for a smooth transition from a first to a second area of constant coronal curvature.

In select high flexion designs, one or more of the posterior condyle curvature, implant thickness, edge thickness, bone cut orientation, and bone cut depth, can be adapted to maximize flexion. For example, the posterior bone cut can be offset more anteriorly for a given minimum thickness of the implant. This anterior offsetting of the posterior cut can be combined with a taper of the posterior implant bearing surface. Other strategies to enhance a patient's deep knee flexion include adding or extending the implant component posteriorly, at the end bearing surface in high flexion. By extending the bearing surface the knee can be flexed more deeply. Accordingly, in certain embodiments, the posterior edge and/or posterior bearing surface is patient-engineered to enhance deep knee flexion for the particular patient.

Patellar revision can be very challenging and bone preservation is preferred in the patella. In certain embodiments, two or more patellar resection facets and two or more patellar implant component bone cuts are employed to preserve patellar bone stock. One or both of the two or more patellar facets can be substantially tangent or parallel to the medial and/or lateral uncut patellar surfaces. Optionally, particularly with more than two patellar resection facets, facets can be substantially tangent or parallel to uncut patellar superior and/or inferior surfaces. In certain embodiments, the patellar-facing surface of an implant component can be patient-specific, i.e., designed to match the patient's normal trochlear groove or patellar shape (e.g. patellar cartilage or subchondral bone). Alternatively, the patellar-facing surface of the implant component can be engineered from patient-specific data to optimize one or more parameters, for example, kinematics or wear between component surfaces. A method for designing a patient-adapted implant to optimize tracking of the patella along the trochlear groove of a femoral implant component is described below in Example 8. Specifically, the exemplary implant design in Example 8 uses a patient-specific sagittal curvature, at least in part, and an engineered coronal curvature, at least in part, to allow the patella component to track properly in the trochlear groove. In certain other embodiments, the coronal curvature additionally can be patient-specific. In certain embodiments, the coronal curvature is patient-specific and the sagittal curvature is standard or engineered.

Figure 39:
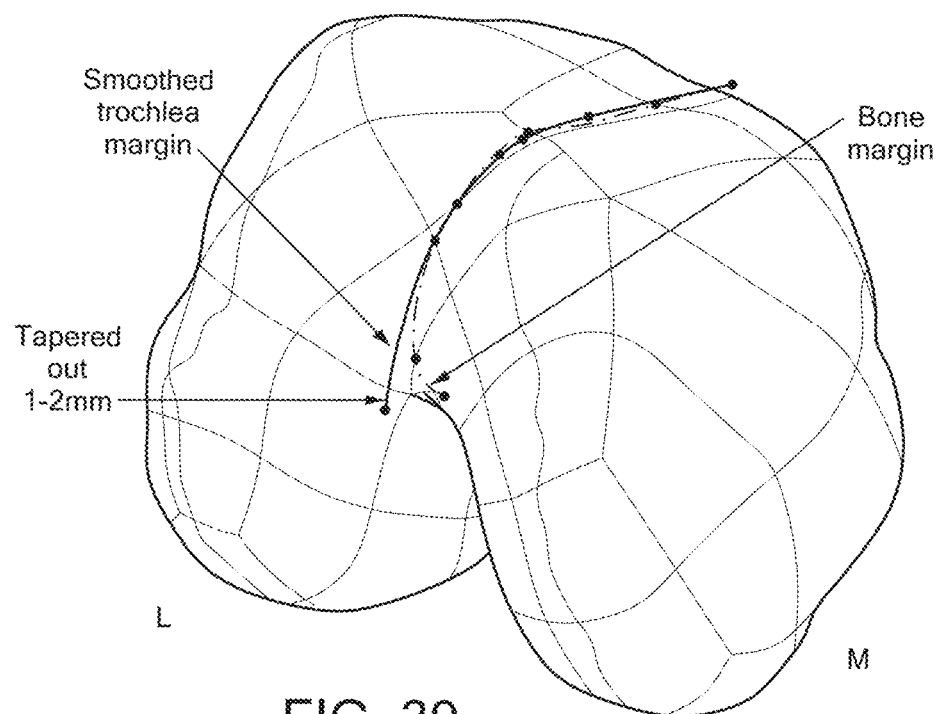
FIG. 39 illustrates a trochlear J-curve on a model of a femur.

In certain embodiments, one or more trochlear groove features (e.g., trochlear J-curve, sulcus displacement, and/or other features) and corresponding patella features (articular surface contour and/or curvature, ML, SI, and/or AP shape) can be patient-specific, patient-engineered, and/or standard, in part or in whole. For example, FIG. 39 shows the line of a trochlear J-curve defined anteriorly by the lowermost point of the patient's trochlear groove (i.e., sulcus) and superimposed on the patient's distal femur. As indicated by the figure, an implant's trochlear J-curve can substantially or partially match the patient's trochlear J-curve (e.g., curve of sulcus viewed in the sagittal plane) in one or more locations, for example, in the anterior portion of the trochlear J-curve. The substantially matching trochlear J-curve can include portions that are smoothed relative to the patient's curvature. The partially matching trochlear J-curve can include portions that are engineered or patient derived and smoothed or constant relative to the patient's curvature. At the same time, the trochlear J-curve and/or sulcus position (e.g., shift in the trochlear J-curve in the ML direction) of the implant can be engineered, in part or in whole, from the patient's anatomy, e.g., to improve kinematics. For example, as shown in FIG. 39, the distal portion of the trochlear J-curve is tapered out 1-2 mm, relative to the patient's trochlear J-curve. As discussed in detail below, the patellar implant component can include be selected and/or designed to include one or more features that correspond to one or more trochlear features of the femoral implant component.

In preferred embodiments, the implant's trochlear groove is slightly larger (e.g., a curvature that is wider in the ML dimension and/or having a deeper sulcus) than the corresponding engaging surface of the patella, and/or slightly larger than the patient's corresponding trochlear groove. For example, in certain embodiments, the implant component includes a trochlear groove coronal curvature that is engineered to be slightly wider and/or deeper than the patient's trochlear groove coronal curvature.

Figure 40:
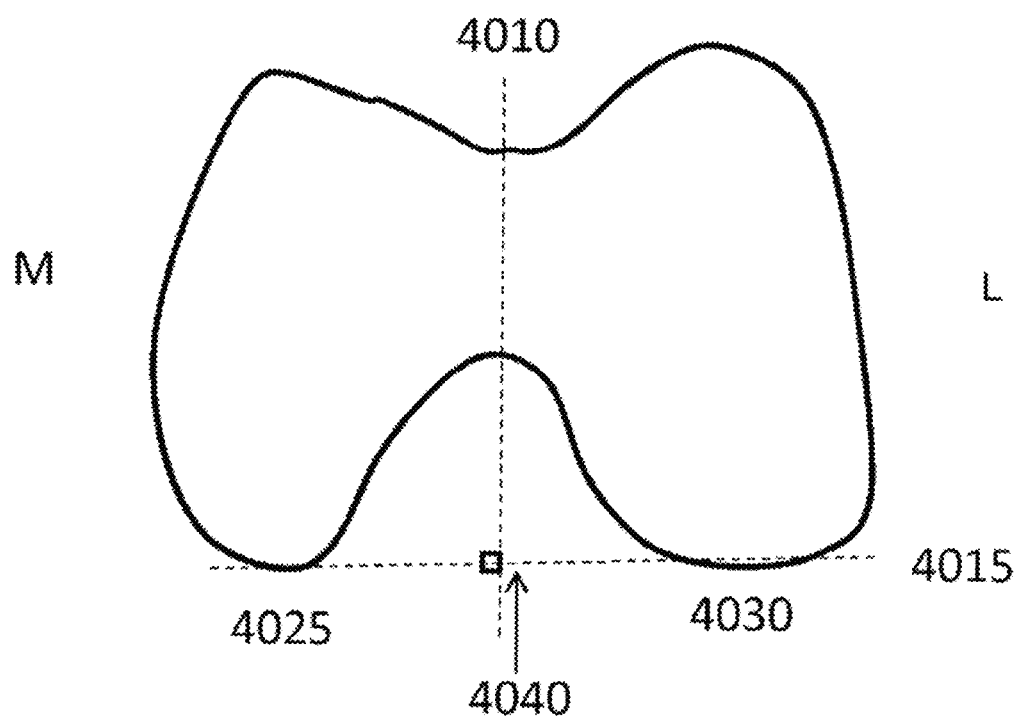
FIG. 40 illustrates a sulcus line of a femoral implant component.

Moreover, the implant component can include a trochlear groove and/or sulcus that are shifted and/or angled in part or in whole, for example, in order to optimize the biomechanical situation during knee motion. For example, the implant component's trochlear groove and/or sulcus can be offset by 2-5 mm medially, by 2-5 mm laterally, by about 2 mm medially, by about 2 mm laterally, by 1-2 mm medially, by 1-2 mm laterally, by less than 1 mm medially, or by less than 1 mm laterally, for example, relative to the patient's trochlear groove and/or sulcus and/or relative to one or both of the medial and/or lateral condyles. For example, as shown in FIG. 40, in certain embodiments, a line 4010 intersecting the sulcus of the implant component and perpendicular to a baseline 4015 connecting the lowermost points 4025, 4030 of the medial and lateral condyles can be medial to the point 4040 on the baseline that bisects the lowermost points of the medial and lateral condyles. Alternatively or in addition, the implant component's trochlear groove and/or sulcus can be angled relative to the patient's trochlear groove and/or sulcus. For example, in certain embodiments the trochlear groove or sulcus of the implant component can be positioned to include the patient's posterior aspect of the femoral trochlear notch or sulcus but then angle away anteriorly (e.g., by less than 10 degree, such as by 5-7 degrees) from the patient's trochlear groove or sulcus either in the medial direction or in the lateral direction.

Figure 41A:
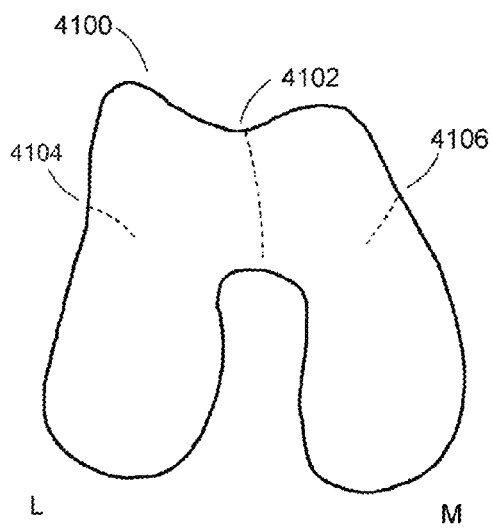
FIG. 41A depicts an axial view of a particular patient's femoral shape.
Figure 41B:
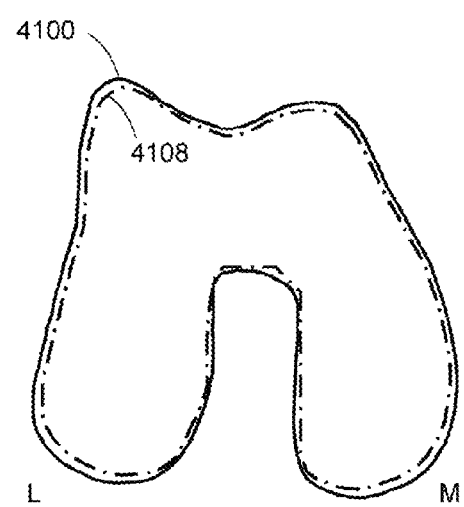
FIGS. 41B through 41V depict overlays of an implant component's articulating surface over the particular patient's femoral shape in axial (FIGS. 41B-41N) and sagittal (FIG. 41O-41V) views.
Figure 41C:
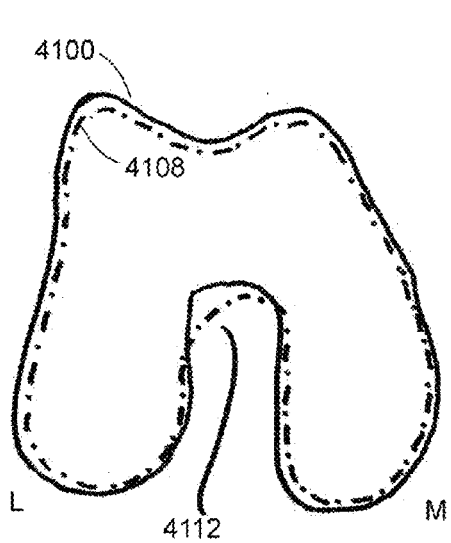

In certain embodiments, the trochlear articulating surface of the femoral implant component can include an overall shape that substantially positively matches the shape of the patient's trochlear articulating surface, as shown in FIGS. 41A and 41B. In particular, FIG. 41A depicts an axial view of a particular patient's femoral shape 4100, with the trochlear groove 4102, lateral anterior sulcus 4104, and medial anterior sulcus 4106 indicated by dashed lines. FIG. 41B depicts an overlay of an implant component's articulating surface 4108 (dash-dot line) and the particular patient' femoral shape 4100 (solid line). In this figure, the shape of the implant component 4108 (from the axial view) is patient-specific such that it substantially positively matches the particular patient's femoral shape 4100 (from the axial view). Alternatively or in addition, one or more aspects of the implant component's shape 4108 can be patient-engineered (e.g., derived from patient-specific data and optimized relative to the shape of the patient's femur 4100. For example, as shown in FIG. 41C, the implant component's trochlear articulating surface includes an overhanging flange or extension 4110 at the intercondylar notch 4110. As shown in the figure, the overhanging flange or extension 4110 extends from the lateral aspect of the intercondylar notch; however, in certain embodiments it can extend from the lateral or medial aspect, or both, of the intercondylar notch. This overhanging feature 4110 can be beneficial in patients with a wider intercondylar notch distance, in particular if a standard patellar button (i.e., patellar implant component) is used that could, for example, be less wide than the intercondylar distance in select patients. The extension or flange can assist to help avoid patellar clicking or capture, for example, if a smaller patellar button may "fall" into the intercondylar notch region during motion of the knee.

Figure 41D:
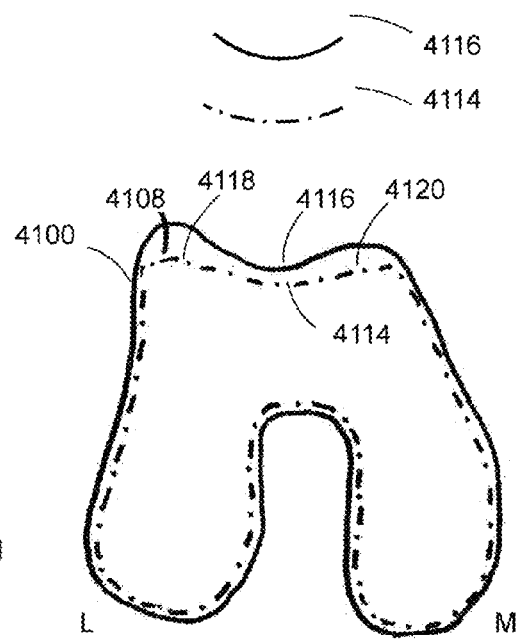
Figure 41E:
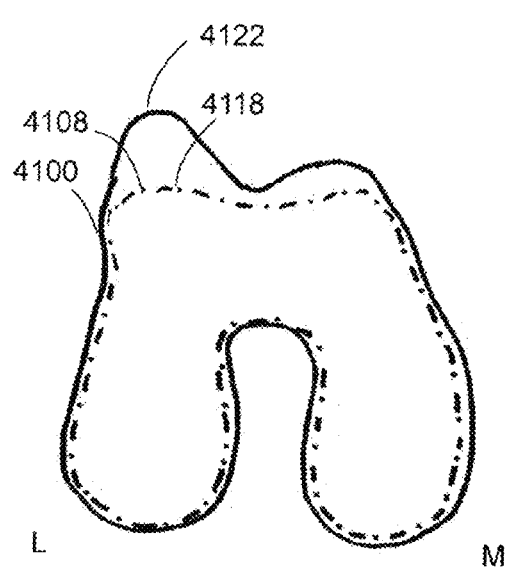

In certain embodiments, the implant component can substantially match one or more of the patient's femoral or femoral condyle dimensions or surface shapes (e.g., the shape of the patient's femoral bone or cartilage) on the joint-facing surface (e.g., at the bearing surface that engages the tibia) and, optionally, also on the bone-facing surface. At the same time, the trochlear's outer, articulating shape can, however, be partially matched to the patient's articular surface or, instead, patient-engineered from patient data but not designed to match the patient's surface feature. For example, as shown in FIG. 41D, the implant component can include a shallower trochlear groove 4114 than the patient's trochlear groove 4116. In the figure, the trochlear groove curvatures 4114, 4116 are shown above the axial view of the femur 4100 and implant component 4108. This shallower trochlear groove 4114 can be engineered by using a shallower lateral side of the trochlear surface 4118 and/or a shallower medial side of the trochlea 4120, for example relative to the patient's lateral and medial sides. A shallower lateral shape of the implant component's trochlea surface 4118 can, for example, assist in achieving more normal patellofemoral motion in select patellofemoral tracking abnormalities. For example, as shown in FIG. 41E, a shallower lateral shape of the implant component's trochlea surface 4118 can be used to correct a patient's tracking abnormality relating to the patient's lateral trochlear shape 4122. A shallower medial shape of the implant component's trochlea surface 4120 can, for example, assist in achieving more normal patellofemoral motion in select patellofemoral tracking abnormalities.

Figure 41F:
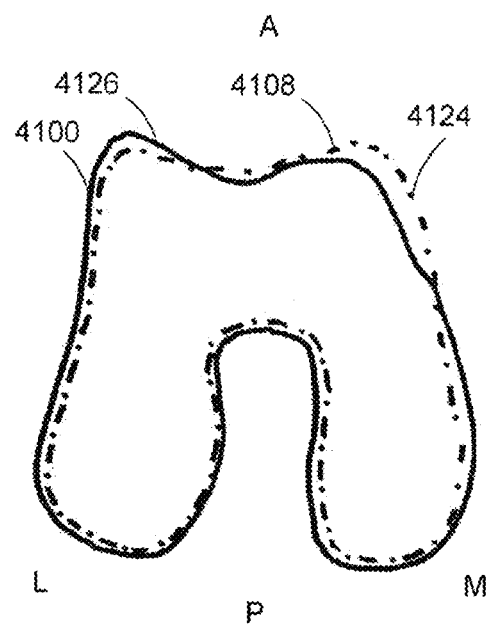

The partially (e.g., coronal plane only or lateral trochlear surface only) or completely engineered (e.g., coronal plane and sagittal plane or medial and lateral trochlear surface) trochlear surface of the implant component can be, at least in part, anterior to the patient's native, uncut bone or it can be, at least in part, posterior to the patient's native, uncut bone, or both. For example, as shown in FIG. 41F, the implant component surface 4108 can be anterior to the patient's uncut medial trochlear bone surface 4124 but posterior to the patient's uncut lateral trochlear bone 4126. As shown in FIG. 41F, the implant component surface 4108 can be anterior to the patient's uncut medial trochlear bone surface 4122 but posterior to the patient's uncut lateral trochlear bone 4124. The most posterior point of the partially or completely engineered trochlear articulating surface of the implant can be anterior to, coincident with, or co-planar with, or posterior to the most posterior point of the patient's native, uncut trochlear in any location of the trochlea, e.g., superior, central, or inferior.

Figure 41G:
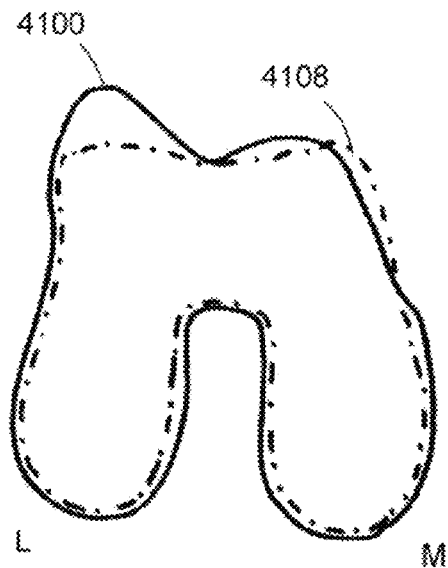
Figure 41H:
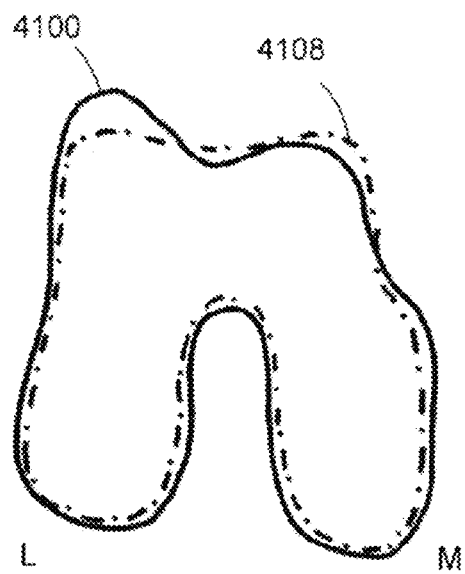

The coronal curvature also can be non-patient-matched or derived, or engineered or constant. Each of FIGS. 41G and 4111 depict an exemplary implant component surface 4108 having a constant trochlear coronal curvature that does not follow the patient's trochlear coronal curvature. However, as shown by the figures, other implant component features (e.g., surface outline 4108) are patient-specific with respect (e.g., with respect to the patient's femoral surface outline 4100).

The trochlear articular surface can be patient-specific in all dimensions and aspects; patient-engineered in all dimensions or aspects; partially patient-specific and partially patient-engineered; partially patient-specific and partially standard; partially patient-engineered and partially standard; or partially patient-specific, partially patient-engineered, and partially standard. Combinations include, for example, those described in Table 9.

TABLE 9

Exemplary features of implant component trochlear surface

| A first implant component feature | A second implant component feature |
|---|---|
| Coronal J-curve patient-engineered | Sagittal J-curve patient-specific |
| Sagittal J-curve patient-engineered | Coronal J-curve patient-specific |
| Medial trochlear surface patient-engineered | Lateral trochlear surface patient-specific |
| Lateral trochlear surface patient-engineered | Medial trochlear surface patient-specific |
| Superiorly patient-engineered | Inferiorly patient-specific |
| Inferiorly patient-engineered | Superiorly patient-specific |

Of note, an engineered surface can still include patient-derived parameters. For example, the patient's trochlear coronal curvature can be measured in multiple locations and an average can be derived. The average or constant coronal curvature can then be applied to the articulating surface of the implant. Optionally, a matching patellar implant component can be selected or designed.

The trochlear groove location can be patient derived, e.g., derived from the location of the patient's uncut trochlear groove determined from an imaging test. A desired trochlear groove location can be derived based on these measurements, for example by calculating a straight line intersecting the patient's curved trochlear groove. Mathematical or kinematic modeling can be used to derive the patient-derived, engineered trochlear groove location.

The sagittal curvature of the articulating trochlear surface of the femoral component can be matched to the patient's sagittal trochlear shape in one or more locations, e.g., trochlear groove, medial trochlea or lateral trochlea or combinations thereof;
  matched to the patient's sagittal trochlear shape superiorly, but engineered inferiorly, e.g., in the trochlear groove, medial trochlea or lateral trochlea or combinations thereof;
  matched to the patient's sagittal trochlear shape inferiorly, but engineered superiorly, e.g., in the trochlear groove, medial trochlea or lateral trochlea or combinations thereof; and/or
  anterior or posterior or combinations thereof to the patient's uncut trochlea in different sections of the patient's trochlea.

Figure 41I:
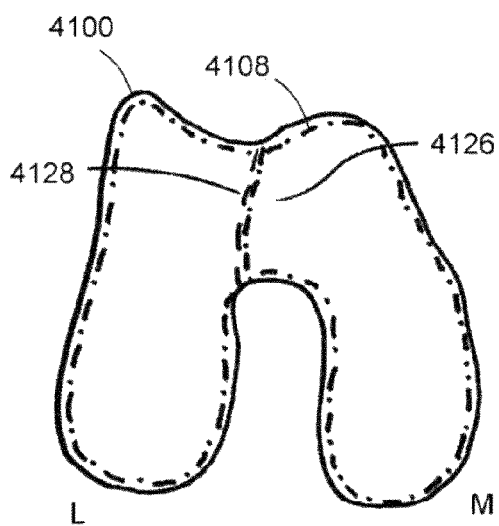
Figure 41J:
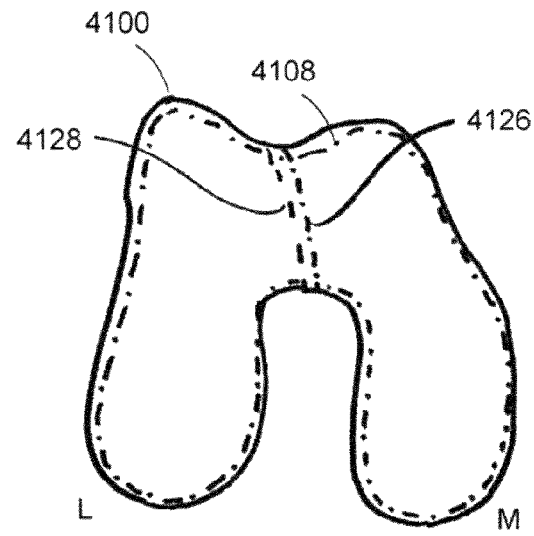
Figure 41K:
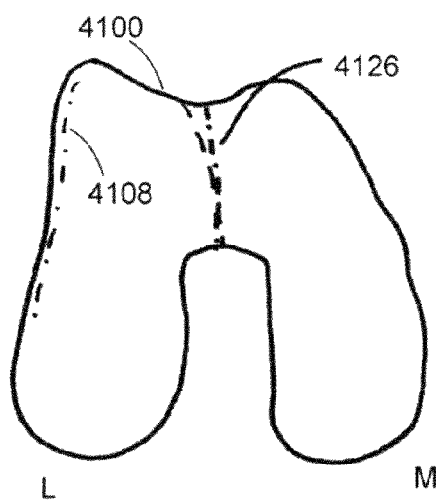
Figure 41L:
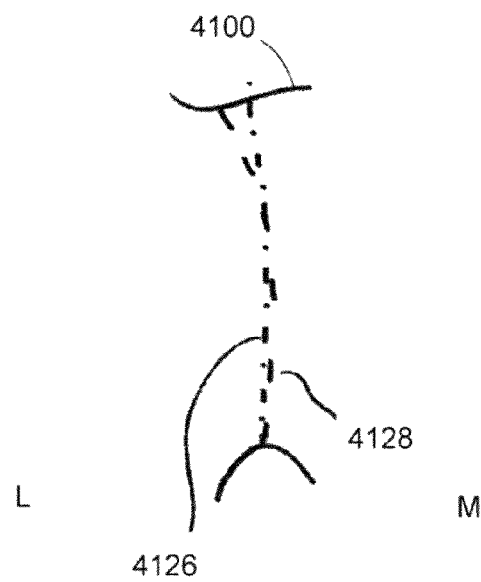

The trochlear groove curvature and/or location can be patient-specific on the implant articulating surface, i.e., replicating the location of the patient's native, uncut trochlear groove, for example as it extends from superior to inferior. For example, FIG. 41I depicts an implant component trochlear groove 4126 that is patient-specific to substantially match the patient's trochlear groove curvature 4128 and position. The trochlear groove location can be patient-engineered, e.g., to include one or more straight, curved, straight oblique, and/or curved oblique sections that may deviate from the patient's trochlear groove. The trochlear groove can be a combination of patient-specific and patient-engineered. For example, FIG. 41K depicts an implant component trochlear groove 4126 that is patient-specific in its shape to substantially positively match the shape of the patient's trochlear groove curvature 4128; however, the implant component trochlear groove 4126 is offset laterally in its location relative to the patient's trochlear groove curvature 4128. Moreover, FIGS. 41K and 41L (FIG. 41L is a blown-up image of the trochlear groove depicted in FIG. 41K) depict an implant component trochlear groove 4126 that is a patient-derived to be patient-specific in part and patient-engineered in part to yield a straight trochlear groove 4126. In particular, the location and curvature of the patient's trochlear groove is measured and then, in the implant component, the trochlear groove is patient-specific where the patient's groove is straight and patient-engineered where the patient's groove curves. Alternatively a patient-engineered straight trochlear groove can be derived as an average straight line based on the patient's groove. Alternative, the patient-engineered line can be forced to follow an oblique line rather than a straight line.

Figure 41M:
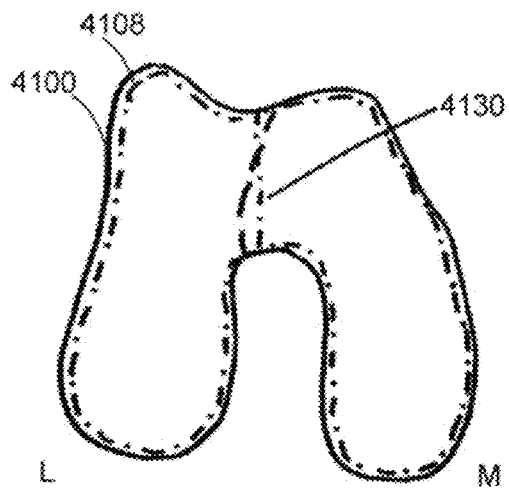
Figure 41N:
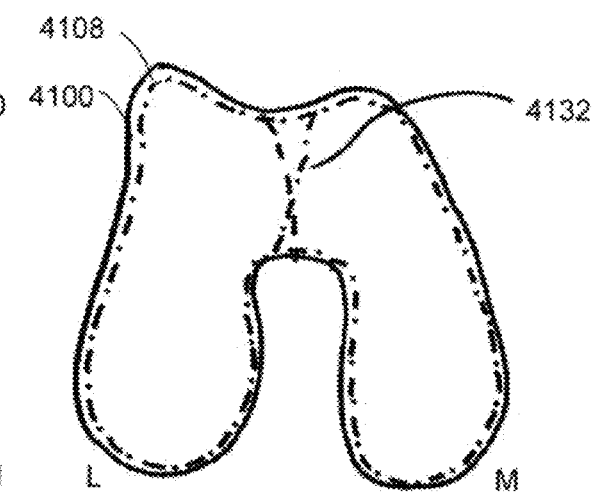

Alternatively, the implant component trochlear groove 4126 can be a standard straight line 4130 or oblique line 4132, as shown in FIGS. 41M and 41N, respectively.

Figure 41O:
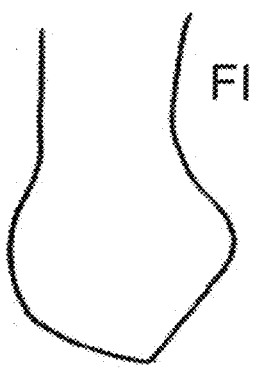
Figure 41P:
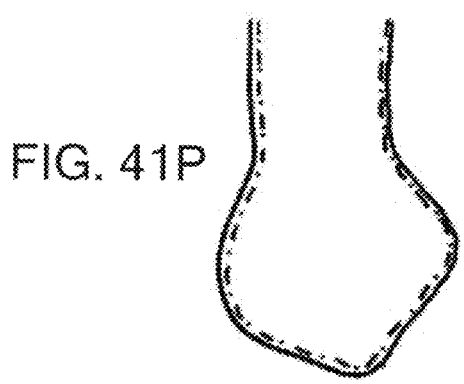
Figure 41Q:
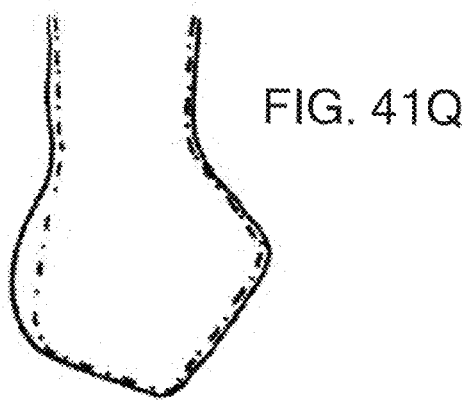
Figure 41R:
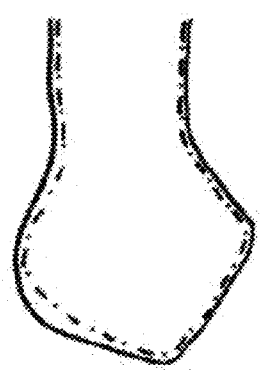
Figure 41S:
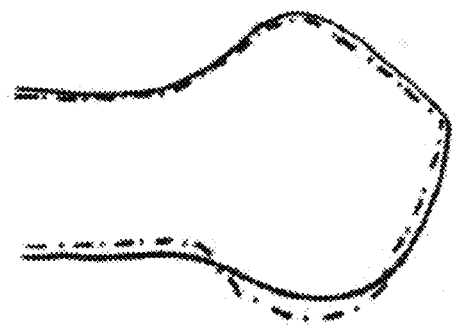
Figure 41T:
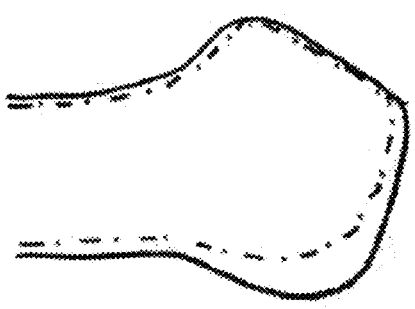
Figure 41U:
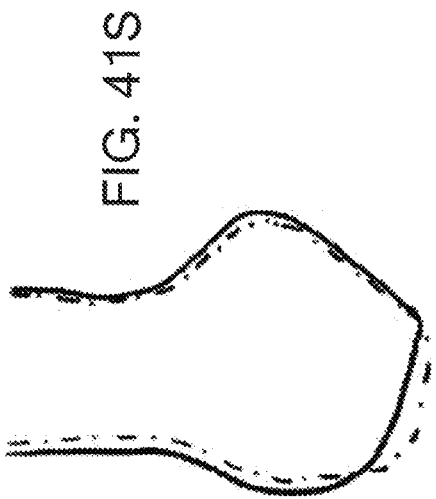
Figure 41V:
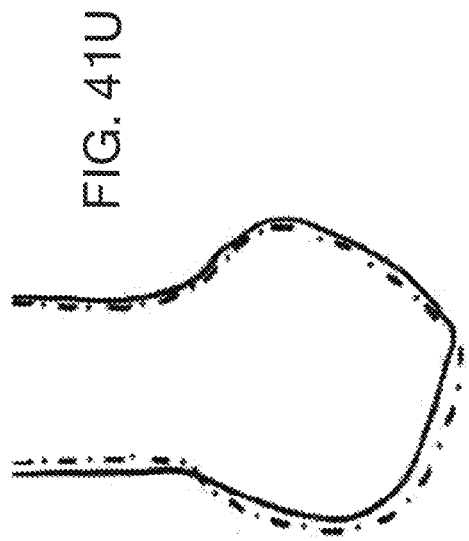

FIG. 41O depicts a patient anatomy sagittal cross-section through the trochlear groove and FIGS. 41P through 41V depict the same patient anatomy sagittal cross-section (solid line) overlaid with an implant component sagittal cross-section through the trochlear groove. In particular, FIG. 41P depicts an implant component having a sagittal shape that is patient-specific to match the patient's sagittal shape. FIGS. 41Q and 41T depict implant components having a sagittal shape that is patient-specific with respect to the inferior trochlea shape and patient-engineered with respect to the superior trochlea shape. FIGS. 41R and 41S depict implant components having a sagittal shape that is patient-specific with respect to the superior trochlea shape and patient-engineered with respect to the inferior trochlea shape. FIGS. 41U and 41V depict implant components that are patient-specific and have a completely engineered sagittal trochlear curvature.

As noted above, with traditional knee implants the patient's bone is resected to fit the standard shape of the bone-facing surface of the traditional femoral implant component. On its bone-facing surface, the traditional femoral implant component includes five standard bone cuts, as exemplified by the implant shown in FIG. 42A. Specifically, a traditional total knee implant includes a distal or horizontal cut 4210, an anterior cut 4220, a posterior cut 4230 along each femoral condyle, an anterior chamfer cut 4240, and a posterior chamfer cut 4250.

In certain embodiments, one or more portions of the bone-facing surface of the femoral implant are designed based on patient-specific data to substantially negatively-match the uncut surface of the patient's femur, for example, the subchondral bone surface of the femur. In such embodiments, the surgical procedure includes resurfacing (i.e., removing cartilage, at least in part, while substantially retaining the surface of subchondral bone (i.e. cutting away bone), the joint-facing surface of the patient's femur. In certain embodiments, the bone-facing surface(s) of the implant component are designed and/or selected preoperatively, based on patient-specific data, to optimize one or more parameters, such as bone preservation (e.g., minimizing the amount of bone that is resected during the implant procedure).

In certain embodiments one or more portions of the bone-facing surface of the femoral implant includes two or more bone cuts, for example, two, three, four, five, six, seven, eight, nine, or more bone cuts. For example, a femoral implant component can include less than or greater than five bone cuts. In a preferred embodiment, the femoral implant includes six bone cuts, as shown in FIG. 42B. In another preferred embodiment, the femoral implant includes seven bone cuts, as shown in FIG. 6B. One or more of the implant bone cuts can be curvilinear or the entire bone-facing surface of the implant component can be curvilinear bone cut.

Figure 42C:
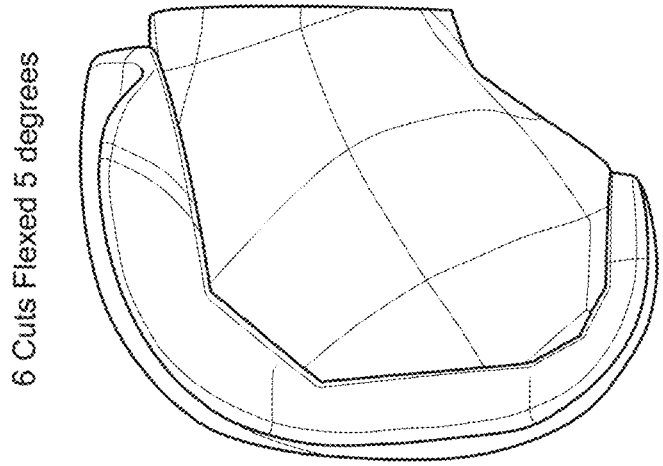
FIGS. 42A through 42C illustrate femoral implant components includes five bone cuts, six bone cuts, and six flexed bone cuts, respectively.
Figure 42B:
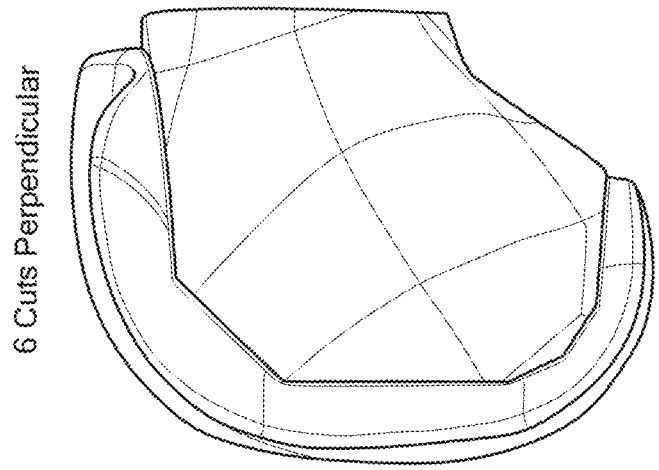
Figure 42A:
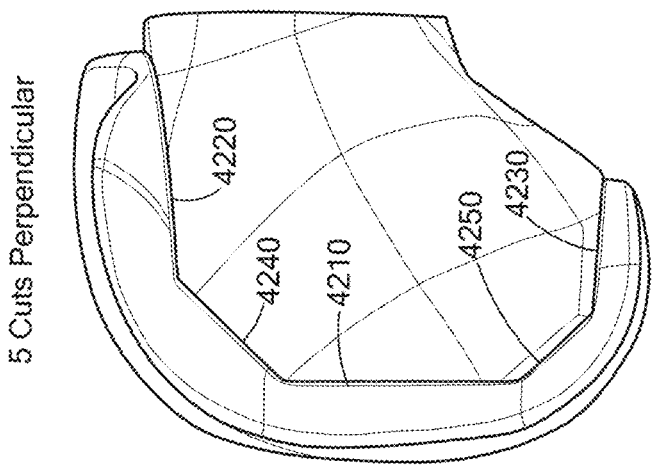

As exemplified in FIG. 42C, in certain embodiments the femoral implant and design can include bone cuts that are rotated or oriented based on a certain flexion angle of the knee, e.g., rotated in the sagittal plane. An example of a flexed-fit cut design is described in Example 2, below. Any number of bone cuts can be included in an implant device designed with flexed-fit cuts. For example, two, three, four, five, six, seven, eight, nine or more cut planes can be included in a flexed-fit design. One or more of the cuts can be curvilinear or the entire bone-facing surface can be curvilinear. Moreover, any one or more bone cuts can include two or more non-coplanar facets, as described below. The cuts can be oriented at any rotation, for example, at 5, greater than 5, 10, greater than 10, 15, greater than 15, 20, greater than 20, 25, or greater than 25 degrees flexion.

In certain embodiments, the femoral implant component can include one or more bone cuts oriented one or more dimensions, e.g., not only in the sagittal plane, but also in the coronal plane and/or in the axial plane. FIGS. 43A through 43F show exemplary cross-sections of femoral implant components with bone cuts shown as dashed lines. FIGS.

Figure 43A:
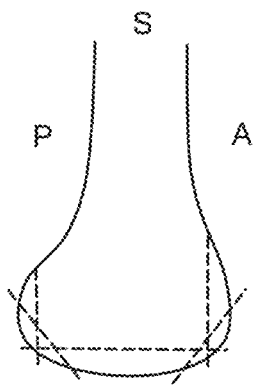
FIGS. 43A through 43F show exemplary cross-sections of femoral implant components with bone cuts shown as dashed lines.
Figure 43B:
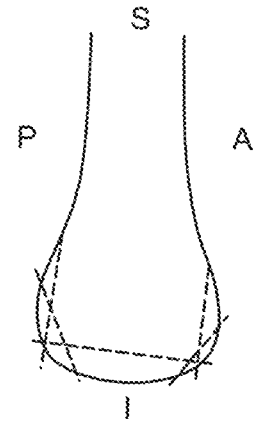
Figure 43C:
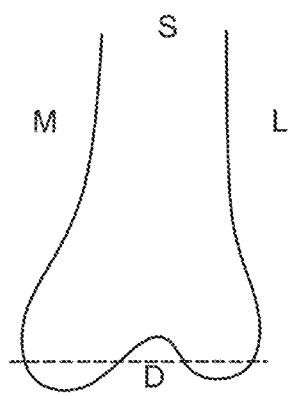
Figure 43D:
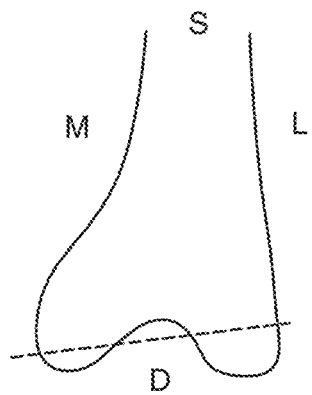
Figure 43E:
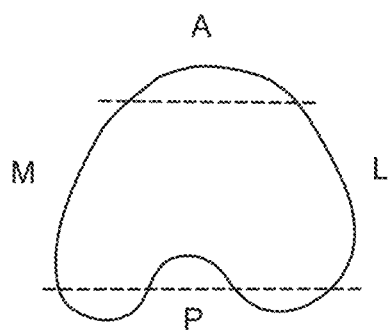
Figure 43F:
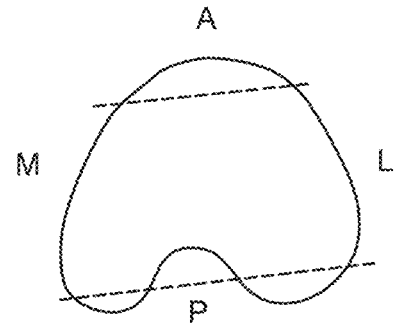

43A and 43B show an implant component with traditional bone cuts (FIG. 43A) as compared to an implant component with bone cuts rotated in the sagittal plane (FIG. 43B). FIGS. 43C and 43D show an implant component with traditional bone cuts (FIG. 43C) as compared to an implant component with bone cuts rotated in the coronal plane (FIG. 43D). FIGS. 43E and 43F show an implant component with traditional bone cuts (FIG. 43E) as compared to an implant component with bone cuts rotated in the axial plane (FIG. 43F). Such bone cut rotations can help to further optimize bone preservation.

As shown in FIGS. 44A-44C and 45A-45B, in certain embodiments an implant component bone cut can include one or more non-parallel and non-coplanar facets. As shown, the implant component in FIG. 44A includes six bone cuts while the implant component in FIG. 45A includes an extra posterior chamfer bone cut for a total of seven bone cuts. Non-coplanar facets can include facets that lie in parallel but different planes and/or facets that lie in non-parallel planes. As exemplified by the implant component shown in FIGS. 44A-44B and by the implant component shown in FIGS. 45A-45B, the medial and lateral facets of a bone cut can be non-parallel and non-coplanar for one or more bone cuts, for example, for one or more of the distal bone cut 4410, the posterior bone cut 4430, the first posterior chamfer bone cut 4452, and the second posterior chamfer bone cut 4454. Alternatively or in addition, one or more corresponding facets of a bone cut can include different thicknesses. For example, the implant component shown in FIG. 44A includes a maximum distal medial facet thickness of 6.2 mm and a maximum distal lateral facet thickness of 6.3 mm. The independent and optionally patient-derived thicknesses on corresponding bone cut facets can apply to one or more thickness measurements, for example, one or more of maximum thicknesses, minimum thickness, and an average thickness, for example, to match or optimize the particular patient's anatomy. Moreover, a single bone cut or bone cut facet can include a variable thickness (e.g., a variable thickness profile across its M-L and/or A-P dimensions. For example, a bone cut or bone cut facet can include a thickness profile in one or more dimensions that is patient-derived (e.g., to match or optimize the patient's anatomy). The implant component in FIG. 45A includes an anterior chamfer with an 11 mm thickness on the medial side (which includes the medial implant component peg or post 4465) and a different thickness on the lateral side. As shown, the implant component in FIG. 45A was selected and/or designed to have a flex-fit (e.g., having bone cuts rotated posteriorly about the transepicondylar axis, which can enhance implant component coverage of the posterior portion of the femur and provide the patient with deeper knee flexion with the implant.

Figure 44B:
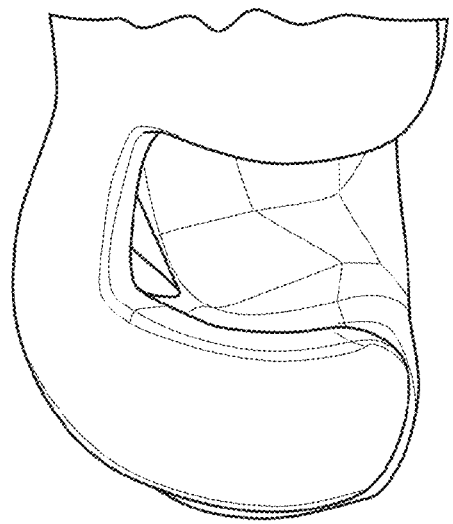
FIGS. 44A-44C illustrate a femoral implant component having six bones cuts that include one or more parallel and non-coplanar facets.
Figure 44C:
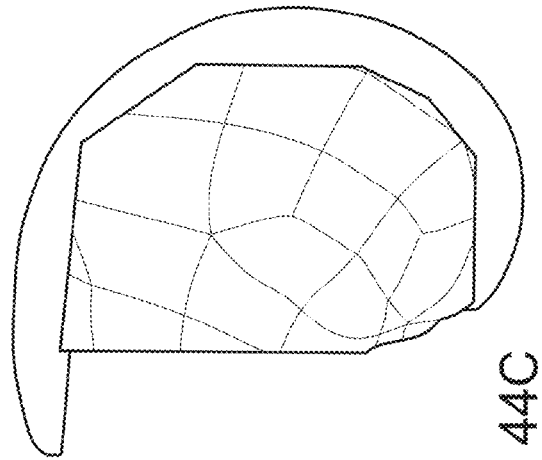
Figure 44A:
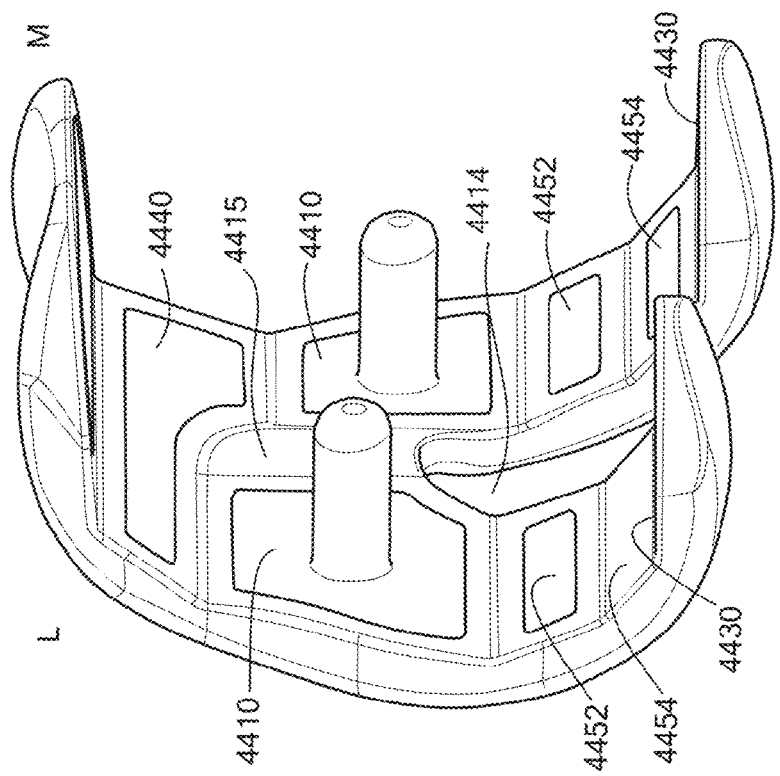

Alternatively or in addition, one or more corresponding facets of a bone cut can include different surface areas or volumes. For bone cuts having facets separated by the intercondylar space and asymmetric with respect to the A-P plane bisecting the implant component, the asymmetric facets appear dissimilar in shape and/or size (e.g., two-dimensional area). For example, the implant components shown in FIGS. 44A and 45A include one or more corresponding facets (e.g., distal medial and lateral facets, posterior medial and lateral facets, and/or posterior chamfer medial and lateral facets) having different medial facet and lateral facet bone-facing surface areas, joint-facing surface areas, and/or volumes in between the two surfaces. In particular, as shown in FIG. 44A and in 45A, the medial and lateral facets of the distal bone cut 4410 are asymmetric and appear dissimilar in both shape (e.g., surface area perimeter shape) and size (e.g., volume under the surface area). The independent facet surface areas and/or volumes optionally can be patient-derived (e.g., to match or optimize the patient's anatomy).

As shown in FIG. 44A, non-coplanar facets can be separated by an intercondylar space 4414 and/or by a step cut 4415. For example, as shown in the figure, the distal bone cut 4410 includes non-coplanar medial and lateral facets that are separated, in part, by the intercondylar space 4414 and, in part, by a step cut 4415.

Figure 45B:
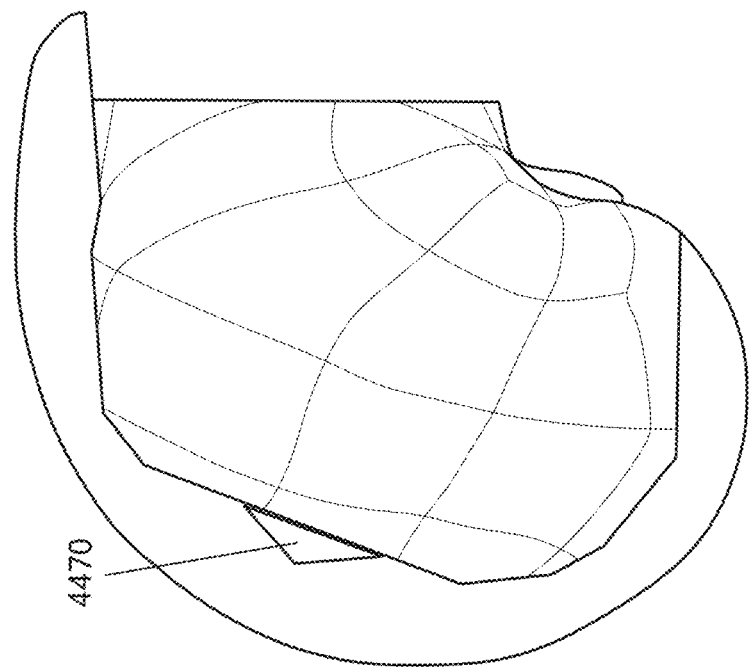
FIGS. 45A-45B illustrate a femoral implant component having seven bones cuts that include one or more parallel and non-coplanar facets.

In certain embodiments, one or more resection cuts can be selected and/or designed to so that one or more resected cut or facet surfaces substantially matches one or more corresponding bone cuts or bone cut facets. For example, FIG. 44C shows six resection cut facets that substantially match the corresponding implant component bone cut facets shown in FIG. 44A. FIG. 45B shows seven resection cut facets that substantially match the corresponding implant component bone cut facets of the medial side of the implant component shown in FIG. 44A. The portion 4470 represents additional bone conserved on the lateral side of the of the femur corresponding to the bone-cut intersection between the lateral distal bone cut facet 4410 and the adjacent anterior chamfer bone cut 4440.

Figure 46:
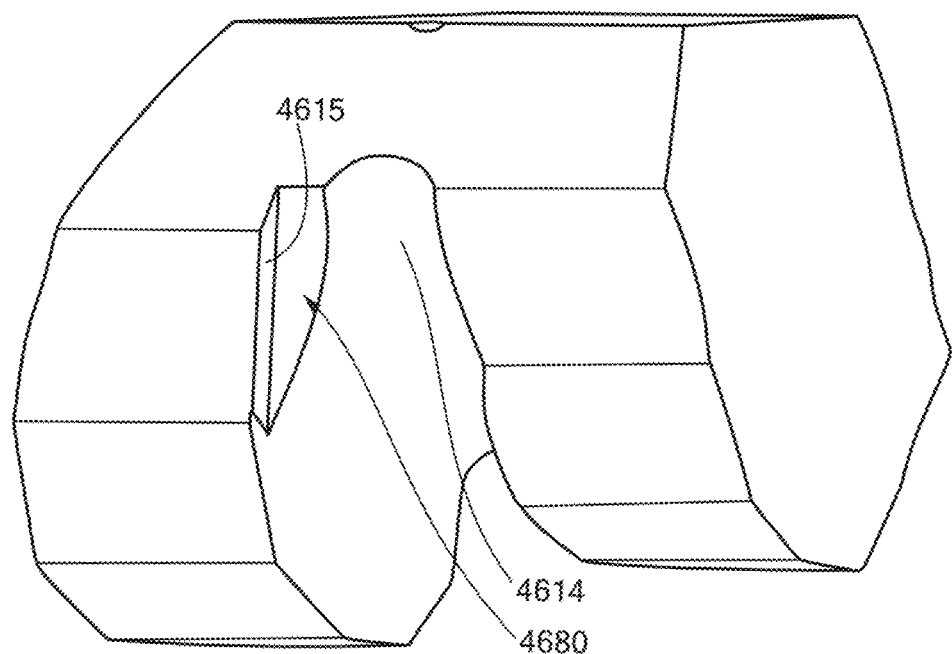
FIG. 46 illustrates a resection cut facet separated from one or more corresponding facets by an intercondylar space and/or by a step cut.

In certain embodiments, a bone-cut facet and/or a resection cut facet can span the intercondylar space and be separated from another facet by a step cut. For example, as exemplified in FIG. 46, predetermined resection cuts can be selected and/or designed to include a facet or part of a facet 4680 separated from one or more corresponding facets by an intercondylar space 4614 and/or by a step cut 4615.

Figure 45A:
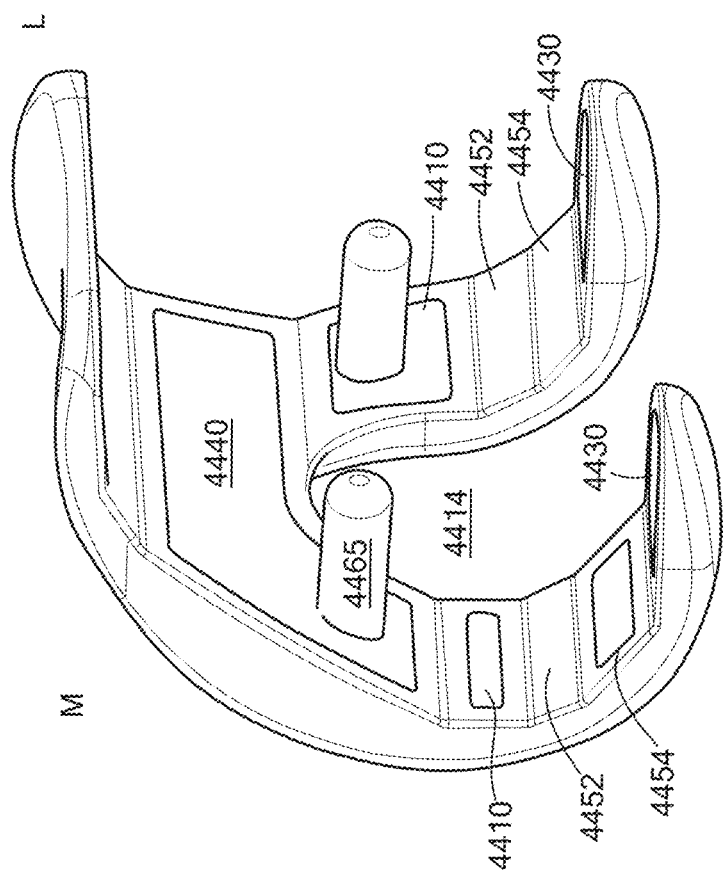

In addition or alternatively, in certain embodiments one or more of the implant bone cuts can be asymmetric, for example, asymmetric with respect to a sagittal or A-P plane, or to a coronal or M-L plane, bisecting the implant component. For example, as shown in FIGS. 44A and 45A, the anterior chamfer bone cut 4440 is asymmetric with respect to an A-P plane bisecting the implant component. In addition, in both figures the lateral distal bone cut facet 4410 is is asymmetric with respect to an A-P plane bisecting the implant component.

The bone cut designs described above, for example, an implant component bone-facing surface having various numbers of bone cuts, flexed bone cuts, non-coplanar bone cut facets, step cuts used to separate facets, and asymmetric bone cuts and bone cut facets, can be employed on a bone-facing surface of a femoral implant component to save substantial portions of bone. Table 10 shows the different amounts of bone to be resected from a patient for fitting an implant component with bone cuts shown in FIG. 44A, an implant component with bone cuts shown in FIG. 44A, and a traditional implant component with traditional bone cuts. As compared to the traditional implant component, the implant component shown in FIG. 44A saves 44% of resected patient bone and the implant component shown in FIG. 45A saves 38% of resected patient bone. However, the implant component in FIG. 45A is flexed, which can provide enhanced deep knee flexion for the patient. In certain embodiments, the surgeon or operator can select or apply a weighting to these two parameters (bone preservation and kinematics) and optionally other parameters to identify an optimum patient-adapted implant component and, optionally, a corresponding resection cut strategy, that meets the desired parameters and/or parameter weightings for the particular patient.

TABLE 10

Bone preservation comparison using different bone cut designs

| Bone Cut | FIG. 9D Implant (Stepped) | FIG. 9E Implant (Flexed no step) | Traditional Implant |
|---|---|---|---|
| Distal Medial | 3626 | 2675 | 5237 |
| Distal Lateral | 2593 | 3077 | 2042 |
| Medial Posterior Chamfer 1 | 942 | 694 | 3232 |
| Lateral Posterior Chamfer 1 | 986 | 715 | 648 |
| Medial Posterior Chamfer 2 | 816 | 921 | — |
| Lateral Posterior Chamfer 2 | 612 | 582 | — |
| Medial Posterior Cut | 945 | 1150 | 2816 |
| Lateral Posterior Cut | 770 | 966 | 649 |
| Anterior Chamfer 1 | 1667 | 6081 | 9872 |
| Anterior Chamfer 2 | — | 1845 | — |
| Anterior Cut | 3599 | 2717 | 4937 |
| Total bone resection (mm$^3$)* | 16556 | 18346 | 29433 |
| Reduction in bone resected as compared to traditional implant | 44% | 38% | — |

Figure 47A:
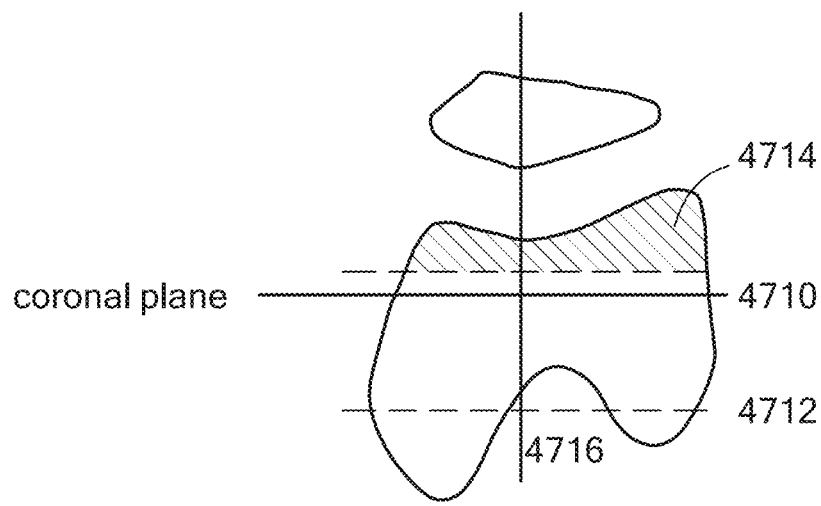
FIGS. 47A and 47B are schematic views of a femur and patella and exemplary resection cut planes.
Figure 47B:
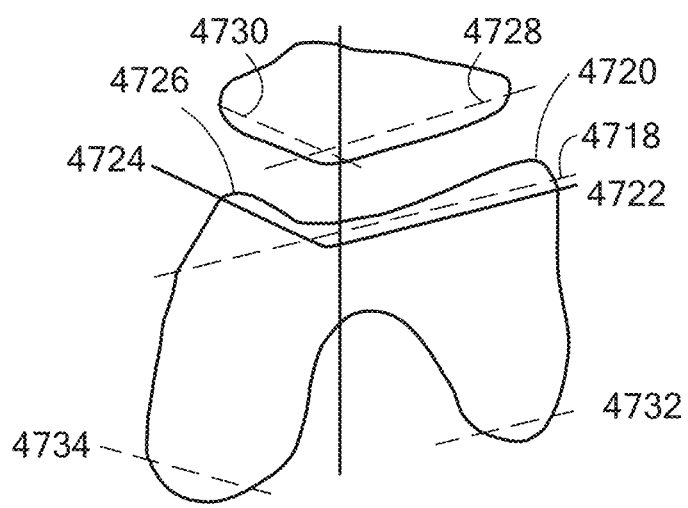

In traditional femoral implant components, the anterior or trochlear bone cut is located substantially in the coronal plane and is parallel to the posterior condylar bone cut, as indicated by the dashed anterior resection cut 4710 and dashed posterior resection cut 4712 shown in FIG. 47A. This can result in a substantial amount of bone lost from those portions of the patient's femur 4714, 4716. However, in certain embodiments described herein, the implant's anterior or trochlear bone cut is substantially non-parallel to the coronal plane, as shown by the dashed and straight line 4718 in FIG. 47B. For example, the implant's anterior or trochlear bone cut can substantially match the patient's resected trochlear surface, which can be selected and/or designed to be parallel to a tangent through the corresponding peak 4720 and an uncut trochlear surface portion of the patient's trochlea, as shown in FIG. 47B. By placing the implant bone cut 4718 and the resected surface at an angle relative to the patient's coronal plane, for example, parallel to a tangent of one or both medial and lateral trochlear peak and/or the adjacent trochlear surface, a substantial amount of bone can be preserved.

In certain embodiments, the implant component can include a trochlear bone cut with two or more non-coplanar facets, as shown by the intersecting solid lines 4722, 4724 in FIG. 47B. For example, one of the two or more facets (and the patient's corresponding resected surface) can be substantially parallel to the patient's lateral uncut trochlear peak 4720 and/or the adjacent uncut trochlear surface. A second facet (and the patient's corresponding resected surface) can be substantially parallel to the patient's medial uncut trochlear peak 4726 and/or the adjacent uncut trochlear surface. This can further enhance the degree of bone preservation.

In certain embodiments, two or more trochlear bone cut facets can be substantially tangent to the lateral and medial patellar surfaces 4728, 4730 of the patient's uncut bone. In addition or alternatively, two or more trochlear bone cuts can be substantially tangent or parallel to the superior and inferior patellar facets, in particular, when more than two implant trochlear bone cut facets are used. In certain embodiments, one or more trochlear bone cut facets can be curvilinear.

In a traditional femoral implant component, the posterior bone cut includes portions on the medial and lateral condyles that are in the same plane and parallel to each other, and substantially parallel to the anterior cut. However, in certain embodiments described herein, the implant component can include posterior condylar bone cut facets on the medial and lateral condyles, respectively, that are non-coplanar 4732, 4734. Alternatively, or additionally, the implant component can include one or more posterior condylar facets that are substantially non-parallel with one or more facts of the anterior bone cut.

Figure 48:
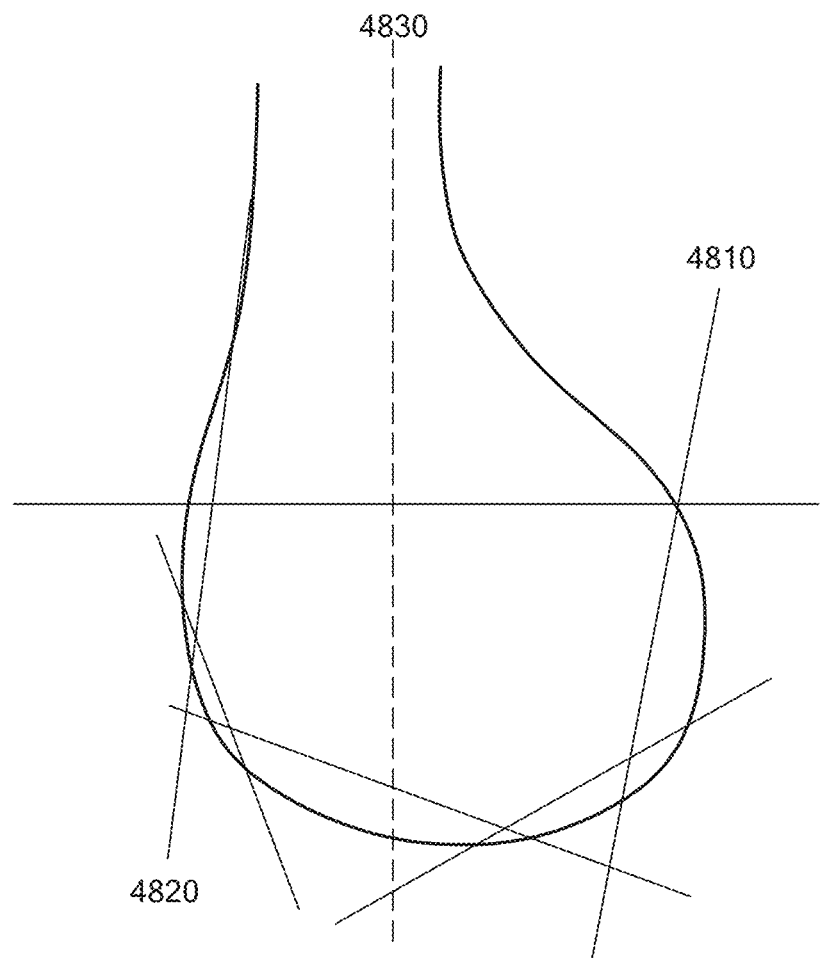
FIG. 48 is a schematic view of a sagittal plane of a femur with facet cuts indicated.

In certain preferred embodiments, the posterior condylar bone cut includes a facet on the medial condyle that is substantially perpendicular to the long axis of the medial condyle. Optionally, the facet on the lateral condyle can be perpendicular to the long axis of the lateral condyle. As depicted in FIG. 48, in certain embodiments, the anterior bone cut and corresponding resection cut 4810 and posterior bone cut 4820 can be substantially non-parallel to the coronal plane 4830 in the superoinferior orientation.

In certain embodiments, the posterior bone cut medial and lateral facets of an implant component can be asymmetric with respect to an A-P plane bisecting the implant component. Moreover, one or more posterior bone cut facets can be curvilinear.

In certain embodiments, the distal bone cut of a femoral implant component includes medial and lateral condylar facets that are in the same plane as each other and/or are substantially parallel to each other. The facets can be separated by the intercondylar space and/or by a step cut. In certain embodiments, the implant component can include a distal bone cut having medial and lateral condylar facets that are non-coplanar and/or non-parallel.

In certain embodiments, the distal bone cut or bone cut facets is/are asymmetric with respect to an A-P plane bisecting the implant component. Moreover, the distal bone cut and/or one or more distal bone cut facets can be curvilinear.

Traditional femoral implant components include one anterior chamfer bone cut and one posterior chamfer bone cut. However, in certain embodiments described herein, additional chamfer bone cuts can be included. By increasing the number of chamfer bone cuts on the implant and placing the cuts in close proximity to the tangent of the articular surface, additional bone can be preserved. One or more additional chamfer bone cuts can be substantially tangent to the articular surface. For example, in certain embodiments, the implant component can include one or more additional anterior chamfer cuts and/or one or more additional posterior chamfer cuts.

In certain embodiments, the implant component can include a posterior chamfer bone cut that includes medial and lateral condylar facets that are non-coplanar and/or non-parallel. In certain embodiments, a posterior chamfer bone cut of the implant component can include facets that are asymmetric with respect to an A-P plane bisecting the implant component. Moreover, one or more posterior chamfer bone cuts and/or one or more posterior chamfer bone cut facets can be curvilinear.

In certain embodiments, the implant component can include an anterior chamfer bone cut that includes medial and lateral condylar facets that are non-coplanar and/or non-parallel. In certain embodiments, an anterior chamfer bone cut of the implant component can be asymmetric and/or can include facets that are asymmetric with respect to an anterior-posterior (A-P) plane bisecting the implant component. Moreover, one or more anterior chamfer bone cuts and/or bone cut facets can be curvilinear.

In certain embodiments, the cut plane for one or more bone cuts of the implant component, for example, the distal bone cut and/or one or more of the anterior chamfer bone cuts, can be defined, in part, by the extent of the trochlear gap in the patient's joint. Specifically, one or more of these bone cuts can be designed based on patient-specific data to include a perimeter that matches the contour of the patient's trochlear notch. In certain embodiments, the implant component is patient-adapted so that there is no exposed implant surface on the bone-facing side of the implant component at the trochlear gap. Moreover, one or more of these bone cuts can be designed so that there is no, or minimally exposed, resected bone surface at the trochlear notch.

Computer software can be used that calculates the closest location possible for resected surfaces and resected cuts relative to the articular surface of the uncut bone, e.g., so that all intersects of adjoining resected surfaces are just within the bone, rather than outside the articular surface. The software can move the cuts progressively closer to the articular surface. When all intersects of the resected cuts reach the endosteal bone level, the subchondral bone level, and/or an established threshold implant thickness, the maximum exterior placement of the resected surfaces is achieved and, with that, the maximum amount of bone preservation.

Figure 49B:
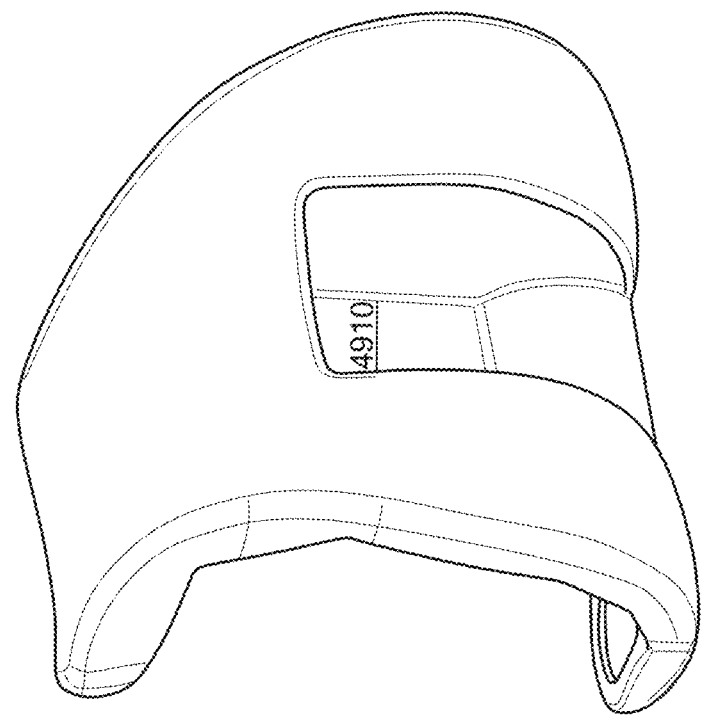
FIGS. 49A and 49B illustrate a femoral implant component comprising an intercondylar housing (sometimes referred to as a "box")
Figure 49A:
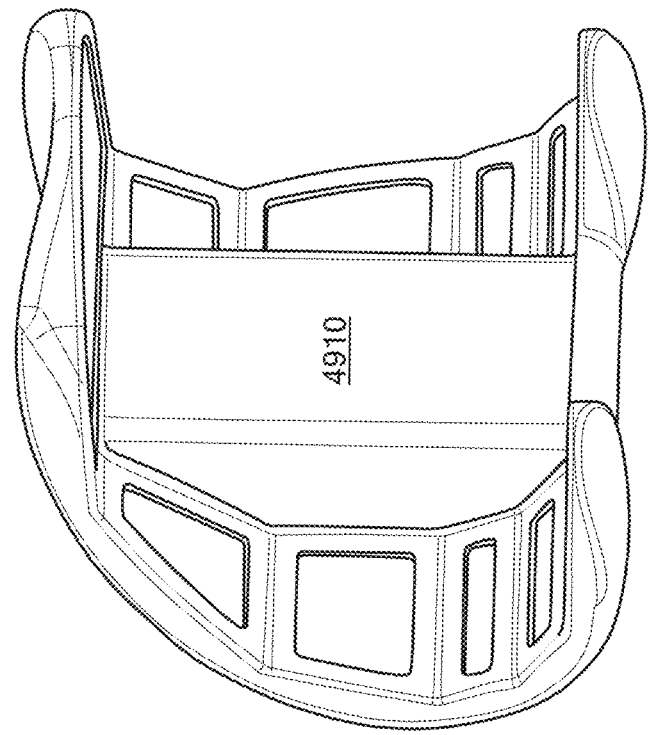

In addition to the implant component features described above, certain embodiments can include features and designs for cruciate substitution. These features and designs can include, for example, an intercondylar housing (sometimes referred to as a "box") 4910, as shown in FIGS. 49A and 49B, and/or one or more intercondylar bars 5010, as shown in FIGS. 50A and 50B, as a receptacle for a tibial post or projection. The intercondylar housing, receptacle, and/or bars can be used in conjunction with a projection or post on a tibial component as a substitute for a patient's posterior cruciate ligament ("PCL"), which may be sacrificed during the implant procedure. Specifically, as shown in FIGS. 50A and 50B, the intercondylar housing, receptacle or bars engage the projection or post on the tibial component to stabilize the joint during flexion, particular during high flexion.

Figure 51:
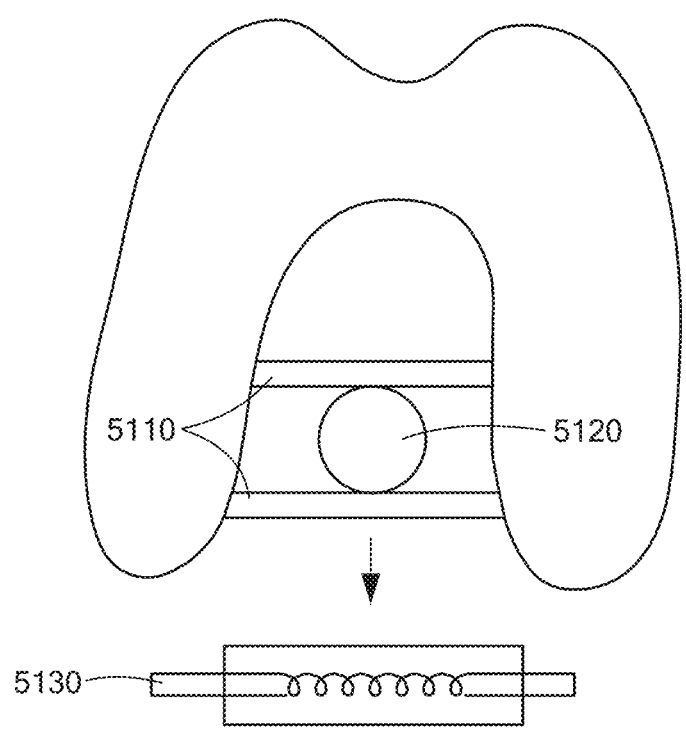
FIG. 51 illustrates a femoral implant component comprising modular intercondylar bars or a modular intercondylar box.

In certain embodiments, the femoral implant component can be designed and manufactured to include the housing, receptacle, and/or bars as a permanently integrated feature of the implant component. However, in certain embodiments, the housing, receptacle, and/or bars can be modular. For example, the housing, receptacle, and/or bars can be designed and/or manufactured separate from the femoral implant component and optionally joined with the component, either prior to (e.g., preoperatively) or during the implant procedure. Methods for joining the modular intercondylar housing to an implant component are described in the art, for example, in U.S. Pat. No. 4,950,298. As shown in FIG. 51, modular bars 5110 and/or a modular box 5120 can be joined to an implant component at the option of the surgeon or practitioner, for example, using spring-loaded pins 5130 at one or both ends of the modular bars. The spring-loaded pins can slideably engage corresponding holes or depressions in the femoral implant component.

The portion of the femoral component that will accommodate the housing, receptacle or bar can be standard, i.e., not-patient matched. In this manner, a stock of housings, receptacles or bars can be available in the operating room and added in case the surgeon sacrifices the PCL. In that case, the tibial insert can be exchanged for a tibial insert with a post mating with the housing, receptacle or bar for a posterior stabilized design.

The intercondylar housing, receptacle, and/or one or more intercondylar bars can include features that are patient-adapted (e.g., patient-specific or patient-engineered). In certain embodiments, the intercondylar housing, receptacle, and/or one or more intercondylar bars includes one or more features that are designed and/or selected preoperatively, based on patient-specific data including imaging data, to substantially match one or more of the patient's biological features. For example, the intercondylar distance of the housing or bar can be designed and/or selected to be patient-specific. Alternatively or in addition, one or more features of the intercondylar housing and/or one or more intercondylar bars can be engineered based on patient-specific data to provide to the patient an optimized fit with respect to one or more parameters. For example, the material thickness of the housing or bar can be designed and/or selected to be patient-engineered. One or more thicknesses of the housing, receptacle, or bar can be matched to patient-specific measurements. One or more thicknesses of the housing, receptacle, and/or bar can be adapted based on one or more implant dimensions, which can be patient-specific, patient-engineered or standard. One or more thicknesses of the housing, receptacle or bar can be adapted based on one or more of patient weight, height, sex and body mass index. In addition, one or more features of the housing and/or bars can be standard.

Different dimensions of the housing, receptacle or bar can be shaped, adapted, or selected based on different patient dimensions and implant dimensions. Examples of different technical implementations are provided in Table 11. These examples are in no way meant to be limiting. Someone skilled in the art will recognize other means of shaping, adapting or selecting a housing, receptacle or bar based on the patient's geometry including imaging data.

TABLE 11

Examples of different technical implementations of a cruciate-sacrificing femoral implant component

| Box, receptacle or bar or space defined by bar and condylar implant walls | Patient anatomy, e.g., derived from imaging studies or intraoperative measurements |
| --- | --- |
| Mediolateral width | Maximum mediolateral width of patient intercondylar notch or fraction thereof |
| Mediolateral width | Average mediolateral width of intercondylar notch |
| Mediolateral width | Median mediolateral width of intercondylar notch |
| Mediolateral width | Mediolateral width of intercondylar notch in select regions, e.g. most inferior zone, most posterior zone, superior one third zone, mid zone, etc. |
| Superoinferior height | Maximum superoinferior height of patient intercondylar notch or fraction thereof |
| Superoinferior height | Average superoinferior height of intercondylar notch |
| Superoinferior height | Median superoinferior height of intercondylar notch |
| Superoinferior height | Superoinferior height of intercondylar notch in select regions, e.g. most medial zone, most lateral zone, central zone, etc. |

TABLE 11-continued

Examples of different technical implementations of a cruciate-sacrificing femoral implant component

| Box, receptacle or bar or space defined by bar and condylar implant walls | Patient anatomy, e.g., derived from imaging studies or intraoperative measurements |
| --- | --- |
| Anteroposterior length | Maximum anteroposterior length of patient intercondylar notch or fraction thereof |
| Anteroposterior length | Average anteroposterior length of intercondylar notch |
| Anteroposterior length | Median anteroposterior length of intercondylar notch |
| Anteroposterior length | Anteroposterior length of intercondylar notch in select regions, e.g. most anterior zone, most posterior zone, central zone, anterior one third zone, posterior one third zone etc. |

The height or M-L width or A-P length of the intercondylar notch can not only influence the length but also the position or orientation of a bar or the condylar walls.

The dimensions of the housing, receptacle or bar can be shaped, adapted, or selected not only based on different patient dimensions and implant dimensions, but also based on the intended implantation technique, for example intended femoral component flexion or rotation. For example, at least one of an anteroposterior length or superoinferior height can be adjusted if an implant is intended to be implanted in 7 degrees flexion as compared to 0 degrees flexion, reflecting the relative change in patient or trochlear or intercondylar notch or femoral geometry when the femoral component is implanted in flexion.

In another example, the mediolateral width can be adjusted if an implant is intended to be implanted in internal or external rotation, reflecting, for example, an effective elongation of the intercondylar dimensions when a rotated implantation approach is chosen. The housing, receptacle, or bar can include oblique or curved surfaces, typically reflecting an obliquity or curvature of the patient's anatomy. For example, the superior portion of the housing, receptacle, or bar can be curved reflecting the curvature of the intercondylar roof. In another example, at least one side wall of the housing or receptacle can be oblique reflecting an obliquity of one or more condylar walls.

The internal shape of the housing, receptacle or bar can include one or more planar surfaces that are substantially parallel or perpendicular to one or more anatomical or biomechanical axes or planes. The internal shape of the housing, receptacle, or bar can include one or more planar surfaces that are oblique in one or two or three dimensions. The internal shape of the housing, receptacle, or bar can include one or more curved surfaces that are curved in one or two or three dimensions. The obliquity or curvature can be adapted based on at least one of a patient dimension, e.g., a femoral notch dimension or shape or other femoral shape including condyle shape, or a tibial projection or post dimension. The internal surface can be determined based on generic or patient-derived or patient-desired or implant-desired kinematics in one, two, three or more dimensions. The internal surface can mate with a substantially straight tibial projection or post, e.g., in the ML plane. Alternatively, the tibial post or projection can have a curvature or obliquity in one, two or three dimensions, which can optionally be, at least in part, reflected in the internal shape of the box. One or more tibial projection or post dimensions can be matched to, designed to, adapted to, or selected based on one or more patient dimensions or measurements. Any combination of planar and curved surfaces is possible.

In certain embodiments, the position and/or dimensions of the tibial plateau projection or post can be adapted based on patient-specific dimensions. For example, the post can be matched with the position of the posterior cruciate ligament or the PCL insertion. It can be placed at a predefined distance from anterior or posterior cruciate ligament or ligament insertion, from the medial or lateral tibial spines or other bony or cartilaginous landmarks or sites. By matching the position of the post with the patient's anatomy, it is possible to achieve a better functional result, better replicating the patient's original anatomy.

Similarly, the position of the box or receptacle or bar on the femoral component can be designed, adapted, or selected to be close to the PCL origin or insertion or at a predetermined distance to the PCL or ACL origin or insertion or other bony or anatomical landmark. The orientation of the box or receptacle or bar can be designed or adapted or selected based on the patient's anatomy, e.g. notch width or ACL or PCL location or ACL or PCL origin or insertion.

Figure 52A:
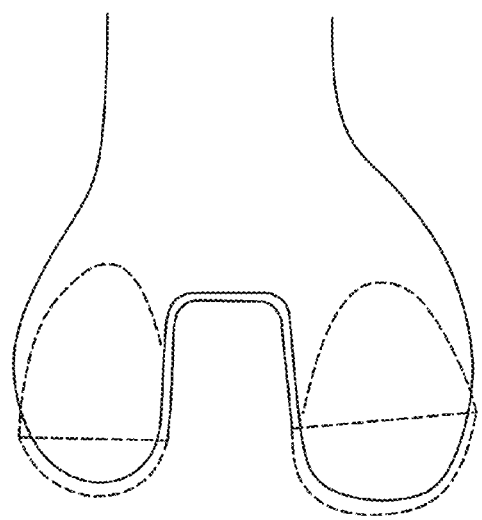
FIGS. 52A through 52K show various embodiments and aspects of cruciate-sacrificing femoral implant components and FIGS. 52L through 52P show lateral views of different internal surfaces of intercondylar boxes.
Figure 52B:
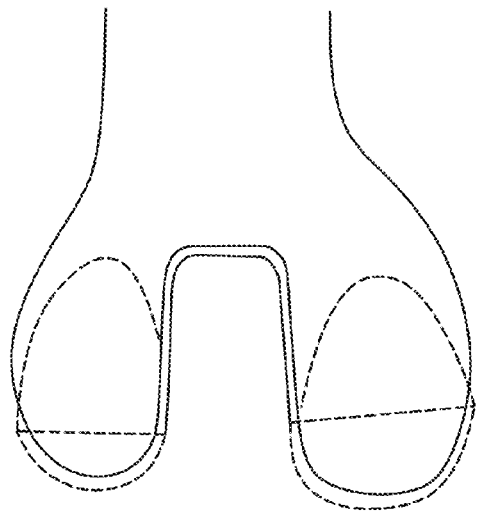
Figure 52C:
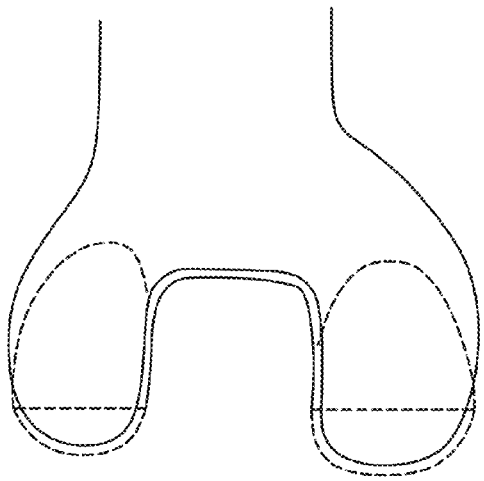
Figure 52D:
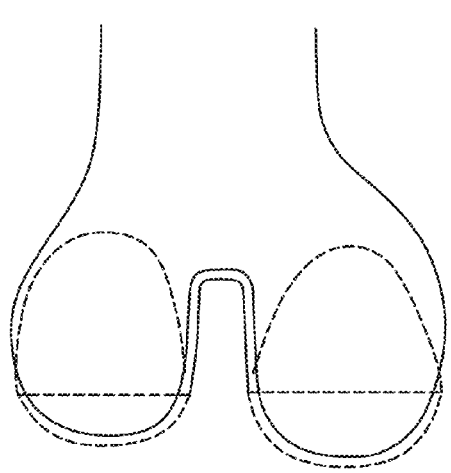
Figure 52E:
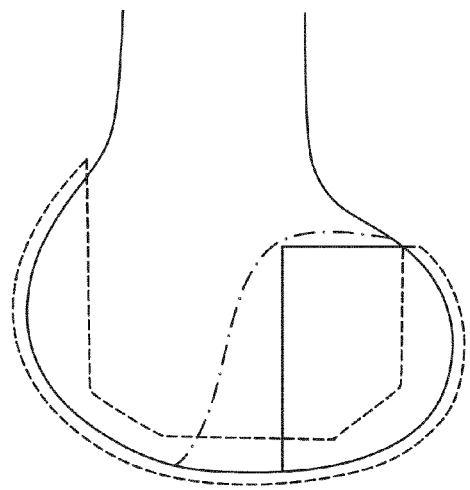
Figure 52F:
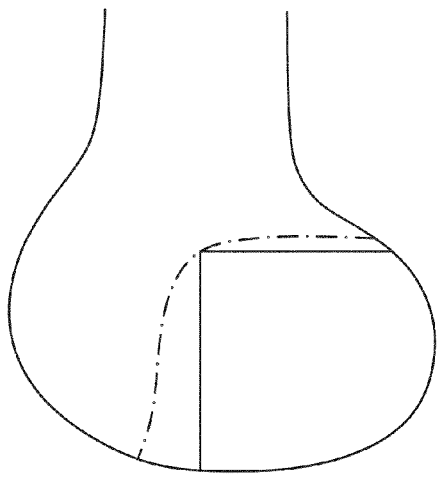
Figure 52G:
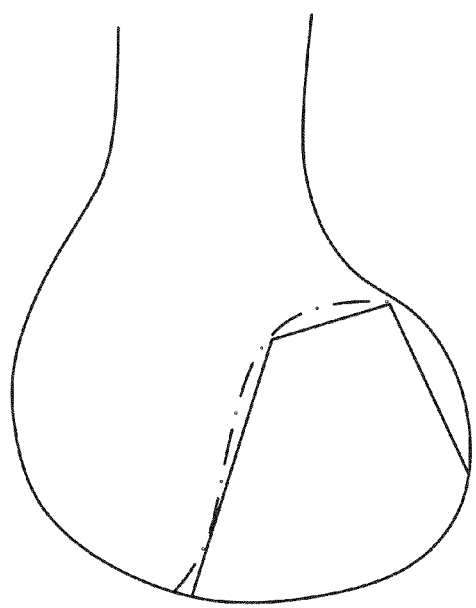
Figure 52H:
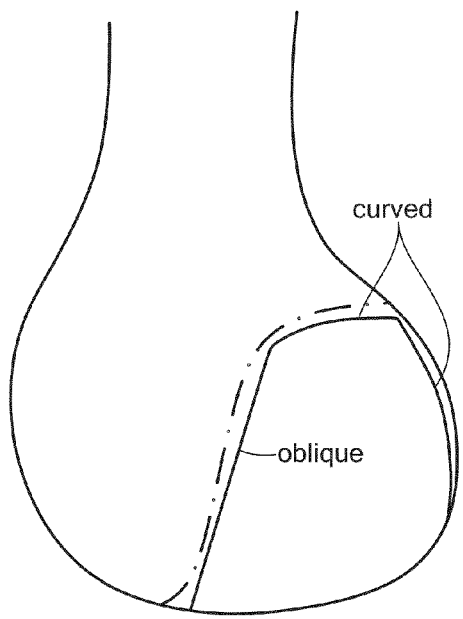
Figure 52J:
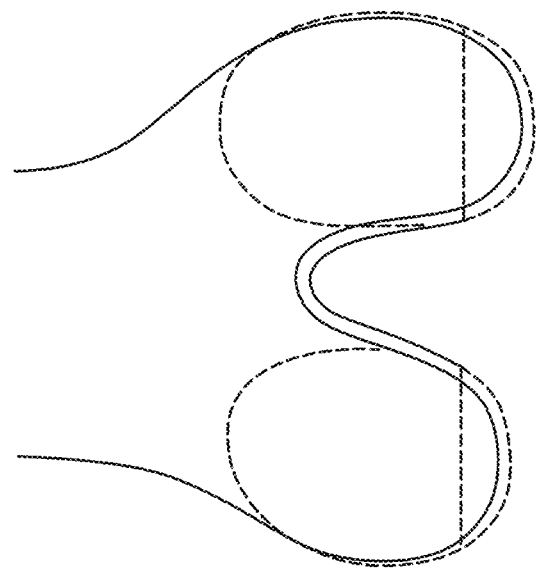
Figure 52I:
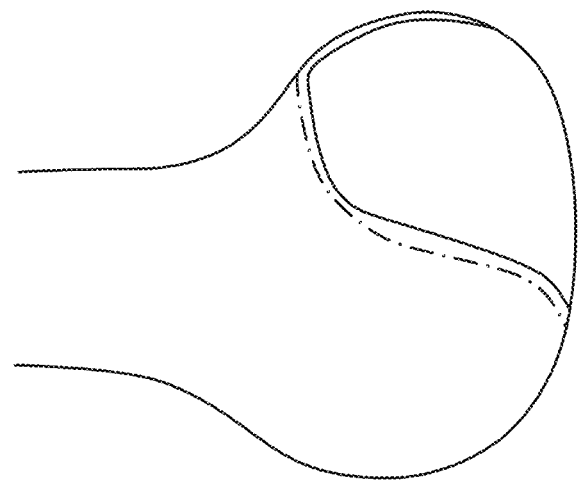
Figure 52L:
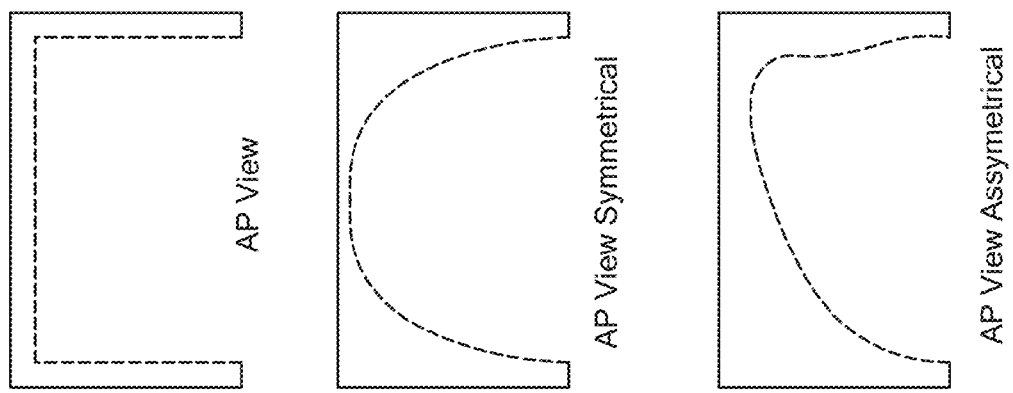
Figure 52K:
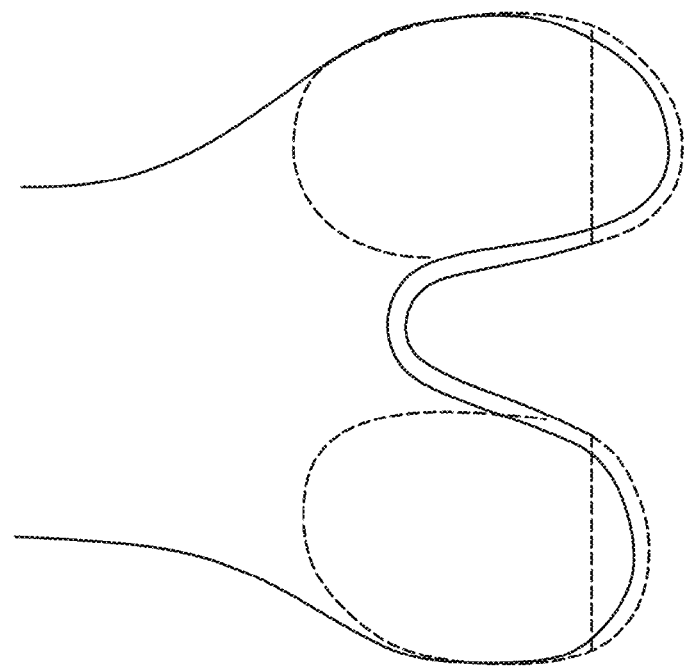
Figure 52N:
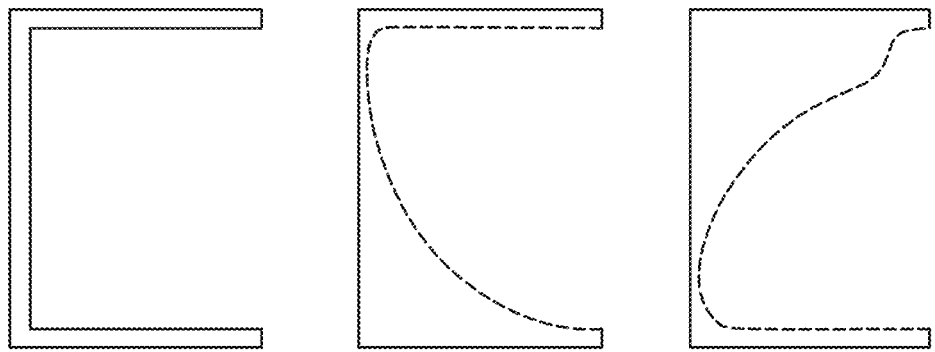
Figure 52M:
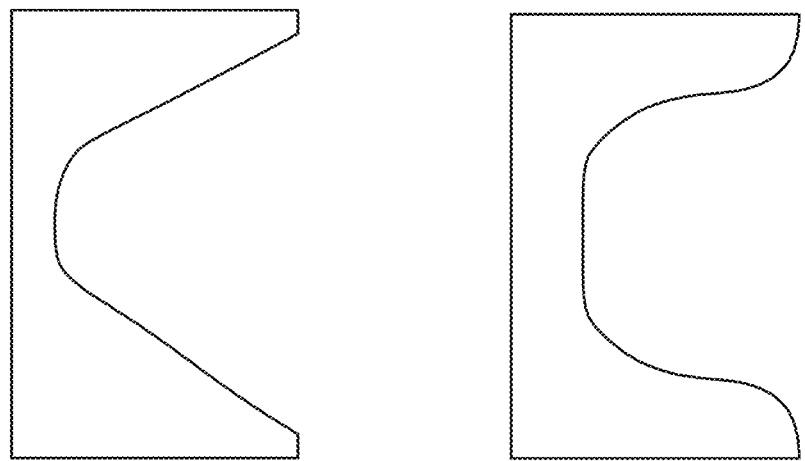
Figures 52O, 52P:
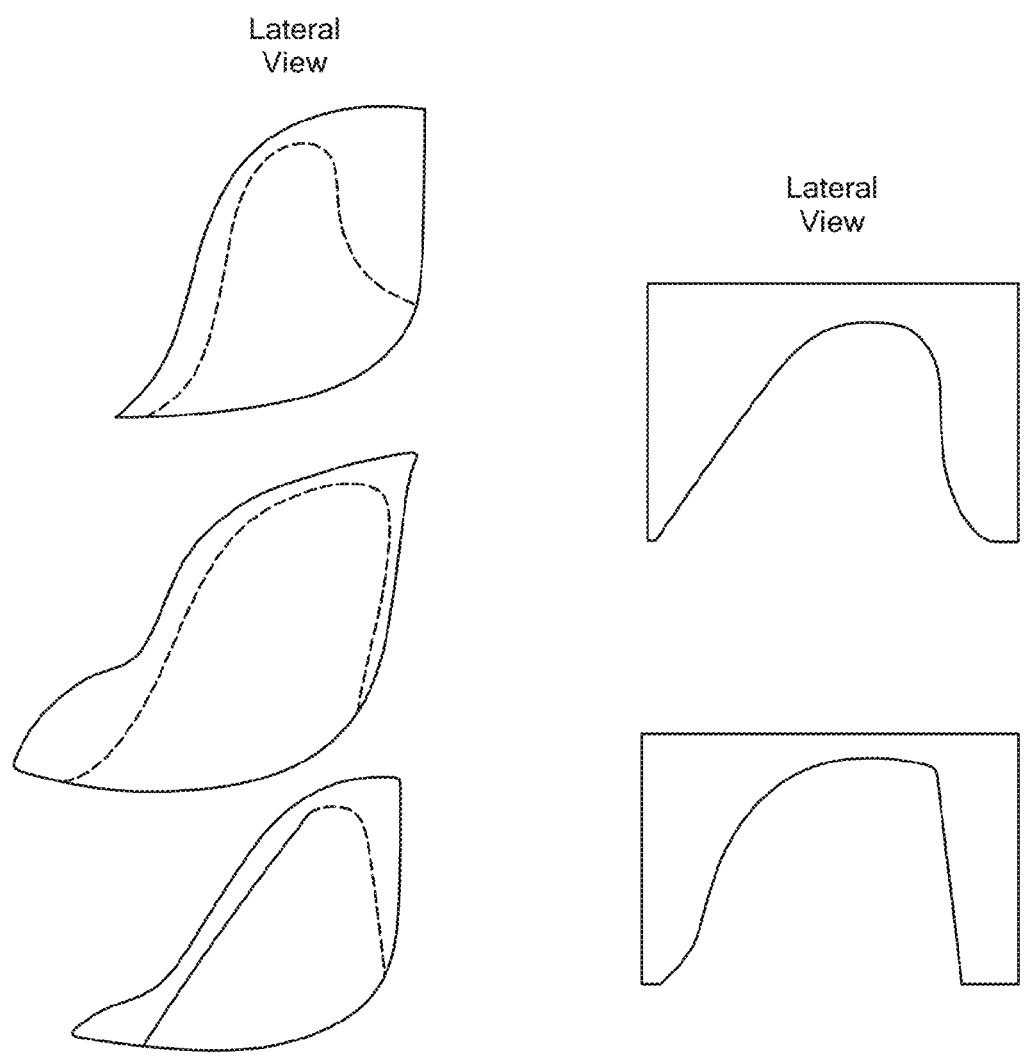

FIGS. 52A through 52K show various embodiments and aspects of cruciate-sacrificing femoral implant components. FIG. 52A shows a box height adapted to superoinferior height of intercondylar notch. The dotted outlines indicate portions of the bearing surface and posterior condylar surface as well as the distal cut of the implant. FIG. 52B shows a design in which a higher intercondylar notch space is filled with a higher box or receptacle, for example, for a wide intercondylar notch. FIG. 52C shows a design in which a wide intercondylar notch is filled with a wide box or receptacle. The mediolateral width of the box is designed, adapted or selected to the wide intercondylar notch. FIG. 52D shows an example of an implant component having a box designed for a narrow intercondylar notch. The mediolateral width of the box is designed, adapted or selected for the narrow intercondylar notch. FIG. 52E shows an example of an implant component having a box for a normal size intercondylar notch. The box or receptacle is designed, adapted or selected for its dimensions. (Notch outline: dashed and stippled line; implant outline:dashed lines). FIG. 52F shows an example of an implant component for a long intercondylar notch. The box or receptacle is designed, adapted or selected for its dimensions (only box, not entire implant shown). FIG. 52G is an example of one or more oblique walls that the box or receptacle can have in order to improve the fit to the intercondylar notch. FIG. 52H is an example of a combination of curved and oblique walls that the box or receptacle can have in order to improve the fit to the intercondylar notch. FIG. 52I is an example of a curved box design in the A-P direction in order to improve the fit to the intercondylar notch. FIG. 52J is an example of a curved design in the M-L direction that the box or receptacle can have in order to improve the fit to the intercondylar notch. Curved designs are possible in any desired direction and in combination with any planar or oblique planar surfaces. FIG. 52K is an example of oblique and curved surfaces in order to improve the fit to the intercondylar notch. FIGS. 52L through 52P show lateral views of different internal surfaces of boxes.

Femoral implant components of certain embodiments also can include other features that are patient-specific and/or optimized according to one or more of the parameters discussed above.

Figure 53A:
FIG. 53A illustrates a variety of peg configurations that can be used for the implant components described herein.
Figure 53B:
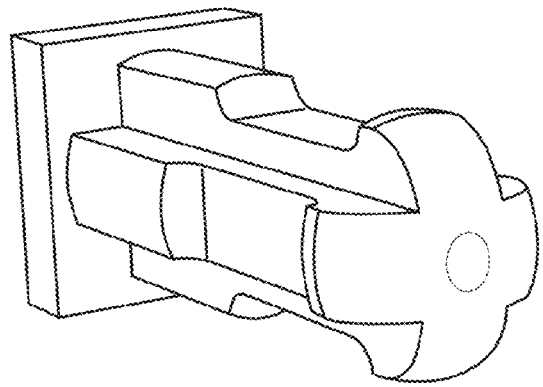
FIG. 53B illustrates an embodiments of a peg having a cross-section that includes a "+" or cross-like configuration.

A variety of peg configurations can be used for the implant components described herein (femoral implant components as well as other implant components). Exemplary configurations are illustrated in FIG. 53A. In certain embodiments, the peg cross-section can be round. In certain embodiments, as illustrated in FIG. 53B, the peg cross-section can include a "+" or cross-like configuration, which may aid in manufacturing. For example, in layering processes (used to create a casting blank), such as stereolithography (SLA), selective laser sintering (SLS), or fused deposition modeling (FDM), (generating or building) the curved edges of a blank typically is more difficult than that of the straight-edges of a blank. Accordingly, the straight-edges of the "+" configured peg may allow for a simpler (and better defined) blank used in the casting process as compared to a round peg.

A variety of peg sizes can be used for a bicompartmental implant or implant component. For example, a 5 mm peg, a 6 mm peg, a 7 mm peg, or another peg size can be used. The peg can reflect a variety of configurations, for example, a "+" configured peg, can be used. The peg can be oriented on the device at any angle. For example, one or more pegs can be oriented in line with the femoral mechanical axis. Alternatively, one or more pegs can be oriented at an anterior-leaning angle as the peg extends from the implant. For example, one or more pegs can be oriented anteriorly 5 degrees, 5-10 degrees, 10 degrees, 10-15 degrees, and/or 15 degrees in an anterior-leaning angle relative to the femoral mechanism axis. The pegs can be oriented at the same angle or at different angles as one or both of the anterior and posterior cuts of the implant component. Pegs on a single implant component can have different diameters, lengths or other features in accordance with independently designed portions of the implant component.

Figure 54B:
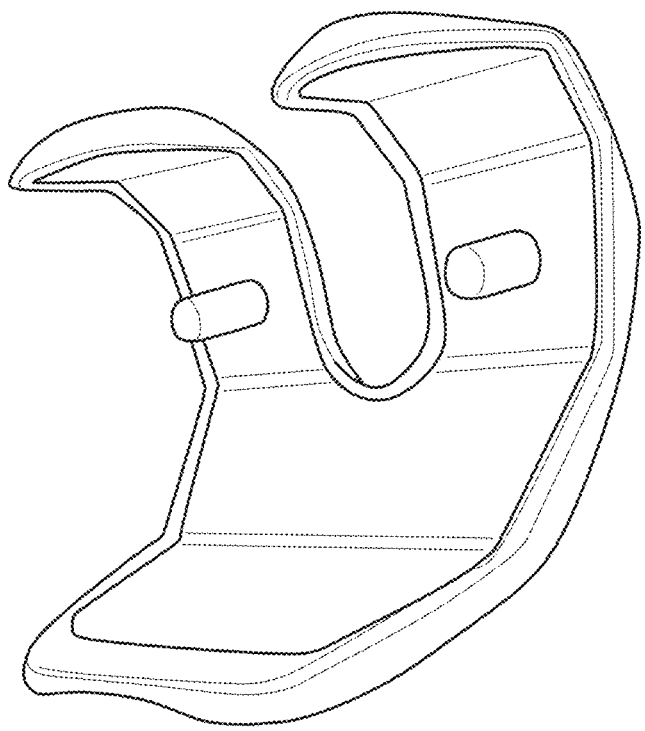
FIGS. 54A and 54B show bone cement pockets in an embodiment of an implant component (FIG. 54A) and in a traditional component (FIG. 54B)
Figure 54A:
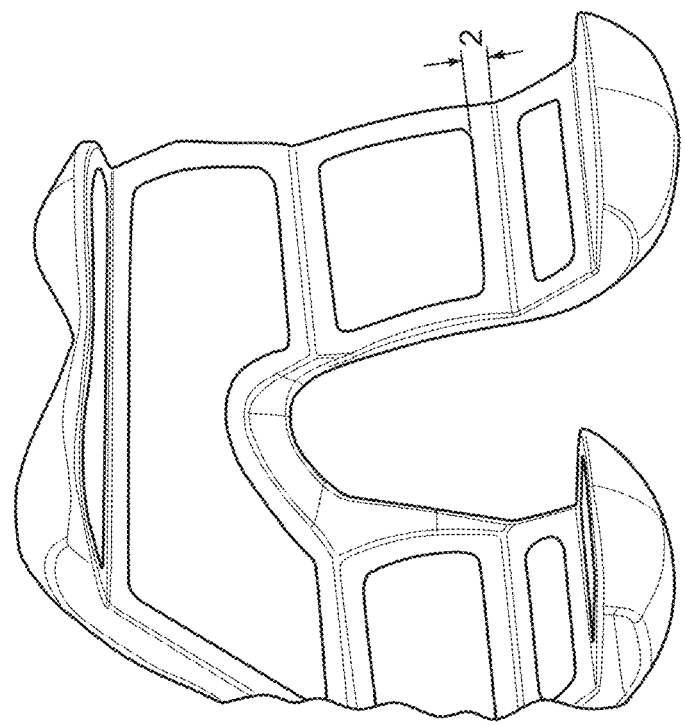

The design of a bone cement pocket or pockets of an implant component also may include features that are patient-specific and/or optimized according to one or more of the parameters discussed above. FIGS. 54A and 54B show bone cement pockets in a component of certain embodiments (FIG. 54A) and in a traditional component (FIG. 54B). As shown in FIG. 54A, each section or facet of the bone-facing surface of the component can have an independent cement pocket. One or more of the cement pockets can be offset from the periphery by 2 mm or more. Each pocket can have a maximum depth of less than 0.9 mm, for example, 0.5 mm or less.

Figure 55B:
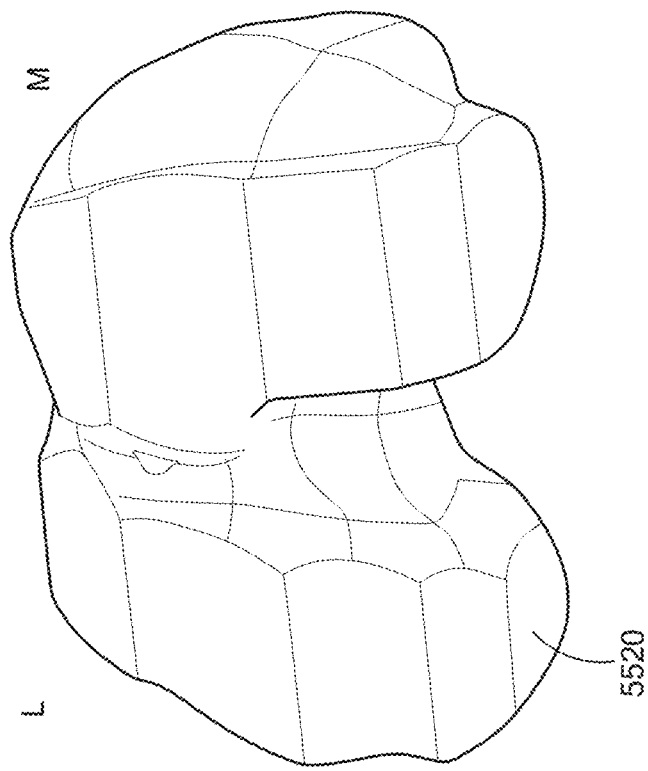
FIGS. 55A through 55F illustrate a preferred embodiment of the femoral implant component and resection cuts.
Figure 55A:
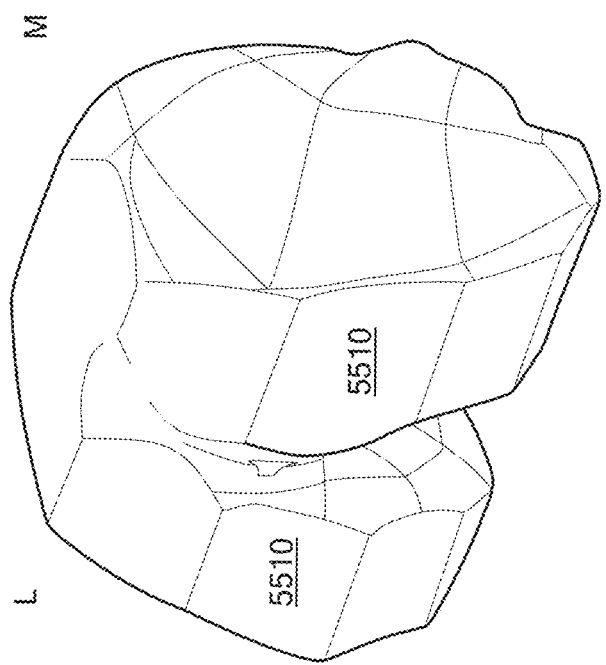
Figure 55D:
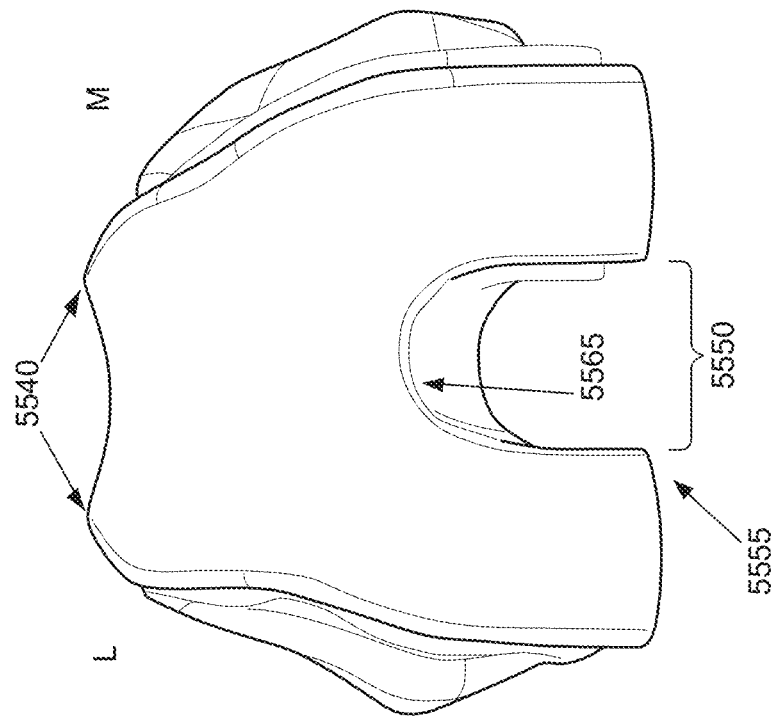
Figure 55C:
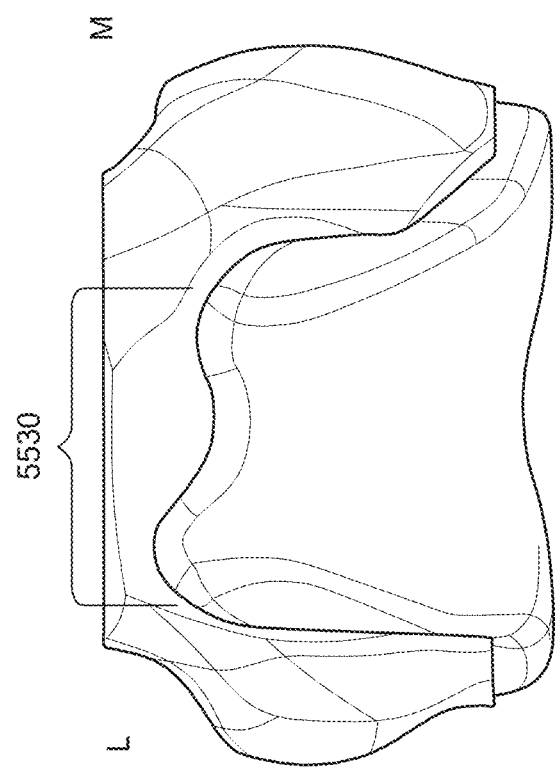
Figure 55F:
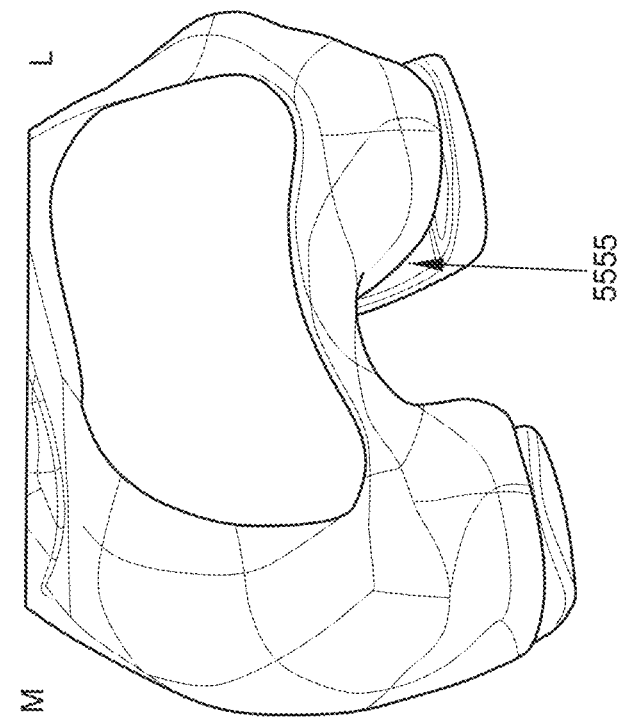
Figure 55E:
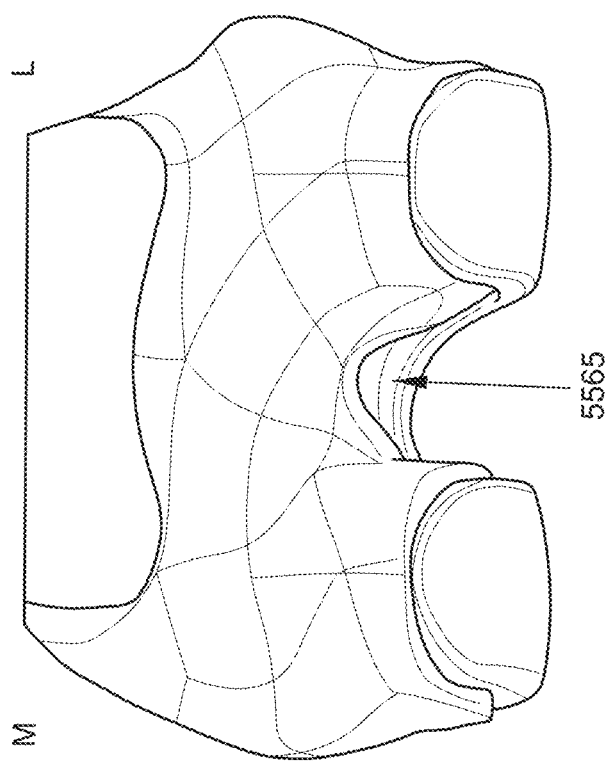

A preferred embodiment of the femoral implant component and resection cuts is illustrated in FIGS. 55A through 55F. As shown FIGS. 55A and 55B, the distal resection cuts are symmetric 5510 with less bone resected from the lateral posterior resection cut 5520. These features are matched on the inner, bone-facing surface of the implant. As shown in FIG. 55C, the anterior surface of the implant component includes a unique superior edge 5530. As shown, the superior edge includes lateral and medial superior curvatures with a trough in between. The lateral superior curvature is higher (e.g., more superior to) the medial superior curvature, and is about 2× higher relative to the lowest point in the trough between them. As shown in FIG. 55D, the trochlear peaks 5540 of the implant are lower than the patient's natural trochlear peaks and an 18 mm intercondylar distance 5550 is used with the implant component. To achieve this intercondylar distance, the lateral condyle of the implant is slightly medialized 5555 relative to the patient's lateral condyle, and intercondylar notch coverage 5560 is increased relative to the patient's intercondylar notch. FIGS. 55E and 55F illustrate the implant component from the opposite direction to show the notch roof with slightly overhanging coverage 5565 on the lateral intercondylar (FIG. 55E) and the slightly medialized lateral condyle 5555 resulting in exposed bone-facing surface on the medial side of the implant's lateral condyle (FIG. 55F).

6.2 Patella Implant Component

In a traditional patellar implant procedure, the articular surface (i.e., the bearing surface and/or joint-facing surface) of a patient's patella can be resected, typically using a bone cut across the patella, and a patellar implant component having standard dimensions can be mounted to the resected surface of the remaining portion of the patient's patella. The patella implant components have off-the-shelf standard dimensions and are typically selected intraoperatively.

In certain embodiments, an imaging test such as x-ray imaging, digital tomosynthesis, cone beam CT, a CT scan including a spiral CT scan, MRI scan including 3D acquisitions, ultrasound scan, laser scan, optical coherence tomography or combinations thereof can be used to define the shape or geometry of a patient's patella and, optionally one or more other biological or kinematic features. The scan data can be utilized to measure or derive information on the shape or geometry of the patient's patella. For example, a superoinferior or mediolateral or oblique dimension or an anteroposterior width can be measured. One or more patellar axes can be determined, e.g., a sagittal axis, coronal axis, axial axis, a tracking axis, one or more axes describing patellar motion in relationship to the trochlea, e.g., mediolateral or superoinferior or oblique, as well as select femoral axes, e.g., a posterior condylar axis, epicondylar axis, Whiteside's line, a mechanical axis and/or one more other axes. Someone skilled in the art will recognize other patellar- and axis-related measurements that can be obtained. In principal, any anatomic or functional measurement applicable to a patellar geometry or function and kinematics can be obtained or derived. Once one or more geometric, functional, and kinematic measurements have been obtained or derived, the information can be utilized to select or design a patellar implant or component that is best suited for a particular patient.

For example, an AP dimension of the patella can be measured and a patellar implant or component best matching the AP dimension can be selected and/or designed. The selection or design can be adapted based on an intended resection depth. An ML dimension of a patellar implant or component can be measured and a patellar implant or component best matching the ML dimension can be selected or designed. The selection or design can be adapted based on an intended resection depth. The AP measurement or ML measurement or any other measurement can be adapted or derived for a preferred resection depth or cut depth. Resection for placing the patellar implant or component can be achieved with any technique known in the art, such as sawing, burring, drilling, and/or other known techniques.

Figure 56C:
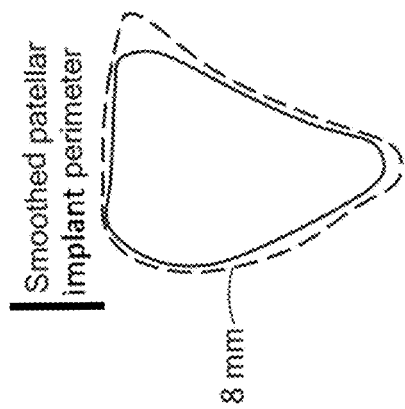
FIGS. 56A to 56C illustrates how a patellar resection depth alters the resultant patellar resection profile.
Figure 56B:
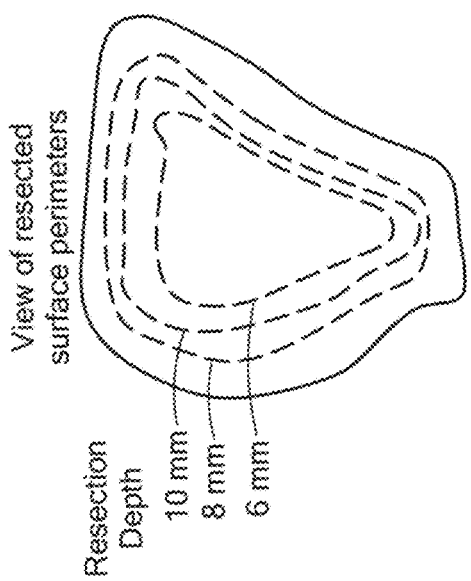
Figure 56A:
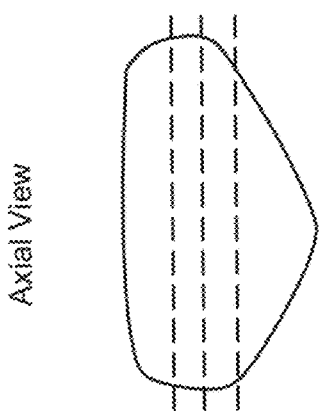

FIGS. 56A to 56C demonstrate how a patellar resection depth alters the resultant patellar resection profile (e.g., the profile of the cut surface on the remaining patella). In general, as the resection plane moves away from the patellar articulating surface cartilage or subchondral bone and deeper into the patella, a greater resultant AP and/or ML resection dimension is produced until about the half point has been crossed; at which point, typically, the resection profile starts to decrease in thickness resulting in a decrease in the AP and/or ML dimension of the resected profile. Thus, as shown in FIGS. 56A and 56B, a patellar implant or component can include a perimeter selected and/or designed for a particular resection depth. The resection can be planned on a 2D image or a series of 2D images, or a 3D image or representation. The implant can be selected and/or designed on the 2D image or series of 2D images, or 3D image or representation, for example by superimposing a 2D or 3D outline of the implant. Multiple outlines can be available. Alternatively, as shown in FIG. 56C, a 2D or 3D outline can be smoothed or deformed to achieve the best or desired fit.

For example, in certain embodiments, the patellar implant or implant component can be selected and/or designed so that it is substantially matches one or more AP or ML or oblique or other dimensions in at least a portion of the uncut patella and/or in at least a portion of the patella resection profile. Alternatively or in addition, the patellar implant or component can be selected and/or designed so that it is smaller than one or more of the AP or ML or oblique or other dimensions in at least a portion of the uncut patella and/or in at least a portion of the patella resection profile. For example, in one or more select dimensions the patellar implant or component can be selected and/or designed to be less than 5%, 10%, 15%, 20%, or other percentage relative to the patellar profile or resected patellar profile for a given resection depth. The patellar implant can be selected and/or designed to achieve a desired fit in one or more of those dimensions or other dimensions so that the fit is applicable to two or more resection depths. In this manner, the surgeon has the ability to change his resection depth intraoperatively, while, for example, still avoiding implant overhang.

A patellar implant also can be selected or designed, for example, based on the patient's original patellar surface shape. For example, if the patella has a dome shape, a substantially dome shaped implant or component can be selected or designed. If the patella has a relatively flat shape, a more flat implant or component can be selected or designed. If the patella has a relatively spherical shape, a more spherical implant or component can be selected or designed. The patellar implant or component can be round or elliptical. Other shapes are possible. The patellar implant or component can be longer laterally than medially. The lateral and medial lengths can be matched to the native patella. Alternatively, the lateral or medial lengths can be matched to the patient's trochlea. Alternatively, the lateral or medial lengths can be matched to the trochlear implant dimensions, which can be patient adapted or standard off the shelf. In this embodiment, a patellar shape can be selected or designed that closely mimics the patient's original patellar shape, for example by following, at least in part, the shape or contour of the cartilage or subchondral bone or portions thereof, for example in a median ridge, lateral facet, medial facet, trochlea, trochlear groove, and/or in one or more other dimensions. In instances when the patella has been distorted in shape by arthritic deformity, the patient's original patellar shape can be derived or estimated based on patient-specific data, for example, based on data regarding the patient's surrounding or contralateral biological features and/or on data regarding the patient's distorted biological features. Mathematical computations can be performed using the data to estimate or derive an approximate shape. Such mathematical computations can use, for example, patella dimensions, trochlear dimensions or femoral dimensions to estimate the original or a preferred patellar shape. Any of these dimensions can be matched to a reference database of normal individuals to select a trochlear or patellar shape for any of the implant components. The database can be age matched, gender matched, weight matched, race matched and/or matched with respect to one or more other features known in the art.

The patellar implant or component shape can, optionally, also be selected and/or designed based on the patient's trochlear shape or based on the shape of the trochlear implant profile, e.g. of a total knee implant.

The patellar implant or component can be selected based on a single measured or derived parameter. Alternatively, the patellar implant or component can be selected based on multiple parameters, e.g., AP and ML dimensions or AP, ML and oblique dimensions, or AP, ML, and oblique dimensions and desired resection depth, or AP, ML, and oblique dimensions, and/or desired resection depth and/or trochlear shape or trochlear implant shape. A weighting can be applied to different parameters. Mathematical or statistical models can be applied for deriving the preferred patellar shape and for designing or selecting an implant based on a multiparametric fit or optimization. These fits or optimization can include kinematic modeling, estimations and measurements.

The resection depth determination can be based on the desired thickness of the patellar implant or patellar component. For example, the resection depth can be at a distance from the native articulating surface patellar cartilage or subchondral bone that is substantially equal to the thickness of the patellar implant or component. In another embodiment, for example if a femoral component is chosen that removes more of the patient's trochlear bone and that has, for example, a femoral component trochlear articulating surface that is posterior to the patient's uncut trochlea, the patellar resection depth may be further posterior, i.e., less bone is removed from the articulating surface the patellar implant or component to extend the patellar implant further toward the femur than the native patella. In this instance, the patellar resection depth can be derived using the following exemplary approach:

1. Start at the patellar articular cartilage or subchondral bone surface.
2. Move resection cut plane into the patella to the point that it substantially matches the patellar implant/component thickness.
3. Move the resection cut plane back toward the patellar articular surface (or, in select circumstances anterior) by an amount sufficient to offset the difference between the femoral component trochlear articulating surface and the native trochlear cartilage or subchondral bone surface.

The above embodiments are applicable to patellar implants or components that are designed or derived for a particular patient as well as to implants that are pre-manufactured and selected based on one or more measurements.

The patellar component can be made of a plastic, e.g., a polyethylene, a metal or ceramic. The patellar component can, for example, include a metal backing. The patellar implant can be cemented or uncemented. The patellar implant component can be symmetrical or asymmetrical. It can be spherical or aspherical. The patellar implant component can include symmetric portions and asymmetric portions. For example, the patellar implant component can be symmetric in the AP dimension and asymmetric in the ML dimension. The patellar implant component can be round or elliptical. Other shapes are possible. The patellar implant or component can be longer laterally than medially.

In certain embodiments, a patella implant or implant component having one or more patient-specific features is included. In addition or alternatively, certain embodiments include, for example, a patella implant or implant component having one or more features that are patient-optimized (i.e, patient-engineered), e.g., designed based on patient-specific data to enhance one or more parameters, such as (1) deformity correction and limb alignment; (2) preserving bone, cartilage, or ligaments; (3) preserving and/or optimizing features of the patient's anatomy such as patella, trochlea and trochlear shape; (4) restoring and/or optimizing joint kinematics or biomechanics including patellofemoral tracking, and/or (5) restoring or optimizing joint-line location and/or joint gap width. For example, a patella implant or implant component feature can be patient-optimized or patient-engineered to enhance the kinematics between the patellar component and the femoral component. The patient-specific and/or patient-optimized patellar implant features and dimensions described herein can be applied, as appropriate, to either a patellar implant that completely replaces a patient's patella or to a patellar implant that amounts to a resected surface of a patient's patella. Embodiments that include patient-specific and/or patient-optimized aspects also can include one or more standard aspects, for example a standard bearing surface.

In certain embodiments, one or more features of a patellar implant or implant component are patient-specific. For example, certain embodiments of patellar implants can be directed to restoring or maintaining the patient's original patella thickness in one or more locations, which can help to preserve bone and restore patella-femoral ("P-F") kinematics, for example, by restoring the patient's P-F joint-line. Accordingly, in certain embodiments, the thickness of the patella implant substantially positively-matches the thickness of the patient's patella in one or more locations. Patient-specific images of the patient's joint, for example, from a CT or MRI scan, can be used for this purpose. The scan can be obtained preoperatively to determine the patient's patellar thickness including at least one of bone and articular cartilage or combinations thereof in different locations of the patella, e.g., the superior dome, superior third, mid-portion, inferior third, inferior tip, lateral third, central third, and medial third.

In certain embodiments, patellar implants can be directed to maintaining the patient's patella surface (e.g., articulating surface) in one or more locations. Accordingly, in certain embodiments, the surface of the patella implant substantially positively-matches the surface of the patient's patella, e.g. cartilage or subchondral bone, in one or more locations. Certain embodiments of patellar implants can be directed to maintaining the patient's patella perimeter in one or more planes. Accordingly, in certain embodiments, the perimeter of the patella implant substantially positively-matches the uncut or cut perimeter of the patient's patella in one or more planes, e.g., for one or more resection depths. Thus, the implant can be selected or designed to achieve a desired fit or match with the uncut or cut perimeter in one or more dimensions. Certain embodiments of patellar implants can be directed to maintaining the patient's patella volume. Accordingly, in certain embodiments, the volume of the patella implant substantially positively-matches the volume of the patient's patella. By matching the patellar dimensions or volume, patellar overstuffing or understuffing can optionally be avoided. The volume can be adapted by adding or subtracting based on the shape of the opposing trochlear component. For example, if a trochlear component extends anterior to the patient's native bone, the shape of the patellar component can be adapted so that the volume or dimensions are decreased to account for the anterior extension of the trochlear component. If the trochlear component rests posterior to the native trochlear bone, for example with use of an anterior trochlear bone cut, the shape of the patellar components can be adapted so that the volume or dimensions are increased to account for the more posterior location of at least portions of the trochlear components. Any of these embodiments can include one or more patient-specific aspects, patient-engineered aspects, and/or standard aspects.

Figure 58D:
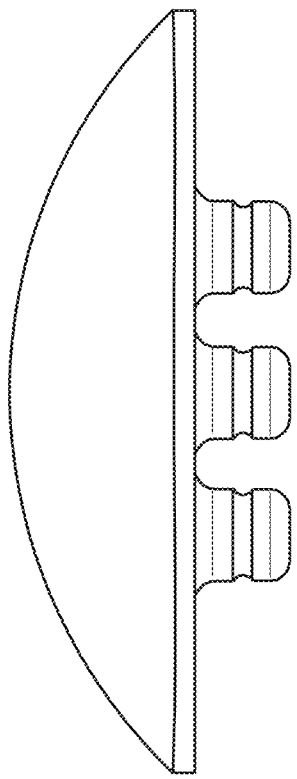
Figure 58C:
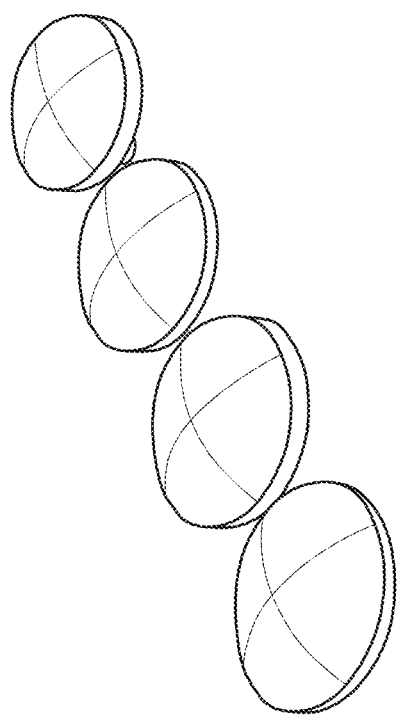

In certain embodiments, one or more aspects of a patella implant include one or more patient-optimized features, for example, to optimally engage an engineered or a patient-derived trochlear groove of a femoral implant component. In certain embodiments, a patella implant component can include a joint-facing surface that is not derived from a sphere. For example, in certain embodiments, the joint-facing surface of a patella implant can be derived from a prolate spheroid shape (i.e., an elongated shape, like a football or lemon), for example, the prolate spheroid cut longitudinally 5710, as shown in FIG. 57. For example, the top-side of the patella implant can be lemon shaped such that it has a differing medial-lateral versus vertical radius. This design can allow for a reduced thickness of the leading edges of the implant during flexion/extension. In certain embodiments, the apex of a dome-shaped or prolate-shaped outer, joint-surface topography is lateralized relative to apex of the patient's patella. For example, the patellar implant optionally can be lateralized 1 mm, 2 mm, 3 mm, 4 mm 5 mm, 1-5 mm, and/or 2-4 mm lateralized. A patella component designed in this way can be used to address poor ML and/or AP fit of traditional designs and/or restore the patient's normal patella topography. In addition or alternatively, the thickness of the patella implant can be less than about 13 mm, less than about 12 mm, less than about 11 mm, less than about 10 mm, less than 9 mm, less than about 8.5 mm, about 8 mm, less than about 8 mm, about 7 mm, and/or less than 7 mm. Further aspects of embodiments of patella implant components are shown in FIGS. 58A-58C. For example, FIG. 58A depicts a patellar implant component (e.g., in an axial plane) having a sombrero-shaped profile for its surface that articulates with the trochlea. As shown, the peak of the articulating surface is offset about 2 mm laterally; however, the peak can be offset laterally or medially less than about 2 mm (e.g., about 0.5 to 2 mm) or greater than about 2 mm (e.g., about 2 to 6 mm or about 2 to 4 mm, or about 2 to 3 mm). The implant component shown in FIG. 58A includes a resection coverage having an elliptical shape and is more similar to a typical anatomical patella as compared to the dome-shaped patella shown in FIG. 58B. FIG. 58B depicts a patellar implant component (e.g., in an axial plane) having a dome-shaped profile for its surface that articulates with the trochlea and includes a resection coverage having an elliptical shape. This dome-shaped patellar implant component has enhanced congruence and therefore lower stress and it can tilt and roll easily in the trochlear groove (i.e., is less constrained). Additional details about embodiments of patellar implant components are shown with reference to FIGS. 58C and 58D. For example, in certain embodiments, the peak of the dome or other shaped patellar implant component can be offset laterally or medially by, for example, 1 mm, 2 mm, 3 mm or more. The dome can be symmetric or asymmetric. The shape of the component perimeter that engages the trochlea can be circular or elongated like the 2D shape of a football or lemon. The edge between the trochlea-engaging surface and the patella-engaging surface can be a uniform thickness or a non-uniform thickness. For example, the edge can be thinner on one or both of the proximal and distal edges (e.g., in the direction of motion) and wider on the medial and/or lateral sides. Exemplary sizes, heights, and edge thicknesses are described in the table in FIG. 58D. Any of the foregoing is applicable to off-the-shelf implants that are, for example, selected using one or more parameters that are measured or derived from an imaging study, or to implants that are designed for a particular patient.

Certain embodiments are directed to designing, selecting, and/or making a patellar implant having one or more patient-specific and/or patient-optimized aspects. For example, a procedure can include one or more steps of: (a) determining a patellar resection depth; (b) determining the perimeter shape of the resected surface; and (c) selecting, designing and/or making an implant that substantially positively-matches, in one or more locations, one or both of the resection depth from (a) and the perimeter shape from (b). One or more of these steps can be performed preoperatively. The steps optionally can be varied in sequence. For example, a patellar implant thickness can be selected first, then a resection depth is selected, then, optionally, the perimeter of the implant can be cut or machined or altered to match the patellar perimeter in one or more dimensions at the selected resection depth. Alternatively, a procedure can include one or more steps of: (a) preoperatively determining a patellar resection depth, for example based on a trochlear component location and/or a desired patellar implant thickness and/or shape; (b) preoperatively determining the perimeter shape of the resected surface; (c) optionally selecting a blank implant having a height that substantially positively-matches in one or more locations the resection depth from (a) and having a standard perimeter; and (d) making (e.g., machining, cutting, etc.) the perimeter for the blank selected in step (c) to substantially positively-match the resected surface determined in step (a), wherein said match can be in one or more dimensions and wherein said match can be a partial or near complete match. One or more of these steps can be performed preoperatively.

Figure 59A:
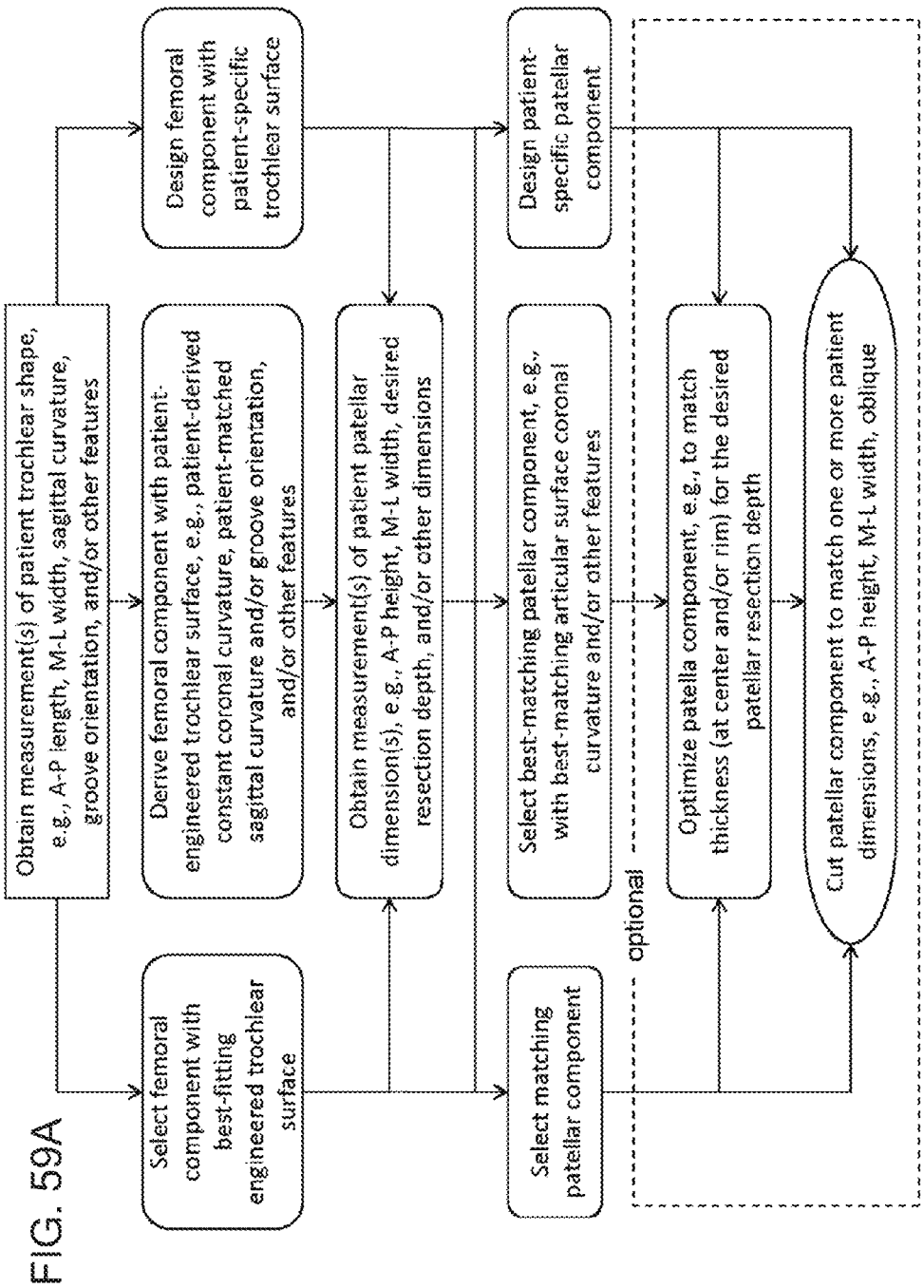
FIGS. 59A and 59B show flow charts of exemplary processes for optimizing selecting and/or designing, and optionally optimizing, a patellar component based on one or more patient-specific biological features.
Figure 59B:
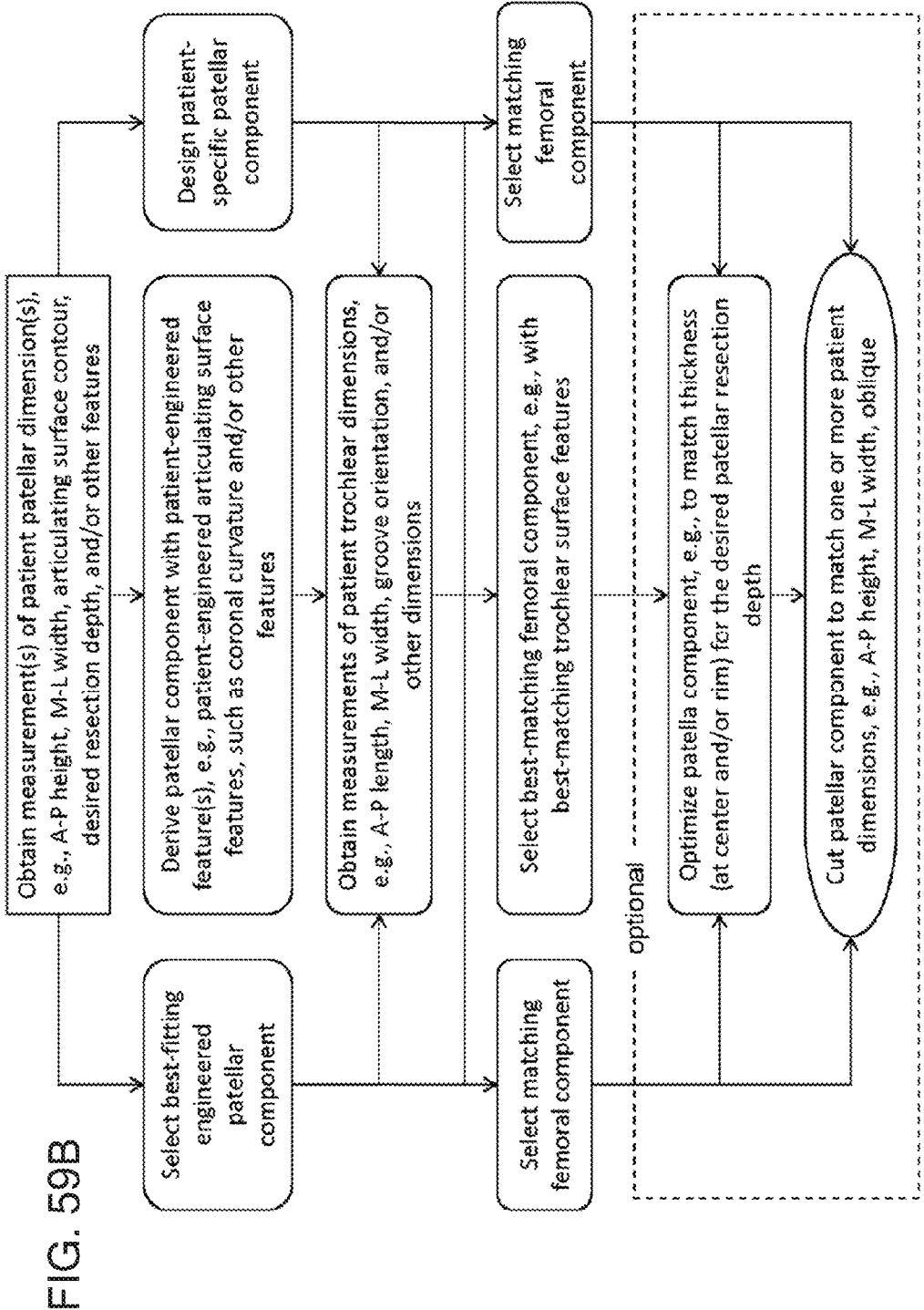

The blank can have different basic features, for example, a dome-shaped articular surface, a sombrero-shaped articular surface, symmetrically- or asymmetrically-shaped features, spherical or elliptical features, and/or one or more additional basic features, as described above or known in the art. The step of selecting the blank can also account for the resultant peripheral or margin thickness of the blank once it is cut for a given perimeter or a given AP or ML dimension at a desired resection depth. Thus, for example, a blank can be selected so that once it is cut the resultant margin thickness does not fall below a desired minimum material thickness and does not exceed a desired maximal material thickness. Thus, the steps of selecting a blank and cutting that blank can include not only adaptations relative to one or more parameters such as a patient's native anatomy and/or dimensions or kinematics, a resection depth, an implant or component thickness, a trochlear shape, but also a desired minimal and maximal implant thickness in the periphery. Alternatively, a procedure can include one or more steps of: (a) preoperatively determining a patellar resection depth, for example based on a trochlear component location and/or a desired patellar implant thickness and/or shape; (b) preoperatively determining the perimeter shape of the resected surface; (c) optionally designing an implant having a height that substantially positively-matches in one or more locations the resection depth; and (d) making (e.g., machining, cutting, printing, injection molding etc.) the implant designed in step (c) to substantially positively-match the resected surface determined in step (a), wherein said match can be in one or more dimensions and wherein said match can be a partial or near complete match. One or more of these steps can be performed preoperatively. FIGS. 59A and 59B show flow charts of exemplary processes for optimizing selecting and/or designing, and optionally optimizing, a patellar component based on one or more patient-specific biological features.

In certain embodiments, the step of (a) determining a patellar resection depth can be performed by determining minimal implant material thickness based on patient-specific data. For example, patient-specific information, such as one or more of weight, activity level, femur size, femur implant aspects such as surface geometry (e.g., trochlear geometry), patellar size, patellar bone decay, femoral shape or geometry, patellar and/or trochlear and/or femoral kinematics, and other information can be used to determine a minimal implant material thickness appropriate for the patient. Alternatively or in addition, the step of (a) determining a patellar resection depth can be determined based on the features of one or more resection cuts or other implant components selected for the patient, which have patient-specific features, patient-engineered, or combinations thereof. Then, the patella resection depth and the patella implant can be designed or selected to match this minimal material thickness. Alternatively, once the implant minimal material thickness is determined, a patella implant can be selected from a family of implants having variable thicknesses and the patellar resection depth is designed to match the thickness of the selected patellar implant. For example, a family of patellar implants can include implants with thicknesses of two or more of 4 mm, 6 mm, 8 mm, 10 mm, 10.5 mm, and 11 mm. FIGS. 56A through 56C illustrate this procedure.

In certain embodiments, the step of designing, selecting, and/or making (e.g., cutting from a blank) the implant perimeter to be substantially positively-match the determined resected perimeter or a percentage thereof in one or more dimensions can include smoothing the line of the surface perimeter on the implant, as illustrated in FIGS. 56A and 56C.

Accordingly, certain embodiments are directed to patellar implants and procedures that include one or more of (a) a preoperatively selected minimal implant thickness based on patient-specific information, such as femoral geometry and patellar size, (b) a preoperatively determined patellar resection depth that matches the selected minimal implant thickness and/or trochlear component thickness and/or external femoral component trochlea surface, and (c) a perimeter on patellar bone-facing surface of the implant that substantially positively-matches the perimeter of the resected surface, with optional smoothing of the implant perimeter. A significant advantage to having matching implant surface and resected surface perimeters is that it minimizes exposed resected bone and thereby minimizes bleeding, clot formation, and scar formation. Moreover, it can result in more bone preservation and/or improved kinematics.

In certain embodiments, the patella uses an external shape that is standard. In this case, the trochlea can also include a standard shape, typically mating with said patellar shape.

In another embodiment, the patellar shape can be standard. The trochlear shape on a patellofemoral replacement or a total knee system can be designed or selected to substantially match the patellar implant or component profile in mediolateral direction. The trochlear shape of a patellofemoral replacement or a total knee system can have a standard geometry in sagittal direction. Alternatively, the sagittal geometry of the trochlear surface of the implant can be derived from or adapted to the patient's sagittal trochlear geometry.

Exemplary combinations are described in Table 12.

TABLE 12

Exemplary patellar and trochlear combinations

| Patellar ML shape | Patellar AP shape | Trochlea ML shape | Trochlea sagittal shape | Trochlea groove orientation |
|---|---|---|---|---|
| Standard | Standard | Standard | Standard | Standard, e.g. substantially sagittal plane or oblique pointing internal or external from superior to inferior, straight or curved |
| Standard | Standard | Standard, e.g. constant coronal curvature | Patient-specific or patient derived | Standard, e.g. substantially sagittal plane or oblique pointing internal or external from superior to inferior, straight or curved |
| Standard | Standard | Standard | Patient-specific or patient derived | Patient-specific or patient derived, optionally corrected for tracking abnormalities |
| Patient-specific or patient-derived | Standard | Standard | Standard | Standard, e.g. substantially sagittal plane or oblique pointing internal or external from superior to inferior, straight or curved |
| Standard | Patient-specific or patient derived | Standard | Standard | Standard, e.g. substantially sagittal plane or oblique pointing internal or external from superior to inferior, straight or curved |
| Patient-specific or patient derived | Patient-specific or patient derived | Standard | Standard | Standard, e.g. substantially sagittal plane or oblique pointing internal or external from superior to inferior, straight or curved |
| Standard | Patient-specific or patient derived | Standard | Patient-specific or patient derived | Patient-specific or patient derived, optionally corrected for tracking abnormalities |
| Standard | Patient-specific or patient derived | Standard | Patient-specific or patient derived | Standard, e.g. substantially sagittal plane or oblique pointing internal or external from superior to inferior, straight or curved |
| Patient-specific or patient derived | Standard | Patient-specific or patient derived | Standard | Patient-specific or patient derived, optionally corrected for tracking abnormalities |
| Patient-specific or patient derived | Standard | Patient-specific or patient derived | Standard | Standard, e.g., substantially sagittal plane or oblique pointing internal or external from superior to inferior, straight or curved |
| Patient-specific or patient derived | Patient-specific or patient derived | Patient-specific or patient derived | Patient-specific or patient derived | Standard, e.g., substantially sagittal plane or oblique pointing internal or external from superior to inferior, straight or curved |
| Patient-specific or patient derived | Patient-specific or patient derived | Patient-specific or patient derived | Patient-specific or patient derived | Patient-specific or patient derived, optionally corrected for tracking abnormalities |

The shape and/or dimensions of the trochlea and the selection of a trochlear implant surface or the design of a trochlear implant surface can assist in the selection or design of a mating patellar implant and/or implant surface. Alternatively, the shape and/or dimensions of a patella and selected or designed patellar implant can assist in the selection or design of a mating trochlear implant surface and/or shape and/or dimensions.

A multiparametric fit or optimization can be performed that includes, for example, trochlea shape and/or dimensions, patella fit and/or dimensions, patella implant/component thickness at center and/or rim, patellar component shape, patellar and/or trochlear implant/component shapes, anterior femoral resection depth, and patellar kinematics in order to select or design the optimal combination of patellar and trochlear implant surfaces or components.

As indicated above, in certain embodiments an implant includes a patellar component, a femoral component, and, optionally, a tibial component. As depicted in FIGS. 59A and 59B, one or more features on the femoral articular surface and/or one or more features on the patellar articular surface can be selected and/or designed based on one or more of the corresponding component features. For example, one or more femoral component features, such as trochlear surface contour, trochlear groove width and/or depth, trochlear j-curve, sulcus dimension(s), mediolateral displacement of trochlear groove and/or sulcus (e.g., from anterior to posterior), medial and/or lateral condylar coronal curvature(s) along one or more surface sections (e.g., the anterior surface section), medial and/or lateral condylar sagittal curvature(s) (j-curves) along one or more sections (e.g., the anterior surface section), and/or other features can be selected and/or designed to include standard, patient-specific, and/or patient-engineered dimensions. Then, one or more of the patellar component features, such as the articular surface contour, thickness, perimeter or rim profile, AP distance, ML distance, oblique distance and other features can be selected and/or designed based on one or more of those femoral component features. Conversely, one or more femoral component features can be selected and/or designed based on one or more of patellar component features.

For example, the trochlear surface of the femoral component can include one or more patient-specific features, such as a patient-specific trochlear j-curve, trochlear groove coronal curvature, and the corresponding AP dimension(s) of the patellar component and/or its articular surface can be selected and/or designed to optimize kinematic fit with the trochlear j-curve. Alternatively or in addition, the trochlear surface of the femoral component can include one or more patient-engineered (i.e., patient-optimized) features, such as the trochlear coronal profile, and the ML dimension of the patellar component and/or its articular surface can be selected and/or designed to optimize kinematic fit with the engineered trochlear coronal profile.

6.3 Tibial Implant Component

In various embodiments described herein, one or more features of a tibial implant component are designed and/or selected, optionally in conjunction with an implant procedure, so that the tibial implant component fits the patient. For example, in certain embodiments, one or more features of a tibial implant component and/or implant procedure are designed and/or selected, based on patient-specific data, so that the tibial implant component substantially matches (e.g., substantially negatively-matches and/or substantially positively-matches) one or more of the patient's biological structures. Alternatively or in addition, one or more features of a tibial implant component and/or implant procedure can be preoperatively engineered based on patient-specific data to provide to the patient an optimized fit with respect to one or more parameters, for example, one or more of the parameters described above. For example, in certain embodiments, an engineered bone preserving tibial implant component can be designed and/or selected based on one or more of the patient's joint dimensions as seen, for example, on a series of two-dimensional images or a three-dimensional representation generated, for example, from a CT scan or Mill scan. Alternatively or in addition, an engineered tibial implant component can be designed and/or selected, at least in part, to provide to the patient an optimized fit with respect to the engaging, joint-facing surface of a corresponding femoral implant component.

Certain embodiments include a tibial implant component having one or more patient-adapted (e.g., patient-specific or patient-engineered) features and, optionally, one or more standard features. Optionally, the one or more patient-adapted features can be designed and/or selected to fit the patient's resected tibial surface. For example, depending on the patient's anatomy and desired postoperative geometry or alignment, a patient's lateral and/or medial tibial plateaus may be resected independently and/or at different depths, for example, so that the resected surface of the lateral plateau is higher (e.g., 1 mm, greater than 1 mm, 2 mm, and/or greater than 2 mm higher) or lower (e.g., 1 mm, greater than 1 mm, 2 mm, and/or greater than 2 mm lower) than the resected surface of the medial tibial plateau.

Figure 60A:
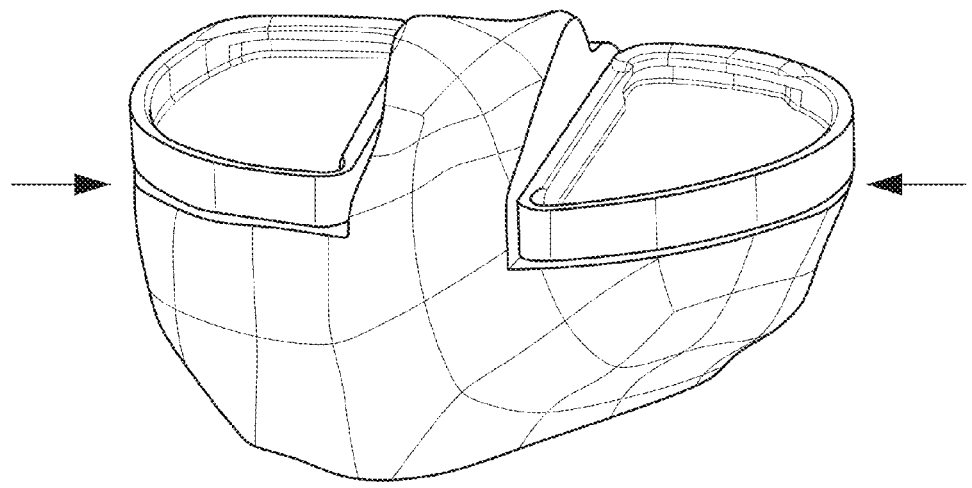
FIGS. 60A and 60B show exemplary unicompartmental medial and lateral tibial implant components without (FIG. 60A) and with (FIG. 60B) a polyethylene layer or insert.
Figure 60B:
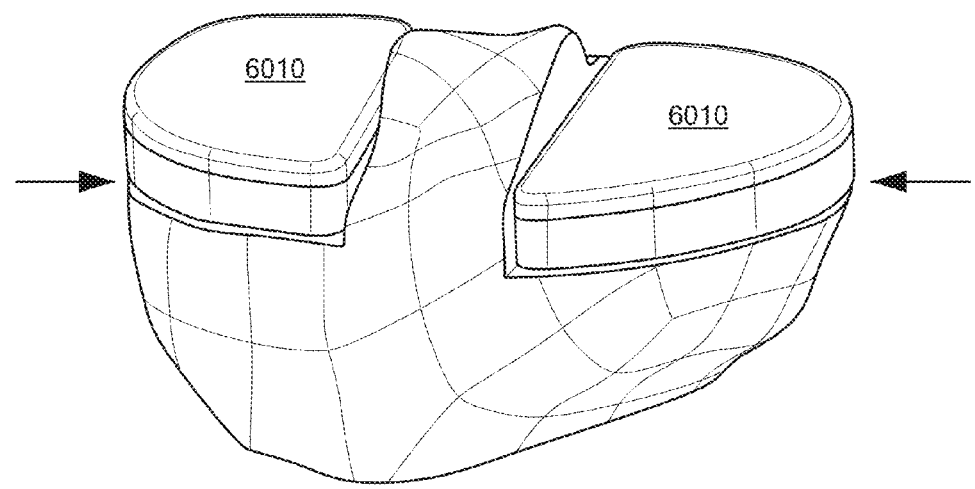

Accordingly, in certain embodiments, tibial implant components can be independently designed and/or selected for each of the lateral and/or medial tibial plateaus. For example, the perimeter of a lateral tibial implant component and the perimeter of a medial tibial implant component can be independently designed and/or selected to substantially match the perimeter of the resection surfaces for each of the lateral and medial tibial plateaus. FIGS. 60A and 60B show exemplary unicompartmental medial and lateral tibial implant components without (FIG. 60A) and with (FIG. 60B) a polyethylene layer or insert. As shown, the lateral tibial implant component and the medial tibial implant component have different perimeters shapes, each of which substantially matches the perimeter of the corresponding resection surface (see arrows). In addition, the polyethylene layers or inserts 6010 for the lateral tibial implant component and the medial tibial implant component have perimeter shapes that correspond to the respective implant component perimeter shapes. In certain embodiments, one or both of the implant components can be made entirely of a plastic or polyethylene (rather than having a having a polyethylene layer or insert) and each entire implant component can include a perimeter shape that substantially matches the perimeter of the corresponding resection surface.

Moreover, the height of a lateral tibial implant component and the height of a medial tibial implant component can be independently designed and/or selected to maintain or alter the relative heights generated by different resection surfaces for each of the lateral and medial tibial plateaus. For example, the lateral tibial implant component can be thicker (e.g., 1 mm, greater than 1 mm, 2 mm, and/or greater than 2 mm thicker) or thinner (e.g., 1 mm, greater than 1 mm, 2 mm, and/or greater than 2 mm thinner) than the medial tibial implant component to maintain or alter, as desired, the relative height of the joint-facing surface of each of the lateral and medial tibial implant components. As shown in FIG. 60A and FIG. 60B, the relative heights of the lateral and medial resection surfaces 6020 is maintained using lateral and medial implant components (and lateral and medial polyethylene layers or inserts) that have the same thickness. Alternatively, the lateral implant component (and/or the lateral polyethylene layer or insert) can have a different thickness than the medial implant component (and/or the medial polyethylene layer or insert). For embodiments having one or both of the lateral and medial implant components made entirely of a plastic or polyethylene (rather than having a having a polyethylene layer or insert) the thickness of one implant component can be different from the thickness of the other implant component.

Figure 61A:
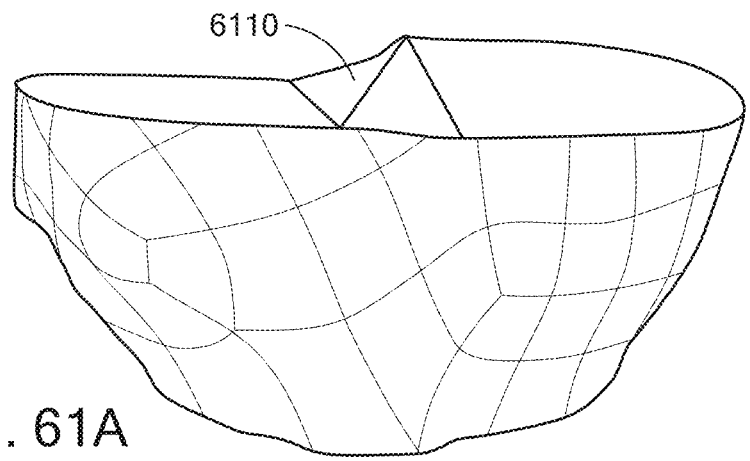
FIGS. 61A to 61C depict three different types of step cuts separating medial and lateral resection cut facets on a patient's proximal tibia.
Figure 61B:
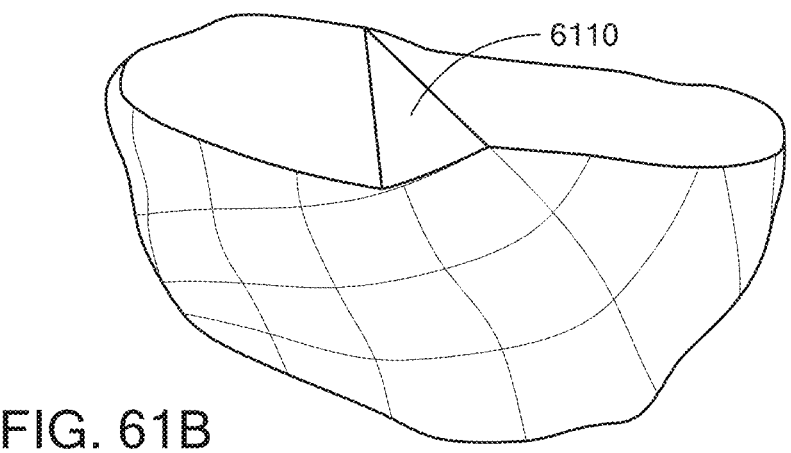
Figure 61C:
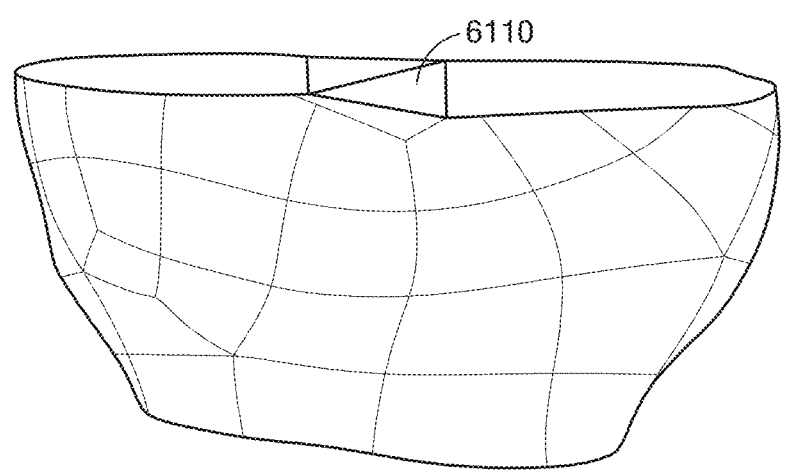

Different medial and lateral tibial cut heights also can be applied with a one piece implant component, e.g., a monolithically formed, tibial implant component. In this case, the tibial implant component and the corresponding resected surface of the patient's femur can have an angled surface or a step cut connecting the medial and the lateral surface facets. For example, FIGS. 61A to 61C depict three different types of step cuts separating medial and lateral resection cut facets on a patient's proximal tibia. In certain embodiments, the bone-facing surface of the tibial implant component is selected and/or designed to match these surface depths and the step cut angle, as well as other optional features such as perimeter shape.

Tibial components also can include the same medial and lateral cut height.

In certain embodiments, the medial tibial plateau facet can be oriented at an angle different than the lateral tibial plateau facet or it can be oriented at the same angle. One or both of the medial and the lateral tibial plateau facets can be at an angle that is patient-specific, for example, similar to the original slope or slopes of the medial and/or lateral tibial plateaus, for example, in the sagittal plane. Moreover, the medial slope can be patient-specific, while the lateral slope is fixed or preset or vice versa, as exemplified in Table 13.

TABLE 13

Exemplary designs for tibial slopes

| MEDIAL SIDE IMPLANT SLOPE | LATERAL SIDE IMPLANT SLOPE |
|---|---|
| Patient-matched to medial plateau | Patient-matched to lateral plateau |
| Patient-matched to medial plateau | Patient-matched to medial plateau |
| Patient-matched to lateral plateau | Patient-matched to lateral plateau |
| Patient-matched to medial plateau | Not patient-matched, e.g., preset, fixed or intraoperatively adjusted |
| Patient-matched to lateral plateau | Not patient-matched, e.g., preset, fixed or intraoperatively adjusted |
| Not patient matched, e.g. preset, fixed or intraoperatively adjusted | Patient-matched to lateral plateau |
| Not patient matched, e.g., preset, fixed or intraoperatively adjusted | Patient-matched to medial plateau |
| Not patient matched, e.g. preset, fixed or intraoperatively adjusted | Not patient-matched, e.g. preset, fixed or intraoperatively adjusted |

The exemplary combinations described in Table 13 are applicable to implants that use two unicompartmental tibial implant components with or without metal backing, one medial and one lateral. They also can be applicable to implant systems that use a single tibial implant component including all plastic designs or metal backed designs with inserts (optionally a single insert for the medial and lateral plateau, or two inserts, e.g., one medial and one lateral), for example PCL retaining, posterior stabilized, or ACL and PCL retaining implant components. The slope preferably is between 0 and 7 degrees, but other embodiments with other slope angles outside that range can be used. The slope can vary across one or both tibial facets from anterior to posterior. For example, a lesser slope, e.g. 0-1 degrees, can be used anteriorly, and a greater slope can be used posteriorly, for example, 4-5 degrees. Variable slopes across at least one of a medial or a lateral tibial facet can be accomplished, for example, with use of burrs (for example guided by a robot) or with use of two or more bone cuts on at least one of the tibial facets. In certain embodiments, two separate slopes can be used medially and laterally. Independent tibial slope designs can be useful for achieving bone preservation. In addition, independent slope designs can be advantageous in achieving implant kinematics that will be more natural, closer to the performance of a normal knee or the patient's knee.

Figure 62A:
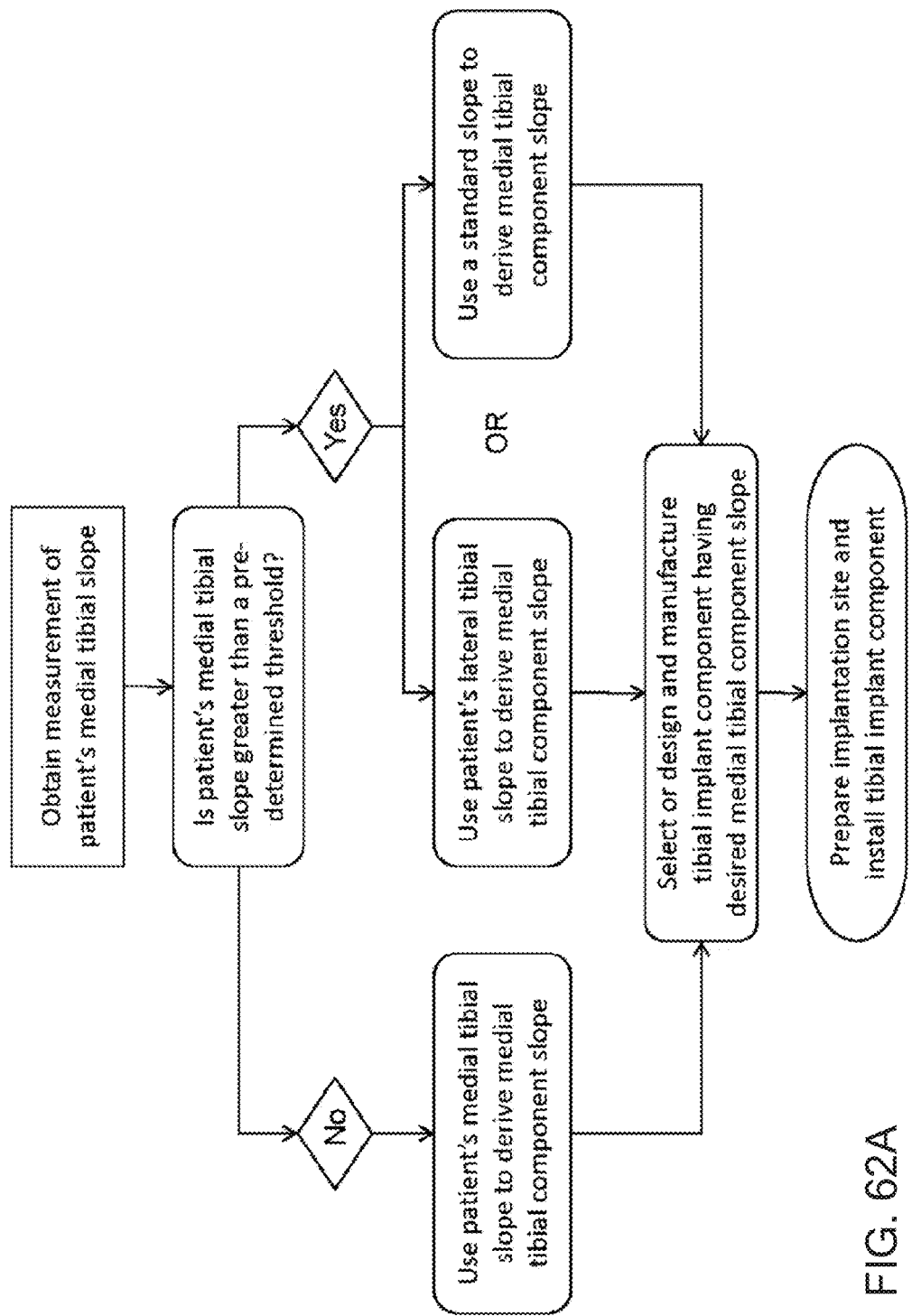
FIGS. 62A and 62B show exemplary flow charts for deriving a medial tibial component slope (FIG. 62A) and/or a lateral tibial component slope (FIG. 62B) for a tibial implant component.
Figure 62B:
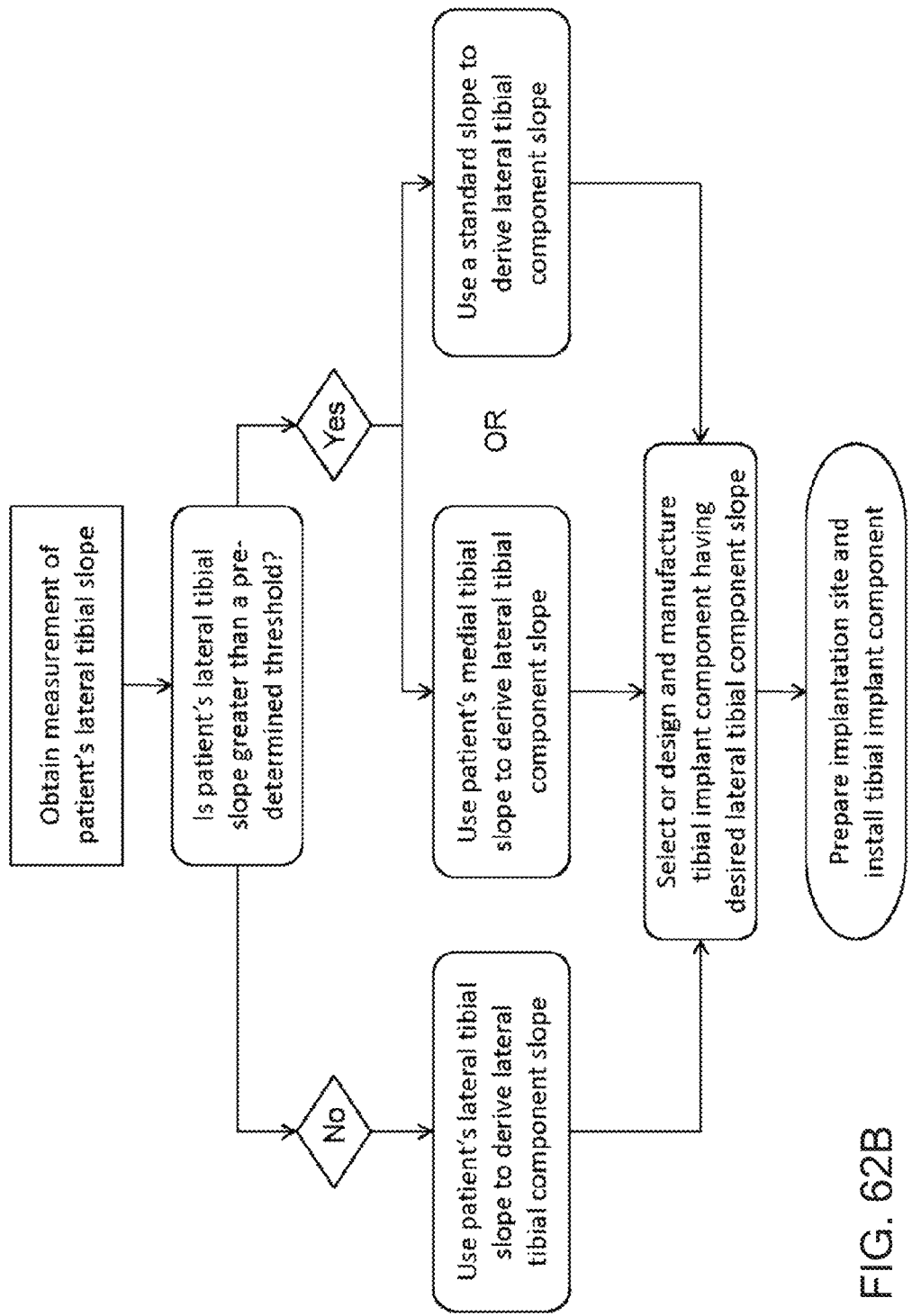
Figures 63A, 63B:
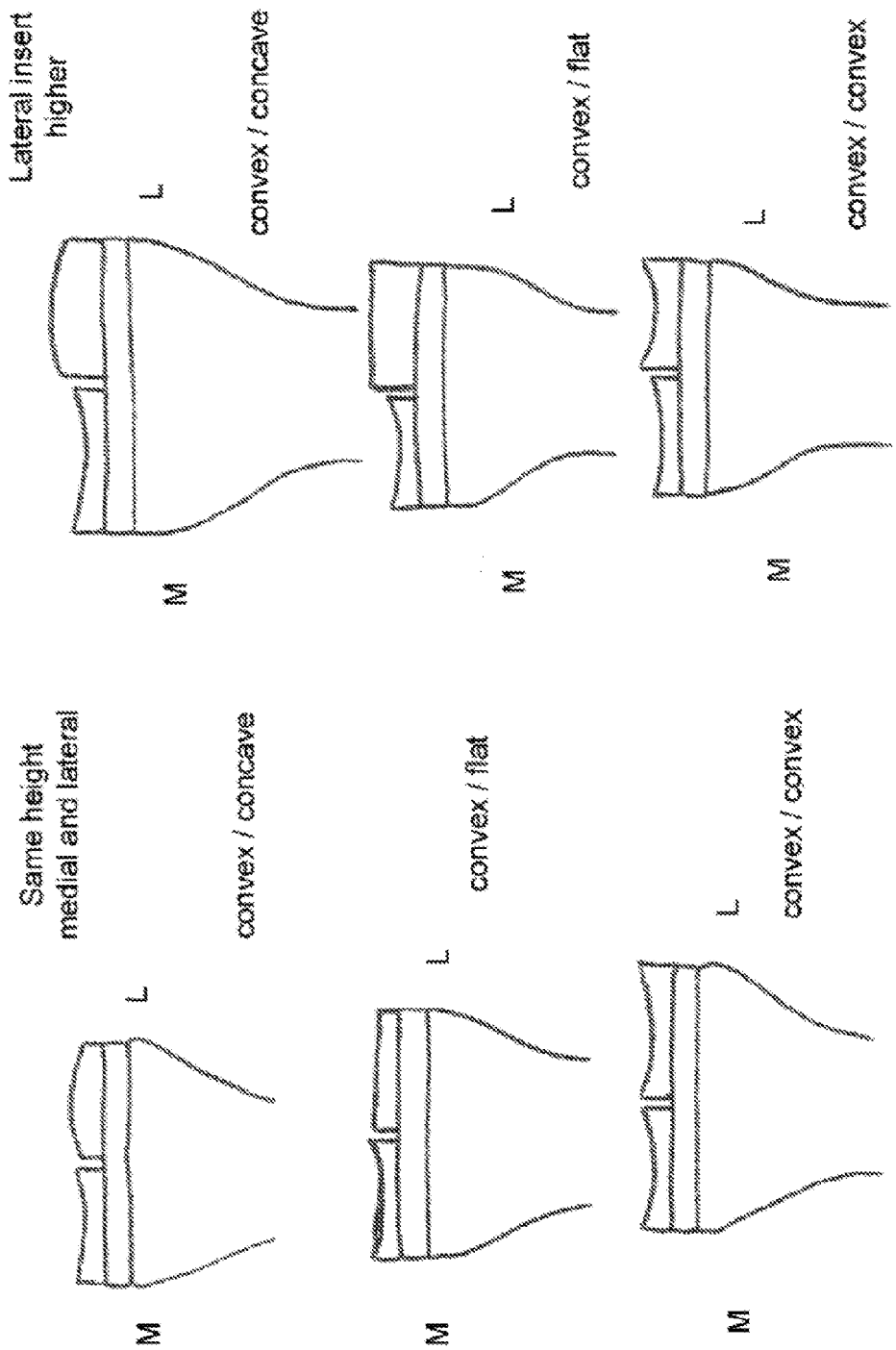
Figure 63E:
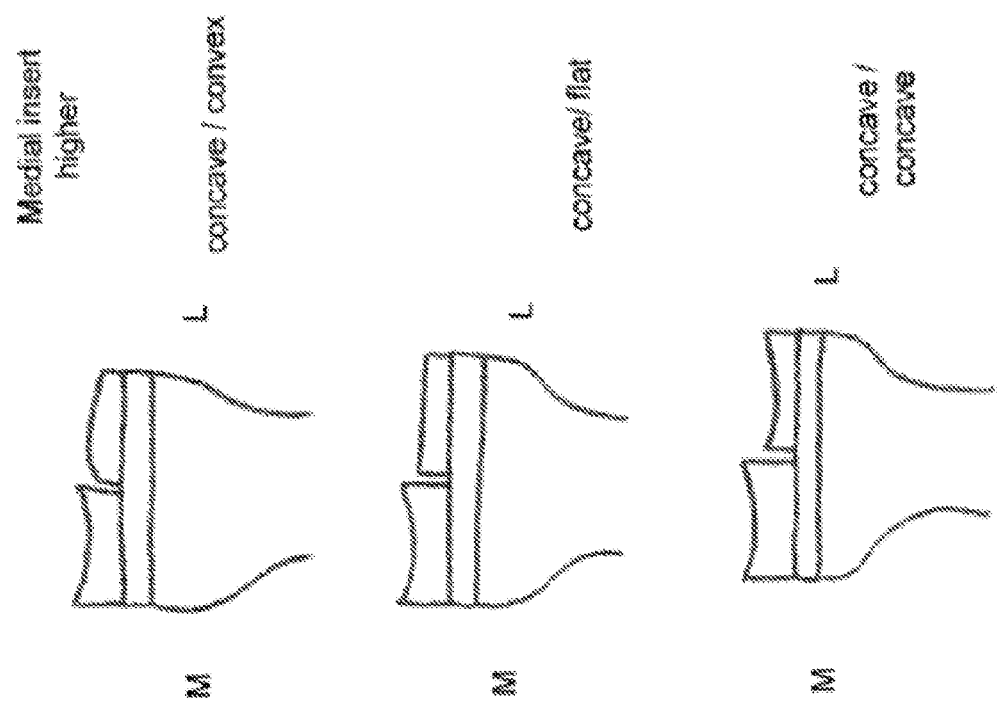
Figure 63F:
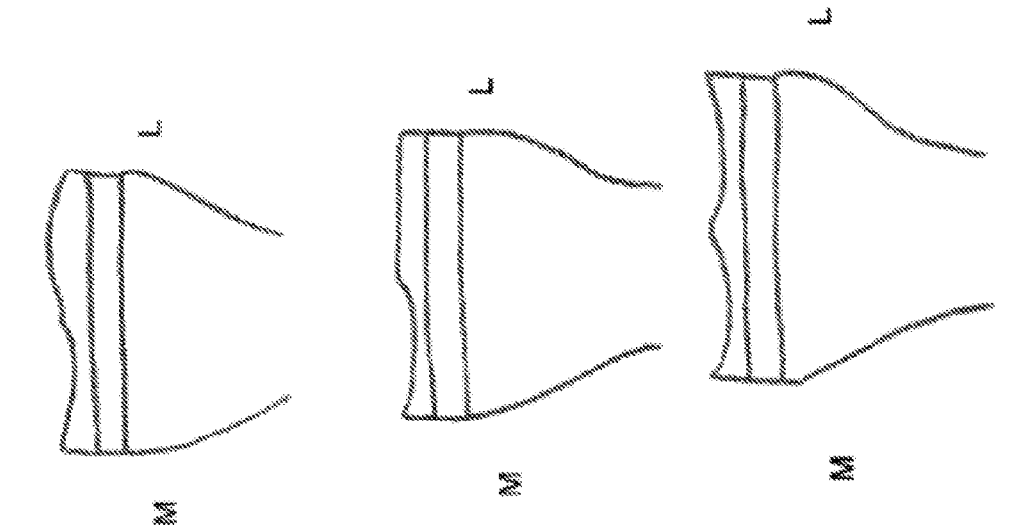
Figure 63H:
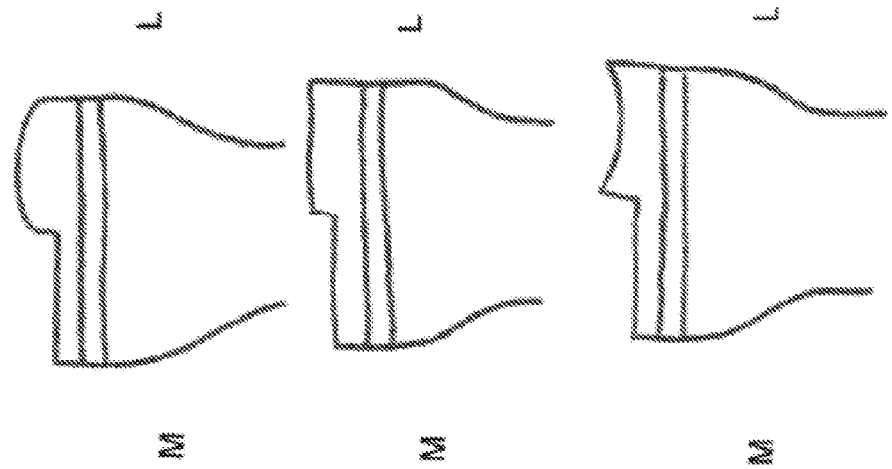
Figure 63G:
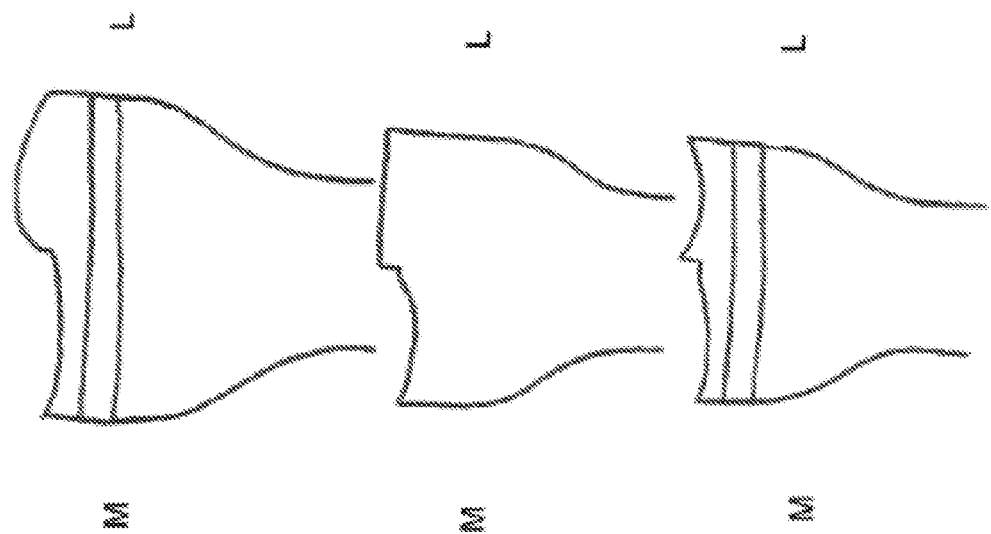
Figure 63J:
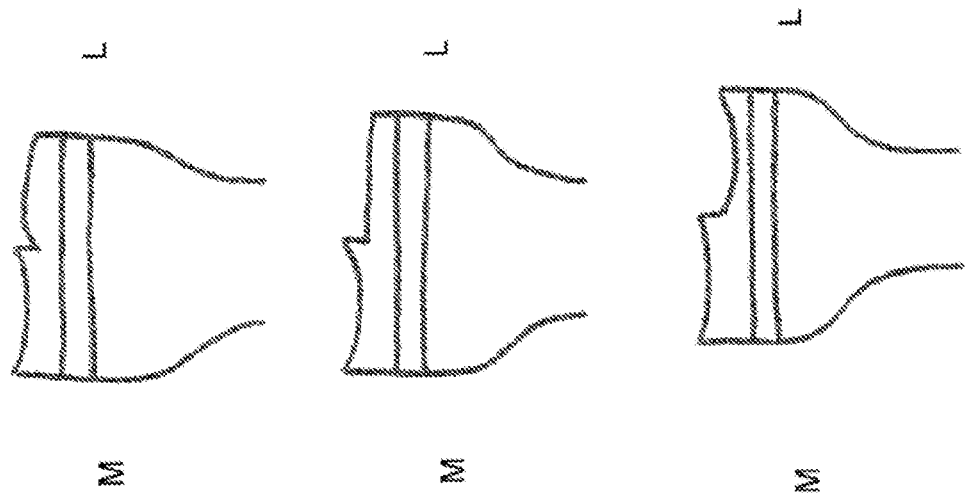
Figure 63I:
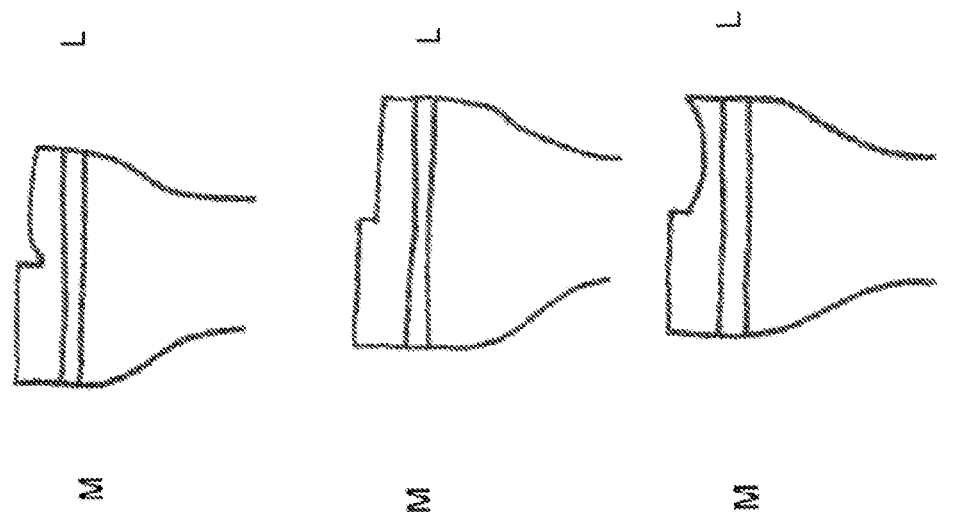
Figures 64A, 64B:
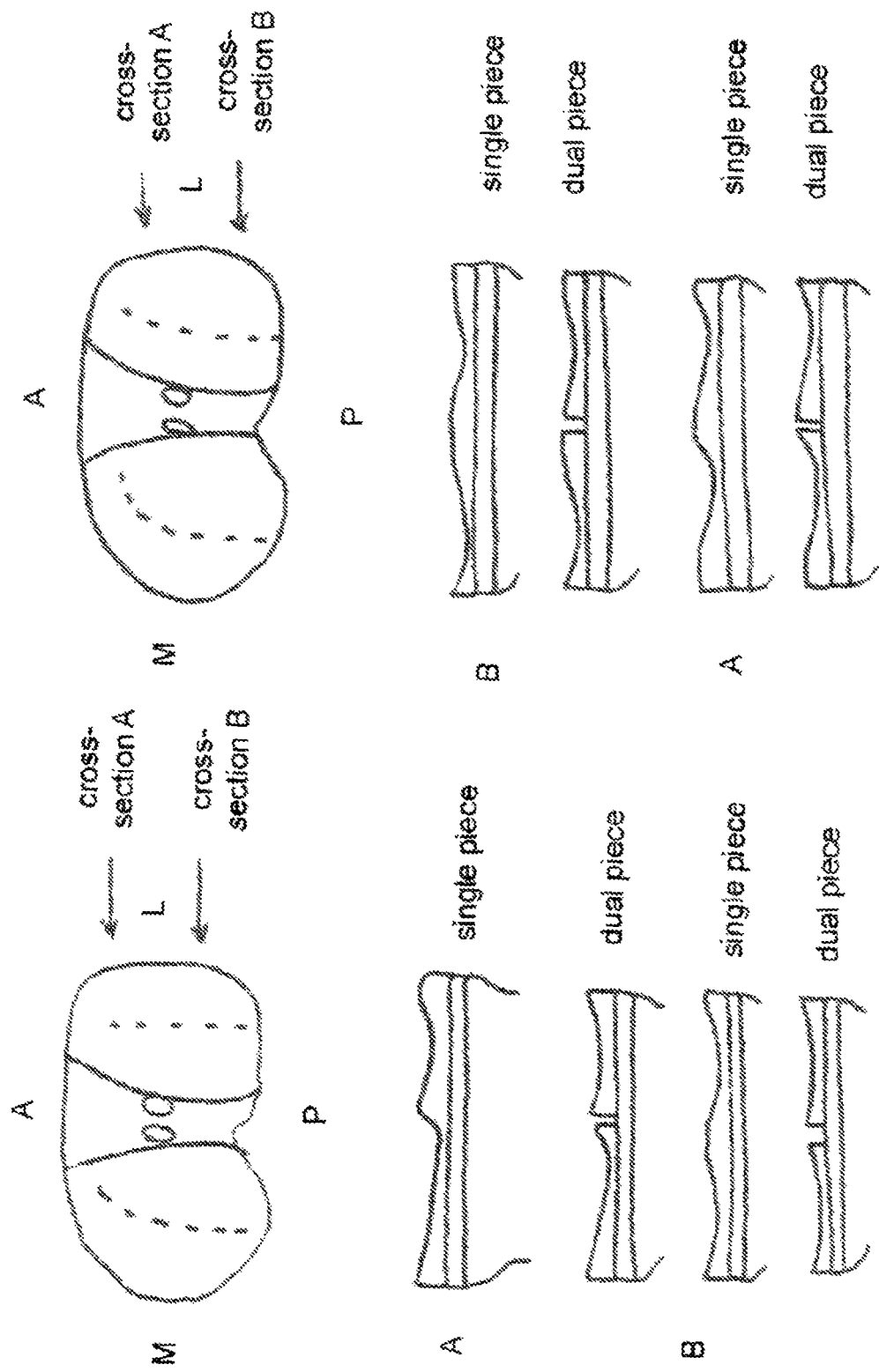
FIGS. 64A through 64F include additional embodiments of tibial implant components that are cruciate retaining.
Figure 64D:
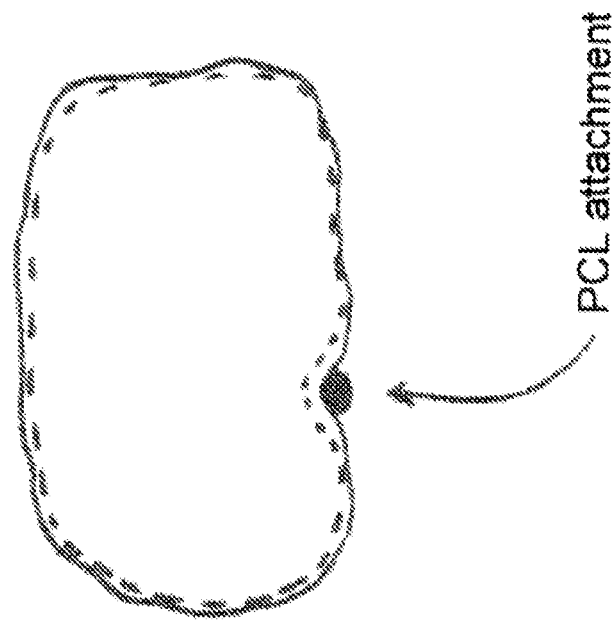
Figure 64C:
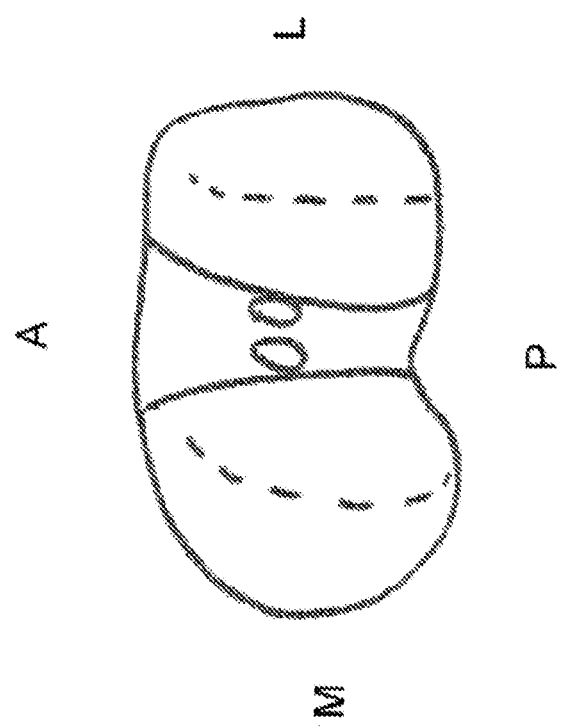
Figures 64E, 64F:
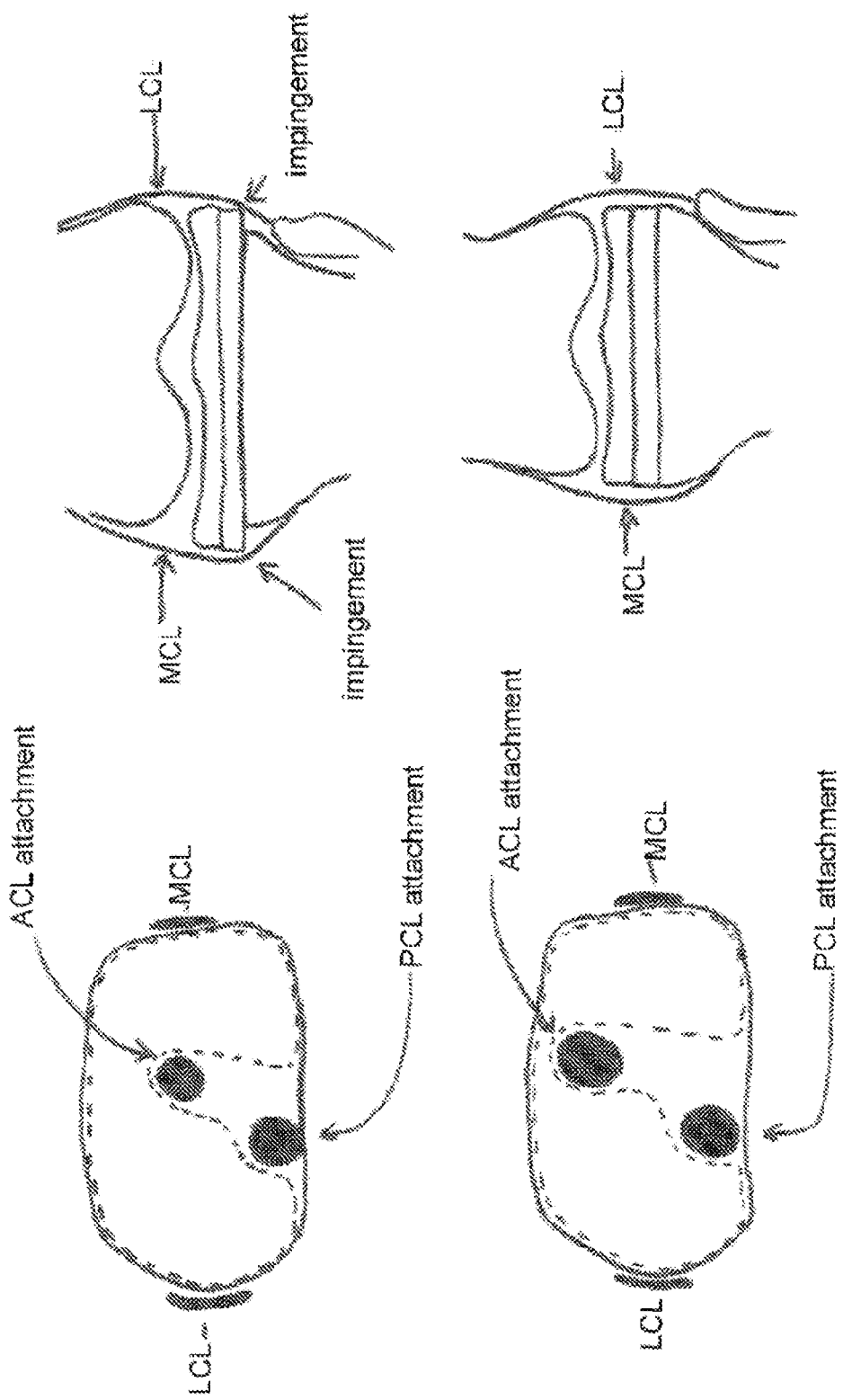

In certain embodiments, the slope can be fixed, e.g. at 3, 5 or 7 degrees in the sagittal plane. In certain embodiments, the slope, either medial or lateral or both, can be patient-specific. The patient's medial slope can be used to derive the medial tibial component slope and, optionally, the lateral component slope, in either a single or a two-piece tibial implant component. The patient's lateral slope can be used to derive the lateral tibial component slope and, optionally, the medial component slope, in either a single or a two-piece tibial implant component. A patient's slope typically is between 0 and 7 degrees. In select instances, a patient may show a medial or a lateral slope that is greater than 7 degrees. In this case, if the patient's medial slope has a higher value than 7 degrees or some other pre-selected threshold, the patient's lateral slope can be applied to the medial tibial implant component or to the medial side of a single tibial implant component. If the patient's lateral slope has a higher value than 7 degrees or some other pre-selected threshold, the patient's medial slope can be applied to the lateral tibial implant component or to the lateral side of a single tibial implant component. Alternatively, if the patient's slope on one or both medial and lateral sides exceeds a pre-selected threshold value, e.g., 7 degrees or 8 degrees or 10 degrees, a fixed slope can be applied to the medial component or side, to the lateral component or side, or both. The fixed slope can be equal to the threshold value, e.g., 7 degrees or it can be a different value. FIGS. 62A and 62B show exemplary flow charts for deriving a medial tibial component slope (FIG. 62A) and/or a lateral tibial component slope (FIG. 62B) for a tibial implant component.

A fixed tibial slope can be used in any of the embodiments described herein.

In another embodiment, a mathematical function can be applied to derive a medial implant slope and/or a lateral implant slope, or both (wherein both can be the same). In certain embodiments, the mathematical function can include a measurement derived from one or more of the patient's joint dimensions as seen, for example, on a series of two-dimensional images or a three-dimensional representation generated, for example, from a CT scan or MRI scan. For example, the mathematical function can include a ratio between a geometric measurement of the patient's femur and the patient's tibial slope. Alternatively or in addition, the mathematical function can be or include the patient's tibial slope divided by a fixed value. In certain embodiments, the mathematical function can include a measurement derived from a corresponding implant component for the patient, for example, a femoral implant component, which itself can include patient-specific, patient-engineered, and/or standard features. Many different possibilities to derive the patient's slope using mathematical functions can be applied by someone skilled in the art.

In certain embodiments, the medial and lateral tibial plateau can be resected at the same angle. For example, a single resected cut or the same multiple resected cuts can be used across both plateaus. In other embodiments, the medial and lateral tibial plateau can be resected at different angles. Multiple resection cuts can be used when the medial and lateral tibial plateaus are resected at different angles. Optionally, the medial and the lateral tibia also can be resected at a different distance relative to the tibial plateau. In this setting, the two horizontal plane tibial cuts medially and laterally can have different slopes and/or can be accompanied by one or two vertical or oblique resection cuts, typically placed medial to the tibial plateau components. FIG. 16 and FIGS. 61A to 61C show several exemplary tibial resection cuts, which can be used in any combination for the medial and lateral plateaus.

The medial tibial implant component plateau can have a flat, convex, concave, or dished surface and/or it can have a thickness different than the lateral tibial implant component plateau. The lateral tibial implant component plateau can have a flat, convex, concave, or dished surface and/or it can have a thickness different than the medial tibial implant component plateau. The different thickness can be achieved using a different material thickness, for example, metal thickness or polyethylene or insert thickness on either side. In certain embodiments, the lateral and medial surfaces are selected and/or designed to closely resemble the patient's anatomy prior to developing the arthritic state.

The height of the medial and/or lateral tibial implant component plateau, e.g., metal only, ceramic only, metal backed with polyethylene or other insert, with single or dual inserts and single or dual tray configurations can be determined based on the patient's tibial shape, for example using an imaging test.

Alternatively, the height of the medial and/or lateral tibial component plateau, e.g. metal only, ceramic only, metal backed with polyethylene or other insert, with single or dual inserts and single or dual tray configurations can be determined based on the patient's femoral shape. For example, if the patient's lateral condyle has a smaller radius than the medial condyle and/or is located more superior than the medial condyle with regard to its bearing surface, the height of the tibial component plateau can be adapted and/or selected to ensure an optimal articulation with the femoral bearing surface. In this example, the height of the lateral tibial component plateau can be adapted and/or selected so that it is higher than the height of the medial tibial component plateau. Since polyethylene is typically not directly visible on standard x-rays, metallic or other markers can optionally be included in the inserts in order to indicate the insert location or height, in particular when asymmetrical medial and lateral inserts or inserts of different medial and lateral thickness are used.

Alternatively, the height of the medial and/or lateral tibial component plateau, e.g. metal only, ceramic only, metal backed with polyethylene or other insert, with single or dual inserts and single or dual tray configurations can be determined based on the shape of a corresponding implant component, for example, based on the shape of certain features of the patient's femoral implant component. For example, if the femoral implant component includes a lateral condyle having a smaller radius than the medial condyle and/or is located more superior than the medial condyle with regard to its bearing surface, the height of the tibial implant component plateaus can be adapted and/or selected to ensure an optimal articulation with the bearing surface(s) of the femoral implant component. In this example, the height of the lateral tibial implant component plateau can be adapted and/or selected to be higher than the height of the medial tibial implant component plateau.

Moreover, the surface shape, e.g. mediolateral or anteroposterior curvature or both, of the tibial insert(s) can reflect the shape of the femoral component. For example, the medial insert shape can be matched to one or more radii on the medial femoral condyle of the femoral component. The lateral insert shape can be matched to one or more radii on the lateral femoral condyle of the femoral component. The lateral insert may optionally also be matched to the medial condyle. The matching can occur, for example, in the coronal plane. This has benefits for wear optimization. A pre-manufactured insert can be selected for a medial tibia that matches the medial femoral condyle radii in the coronal plane with a pre-selected ratio, e.g. 1:5 or 1:7 or 1:10. Any combination is possible. A pre-manufactured insert can be selected for a lateral tibia that matches the lateral femoral condyle radii in the coronal plane with a pre-selected ratio, e.g. 1:5 or 1:7 or 1:10. Any combination is possible. Alternatively, a lateral insert can also be matched to a medial condyle or a medial insert shape can also be matched to a lateral condyle. These combinations are possible with single and dual insert systems with metal backing. Someone skilled in the art will recognize that these matchings can also be applied to implants that use all polyethylene tibial components; i.e. the radii on all polyethylene tibial components can be matched to the femoral radii in a similar manner.

The matching of radii can also occur in the sagittal plane. For example, a cutter can be used to cut a fixed coronal curvature into a tibial insert or all polyethylene tibia that is matched to or derived from a femoral implant or patient geometry. The path and/or depth that the cutter is taking can be driven based on the femoral implant geometry or based on the patient's femoral geometry prior to the surgery. Medial and lateral sagittal geometry can be the same on the tibial inserts or all poly tibia. Alternatively, each can be cut separately. By adapting or matching the tibial poly geometry to the sagittal geometry of the femoral component or femoral condyle, a better functional result may be achieved. For example, more physiologic tibiofemoral motion and kinematics can be enabled.

The medial and/or the lateral component can include a trough. The medial component can be dish shaped, while the lateral component includes a trough. The lateral component can be dish shaped, while the medial component includes a trough. The lateral component can be convex, while the medial component includes a trough. The shape of the medial or lateral component can be patient derived or patient matched in one, two or three dimensions, for example as it pertains to its perimeter as well as its surface shape. The convex shape of the lateral component can be patient derived or patient matched in one, two or three dimensions. The trough can be straight. The trough can also be curved. The curvature of the trough can have a constant radius of curvature or it can include several radii of curvature. The radii can be patient matched or patient derived, for example based on the femoral geometry or on the patient's kinematics. These designs can be applied with a single-piece tibial polyethylene or other plastic insert or with two-piece tibial polyethylene or other plastic inserts. FIGS. 63A through 63J show exemplary combinations of tibial tray designs. FIGS. 64A through 64F include additional embodiments of tibial implant components that are cruciate retaining.

The perimeter of the tibial component, metal backed, optionally poly inserts, or all plastic or other material, can be matched to or derived from the patient's tibial shape, and can be optimized for different cut heights and/or tibial slopes. In a preferred embodiment, the shape is matched to the cortical bone of the cut surface. The surface topography of the tibial bearing surface can be designed or selected to match or reflect at least a portion of the tibial geometry, in one or more planes, e.g., a sagittal plane or a coronal plane, or both. The medial tibial implant surface topography can be selected or designed to match or reflect all or portions of the medial tibial geometry in one or more planes, e.g., sagittal and coronal. The lateral tibial implant surface topography can be selected or designed to match or reflect all or portions of the lateral tibial geometry in one or more planes, e.g., sagittal and coronal. The medial tibial implant surface topography can be selected or designed to match or reflect all or portions of the lateral tibial geometry in one or more planes, e.g., sagittal and coronal. The lateral tibial implant surface topography can be selected or designed to match or reflect all or portions of the medial tibial geometry in one or more planes, e.g., sagittal and coronal.

The surface topography of the tibial bearing surface(s) can be designed or selected to match or reflect at least portions of the femoral geometry or femoral implant geometry, in one or more planes, e.g., a sagittal plane or a coronal plane, or both. The medial implant surface topography can be selected or designed to match or reflect all or portions of the medial femoral geometry or medial femoral implant geometry in one or more planes. The lateral implant surface topography can be selected or designed to match or reflect all or portions of the lateral femoral geometry or lateral femoral implant geometry in one or more planes. The medial implant surface topography can be selected or designed to match or reflect all or portions of the lateral femoral geometry or lateral femoral implant geometry in one or more planes. The lateral implant surface topography can be selected or designed to match or reflect all or portions of the medial femoral geometry or medial femoral implant geometry in one or more planes. The medial and/or the lateral surface topography can be fixed in one, two or all dimensions. The latter can typically be used when at least one femoral geometry, e.g., the coronal curvature, is also fixed.

The implant surface topography can include one or more of the following:
  Curvature of convexity in sagittal plane, optionally patient derived or matched, e.g., based on tibial or femoral geometry
  Curvature of convexity in coronal plane, optionally patient derived or matched, e.g., based on tibial or femoral geometry
  Curvature of concavity in sagittal plane, optionally patient derived or matched, e.g., based on tibial or femoral geometry
  Curvature of concavity in coronal plane, optionally patient derived or matched, e.g., based on tibial or femoral geometry
  Single sagittal radius of curvature, optionally patient derived or matched, e.g., based on tibial or femoral geometry
  Multiple sagittal radii of curvature, optionally patient derived or matched, e.g., based on tibial or femoral geometry
  Single coronal radius of curvature, optionally patient derived or matched, e.g., based on tibial or femoral geometry
  Multiple coronal radii of curvature, optionally patient derived or matched, e.g., based on tibial or femoral geometry
  Depth of dish, optionally patient derived or matched, e.g., based on tibial or femoral geometry
  AP length of dish, optionally patient derived or matched, e.g., based on tibial or femoral geometry
  ML width of dish, optionally patient derived or matched, e.g., based on tibial or femoral geometry
  Depth of trough, optionally patient derived or matched, e.g., based on tibial or femoral geometry
  AP length of trough, optionally patient derived or matched, e.g., based on tibial or femoral geometry
  ML width of trough, optionally patient derived or matched, e.g., based on tibial or femoral geometry
  Curvature of trough, optionally patient derived or matched, e.g., based on tibial or femoral geometry All of the tibial designs discussed can be applied with a:
  single piece tibial polyethylene insert, for example with a single metal backed component
  single piece tibial insert of other materials, for example with a single metal backed component
  two piece tibial polyethylene inserts, for example with a single metal backed component
  two piece tibial inserts of other materials, for example with a single metal backed component
  single piece all polyethylene tibial implant
  two piece all polyethylene tibial implant, e.g. medial and lateral
  single piece metal tibial implant (e.g., metal on metal or metal on ceramic)
  two piece metal tibial implant, e.g., medial and lateral (e.g., metal on metal or metal on ceramic)
  single piece ceramic tibial implant
  two piece ceramic tibial implant, e.g., medial and lateral
Any material or material combination currently known in the art and developed in the future can be used.

Certain embodiments of tibial trays can have the following features, although other embodiments are possible: modular insert system (polymer); cast cobalt chrome; standard blanks (cobalt portion and/or modular insert) can be made in advance, then shaped patient-specific to order; thickness based on size (saves bone, optimizes strength); allowance for 1-piece or 2-piece insert systems; and/or different medial and lateral fins.

In certain embodiments, the tibial tray is designed or cut from a blank so that the tray periphery matches the edge of the cut tibial bone, for example, the patient-matched peripheral geometry achieves >70%, >80%, >90%, or >95% cortical coverage. In certain embodiments, the tray periphery is designed to have substantially the same shape, but be slightly smaller, than the cortical area.

The patient-adapted tibial implants of certain embodiments allow for design flexibility. For example, inserts can be designed to compliment an associated condyle of a corresponding femoral implant component, and can vary in dimensions to optimize design, for example, one or more of height, shape, curvature (preferably flat to concave), and location of curvature to accommodate natural or engineered wear pattern.

In the knee, a tibial cut can be selected so that it is, for example, 90 degrees perpendicular to the tibial mechanical axis or to the tibial anatomical axis. The cut can be referenced, for example, by finding the intersect with the lowest medial or lateral point on the plateau.

The slope for tibial cuts typically is between 0 and 7 or 0 and 8 degrees in the sagittal plane. Rarely, a surgeon may elect to cut the tibia at a steeper slope. The slope can be selected or designed into a patient-specific cutting jig using a preoperative imaging test. The slope can be similar to the patient's preoperative slope on at least one of a medial or one of a lateral side. The medial and lateral tibia can be cut with different slopes. The slope also can be different from the patient's preoperative slope on at least one of a medial or one of a lateral side.

The tibial cut height can differ medially and laterally, as shown in FIG. 16 and FIGS. 61A to 61C. In some patients, the uncut lateral tibia can be at a different height, for example, higher or lower, than the uncut medial tibia. In this instance, the medial and lateral tibial cuts can be placed at a constant distance from the uncut medial and the uncut lateral tibial plateau, resulting in different cut heights medially or laterally. Alternatively, they can be cut at different distances relative to the uncut medial and lateral tibial plateau, resulting in the same cut height on the remaining tibia. Alternatively, in this setting, the resultant cut height on the remaining tibia can be elected to be different medially and laterally. In certain embodiments, independent design of the medial and lateral tibial resection heights, resection slopes, and/or implant component (e.g., tibial tray and/or tibial tray insert), can enhance bone perseveration on the medial and/or lateral sides of the proximal tibia as well as on the opposing femoral condyles.

In certain embodiments, a patient-specific proximal tibia cut (and the corresponding bone-facing surface of the tibial component) is designed by: (1) finding the tibial axis perpendicular plane ("TAPP"); (2) lowering the TAPP, for example, 2 mm below the lowest point of the medial tibial plateau; (3) sloping the lowered TAPP 5 degrees posteriorly (no additional slope is required on the proximal surface of the insert); (4) fixing the component posterior slope, for example, at 5 degrees; and (5) using the tibial anatomic axis derived from Cobb or other measurement technique for tibial implant rotational alignment. As shown in FIG. 65, resection cut depths deeper than 2 mm below the lowest point of the patient's uncut medial or lateral plateau (e.g., medial plateau) may be selected and/or designed, for example, if the patient's anatomy includes an abnormality or diseased tissue below this point, or if the surgeon prefers a lower cut. For example, resection cut depths of 2.5 mm, 3 mm, 3.5 mm, 4 mm, 4.5 mm, or 5 mm can be selected and/or designed and, optionally, one or more corresponding tibial and/or femoral implant thicknesses can be selected and/or designed based on this patient-specific information.

In certain embodiments, a patient-specific proximal tibial cut (and the corresponding bone-facing surface of the tibial component) uses the preceding design except for determining the A-P slope of the cut. In certain embodiments, a patient-specific A-P slope can be used, for example, if the patient's anatomic slope is between 0 degrees and 7 degrees, or between 0 degrees and 8 degrees, or between 0 degrees and 9 degrees; a slope of 7 degrees can be used if the patient's anatomic slope is between 7 degrees and 10 degrees, and a slope of 10° can be used if the patient's anatomic slope is greater than 10 degrees.

In certain embodiments, a patient-specific A-P slope is used if the patient's anatomic slope is between 0 and 7 degrees and a slope of 7 degrees is used if the patient's anatomic slope is anything over 7 degrees. Someone skilled in the art will recognize other methods for determining the tibial slope and for adapting it during implant and jig design to achieve a desired implant slope.

A different tibial slope can be applied on the medial and the lateral side. A fixed slope can be applied on one side, while the slope on the other side can be adapted based on the patient's anatomy. For example, a medial slope can be fixed at 5 degrees, while a lateral slope matches that of the patient's tibia. In this setting, two unicondylar tibial inserts or trays can be used. Alternatively, a single tibial component, optionally with metal backing, can be used wherein said component does not have a flat, bone-facing surface, but includes, for example, an oblique portion to connect the medial to the lateral side substantially negatively-match resected lateral and medial tibial surfaces as shown, for example, in FIG. 16 and FIGS. 61A to 61C.

In certain embodiments, the axial profile (e.g., perimeter shape) of the tibial implant can be designed to match the axial profile of the patient's cut tibia, for example as described in U.S. Patent Application Publication No. 2009/0228113. Alternatively or in addition, in certain embodiments, the axial profile of the tibial implant can be designed to maintain a certain percentage or distance in its perimeter shape relative to the axial profile of the patient's cut tibia. Alternatively or in addition, in certain embodiments, the axial profile of the tibial implant can be designed to maintain a certain percentage or overhang in its perimeter shape relative to the axial profile of the patient's cut tibia.

Any of the tibial implant components described above can be derived from a blank that is cut to include one or more patient-specific features.

Figure 66:
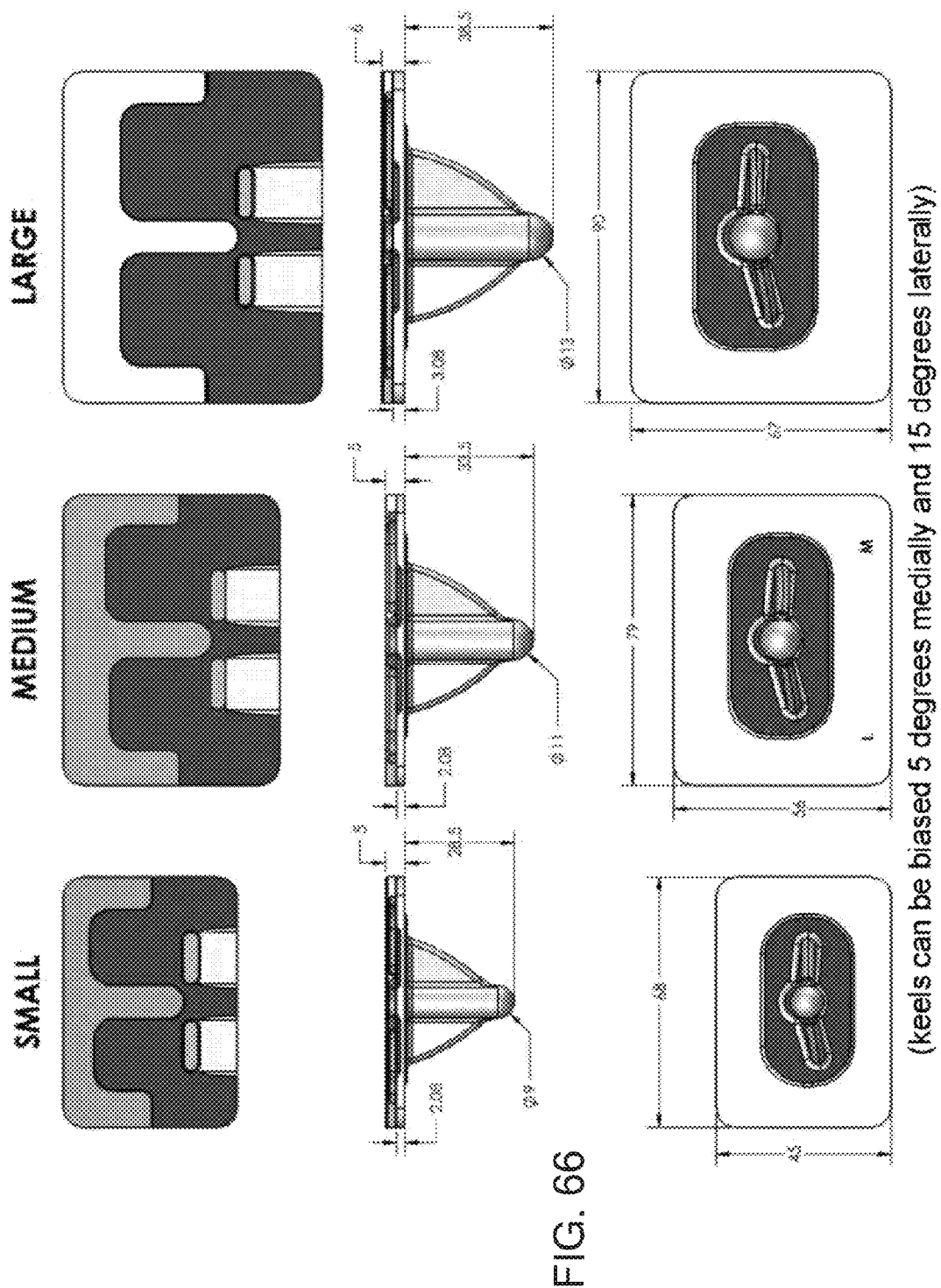
FIG. 66 shows exemplary small, medium and large blank tibial trays.

Tibial tray designs can include patient-specific, patient-engineered, and/or standard features. For example, in certain embodiments the tibial tray can have a front-loading design that requires minimal impaction force to seat it. The trays can come in various standard or standard blank designs, for example, small, medium and large standard or standard blank tibial trays can be provided. FIG. 66 shows exemplary small, medium and large blank tibial trays. As shown, the tibial tray perimeters include a blank perimeter shape that can be designed based on the design of the patient's resected proximal tibia surface. In certain embodiments, small and medium trays can include a base thickness of 2 mm (e.g., such that a patient's natural joint line may be raised 3-4 mm if the patient has 2-3 mm of cartilage on the proximal tibia prior to the disease state). Large trays can have a base thickness of 3 mm (such that in certain embodiments it may be beneficial to resect an additional 1 mm of bone so that the joint line is raised no more than 2-3 mm (assuming 2-3 mm of cartilage on the patient's proximal tibia prior to the disease state).

Figure 67:
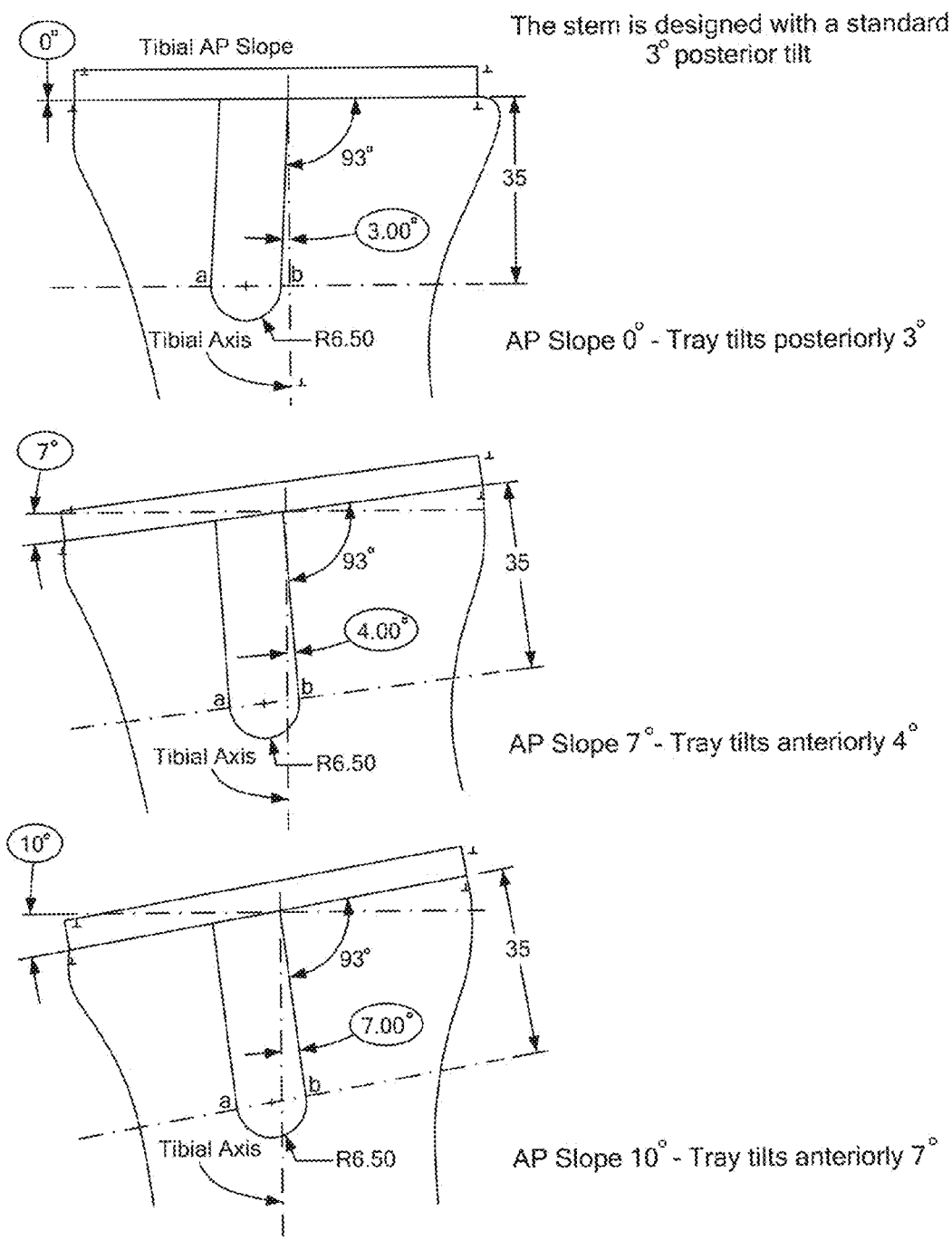
FIG. 67 shows exemplary A-P and peg angles for tibial trays.

A patient-specific peg alignment (e.g., either aligned to the patient's mechanical axis or aligned to another axis) can be combined with a patient-specific A-P cut plane. For example, in certain embodiments the peg alignment can tilt anteriorly at the same angle that the A-P slope is designed. In certain embodiments, the peg can be aligned in relation to the patient's sagittal mechanical axis, for example, at a predetermined angle relative to the patient's mechanical axis. FIG. 67 shows exemplary A-P and peg angles for tibial trays.

The joint-facing surface of a tibial implant component includes a medial bearing surface and a lateral bearing surface. Like the femoral implant bearing surface(s) described above, a bearing surface on a tibial implant (e.g., a groove or depression or a convex portion (on the lateral side) in the tibial surface that receives contact from a femoral component condyle) can be of standard design, for example, available in 6 or 7 different shapes, with a single radius of curvature or multiple radii of curvature in one dimension or more than one dimension. Alternatively, a bearing surface can be standardized in one or more dimensions and patient-adapted in one or more dimensions. A single radius of curvature and/or multiple radii of curvature can be selected in one dimension or multiple dimensions. Some of the radii can be patient-adapted.

Each of the two contact areas of the polyethylene insert of the tibial implant component that engage the femoral medial and lateral condyle surfaces can be any shape, for example, convex, flat, or concave, and can have any radii of curvature. In certain embodiments, any one or more of the curvatures of the medial or lateral contact areas can include patient-specific radii of curvature. Specifically, one or more of the coronal curvature of the medial contact area, the sagittal curvature of the medial contact area, the coronal curvature of the lateral contact area, and/or the sagittal curvature of the lateral contact area can include, at least in part, one or more patient-specific radii of curvature. In certain embodiments, the tibial implant component is designed to include one or both medial and lateral bearing surfaces having a sagittal curvature with, at least in part, one or more patient-specific radii of curvature and a standard coronal curvature. In certain embodiments, the bearing surfaces on one or both of the medial and lateral tibial surfaces can include radii of curvature derived from (e.g., the same length or slightly larger, such as 0-10% larger than) the radii of curvature on the corresponding femoral condyle. Having patient-adapted sagittal radii of curvature, at least in part, can help achieve normal kinematics with full range of motion.

Alternatively, the coronal curvature can be selected, for example, by choosing from a family of standard curvatures the one standard curvature having the radius of curvature or the radii of curvature that is most similar to the coronal curvature of the patient's uncut femoral condyle or that is most similar to the coronal curvature of the femoral implant component.

In preferred embodiments, one or both tibial medial and lateral contact areas have a standard concave coronal radius that is larger, for example slightly larger, for example, between 0 and 1 mm, between 0 and 2 mm, between 0 and 4 mm, between 1 and 2 mm, and/or between 2 and 4 mm larger, than the convex coronal radius on the corresponding femoral component. By using a standard or constant coronal radius on a femoral condyle with a matching standard or constant coronal radius or slightly larger on a tibial insert, for example, with a tibial radius of curvature of from about 1.05× to about 2×, or from about 1.05× to about 1.5×, or from about 1.05× to about 1.25×, or from about 1.05× to about 1.10×, or from about 1.05× to about 1.06×, or about 1.06× of the corresponding femoral implant coronal curvature. The relative convex femoral coronal curvature and slightly larger concave tibial coronal curvature can be selected and/or designed to be centered to each about the femoral condylar centers.

In the sagittal plane, one or both tibial medial and lateral concave curvatures can have a standard curvature slightly larger than the corresponding convex femoral condyle curvature, for example, between 0 and 1 mm, between 0 and 2 mm, between 0 and 4 mm, between 1 and 2 mm, and/or between 2 and 4 mm larger, than the convex sagittal radius on the corresponding femoral component. For example, the tibial radius of curvature for one or both of the medial and lateral sides can be from about 1.1× to about 2×, or from about 1.2× to about 1.5×, or from about 1.25× to about 1.4×, or from about 1.30× to about 1.35×, or about 1.32× of the corresponding femoral implant sagittal curvature. In certain embodiments, the depth of the curvature into the tibial surface material can depend on the height of the surface into the joint gap. As mentioned, the height of the medial and lateral tibial component joint-facing surfaces can be selected and/or designed independently. In certain embodiments, the medial and lateral tibial heights are selected and/or designed independently based on the patient's medial and lateral condyle height difference. In addition or alternatively, in certain embodiments, a threshold minimum or maximum tibial height and/or tibial insert thickness can be used. For example, in certain embodiments, a threshold minimum insert thickness of 6 mm is employed so that no less than a 6 mm medial tibial insert is used.

By using a tibial contact surface sagittal and/or coronal curvature selected and/or designed based on the curvature(s) of the corresponding femoral condyles or a portion thereof (e.g., the bearing portion), the kinematics and wear of the implant can be optimized. For example, this approach can enhance the wear characteristics a polyethylene tibial insert. This approach also has some manufacturing benefits.

Figure 68B:
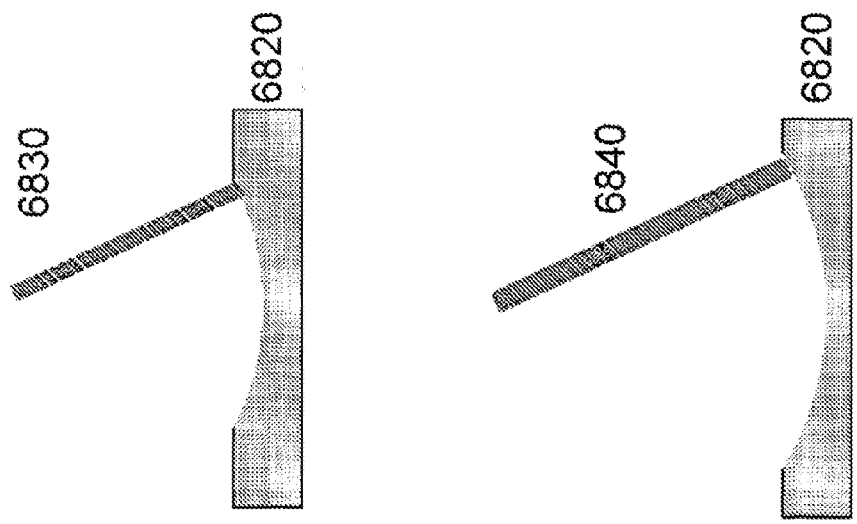
FIG. 68B shows a sagittal view of two exemplary tools sweeping from different distances into the polyethylene insert.
Figure 68A:
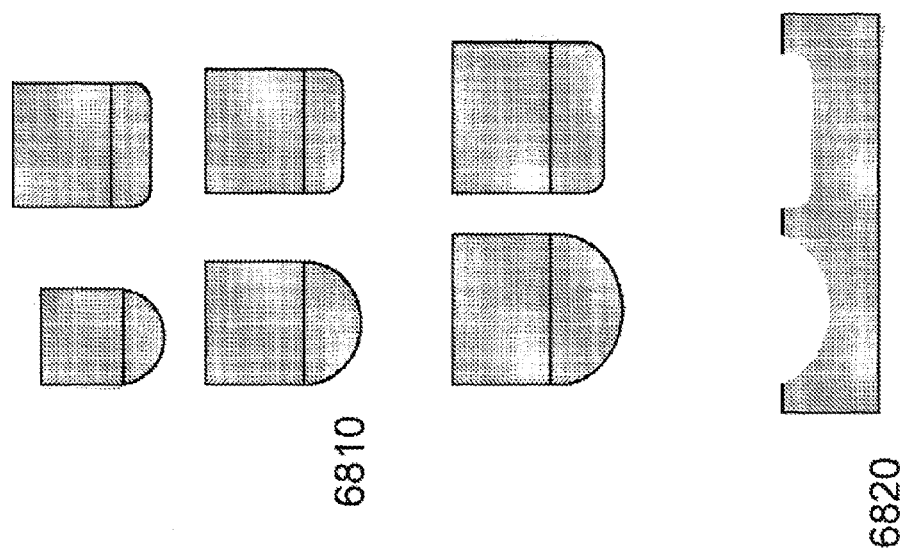
FIG. 68A shows six exemplary tool tips a polyethylene insert for a tibial implant component.

For example, a set of different-sized tools can be produced wherein each tool corresponds to one of the pre-selected standard coronal curvatures. The corresponding tool then can be used in the manufacture of a polyethylene insert of the tibial implant component, for example, to create a curvature in the polyethylene insert. FIG. 68A shows six exemplary tool tips 6810 and a polyethylene insert 6820 in cross-section in the coronal view. The size of the selected tool can be used to generate a polyethylene insert having the desired coronal curvature. In addition, FIG. 68A shows an exemplary polyethylene insert having two different coronal curvatures created by two different tool tips. The action of the selected tool on the polyethylene insert, for example, a sweeping arc motion by the tool at a fixed point above the insert, can be used to manufacture a standard or patient-specific sagittal curvature. FIG. 68B shows a sagittal view of two exemplary tools 6830, 6840 sweeping from different distances into the polyethylene insert 6820 of a tibial implant component to create different sagittal curvatures in the polyethylene insert 6820.

In certain embodiments, one or both of the tibial contact areas includes a concave groove having an increasing or decreasing radius along its sagittal axis, for example, a groove with a decreasing radius from anterior to posterior.

Figure 69A:
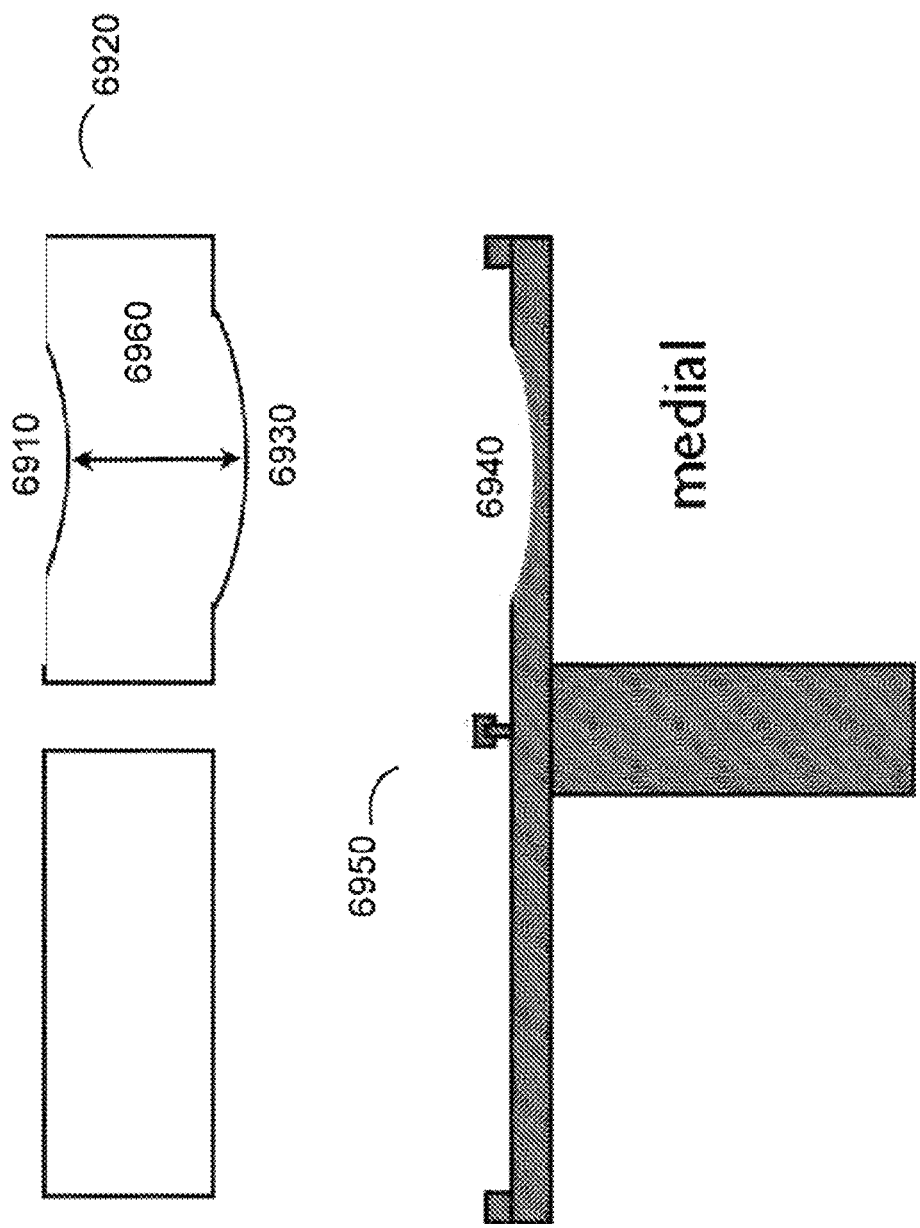
FIG. 69A shows an embodiment in which the shape of the concave groove on the medial side of the joint-facing surface of the tibial insert is matched by a convex shape on the opposing surface of the insert and by a concavity on the engaging surface of the tibial tray.
Figure 69B:
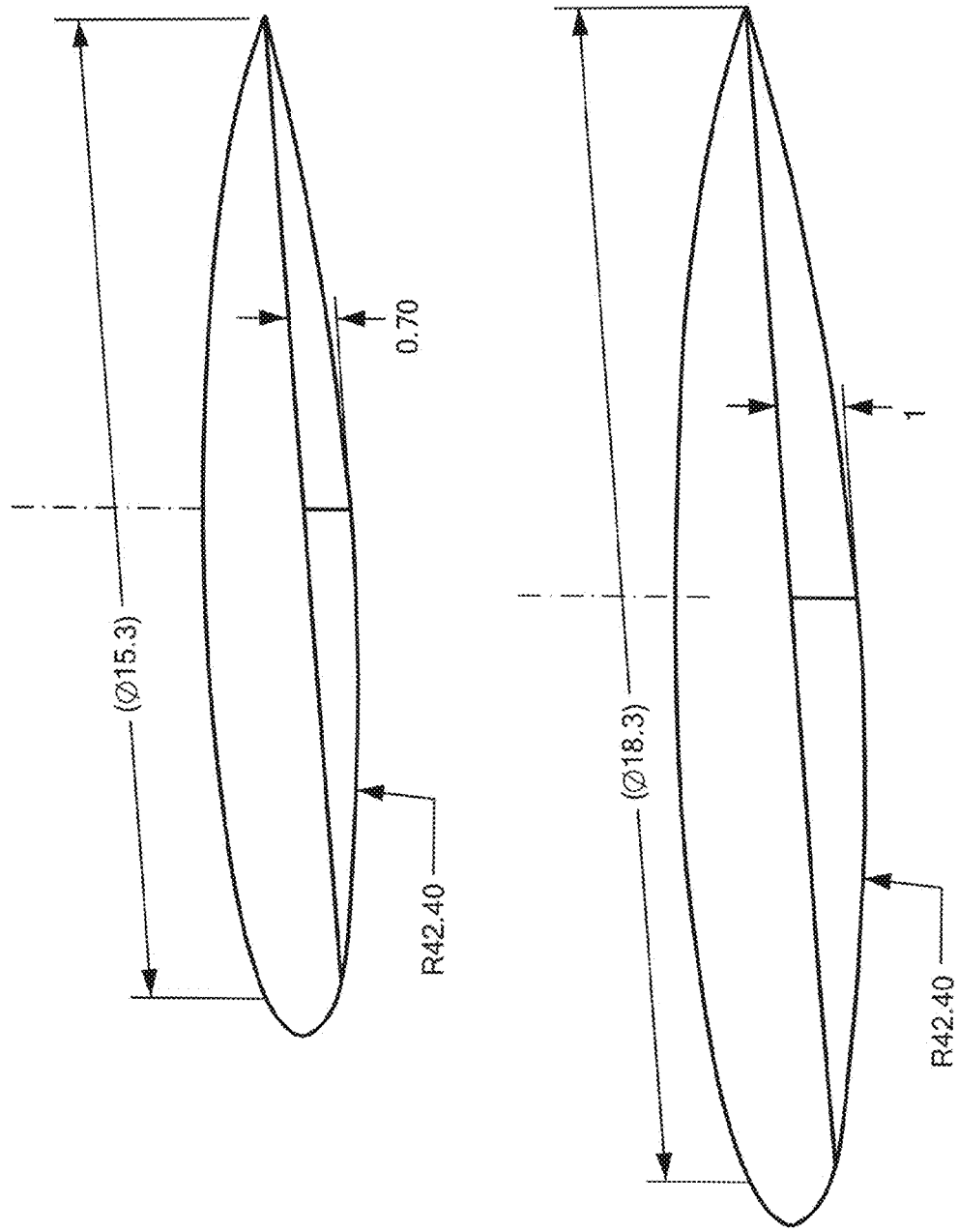
FIG. 69B illustrates two exemplary concavity dimensions for the bearing surface of a tibial implant component.

As shown in FIG. 69A, in certain embodiments the shape of the concave groove 6910 on the lateral and/or on the medial sides of the joint-facing surface of the tibial insert 6920 can be matched by a convex shape 6930 on the opposing side surface of the insert and, optionally, by a concavity 6940 on the engaging surface of the tibial tray 6950. This can allow the thickness of the component to remain constant 6960, even though the surfaces are not flat, and thereby can help maintain a minimum thickness of the material, for example, plastic material such as polyethylene. For example, an implant insert can maintain a constant material thickness (e.g., less than 5.5 mm, 5.5 mm, 5.6 mm, 5.7 mm, 5.8 mm, 5.9 mm, 6.0 mm, 6.1 mm, or greater than 6.1 mm) even though the insert includes a groove on the joint-facing surface. The constant material thickness can help to minimize overall minimum implant thickness while achieving or maintaining a certain mechanical strength (as compared to a thicker implant). The matched shape on the metal backing can serve the purpose of maintaining a minimum polyethylene thickness. It can, however, also include design features to provide a locking mechanism between the polyethylene or other insert and the metal backing. Such locking features can include ridges, edges, or an interference fit. In the case of an interference fit, the polyethylene can have slightly larger dimensions at the undersurface convexity than the matching concavity on the metal tray. This can be stabilized against rails or dove tail locking mechanisms in the center or the sides of the metal backing. Other design options are possible. For example, the polyethylene extension can have a saucer shape that can snap into a matching recess on the metal backing. In addition, as shown in FIG. 69A, any corresponding pieces of the component, such as a metal tray, also can include a matching groove to engage the curved surface of the plastic material. Two exemplary concavity dimensions are shown in FIG. 69B. As shown in the figure, the concavities or scallops have depths of 1.0 and 0.7 mm, based on a coronal geometry of R42.4 mm. At a 1.0 mm depth, the footprint width is 18.3 mm. At a 0.70 mm depth, the footprint width is 15.3 mm. These dimensions are only of exemplary nature. Many other configurations are possible.

Figure 70B:
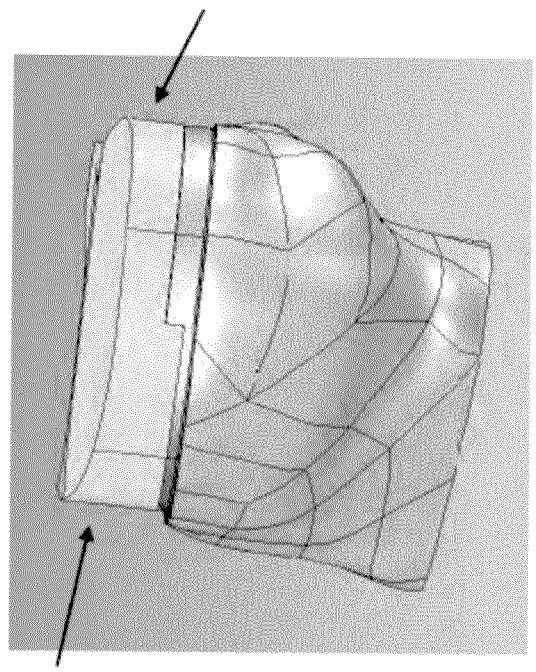
FIGS. 70A and 70B illustrate two embodiments of tibial implant components having slop[p]ed sagittal J-curves.
Figure 70A:
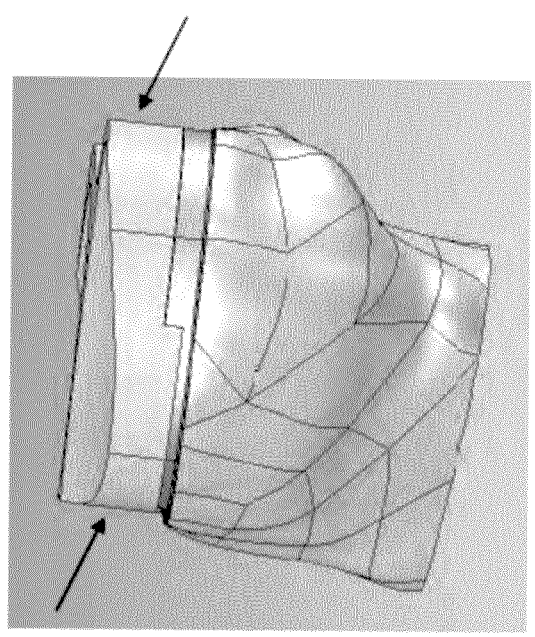

In certain embodiments, the sagittal curvature of the femoral component can be designed to be tilted, as suggested by FIGS. 70A and 70B. The corresponding curvature of the tibial surface can be tilted by that same slope, which can allow for thicker material on the corresponding tibial implant, for example, thicker poly at the anterior or posterior aspect of the tibial implant. The femoral component J-curve, and optionally the corresponding curvature for the tibial component, can be tilted by the same slope in both the medial and lateral condyles, just in the medial condyle or just in the lateral condyle or both independently or coupled. In certain embodiments, some additional material can be removed or the material thickness can be adapted from the posterior aspect of the femoral and/or tibial curvatures to allow for rotation.

In addition to the implant component features described above, certain embodiments can include features and designs for cruciate substitution. These features and designs can include, for example, a keel, post, or projection that projects from the bone-facing surface of the tibial implant component to engage on the corresponding an intercondylar housing, receptacle, or bars on the corresponding femoral implant component.

FIGS. 49A and 49B, 50A and 50B, 51, and 52A through 52P depict various features of intercondylar bars or in intercondylar housing for a cruciate-substituting femoral implant component. In addition, FIGS. 50A and 50B show a tibial implant component having a post or projection that can be used in conjunction with an intercondylar housing, receptacle, and/or bars on a femoral implant component as a substitute for a patient's PCL", which may be sacrificed during the implant procedure. Specifically, the post or projection on the tibial component engages the intercondylar housing, receptacle or bars on the femoral implant component to stabilize the joint during flexion, particular during high flexion.

FIGS. 71A and 71B depict exemplary cross-sections of tibial implant components having a post (or keel or projection) projecting from the bone-facing surface of the implant component. In particular, FIG. 71A shows (a) a tibial implant component with a straight post or projection and (b)-(d) tibial implant components having posts or projections oriented laterally, with varying thicknesses, lengths, and curvatures. FIG. 71B shows (a)-(e) tibial implant components having posts or projections oriented medially, with varying thicknesses, lengths, and curvatures.

As shown in the figures, the upper surface of the tray component has a "keel type" structure in between the concave surfaces that are configured to mate with the femoral condyle surfaces of a femoral implant. This "keel type" structure can be configured to slide within a groove in the femoral implant. The groove can comprise stopping mechanisms at each end of the groove to keep the "keel type" structure within the track of the groove. This "keel type" structure and groove arrangement may be used in situations where a patient's posterior cruciate ligament is removed as part of the surgical process and there is a need to posteriorly stabilize the implant within the joint.

In certain embodiments, the tibial implant component can be designed and manufactured to include the post or projection as a permanently integrated feature of the implant component. However, in certain embodiments, the post or projection can be modular. For example, the post or projection can be designed and/or manufactured separate from the tibial implant component and optionally joined with the component, either prior to (e.g., preoperatively) or during the implant procedure. For example, a modular post or projection and a tibial implant component can be mated using an integrating mechanism such as respective male and female screw threads, other male-type and female-type locking mechanisms, or other mechanism capable of integrating the post or projection into or onto the tibial implant component and providing stability to the post or projection during normal wear. A modular post or projection can be joined to a tibial implant component at the option of the surgeon or practitioner, for example, by removing a plug or other device that covers the integrating mechanism and attaching the modular post or projection at the uncovered integrating mechanism.

The post or projection can include features that are patient-adapted (e.g., patient-specific or patient-engineered). In certain embodiments, the post or projection includes one or more features that are designed and/or selected preoperatively, based on patient-specific data including imaging data, to substantially match one or more of the patient's biological features. For example, the length, width, height, and/or curvature of one or more portions of the post or projection can be designed and/or selected to be patient-specific, for example, with respect to the patient's intercondylar distance or depth, femoral shape, and/or condyle shape. Alternatively or in addition, one or more features of the post or projection can be engineered based on patient-specific data to provide to the patient an optimized fit. For example, the length, width, height, and/or curvature of one or more portions of the post or projection can be designed and/or selected to be patient-engineered. One or more thicknesses of the housing, receptacle, or bar can be matched to patient-specific measurements. One or more dimensions of the post or projection can be adapted based on one or more implant dimensions (e.g., one or more dimensions of the housing, receptacle or bar on the corresponding femoral implant component), which can be patient-specific, patient-engineered or standard. One or more dimensions of the post or projection can be adapted based on one or more of patient weight, height, sex, and body mass index. In addition, one or more features of the post or projection can be standard.

Optionally, referring to FIGS. 71A and 71B, an exemplary "keel type" structure or post can be adapted to the patient's anatomy. For example, the post can be shaped to enable a more normal, physiologic glide path of the femur relative to the tibia. Thus, the post can deviate medially or lateral as it extends from its base to its tip. This medial or lateral deviation can be designed to achieve a near physiologic rolling and rotating action of the knee joint. The medial and lateral bending of the post can be adapted based on patient specific imaging data. For example, the mediolateral curve or bend of the post or keel can be patient-derived or patient-matched (e.g., to match the physical or force direction of PCL or ACL). Alternatively or in addition, the post or keel can deviate at a particular AP angle or bend, for example, the sagittal curve of the post or keel can be reflection of PCL location and orientation or combinations of ACL and PCL location and orientation. The post can optionally taper or can have different diameters and cross-sectional profiles, e.g. round, elliptical, ovoid, square, rectangular at different heights from its base.

Different dimensions of the post or projection can be shaped, adapted, or selected based on different patient dimensions and implant dimensions. Examples of different technical implementations are provided in Table 14. These examples are in no way meant to be limiting. Someone skilled in the art will recognize other means of shaping, adapting or selecting a tibial implant post or projection based on the patient's geometry including imaging data.

TABLE 14

Examples of different technical implementations of a cruciate-sacrificing tibial implant component

| Post or projection feature | Corresponding patient anatomy, e.g., derived from imaging studies or intraoperative measurements |
|---|---|
| Mediolateral width | Maximum mediolateral width of patient intercondylar notch or fraction thereof |
| Mediolateral width | Average mediolateral width of intercondylar notch |
| Mediolateral width | Median mediolateral width of intercondylar notch |
| Mediolateral width | Mediolateral width of intercondylar notch in select regions, e.g. most inferior zone, most posterior zone, superior one third zone, mid zone, etc. |
| Superoinferior height | Maximum superoinferior height of patient intercondylar notch or fraction thereof |
| Superoinferior height | Average superoinferior height of intercondylar notch |
| Superoinferior height | Median superoinferior height of intercondylar notch |
| Superoinferior height | Superoinferior height of intercondylar notch in select regions, e.g. most medial zone, most lateral zone, central zone, etc. |
| Anteroposterior length | Maximum anteroposterior length of patient intercondylar notch or fraction thereof |
| Anteroposterior length | Average anteroposterior length of intercondylar notch |
| Anteroposterior length | Median anteroposterior length of intercondylar notch |
| Anteroposterior length | Anteroposterior length of intercondylar notch in select regions, e.g. most anterior zone, most posterior zone, central zone, anterior one third zone, posterior one third zone etc. |

The height or M-L width or A-P length of the intercondylar notch can not only influence the length but also the position or orientation of a post or projection from the tibial implant component.

The dimensions of the post or projection can be shaped, adapted, or selected not only based on different patient dimensions and implant dimensions, but also based on the intended implantation technique, for example, the intended tibial component slope or rotation and/or the intended femoral component flexion or rotation. For example, at least one of an anteroposterior length or superoinferior height can be adjusted if a tibial implant is intended to be implanted at a 7 degrees slope as compared to a 0 degrees slope, reflecting the relative change in patient or trochlear or intercondylar notch or femoral geometry when the tibial component is implanted. Moreover, at least one of an anteroposterior length or superoinferior height can be adjusted if the femoral implant is intended to be implanted in flexion, for example, in 7 degrees flexion as compared to 0 degrees flexion. The corresponding change in post or projection dimension can be designed or selected to reflect the relative change in patient or trochlear or intercondylar notch or femoral geometry when the femoral component is implanted in flexion.

In another example, the mediolateral width can be adjusted if one or both of the tibial and/or femoral implant components are intended to be implanted in internal or external rotation, reflecting, for example, an effective elongation of the intercondylar dimensions when a rotated implantation approach is chosen. Features of the post or projection can be oblique or curved to match corresponding features of the femoral component housing, receptacle or bar. For example, the superior portion of the post projection can be curved, reflecting a curvature in the roof of the femoral component housing, receptacle, or bar, which itself may reflect a curvature of the intercondylar roof. In another example, a side of a post or projection may be oblique to reflect an obliquity of a side wall of the housing or receptacle of the femoral component, which itself may reflect an obliquity of one or more condylar walls. Accordingly, an obliquity or curvature of a post or projection can be adapted based on at least one of a patient dimension or a femoral implant dimension. Alternatively, the post or projection of the tibial implant component can be designed and/or selected based on generic or patient-derived or patient-desired or implant-desired kinematics in one, two, three or more dimensions. Then, the corresponding surface(s) of the femoral implant housing or receptacle can be designed and/or selected to mate with the tibial post or projection, e.g., in the ML plane. Alternatively, the post or projection of the femoral receptacle or box or bar or housing can be designed and/or selected based on generic or patient-derived or patient-desired or implant-desired kinematics in one, two, three or more dimensions. Then, the corresponding surface(s) of the post or projection of the tibial implant can be designed and/or selected to mate with the tibial post or projection, e.g., in the ML plane.

The tibial post or projection can be straight. Alternatively, the tibial post or projection can have a curvature or obliquity in one, two or three dimensions, which can optionally be, at least in part, reflected in the internal shape of the box. One or more tibial projection or post dimensions can be matched to, designed to, adapted to, or selected based on one or more patient dimensions or measurements. Any combination of planar and curved surfaces is possible.

In certain embodiments, the position and/or dimensions of the tibial implant component post or projection can be adapted based on patient-specific dimensions. For example, the post or projection can be matched with the position of the posterior cruciate ligament or the PCL insertion. It can be placed at a predefined distance from anterior or posterior cruciate ligament or ligament insertion, from the medial or lateral tibial spines or other bony or cartilaginous landmarks or sites. By matching the position of the post with the patient's anatomy, it is possible to achieve a better functional result, better replicating the patient's original anatomy.

The tray component can be machined, molded, casted, manufactured through additive techniques such as laser sintering or electron beam melting or otherwise constructed out of a metal or metal alloy such as cobalt chromium. Similarly, the insert component may be machined, molded, manufactured through rapid prototyping or additive techniques or otherwise constructed out of a plastic polymer such as ultra high molecular weight polyethylene. Other known materials, such as ceramics including ceramic coating, may be used as well, for one or both components, or in combination with the metal, metal alloy and polymer described above. It should be appreciated by those of skill in the art that an implant may be constructed as one piece out of any of the above, or other, materials, or in multiple pieces out of a combination of materials. For example, a tray component constructed of a polymer with a two-piece insert component constructed one piece out of a metal alloy and the other piece constructed out of ceramic.

Each of the components may be constructed as a "standard" or "blank" in various sizes or may be specifically formed for each patient based on their imaging data and anatomy. Computer modeling may be used and a library of virtual standards may be created for each of the components. A library of physical standards may also be amassed for each of the components.

Imaging data including shape, geometry, e.g., M-L, A-P, and S-I dimensions, then can be used to select the standard component, e.g., a femoral component or a tibial component or a humeral component and a glenoid component that most closely approximates the select features of the patient's anatomy. Typically, these components will be selected so that they are slightly larger than the patient's articular structure that will be replaced in at least one or more dimensions. The standard component is then adapted to the patient's unique anatomy, for example by removing overhanging material, e.g. using machining.

Figure 72B:
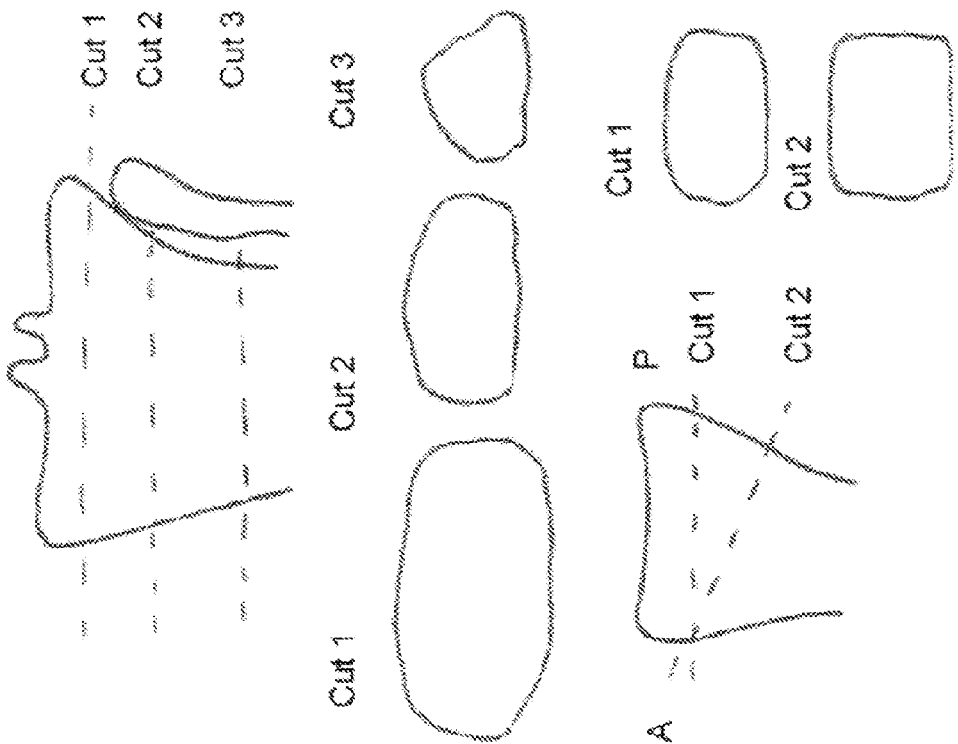
FIG. 72B illustrates various tibial cuts and corresponding surface features.
Figure 72A:
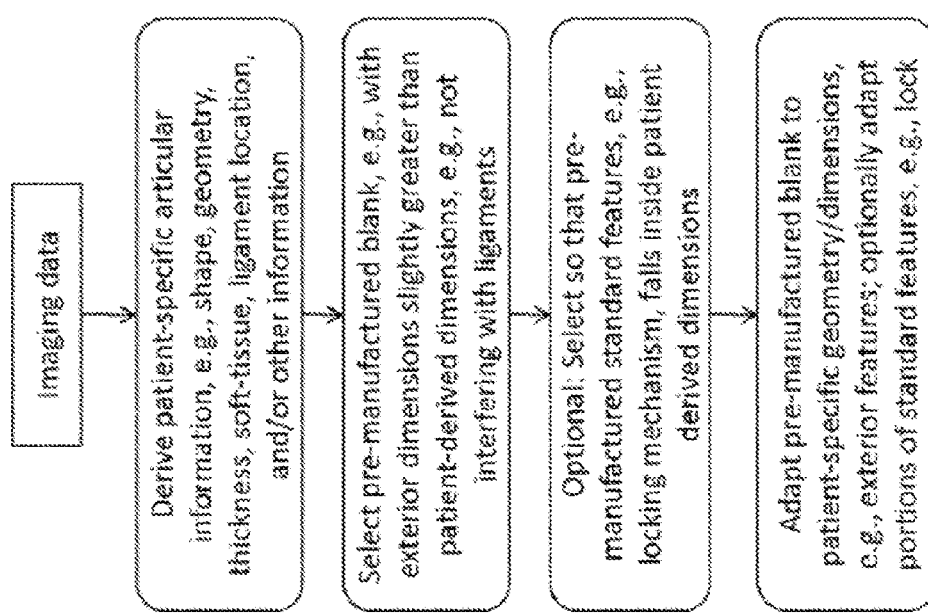
FIG. 72A is a flow chart for adapting a blank implant component for a particular patient.

Thus, referring to the flow chart shown in FIG. 72A, in a first step, the imaging data will be analyzed, either manually or with computer assistance, to determine the patient specific parameters relevant for placing the implant component. These parameters can include patient specific articular dimensions and geometry and also information about ligament location, size, and orientation, as well as potential soft-tissue impingement, and, optionally, kinematic information.

In a second step, one or more standard components, e.g., a femoral component or a tibial component or tibial insert, are selected. These are selected so that they are at least slightly greater than one or more of the derived patient specific articular dimensions and so that they can be shaped to the patient specific articular dimensions. Alternatively, these are selected so that they will not interfere with any adjacent soft-tissue structures. Combinations of both are possible.

If an implant component is used that includes an insert, e.g., a polyethylene insert and a locking mechanism in a metal or ceramic base, the locking mechanism can be adapted to the patient's specific anatomy in at least one or more dimensions. The locking mechanism can also be patient adapted in all dimensions. The location of locking features can be patient adapted while the locking feature dimensions, for example between a femoral component and a tibial component, can be fixed. Alternatively, the locking mechanism can be pre-fabricated; in this embodiment, the location and dimensions of the locking mechanism will also be considered in the selection of the pre-fabricated components, so that any adaptations to the metal or ceramic backing relative to the patient's articular anatomy do not compromise the locking mechanism. Thus, the components can be selected so that after adaptation to the patient's unique anatomy a minimum material thickness of the metal or ceramic backing will be maintained adjacent to the locking mechanism.

Since the tibia has the shape of a champagne glass, i.e., since it tapers distally from the knee joint space down, moving the tibial cut distally will result in a smaller resultant cross-section of the cut tibial plateau, e.g., the ML and/or AP dimension of the cut tibia will be smaller. For example, referring to FIG. 72B, increasing the slope of the cut will result in an elongation of the AP dimension of the cut surface—requiring a resultant elongation of a patient matched tibial component. Thus, in one embodiment it is possible to select an optimal standard, pre-made tibial blank for a given resection height and/or slope. This selection can involve (1) patient-adapted metal with a standard poly insert; or (2) metal and poly insert, wherein both are adapted to patient anatomy. The metal can be selected so that based on cut tibial dimensions there is always a certain minimum metal perimeter (in one, two or three dimensions) guaranteed after patient adaptation so that a lock mechanism will not fail. Optionally, one can determine minimal metal perimeter based on finite element modeling (FEA) (once during initial design of standard lock features, or patient specific every time e.g. via patient specific FEA modeling).

The tibial tray can be selected (or a metal base for other joints) to optimize percent cortical bone coverage at resection level. This selection can be (1) based on one dimension, e.g., ML; (2) based on two dimensions, e.g. ML and AP; and/or (3) based on three dimensions, e.g., ML, AP, SI or slope.

The selection can be performed to achieve a target percentage coverage of the resected bone (e.g. area) or cortical edge or margin at the resection level (e.g. AP, ML, perimeter), e.g. 85%, 90%, 95%, 98% or 100%. Optionally, a smoothing function can be applied to the derived contour of the patient's resected bone or the resultant selected, designed or adapted implant contour so that the implant does not extend into all irregularities or crevaces of the virtually and then later surgically cut bone perimeter.

Optionally, a function can be included for deriving the desired implant shape that allows changing the tibial implant perimeter if the implant overhangs the cortical edge in a convex outer contour portion or in a concave outer contour portion (e.g. "crevace"). These changes can subsequently be included in the implant shape, e.g. by machining select features into the outer perimeter.

Those of skill in the art will appreciate that a combination of standard and customized components may be used in conjunction with each other. For example, a standard tray component may be used with an insert component that has been individually constructed for a specific patient based on the patient's anatomy and joint information.

Another embodiment incorporates a tray component with one half of a two-piece insert component integrally formed with the tray component, leaving only one half of the two-piece insert to be inserted during surgery. For example, the tray component and medial side of the insert component may be integrally formed, with the lateral side of the insert component remaining to be inserted into the tray component during surgery. Of course, the reverse could also be used, wherein the lateral side of the insert component is integrally formed with the tray component leaving the medial side of the insert component for insertion during surgery.

Each of these alternatives results in a tray component and an insert component shaped so that once combined, they create a uniformly shaped implant matching the geometries of the patient's specific joint.

The above embodiments are applicable to all joints of a body, e.g., ankle, foot, elbow, hand, wrist, shoulder, hip, spine, or other joint.

For example, in a hip, an acetabular component can be designed or selected or adapted so that its peripheral margin will be closely matched to the patient patient specific acetabular rim or perimeter. Optionally, reaming can be simulated for placement of an acetabular cup and the implant can then be designed or selected or adapted so that it will be closely matched to the resultant acetabular rim after reaming. Thus, the exterior dimensions of the implant can be matched to the patient's geometry in this fashion. Optionally, standard, round dimensions of a polyethylene insert can be used with this embodiment. Similarly, a glenoid component can be matched to the glenoid rim, optionally after surgically preparing or resectioning all or portions of the glenoid rim. Thus, edge matching, designing, selecting or adapting implants including, optionally lock features, can be performed for implants used in any joint of the body.

An implant component can include a fixed bearing design or a mobile bearing design. With a fixed bearing design, a platform of the implant component is fixed and does not rotate. However, with a mobile bearing design, the platform of the implant component is designed to rotate e.g., in response to the dynamic forces and stresses on the joint during motion.

A rotating platform mobile bearing on the tibial implant component allows the implant to adjust and accommodate in an additional dimension during joint motion. However, the additional degree of motion can contribute to soft tissue impingement and dislocation. Mobile bearings are described elsewhere, for example, in U.S. Patent Application Publication No. 2007/0100462.

In certain embodiments, an implant can include a mobile-bearing implant that includes one or more patient-specific features, one or more patient-engineered features, and/or one or more standard features. For example, for a knee implant, the knee implant can include a femoral implant component having a patient-specific femoral intercondylar distance; a tibial component having standard mobile bearing and a patient-engineered perimeter based on the dimensions of the perimeter of the patient's cut tibia and allowing for rotation without significant extension beyond the perimeter of the patient's cut tibia; and a tibial insert or top surface that is patient-specific for at least the patient's intercondylar distance between the tibial insert dishes to accommodate the patient-specific femoral intercondylar distance of the femoral implant.

As another example, in certain embodiments a knee implant can include a femoral implant component that is patient-specific with respect to a particular patient's M-L dimension and standard with respect to the patient's femoral intercondylar distance; a tibial component having a standard mobile bearing and a patient-engineered perimeter based on the dimensions of the perimeter of the patient's cut tibia and allowing for rotation without significant extension beyond the perimeter of the patient's cut tibia; and a tibial insert or top surface that includes a standard intercondylar distance between the tibial insert dishes to accommodate the standard femoral intercondylar distance of the femoral implant.

7. Optimizing Soft-Tissue Tension, Ligament Tension, Balancing, Flexion and Extension Gap The surgeon can, optionally, make adjustments of implant position and/or orientation such as rotation, bone cuts, cut height and selected component thickness, insert thickness or selected component shape or insert shape. In this manner, an optimal compromise can be found, for example, between biomechanical alignment and joint laxity or biomechanical alignment and joint function, e.g., in a knee joint flexion gap and extension gap. Thus, multiple approaches exist for optimizing soft-tissue tension, ligament tension, ligament balance, and/or flexion and extension gap. These include, for example, one or more of the exemplary options described in Table 15.

TABLE 15

Exemplary approach options for optimizing soft-tissue tension, ligament tension, ligament balance, and/or flexion and extension gap

| Option # | Description of Exemplary Option |
| --- | --- |
| 1 | Position of one or more femoral bone cuts |
| 2 | Orientation of one or more femoral bone cuts |
| 3 | Location of femoral component |
| 4 | Orientation of femoral component, including rotational alignment in axial, sagittal and coronal direction |
| 5 | Position of one or more tibial bone cuts |
| 6 | Orientation of one or more tibial bone cuts including sagittal slope, mediolateral orientation |
| 7 | Location of tibial component |
| 8 | Orientation of tibial component, including rotational alignment in axial, sagittal and coronal direction |
| 9 | Tibial component height |
| 10 | Medial tibial insert or component or composite height |
| 11 | Lateral tibial insert or component or composite height |
| 12 | Tibial component profile, e.g., convexity, concavity, trough, radii of curvature |
| 13 | Medial tibial insert or component or composite profile, e.g. convexity, concavity, trough, radii of curvature |
| 14 | Lateral tibial insert or component or composite profile, e.g. convexity, concavity, trough, radii of curvature |
| 15 | Select soft-tissue releases, e.g. partial or full releases of retinacula and/or ligaments, "pie-crusting" etc. |

Any one option described in Table 15 can be optimized alone or in combination with one or more other options identified in the table and/or known in the art for achieving different flexion and extension, abduction, or adduction, internal and external positions and different kinematic requirements.

In one embodiment, the surgeon can initially optimize the femoral and tibial resections. Optimization can be performed by measuring soft-tissue tension or ligament tension or balance for different flexion and extension angles or other joint positions before any bone has been resected, once a first bone resection on a first articular surface has been made and after a second bone resection on a first or second articular surface has been made, such as a femur and a tibia, humerus and a glenoid, femur and an acetabulum.

The position and orientation between a first implant component and a second, opposing implant component or a first articular surface and a trial implant or a first trial implant and a second trial implant or an alignment guide and an instrument guide and any combinations thereof can be optimized with the use of, for example, interposed spacers, wedges, screws and other mechanical or electrical methods known in the art. A surgeon may desire to influence joint laxity as well as joint alignment. This can be optimized for different flexion and extension, abduction, or adduction, internal and external rotation angles. For this purpose, spacers can be introduced at or between one or more steps in the implant procedure. One or more of the spacers can be attached or in contact with one or more instruments, trials or, optionally, patient-specific molds. The surgeon can intraoperatively evaluate the laxity or tightness of a joint using spacers with different thicknesses or one or more spacers with the same thickness. For example, spacers can be applied in a knee joint in the presence of one or more trials or instruments or patient-specific molds and the flexion gap can be evaluated with the knee joint in flexion. The knee joint can then be extended and the extension gap can be evaluated. Ultimately, the surgeon selects for a given joint an optimal combination of spacers and trial or instrument or patient-specific mold. A surgical cut guide can be applied to the trial or instrument or patient-specific mold with the spacers optionally interposed between the trial or instrument or patient-specific mold and the cut guide. In this manner, the exact position of the surgical cuts can be influenced and can be adjusted to achieve an optimal result. Someone skilled in the art will recognize other means for optimizing the position of the surgical cuts. For example, expandable or ratchet-like devices can be utilized that can be inserted into the joint or that can be attached or that can touch the trial or instrument or patient-specific mold. Hinge-like mechanisms are applicable. Similarly, jack-like mechanisms are useful. In principal, any mechanical or electrical device useful for fine tuning the position of a cut guide relative to a trial or instrument or patient-specific mold can be used.

A surgeon may desire to influence joint laxity as well as joint alignment. This can be optimized for different flexion and extension, abduction, or adduction, internal and external rotation angles. For this purpose, for example, spacers can be introduced that are attached or that are in contact with one or more trials or instruments or patient-specific molds. The surgeon can intraoperatively evaluate the laxity or tightness of a joint using spacers with different thickness or one or more spacers with the same thickness. For example, spacers can be applied in a knee joint in the presence of one or more instruments or trials or molds and the flexion gap can be evaluated with the knee joint in flexion. Different thickness trials can be used. The terms spacer or insert can be used interchangeably with the term trial.

In certain embodiments, the surgeon can elect to insert different trials or spacers or instruments of different thicknesses in the medial and/or lateral joint space in a knee. This can be done before any bone has been resected, once a first bone resection on a first articular surface has been made and after a second bone resection on a first or second articular surface has been made, such as a femur and a tibia or a medial and a lateral condyle or a medial and a lateral tibia. The joint can be tested for soft-tissue tension, ligament tension, ligament balance and/or flexion or extension gap for different orientations or kinematic requirements using different medial and lateral trial or spacer thicknesses, e.g., at different flexion and extension angles. Surgical bone cuts can subsequently optionally be adapted or changed. Alternatively, different medial and lateral insert thickness or profiles or composite heights can be selected for the tibial component(s). For example, combinations of medial and lateral spacers or trials having thicknesses described in Table 16 can be inserted.

TABLE 16

Exemplary medial and lateral spacer, trial, and/or insert heights that can be used in combination

| Medial spacer, trial, and/or insert height | Lateral spacer, trial, and/or insert height | Note |
|---|---|---|
| 6 mm | 6 mm | Same medial and lateral spacer, trial, and/or insert height |
| 7 mm | 7 mm | |
| 8 mm | 8 mm | |
| 9 mm | 9 mm | |
| 10 mm | 10 mm | |
| 11 mm | 11 mm | |
| 12 mm | 12 mm | |
| 13 mm | 13 mm | |
| 14 mm | 14 mm | |
| 15 mm | 15 mm | |
| 16 mm | 16 mm | |
| 6 mm | 7 mm | Different medial and lateral spacer, trial, and/or insert (6 mm medial spacer, trial, and/or insert height with various lateral spacer, trial, and/or insert heights) |
| 6 mm | 8 mm | |
| 6 mm | 9 mm | |
| 6 mm | 10 mm | |
| 6 mm | 11 mm | |
| 6 mm | 12 mm | |
| 6 mm | 13 mm | |
| 6 mm | 14 mm | |
| 6 mm | 15 mm | |
| 6 mm | 16 mm | |
| 7 mm | 6 mm | Different medial and lateral spacer, trial, and/or insert height (7 mm medial spacer, trial, and/or insert height with various lateral spacer, trial, and/or insert heights) |
| 7 mm | 8 mm | |
| 7 mm | 9 mm | |
| 7 mm | 10 mm | |

TABLE 16-continued

Exemplary medial and lateral spacer, trial, and/or insert heights that can be used in combination

| Medial spacer, trial, and/or insert height | Lateral spacer, trial, and/or insert height | Note |
|---|---|---|
| 7 mm | 11 mm | |
| 7 mm | 12 mm | |
| 7 mm | 13 mm | |
| 7 mm | 14 mm | |
| 7 mm | 15 mm | |
| 7 mm | 16 mm | |
| 8 mm | 6 mm | Different medial and lateral spacer, trial, and/or insert height (8 mm medial spacer, trial, and/or insert height with various lateral spacer, trial, and/or insert heights) |
| 8 mm | 7 mm | |
| 8 mm | 9 mm | |
| 8 mm | 10 mm | |
| 8 mm | 11 mm | |
| 8 mm | 12 mm | |
| 8 mm | 13 mm | |
| 8 mm | 14 mm | |
| 8 mm | 15 mm | |
| 8 mm | 16 mm | |
| 9 mm | 6 mm | Different medial and lateral spacer, trial, and/or insert height (9 mm medial spacer, trial, and/or insert height with various lateral spacer, trial, and/or insert heights) |
| 9 mm | 7 mm | |
| 9 mm | 8 mm | |
| 9 mm | 10 mm | |
| 9 mm | 11 mm | |
| 9 mm | 12 mm | |
| 9 mm | 13 mm | |
| 9 mm | 14 mm | |
| 9 mm | 15 mm | |
| 9 mm | 16 mm | |
| 10 mm | 6 mm | Different medial and lateral spacer, trial, and/or insert height (10 mm medial spacer, trial, and/or insert height with various lateral spacer, trial, and/or insert heights) |
| 10 mm | 7 mm | |
| 10 mm | 8 mm | |
| 10 mm | 9 mm | |
| 10 mm | 11 mm | |
| 10 mm | 12 mm | |
| 10 mm | 13 mm | |
| 10 mm | 14 mm | |
| 10 mm | 15 mm | |
| 10 mm | 16 mm | |
| 11 mm | 6 mm | Different medial and lateral spacer, trial, and/or insert height (11 mm medial spacer, trial, and/or insert height with various lateral spacer, trial, and/or insert heights) |
| 11 mm | 7 mm | |
| 11 mm | 8 mm | |
| 11 mm | 9 mm | |
| 11 mm | 10 mm | |
| 11 mm | 12 mm | |
| 11 mm | 13 mm | |
| 11 mm | 14 mm | |
| 11 mm | 15 mm | |
| 11 mm | 16 mm | |
| 12 mm | 6 mm | Different medial and lateral spacer, trial, and/or insert height (12 mm medial spacer, trial, and/or insert height with various lateral spacer, trial, and/or insert heights) |
| 12 mm | 7 mm | |
| 12 mm | 8 mm | |
| 12 mm | 9 mm | |
| 12 mm | 10 mm | |
| 12 mm | 11 mm | |
| 12 mm | 13 mm | |
| 12 mm | 14 mm | |
| 12 mm | 15 mm | |
| 12 mm | 16 mm | |
| 13 mm | 6 mm | Different medial and lateral spacer, trial, and/or insert height (13 mm medial spacer, trial, and/or insert height with various lateral spacer, trial, and/or insert heights) |
| 13 mm | 7 mm | |
| 13 mm | 8 mm | |
| 13 mm | 9 mm | |
| 13 mm | 10 mm | |
| 13 mm | 11 mm | |
| 13 mm | 12 mm | |
| 13 mm | 14 mm | |
| 13 mm | 15 mm | |
| 13 mm | 16 mm | |
| 14 mm | 6 mm | Different medial and lateral spacer, trial, and/or insert height (14 mm medial spacer, trial, and/or insert height with various lateral spacer, trial, and/or insert heights) |
| 14 mm | 7 mm | |
| 14 mm | 8 mm | |
| 14 mm | 9 mm | |
| 14 mm | 10 mm | |
| 14 mm | 11 mm | |
| 14 mm | 12 mm | |

TABLE 16-continued

Exemplary medial and lateral spacer, trial, and/or insert heights that can be used in combination

| Medial spacer, trial, and/or insert height | Lateral spacer, trial, and/or insert height | Note |
|---|---|---|
| 14 mm | 13 mm | |
| 14 mm | 15 mm | |
| 14 mm | 16 mm | |
| 15 mm | 6 mm | Different medial and lateral spacer, trial, and/or insert height (15 mm medial spacer, trial, and/or insert height with various lateral spacer, trial, and/or insert heights) |
| 15 mm | 7 mm | |
| 15 mm | 8 mm | |
| 15 mm | 9 mm | |
| 15 mm | 10 mm | |
| 15 mm | 11 mm | |
| 15 mm | 12 mm | |
| 15 mm | 13 mm | |
| 15 mm | 14 mm | |
| 15 mm | 16 mm | |
| 16 mm | 6 mm | Different medial and lateral spacer, trial, and/or insert height (16 mm medial spacer, trial, and/or insert height with various lateral spacer, trial, and/or insert heights) |
| 16 mm | 7 mm | |
| 16 mm | 8 mm | |
| 16 mm | 9 mm | |
| 16 mm | 10 mm | |
| 16 mm | 11 mm | |
| 16 mm | 12 mm | |
| 16 mm | 13 mm | |
| 16 mm | 14 mm | |
| 16 mm | 15 mm | |

Thus, by using separate medial and/or lateral spacers or trials or inserts, it is possible to determine an optimized combination of medial or lateral tibial components, for example with regard to medial and lateral composite thickness, insert thickness or medial and lateral implant or insert profile. Thus, medial and/or lateral tibial implant or component or insert thickness can be optimized for a desired soft-tissue or ligament tension or ligament balance for different flexion and extension angles and other joint poses. This offers a unique benefit beyond traditional balancing using bone cuts and soft-tissue releases. In one embodiment, the surgeon can place the tibial and femoral surgical bone cuts and perform the proper soft-tissue or ligament tensioning or balancing entirely via selection of a medial or lateral tibial insert or composite thickness and/or profile. Additional adaptation and optimization of bone cuts and soft-tissue releases is possible.

FIGS. 73A through 75C show various exemplary spacers or trials or inserts for adjusting and optimizing alignment, tension, balance, and position (e.g., as described in Table 15 above) during a knee implant surgery. In particular, FIG. 73A depicts a medial balancer chip insert from top view to show the superior surface of the chip. FIG. 73B depicts a side view of a set of four medial balancer chip inserts that incrementally increase in thickness by 1 mm. A corresponding set of lateral balancing chip inserts (having a range of thicknesses) can be used in conjunction with a set of medial balancing chip inserts. In this way, the joint can be optimized using independent medial and lateral balancing chips inserts having different thicknesses. As indicated with the first chip in the figure, the superior surface 7302 of a balancing chip insert engages the femur and the inferior surface 7304 engages the tibia. In certain embodiments, one or both of the superior surface 7302 and/or the inferior surface 7304 can be patient-adapted to fit the particular patient. In certain embodiments, a balancing chip can include a resection surface to guide a subsequent surgical bone cut.

FIG. 73C depicts a medial balancing chip being inserted in flexion between the femur and tibia. FIG. 73D depicts the medial balancing chip insert in place while the knee is brought into extension. Optionally, a lateral balancing chip also can be placed between the lateral portions of the femur and tibia. Medial and lateral balancing chips having different thicknesses can be placed as shown in FIGS. 73C and 73D, until a desired tension is observed medially and laterally throughout the patient's range of motion. As shown in FIG. 73E, in certain embodiments, a cutting guide can be attached to the medial balancing chip insert, to the lateral balancing chip insert, or to both, so that the resection cuts are made based on the selected medial and lateral balancing chip inserts. Optionally, one or more surfaces of one or both balancing chips also can act as a cutting guide. As shown in FIG. 73F, the inferior surface of the medial balancing chip can act as cutting guide surface for resectioning the medial portion of the tibia.

Figure 74C:
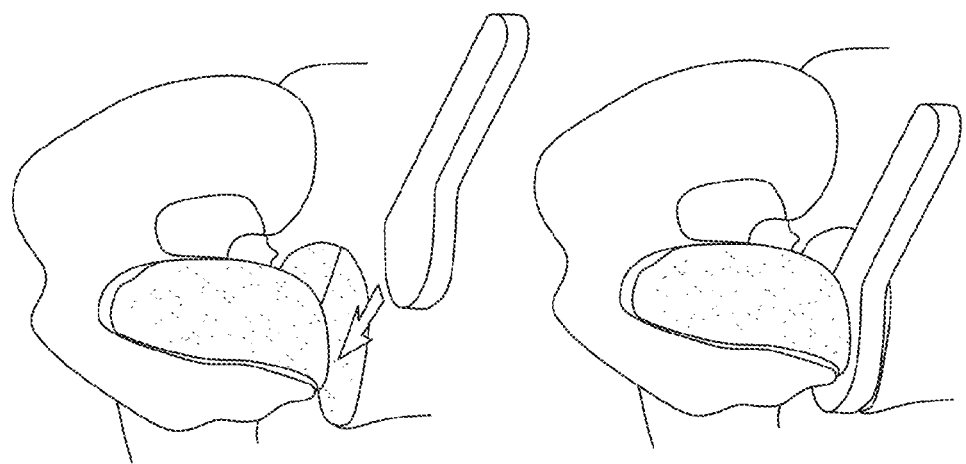
FIG. 74C depicts a medial femoral trial in place and a spacer block being inserted to evaluate the balance of the knee in flexion and extension.
Figure 74B:
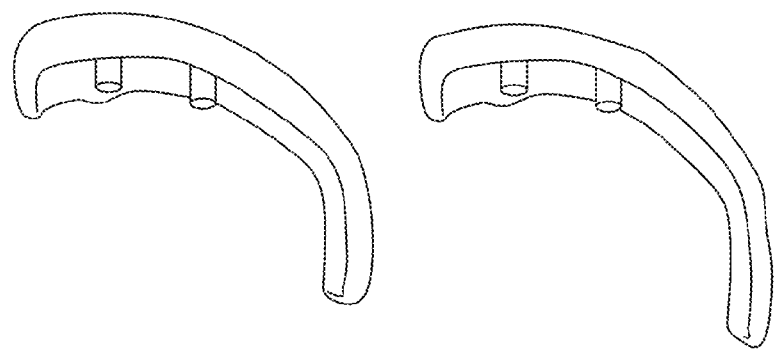
FIG. 74B depicts a set of two medial femoral trials having incrementally increasing thicknesses.
Figure 74A:
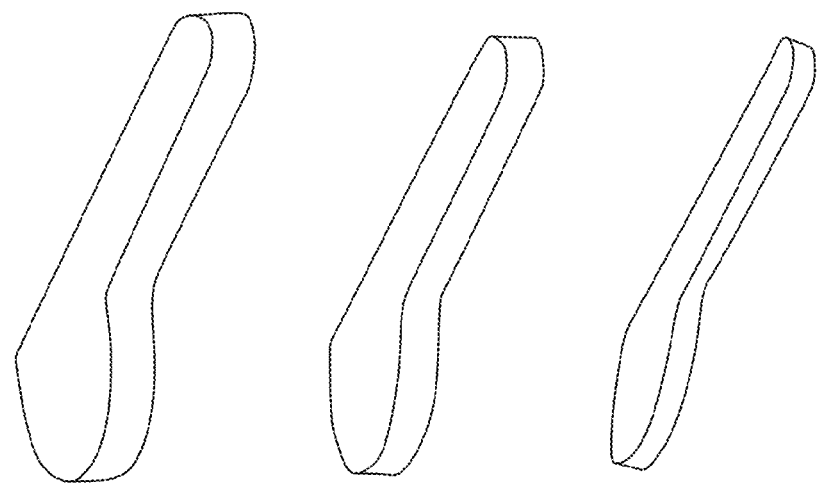
FIG. 74A depicts a set of three medial spacer block inserts having incrementally increasing thicknesses.

FIG. 74A depicts a set of three medial spacer block inserts having incrementally increasing thicknesses, for example, thicknesses that increase by 1 mm, by 1.5 mm, or by 2 mm. A corresponding set of lateral medial spacer block inserts (having a range of thicknesses) can be used in conjunction with a set of medial spacer block inserts. A spacer block insert can be used, for example, to provide the thickness of a tibial implant component (optionally with or without the additional thickness of a tibial implant component insert) during subsequent implantation steps and prior to placement of the tibial implant component. In certain embodiments, the spacer block insert can include a portion for attaching a trial a tibial implant component insert, so that the precise thicknesses of different combinations of tibial implant components and component inserts can be assessed. By using medial and lateral spacer block inserts of different thicknesses, the balancing, tensioning, alignment, and/or positioning of the joint can continue to be optimized throughout the implantation procedure. In certain embodiments, one or more features of a spacer block insert can be patient-adapted to fit the particular patient. In certain embodiments, a spacer block insert can include a feature for attaching or stabilizing a cutting guide and/or a feature for guiding a cutting tool.

FIG. 74B depicts a set of two medial femoral trials having incrementally increasing thicknesses, for example, thicknesses that increase by 1 mm, by 1.5 mm, or by 2 mm. A corresponding set of lateral femoral trials (having a range of thicknesses) can be used in conjunction with the set of medial femoral trials. A femoral trial can be used, for example, to test variable thicknesses and/or features of a femoral implant component during implantation steps prior to placement of the tibial implant component. By using medial and lateral femoral trials of different thicknesses, the balancing, tensioning, alignment, and/or positioning of the joint can continue to be optimized throughout the implantation procedure. In certain embodiments, one or more features of a femoral trial can be patient-adapted to fit the particular patient. In certain embodiments, a femoral trial can include a feature for attaching or stabilizing a cutting guide and/or a feature for guiding a cutting tool.

FIG. 74C depicts a medial femoral trial in place and a spacer block being inserted to evaluate the balance of the knee in flexion and extension. Spacer blocks having different thicknesses can be inserted and evaluated until an optimized thickness is identified. Optionally, a lateral femoral trial also can be placed between the lateral portions of the femur and tibia and a lateral spacer block inserted and evaluated along with the medial spacer block. Medial and lateral spacer blocks having different thicknesses can be placed and removed until a desired tension is observed medially and laterally throughout the patient's range of motion. Then, a tibial implant component and/or tibial implant component insert can be selected to have a thickness based on the thickness identified by evaluation using the femoral trial and spacer block. In this way, the selected medial a tibial implant component (and/or tibial implant component insert) and the lateral tibial implant component (and/or tibial implant component insert) can have different thicknesses.

FIG. 75A depicts a set of three medial tibial component insert trials having incrementally increasing thicknesses, for example, thicknesses that increase by 0.5 mm, by 1 mm, by 1.5 mm, or by 2 mm. A corresponding set of lateral tibial component insert trials (having a range of thicknesses) can be used in conjunction with the set of medial tibial component insert trials. A tibial component insert trial can be used, for example, to determine the best insert thickness and/or features of a tibial component insert during the final implantation steps. By using medial and lateral tibial component insert trials of different thicknesses and/or configurations, the balancing, tensioning, alignment, and/or positioning of the joint can be optimized even in the final steps of the procedure. In certain embodiments, one or more features of a tibial component insert trial can be patient-adapted to fit the particular patient. FIG. 75B depicts the process of placing and adding various tibial component insert trials and FIG. 75C depicts the process of placing the selected tibial component insert.

The sets of exemplary spacers, trials, and inserts described in connection with FIGS. 73A through 75C can be expanded to include spacers, trials, and/or inserts having various intermediate thicknesses (e.g., in increments of 0.5 mm, 0.25 mm, and/or 0.1 mm) and/or having various other selection features. For example, sets of femoral and/or tibial insert trials can include different bone-facing and/or joint-facing surfaces from which the surgeon can select the optimum available surface for further steps in the procedure.

Using the various spacers, trials, and inserts described above, the knee joint can be flexed and the flexion gap can be evaluated. In addition, the knee can be extended and the extension gap can be evaluated. Ultimately, the surgeon will select an optimal combination of spacers or trials for a given joint, instrument, trial or mold. A surgical cut guide can be applied to the trial, instrument, or mold with the spacers optionally interposed between the trial, instrument or mold and the cut guide. In this manner, the exact position of the surgical cuts can be influenced and can be adjusted to achieve an optimal result. Someone skilled in the art will recognize other means for optimizing the position of the surgical cuts. For example, expandable or ratchet-like devices can be utilized that can be inserted into the joint or that can be attached or that can touch the trial, instrument or mold. Hinge-like mechanisms are applicable. Similarly, jack-like mechanisms are useful. In principal, any mechanical or electrical device useful for fine tuning the position of the cut guide relative to the trial or instrument or molds can be used. The trials or instruments or molds and any related instrumentation such as spacers or ratchets can be combined with a tensiometer to provide a better intraoperative assessment of the joint. The tensiometer can be utilized to further optimize the anatomic alignment and tightness or laxity of the joint and to improve post-operative function and outcomes. Optionally local contact pressures may be evaluated intraoperatively, for example using a sensor like the ones manufactured by Tekscan, South Boston, Mass.

8. Guide Tools for Installing a Joint Implant

A variety of traditional guide tools are available to assist surgeons in preparing a joint for an implant, for example, for resectioning one or more of a patient's biological structures during a joint implant procedure. However, these traditional guide tools typically are not designed to match the shape (contour) of a particular patient's biological structure(s). Moreover, these traditional guide tools typically are not designed to impart patient-optimized placement for the resection cuts. Thus, using and properly aligning traditional guide tools, as well as properly aligning a patient's limb (e.g., in rotational alignment, in varus or valgus alignment, or alignment in another dimension) in order to orient these traditional guide tools, can be an imprecise and complicated part of the implant procedure.

Certain embodiments described herein provide improved surgical guide tools and methods for preparing a patient's biological structure during a joint implant procedure.

8.1 Patient-Specific Guide Tools

Certain embodiments include a guide tool having at least one patient-specific bone-facing surface portion that substantially negatively-matches at least a portion of a biological surface at the patient's joint. The guide tool further can include at least one aperture for directing movement of a surgical instrument, for example, a securing pin or a cutting tool. One or more of the apertures can be designed to guide the surgical instrument to deliver a patient-optimized placement for, for example, a securing pin or resection cut. In addition or alternatively, one or more of the apertures can be designed to guide the surgical instrument to deliver a standard placement for, for example, a securing pin or resection cut. As used herein, "jig" also can refer to guide tools, for example, to guide tools that guide resectioning of a patient's biological structure. Alternatively, certain guide tools can be used for purposes other than guiding a drill or cutting tool. For example, balancing and trial guide tools can be used to assess knee alignment and/or fit of one or more implant components or inserts.

Certain embodiments can include a guide tool that includes at least one patient-specific bone-facing surface that substantially negatively-matches at least a portion of a biological surface at the patient's joint. The patient's biological surface can include cartilage, bone, tendon, and/or other biological surface. For example, in certain embodiments, patient-specific data such as imaging data of a patient's joint can be used to select and/or design an area on the articular surface that is free of articular cartilage. The area can be free of articular cartilage because it was never cartilage covered or because the overlying cartilage has been worn away. The imaging test can be specifically used to identify areas of full or near full thickness cartilage loss for designing the contact surface on the bone-facing surface of a patient-specific guide tool. Alternatively, the area can be free of articular cartilage because an osteophyte has formed and is extending outside the cartilage. The guide tool then can rest directly on the bone, e.g., subchondral bone, marrow bone, endosteal bone or an osteophyte. By selecting and/or designing an area of the articular surface that is free of articular cartilage, it is possible to (a) reference the guide tool against the articular surface and (b) reference it against bone rather than cartilage.

In certain embodiments, patient-specific data such as imaging test data of a patient's joint can be used to identify a contact area on the articular surface for deriving an area on the bone-facing surface of a guide tool to substantially negatively-match the contact area on the subchondral bone surface. While the area may be covered by articular cartilage, the guide tool surface area can be specifically designed to match the subchondral bone contact area. The guide tool can have one or multiple areas that substantially negatively-match one or multiple contact areas on the subchondral bone surface. Intraoperatively, the surgeon can elect to place the guide tool on the residual cartilage. Optionally, the surgeon then can mark the approximate contact area on the cartilage and remove the overlying cartilage in the marked area before replacing the guide tool directly onto the subchondral bone. In this manner, the surgeon can achieve more accurate placement of the guide tools that substantially negatively-matches subchondral bone.

In certain embodiments, patient-specific data such as imaging test data of a patient's joint can be used to identify a contact area on the articular surface for deriving an area on the bone-facing surface of a guide tool that substantially negatively-matches the endosteal bone or bone marrow contact area. While the area may be covered by articular cartilage, the guide tool surface area can be specifically designed to match the endosteal bone or bone marrow. The guide tool can have one or multiple areas that substantially negatively-match one or multiple areas on the endosteal bone or bone marrow. Intraoperatively, the surgeon can elect to place the guide tool on the residual cartilage. Optionally, the surgeon then can mark the approximate contact area on the cartilage and subsequently remove the overlying cartilage in the marked area before replacing the guide tool directly onto the endosteal bone or bone marrow. In this manner, the surgeon can achieve more accurate placement of guide tools that match endosteal bone or bone marrow.

In certain embodiment, the articular surface or the margins of the articular surface can include one or more osteophytes. The guide tool can rest on the articular surface, e.g., on at least one of normal cartilage, diseased cartilage or subchondral bone, and it can include the shape of the osteophyte. In certain embodiments, patient-specific data such as imaging test data of a patient's joint can be used to derive an area on the bone-facing surface of the guide tool that substantially negatively-matches the patient's articular surface including the osteophyte. In this manner, the osteophyte can provide additional anatomic referencing for placing the guide tool. In certain embodiments, the osteophyte can be virtually removed from the joint on the 2D or 3D images and the contact surface of the guide tool can be derived based on the corrected surface without the osteophyte. In this setting, the surgeon can remove the osteophyte intraoperatively prior to placing the guide tool.

Certain embodiments can include a guide tool that is flexible. The guide tool's flexibility, optionally in combination with a patient-specific bone-facing surface, can allow it to snap-fit into position onto the patient's biological structure. For example, the guide tool can be snap-fit to a patient's biological structure by applying force to the guide tool to cause it to expand and engage the structure. During or following the expansion and engagement, the tool can be adjusted so that the bone-facing surface engages the corresponding surface of the biological structure.

The flexibility of the guide tool can be altered or enhanced using materials and processes known in the art. For example, various types and/or combinations of polymers and polymer manufacturing techniques can be used to make a guide tool with the appropriate flexibility to provide a snap-fit.

The bone-facing surface of the guide tool can be patient-specific (e.g., substantially negatively-match) for one or more surface dimensions or features of the patient's biological surface including, for example, width, area, height, distance, angle, and curvature. For example, in certain embodiments, a dimension or feature of the patient's biological structure can be assessed to include the cartilage on its surface. In certain other embodiments, a dimension or feature can be assessed based on the patient's bone surface, for example, subchondral bone surface.

If a subchondral bone surface is used to assess the patient's biological surface, a standard cartilage thickness (e.g., 2 mm), or an approximate cartilage thickness derived from patient-specific data (e.g., age, joint-size, contralateral joint measurements, etc.) can be used as part of the design for the guide tool, for example, to design the size and bone-facing surface of the guide tool. The standard or approximate cartilage thickness can vary in thickness across the assessed surface area. In certain embodiments, this design can be used with a similarly designed implant, for example, an implant designed to include a standard or approximate cartilage thickness.

8.2 Patient-Engineered Guide Tools

In certain embodiments, a guide tool includes at least one feature for directing a surgical instrument to deliver a patient-engineered feature to the patient's biological structure, for example, a resected hole or a resection cut for engaging a patient-engineered implant peg or a patient-engineered implant bone-facing surface. In addition to the patient-engineered feature, in certain embodiments one or more of the guide tool's bone-facing surfaces can be designed to be patient-specific so that it substantially negatively-matches a portion of the patient's joint surface. In addition or alternatively, one or more of the guide tool's bone-facing surfaces can be standard in shape.

Example 14 below describes a set of patient-optimized guide tools that can be used to perform patient-optimized resection cuts to the femur in preparation for implanting a femoral knee implant component having patient-optimized bone cuts. As described in Example 14, one or more guide tools can be used to prepare a joint for a patient-engineered implant.

8.3 Exemplary Guide Tool Configurations

The guide tools described herein can include any combination of patient-specific features, patient-engineered features, and/or standard features. For example, a patient-specific guide tool includes at least one feature that is preoperatively designed and/or selected to substantially match one or more of the patient's biological features. A patient-engineered guide tool includes at least one feature that is designed or selected based on patient-specific data to optimize one or more of the patient's biological features to meet one or more parameters, for example, as described elsewhere here, such as in Section 4. A standard guide tool includes at least one feature that is selected from among a family of limited options, for example, selected from among a family of 5, 6, 7, 8, 9, or 10 options. Accordingly, any one guide tool can be both patient-specific in view of its patient-specific features and patient-engineered in view of its patient-engineered features. Such a guide tool also can include standard features as well. Table 17 describes the various combinations of three features of a single guide tool with regard to being patient-specific features, patient-engineered features, and/or standard features of the exemplary guide tools. Moreover, in certain embodiments a set or kit of guide tools is provided in which certain guide tools in the set or kit include patient-specific, patient-engineered, and/or standard features. For example, a set or kit of guide tools can include any two or more guide tools described in Table 17.

resected holes, to establish resected cuts, and to balance or estimate fit of a joint implant.

Figure 76:
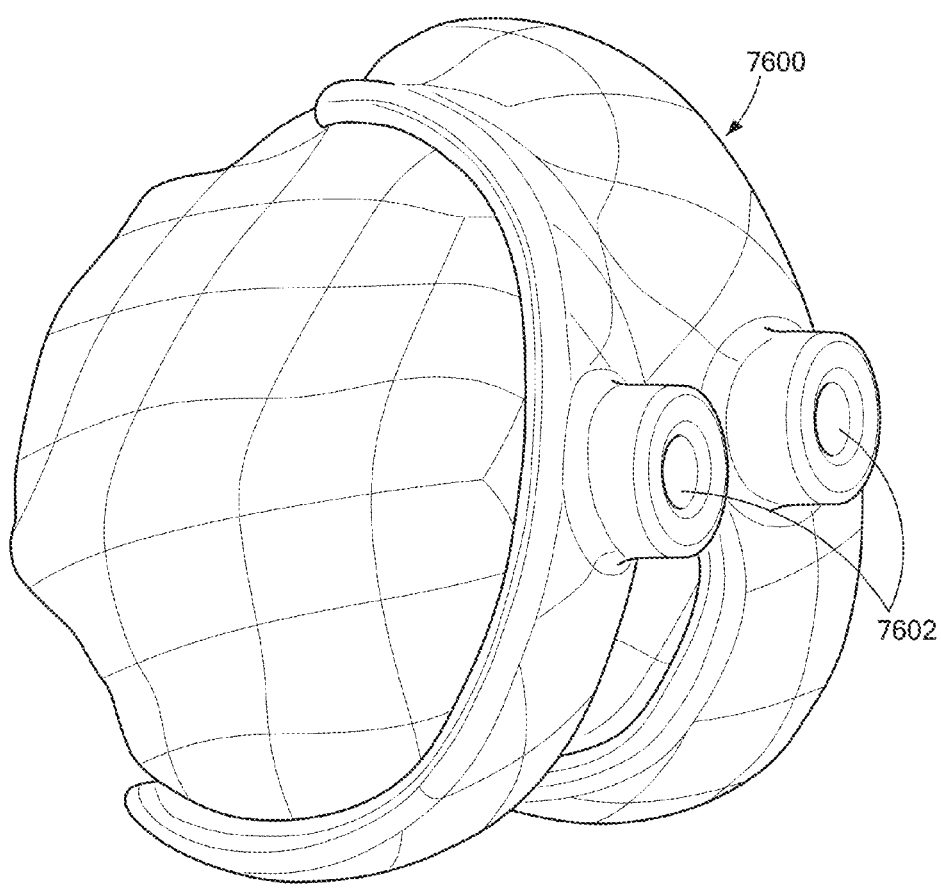
FIG. 76 illustrates a guide tool having one or more apertures for establishing resected holes in a patient's biological structure.

As shown in FIG. 76, a guide tool 7600 can include one or more apertures 7602 for establishing resected holes in a patient's biological structure. One or more of these resected holes can be used to engage a peg, which can be used to secure one or more subsequently used guide tools, e.g., guide tools for establishing resection cuts, into proper position on the biological surface. For example, a subsequently used guide tool can include one or more attached pegs that correspond to the one or more holes resected using, for example, using the guide tool of FIG. 76. In particular, the subsequently used guide tool can be secured onto the biological surface by sliding the pegs into the appropriate resected holes. Alternatively, an independent peg can be placed into the resected hole and, then, a subsequently used guide tool having apertures corresponding to the independent pegs can be secured onto the biological surface by sliding the apertures over the independent pegs. In certain embodiments, the exemplary guide tool shown in FIG. 76 can include anterior and posterior portions that are extended and the material is pliable so that the guide tool can snap-fit onto the femur.

In certain embodiments, one or more attached pegs (i.e., attached to a guide tool) can be detachable, so that, once detached, they can be used to secure a subsequent guide tool or implant component having a corresponding aperture. In

TABLE 17

Patient-specific, patient-engineered, and standard features of exemplary guide tools

| Exemplary Guide tool | Feature #1 | Feature #2 | Feature #3 |
|---|---|---|---|
| A guide tool that includes at least 3 PS features | P | P | P |
| A guide tool that includes at least 3 PE features | PE | PE | PE |
| A guide tool that includes at least 3 S features | St | St | St |
| A guide tool that includes at least 2 PS features and at least 1 PE feature | P | P | PE |
|  | P | PE | P |
|  | PE | P | P |
| A guide tool that includes at least 2 PS features and at least 1 S feature | P | P | St |
|  | P | St | P |
|  | St | P | P |
| A guide tool that includes at least 1PS feature and at least 2 PE features | PE | PE | P |
|  | PE | P | PE |
|  | P | PE | PE |
| A guide tool that includes at least 1PS feature and at least 2 S feature | St | St | P |
|  | St | P | St |
|  | P | St | St |
| A guide tool that includes at least 2PE features and at least 1 S feature | PE | PE | St |
|  | PE | St | PE |
|  | St | PE | PE |
| A guide tool that includes at least 1PE feature and at least 2 S features | St | St | PE |
|  | St | PE | St |
|  | PE | St | St |
| A guide tool that includes at least 1PS feature. at least 1 PE feature, and at least 1 S feature | P | PE | St |
|  | P | St | PE |
|  | PE | P | St |
|  | PE | St | P |
|  | St | P | PE |
|  | St | PE | P |

P indicates a patient-specific feature,
PE indicates a patient-engineered feature, and
St indicates a standard feature A guide tool can be used for one or more purposes during an implant procedure. For example, one or more guide tools can be used to establish resected holes in a patient's biological structure, to establish resected cuts in a patient's biological structure, and/or to balance or estimate fit of a joint implant. The following subsections describe exemplary guide tools and guide tool features that can help to establish certain embodiments, a first guide tool can be secured to the biological structure and a second guide can be secured to the first guide tool. For example, an attached or independent peg can extend from the resected hole, through the aperture of the first guide tool and into a corresponding aperture of the second guide tool. Alternatively or in addition, the second guide tool can include a feature that engages an aspect of the aperture on the first implant. For example, a portion of the aperture on the second guide tool can be wider than the aperture on the first guide tool and engage a raised aperture collar surrounding the aperture on the first guide tool. Alternatively, the second aperture can include a sleeve that slide into the aperture on the first guide tool.

Alternatively or in addition, one or more of these resected holes can be used to secure an implant component. For example, one or more pegs projecting from the bone-facing surface of the implant component can be placed into the resected hole to fix the placement of the implant component. In certain embodiments, cement can be applied to the resected hole and/or the implant component peg to secure the placement of the implant.

A variety of aperture configurations can be used for the guide tools described herein. In certain embodiments, a guide tool aperture configuration can be patient-engineered to engage a particular patient-engineered peg configuration on the corresponding implant component. Moreover, aperture features such as size, shape, angle, and optionally, stop depth, can be designed to substantially match the peg features for the corresponding implant component. For example, in certain embodiments the aperture cross-section can be round to match a round peg on the implant component. However, in certain embodiments, as suggested by FIG. 53B, the aperture cross-section can include a "+" or cross-like configuration to match the corresponding peg on the implant component.

A variety of aperture sizes can be used. For example, a 7 mm diameter aperture can be used. Moreover, the aperture can be oriented to establish a resected hole at any angle. For example, an aperture can be oriented to establish a resected hole in line with the femoral mechanical axis. Alternatively, an aperture can be oriented to establish a resected hole at an anterior-leaning angle to match the angle of the corresponding implant peg. For example, one or more apertures can be oriented anteriorly to establish a 5 degree, 5-10 degree, 10 degree, 10-15 degree, and/or 15 degree anterior-leaning angle relative to the femoral mechanism axis. The aperture can be oriented to establish a resected hole that is oriented at the same angle or at different angles as one or both of the anterior and posterior cuts of the implant component. In certain embodiments, a depth-stop can be used so that the aperture allows a resected hole having a certain maximum depth.

Figure 77:
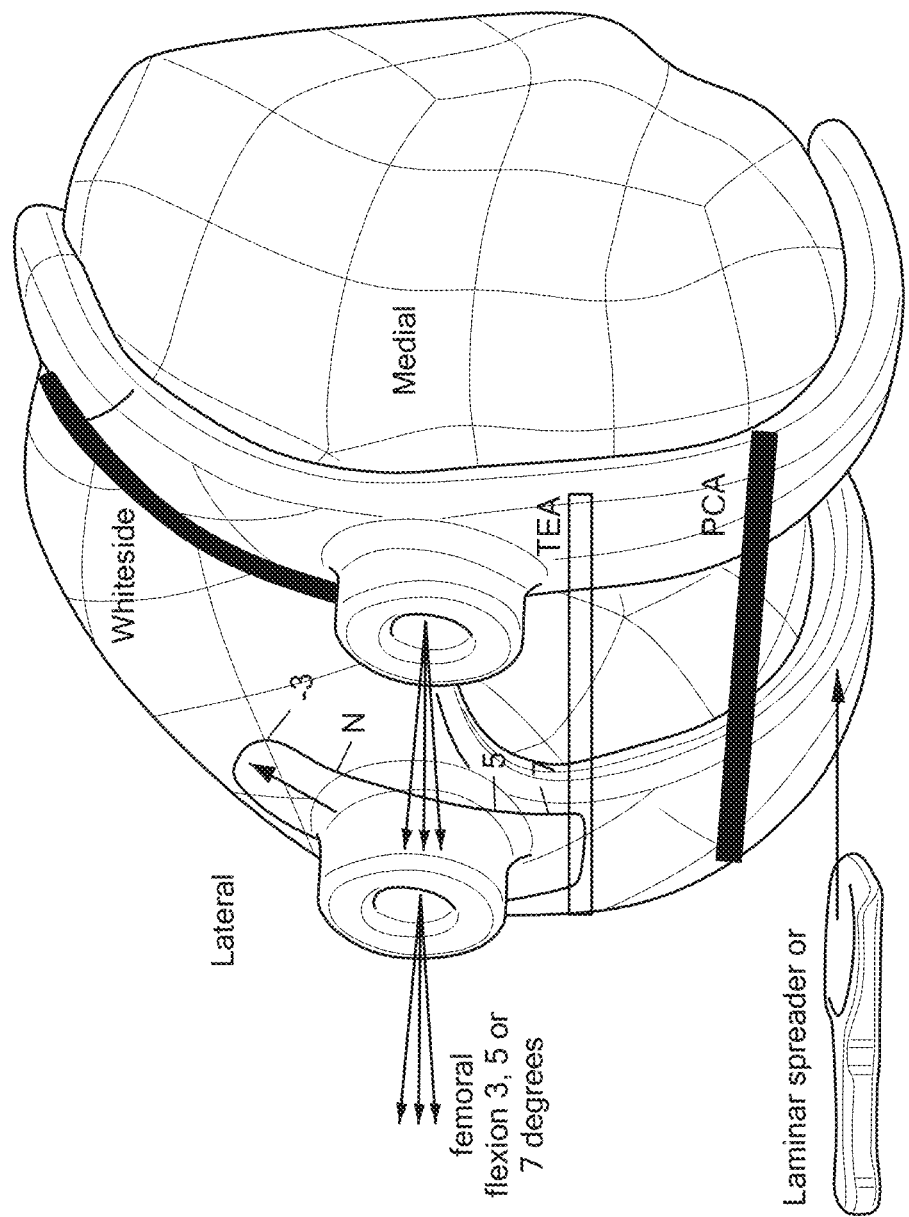
FIG. 77 illustrates a guide tool having a moveable aperture and bushing.

In certain embodiments, a guide tool includes at least one moveable aperture and, optionally, a moveable corresponding bushing. FIG. 77 depicts a guide tool having a moveable lateral aperture and bushing. Specifically, the lateral aperture and bushing in the figure are moveable in the A-P direction. However, a moveable aperture (and, optionally, a moveable bushing) can be moveable in the A-P direction, in the M-L direction, or in all directions from the aperture center (e.g., can be rotated in a circular pattern). Moreover, the guide tool can include two or more moveable apertures. For example, a lateral aperture and a medial aperture, and optionally one or both corresponding bushings, can be moveable. Alternatively, one or more apertures (and optional bushings) can be fixed, for example, as is the medial aperture and bushing in FIG. 77.

The guide tool that includes one or more moveable apertures also can include one or more patient-specific features, one or more patient-optimized features, and/or one or more standard features. Moreover, the guide tool can be used with a subsequently used guide tool or implant that includes one or more patient-specific features, one or more patient-optimized features, and/or one or more standard features.

A guide tool that includes one or more moveable apertures for establishing resected holes can be used during surgery to adjust the orientation of subsequently placed guide tools and/or implant components. For example, one or more moveable apertures in a femoral guide tool can be used to adjust the femoral flexion, femoral rotation, and/or tibial external rotation of the particular patient's femoral implant.

With reference to the exemplary guide tool shown in FIG. 77, a surgeon can snap-fit the guide tool on the femur, observe placement of the moveable aperture as well as other guide tool features relative to one or more biological landmarks, and, if appropriate, move the moveable aperture in order to adjust the orientation of the subsequently installed femoral implant component on the femur. For example, if the surgeon moves the lateral aperture posteriorly to the 3 degree mark, as shown in the figure, the lateral resected hole and engaging lateral peg of the subsequently installed femoral implant component also would be shifted posteriorly. With the medial aperture fixed, this would posteriorly flex the lateral side of the implant component and axially rotate the orientation of the implant component on the femur. As shown in FIG. 77, the movable bushing can be limited to one or more ranges of motion and can be accompanied by markings and/or values displayed on the tool surface indicating the rotation in relation to one or more axes. Moreover, in certain embodiments, patient-specific information and/or standard rules can be used to limit the extent of movement of the moveable aperture. For example, the limit of posterior movement of the aperture in the guide tool can be established as the point that allows a subsequent guide tool to guide a lateral posterior bone resection that removes some minimum amount of bone, for example, so that the intersect between the posterior resection cut and posterior chamfer cut is below the bone surface.

In certain embodiments, the movable aperture also could allow for a balancing technique. For example, a navigation chip can be placed into the lateral joint in flexion, e.g., as a laminar spreader. This rotates the femur internally and the joint gap can be balanced by moving the lateral aperture, for example, posteriorly. So we have all four techniques integrated into our system and everyone's believe would be satisfied. The surgeon could then decide what he wants right there at surgery.

In certain embodiments, the extent limit of movement of the moveable aperture in the A-P direction can be limited to 3 degrees, less than 3 degrees, 5 degrees, less than 5 degrees, 7 degrees, and/or less than 7 degrees.

In certain embodiments, instead of including a moveable aperture, the guide tool can include one or more alterative apertures and/or an extended opening, for example, and opening that includes the approximate area through which a moveable aperture can move. Then, a bushing (e.g., metal or plastic) or other device can snap, slide, or lock into place onto one of the alternative apertures or at a certain location in the extended opening. For example, the bushing or other device could lock into place at alternative apertures or in the extended opening at 3, 5 and 7 degrees. In this way, the surgeon can alter the implant orientation as he or she deems appropriate. Alternatively, a guide tool can include an aperture bushing that is fixed in one location but can swivel (e.g., tilt). For example, in certain embodiments, a bushing can swivel or tilt in one direction, in two directions, or all directions about a fixed point. The amount of swivel or tilt can be, for example, between 0 and 7 degrees, up to 7 degrees, between 1 and 7 degrees, and/or between 3 and 7 degrees in one or more directions.

The guide tools described herein can include features and apertures for various steps in a joint replacement procedure. For example, in certain embodiments, one or more guide tools can be used to establish all the resection cuts associated with installation of a particular implant component. As noted above, one or more of the guide tools can include one more patient-specific features and/or one or more patient-engineered features and/or one or more standard features.

Figure 79B:
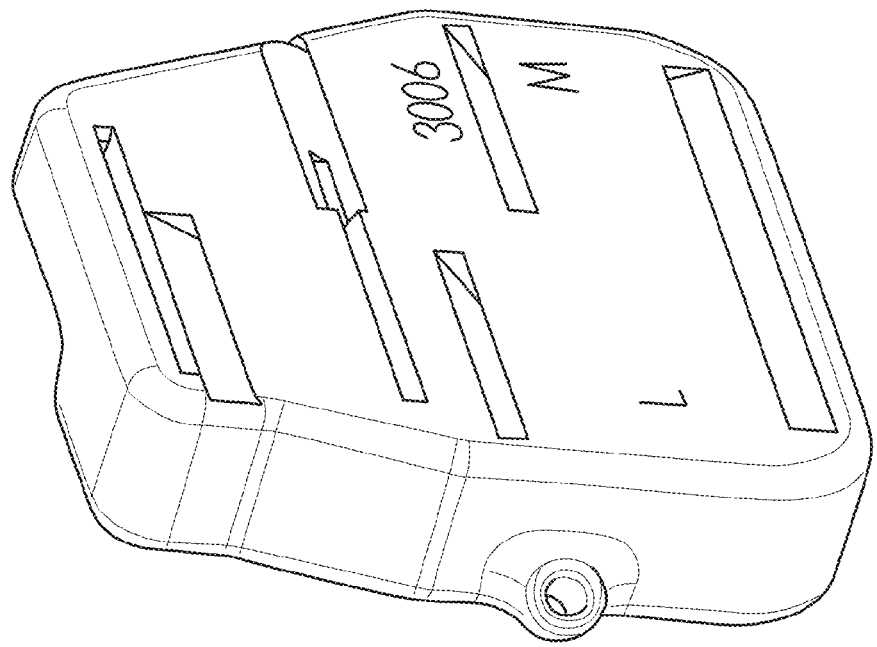
FIGS. 79A and 79B show two options for a third guide tool for making anterior and posterior chamfer cuts.
Figure 79A:
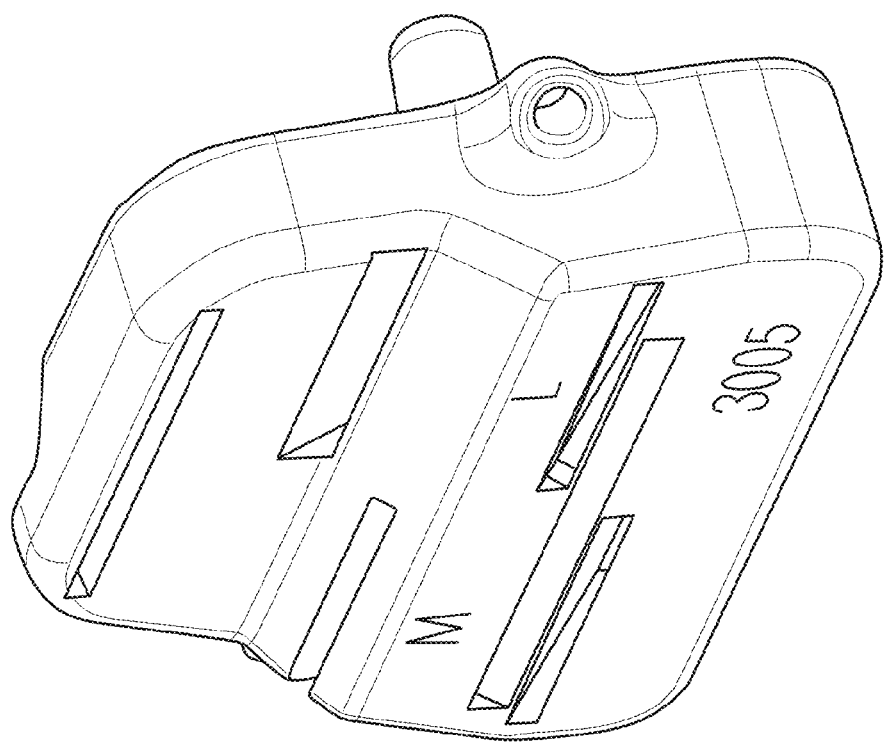

In certain embodiments, a set of three guide tools can be used to establish all the resection cuts associated with installation of a particular implant component. For example, the three guide tools shown in FIG. 76 or 77, FIG. 78, and FIGS. 79A and 79B can be used together to establish all the resection cuts associated with installation of a femoral implant component. In particular, FIGS. 76 and 77 each shows a peg hole driver guide tool for establishing pin or peg holes for subsequent guide tools and, optionally, for the femoral implant component. This tool can be used to establish the direction of pegs used by subsequent tools and/or the implant component and can be specifically matched to the patient just like the implant component. Subsequently placed guide tools can be placed with respect to these peg hole features to ensure that the bone preparation is performed per the intended implant design. FIG. 78 shows a guide tool for making distal and posterior resection cuts to the distal femur and FIGS. 79A and 79B show two options for a third guide tool for making anterior and posterior chamfer cuts. The particular set of guide tools shown in these figures is designed for a tibia first technique; however, the features of the guide tools for preparing a knee joint as described herein can be applied to both a tibia first technique and to a femur first technique.

Furthermore, a spacer, such as a lateral spacer, can be used for balancing to equal distal asymmetry. The spacer can include patient-specific and/or patient-engineered features. A series of balancer chips with thicknesses can be included, for example a series of chips having 1 mm increases in thickness. Alternatively or in addition, a guide tool can include an integrated spacer thickness to allow surgeon to assess tension without needing a spacer. For example, a guide tool for establishing femoral resection cuts can include an integrated space having a tibial resection depth added to the guide tool external surface.

One or more guide tools can be selected and/or designed to include patient-specific and/or patient-engineered features. For example, the peg hole driver guide tool shown in FIG. 76 can include, at least in part, a patient-specific bone-facing surface that substantially matches a particular patient's femoral surface. Moreover, such guide tools can include flexible material, such as nylon plastic, to allow the tool to snap-fit onto the particular patient's femur, as suggested by the peg hole driver guide tool shown in FIG. 76. Other features, such as peg hole angle, peg hole placement, peg hole size, tool thickness, joint-facing surface, and other features can be patient-specific or patient-engineered. Alternatively or in addition, one or more features can be standard. For example, for the peg hole driver guide tool shown in FIG. 76, the peg size is 6 mm, which can accommodate a quarter-inch drill size; however, any peg hole size can be used.

Resection cut guide tools can be designed to be patient-specific on their bone-facing surface to allow a snap-fit onto a particular patient's femur. Moreover, other features, such as thickness, joint-facing surface, and peg placement and size, also can be patient-specific or patient-engineered. Alternatively or in addition, one or more features can be standard. The cut guide tool shown in FIG. 78 can be designed to rest on 2 mm thick cartilage relative to CT data and can include a standard tool thickness of 4 mm; however other standard thicknesses can be used, for example, a 2 mm or a 3 mm thickness. Moreover, the cut guide tool shown in FIG. 78 can include three optional pin placements for stabilization and a posterior beam to give stability and rigidity to the tool. The lateral spacer shown on the left side of FIG. 78 can rest on cut tibia to approximate the thickness of asymmetry.

The cut tools shown in FIGS. 79A and 79B are designed to follow the cut tool shown in FIG. 78 and can complete the remaining chamfer cuts for the distal femur. Each of the cut tools shown in the figure includes two pin placements for stabilization. The tool on the left includes short pegs to be positioned in the peg holes established by a peg hole driver guide tool, for example, as shown in FIGS. 76 and 77. The tool on the right includes no lateral peg to allow for external rotation of the guide tool to establish rotated chamfer cuts.

Figure 80:
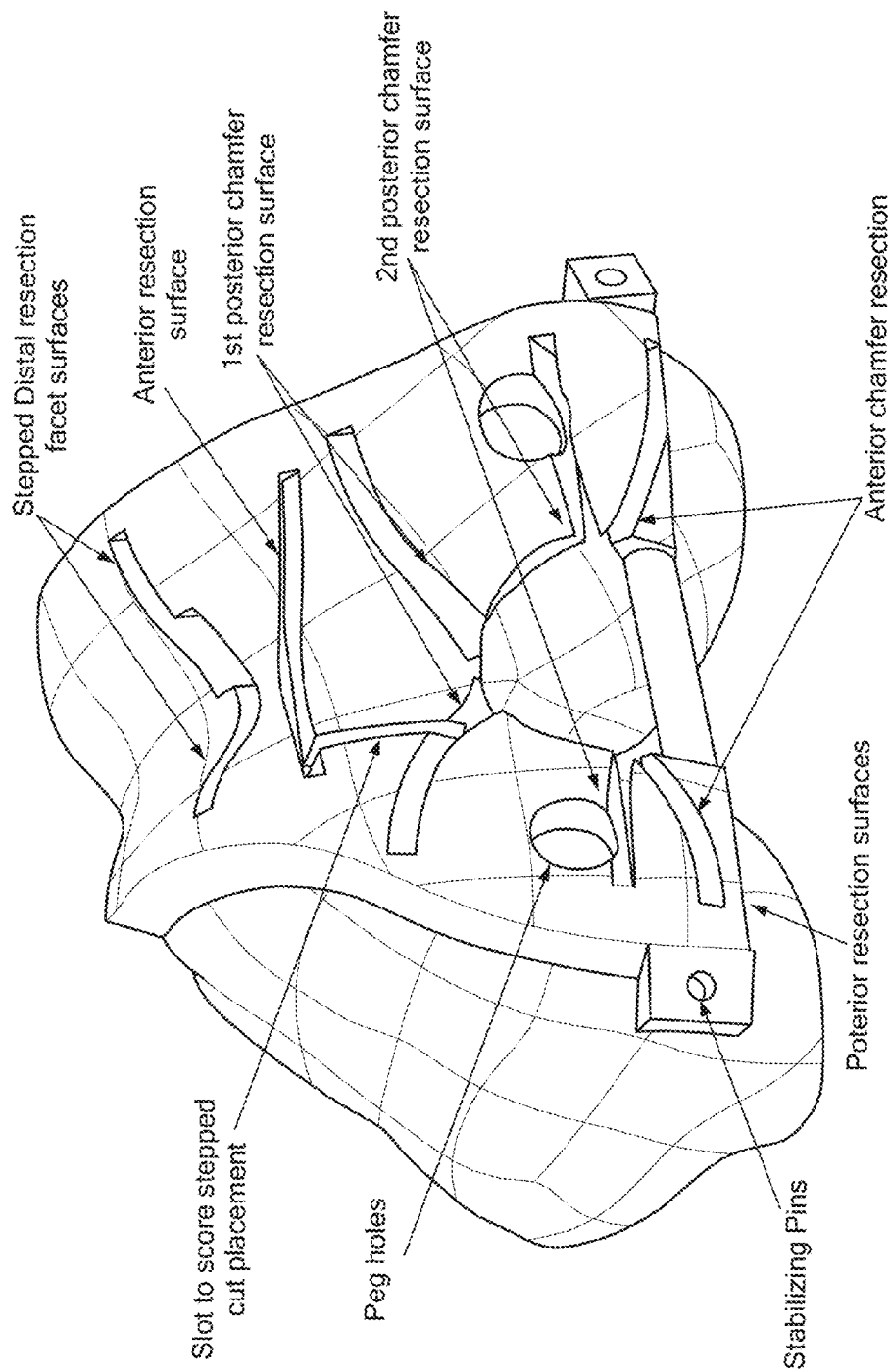
FIG. 80 illustrates a single, "all-in-one" guide tool that can be used to establish all the resection cuts associated with installation of a femoral implant component.
Figure 81A:
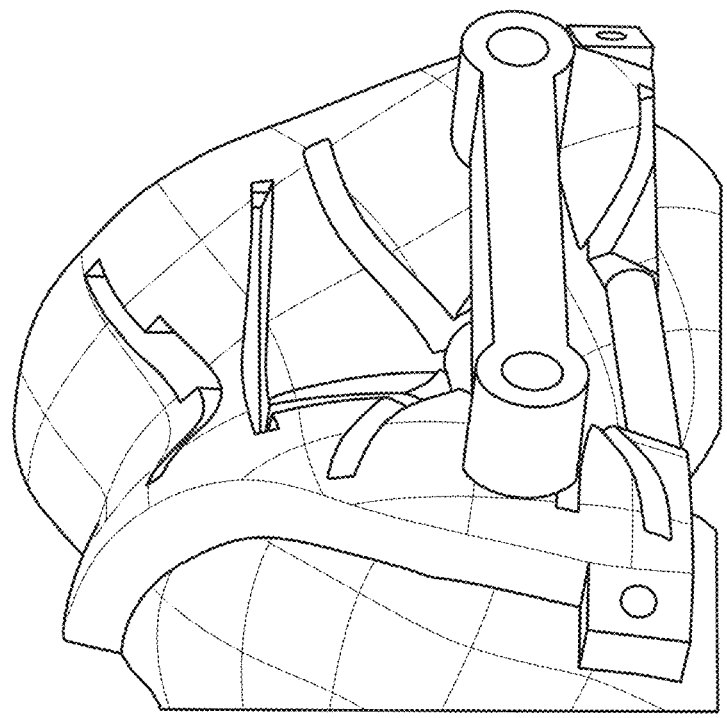
FIGS. 81A and 81B illustrate optional guide tool attachments that can be used to enhance one or more cutting or drilling surfaces.
Figure 81B:
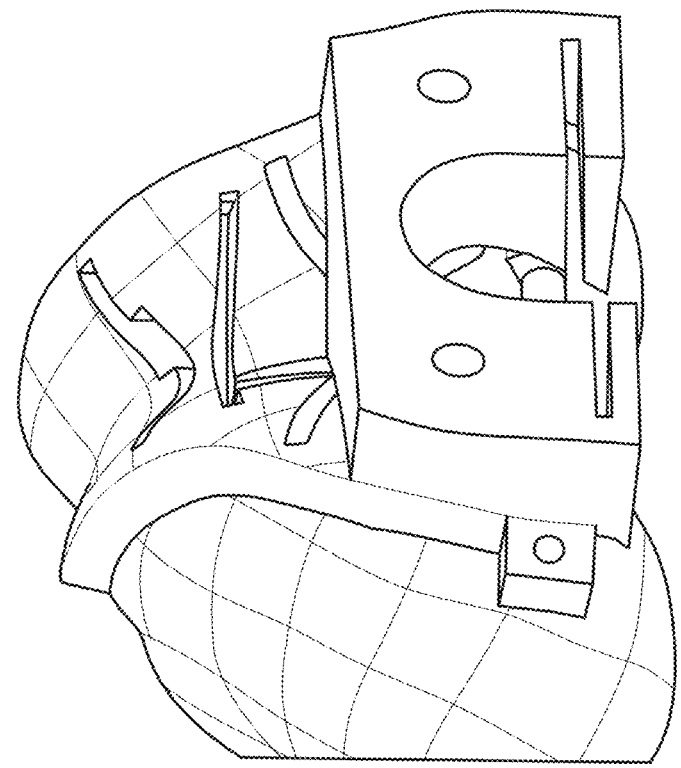

In certain embodiments, fewer than three guide tools, for example, two guide tools or one guide tool can be used to establish the peg holes and all the resection cuts associated with installation of a particular implant component. For example, the single guide tool shown in FIG. 80 can be used to establish all the resection cuts associated with installation of a femoral implant component, including, for example, a distal cut with one more facets, a posterior cut with one or more facets, an anterior cut, an anterior chamfer cut with one or more facets, one or more posterior chamfer cuts each with one or more facets, and one or more step cuts, for example, between two facets of a cut. The apertures (e.g., holes and slots) in the guide tool and edges of the guide tools can be used to guide peg hole placement and resection cuts. For example, the posterior surface of the guide tool shown in FIG. 80 can be used to establish the posterior resection cuts. Optional guide tool attachments can be used to enhance the guidance for one or more of the cutting holes or slots in the cut guide tool. For example, the optional guide tool attachments shown in FIGS. 81A and 81B can be used to enhance one or more cutting or drilling surfaces.

Figure 82C:
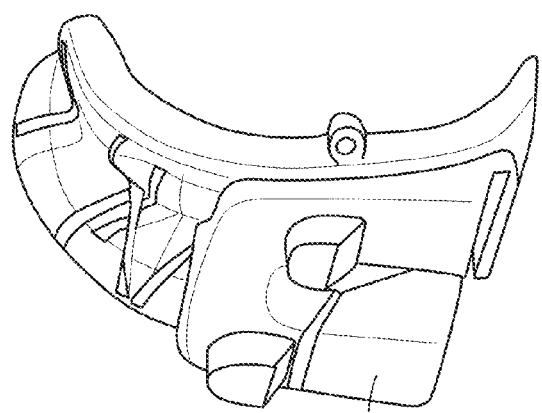
FIGS. 82B and 82C illustrate three optional guide tool attachments for enhancing the cutting or drilling surfaces of the single guide tool.
Figure 82B:
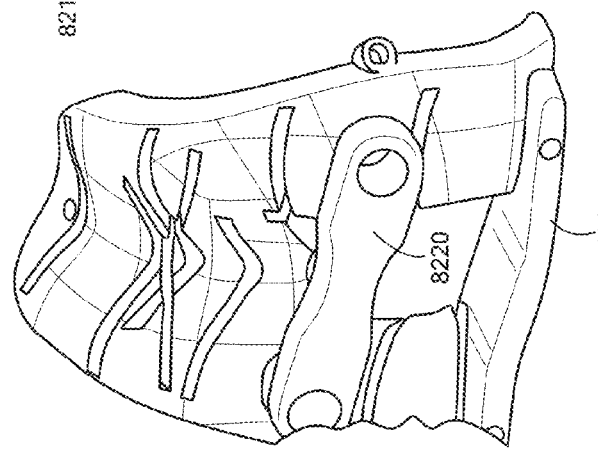
Figure 82A:
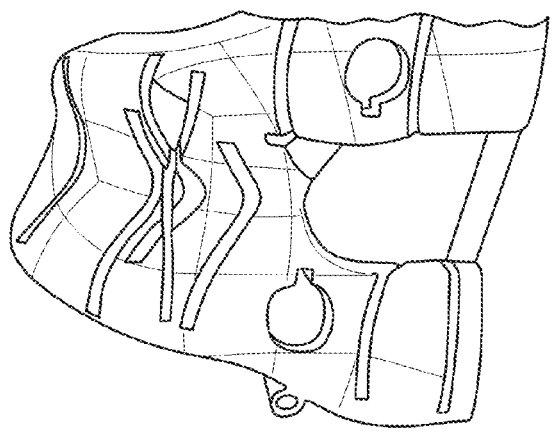
FIG. 82A illustrates an embodiment of a single guide tool that can be used to establish the peg holes and all the resection cuts associated with installation of a femoral implant component.
Figure 82D:
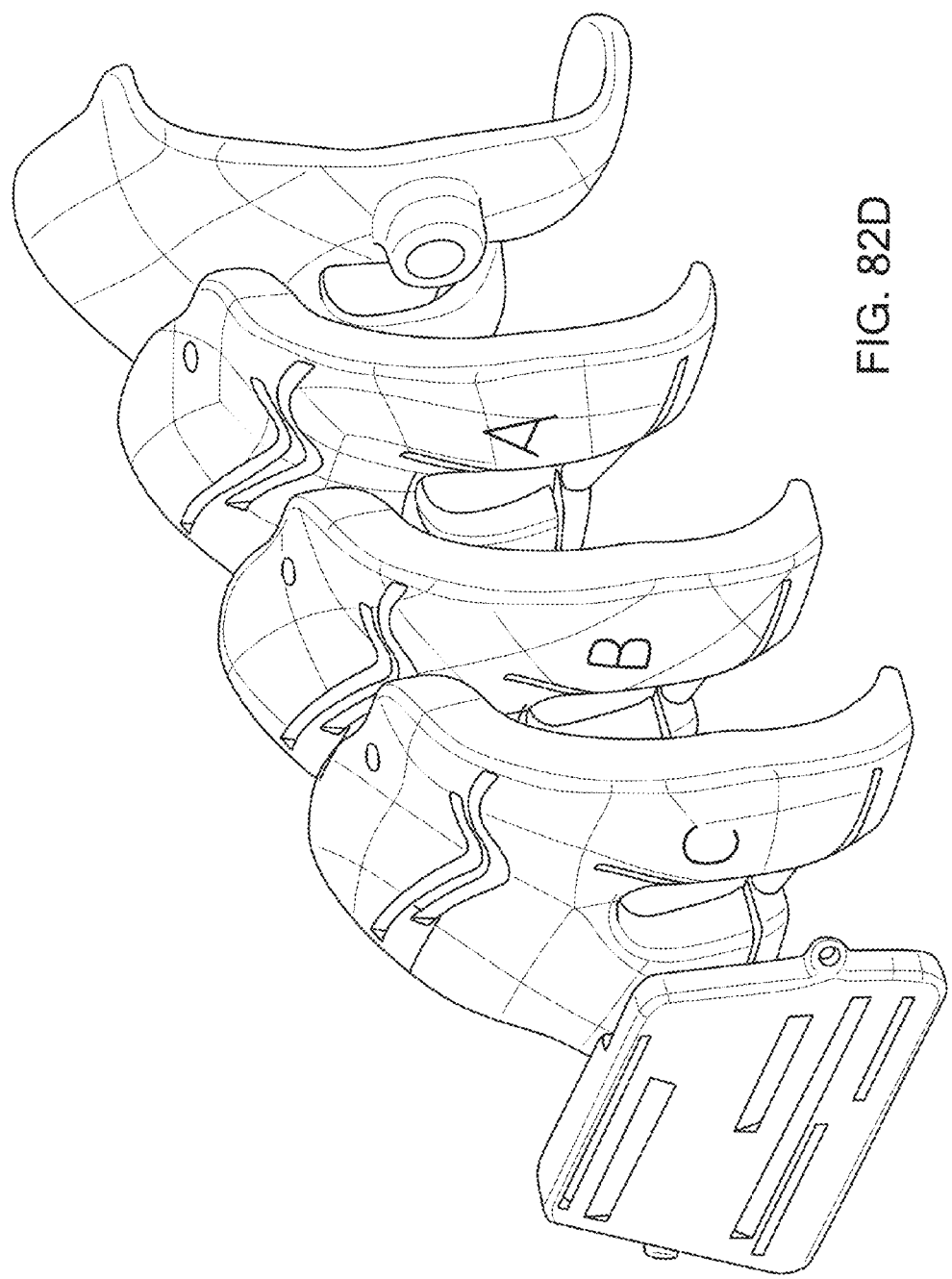
FIG. 82D illustrates a set of resection cut guide tools that together can be used to facilitate peg holes and resection cuts for a patient's femur.

FIG. 82A shows an additional embodiment of a single guide tool that can be used to establish the peg holes and all the resection cuts associated with installation of a femoral implant component. In particular, the single guide tool is presented with three different thicknesses, which corresponds to each of images shown on the figure. Having the single guide tool in different thicknesses allows a surgeon to select the optimum thickness for balancing before initiating the resection cuts. The guide tool can come in 2, 3, 4, 5, 6, 7, 8, 9, 10, or more thicknesses. One the surgeon has selected the guide tool with the appropriate thickness, the distal resection cut and all subsequent resection cuts can be made using the selected guide tool. This allows the distal resection cut to be placed at the appropriate position from the joint-line. In addition, FIGS. 82B and 82C show three optional guide tool attachments 8210, 8220, 8230 for enhancing the cutting or drilling surfaces of the single guide tool. One or more guide tool attachments can be used to enhance the cutting and/or drilling surfaces for one, two, more than two, or all of the apertures in a single guide tool. In this embodiment, numbers are included on the surface of the guide tools to indicate the order of the resection cuts. FIG. 82D shows a set of resection cut guide tools that together can be used to facilitate the same peg holes and resection cuts that can be facilitated with the single guide tool described above. The middle three guide tools (labeled A, B, and C)

include the same resection cuts but have different thicknesses to allow for balancing, as described above. This group of guide tools can be included in a kit along with the single guide tool described above, for example, to act as a back-up set of guide tools.

Figure 82F:
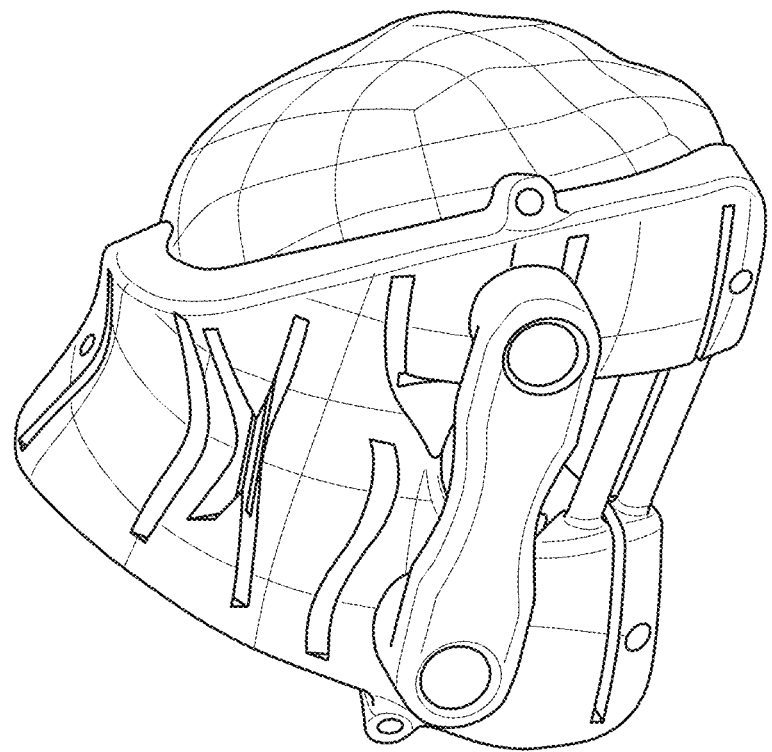
FIGS. 82E to 82H show another embodiment of a single guide tool and attachments that can be used to establish the peg holes and all the resection cuts associated with installation of a femoral implant component.
Figure 82E:
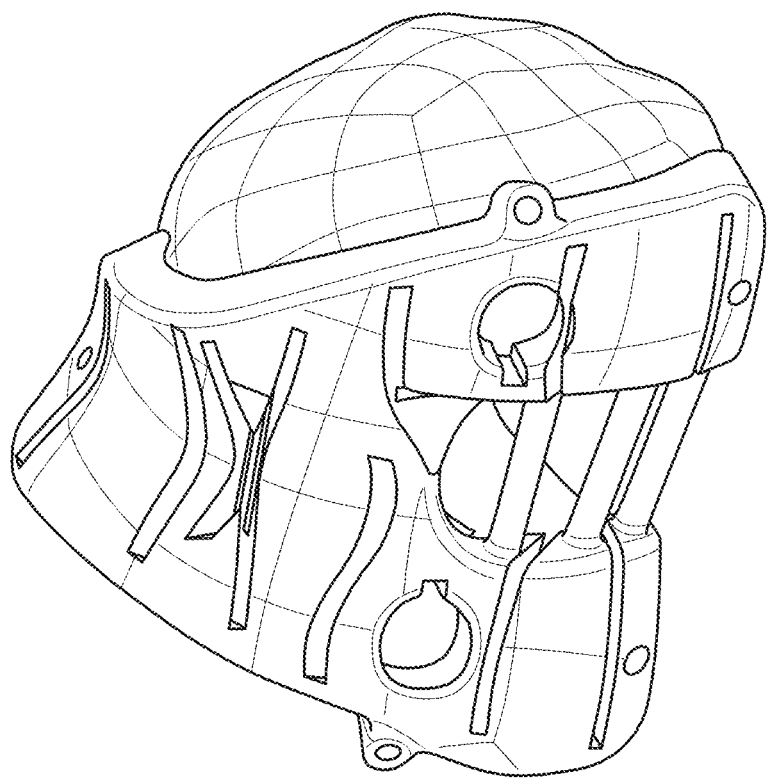
Figure 82H:
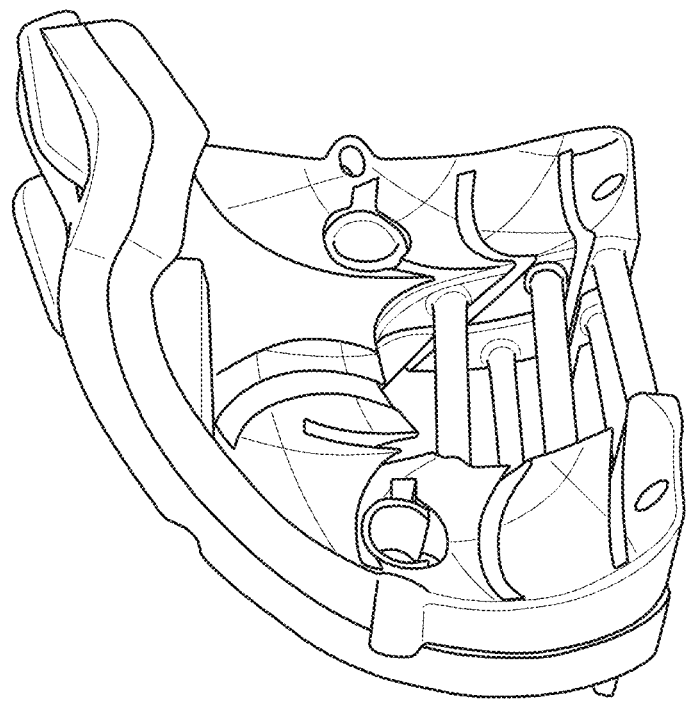
Figure 82G:
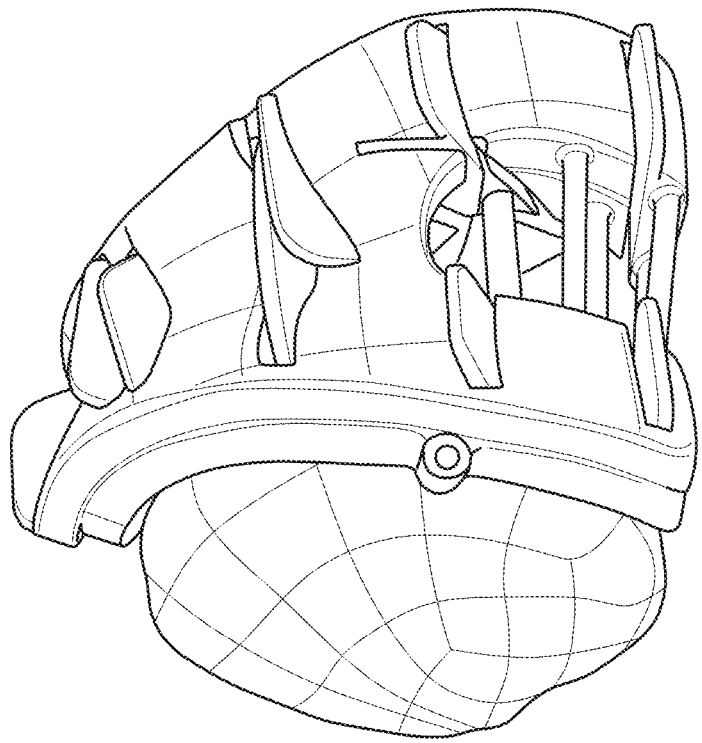

FIGS. 82E to 82H show another embodiment of a single guide tool and attachments that can be used to establish the peg holes and all the resection cuts associated with installation of a femoral implant component. In particular, the guide tool shown in FIG. 82E includes three reinforcement bars between the implant component condyles. This guide tool can be presented in one or more thicknesses. As noted above, a guide tool having an appropriate thickness can be used to balance the knee before the surgeon performs any femoral cutting. FIG. 82F shows the guide tool of FIG. 82E with an additional attachment to supply additional surface area to guide to a drilling tool in making the two peg holes. FIG. 82G shows the guide tool of FIG. 82E with an additional attachment to supply additional surface area to guide a cutting tool in making the numbered resection cuts. As shown in the figure, the attachment covers the entire surface area of the guide tool. The attachment also include flanges adjacent to each cutting hole that supply additional surface area for guiding the cutting tool. FIG. 82H shows the reverse side of the guide tool and attachment shown in FIG. 82G. As shown, the attachment can be fixed in place on the guide tool using an interface that can include fitting a peg from the attachment into one or both peg guide holes of the guide tool.

One or more resection cut slots in a particular guide tool can be substantially, horizontal, substantially diagonal, or substantially vertical, for example, as compared to the patient's mechanical axis and/or anatomical axis. Moreover, one or more of the resection cut slots can allow for a complete resection cut or a partial resection cut, e.g., scoring of the patient's bone to establish a resection cut that can be finished after removing the tool. This approach can be advantageous by allowing for faster resection in the absence of the guide tool. Moreover, one or more resection cut slots can include a blade-depth stop. This is particularly useful for step resection cuts, for example, vertical step resection cuts, that connect two facets or planes of a resected surface.

8.4 Guide Tool Markings

In certain embodiments, one or more guide tools described herein can include markings to identify relevant features, for example, alignment indicators for anatomical and/or biomechanical axes. Such markings can intraoperatively guide a surgeon in the installation procedure. For example, the guide tool shown in FIG. 77 includes on its surface alignment indicators for the patient's Whiteside's AP trochlear line, the transepicondylar axis (TEA), and the posterior condylar axis (PEA). These indicators can be in colors and/or in raised geometries to strengthen the guide tool.

Moreover, as shown in FIG. 82A, resection cut apertures on a guide tool can include numbers or other instructions to direct a surgeon in the proper resection procedure.

Guide tools for establishing tibial resection cuts can include one or more patient-specific features and/or one or more patient-engineered features, and/or one or more standard features. For example, the bone-facing surface of a tibial resection guide tool can include patient-specific features that conform to the uncut tibial surface, e.g., bone and/or cartilage surface. Embodiments of patient-specific tibial resection guide tools are shown in FIGS. 83A to 83H and in FIGS. 84A and 84B.

FIGS. 83A to 83F show a tibial guide tool 8310, a tibial guide rod 8320, and a tibial+2 mm additional resection cut guide 8330. The tibial guide tool having a large anterior portion provide a patient-specific surface area that matches a portion of the contour of the tibia. The anterior portion also is relatively thin to make the tool low profile. As shown in the figures, the guide tool includes parallel pins for ease of removal and installation, and a cutting slot that extends laterally (e.g., 10 mm laterally) and is 1.32 mm in diameter to better control the blade flex during cutting. In certain embodiments, the tibial guide tool includes a large medial surface that can be patient-specific for a portion of the patient's corresponding biological structure (e.g., bone or cartilage surface). In this way, the conforming guide tool fits optimally on the particular patient's bone and thereby provides a secure cutting surface. In certain embodiments, the tibial guide tool can include a feature for attaching a tibial guide rod, for example, at the anterior portion of the guide tool. In particular, the tibial guide rod can mate with the anterior feature of the tibial guide via a rectangular boss and hole. As with the guide tool, the guide rod can include one or more patient-specific features and/or one or more patient-engineered features and/or one or more standard features. For the example, the diameter and/or length of the guide rod can be designed based on the specific patient information, such as information derived from one or more patient images. The guide rod depicted in the figure includes a diameter of 8.5 mm and a length of 250 mm.

Figures 83E, 83F:
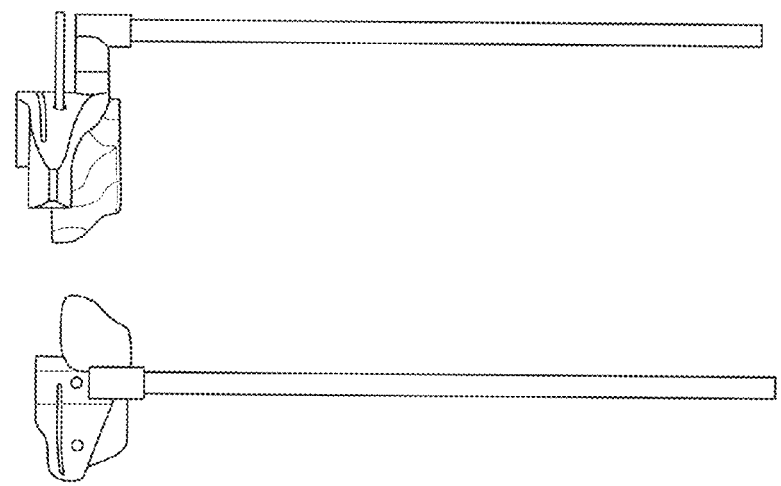
FIGS. 83A to 83F illustrate a tibial guide tool, a tibial guide rod, and a tibial+2 mm additional resection cut guide.
Figures 83B, 83C, 83D:
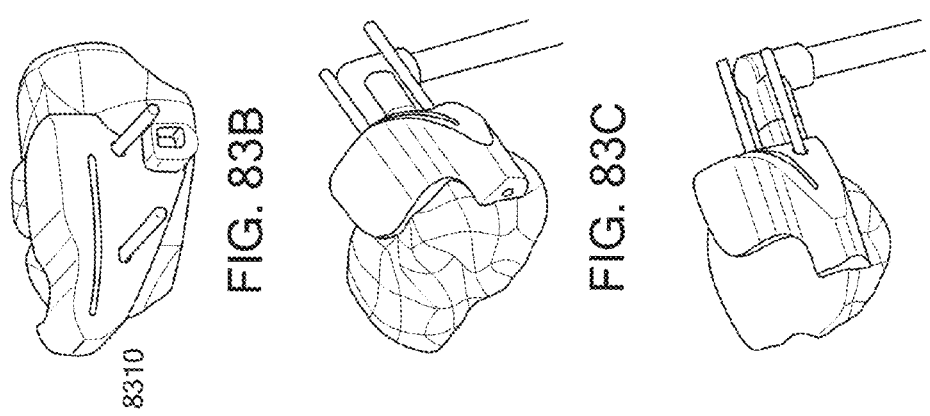
Figure 83A:
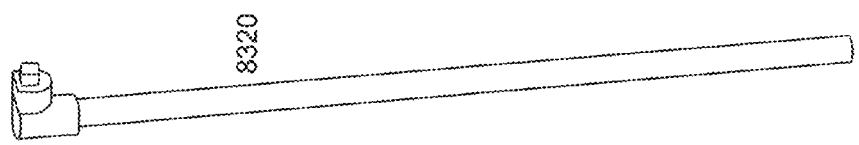
Figure 83G:
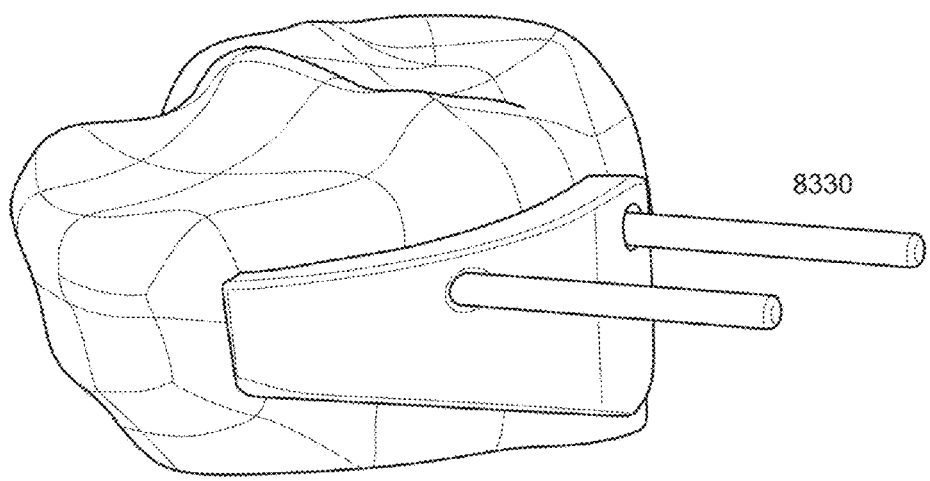
FIGS. 83G and 83H illustrate one or more additional guide tools that can be included and used to remove additional bone from the proximal surface of the tibia.
Figure 83H:
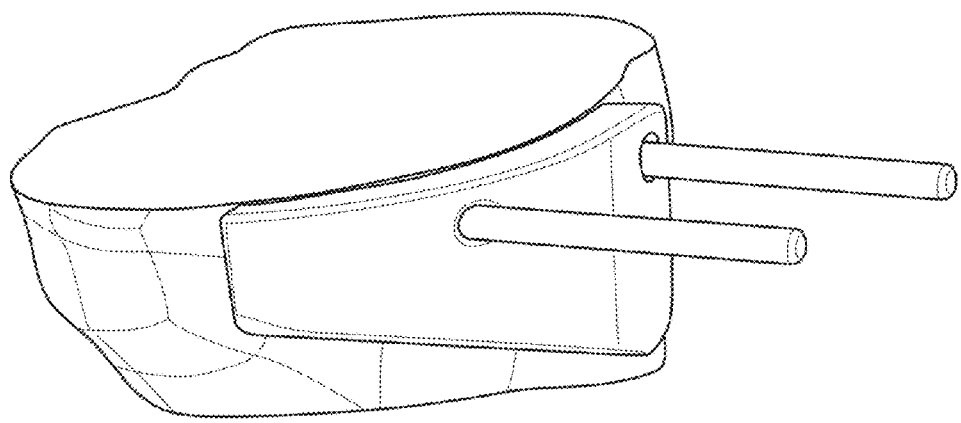

As shown in FIGS. 83G and 83H, one or more additional guide tools can be included and used to remove additional bone from the proximal surface of the tibia. For example, as shown in the figure, an additional guide tool can provide a 2 mm deeper resection than is available with a first guide tool. Alternatively, one or more additional guide tools can allow for resection of an additional 1 mm, 3 mm, 4 mm, and/or 5 mm (or any amount in between these values) off the patient's proximal tibia. A single additional guide tool can include one or more resection slots to allow for more than one additional resection depth to be achieved with that single guide tool. The one or more additional guide tools can include one or more patient-specific features, one or more patient-engineered features, and one or more standard features.

FIG. 84A shows a tibial guide tool for making the same resection cut as shown for FIGS. 83A to 83F. However, the guide tool shown in FIG. 84A includes additional patient-adapted surface area that conforms to the patient's biological surface. This patient-adapted surface area can be designed to conform with the patient's biological structure, e.g., subchondral bone and/or cartilage surface, based on one or more images of the patient's joint. Alternatively, this conforming surface area can be engineered based on patient-specific images to conform to an expanded outline of the patient's biological structure, e.g., the patient's subchondral bone surface expanded to include estimated amount of cartilage, for example, expanded 1 mm, 1.5 mm, or 2 mm. For example, the guide tool shown in FIG. 84A can be used to make a 2 mm cut at a 5 degree A-P slope. The guide rod can be as described above.

Figure 84B:
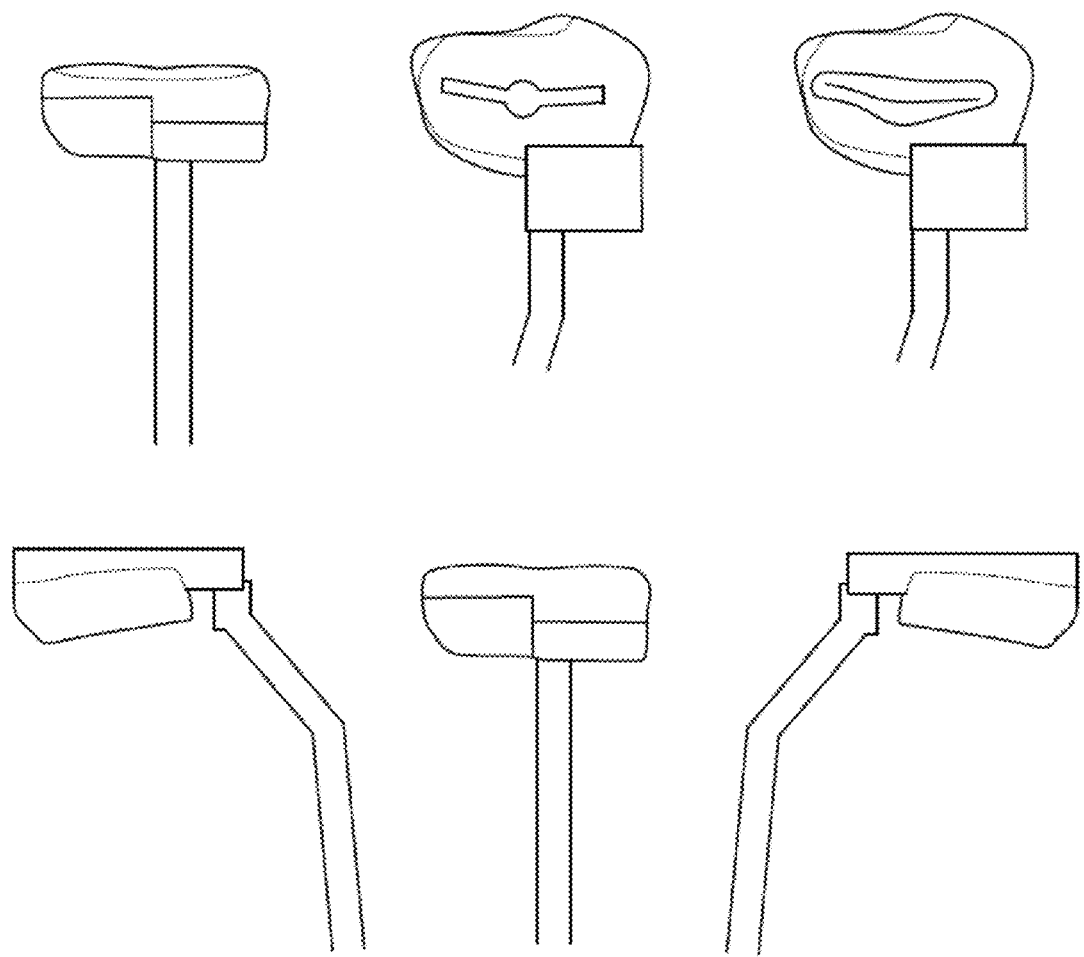
FIG. 84B shows a tibial guide tool to resect into the resected tibial surface to create a notch for accepting the keel of a tibial implant component, the profile of the guide is an exact match to the profile of cut tibia, the stem hole is created using a 14 mm drill bit, a Keel Prep Guide seats in the drilled stem hole, and the keel slot is created with 3 holes on each side using a 4 mm drill bit and an osteotome.
Figures 86A, 86B, 86C, 86D:
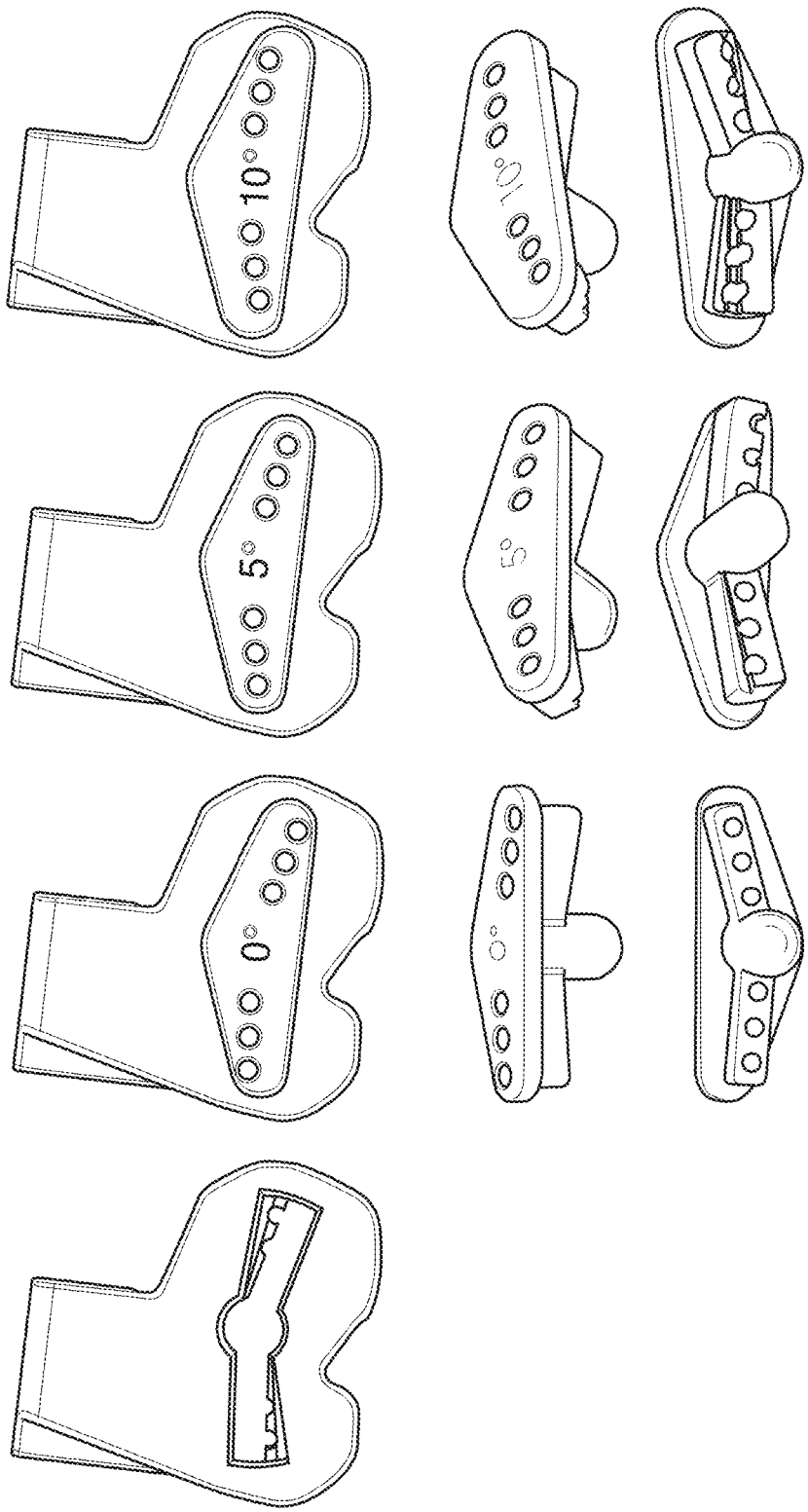
FIGS. 86A through 86D show the same front view of the guide tools and inserts shown in FIGS. 85A through 85D and, in addition, show front and back view of three exemplary inserts.

FIG. 84B shows a tibial guide tool to resect into the cut tibial surface to create a notch for accepting the keel of a tibial implant component. In certain embodiments, the perimeter of this tool can be patient-specific to match the perimeter of the patient's cut tibial surface. In certain embodiments, the perimeter of this tool can match the perimeter of the tibial implant component that will rest on the cut tibial surface. Alternatively, the perimeter of this tool can be engineered to be some amount less than the perimeter of the patient's cut tibia. The amount that the perimeter is less that the cut tibia can be, for example, a percentage of surface area or circumferential distance, for example, 2% less, 4% less, 5% less, 6% less, 8% less, 10% less, or some other percent less than the corresponding measure on the patient's cut tibia. Alternatively, the tibial guide tool and also, optionally, the tibial implant component, can include a perimeter that is less than the corresponding measure on the patient's cut tibia by an amount calculated to allow for a certain level of intraoperative rotation of the tibial implant component without any overhang of the tibial implant component perimeter.

Various methods can be used to allow for intraoperative rotation of the tibial implant component during installation of the implant. Being able to rotate and install a rotated tibial implant component can be important in balancing the joint with the implant. One example of a method for intraoperatively preparing a rotated tibial implant component is shown in FIGS. 85A through 85D. In particular, FIGS. FIGS. 85A through 85D show the front and back views of the same tibial guide tool to resect into the cut tibial surface to create a notch for accepting the keel of a tibial implant component. FIGS. FIGS. 85B through 85D each additionally show an insert with holes for guiding a drilling tool. The holes in each figure are oriented at different angles. Specifically, the insert in FIG. 85B can create holes at a 0 degree rotation angle; the insert in FIG. 85C can create holes at a 5 degree rotation angle; and the insert in FIG. 85D can create holes at a 5 degree rotation angle. Accordingly, by supplying along with the guide tool a series of inserts with holes at various angles, the resected holes and subsequent notch can be rotated at any desired angle (for which an insert has been supplied), which in turn will rotate the tibial implant component by the same angle as its keel is placed into the notch. Inserts can be included to have any degree of rotated holes, for example, inserts can be included to rotate the notch and implant 1, 2, 3, 4, 5, 6, 7, 8, 9, 10 degrees or more. Any number of inserts with different hole rotations can be included. In certain embodiments, the a maximum rotation for a given tibial implant component can be calculated as the rotation at which an undersized component perimeter extends beyond (i.e., overhangs) the perimeter of the patient's cut tibial surface, and inserts can be limited to this maximum rotation. FIGS. 86A through 86D show the same front view of the guide tools and inserts shown in FIGS. 85A through 85D and, in addition, show front and back view of three exemplary inserts. As shown in the figures, in certain embodiments the inserts can include differently keyed insert shapes.

9. Manufacturing

The step of designing an implant component and/or guide tool as described herein can include both configuring one or more features, measurements, and/or dimensions of the implant and/or guide tool (e.g., derived from patient-specific data from a particular patient and adapted for the particular patient) and manufacturing the implant. In certain embodiments, manufacturing can include making the implant component and/or guide tool from starting materials, for example, metals and/or polymers or other materials in solid (e.g., powders or blocks) or liquid form. In addition or alternatively, in certain embodiments, manufacturing can include altering (e.g., machining) an existing implant component and/or guide tool, for example, a standard blank implant component and/or guide tool or an existing implant component and/or guide tool (e.g., selected from a library). The manufacturing techniques to making or altering an implant component and/or guide tool can include any techniques known in the art today and in the future. Such techniques include, but are not limited to additive as well as subtractive methods, i.e., methods that add material, for example to a standard blank, and methods that remove material, for example from a standard blank.

Various technologies appropriate for this purpose are known in the art, for example, as described in *Wohlers Report 2009, State of the Industry Annual Worldwide Progress Report on Additive Manufacturing*, Wohlers Associates, 2009 (ISBN 0-9754429-5-3), available from the web www-.wohlersassociates.com, Pham and Dimov, *Rapid manufacturing*, Springer-Verlag, 2001 (ISBN 1-85233-360-X); Grenda, *Printing the Future, The 3D Printing and Rapid Prototyping Source Book*, Castle Island Co., 2009; *Virtual Prototyping & Bio Manufacturing in Medical Applications*, Bidanda and Bartolo (Eds.), Springer, Dec. 17, 2007 (ISBN: 10: 0387334297; 13: 978-0387334295); *Bio-Materials and Prototyping Applications in Medicine*, Bartolo and Bidanda (Eds.), Springer, Dec. 10, 2007 (ISBN: 10: 0387476822; 13: 978-0387476827); Liou, *Rapid Prototyping and Engineering Applications: A Toolbox for Prototype Development*, CRC, Sep. 26, 2007 (ISBN: 10: 0849334098; 13: 978-0849334092); *Advanced Manufacturing Technology for Medical Applications: Reverse Engineering, Software Conversion and Rapid Prototyping*, Gibson (Ed.), Wiley, January 2006 (ISBN: 10: 0470016884; 13: 978-0470016886); and Branner et al., "Coupled Field Simulation in Additive Layer Manufacturing," 3rd International Conference PMI, 2008 (10 pages).

Exemplary techniques for adapting an implant to a patient's anatomy include, but are not limited to those shown in Table 18.

TABLE 18

Exemplary techniques for forming or altering a patient-specific and/or patient-engineered implant component for a patient's anatomy

| Technique | Brief description of technique and related notes |
|---|---|
| CNC | CNC refers to computer numerically controlled (CNC) machine tools, a computer-driven technique, e.g., computer-code instructions, in which machine tools are driven by one or more computers. Embodiments of this method can interface with CAD software to streamline the automated design and manufacturing process. |
| CAM | CAM refers to computer-aided manufacturing (CAM) and can be used to describe the use of software programming tools to efficiently manage manufacturing and production of products and prototypes. CAM can be used with CAD to generate CNC code for manufacturing three-dimensional objects. |
| Casting, including casting using rapid | Casting is a manufacturing technique that employs a mold. Typically, a mold includes the negative of the desired shape of a |

TABLE 18-continued

Exemplary techniques for forming or altering a patient-specific and/or patient-engineered implant component for a patient's anatomy

| Technique | Brief description of technique and related notes |
|---|---|
| prototyped casting patterns | product. A liquid material is poured into the mold and allowed to cure, for example, with time, cooling, and/or with the addition of a solidifying agent. The resulting solid material or casting can be worked subsequently, for example, by sanding or bonding to another casting to generate a final product. |
| Welding | Welding is a manufacturing technique in which two components are fused together at one or more locations. In certain embodiments, the component joining surfaces include metal or thermoplastic and heat is administered as part of the fusion technique. |
| Forging | Forging is a manufacturing technique in which a product or component, typically a metal, is shaped, typically by heating and applying force. |
| Rapid prototyping | Rapid prototyping refers generally to automated construction of a prototype or product, typically using an additive manufacturing technology, such as EBM, SLS, SLM, SLA, DMLS, 3DP, FDM and other technologies |
| EBM ® | EBM ® refers to electron beam melting (EBM ®), which is a powder-based additive manufacturing technology. Typically, successive layers of metal powder are deposited and melted with an electron beam in a vacuum. |
| SLS | SLS refers to selective laser sintering (SLS), which is a powder-based additive manufacturing technology. Typically, successive layers of a powder (e.g., polymer, metal, sand, or other material) are deposited and melted with a scanning laser, for example, a carbon dioxide laser. |
| SLM | SLM refers to selective laser melting ™ (SLM), which is a technology similar to SLS; however, with SLM the powder material is fully melted to form a fully-dense product. |
| SLA or SL | SLA or SL refers to stereolithography (SLA or SL), which is a liquid-based additive manufacturing technology. Typically, successive layers of a liquid resin are exposed to a curing, for example, with UV laser light, to solidify each layer and bond it to the layer below. This technology typically requires the additional and removal of support structures when creating particular geometries. |
| DMLS | DMLS refers to direct metal laser sintering (DMLS), which is a powder-based additive manufacturing technology. Typically, metal powder is deposited and melted locally using a fiber optic laser. Complex and highly accurate geometries can be produced with this technology. This technology supports net-shaping, which means that the product generated from the technology requires little or no subsequent surface finishing. |
| LC | LC refers to LaserCusing ®(LC), which is a powder-based additive manufacturing technology. LC is similar to DMLS; however, with LC a high-energy laser is used to completely melt the powder, thereby creating a fully-dense product. |
| 3DP | 3DP refers to three-dimensional printing (3DP), which is a high-speed additive manufacturing technology that can deposit various types of materials in powder, liquid, or granular form in a printer-like fashion. Deposited layers can be cured layer by layer or, alternatively, for granular deposition, an intervening adhesive step can be used to secure layered granules together in bed of granules and the multiple layers subsequently can be cured together, for example, with laser or light curing. |
| LENS | LENS ® refers to Laser Engineered Net Shaping ™ (LENS ®), which is a powder-based additive manufacturing technology. Typically, a metal powder is supplied to the focus of the laser beam at a deposition head. The laser beam melts the powder as it is applied, in raster fashion. The process continues layer by and layer and requires no subsequent curing. This technology supports net-shaping, which means that the product generated from the technology requires little or no subsequent surface finishing. |
| FDM | FDM refers to fused deposition modeling ™ (FDM) is an extrusion-based additive manufacturing technology. Typically, beads of heated extruded polymers are deposited row by row and layer by layer. The beads harden as the extruded polymer cools. |

9.1 Implant Components Generated from Different Manufacturing Methods

Implant components generated by different techniques can be assessed and compared for their accuracy of shape relative to the intended shape design, for their mechanical strength, and for other factors. In this way, different manufacturing techniques can supply another consideration for achieving an implant component design with one or more target features. For example, if accuracy of shape relative to the intended shape design is critical to a particular patient's implant component design, then the manufacturing technique supplying the most accurate shape can be selected. If a minimum implant thickness is critical to a particular patient's implant component design, then the manufacturing technique supplying the highest mechanical strength and therefore allowing the most minimal implant component thickness, can be selected. Branner et al. describe a method a method for the design and optimization of additive layer manufacturing through a numerical coupled-field simulation, based on the finite element analysis (FEA). Branner's method can be used for assessing and comparing product mechanical strength generated by different additive layer manufacturing techniques, for example, SLM, DMLS, and LC.

In certain embodiments, an implant can include components and/or implant component parts produced via various methods. For example, in certain embodiments for a knee implant, the knee implant can include a metal femoral implant component produced by casting or by an additive manufacturing technique and having a patient-specific femoral intercondylar distance; a tibial component cut from a blank and machined to be patient-specific for the perimeter of the patient's cut tibia; and a tibial insert having a standard lock and a top surface that is patient-specific for at least the patient's intercondylar distance between the tibial insert dishes to accommodate the patient-specific femoral intercondylar distance of the femoral implant.

As another example, in certain embodiments a knee implant can include a metal femoral implant component produced by casting or by an additive manufacturing technique that is patient-specific with respect to a particular patient's M-L dimension and standard with respect to the patient's femoral intercondylar distance; a tibial component cut from a blank and machined to be patient-specific for the perimeter of the patient's cut tibia; and a tibial insert having a standard lock and a top surface that includes a standard intercondylar distance between the tibial insert dishes to accommodate the standard femoral intercondylar distance of the femoral implant.

9.2 Repair Materials

A wide variety of materials find use in the practice of the embodiments described herein, including, but not limited to, plastics, metals, crystal free metals, ceramics, biological materials (e.g., collagen or other extracellular matrix materials), hydroxyapatite, cells (e.g., stem cells, chondrocyte cells or the like), or combinations thereof. Based on the information (e.g., measurements) obtained regarding the defect and the articular surface and/or the subchondral bone, a repair material can be formed or selected. Further, using one or more of these techniques described herein, a cartilage replacement or regenerating material having a curvature that will fit into a particular cartilage defect, will follow the contour and shape of the articular surface, and will match the thickness of the surrounding cartilage. The repair material can include any combination of materials, and typically includes at least one non-pliable material, for example materials that are not easily bent or changed.

Currently, joint repair systems often employ metal and/or polymeric materials including, for example, prostheses which are anchored into the underlying bone (e.g., a femur in the case of a knee prosthesis). See, e.g., U.S. Pat. No. 6,203,576 to Afriat et al. issued Mar. 20, 2001 and U.S. Pat. No. 6,322,588 to Ogle, et al. issued Nov. 27, 2001, and references cited therein. A wide-variety of metals is useful in the practice of the embodiments described herein, and can be selected based on any criteria. For example, material selection can be based on resiliency to impart a desired degree of rigidity. Non-limiting examples of suitable metals include silver, gold, platinum, palladium, iridium, copper, tin, lead, antimony, bismuth, zinc, titanium, cobalt, stainless steel, nickel, iron alloys, cobalt alloys, such as Elgiloy®, a cobalt-chromium-nickel alloy, and MP35N, a nickel-cobalt-chromiummolybdenum alloy, and Nitinol T™, a nickel-titanium alloy, aluminum, manganese, iron, tantalum, crystal free metals, such as Liquidmetal® alloys (available from LiquidMetal Technologies, www.liquidmetal.com), other metals that can slowly form polyvalent metal ions, for example to inhibit calcification of implanted substrates in contact with a patient's bodily fluids or tissues, and combinations thereof.

Suitable synthetic polymers include, without limitation, polyamides (e.g., nylon), polyesters, polystyrenes, polyacrylates, vinyl polymers (e.g., polyethylene, polytetrafluoroethylene, polypropylene and polyvinyl chloride), polycarbonates, polyurethanes, poly dimethyl siloxanes, cellulose acetates, polymethyl methacrylates, polyether ether ketones, ethylene vinyl acetates, polysulfones, nitrocelluloses, similar copolymers and mixtures thereof. Bioresorbable synthetic polymers can also be used such as dextran, hydroxyethyl starch, derivatives of gelatin, polyvinylpyrrolidone, polyvinyl alcohol, poly[N-(2-hydroxypropyl) methacrylamide], poly(hydroxy acids), poly(epsilon-caprolactone), polylactic acid, polyglycolic acid, poly(dimethyl glycolic acid), poly(hydroxy butyrate), and similar copolymers.

Other appropriate materials include, for example, the polyketone known as polyetheretherketone (PEEKT). This includes the material PEEK 450G, which is an unfilled PEEK approved for medical implantation available from Victrex of Lancashire, Great Britain. (Victrex is located at www.matweb.com or see Boedeker www.boedeker.com). Other sources of this material include Gharda located in Panoli, India (www.ghardapolymers.com).

It should be noted that the material selected can also be filled. For example, other grades of PEEK are also available and contemplated, such as 30% glass-filled or 30% carbon filled, provided such materials are cleared for use in implantable devices by the FDA, or other regulatory body. Glass filled PEEK reduces the expansion rate and increases the flexural modulus of PEEK relative to that portion which is unfilled. The resulting product is known to be ideal for improved strength, stiffness, or stability. Carbon filled PEEK is known to enhance the compressive strength and stiffness of PEEK and lower its expansion rate. Carbon filled PEEK offers wear resistance and load carrying capability.

As will be appreciated, other suitable similarly biocompatible thermoplastic or thermoplastic polycondensate materials that resist fatigue, have good memory, are flexible, are deflectable, have very low moisture absorption, and/or have good wear and/or abrasion resistance, can be used. The implant can also be comprised of polyctherketoneketone (PEKK).

Other materials that can be used include polyetherketone (PEK), polyetherketoneetherketoneketone (PEKEKK), and polyetheretherketoneketone (PEEKK), and, generally, a polyaryletheretherketone. Further, other polyketones can be used as well as other thermoplastics.

Reference to appropriate polymers that can be used for the implant can be made to the following documents, all of which are incorporated herein by reference. These documents include: PCT Publication WO 02/02158 A1, dated Jan. 10, 2002 and entitled Bio-Compatible Polymeric Materials; PCT Publication WO 02/00275 A1, dated Jan. 3, 2002 and entitled Bio-Compatible Polymeric Materials; and PCT Publication WO 02/00270 A1, dated Jan. 3, 2002 and entitled Bio-Compatible Polymeric Materials.

The polymers can be prepared by any of a variety of approaches including conventional polymer processing methods. Preferred approaches include, for example, injection molding, which is suitable for the production of polymer components with significant structural features, and rapid prototyping approaches, such as reaction injection molding and stereo-lithography. The substrate can be textured or made porous by either physical abrasion or chemical alteration to facilitate incorporation of the metal coating. Other processes are also appropriate, such as extrusion, injection, compression molding and/or machining techniques. Typically, the polymer is chosen for its physical and mechanical properties and is suitable for carrying and spreading the physical load between the joint surfaces.

More than one metal and/or polymer can be used in combination with each other. For example, one or more metal-containing substrates can be coated with polymers in one or more regions or, alternatively, one or more polymer-containing substrate can be coated in one or more regions with one or more metals.

The system or prosthesis can be porous or porous coated. The porous surface components can be made of various materials including metals, ceramics, and polymers. These surface components can, in turn, be secured by various means to a multitude of structural cores formed of various metals. Suitable porous coatings include, but are not limited to, metal, ceramic, polymeric (e.g., biologically neutral elastomers such as silicone rubber, polyethylene terephthalate and/or combinations thereof or combinations thereof. See, e.g., U.S. Pat. No. 3,605,123 to Hahn, issued Sep. 20, 1971. U.S. Pat. No. 3,808,606 to Tronzo issued May 7, 1974 and U.S. Pat. No. 3,843,975 to Tronzo issued Oct. 29, 1974; U.S. Pat. No. 3,314,420 to Smith issued Apr. 18, 1967; U.S. Pat. No. 3,987,499 to Scharbach issued Oct. 26, 1976; and German Offenlegungsschrift 2,306,552. There can be more than one coating layer and the layers can have the same or different porosities. See, e.g., U.S. Pat. No. 3,938,198 to Kahn, et al., issued Feb. 17, 1976.

The coating can be applied by surrounding a core with powdered polymer and heating until cured to form a coating with an internal network of interconnected pores. The tortuosity of the pores (e.g., a measure of length to diameter of the paths through the pores) can be important in evaluating the probable success of such a coating in use on a prosthetic device. See, also, U.S. Pat. No. 4,213,816 to Morris issued Jul. 22, 1980. The porous coating can be applied in the form of a powder and the article as a whole subjected to an elevated temperature that bonds the powder to the substrate. Selection of suitable polymers and/or powder coatings can be determined in view of the teachings and references cited herein, for example based on the melt index of each.

EXAMPLES

Example 1 describes an exemplary process for designing a patient-adapted implant component. Example 2 describes an exemplary patient-adapted knee implants components and methods for designing the same. Example 3 describes exemplary knee implants components having patient-adapted features and non-traditional features. Example 4 illustrates an implant and implant design having straight and curvilinear bone cuts. Example 5 illustrates an implant and implant design having resurfacing and one or no bone cuts. Example 6 describes an exemplary femoral implant component having non-traditional bone cuts on its inner, bone-facing surface. Example 7 describes an exemplary femoral implant component with an enhanced articular surface. Example 8 illustrates a patient-adapted implant design for an implant having a femoral component and a patella component. Example 9 illustrates an exemplary process for virtually aligning a patient's lower extremity, in preparation for designing a knee implant component. Example 10 illustrates a finite element analysis ("FEA") used to design and/or assess an implant component.

Example 11 describes and exemplary tibial implant design and related resection techniques. Example 12 describes exemplary tibial tray and insert designs and related jigs and cutting designs. Example 13 describes an exemplary design for a tibial implant component.

Example 14 illustrates a set of jigs for guiding patient-specific bone cuts in a femur-first technique. Example 15 illustrates a set of jigs for guiding patient-specific bone cuts in a tibia-first technique.

Example 1

Exemplary Design Process for Certain Patient-Specific Total Knee Implants

This example describes an exemplary process for selecting and/or designing a patient-adapted total knee implant, for example, a knee implant having one or more patient-specific and/or patient-engineered based on patient-specific data. The steps described in this process can be performed in any order and can be performed more than once in a particular process. For example, one or more steps can be reiterated and refined a second, third, or more times, before, during, or after performing other steps or sets of steps in the process. While this process specifically describes steps for selecting and/or designing a patient-specific total knee implant, it can be adapted to design other embodiments, for example, patient-adapted bicompartmental knee implants, unicompartmental knee implants, and implants for shoulders and hips, vertebrae, and other joints.

1.1 Methods

Figure 87:
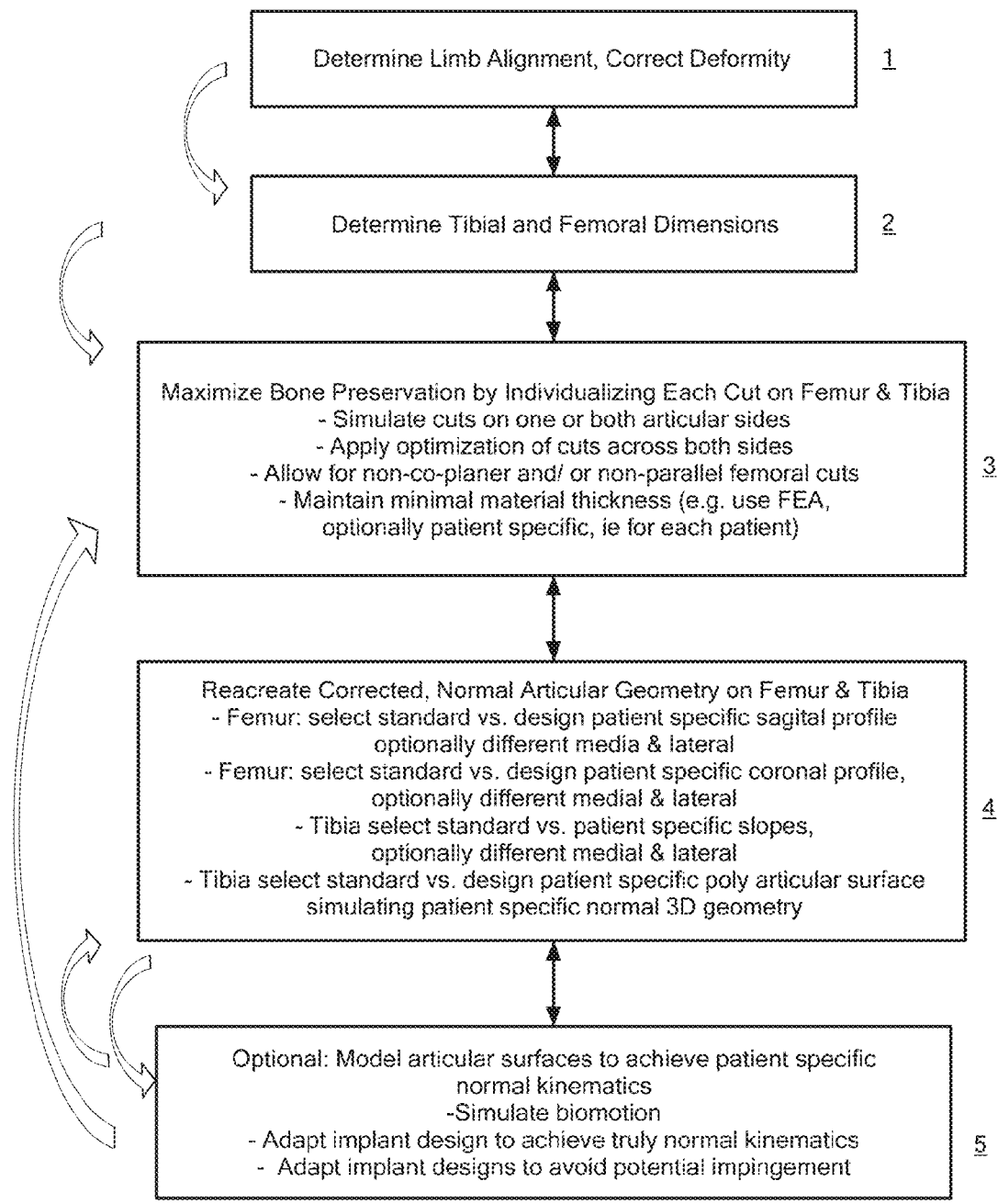
FIG. 87 is a flow chart illustrating an exemplary process for selecting and/or designing a patient-adapted total knee implant.

The exemplary process shown in FIG. 87 includes four general steps and, optionally, can include a fifth general step. Each general step includes various specific steps. The general steps are identified as (1)-(5) in the figure. These steps can be performed virtually, for example, by using one or more computers that have or can receive patient-specific data and specifically configured software or instructions to perform such steps.

In general step (1), limb alignment and deformity corrections are determined, to the extent that either is needed for a specific patient's situation. In general step (2), the requisite tibial and femoral dimensions of the implant components are determined based on patient-specific data obtained, for example, from image data of the patient's knee.

In general step (3), bone preservation is maximized by virtually determining a resection cut strategy for the patient's femur and/or tibia that provides minimal bone loss optionally while also meeting other user-defined parameters such as, for example, maintaining a minimum implant thickness, using certain resection cuts to help correct the patient's misalignment, removing diseased or undesired portions of the patient's bone or anatomy, and/or other parameters. This general step can include one or more of the steps of (i) simulating resection cuts on one or both articular sides (e.g., on the femur and/or tibia), (ii) applying optimized cuts across one or both articular sides, (iii) allowing for non-co-planar and/or non-parallel femoral resection cuts (e.g., on medial and lateral corresponding portions of the femur) and, optionally, non-co-planar and/or non-parallel tibial resection cuts (e.g., on medial and lateral corresponding portions of the tibia), and (iv) maintaining and/or determining minimal material thickness. The minimal material thickness for the implant selection and/or design can be an established threshold, for example, as previously determined by a finite element analysis ("FEA") of the implant's standard characteristics and features. Alternatively, the minimal material thickness can be determined for the specific implant, for example, as determined by an FEA of the implant's standard and patient-specific characteristics and features. This step identifies for a surgeon the bone resection design to perform in the surgical theater and it also identifies the design of the bone-facing surface(s) of the implant components, which substantially negatively-match the patient's resected bone surfaces, at least in part.

In general step (4), a corrected, normal and/or optimized articular geometry on the femur and tibia is recreated virtually. For the femur, this general step can include, for example, the step of: (i) selecting a standard sagittal profile, or selecting and/or designing a patient-engineered or patient-specific sagittal profile; and (ii) selecting a standard coronal profile, or selecting and/or designing a patient-specific or patient-engineered coronal profile. Optionally, the sagittal and/or coronal profiles of one or more corresponding medial and lateral portions (e.g., medial and lateral condyles) can include different curvatures. For the tibia, this general step includes one or both of the steps of: (iii) selecting a standard anterior-posterior slope, and/or selecting and/or designing a patient-specific or patient-engineered anterior-posterior slope, either of which optionally can vary from medial to lateral sides; and (iv) selecting a standard poly-articular surface, or selecting and/or designing a patient-specific or patient-engineered poly-articular surface. The patient-specific poly-articular surface can be selected and/or designed, for example, to simulate the normal or optimized three-dimensional geometry of the patient's tibial articular surface. The patient-engineered poly-articular surface can be selected and/or designed, for example, to optimize kinematics with the bearing surfaces of the femoral implant component. This step can be used to define the bearing portion of the outer, joint-facing surfaces (i.e., articular surfaces) of the implant components.

In optional general step (5), a virtual implant model (for example, generated and displayed using a computer specifically configured with software and/or instructions to assess and display such models) is assessed and can be altered to achieve normal or optimized kinematics for the patient. For example, the outer joint-facing or articular surface(s) of one or more implant components can be assessed and adapted to improve kinematics for the patient. This general step can include one or more of the steps of: (i) virtually simulating biomotion of the model, (ii) adapting the implant design to achieve normal or optimized kinematics for the patient, and (iii) adapting the implant design to avoid potential impingement.

1.2 Results and Discussion

The exemplary process described above yields both a predetermined surgical resection design for altering articular surfaces of a patient's bones during surgery and a design for an implant that specifically fits the patient, for example, following the surgical bone resectioning. Specifically, the implant selection and/or design, which can include manufacturing or machining the implant to the selected and/or designed specifications using known techniques, includes one or more patient-engineered bone-facing surfaces that negatively-match the patient's resected bone surface. The implant also can include other features that are patient-adapted, such as minimal implant thickness, articular geometry, and kinematic design features. This process can be applied to various joint implants and to various types of joint implants. For example, this design process can be applied to a total knee, cruciate retaining, posterior stabilized, and/or ACL/PCL retaining knee implants, bicompartmental knee implants, unicompartmental knee implants, and other joint implants, for example, for the shoulder, hip, elbow, spine, or other joints.

The exemplary process described above, including the resulting patient-adapted implants and predetermined bone resectioning design, offers several advantages over traditional primary and revision implants and related processes. For example, it allows for one or more pre-primary implants such that a subsequent replacement or improvement can take the form of a primary implant. Specifically, because the process described herein can minimize the amount of bone that is resected, enough bone stock may remain such that a subsequent procedure may be performed with a traditional, primary, off-the-shelf implant. This offers a significant advantage for younger patients who may require in their lifetime more than a single revision for an implant. In fact, the exemplary process described above may allow for two or more pre-primary implants or procedures before so much bone stock is sacrificed that a traditional, primary implant is required.

The advantageous minimal bone resectioning and therefore minimal bone loss that is achieved with this process arises from the fact that the bone-facing surfaces of the implants are derived for each patient based on patient-specific data, such as, for example, data derived from images of the patient's joint, size or weight of the patient, size of the joint, and size, shape and/or severity of defects and/or disease in the joint. This patient-adapted approach allows for the bone-facing surface of the implant components to be optimized with respect to any number of parameters, including minimizing bone loss, using any number of resection cuts and corresponding implant component bone cuts and bone cut facets to conserve bone for the patient. With traditional implants, the implant's bone-facing surface includes standard bone cuts and the resection cuts to the patient's bone are made to fit those standard bone cuts.

Another advantage to this process is that the selection and/or design process can incorporate any number of target parameters such that any number of implant component features and resection cuts can be selected and/or designed to meet one or more parameters that are predetermined to have clinical value. For example, in addition to bone preservation, a selection and/or design process can include target parameters to restore a patient's native, normal kinematics, or to provide optimized kinematics. For example, the process for selecting and/or designing an implant and/or resection cuts can include target parameters such as reducing or eliminating the patient's mid-flexion instability, reducing or eliminating "tight" closure, improving or extending flexion, improving or restoring cosmetic appearance, and/or creating or improving normal or expected sensations in the patient's knee. The design for a tibial implant can provide an engineered surface that replicates the patient's normal anatomy yet also allows for low contact stress on the tibia.

For surgeons and medical professionals, this process also provides a simplified surgical technique. The selected and/or designed bone cuts and, optionally, other features that provide a patient-adapted fit for the implant components eliminates the complications that arise in the surgical setting with traditional, misfitting implants. Moreover, since the process and implant component features are predetermined prior to surgery, model images of the surgical steps can be provided to the surgeon as a guide.

As noted above, the design of an implant component can include manufacturing or machining the component in accordance with the implant design specifications. Manufacturing can include, for example, using a designed mold to form the implant component. Machining can include, for example, altering a selected blank form to conform to the implant design specifications. For example, using the steps described above, the femoral implant component can be manufactured from a designed mold and the tibial implant component, including each of a tibial tray and insert, can be customized from a selected starting tray and insert, for example, from blanks.

Example 2

Figure 88B:
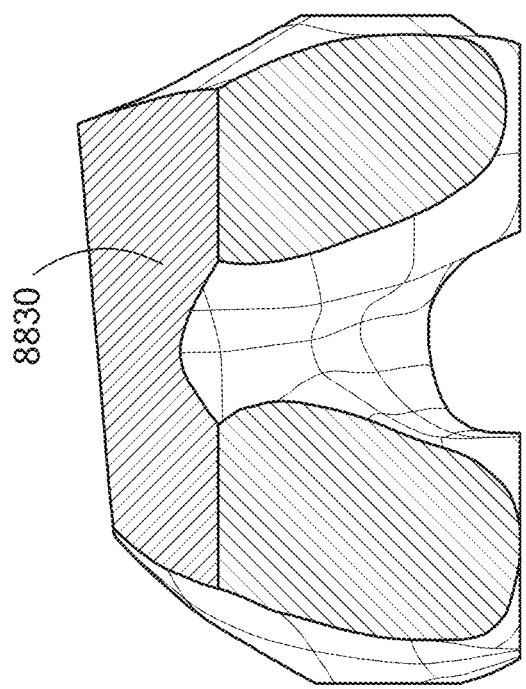
FIG. 88B shows an example of an anterior oblique resection plane 8830.
Figure 88A:
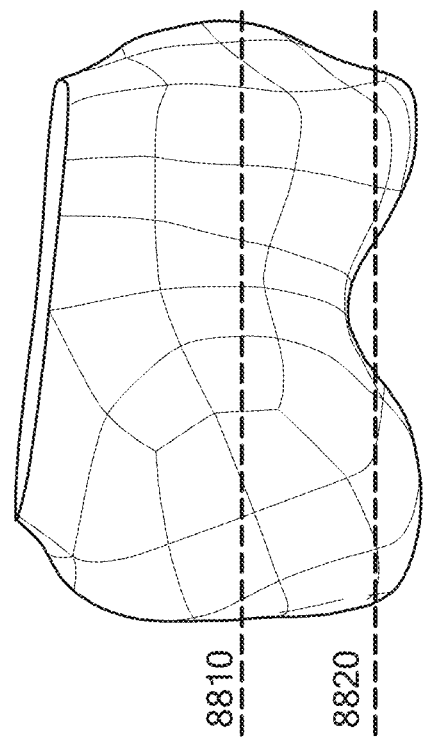
FIG. 88A illustrates a distal femur and a distal resection plane parallel to the epicondylar axis.

Patient-Adapted Femoral Implant Component with Five Bone Cuts and Corresponding Resection Cuts This example describes two exemplary methods for designing resection cuts to a patient's femur and related bone cuts on the bone-facing surface of a femoral implant component designed for the patient. In particular, in both methods, a model of a patient's distal femur is created based on data from patient-specific two- or three-dimensional images of the patient's femur. As shown in FIG. 88A, the epicondylar axis 8810 is determined for the patient's femur. Then, the resection cut planes and cut angles (and corresponding implant component cut planes and cut angles) are assessed and selected using the epicondylar axis 8810 as a reference. Specifically, four of the five cut planes—the distal cut, posterior cut, posterior chamfer cut, and anterior chamfer cut—are designed to be parallel with the epicondylar axis 8810. FIG. 88A shows the distal cut plane 8820 parallel to the epicondylar axis 8810. However, for the particular patient, the anterior cut plane is designed to be oblique to the epicondylar axis 8810, which can minimize the amount of bone resected on the lateral side of the cut. FIG. 88B shows an example of an anterior oblique cut plane 8830.

Figure 89C:
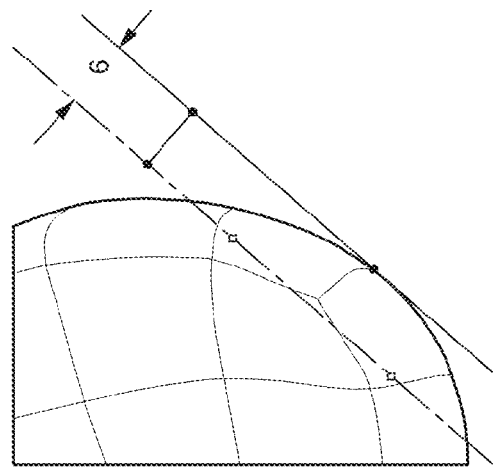
FIGS. 89A to 89E show optimized resection cut planes to a patient's femur based on the medial condyle.
Figure 89B:
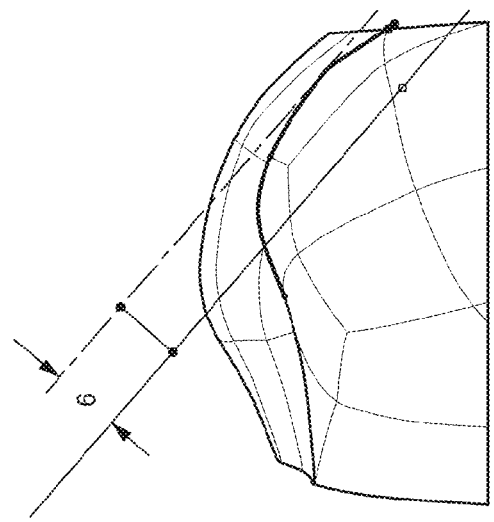
Figure 89A:
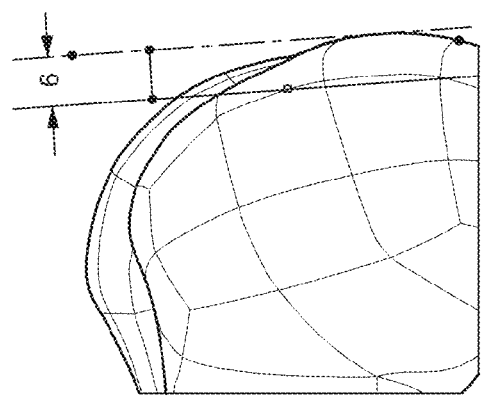
Figure 89E:
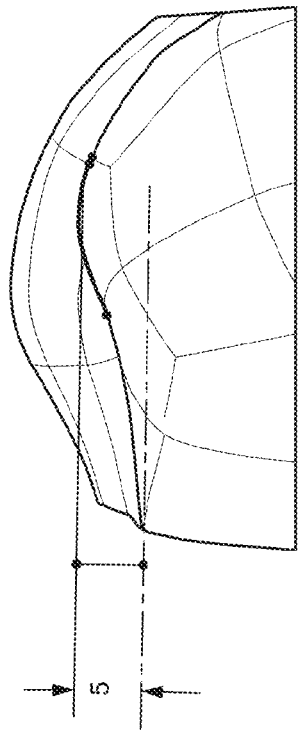
Figure 89D:
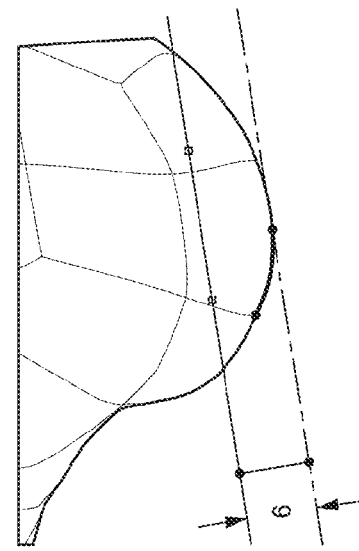

For each of the five cut planes, optimized cuts (i.e., resection cuts) tangent to the bone surface at the angle of each resection plane also is determined. The optimized cuts as shown in FIGS. 89A to 89E included a maximum cut depth of 6 mm for the distal cut plane (FIG. 89A), the anterior chamfer cut plane (FIG. 89B), the posterior chamfer cut (FIG. 89C), and the posterior cut plane (FIG. 89D). The maximum cut depth is 5 mm for the anterior cut plane (FIG. 89E). Optimized cuts can be determined based on one or more parameters, including those described above. In this example, optimized cut were determined, at least in part, to minimize resected bone while providing greater than a threshold minimum implant thickness. Deeper resection cuts allow for a thicker implant, but require greater bone loss. Typically, the thinnest resection cut depth and, accordingly, the minimum implant thickness occurs at the intersections between cut planes. Accordingly, alternatively or in addition to altering cut plane depths, the number of cut planes, the cut plane angles and/or the cut plane orientations can be altered to provide deeper cut plane intersections and corresponding greater minimum implant thickness at the bone cut intersections while also minimizing the amount of bone resected from the patient.

Figure 90B:
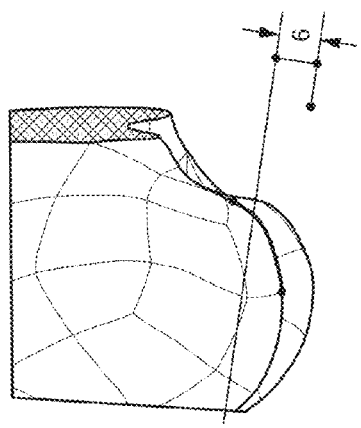
FIGS. 90A and 90B show resection cut planes for a patient's lateral condyle posterior chamfer (FIG. 90A) and lateral condyle posterior (FIG. 90B) cut planes that are independently optimized based on patient-specific data for the lateral condyle.
Figure 90A:
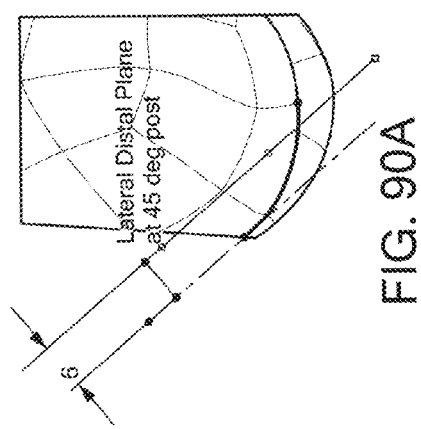

The optimized number of cut planes, depths of cut planes, angles of cut planes and/or orientations of cut planes can be determined independently for each of the medial and lateral femoral condyles. For example, FIGS. 89A to 89E show optimized cut planes based on the medial condyle. However, FIGS. 90A and 90B show cut planes for the lateral condyle posterior chamfer (FIG. 90A) and lateral condyle posterior (FIG. 90B) cut planes that are independently optimized (i.e., relative to the medial condyle posterior chamfer and medial condyle posterior cut planes, respectively) based on patient-specific data for the lateral condyle. This type of independent optimization between condyles can result in a different number of cut plane facets, different angles of cut plane facets, and/or different depths of cut plane facets on corresponding portions of medial and lateral condyles.

Figure 91B:
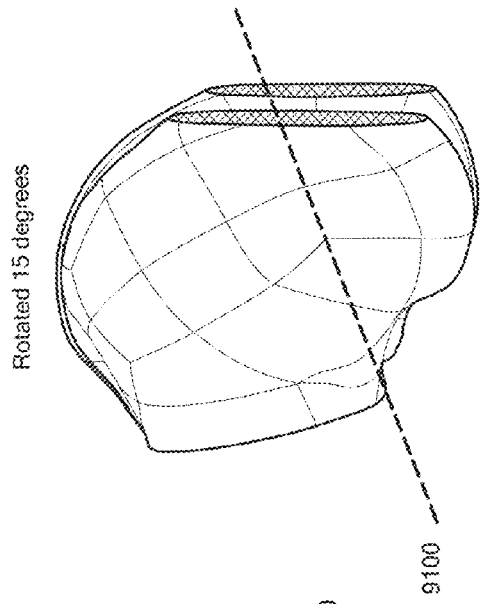
FIGS. 91A and 91B illustrate two exemplary distal resection cut planes for two different cut designs.
Figure 91A:
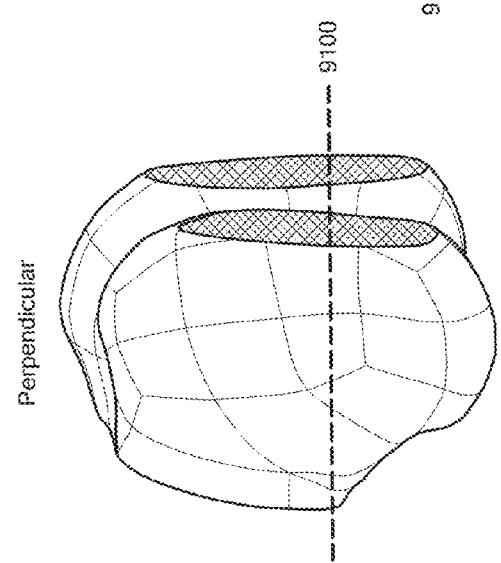

Two exemplary resection cut designs (and corresponding implant component bone cut design e.g., that includes substantially matching cut features of the resection cut design) is based on five cut planes are described in this example. In the first design, shown in FIG. 91A, a distal cut plane is designed perpendicular to the sagittal femoral axis 9100. In the second design, referred to as a "flexed" or "flex-fit" design" and shown in FIG. 91B, the distal cut plane is rotated 15 degrees in flexion from the perpendicular to the sagittal femoral axis. The additional four cut planes are shifted accordingly for each design method, as shown in FIGS. 92A and 92B.

Figure 94B:
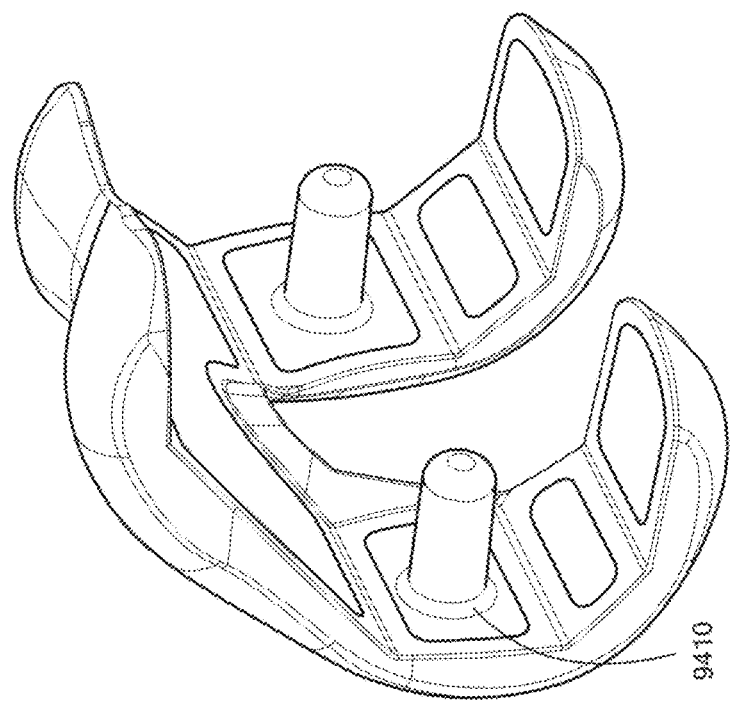
FIG. 94B illustrates an implant component design that includes a peg diameter of 7 mm with a rounded tip.
Figure 94A:
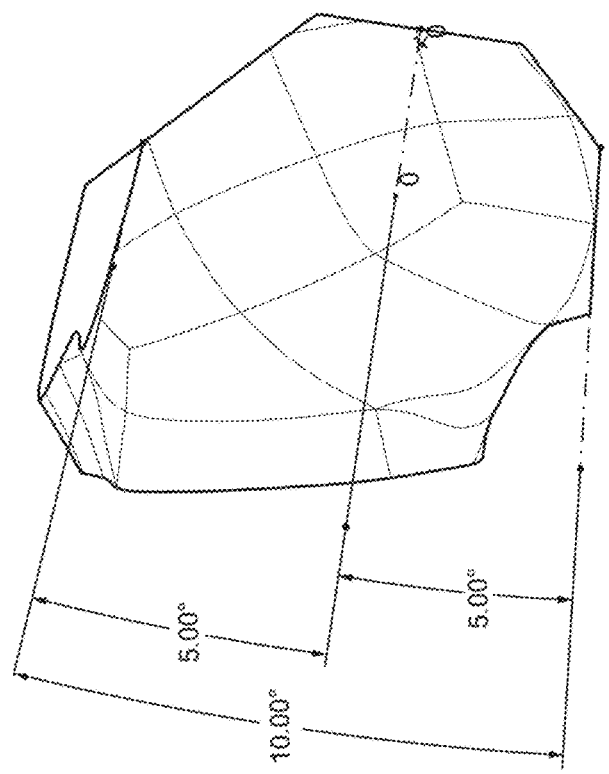
FIG. 94A illustrates an embodiment of a cut plane design having anterior and posterior cut planes that diverge from the component peg axis.

FIGS. 93A and 93B show the completed cut femur models for each cut design. For each design, the maximum resection depth for each cut plane was 6 mm, except for the anterior cut plane, which was 5 mm. The "flex-fit" design can provide more posterior coverage in high flexion. However, it also may require more anterior bone resectioning to achieve sufficient coverage and may require particular attention during actual bone cutting to avoid any incomplete bone removal at the trochlear notch 9310. In certain embodiments of a cut plane design, the anterior and posterior cut planes diverge from the component peg axis by five degrees each, as shown in FIG. 94A. With a traditional femoral implant component, the posterior and anterior cut planes diverge 2 degrees and 7 degrees, respectively, from the peg axis. Moreover, in certain embodiments, the peg can be designed to have various dimensions. For example, the design in FIG. 94B includes a peg diameter of 7 mm tapering to about 6.5 mm, a length of 14 mm with a rounded tip, and a base with a 1 mm fillet 9410.

Figure 95A:
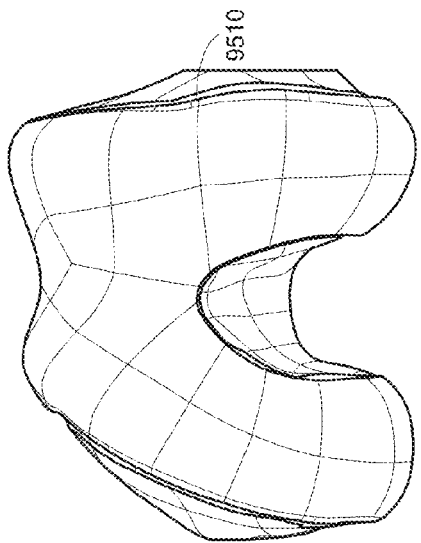
FIGS. 95A and 95B illustrate exemplary bone-facing surfaces of femoral implant component designs that include a patient-adapted peripheral margin.
Figure 95B:
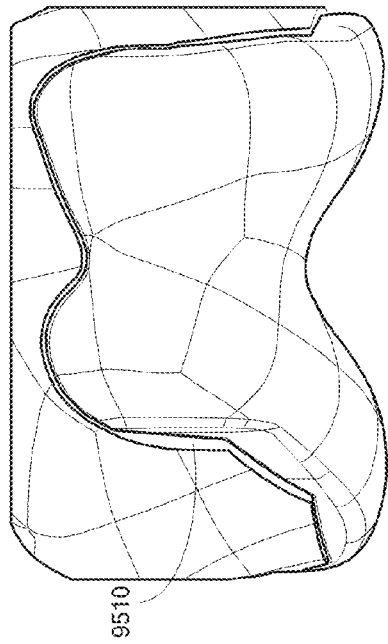
Figure 96A:
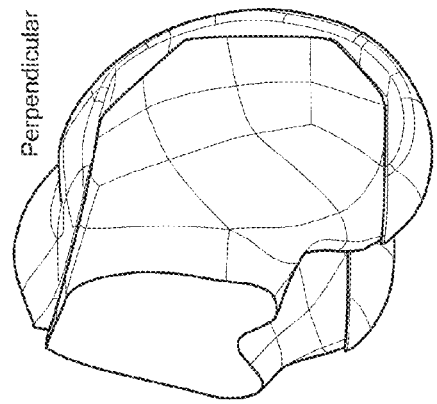
FIGS. 96A and 96B illustrate side views of exemplary femoral implant component designs.
Figure 96B:
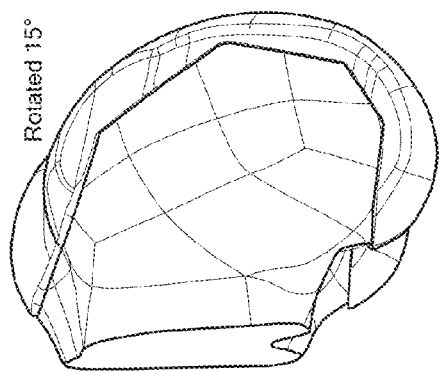

An exemplary bone facing surface of the femoral implant component design is shown in FIGS. 95A and 95B. In addition to optimized cut planes described above, these implant components also include a patient-adapted peripheral margin 9510 that is 0.5 mm from the edge of cut bone. The designs also can include engineered coronal curvatures on the condyles. Side views of the resulting femoral implant component designs for the first and second design methods are shown in FIGS. 96A and 96B. This sagittal view of the implant components shows the difference in anterior and posterior coverage for the two designs. As seen by a comparison of the two figures, the flexed cut design provides greater posterior coverage, which enhances deep knee flexion for the patient. Accordingly, as shown by this example, one or more features or measurements derived from patient-specific data are used to preoperatively select and/or design implant component features that target and achieve more than one parameter, in this case preservation of the patient's bone and preservation, restoration, or enhancement of the patient's joint kinematics.

As mentioned above, the optimization of resection cuts and implant component bone cuts can result in a cut design that has any number of cut planes or facets, depths of cut planes or facets, angles of cut planes or facets, and/or orientations of cut planes or facets. In addition to optimizing the cut planes to minimize bone loss and maximize implant thickness, various other parameters can be included in the cut plane optimization. In this example, the flexed cut design was used to help preserve, restore, or enhance the patient's joint kinematics. Additional parameters that may be included in the determination of optimized resection and bone cuts can include, but are not limited to, one or more of: (1) deformity correction and/or limb alignment (2) maximizing preservation of cartilage, or ligaments, (3) maximizing preservation and/or optimization of other features of the patient's anatomy, such as trochlea and trochlear shape, (4) further restoration and/or optimization of joint kinematics or biomechanics (5) restoration or optimization of joint-line location and/or joint gap width, and (6) preservation, restoration, or enhancement of other target features.

Example 3

Design of a Femoral Component of a Total Knee Replacement with a Bone-Facing Surface that Optimizes Bone Preservation This example describes an exemplary design of femoral implant component. In particular, the femoral component includes seven bone cuts on its inner, bone-facing surface.

3.1 Methods

Figure 98B:
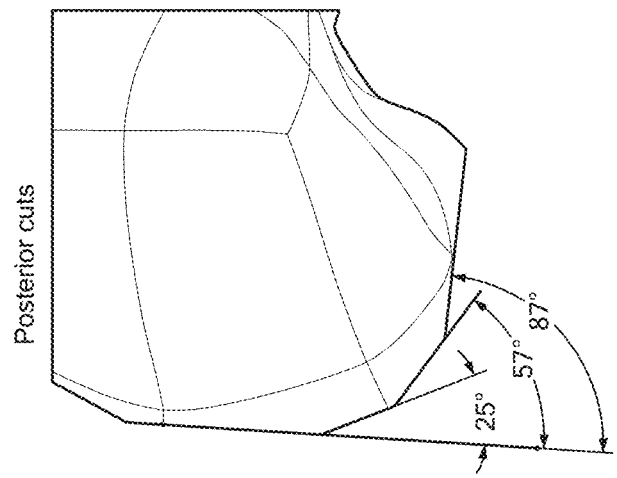
FIG. 98A and FIG. 98B illustrate the resection cut planes for the implant component of FIG. 97.
Figure 98A:
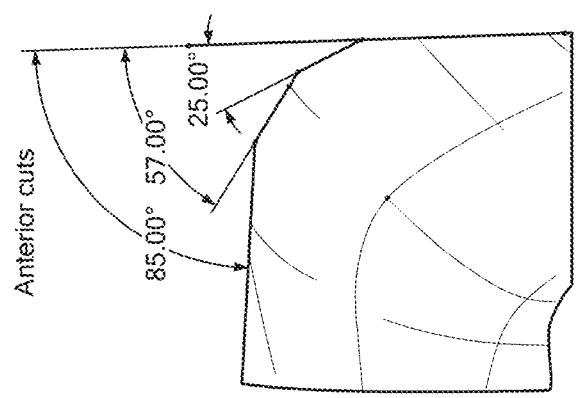
Figure 97:
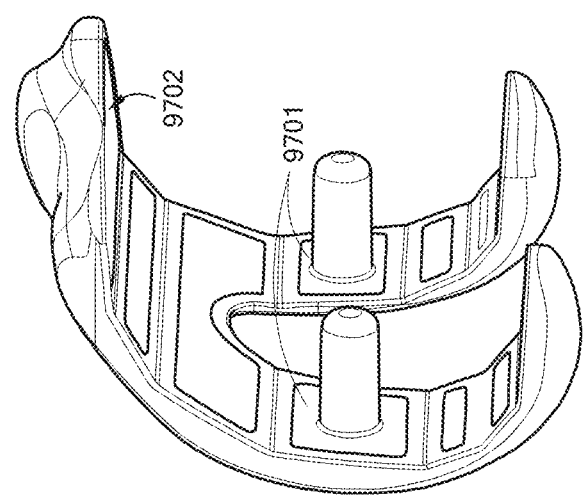
FIG. 97 illustrates a femoral implant component (PCL-retaining) having seven bone cuts.
Figure 99:
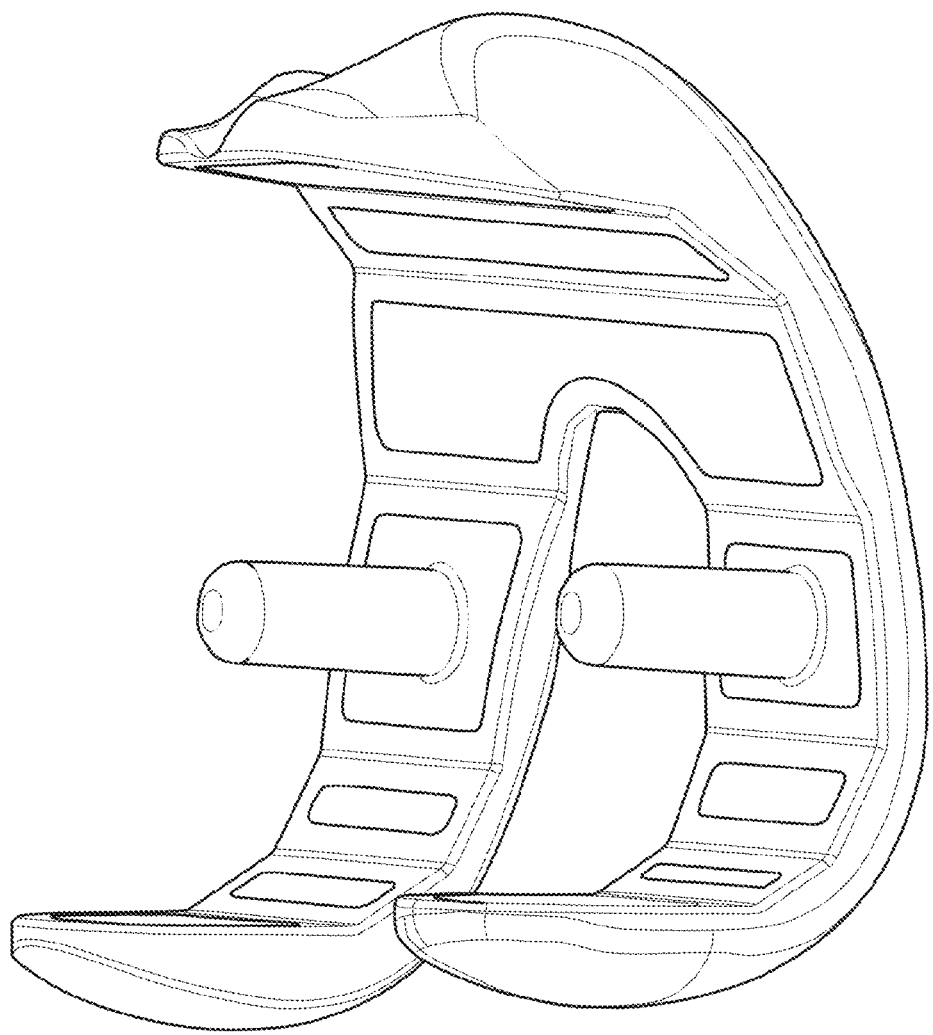
FIG. 99 illustrates the implant component of FIG. 97 from a different angle to show cement pocket and peg features.

A femoral implant component (PCL-retaining) is designed with seven bone cuts for a femur-first implantation technique. The design of the implant component is depicted in FIG. 97. The seven bone cuts on the inner, bone-facing surface of the implant component include a distal bone cut 9701 (including lateral and medial facets) that is perpendicular to the sagittal femoral axis, and an anterior cut 9702. The corresponding resection cut planes are shown in FIG. 98A and in FIG. 98B. Specifically, a first anterior chamfer cut plane is at 25 degrees, a second anterior chamfer cut plane is at 57 degrees, and an anterior cut plane is at 85 degrees relative to the distal femoral cut plane, as shown in FIG. 98A. Moreover, a first posterior chamfer cut plane is at 25 degrees, a second posterior chamfer cut plane is at 57 degrees, and a posterior chamfer cut plane is at 87 degrees relative to the distal femoral cut plane, as shown in FIG. 98B. The femoral implant includes bone cuts that substantially negatively-match (e.g., in cut angle, area, and/or orientation) the resection cuts on these cut planes. The femoral implant component also can include on its bone-facing surface cement cutouts 9704 that are 0.5 mm deep and offset from the outer edge by 2 mm, and a peg protruding from the each of the lateral and medial distal bone cuts facets. The pegs are 7 mm in diameter, 17 mm long and are tapered by 0.5 degrees as they extend from the component. FIG. 99 shows the cement pocket and peg features.

3.2 Results and Discussion

In a traditional femoral implant component, the bone-facing surface consists of five standard bone cuts. However, the femoral component in this example includes seven bone cuts on the bone-facing surface. The additional bone cuts can allow for the corresponding resection cut planes be less deep from the bone surface to insure that the cut plane intersections have a depth below the bone surface that allows for a minimum implant thickness. Accordingly, less bone can be resected for a seven-bone-cut implant component than for a traditional five-bone-cut implant component to provide the same minimum implant component thickness, e.g., at the bone cut intersections. Moreover, the outer, joint-facing surface of the implant component described in this example includes a combination of patient-adapted features and standard features.

Figure 100B:
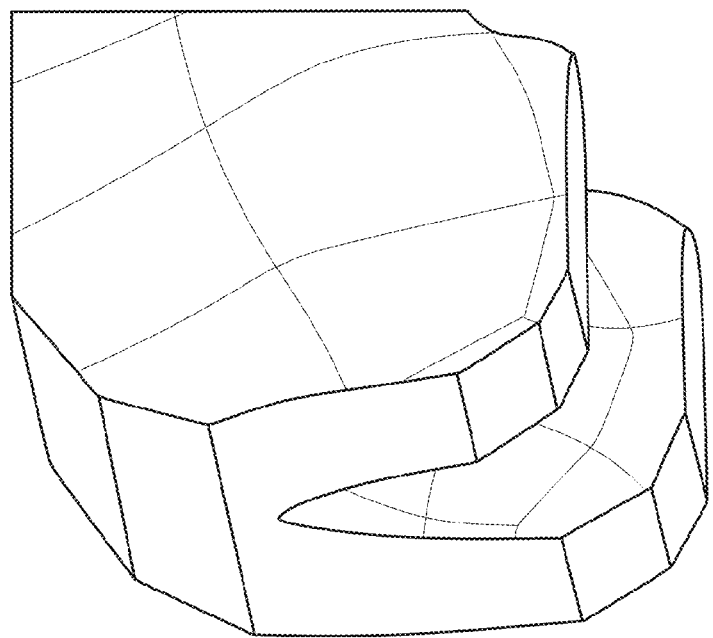
FIG. 100B shows a seven-cut-plane femoral resection design for a femoral implant component having seven bone cuts.
Figure 100A:
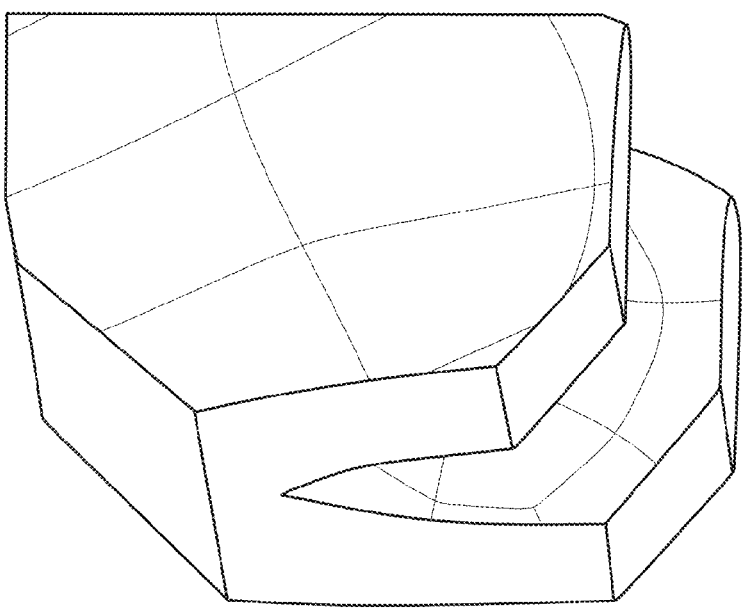
FIG. 100A shows a five-cut-plane femoral resection design for a femoral implant component having five bone cuts.

FIG. 100A shows a five-cut-plane femoral resection design for a femoral implant component having five bone cuts. FIG. 100B shows a seven-cut-plane femoral resection design for a femoral implant component having seven bone cuts. Each cut design was performed on the same patient femur model (i.e., having identical bone volumes). In addition, the corresponding five-bone-cut implant component and seven-bone-cut implant component were both designed meet or exceed the same minimum implant thickness. After performing the resection cuts, the model of the patient's femur having five resection cuts retained bone volume of 103,034 mm$^3$, while the model of the patient's femur having seven bone cuts retained a bone volume of 104,220 mm$^3$. As this analysis shows, the seven-bone-cut implant component saved substantially more of the patient's bone stock, in this case more than 1,000 mm$^3$, as compared to the five-bone cut implant component.

Figure 101B:
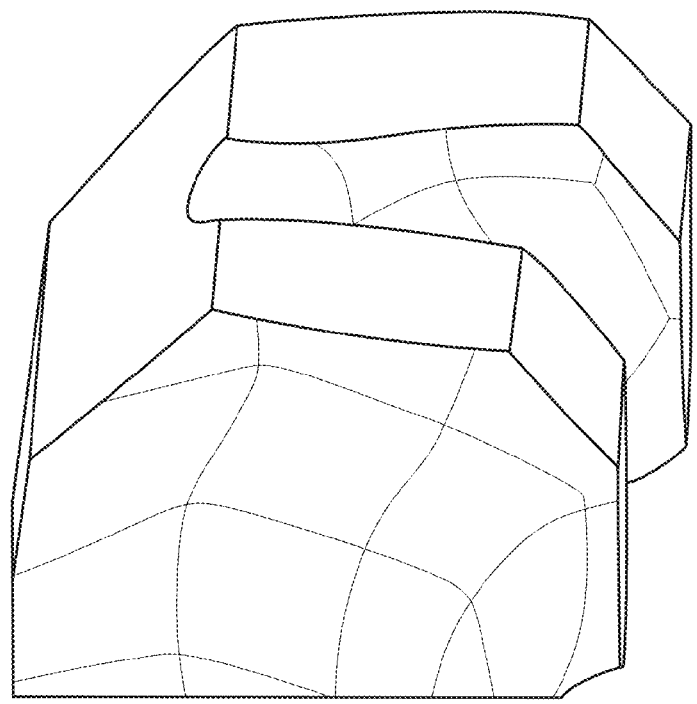
FIG. 101B shows the same femur but with five, flexed resection cuts.
Figure 101A:
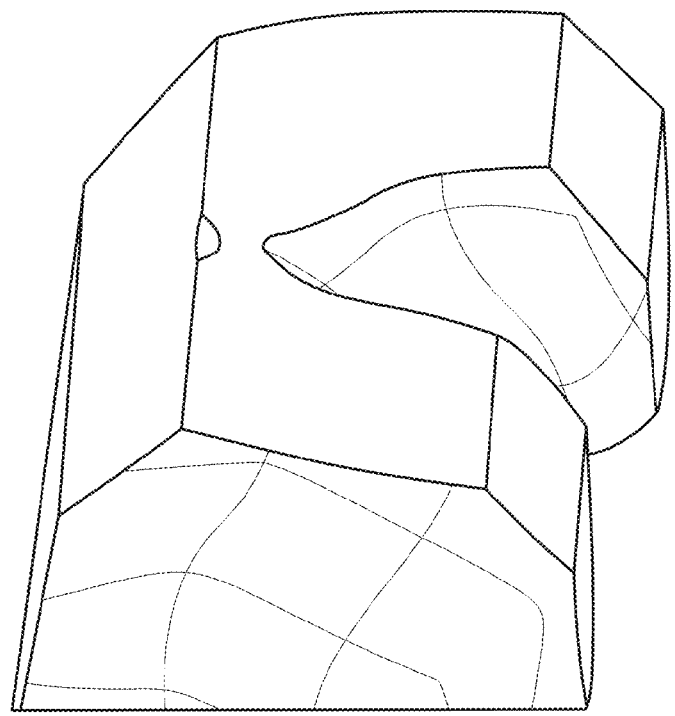
FIG. 101A shows a patient's femur having five, not flexed resection cuts.

A similar analysis was performed to assess relative bone loss between a five-cut design and a five-flexed cut design. FIG. 101A shows a patient's femur having five, not flexed resection cuts and FIG. 101B shows the same femur but with five, flexed resection cuts. As shown, the model having five, not flexed resection cuts retains a bone volume of 109,472 mm$^3$, while the model having five, flexed resection cuts retains a bone volume of 105,760 mm$^3$. As this analysis shows, the not-flexed-five-bone-cut implant component saved substantially more of the patient's bone stock, in this case nearly 4,000 mm$^3$, as compared to the flexed-five-bone-cut cut implant component. However, as noted in Example 2, the flexed cut design can offer other advantages, such as greater posterior coverage and enhanced deep-knee flexion, which can be weighed relative to all selected parameters and accordingly integrated in the selection and/or design of an implant component.

Figure 102B:
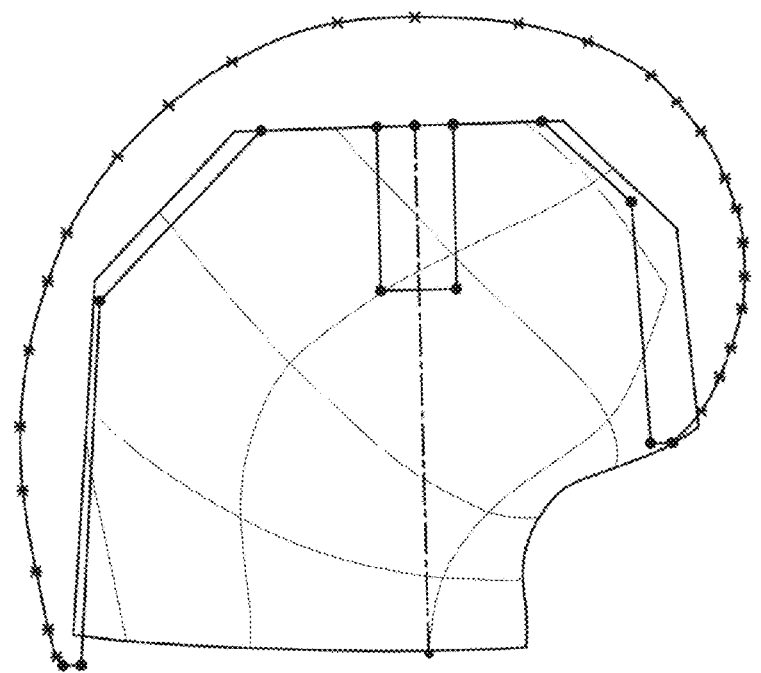
FIGS. 102A to 102D show outlines of a traditional five-cut femoral component (in hatched lines) overlaid with, in 102A, a femur having seven optimized resection cuts for matching an optimized seven-bone-cut implant component.
Figure 102A:
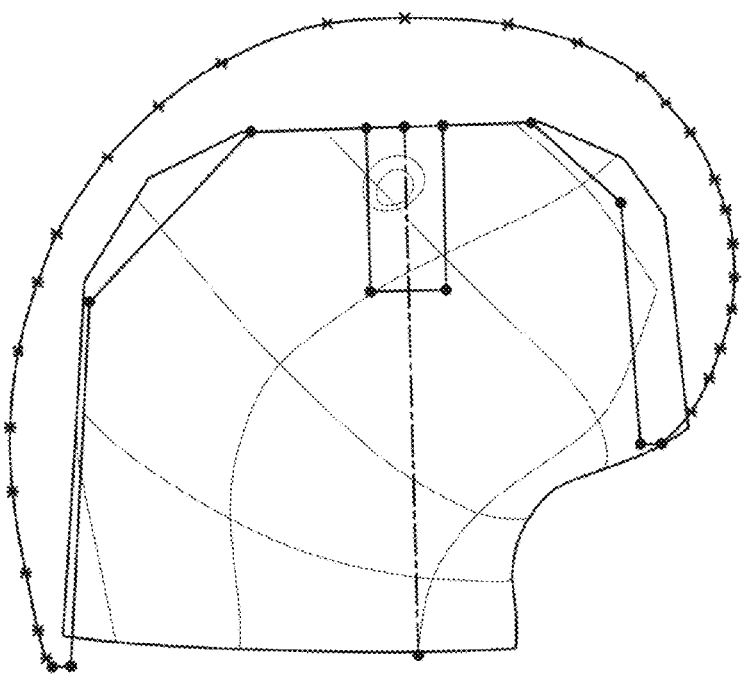
Figure 102D:
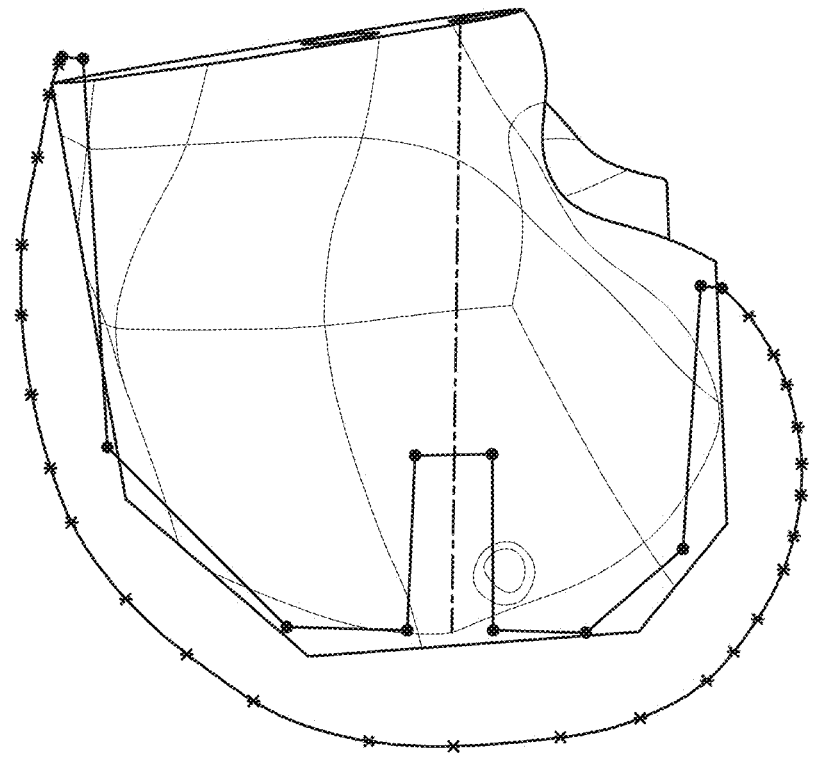
Figure 102C:
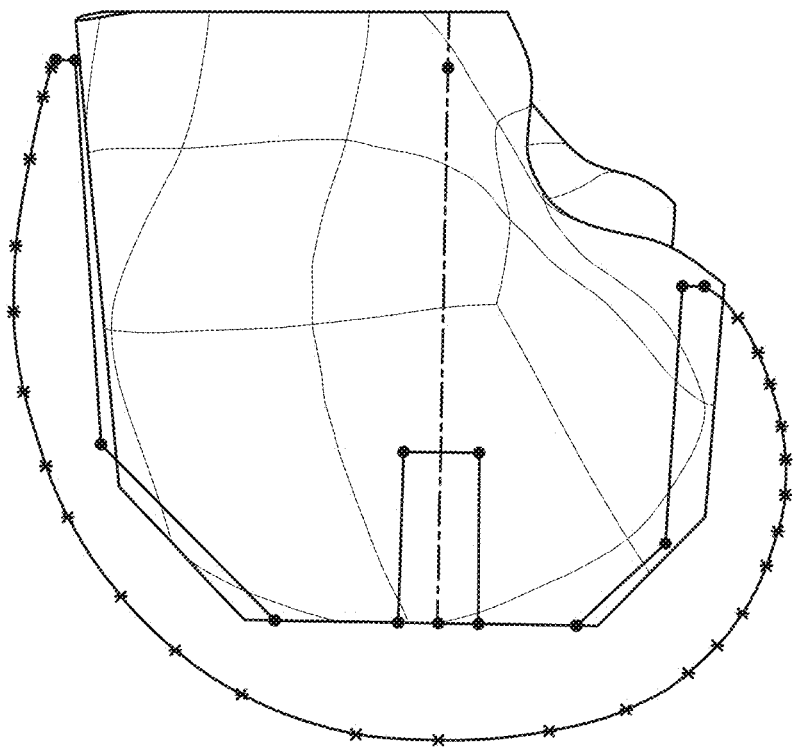

FIGS. 102A to 102D show outlines of a traditional five-cut femoral component (in hatched lines) overlaid with, in 102A, a femur having seven optimized resection cuts for matching an optimized seven-bone-cut implant component; in FIG. 102B, a femur having five optimized resection cuts for matching to an optimized five-bone-cut implant component; in FIG. 102C, a femur having five, not flexed resection cuts for matching to an optimized five-bone-cut implant component; and in FIG. 102D, a femur having five, flexed resection cuts for matching to an optimized five-bone-cut, flexed implant component. As shown in each of these figures, the designed bone cuts save substantial bone as compared to those required by a traditional implant component.

In summary, the component designs described in this example can save patient bone stock as compared to a traditional implant component and thereby allow the implant to be pre-primary. Alternatively or in addition, the implant components may include cut planes (i.e., of resection cuts and bone cuts) that are optimized based on patient-specific data to meet one or more user-defined parameters, as described above. For example, cut planes can be symmetric or asymmetric, parallel or non-parallel, aligned perpendicular to the sagittal plane or not perpendicular, varied from medial to lateral condyle, and/or can include other orientations. The cut plane designs may include a "flexed" (i.e., rotated or offset relative to the biomechanical or anatomical axes) orientation. Moreover, the design of attachment pegs may also be flexed relative to the biomechanical or anatomical axes.

Example 4

Patient-Adapted Implant Components and Guide Tools

This example describes designs and surgical implantation of knee implant components and guide tools having certain patient-specific, patient-engineered, and/or non-traditional standard features. In the studies described in this example, patient-adapted femoral, tibial, and patellar implant components were designed and implanted for each of three cadaveric patients. In addition, corresponding resection cut strategies were designed and performed. Moreover, several different patient-adapted guide tools were designed and used for the implantation procedure.

The implant components and guide tools (also referred to as "jigs" or "iJigs") for each patient were designed based on patient-specific CT-derived data from each patient. Specifically, data from CT images of each patient's knee was selected and imported into computer modeling software. The software was used to generate a model of the biological structures in the patient's knee and to design (e.g., using CAD software) a femoral implant component, a tibial implant component, and related guide tools. The design of the implant components and guide tools included manufacturing, for example, using CAM software and additive and/or casting manufacturing techniques as described above. In addition, predetermined resection cuts to each patient's femur and tibia were designed based on the patient's biology and in conjunction with the patient-adapted features of the implant component. For example, the resection cuts and the corresponding component's bone-facing surfaces were designed based on patient-specific data to substantially negatively match (e.g., in surface area, surface angle, and/or other feature). Then, surgery was performed on the cadaveric patient to perform the predetermined (e.g., designed) resection cuts and to implant the components designed for the particular patient. In addition, one or more guide tools were designed and used for the procedure which also were designed to include patient-adapted features, for example, a bone-facing surface that substantially negatively-matched the patient's anatomy and/or cutting guide slots or drilling guide holes that provided accurate placement for the predetermined resection cuts and holes for the particular patient.

4.1 Methods and Materials

Three surgical procedures were performed to implant femoral and tibial implant components for three different cadaveric patients. Prior to each surgery, patient-adapted implant components (femoral and tibial implant components) and guide tools were designed (including manufacturing) in conjunction with a resection cut design. Then, the guide tools were used during surgery to prepare the predetermined resection cuts and place the implant components.

Femoral Implant Component

Figure 103B:
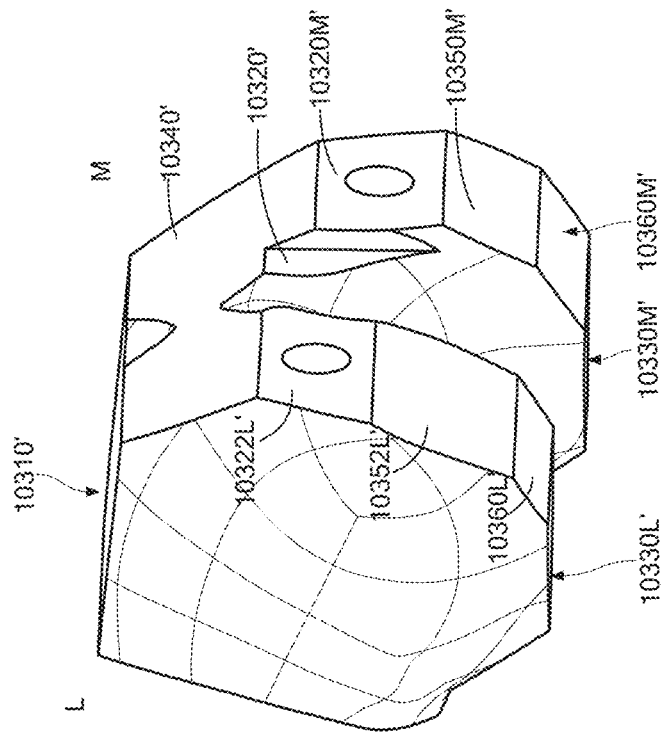
FIGS. 103A to 103F illustrate patient-adapted femoral implants and resection cuts for each of the three patients.
Figure 103A:
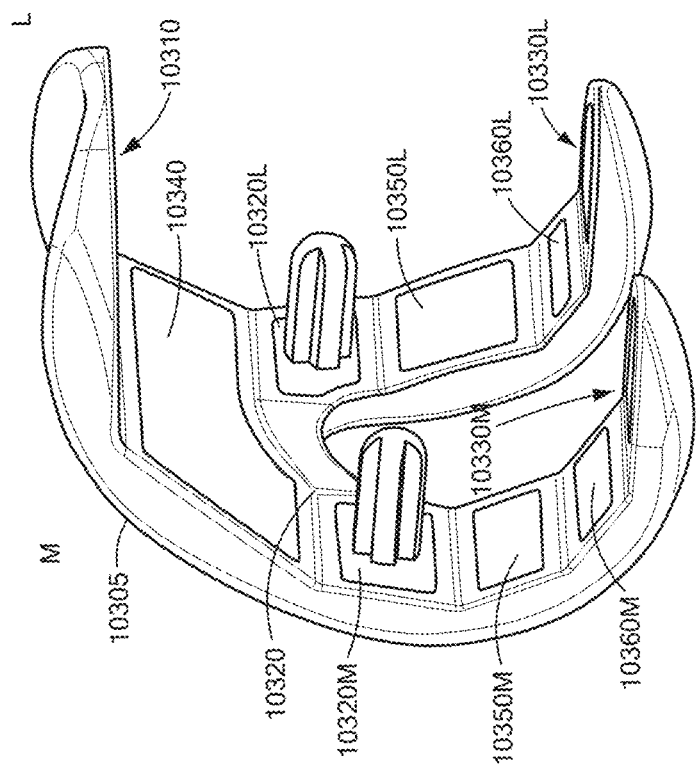
Figure 103C:
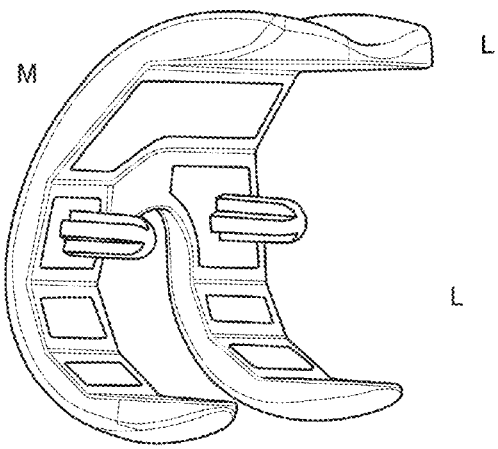

The patient-adapted femoral implant components each included six bone cuts. The bone cut design was designed in conjunction with corresponding resection cuts. FIGS. 103A and 103B, FIGS. 103C and 103D, and FIGS. 103E and 103F, show the patient-adapted femoral implant and resection cuts, respectively, for each of the three patients. As exemplified in FIG. 103A, the six bone cuts included an anterior bone cut 10310, medial 10320M and lateral 10320L facets of a distal bone cut, medial 10330M and lateral 10330L facets of a posterior bone cut, an anterior chamfer bone cut 10340, medial 10350M and lateral 10350L facets of a first posterior chamfer bone cut, and medial 10360M and lateral 10360L facets of a second posterior chamfer bone cut. In addition, the femoral implant component 10305 included a stepped (or "step") cut 10370 between the medial facet 10320M and lateral facet 10320L of the distal bone cut in order to provide enhanced preservation of distal medial bone stock. FIG. 103C relating to the second patient and FIG. 103E relating to the third patient include similar features as those numbered in FIG. 103A. As the figures show, the non-coplanar distal bone cut facets, which can be connected by a stepped cut, allow for independent and optionally minimum resection depths on the medial and lateral portions of an otherwise continuous bone cut (e.g., anterior bone cut, anterior chamfer bone cut, or distal bone cut).

Comparison between each of the three patient-adapted implant components and corresponding resection cuts shows various features of the implant component that specifically match features of the resection cuts and/or of the patient's anatomy. For example, each implant component includes a width, height, and condylar width that is patient-specific (i.e., matches the patient's anatomy) or patient-engineered (i.e., derived from patient-specific data to achieve one or more predetermined parameter thresholds, for example, an implant component peripheral margin that does not overhang the cut surface of the bone and provides no more than 1 mm or 0.5 mm or 0.3 mm exposed resection cut surface 10361).

Figure 103D:
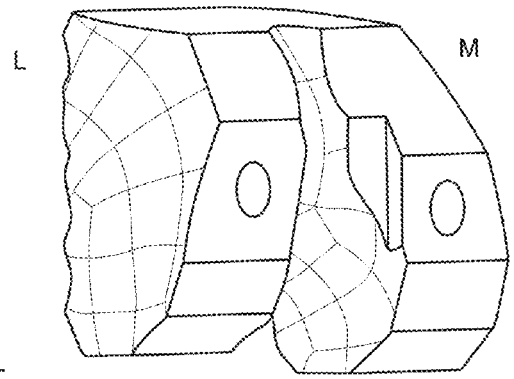
Figure 103E:
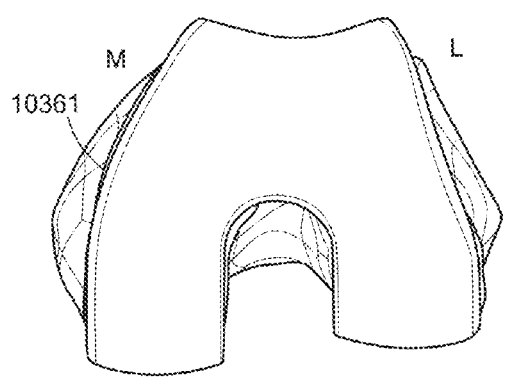
Figure 103F:
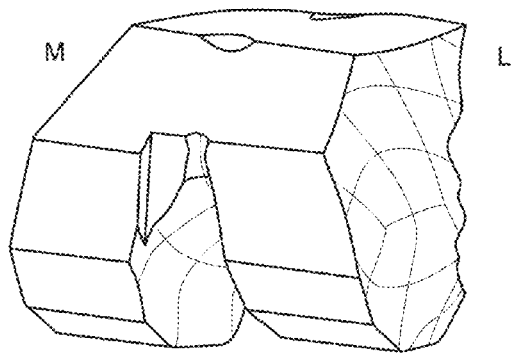

Moreover, as shown by a comparison of the figures, the implant component bone cuts for each patient was engineered to specifically-match the resection cuts for the patient (e.g., in cut and/or facet surface areas, angles, relative orientations, and/or other features). For example, as exemplified in FIG. 103B, the resection cuts included an anterior resection cut 10310', medial 10320M' and lateral 10320L' facets of a distal resection cut, medial 110330M' and lateral 10330L' facets of a posterior resection cut, an anterior chamfer resection cut 10340', medial 10350M' and lateral 10350L' facets of a first posterior chamfer resection cut, and medial 10360M' and lateral 10360L' facets of a second posterior chamfer resection cut. In addition, the femoral implant component included a stepped (or "step") resection cut 10370' between the medial facet 10320M' and lateral facet 10320L' of the distal resection cut. FIG. 103D relating to the second patient and FIG. 103F relating to the third patient include similar features as those numbered in FIG. 103B. As shown by the figures, the stepped cut 10320' saves substantial bone stock, for example, at the distal medial facet 10320M' in comparison to a distal medial facet cut having the same depth as the distal lateral facet cut.

In addition, each patient-adapted femoral implant component included on the joint-facing surface of each condyle a patient-specific J-curve that substantially positively matched the J-curve of the particular patient's femur. Toward the anterior joint-facing surface, each implant component included a trochlear groove profile that was patient-engineered to be offset 2 mm laterally (e.g., relative to the particular patient's trochlear groove), and that was angled laterally. The first two patients' implant components included a trochlear groove that engineered to be angled laterally at approximately 3-5 degrees, while the third patient's implant component included a trochlear groove that was engineered to be angled laterally at approximately 5-7 degrees. The trochlear surface profile was designed to accommodate a dome-shaped (e.g., in profile) patellar implant component. On the bone-surface of the femoral implant component, two pegs 7 mm in diameter projected from the medial 10320M and lateral 10320L facets of the distal bone cut. The receiving peg holes in the patient's distal femur were prepared with an 8 mm drill bit. Each bone cut and bone cut facet on the bone-facing surface of the femoral implant included a cement cutout to hold cement applied during the procedure.

Femoral Guide Tools

Figure 104B:
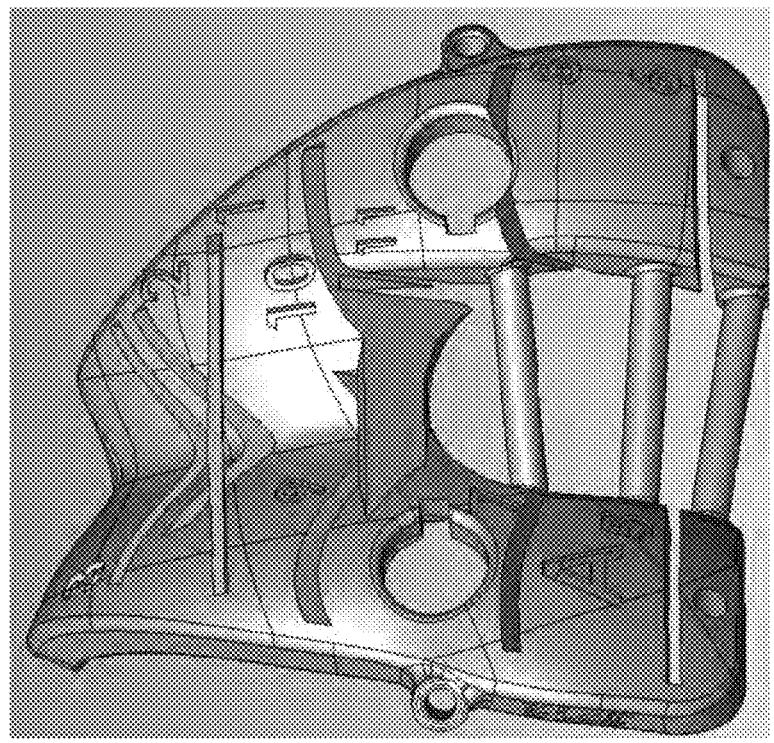
FIGS. 104A and 104B illustrate all-in-one femoral resection guide tools for each of two patients.
Figure 104A:
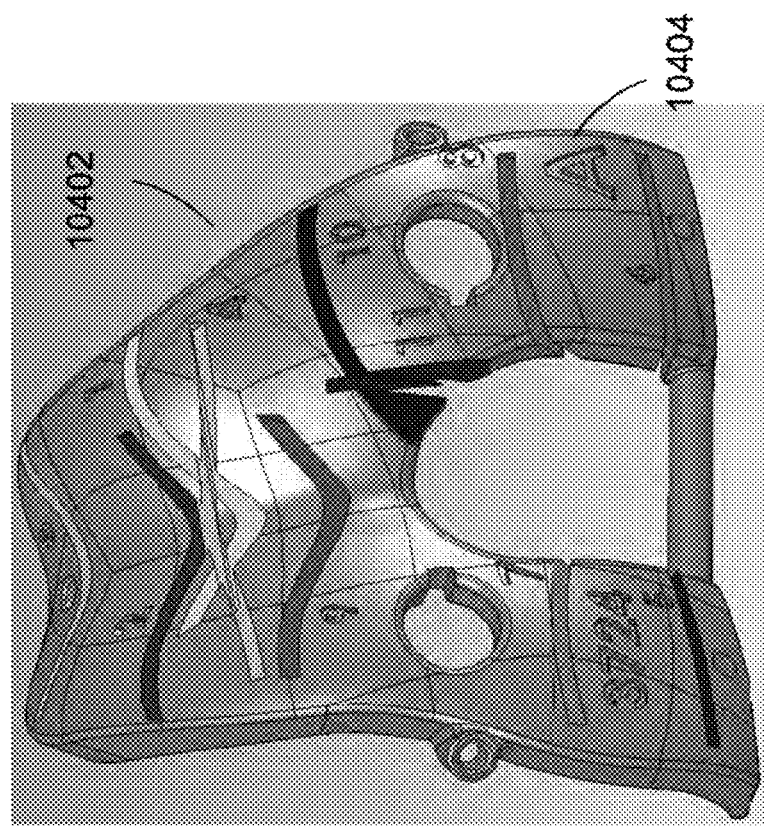

The guide tool designs were based on a tibial-cut-first technique. For the first two patients, a femoral all-in-one guide tool was designed to include guide slots and holes to perform all of the predetermined (e.g., designed based on patient-specific data) femoral resection cuts and peg hole placements. The all-in-one guide tools for each of the two patients are shown in FIGS. 104A and 104B, respectively. As shown in the figures, the guide slots were numbered sequentially 1-11 to guide the surgeon in the cutting steps and to maximize ease of use. The all-in-one guide tools 10402 also were prepared and provided to the surgeon in three different thicknesses denoted by different letters 10404, which allowed the surgeon to select the tool having the best fit, e.g., between the femur in tibia with the knee in extension. Accordingly, this guide tool 10402 aided the surgeon in assessing balance and implant fit, as well as providing guide slots for all cuts and drill holes for the patient's femur. In addition, the bone-facing surface of each all-in-one guide tool was designed to be patient-specific (i.e., designed based on patient-specific data to substantially match the corresponding biological surface of the patient). Moreover, a comparison of the two patient's guide tools, shown in FIGS. 104A and 104B, respectively, shows guide slots in different orientations from each other. These unique guide slot orientations are provided to establish the predetermined resection cuts specifically designed in conjunction with a patient-adapted implant component for each patient based on patient-specific data.

Figure 106A:
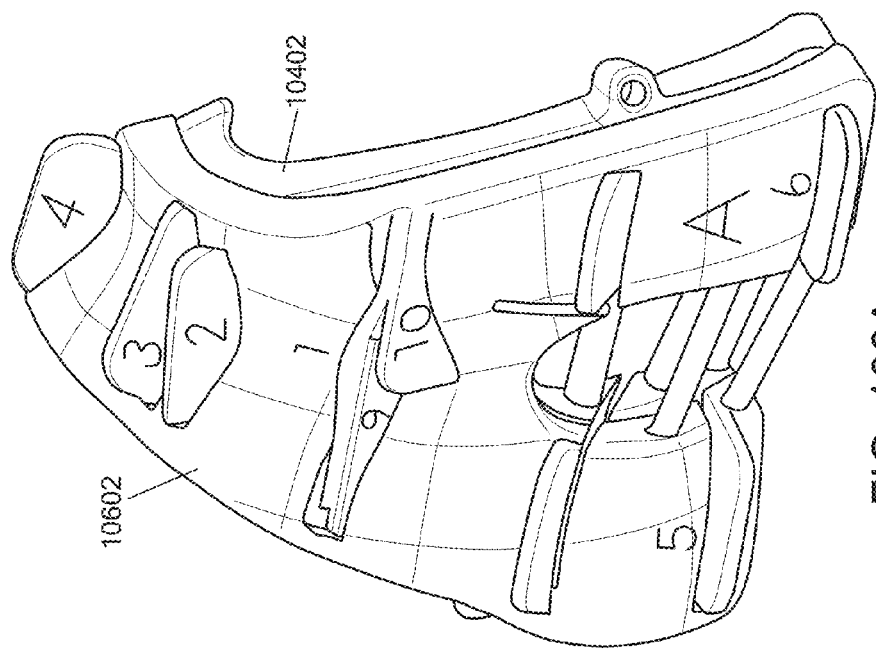
FIGS. 106A, 106B, and 106C show various too attachments for the all-in-one guide tool to extend one or more cutting surfaces.
Figure 105:
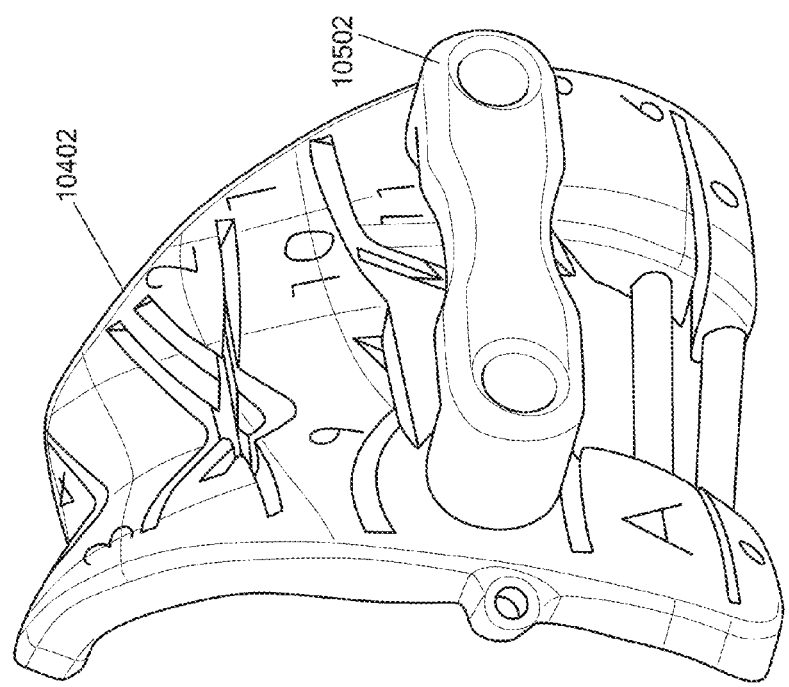
FIG. 105 illustrates a drill guide attachment for attaching to the all-in-one guide tool.
Figure 106C:
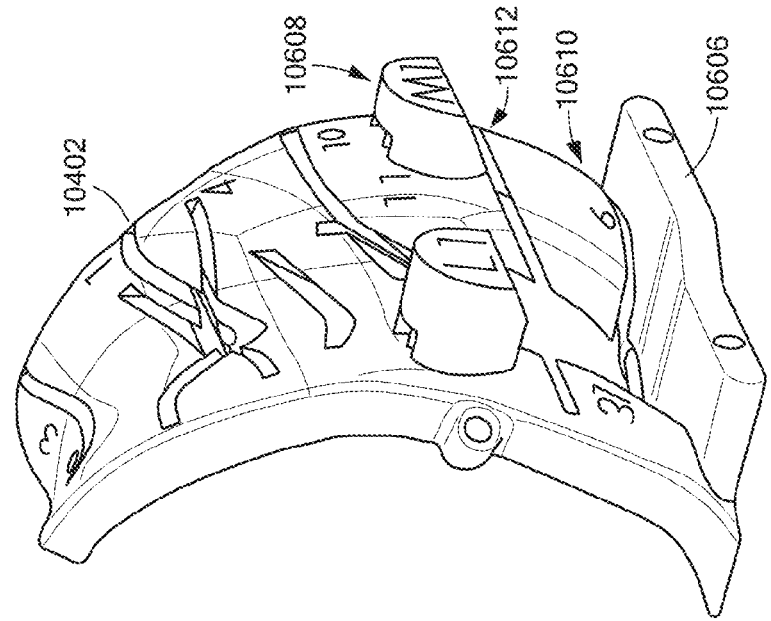
Figure 106B:
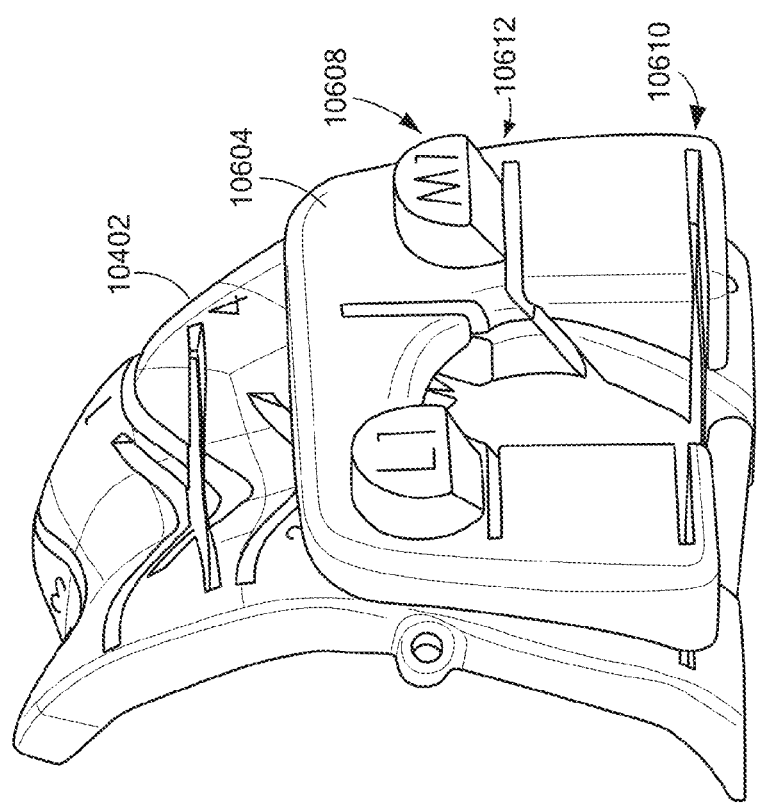

In addition, several guide tool attachments were designed and included for the for the all-in one guide tools 10402. For example, as shown in FIG. 105, a drill guide attachment 10502 was designed and included for attaching to the guide tool 10402 to extend the drilling surface. Moreover, as shown in FIGS. 106A, 106B, and 106C, various too attachments 10602, 10604, 10606, 10608 were designed and included for attaching to the all-in-one guide tool to extend one or more cutting surfaces. For example, the attachment 10602 in FIG. 106A extends the cutting surface area for all cutting slots. The attachment 10604 in FIG. 106B extends the surface area for the posterior resection cut slots 10610 and for posterior chamfer resection cut slots 10612. The attachment 10606 in FIG. 106B extends the surface area for the posterior resection cut slots 10610. In addition, guide peg attachments 10608 were designed and included to provide additional surface area for the posterior chamfer resection cut slots 10612. As shown, the guide pegs 10608 can be integrated with a guide attachment 10604 or can be used independently and, optionally, integrated with the guide tool 10402. In addition or as an alternative to extending a cutting surface, the guide pegs can be used to aid in securing the guide tool 10402 to the patient's femur after peg holes are drilled into the patient's femur.

As an alternative to the all-in-one guide tool 10402, a set of three guide tools also was designed and included for each of the first two patients. FIGS. 107A, 107B, and 107C illustrate the set of three guide tools, which collectively supplied all of the guide slots and holes to perform each of the predetermined femoral resection cuts and peg hole placements available in the single all-in-one guide tool 10402. This set of guide tools was included, for example, in case the all-in-one guide tool 10402 did not suit the needs of the surgeon. As with the all-in-one guide tool 10402, each of the three guide tools in the set included one or more patient-adapted features. As shown in FIG. 107A, the first guide tool 10780 in the set provided guide holes 10782 for drilling into the patient's femur predetermined holes for receiving the femoral implant component pegs. As shown in the figure, the guide tool 10780 is attached to the patient's femoral bone 10784. The bone-facing surface of the first guide tool was designed to snap-fit to 3 mm of cartilage on the patient's distal femur. As shown in FIG. 107B, a second balancing chip guide tool 10786 provided distal facet resection guide slots 10788, a slot to mark the termination of the distal lateral resection 10790 (which can be used to establish the step cut between the distal lateral and medial resection facets), and a guide surface 10792 for making the posterior resection cut. As with the all-in-one guide tool, this tool 10786 also can be used for balancing and assessing implant fit (e.g., based on the fit of the guide tool between the femur and cut tibia in knee extension). As shown in FIG. 107C, a third chamfer cutting guide tool 10794 provided guide slots for the remaining predetermined resection cuts. As shown, the cutting guide slots were identified with numbers 1-6 to identify the order for performing the resection cuts.

For the third patient, a different set of femoral guide tools was designed and included to perform the predetermined femoral resection cuts and peg hole placements, as shown in FIGS. 108A through 108F. As shown in FIG. 108A, a femoral trial guide tool 10830 was designed and included to guide the hole placement for the pegs on the subsequently used guide tools and on the femoral implant component. As shown, this guide tool 10830 includes marks incorporated into its joint-facing surface to indicate to the surgeon the locations representing the Whiteside Line 10832 and Epicondylar Axis 10834. As shown in FIG. 108B, the second guide tool, a balancer chip guide tool 10836, was designed and included for guiding independent distal medial 10838 and distal lateral 10840 facet cuts, as well as the step cut 10842. Both the femoral trial guide tool 10830 and the balancer chip guide tool 10836 included a bone-facing surface derived from patient-specific data and designed to rest on 3 mm of cartilage atop the patient's femoral bone surface. The balancer chip guide tool 10836 was provided in six different thicknesses to allow the surgeon to use the tool 10836 for ligament balancing and assessment of the implant fit (e.g., by observing the space or tightness of the tool 1636 positioned between the femur and cut tibia during flexion and extension). In addition, a spacing paddle tool 10844, as shown in FIG. 108C, was designed and included for representing the extra asymmetric lateral poly thickness when balancing. As shown in FIG. 108D, a chamfer cut guide tool 10846 was designed and included for guiding an anterior resection cut 10848, a anterior chamfer resection cut 10850, and independent posterior medial 10852 and posterior lateral 10854 facet cuts. The a chamfer cut guide tool 10846 was designed with pegs to fit into the previously prepared peg holes in the patient's femur and with each cutting slot numbered for the order in which the cuts were to be performed. As shown in FIGS. 108E and 108F, a pair of angled cut guides 10856, 10858 was designed and included to facilitate the first and second posterior chamfer cuts. As shown, each angled cut guide 10856, 10858 includes a first surface that matches the distal resection surface and, optionally, includes pegs to fit into the previously prepared peg holes in the patient's femur. In the figures, the distal resection surface includes two non co-planar facets, which first cut guide surface matches. In addition, each angled cut guide 10856, 10858 also includes a second cutting guide surface angled at the predetermined angle of the corresponding chamfer cut such that a cutting tool placed against the surface cuts into the patient's bone at the predetermined angle.

Figure 109A:
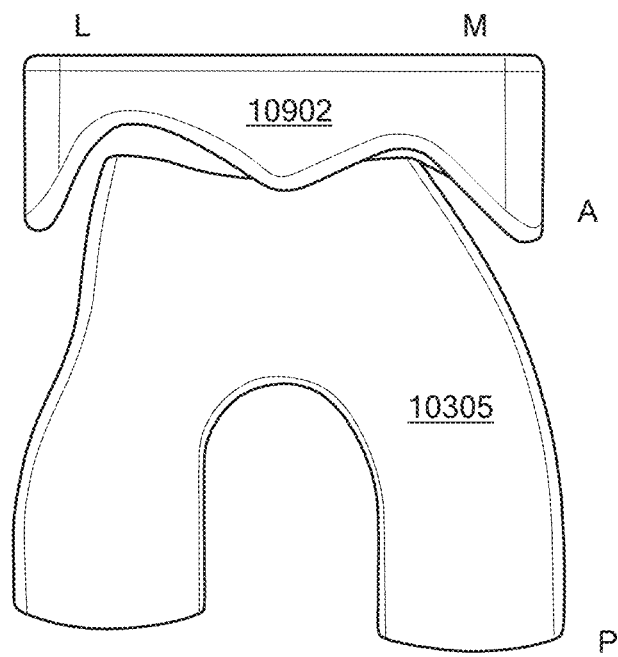
FIGS. 109A and 109B illustrate an anterior profile guide tool for assessing the peak profile at the anterior portion of the femur in the installed implant as compared to the patient's native knee.
Figure 109B:
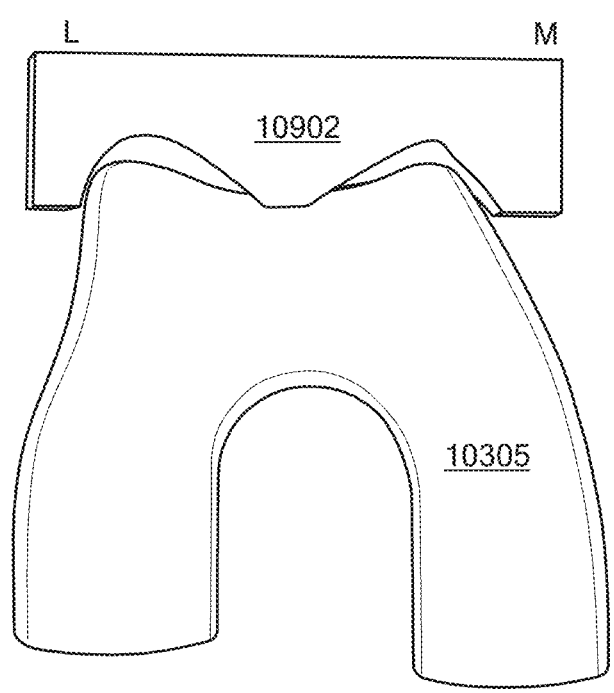

For the first two patients, and as shown in FIGS. 109A and 109B, an anterior profile guide tool 10902 also was designed and included to compare the peak profile at the anterior portion of the femur in the installed implant as compared to the patient's native knee. As discussed above, the trochlear area of the femoral implant component was patient-engineered (e.g., derived and/or optimized from patient-specific data) to include a trochlear groove offset 2 mm laterally and designed to accommodate a dome-shaped patellar implant component. Accordingly, as shown in the figures, the anterior profile of the implant differs from the anterior profile of the patient's native femur, particularly in providing relief on the lateral side of the implant relative to the patient's femur.

Tibial Guide Tools

Several guide tools for resectioning the tibia and/or placing the tibial implant component were designed and included for each patient's surgery. For example, as shown in FIG. 110A, for each patient a cutting guide tool 11002 was designed and included for accurately resectioning the proximal tibia to a predetermined resection depth and angle (e.g., 2 mm below the lowest point of the medial plateau, with an AP slope of 5 degrees and perpendicular to the mechanical axis). The anterior part of the tibial cutting guide tool 11004 was designed with a patient-specific bone-facing surface to substantially negatively-match the corresponding anterior portion of the patient's tibia when the medial edge of the guide was aligned to the medial one-third of the patient's tibial tubercle 11006. The proximal part 11008 of the tibial cutting guide tool 11002 was designed to rest on an estimated 2 mm thick cartilage layer atop the patient's proximal tibia that was identified from patient-specific data. For the first two patients, an alternate tibial cutting guide tool 11010 shown in FIG. 110B also was designed and included. The alternate tibial cutting guide tool 11010 included the same features of tibial cutting guide tool 11002 except that the proximal part 11008 of the alternate tibial guide tool 11010 was designed to rest directly on the bone surface of the patient's proximal tibia was identified from patient-specific data, rather than on a cartilage surface.

The tibial cutting guide tools 11002, 11010 were designed to include a dovetail mating feature 11012 that was attachable to a tibial alignment guide tool 11014 and down rod 11016 to visually check the alignment of the guide tools with the patient's mechanical axis. FIG. 110C depicts the tibial alignment guide tool 11014 and down rod 11016 attached via the dovetail connection to a tibial cutting guide tool 11002, 11010 to confirm prior to cutting the alignment of the cutting guide tool 11002, 11010 with respect to the patient's mechanical axis. The tibial alignment guide tool 11014 included a complementary dovetail mating feature to attach to the tibial cutting guide tools.

For the third patient and, as shown in FIG. 110D, the tibial cutting guide tool 11002 included two small holes on the anterior portion of the tool through which the patient's femur was marked with a pen or other instrument. The two markings on the surface of the cut tibia, as shown in FIG. 110D, served as landmarks for placement of subsequent tools.

Figure 111B:
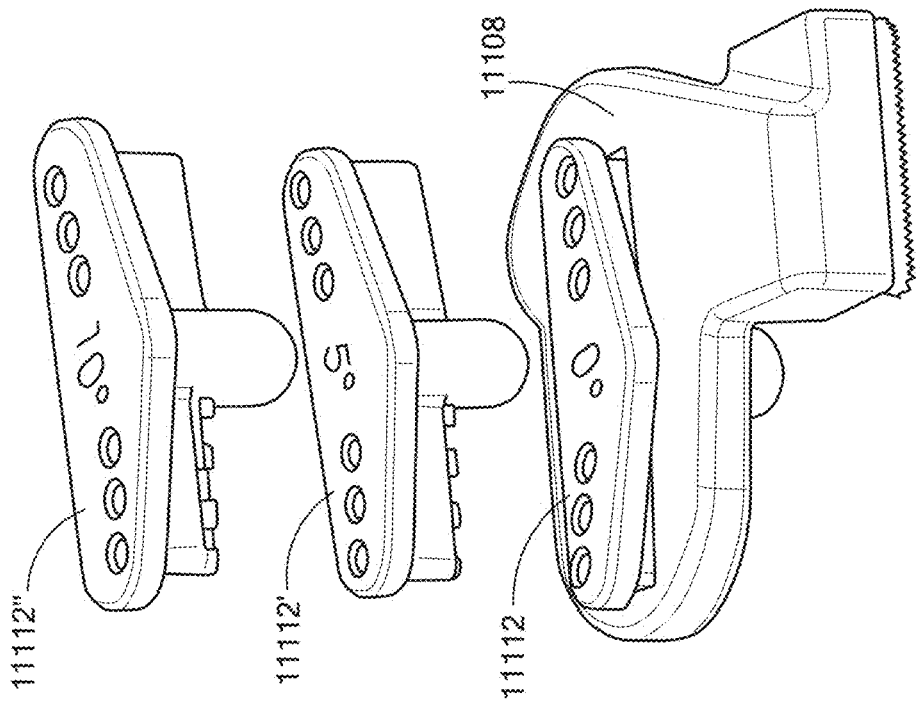
FIG. 111B illustrates a set of tibial keel prep insert guides.
Figure 111A:
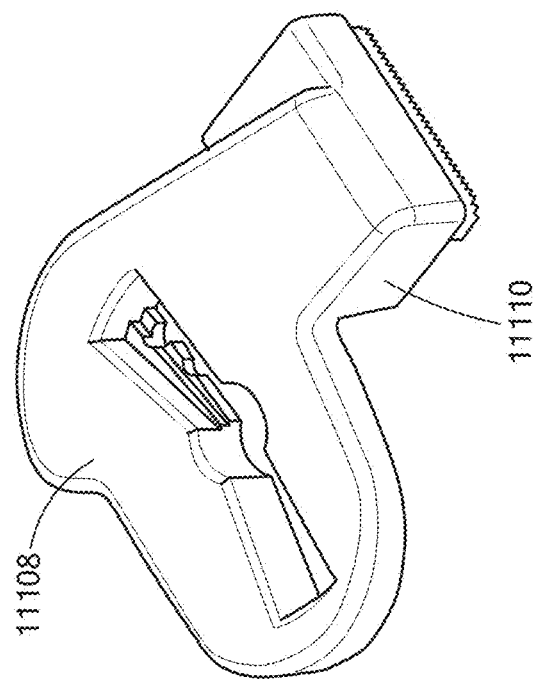
FIG. 111A illustrates a tibial keel prep guide tool.

For each patient, tibial keel preparation guide tools were designed and included to facilitate preparation of the holes and slots into the proximal, resected tibial surface and thereby ensure proper placement of the tibial tray keel and tibial implant component generally. A different set of tibial keel preparation guides were used for each of the three patients. For the first patient and as shown in FIG. 111A, a tibial keel prep guide tool 11108 was designed and included. To help ensure proper placement, the perimeter (except for the handle portion) of the tool 11108 was designed to substantially match the perimeter of the tibial tray implant component, which itself was patient-adapted to substantially match the perimeter of the patient's resected tibial surface. Accordingly, the proper placement of the tibial prep guide tool 11108 could be discerned by the surgeon by aligning the perimeter of the tibial prep guide tool 1608 with the perimeter of the patient's resected tibial surface. In addition, the medial edge of the handle 11110 of the tibial prep guide tool 11108 was designed to align with the medial ⅓ of the tibial tubercle 11006 to further ensure proper tibial implant rotational alignment. The central hole was drilled using a 0.5 inch diameter drill bit. As shown in FIG. 111B, a set of tibial keel prep insert guides 11112, 11112', 11112" was designed to mate with the tibial prep guide 11108 once the central hole was drilled. The tibial keep prep insert guides 11112, 11112', 11112" allow for controlled intra-operative tibial implant rotational alignment according to predetermined amounts of rotation. For example, as indicated in the figure, the set of tibial prep guides included a first tibial keel prep insert guide 1612 that provided 0 degrees of rotation, a second tibial keel prep insert guide 11112' that provided 5 degrees of rotation, and a third tibial keel prep insert guide 11112" that provided 10 degrees of rotation. After the surgeon selected the tibial keel prep guide that desired predetermined amount of rotation, slots were created using the guide holes in the selected tibial keep prep guide to drill multiple angled holes (e.g., six holes corresponding to the six guide holes in the tibial keep prep guide) using a 4 mm drill bit. Once the 4 mm holes were drilled into the patient's resected proximal tibial surface, an osteotome was used to create a rectangular slot for the keels of the tibial tray implant component.

For the second patient and as shown in FIG. 112, a tibial keel prep guide tool 1660 was designed and included for establishing the keel slot in the patient's resected proximal tibial surface. Similar to the tibial keel prep guide tool 11108 for the first patient, the tibial keel prep guide tool 11208 for the second patient included a perimeter (except for the handle portion) designed to substantially match the perimeter of the tibial tray implant component, which itself was patient-adapted to substantially match the perimeter of the patient's resected tibial surface. However, for the second patient an optional drill guide 11210 and a keel saw guide 11212 also were designed and included. The drill guide was available to be inserted into the central opening of the tibial keel prep guide tool 11208 to provide an accurately placed central hole. In addition, once the central hole was established, the keel saw guide 11212 was available to be inserted to provide a narrow channel for sawing an accurately slot for receiving the keel of the tibial implant component.

As shown in FIGS. 113A and 113B, the tibial keel prep guide tool 11308 for the third patient incorporated features from the first patient's tibial keel prep guide tool 11108 and insert guide tool 11112. However, unlike the tibial keel prep guide tools for the first two patients, this tool 11308 did not include a handle. In certain embodiments, more than one such tool 11308 can be included having different orientations of holes to provide different degrees of rotation for the keel and tibial tray. Similar to the tibial keel prep guide tools for the first two patients, this tool 11308 also included a perimeter designed to substantially match the perimeter of the tibial tray implant component, which itself was patient-adapted to substantially match the perimeter of the patient's resected tibial surface. As shown in the figures, an arrow was located on the proximal surface of the tool 11308 that indicated alignment to the medial ⅓ of the tibia tubercle for proper tibial implant rotational alignment (which itself had been marked, as described above). The central hole was drilled using an 9/16" drill bit and the keel holes were drilled using a ⅛" drill bit, before cutting between them with an osteotome to establish the keel slots.

Figure 114B:
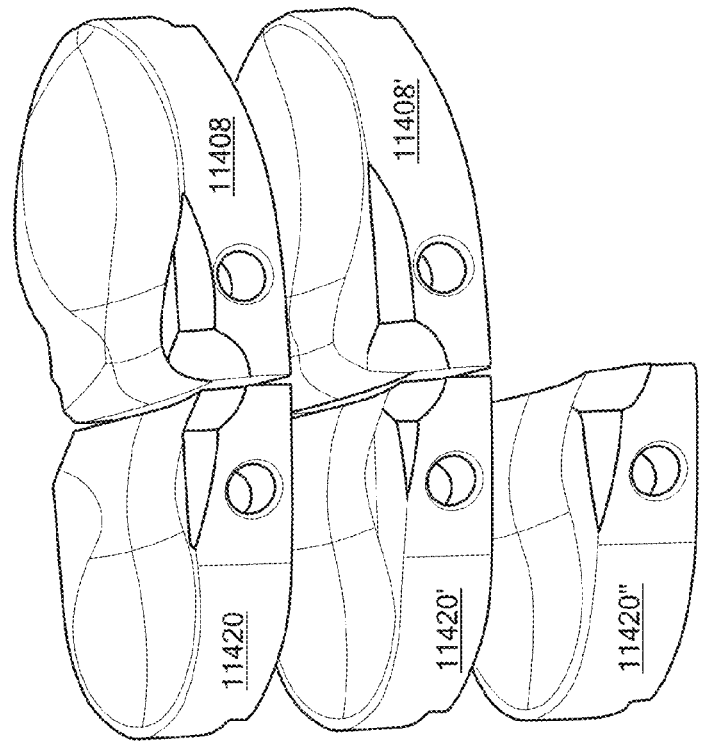
FIG. 114B illustrates a set of tibial implant component trial inserts.
Figure 114A:
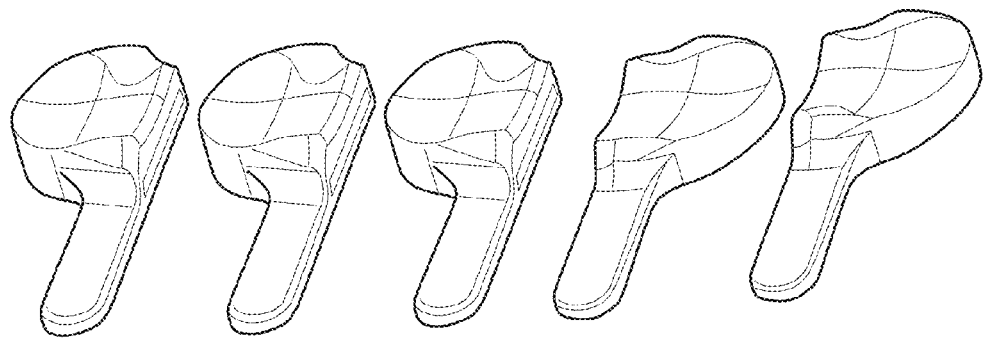
FIG. 114A illustrates a set of tibial trial spacers.

As shown in FIG. 114A, a set of tibial trial spacers was designed and included for the second and third patients. Specifically, for the second patient, two medial trial spacers were provided in thicknesses of 6 mm and 8 mm, respectively (second patient) or 8 mm and 10 mm, respectively (third patient) and three lateral trial spacers were provided in thicknesses of 9 mm, 10 mm, and 11 mm, respectively (second patient) or 10 mm, 11 mm, and 12 mm, respectively (third patient). The spacers were used to assess balance and fit, for example, to assess the tightness and balance of the joint with the spacer in place to represent tibial implant thickness between the cut tibia and femur (and optionally other components in place representing femoral thickness) during flexion and extension of the knee.

For each patient and as shown in FIG. 114B, a set of tibial implant component trial inserts was designed and included for each patient in order for the surgeon to assess the appropriate thicknesses to use for medial and lateral tibial implant component inserts for properly balancing the patient's knee joint. As shown in the figure, two medial trial inserts 111408, 11408' and three lateral trial inserts 11420, 11420', 11420" were designed and included. The two medial trial inserts had thicknesses of 6 mm and 8 mm, respectively, and the lateral trial inserts had thicknesses of 8.5 mm, 9.5 and 10.5 mm, respectively (first patient) or 9 mm, 10 mm, and 11 mm, respectively (second patient) or 8 mm, 9 mm, and 10 mm, respectively (third patient). After assessing the trial inserts and deciding on an appropriate medial and lateral insert thickness for balancing, the surgeon positioned the tibial implant tray and inserts having the appropriate thicknesses medially and laterally.

Tibial Implant Components

Figure 115B:
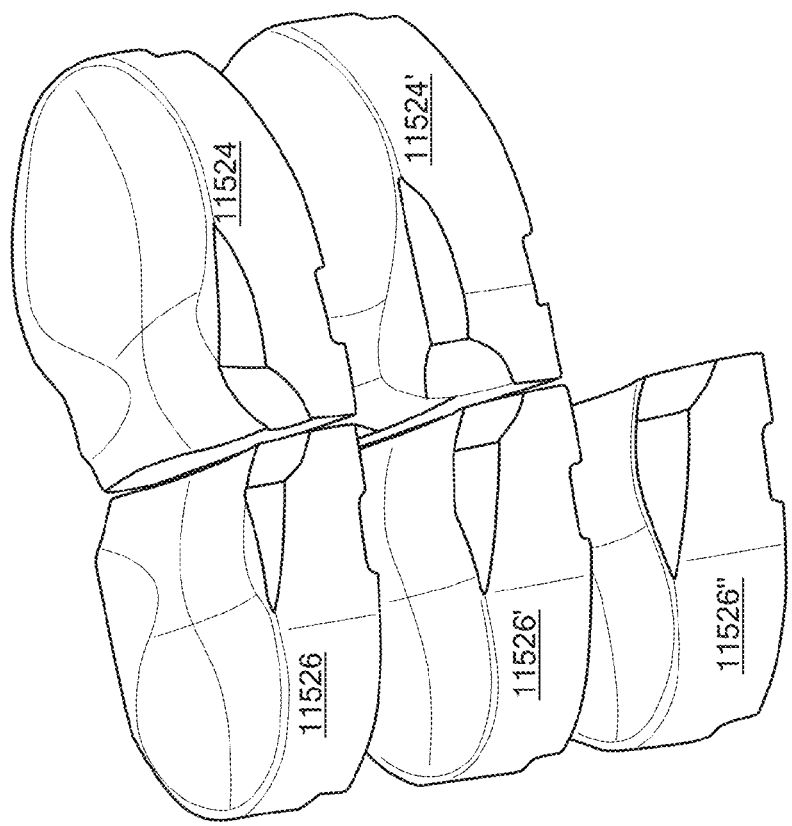
Figure 115A:
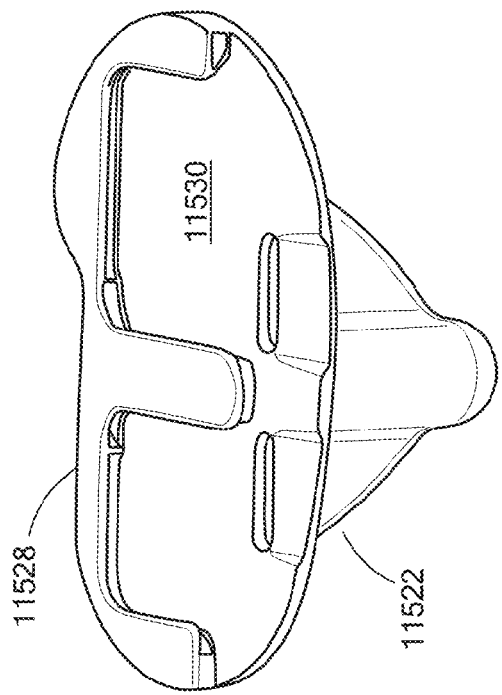

As shown in FIGS. 115A and 115B, the tibial implant components that were designed and included for each patient comprised a tibial tray 11522 and a set of tibial inserts 11524, 11526. The tibial tray 11522 was designed to include a patient-specific perimeter 11528 that substantially matched the perimeter of the patient's resected proximal tibial surface. In addition, the tibial tray 11522 was designed to include a 11 mm×35 mm (first and second patients) or a 13 mm×40 mm (third patient) central stem and 3.5 mm wide keels that were angled posteriorly 5 degrees on the medial and 15° on the lateral side and match the orientation of the holes created by the tibial keel prep guide 11512'. The tibial inserts 11524, 11526 were designed and provided to have the same thicknesses as the tibial trial inserts 11408, 11420 described above. As shown in the figure, the tibial trial inserts 11524, 11526 were designed to have a locking fit onto the tibial tray joint-facing surface 11530.

The perimeters of the trial spacers (except for the handle portion), tibial implant component trial inserts, and tibial inserts were designed to substantially match the perimeter of the tibial tray implant component, which itself was patient-adapted to substantially match the perimeter of the patient's resected tibial surface.

Patellar Guide Tool and Implant Components

In addition to the patient-adapted femoral and tibial implant components that were designed and included, a patient-adapted patellar implant component and related guide tools also were designed and included for the third patient's surgery. For example, as shown in FIG. 116A, a set of patella sizers was designed and included to assess the diameter of the patella. As shown in FIG. 116B, a patellar cutting tool was designed and included to cut the patella to a predetermined depth of resection. In addition, various patella implant trials also were designed (e.g., using 3D print manufacturing) and included. As shown in FIG. 116C, the implant trials included diameters of 32 mm, 35 mm, 38 mm, and 41 mm, respectively. As shown in FIG. 116D, a patellar implant of 41 mm was selected and implanted for the third patient.

4.2 Results and Discussion

The patient-adapted implant components were successfully implanted using the resection cuts and patient-adapted guide tools that were specifically designed for each cadaveric patient based on particular patient data (e.g., image data). Specifically, the tibial cut guide tools showed good fit with the patient's tibial plateau. The alignment guide tool and the drop down rod helped to confirm proper tibial alignment of the cut guide tool prior to resectioning for each patient. The different guide tools used to prepare the stem holes and keel slots in the proximal, resected surface of each patient's femur were found to useful. The tibial guide tools designed to include a patient-derived perimeter were found to fit well with the perimeter of each patient's resected tibia. The matching perimeter was helpful in properly aligning the cut tools to establish the predetermined resection cuts and/or for balancing. Regarding the patient-adapted tibial implant components, the tibial tray perimeter was shown to have a perimeter profile that substantially matched the perimeter of the patient's resected proximal tibial surface, with no excessive overhang or underhang. The tibial trial inserts were helpful in selecting the proper medial and lateral tibial inserts for balancing and fit. The tibial inserts were easily fit into the locking mechanism of the tibial tray. Overall, the predetermined tibial resection cuts, patient-adapted tibial guide tools, and patient-adapted tibial implant components provided a well-fit and aligned implant component.

On the femoral side, the single all-in-one guide tool used with the first two patients was found to have a patient-specific bone-facing surface that fit well to each patient's biological surface. The posterior and distal thickness of the tool was useful to assess balance and tightness/looseness of the joint. The set of femoral guide tools used to resect the third patient's femur were found to be useful for making the predetermined resection cuts. Regarding the patient-adapted femoral implant components, once in place the component for each patient was shown to have good coverage of the resected surfaces of the patient's femur and proper articulation with the tibial component.

FIGS. 117A through 117D show exemplary steps in the surgical procedures described above. In particular, FIG. 117A shows the use of a the tibial cut guide tool attached to an alignment guide tool for guiding the predetermined resection cut to the proximal tibia (for patient #2). FIG. 117B shows the placement of a tibial tray having a patient-adapted perimeter (for patient #2). FIG. 117C shows the use of an all-in-one guide tool for guiding the predetermined resection cuts to the femur (for patient #2). FIG. 117D shows a fluoroscopic image of the implanted femoral and tibial implant components (for patient #3).

Example 5

Implant Component with Curvilinear Bone Cuts

This example illustrates an implant component having both straight and curvilinear bone cuts on its bone-facing surface. Specifically, a femoral implant is designed to include 3 mm curvilinear cut depths and corresponding implant thicknesses along the distal portion of each condyle. The cut depth and implant thickness along each condyle are designed independently of the other condyle. In addition, jigs for performing the curvilinear cuts to the articular bone surface are described.

Using a computer model generated from patient-specific data, posterior and anterior resection cut lines are created in the model, as shown in FIGS. 118A and 118B. To design the curvilinear bone cut line corresponding to the resection cut on the medial condyle, a medial split line is identified on the condyle, as shown in FIG. 119A, and then a 3 mm deep cut line is generated to follow the split line, as shown in FIG. 119B. The resulting virtual curvilinear cut is shown in FIG. 119C. The same steps are performed independently for the lateral condyle, as shown in FIGS. 120A to 120C.

The resulting resection cut model, as shown in FIG. 121A establishes predetermined resection cuts for the surgical procedure and it also can be used to engineer the bone-facing surface of the corresponding patient-specific implant component, as shown in FIGS. 121B and 121C. Specifically, the inner, bone-facing surface of the implant component can be designed and engineered to substantially negatively-match the resection cut surface on the model. Optionally, and as shown in the figures, the outer, joint-facing surface of the implant also can include one or more patient-specific features.

The resulting cut model also can be used to design one or more cutting jigs that are fitted to the bone to guide the bone cutting procedure. For example, FIG. 122A shows a model of a bone along with a jig that allows preparation of predetermined resection holes and, optionally, resection cuts surfaces to match the predetermined resection cuts specific to a patient's particular anatomy. FIGS. 122B and 122C show an alternative set of jigs that can be used with a router-type saw. Specifically, a router-type bit can fit into the central channel of the jig shown in FIG. 122B to cut along the channel to a specific depth, for example, 3 mm. Then, as shown in FIG. 122C, a second jig having two channels that circumvent the channel of the first jig can be applied. The router-type bit can fit into these two channels to cut medial and lateral to the first channel to the same depth, for example, 3 mm.

FIG. 123A shows a model of the prepared bone following jig-guided bone cuts. FIG. 123B shows the model of FIG. 123A with a two-piece patient-specific implant component designed with an inner bone-facing surface that substantially negatively-matches the patient's resected bone surface.

Example 6

Implant and Implant Design with Resurfacing

This example illustrates (a) an implant component and design having a resurfaced portion and a bone cut portion and (b) an implant and implant design having a resurfaced surface with no bone cuts.

Figure 8E:
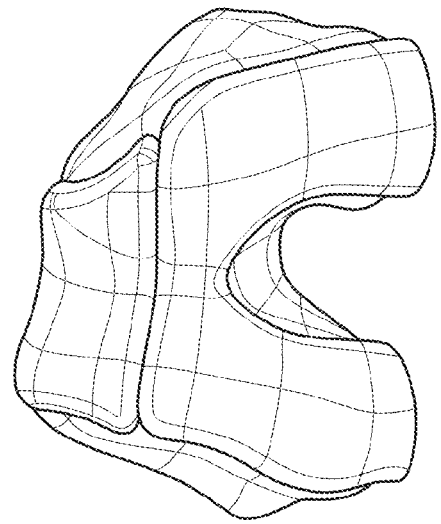
FIGS. 8A-8E show an exemplary design of a two-piece implant component.
Figure 8D:
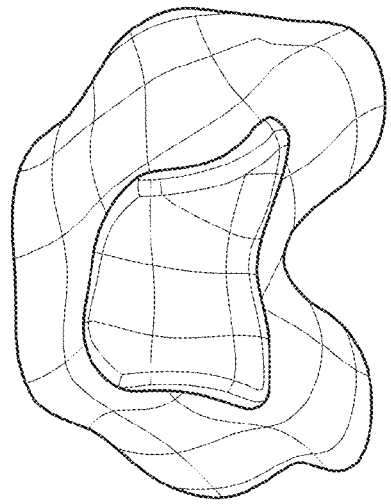
Figure 8C:
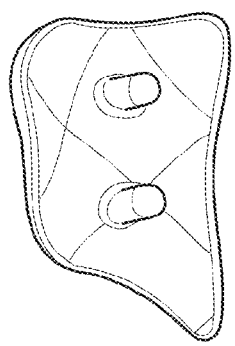
Figure 8A:
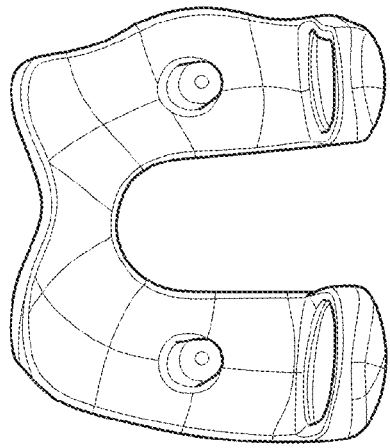
Figure 8B:
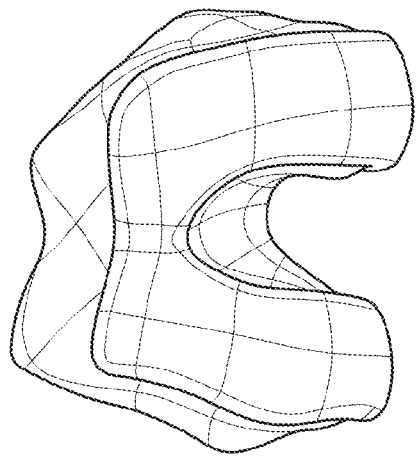

Using a patient-specific model (e.g., CAD model) generated from patient-specific data, a femoral implant is designed to include a single, posterior cut on its inner, bone-facing surface, as shown in FIG. 8A above and in FIGS. 124A and 124B. The remaining portions of the inner, bone-facing surface of the implant are designed to substantially negatively-match the patient's uncut articular bone surface that the implant component engages. Optionally, the outer, joint-facing surface of the implant also can include one or more patient-specific features. As shown in the figures, the patient-specific implant component with a single bone cut is prepared as two pieces or components, which allows for fitting the curved anterior portion of the implant component 12400 around the anterior portion 12402 of the femur.

The femoral implant design shown in FIGS. 125A and 125B and the corresponding implant shown in FIG. 125C also uses a two-piece or two-component design, in part to allow for fitting the curved anterior portion of the implant 12400 around the anterior portion 12402 of the femur. Specifically, using a patient-specific model generated from patient-specific data, a femoral implant was designed to include no bone cuts on its inner, bone-facing surface. Instead, the inner, bone-facing surface of the implant was designed to substantially negatively-match the uncut articular bone surface that the implant component engages. Optionally, the outer, joint-facing surface of the implant also can be designed and engineered to include one or more patient-specific features.

Example 7

A Femoral Component Device with Enhanced Articular Surface

This example illustrates exemplary implant components having enhanced articular surfaces (i.e., joint-facing surfaces). FIG. 126A is a front schematic view of engaging portions of a single compartment (e.g., a single condyle) of a knee implant 12601. FIG. 126B is a cross-sectional schematic view in the coronal plane of a femoral component 12602 of the implant 12601 of FIG. 126A. With reference to FIG. 126A and FIG. 126B, this exemplary embodiment of a patient-specific implant component 12601 includes a femoral component 12602 and a tibial tray component 12603, and it is designed based on patient-specific data. An inner, bone-facing surface 12604 of the femoral component 12602 conforms to the corresponding surface of the femoral condyle. Alternatively, it can conform to one or more optimized bone cuts on the femoral condyle. However, the outer, articular surface 12605 of the femoral component 12602 is enhanced to incorporate a smooth surface having an approximately constant radius in the coronal plane. The corresponding articular surface 12607 of the tibial tray 12603 has a surface contour in the coronal plane that is engineered based on the coronal plane to the outer articular surface 12605 of the femoral component 12602. In this embodiment, the articular surface 12607 has a radius that is five times the radius of the outer articular surface 12605. In certain embodiments, the articular surface 50 of the femoral component 12602 includes a sagittal curvature that matches the patient's existing or healthy sagittal radius.

FIGS. 126C to 126F show cross-sectional schematic views in the coronal plane of respective alternate embodiments of a femoral component.

The design of implant component 12601 has several advantages. First, the design of articular surface 12605 allows the thickness of femoral component to be better controlled as desired. For example, referring to FIG. 126C, if a curve of an articular surface 12608 of a femoral component 12609 is too large, the thickness of the femoral component may be too thick along a centerline 12610 of the implant, thereby requiring an excessive amount of bone to be removed when the implant is placed on the femoral condyle. On the other hand, referring to FIG. 126D, if the same curve 12608 is applied to a device having an appropriate centerline thickness 110, the margins or sidewalls 12612, 12613 of the device may be too thin to provide proper structural support. Similarly, referring to FIG. 126E, if the curve of the outer articular surface 12612 of a femoral component 12613 is too flat, the device does not exhibit the tapering from a centerline 12614 to the margins or sidewalls 12615, 12616 of the device and may not function well.

Referring again to FIGS. 126A and 126B, a second advantage of implant component 10 over certain other embodiments of patient-specific devices is that the smooth articular surface 50 can provide enhanced kinematics as compared to a true representation of the surface of the patient's femoral condyle.

Figure 126F:
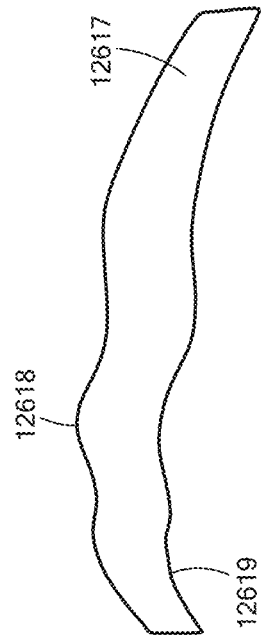
Figure 126C:
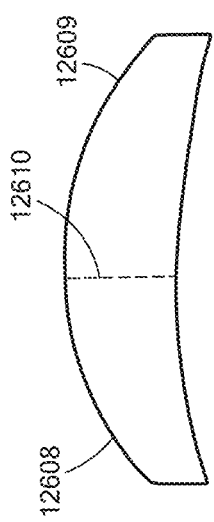
Figure 126D:
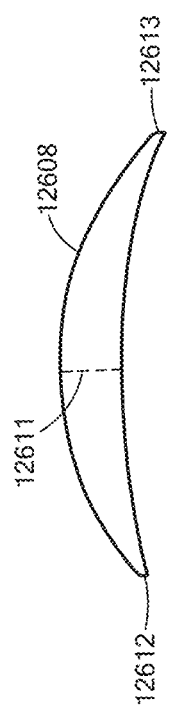

For example, referring also to FIG. 126F, one method of making patient-specific implants is to use a simple offset, in which a femoral component 12617 is designed using a standard offset from each point of the modeled surface of the patient's femoral condyle. Using such a design, the thickness of the device remains essentially constant, and an outer surface 12618 essentially positively-matches or conforms to the underlying inner femoral-facing surface 12619, as well as the modeled surface of the femoral condyle on which it is based. While this provides a truly patient-matched joint-facing surface, it is not necessarily optimal for the kinematics of the resulting implant, due to, for example, rough areas that may produce higher, more localized loading of the implant. By using a smooth surface with an essentially pre-determined shape, the loading of the implant can be better managed and distributed, thereby reducing the wear on the tibial tray component 12603.

A third advantage, which also is related to the loading and overall kinematics of the implant, is in the negative-matching of the tibial articular surface 12607 to the femoral articular surface 12605 in the coronal plane. By providing a radius that is predetermined, for example, five times the radius of the femoral articular surface 50 at its centerline in the present embodiment, the loading of the articular surfaces can be further distributed. Thus, the overall function and movement of the implant is improved, as is the wear on the tibial bearing surface, which can include polyethylene material. While the embodiment described above uses a ratio of five times the radius of the outer surface at its centerline (note that the radius of the outer surface may be slightly different at other locations of the outer surface 50 away from the centerline), other embodiments are possible, including an outer tibial surface that, in the coronal plane, is based on other ratios of curvature, other curvatures, other functions or combinations of curves and/or functions at various points. Additionally, while the embodiments shown in FIG. 126C through FIG. 126F are not considered to be optimal designs generally, they are embodiments that can be generated using automated systems and may have preferable characteristics in some instances.

Example 8

A Patient-Specific Engineered Trochlea Design

This example describes a patient-specific trochlea design that is optimized for proper kinematics of the patella-femoral ("PF") joint.

8.1 Method

Figure 127A:
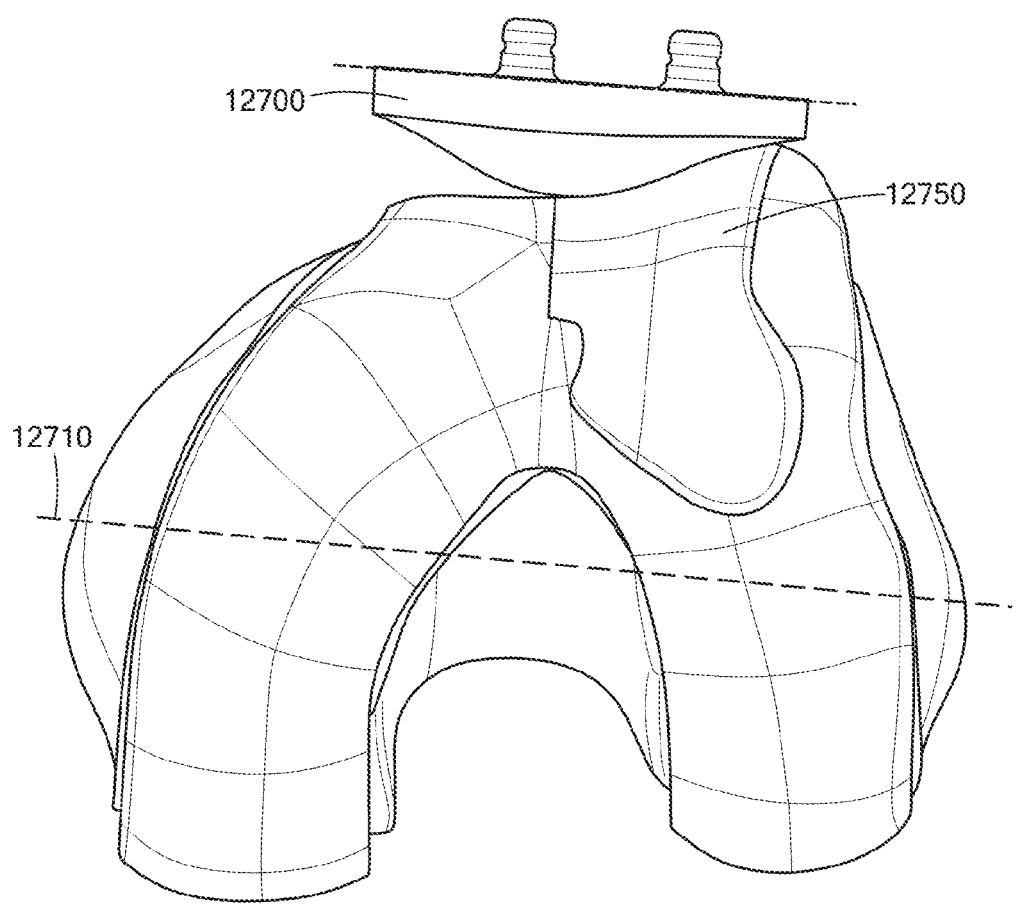
Figure 127B:
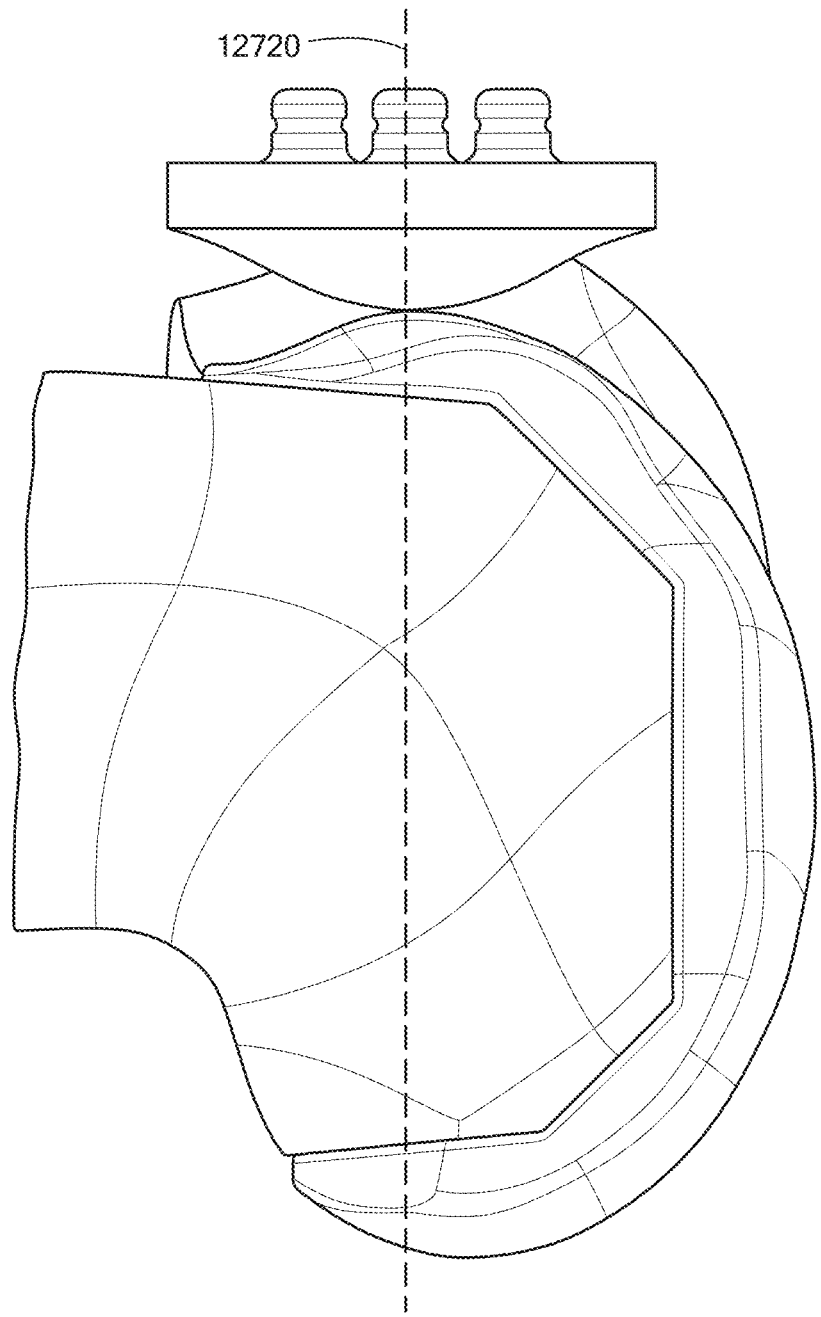
Figure 127C:
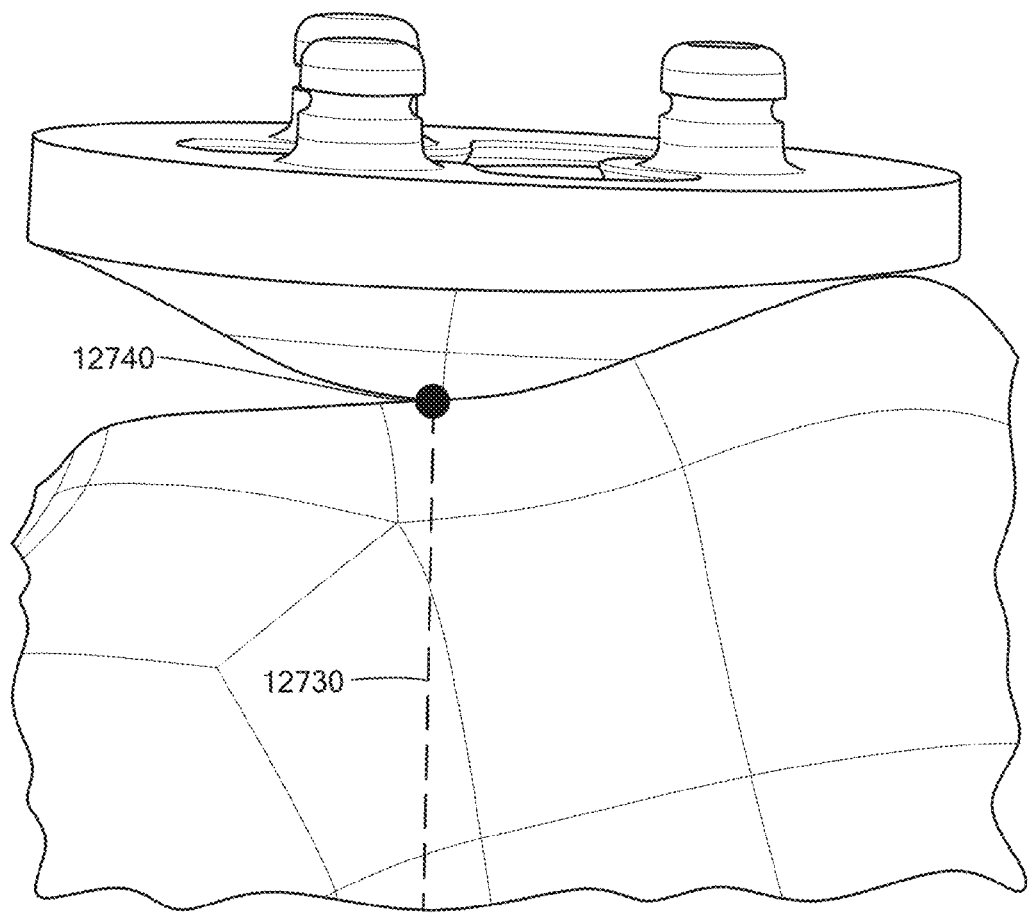
Figure 127D:
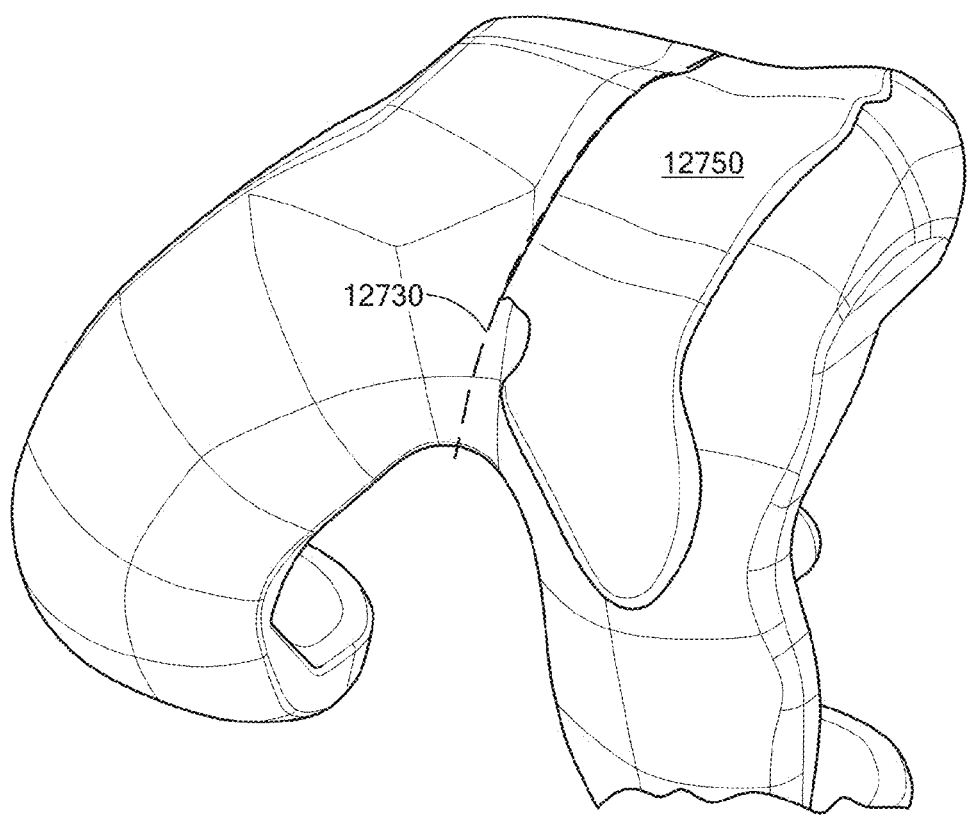
Figure 127F:
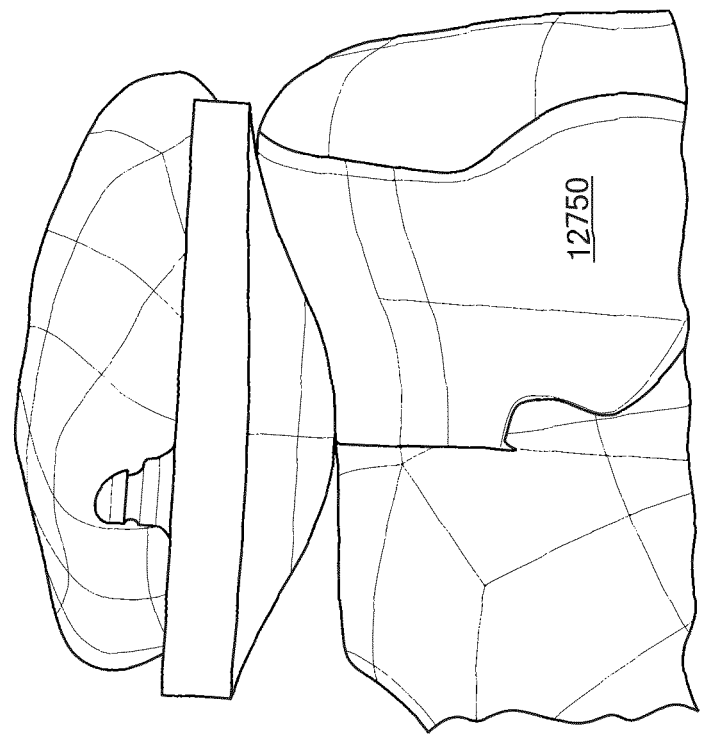
Figure 127E:
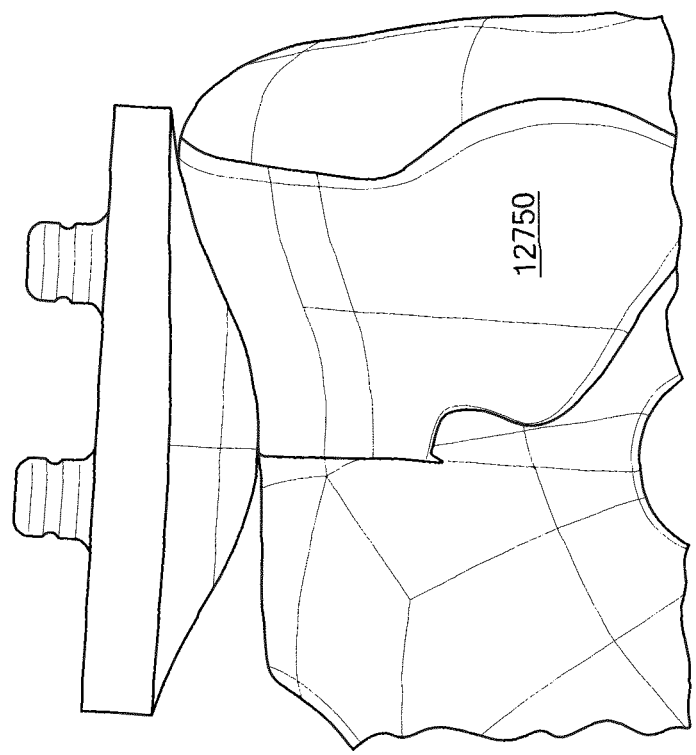

FIGS. 127A to 127F show an exemplary design of a knee implant, including a femoral component and a patella component, with a material cutaway region highlighted (darker) in certain figures. The placement of the patella and material removal was as follows: As shown in FIG. 127A, the flat bone-bearing surface of the patella 12700, was made parallel to the epicondylar axis 12710 in the coronal view. As shown in FIG. 127B, the center plane of the patella implant was made collinear with the epicondylar axis 12720. This allows for general positioning at the peak area of the trochlea. As shown in FIG. 127C, in this position the medial-lateral center or sulcus of the trochlea is identified 12730, and the patella implant component is brought down so the lowest points are coincident 12740. As shown in FIGS. 127D through 127F, the patella profile is swept along the sagittal curve of the trochlear region 12750.

8.2 Results and Discussion

This exemplary implant design uses a patient-specific sagittal curvature and an engineered coronal curvature to allow the patella component to track properly in the trochlear groove. This exemplary implant design for the femoral component and a patella component can allow various advantages including a reduction of lateral overstuffing of the P-F joint and a post-operative patella tracking that is normal or close to the patient's pre-operative and/or pre-disease state. In certain embodiments, the lateral peak can be retained, which may minimize dislocation events. In certain embodiments, the patella implant bone-bearing surface can be or appear to be approximately parallel to the osteochondral junction of the native patella.

Example 9

Exemplary Method for Virtually Aligning a Patient's Lower Extremity

From a three-dimensional perspective, the lower extremity of the body ideally functions within a single plane known as the median anterior-posterior plane (MAP-plane) throughout the flexion-extension arc. In order to accomplish this, the femoral head, the mechanical axis of the femur, the patellar groove, the intercondylar notch, the patellar articular crest, the tibia and the ankle remain within the MAP-plane during the flexion-extension movement. During movement, the tibia rotates as the knee flexes and extends in the epicondylar axis, which is perpendicular to the MAP-plane.

As shown in FIG. 128, the mechanical axis of a patient's lower extremity can be defined by the center of hip 12802 (located at the head 12830 of the femur 12832), the center of the knee 12804 (located at the notch where the intercondylar tubercle 12834 of the tibia 12836 meet the femur) and the center of the ankle 12806. In the figure, the long axis of the tibia 12836 is collinear with the mechanical axis of the lower extremity 12810. The anatomic axis 12820 aligns 5-7 degrees offset θ from the mechanical axis in the valgus, or outward, direction. A variety of image slices can be taken at each joint, for example, at one or more of the knee joint 12850-12850n, the hip joint 12852-12852n, and the ankle joint, to determine the mechanical centerpoint for each joint.

In certain preferred embodiments, anatomic reference points are used to virtually determine a patient's misalignment and the proper mechanical axis of his or her lower extremity. Based on the difference between the patient's misalignment and the proper mechanical axis, a knee implant and implant procedure can be virtually designed to include implant and/or resection cut features that substantially realign the patient's limb to have a proper mechanical axis. The implant design process can include manufacturing the implant (e.g., using CAM software) and, optionally, the implant can be surgically implanted into the patient according to the virtually designed procedure.

In certain embodiments, a patient's proper mechanical axis of the lower extremity, and the extent of misalignment of the extremity, is virtually determined using an appropriate computer-aided design software program, such as Solid-Works software (Dassault Systèmes SolidWorks Corp., 300 Baker Avenue, Concord, Mass. 01742). Using the software, patient-specific information, for example, a collection of anatomic reference points, is used to generate a virtual model that includes the patient's knee joint.

The virtual model also can include reference points from the hip and/or ankle joints. Using the virtual model, a user can determine virtually the misalignment of and mechanical axis of the patient's lower extremity by determining in the model the patient's tibial mechanical axis, femoral mechanical axis, and one or more planes from each axis. For example, the patient's tibial mechanical axis can be determined virtually in the model as a line connecting the center of the patient's ankle and the center of the patient's tibia. The patient's femoral mechanical axis can be determined virtually in the model as a line connecting the center of the patient's hip and the center of the patient's distal femur. The center of the patient's ankle, tibia, hip, and/or distal femur can be determined based on the patient-specific anatomic reference points or landmarks used to generate the virtual model.

Then, the user can align virtually the lower extremity by collinearly aligning the tibial and femoral mechanical axes. This collinear alignment can be achieved by adjusting the angle of the intersecting axes at the knee joint to be zero. The axes can be aligned axially by aligning one or more planes common to both axes, such as the sagittal or coronal planes. FIGS. 129A to 129C each illustrate a model showing the existing misalignment of a patient's lower extremity (dark and solid line) and the virtual alignment (light and dashed line) determined using the model.

Exemplary methods for determining the tibial mechanical axis, the femoral mechanical axis, and the sagittal and coronal planes for each axis are described in more detail in the following subsections.

9.1 Methods for Determining Tibial Mechanical Axis and its Sagittal and Coronal Planes In certain embodiments, the tibial mechanical axis and the tibial sagittal and coronal planes are determined virtually using a model that includes reference points from a patient's knee and ankle joints, as follows:

9.1.1 Tibial Mechanical Axis

Figure 130A:
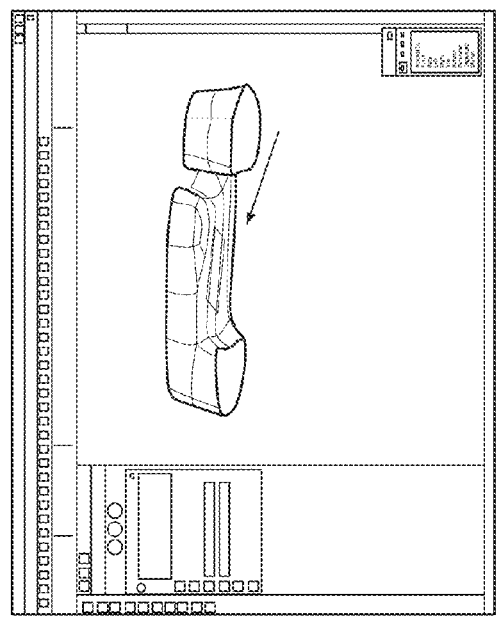

1a. Axial plane of the ankle. As shown in FIG. 130A, an axial plane at the ankle is identified using three or more points at the inferior articular surface of the tibia. The three or more points are selected from the same or closely similar elevation(s) on the inferior articular surface of the tibia. This optional step can be used to establish an initial plane of reference for subsequent virtual determinations.

Figure 130B:
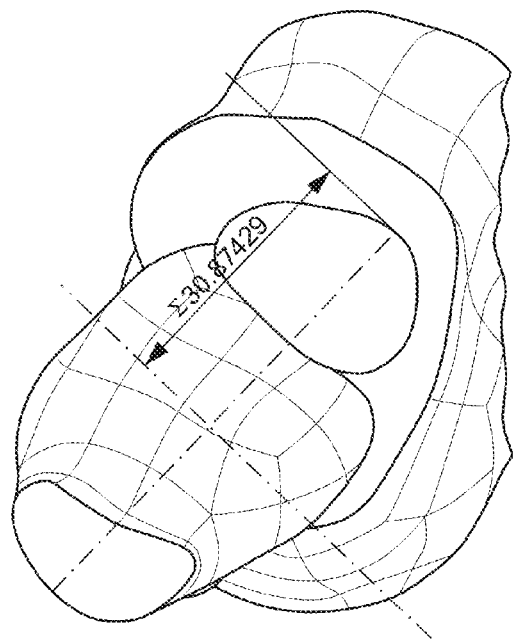

1b. Distal point of the tibial mechanical axis. The distal point of the patient's tibial mechanical axis can be defined as the center of the ankle. As shown in FIG. 130B, the center of the ankle can be determined virtually by connecting a line from the medial to the lateral malleoli and marking 4 percent medial from the center of the line. For example, if the distance between the malleoli is 100, then the center of the line is at 50 and the center of the ankle is 4 percent medial from the center of the line or, in other words, at 46 from the medial malleoli and 54 from the lateral malleoli.

Figure 130C:
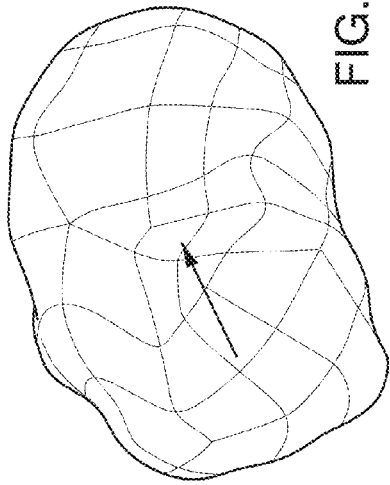

1c. Proximal point of the tibial mechanical axis. The proximal point of the tibial mechanical axis can be determined virtually as the posterior aspect of the ACL insertion point, as shown in FIG. 130C.

Figure 130D:
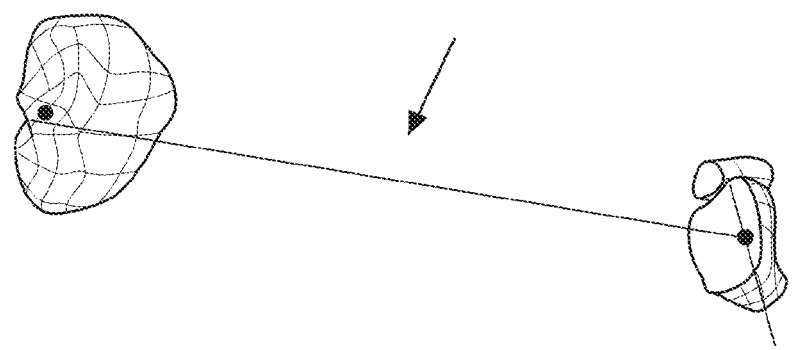

1d. Tibial mechanical axis. The tibial mechanical axis can be determined virtually as the line connecting the distal and the proximal points of the tibial mechanical axis, as shown in FIG. 130D.

9.1.2 Sagittal or A-P Plane of the Tibia

Figure 131A:
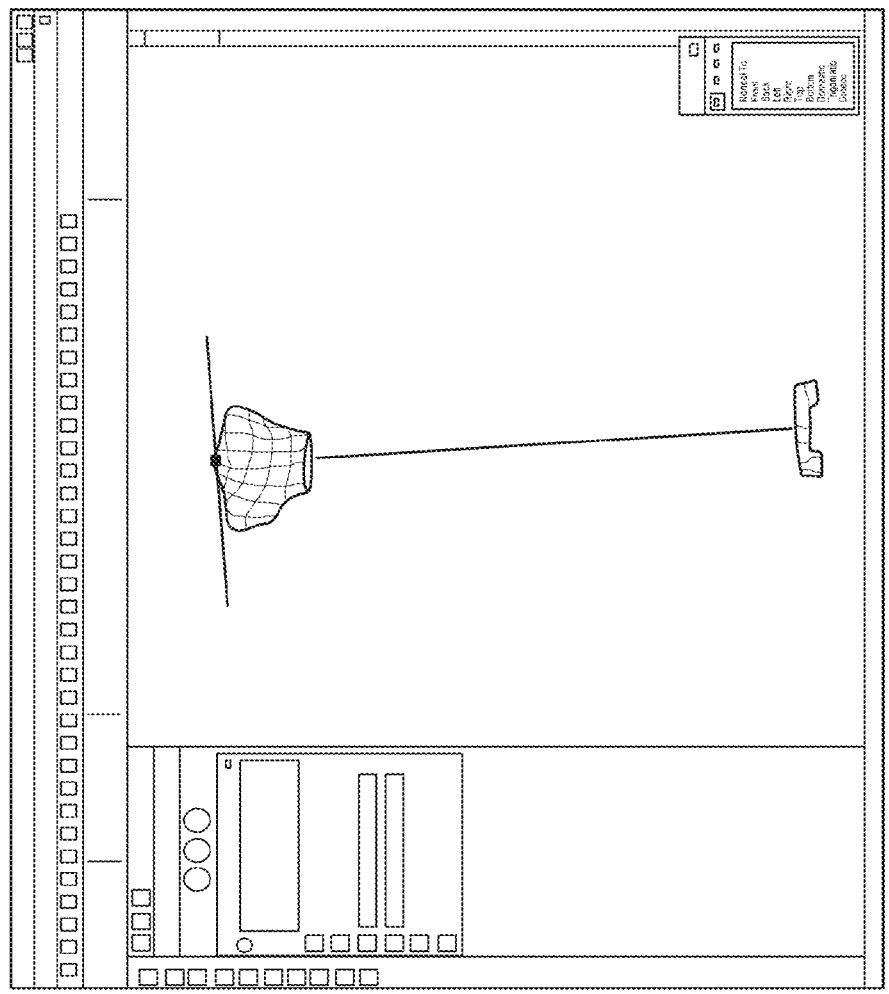

2a. Tibial axis perpendicular plane ("TAPP"). The TAPP can be determined virtually as the plane perpendicular to the tibial mechanical axis line and including the proximal point of the tibial mechanical axis, as shown in FIG. 131A. This optional step can be used to establish a plane of reference for subsequent virtual determinations. The TAPP, optionally tilted in an A-P orientation, also can be used to determine the tibial cut line.

Figure 131B:
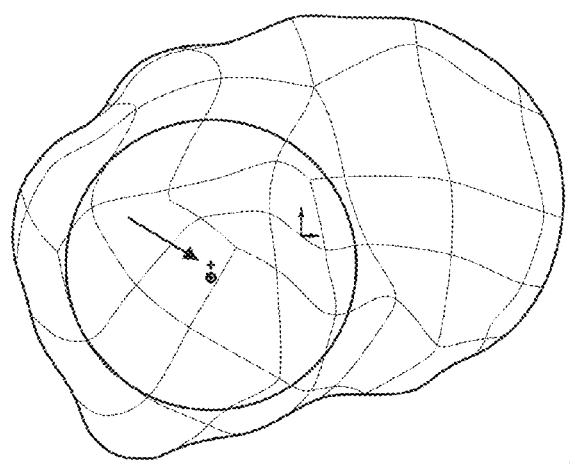
Figure 131C:
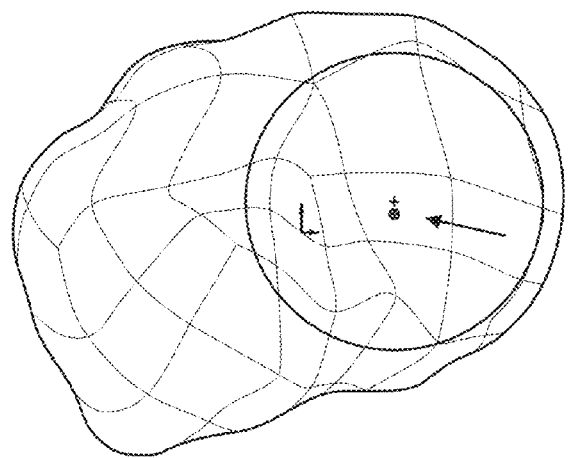

2b. A-P line of the tibia—derived from Cobb method. The A-P line of the tibia can be determined virtually based on method derived from Cobb et al. (2008) "The anatomical tibial axis: reliable rotational orientation in knee replacement" J Bone Joint Surg Br. 90(8):1032-8. Specifically, the A-P line of the tibia can be determined virtually as the line perpendicular to the line connecting the diametric centers of the lateral and medial condyles of the tibia. For example, as shown in FIGS. 131B and 131C, a best-fit circle can be sketched to determine the diametric center of the lateral condyle (i.e., the lateral plateau of the tibia). In addition, a best-fit circle can be sketched to determine the diametric center of the medial condyle (i.e., the medial plateau of the tibia).

In certain embodiments, one or both of the circles can be sketched to best fit the corresponding condyle(s) at the superior articular surface of the tibia. Alternatively, one or both of the circles can be sketched to best fit a portion of the wear pattern at the superior articular surface of the tibia. Still yet, one or both of the circles can be sketched to best fit the condyle(s) at a certain distance distal to the superior articular surface of the tibia. For example, the circle for the medial condyle can be sketched to best fit the medial condyle at 10 mm, 15 mm, 20 mm, 25 mm or more below, or distal to, the superior articular surface of the tibia; and then the circle can be adjusted proximally to lie on the plane of the superior articular surface of the tibia.

Figure 131D:
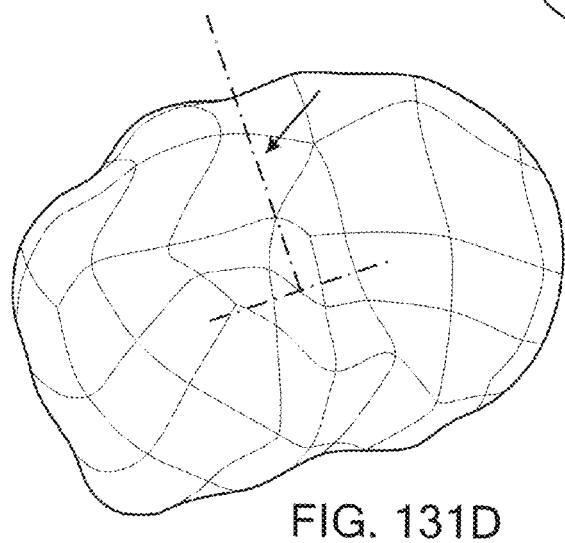

Then, as shown in FIG. 131D, A-P line of the tibia is determined virtually as the line perpendicular to, and including the midpoint of, the line connecting the diametric centers of the lateral and medial condyles of the tibia. If the midpoint of the line connecting the diametric centers of the lateral and medial condyles is not in the same location as the proximal point of the tibial mechanical axis, then the A-P line can be shifted away from the midpoint to include the proximal point of the tibial mechanical axis while remaining perpendicular to the line connecting the diametric centers of the lateral and medial condyles.

A-P line of the tibia—derived from Agaki method. An alternative method for determining virtually the A-P line can be derived from other published methods, such as Agaki (2004) "An Anteroposterior Axis of the Tibia for Total Knee Arthroplasty," Clin Orthop 420: 213-219.

2c. Sagittal or A-P plane of the tibia. As shown in FIG. 131E, the sagittal or A-P plane of the tibia can be determined virtually as the plane including both the A-P line of the tibia and the tibial mechanical axis line. The sagittal or A-P plane also is perpendicular to the TAPP.

9.1.3 Coronal or Medial-Lateral ("M-L") Plane of the Tibia

Figure 131F:
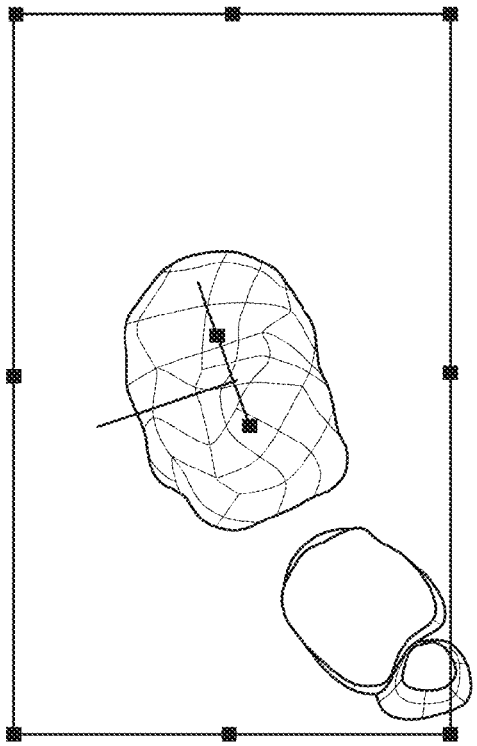
Figure 131E:
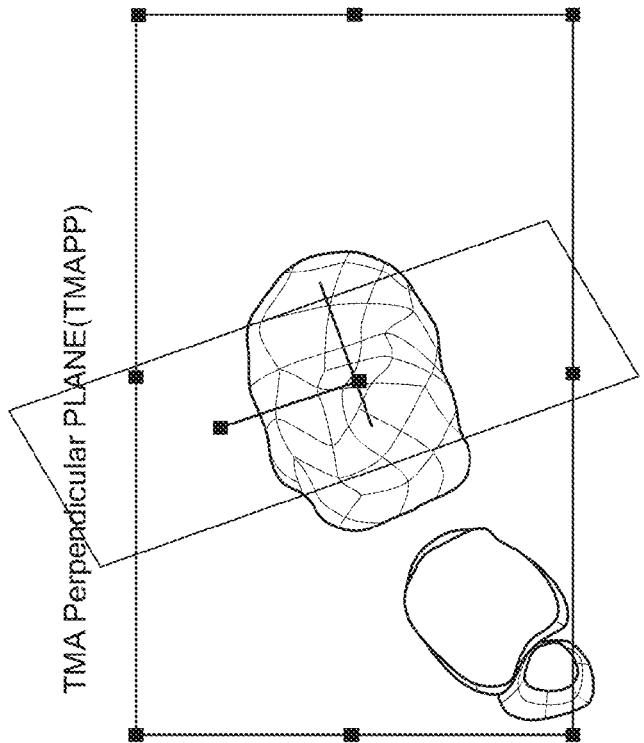

As shown in FIG. 131F, the coronal or M-L plane of the tibia can be determined virtually as the plane perpendicular to the A-P plane (or perpendicular to the A-P line) of the tibia and including the tibial mechanical axis line. The coronal or M-L plane also is perpendicular to the TAPP.

9.2 Methods for Determining Femoral Mechanical Axis and its Sagittal and Coronal Planes In certain embodiments, the femoral mechanical axis and the femoral sagittal and coronal planes are determined virtually using a model that includes reference points from a patient's knee and hip joints, as follows:

9.2.1 Femoral Mechanical Axis

Figure 132B:
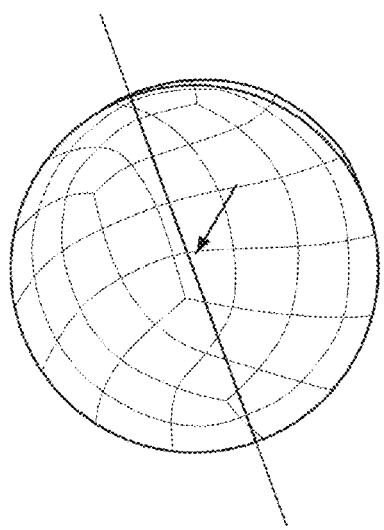
Figure 132D:
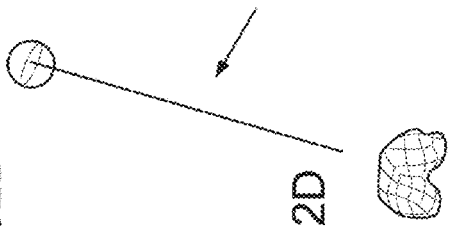
Figure 132A:
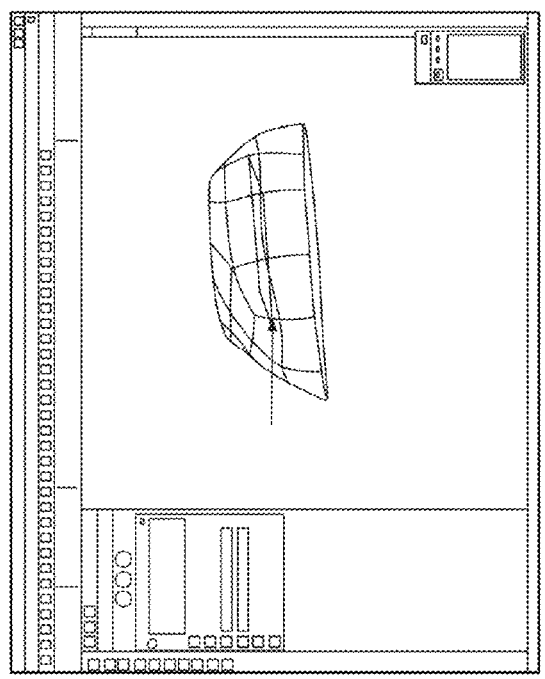

1a. Axial plane of the femur. As shown in FIG. 132A, an axial plane of the femur is selected virtually using three or more points within the spherical femoral head that substantially lie in the same axial plane. This optional step can be used to establish an initial plane of reference for subsequent virtual determinations.

1b. Proximal point of the femoral mechanical axis. As shown in FIG. 132B, the proximal point of the patient's femoral mechanical axis can be determined virtually as the center of the spherical femoral head.

Figure 132C:
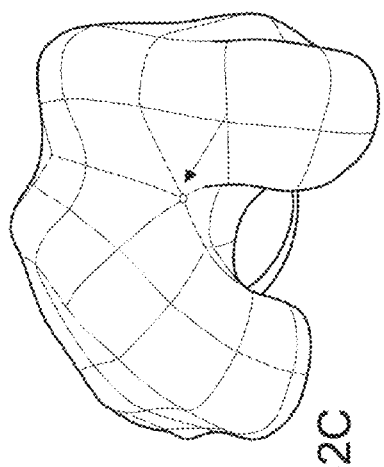

1c. Distal point of the femoral mechanical axis. As shown in FIG. 132C, the distal point of the femoral mechanical axis is determined virtually as the point at the posterior aspect of the femoral trochlear notch or sulcus.

1d. Femoral mechanical axis. The femoral mechanical axis can be determined virtually as the line connecting the distal and the proximal points of the femoral mechanical axis, as shown in FIG. 132D.

9.2.2 Sagittal or A-P Plane of the Femur

2a. Femoral mechanical axis perpendicular plane (FMAPP). The FMAPP can be determined virtually as a plane perpendicular to the femoral mechanical axis line and including the distal point of the femoral mechanical axis, as shown in FIG. 133A. This optional step can be used to establish a plane of reference for subsequent virtual determinations. In certain embodiments of implant procedures that require femoral cuts, the distal femoral cut is applied at the FMAPP.

2b. A-P line of the femur—derived from Whiteside's line. As shown in FIG. 133B, the A-P line of the femur can be determined virtually as the line perpendicular to the epicondylar line and passing through distal point of the femoral mechanical axis. The epicondylar line is the line connecting medial and lateral epicondyles (furthest out points).

2c. Sagittal or A-P plane of the femur. As shown in FIG. 133C, the sagittal or A-P plane of the femur can be determined virtually as the plane including both the A-P line of the femur (derived from the Whiteside's line) and the femoral mechanical axis line. The sagittal or A-P plane also is perpendicular to the plane perpendicular to the femoral axis.

9.2.3 Coronal or Medial-Lateral ("M-L") Plane of the Femur

As shown in FIG. 133D, the coronal or M-L plane of the femur can be determined virtually as the plane perpendicular to the A-P plane (or perpendicular to the A-P line) of the femur and including the femoral mechanical axis line. The coronal or M-L plane also is perpendicular to the plane perpendicular to the femoral axis.

Figure 135B:
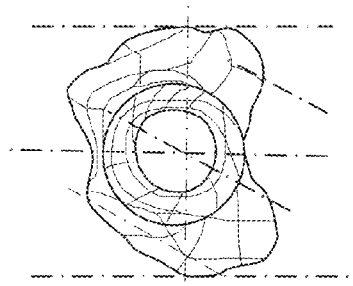
Figure 135D:
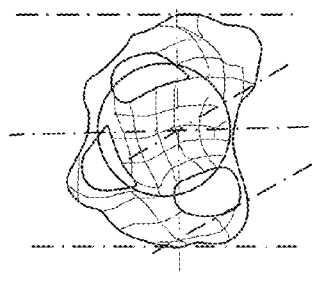
Figure 135G:
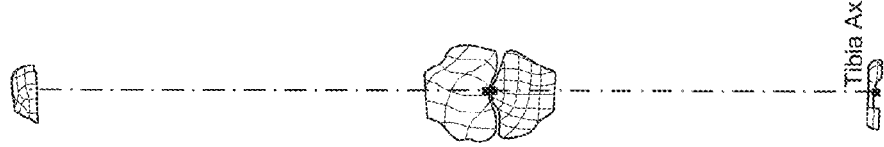
Figure 135F:
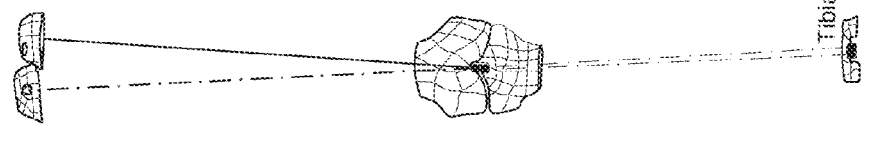
Figure 135E:
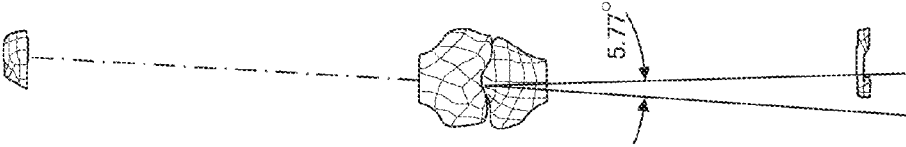
Figure 135A:
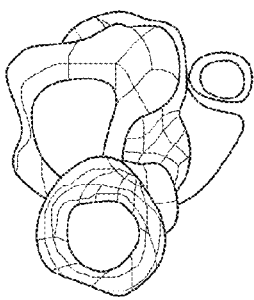
Figure 135C:
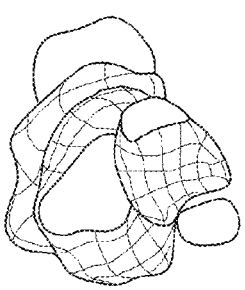

After determining virtually the tibial and femoral mechanical axis, and their sagittal and coronal planes, the lower extremity can be aligned virtually by adjusting the angle of the intersecting mechanical axes at the knee joint to be zero. The axes can be aligned axially by aligning one or both of the sagittal or coronal planes from each axis, as shown in FIGS. 134A and 134B, respectively. FIGS. 135A and 135B show a model before and after virtual alignment as it appears in axial view looking distally from a section of the femoral head, to a section of the distal femur, and on to a section of the tibia. Similarly, FIGS. 135C and 135D show a model before and after virtual alignment as it appears in axial view looking proximally from a section of the distal tibia, to a section of the distal femur, and in FIG. 135C, on to a section of the femoral head. FIGS. 135E to 135G show a model before and after virtual alignment (FIGS. 135E and 135G), and an overlay of both before and after virtual alignment (FIG. 135F).

Various features of the patient-adapted implant components, including bone cut angles, bone cut slopes, bone cut number, implant thickness in one or more portions, joint facing curvature, implant component thickness, and other features, can be selected and/or designed, at least in part, to optimize the parameter of deformity correction and/or limb alignment, for example, using the virtual alignment method described herein. Optionally, one or more other parameters can simultaneously be factored into the selection and/or design of implant component features. For example, in addition to limb alignment, the implant component features also can be selected or designed meet one or more of the following parameters: (1) preserving, restoring, or enhancing the patient's joint kinematics; (2) deformity correction; (3) maximizing preservation of bone cartilage, or ligaments (e.g., resulting from the resection); (4) maximizing preservation and/or optimization of other features of the patient's anatomy, such as trochlea and trochlear shape; (5) restoration or optimization of joint-line location and/or joint gap width, and (6) preservation, restoration, or enhancement of other target features.

Example 10

Finite Element Analysis

This example illustrates an exemplary finite element analysis ("FEA") that can be conducted on a device component of some embodiments as one parameter in the optimization of patient-specific features of the implant. Specifically, this example describes FEA conducted on three variations of a femoral implant component.

10.1 Methods

This analysis investigates the effect of interference fit and loading scenarios on three different large knee femoral implant designs, including, as shown in FIGS. 136A to 136C, respectively, a component with six bone cuts and a perpendicular distal bone cut ("Perp 6-Cuts"); a component with five bone cuts and a perpendicular distal bone cut ("Perp 5-Cuts"); and a component with six bone cuts and flexed bone cuts ("Flexed 6-Cuts"). The three femoral implant component geometries tested represented implants for the largest expected anatomy. FIGS. 137A to 137C each show a traditional implant component overlaid with each of the three tested implant components. In addition, FIG. 138 shows a traditional component overlaid with the 6-Cuts implant component in an overlaid position that respects the actual implant placements based on movement of the joint-line. FIG. 139 shows the joint-facing surface of the 6-Cuts implant component positioned on a femur having six corresponding resection cuts.

Target results of the FEA analysis included identification of maximum principle stresses and displacements. For a general reference on conducting FEA on knee implant components, see "Initial fixation of a femoral knee component: an in vitro and finite element study," Int. J. Experimental and Computational Biomechanics, Vol 1, No. 1, 2009.

FIG. 140 shows set-up information for the testing. For initial runs of the three variations, the models of the femur were setup with 0.35 degrees interference fit angles on the Anterior Shield (A, FIG. 141A), and upper most medial and lateral condyle (B and C, FIG. 141B) surfaces. This angle was set by running iterative analyses until a Max Principal Stress of roughly 240 MPa (the fatigue endurance limit of CoCr) was achieved. Secondary analysis runs were performed with no interference fit on the three Femoral Implant geometries.

All contact surfaces between the implant and femur (D, FIG. 141C) were set up as frictional (0.5 coefficient of friction based on the general reference described above), and the surfaces between the implant and condyle support plates (E, FIG. 141C) were frictionless.

For all cases the top face of the femur (F, FIG. 141D) was fully fixed. The bottom faces of the condyle support plates (G and H, FIG. 141E) were either fixed in all directions or, when the load was applied, allowed to move along the femoral axis only (Z direction shown on visible coordinate system).

Figure 141B:
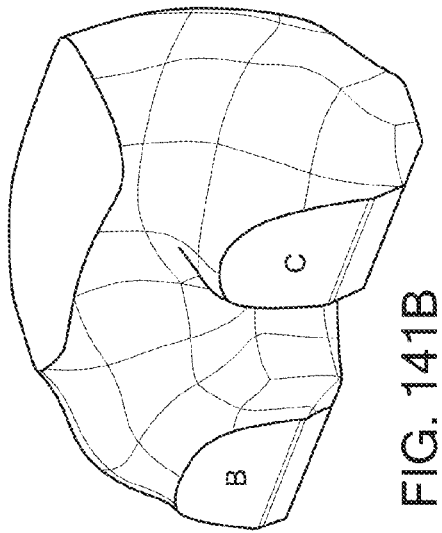
Figure 141D:
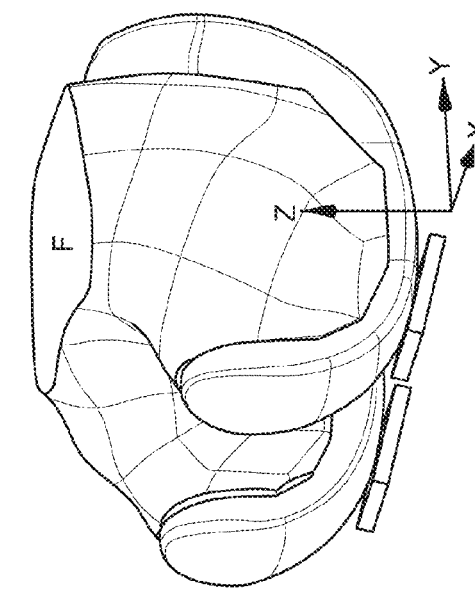
Figure 141A:
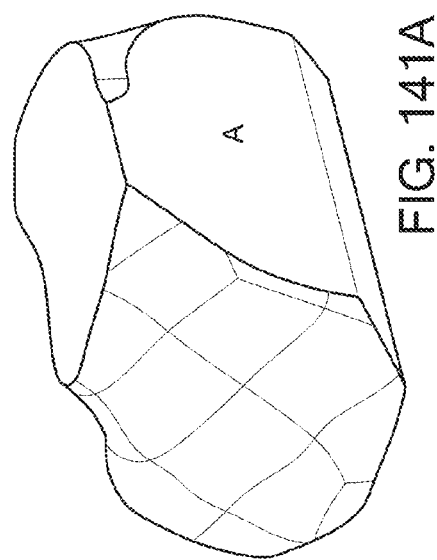
Figure 141C:
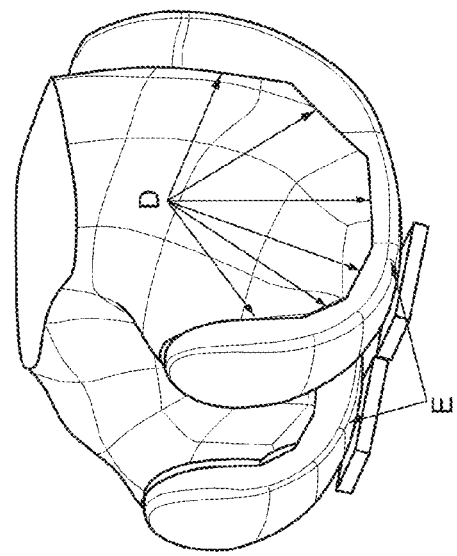
Figure 141E:
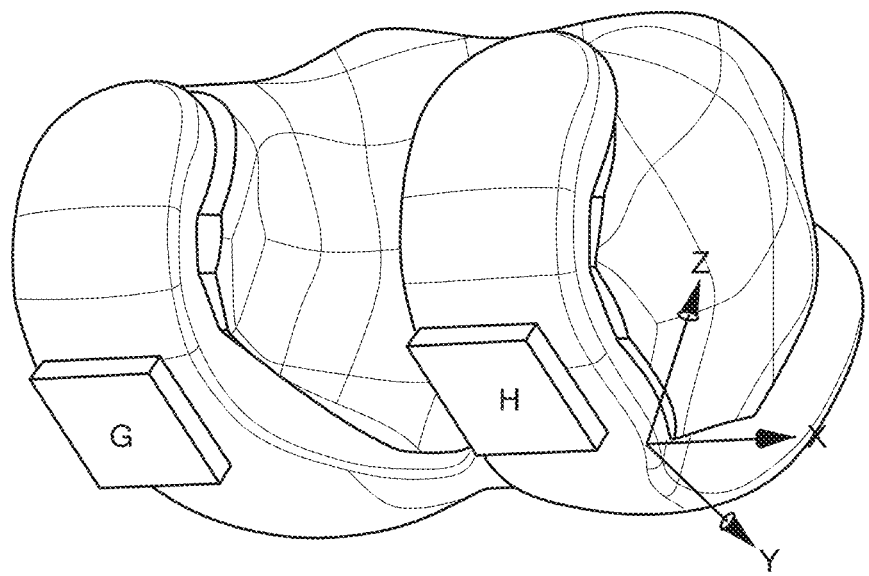
Figure 141F:
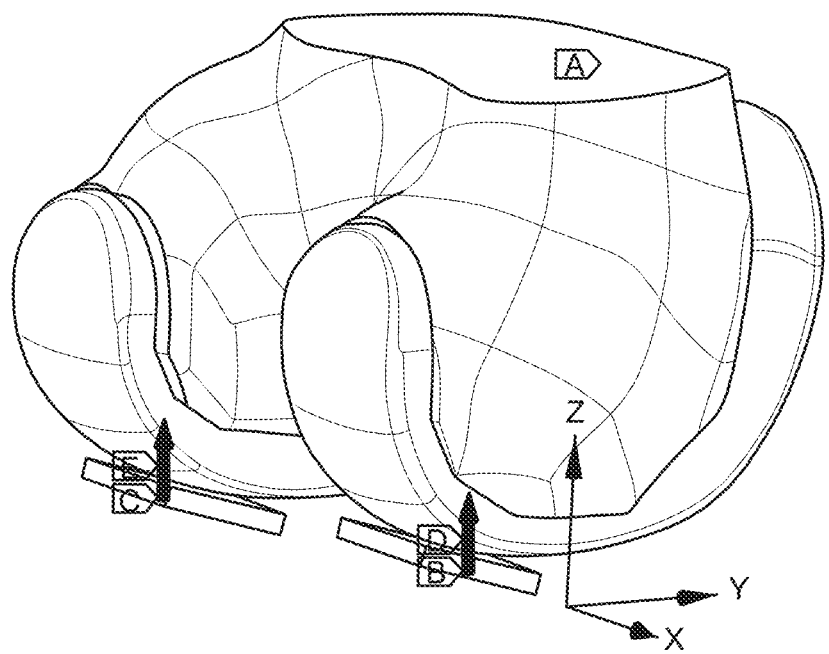
Figure 141H:
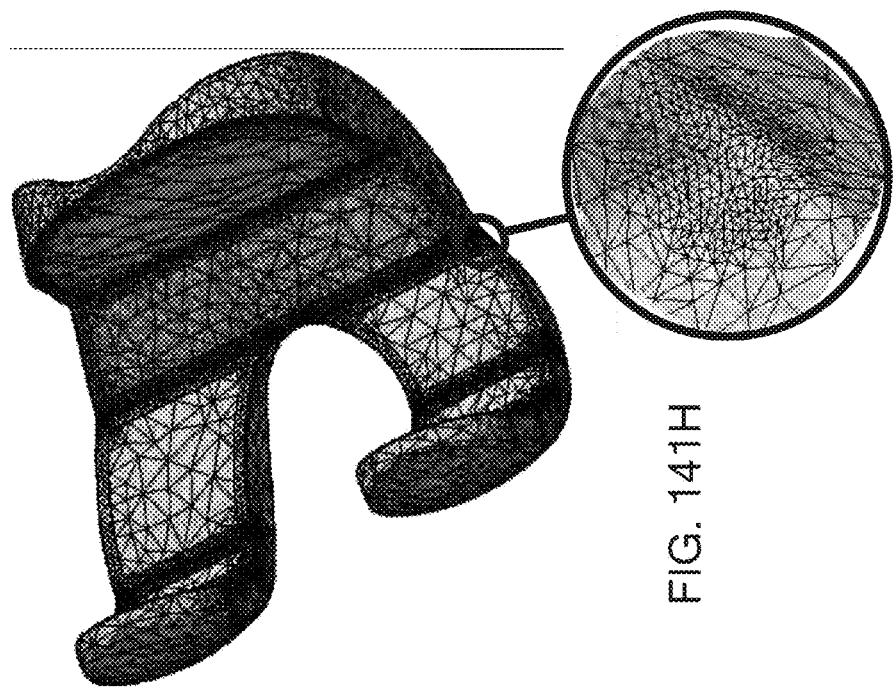
Figure 141G:
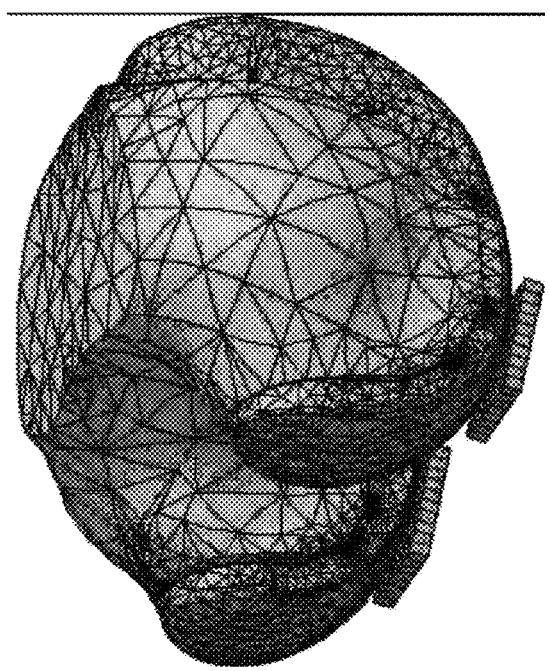

Loads of 1601 N (360 lbs.) to the lateral condyle support plate and 2402 N (540 lbs.) to the medial condyle support plate were applied in the direction of the Femoral Axis (Z axis shown, FIG. 141F). A balance was struck to align model performance with the different contact areas and results. The overall mesh is shown in FIG. 141G. The mesh of the implant component was refined for best results in the high stress areas (FIG. 141H).

10.2 Results and Discussion

The three different large knee femoral implant component geometries that were assessed were sized to correspond to large anatomical knees. The results for Interference No Load, Interference Plus Load, and No Interference Plus Load are shown in Table 19 below. FIGS. 142A, 142B, and 142C show the corresponding high stress locations for the implant components, which was the same for all three models tested. These data can be used in the design of patient-specific implant components, for example, to identify a minimum component thickness for areas of high stress. As shown in the table, there was a 24% reduction in stress with 6 cuts compared to five cuts 221 MPa versus 292 MPa, interference plus no load).

designed to be a certain distance below a particular location on the patient's tibial plateau. For example, the tibial proximal cut height can be selected and/or designed to be 1 mm, 1.5 mm, 2 mm, 2.5 mm, 3 mm, 3.5 mm, or 4 mm or more below the lowest point on the patient's tibial plateau or below the lowest point on the patient's medial tibial plateau or below the lowest point on the patient's lateral tibial plateau. In this example, the tibial proximal cut height was selected and designed to be 2 mm below the lowest point on the patient's medial tibial plateau. For example, as shown in FIG. 143B, anatomic sketches (e.g., using a CAD program to manipulate a model of the patient's biological structure) can be overlaid with the patient's tibial plateau. As shown in FIG. 143C, these sketched overlays can be used to identify the centers of tubercles and the centers of one or both of the lateral and medial plateaus. In addition, as shown in FIGS. 144A to 144C, one or more axes such as the patient's anatomic tibial axis 14420, posterior condylar axis 14430, and/or sagittal axis 14440 can be derived from anatomic sketches, e.g., based on a defined a midpoint line 14450 between the patient's lateral condyle center and medial condyle center. For example, M-L and AP planes can be determined as described in Example 9 above.

As shown in FIG. 145A, the proximal tibial resection was made a 2 mm below the lowest point of the patient's medial tibial plateau with a an A-P slope cut that matched the A-P slope on the patient's medial tibial plateau. As shown in FIGS. 145B and 145C, an implant profile 14500 was selected and/or designed to have 90% coverage of the patient's cut tibial surface. In certain embodiments, the tibial implant profile can be selected and/or designed such that tibial implant is supported entirely or substantially by cortical bone and/or such that implant coverage of the cut tibial surface exceeds 100% and/or has no support on cortical bone.

Figure 146A:
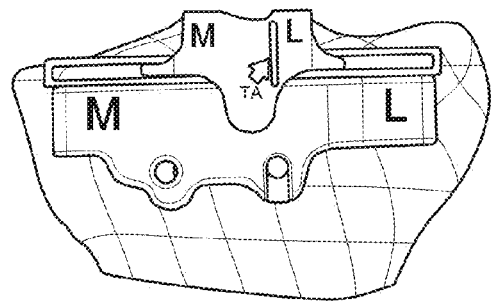
Figure 146B:
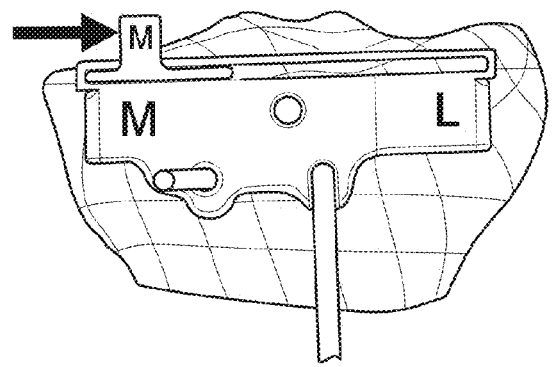

FIGS. 146A to 156C describe exemplary steps for performing resection cuts to the tibia using the anatomical references identified above. For example, as shown in FIGS. 146A and 146B, one step can include aligning the top of the tibial jig stylus to the top of the patient's medial and lateral

TABLE 19

|  | Interference | Inter. + Load | No Inter. + Load | Interference | Inter. + Load | No Inter. + Load | Interference | Inter. + Load | No Inter. + Load |
|---|---|---|---|---|---|---|---|---|---|
|  | Perp-6-Cuts | | | Perp-5-Cuts | | | Flexed-6-Cuts | | |
| Max Principal Stress (MPa) | 246.0 | 221.0 | 98.1 | 241.3 | 292.0 | 120.5 | 261.4 | 214.0 | 83.5 |
|  | Deflections (mm) | | | Deflections (mm) | | | Deflections (mm) | | |
| Lateral Condyle | 0.11 | 0.11 | 0 | 0.10 | 0.10 | 0 | 0.11 | 0.11 | 0 |
| Medial Condyle | 0.08 | 0.08 | 0 | 0.07 | 0.08 | 0 | 0.07 | 0.07 | 0 |
| Anterior Shield | 0.18 | 0.19 | 0.05 | 0.17 | 0.18 | 0.06 | 0.20 | 0.21 | 0.05 |

Example 11

Tibial Implant Design and Bone Cuts

Figure 147A:
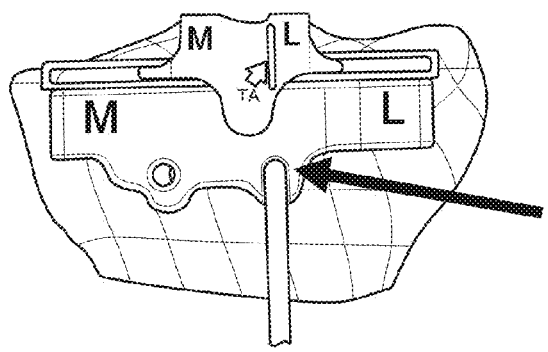
Figure 147B:
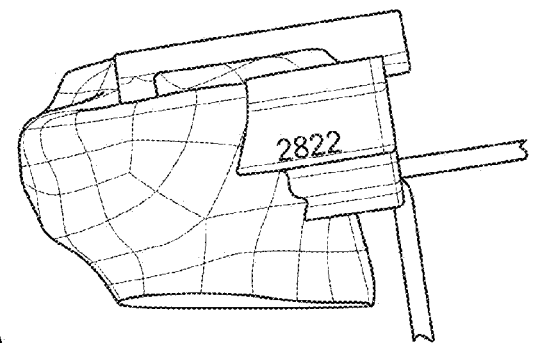
Figure 148:
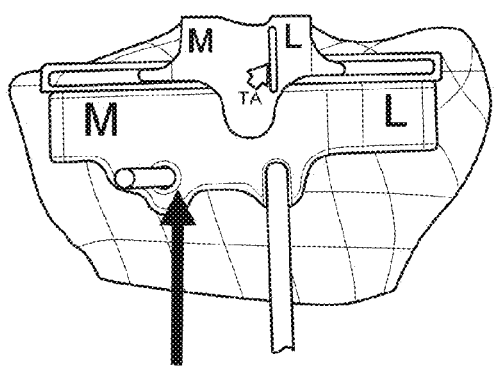
Figure 149:
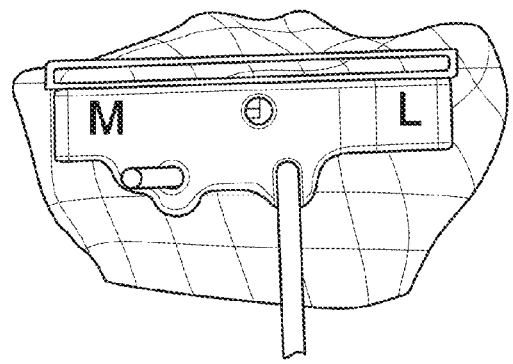
Figure 150:
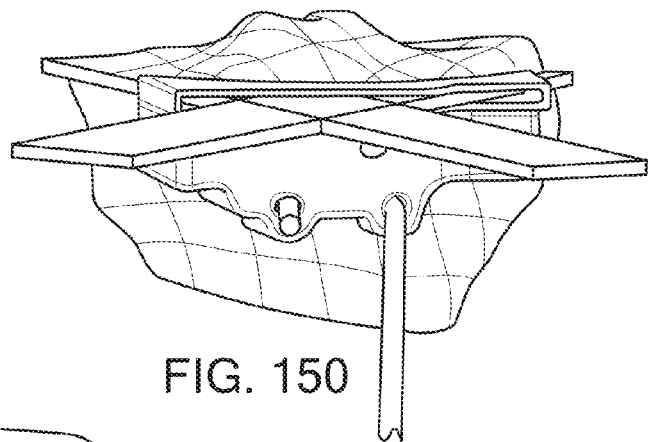
Figure 151:
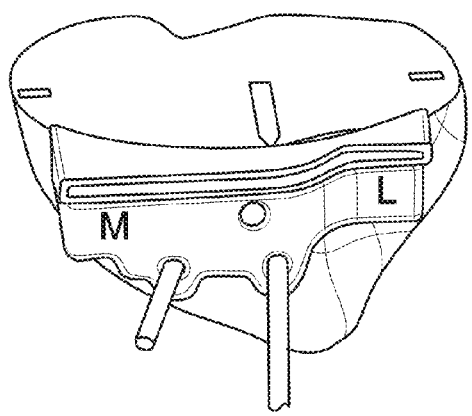
Figure 152:
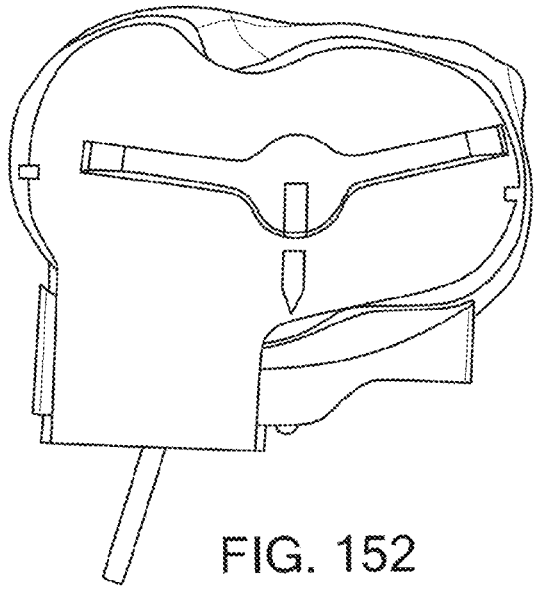
Figure 153:
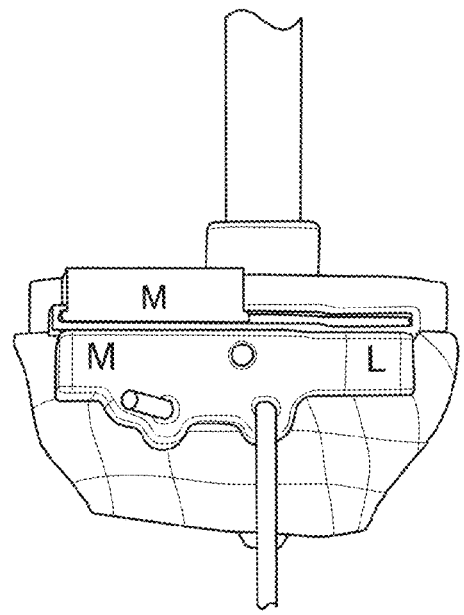
Figure 154:
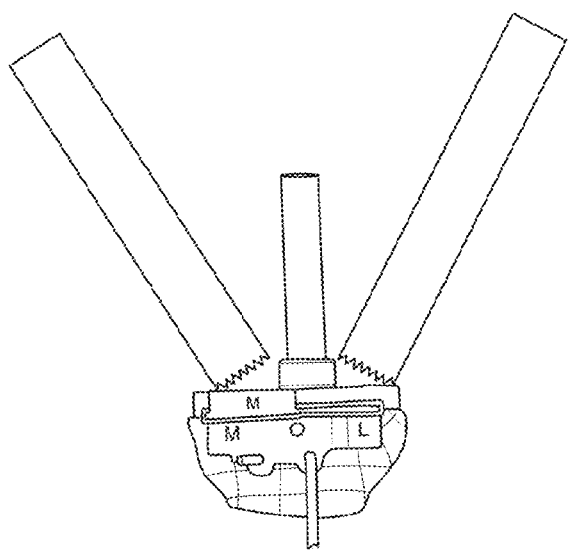
Figure 155:
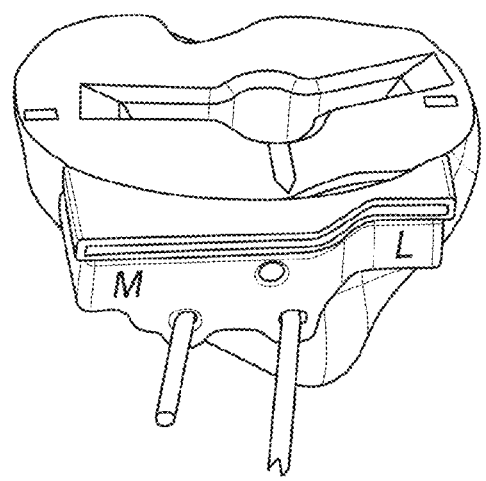
Figure 156C:
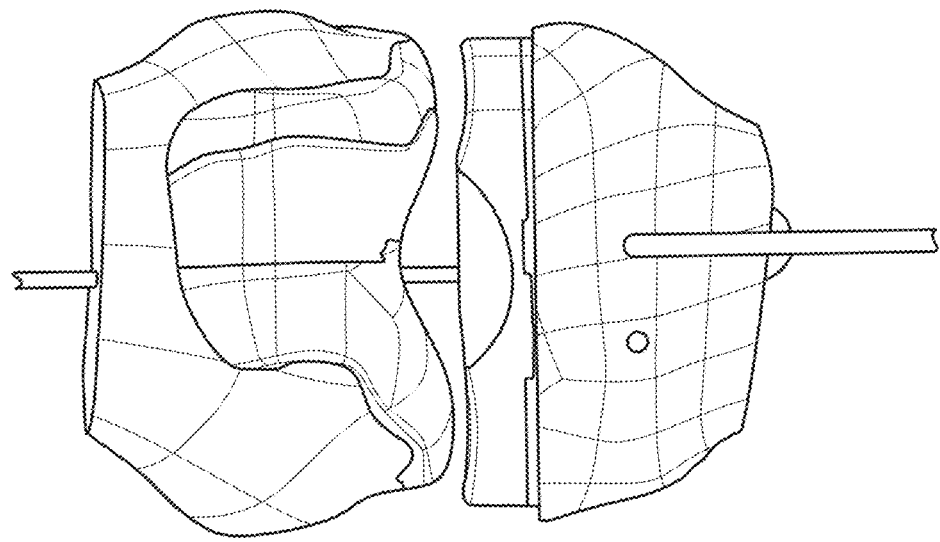
Figure 156B:
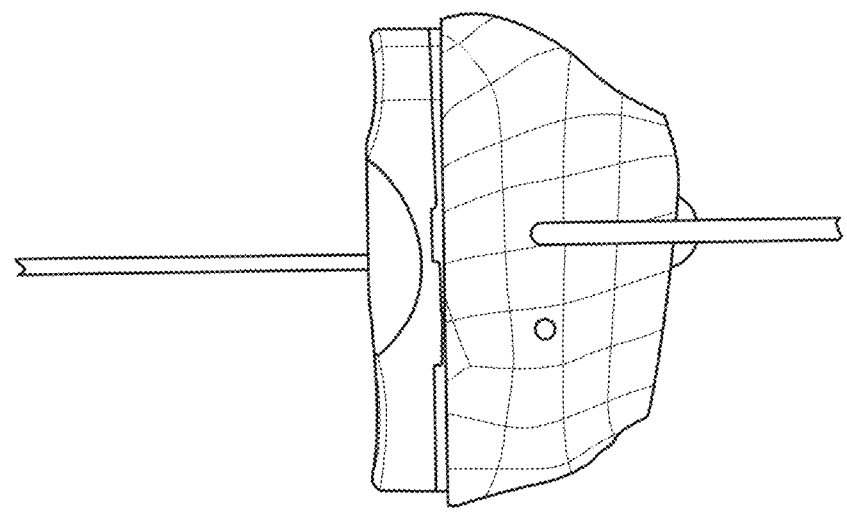
Figure 156A:
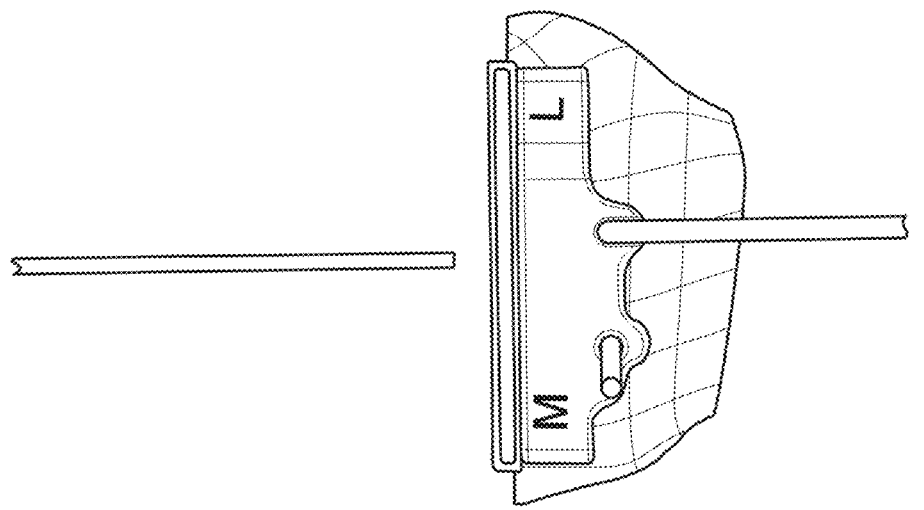

This example illustrates tibial implant components and related designs. This example also describes methods and devices for performing a series of tibial bone cuts to prepare a patient's tibia for receiving a tibial implant component. Patient data, such scans of the patient's joint, can be used to locate the point and features used to identify planes, axes and slopes associated with the patient's joint. As shown in FIG. 143A, the tibial proximal cut can be selected and/or spines (see arrow). As shown in FIGS. 147A and 147B, a second step can include drilling and pinning the tibial axis (see arrow). As shown in FIG. 148, a third step can include drilling and pinning the medial pin (see arrow). As shown in FIG. 149, a fourth step can include removing the stylus. As shown in FIG. 150, a fifth step can include sawing 2 mm of tibial bone from the patient's tibial plateau with the patient's medial AP slope. As shown in FIG. 151, a sixth step can include removing the resected portion of the patient's tibial plateau. As shown in FIG. 152, a seventh step can include assembling stem and keel guide(s) onto the tibial cut guide. As shown in FIG. 153, an eighth step can include drilling, e.g., using a 14 mm drill bit (13 mm×40 mm stem) to drill a central hole into the proximal tibial surface. As shown in FIG. 154, a ninth step can include using a saw or osteotome to create a keel slot, for example, a 3.5 mm wide keel slot. FIG. 155 shows the finished tibial plateau with guide tools still in place. FIGS. 156A-156C show each of a guide tool (FIG. 156A), a tibial implant component (FIG. 156B), and tibial and femoral implant components (FIG. 156C) in the aligned position in the knee.

This example shows that using a patient's joint axes (e.g., as identified from patient-specific data and optionally from a model of the patient's joint) to select and/or design resection cuts, e.g., the tibia, and corresponding guide tools can create resection cuts perpendicular to the patient's tibial axis and based on the patient's medial AP slope. In addition, one or more features of the corresponding implant components (e.g., tibial tray implant thickness) can be selected and/or designed to align the tibial axis with the femoral axis and thereby correct the patient's alignment.

Example 12

Tibial Tray and Insert Designs

This example illustrates exemplary designs and implant components for tibial trays and inserts for certain embodiments described herein. In particular, this example describes a standard blank tibial tray and insert and a method for altering the standard blanks based on patient-specific data to include a patient-adapted feature (e.g., a patient-adapted tray and insert perimeter that substantially match the perimeter of the patient's resected tibia).

FIGS. 157A to 157E illustrate various aspects of an embodiment of a standard blank tibial implant component, including a bottom view (FIG. 157A) of a standard blank tibial tray, a top view (FIG. 157B) of the standard blank tibial tray, a bottom view (FIG. 157C) of a standard blank tibial insert, a top-front (i.e., proximal-anterior) perspective view (FIG. 157D) of the standard blank tibial tray, and a bottom front (i.e., distal anterior) perspective view (FIG. 157E) of a patient-adapted tibial insert. In this example and in certain embodiments, the top surface of the tibial tray can receive a one-piece tibial insert or two-piece tibial inserts. The tibial inserts can include one or more patient-adapted features (e.g., patient-matched or patient-engineered perimeter profile, thickness, and/or joint-facing surface) and/or one or more standard features, in addition to a standard locking mechanism to engage the tibial tray. With reference to FIGS. 157D and 157E, in certain embodiments the locking mechanism on the tray and insert can include, for example, one or more of: (1) a posterior interlock, (2) a central dovetail interlock, (3) an anterior snap, (4) an anterior interlock, and (5) an anterior wedge.

Standard blank tibial trays and/or inserts can be prepared in multiple sizes, e.g., having various AP dimensions, ML dimensions, and/or stem and keel dimensions and configurations. For example, in certain-sized embodiments, the stem can be 13 mm in diameter and 40 mm long and the keel can be 3.5 mm wide, 15 degrees biased on the lateral side and 5 degrees biased on the medial side. However, in other-sized embodiments (e.g., having larger or small tray ML and/or AP dimensions, the step and keel can be larger, smaller, or have a different configuration.

As mentioned above, in this example and in certain embodiments, the tibial tray can receive a one-piece tibial insert or two-piece tibial inserts. FIGS. 158A to 158C show aspects of an embodiment of a tibial implant component that includes a tibial tray and a one-piece insert. FIGS. 159A to 159C show aspects of an embodiment of a tibial implant component that includes a tibial tray and a one-piece insert. Alternatively, a two-piece tibial insert can be used with a two-piece tibial tray. Alternatively, a one-piece tibial insert can be used with a two-piece tibial tray.

FIGS. 160A to 160C show exemplary steps for altering a blank tibial tray and a blank tibial insert to each include a patient-adapted profile, for example, to substantially match the profile of the patient's resected tibial surface. In particular, as shown in FIG. 160A, standard cast tibial tray blanks and standard machined insert blanks (e.g., having standard locking mechanisms) can be finished, e.g., using CAM machining technology, to alter the blanks to include one or more patient-adapted features. For example, as shown in FIG. 160B, the blank tray and insert can be finish machined to match or optimize one or more patient-specific features based on patient-specific data. The patient-adapted features machined into the blanks can include for example, a patient-specific perimeter profile and/or one or more medial coronal, medial sagittal, lateral coronal, lateral sagittal bone-facing insert curvatures. FIG. 160C illustrates a finished tibial implant component that includes a patient-specific perimeter profile and/or one or more patient-adapted bone-facing insert curvatures.

Example 13

Tibial Implant Component Design

This example illustrates tibial implant component selection and/or design to address tibial rotation. FIGS. 161A to 161B describe exemplary techniques for determining tibial rotation for a patient and FIG. 161C shows resulting alignment data for the second technique. With regard to FIG. 161A, a "Floating Insert" Technique includes putting the knee through a full range of flexion and extension allowing the tibial trial to orientate itself in the best position relative to the femoral component. The orientation is marked on the anterior tibial cortex and the tibial component is implanted to match this mark. With regard to FIG. 161B, an anatomic landmark technique (see Mizuuchi et al, Effect of Ankle Rotation on Cutting of the Tibia in TKA, JBJS 2006; Vol 88; Pages 2632-2636) utilizes the AP Axis of the ankle joint and the line perpendicular to the anterior cortical line.

Various tibial implant component features can optimized to ensure proper tibial rotation. For example, FIG. 162 illustrates exemplary stem design options for a tibial tray including using stem and keel dimensions that increase or decrease depending on the size of the tibial implant component (e.g., in the ML and/or AP dimension). Moreover, cement pockets can be employed to enhance stabilization upon implantation, In addition, patient-specific stem and keel guide tools can be selected and/or designed so that the prepared stem and keel holes in a patient's proximal tibia are properly sized, which can minimize rotation (e.g., of a keel in a keel hole that is too large).

Another tibial implant component that can be used to address tibial rotation is selecting and/or designing a tibial tray perimeter profile and/or a tibial insert perimeter profile that minimizes overhang from the patient's bone (which may catch and cause rotation) and, optionally, that maximizes seating of the implant component on cortical bone. Accordingly, in certain embodiments, the tibial tray perimeter profile and/or a tibial insert perimeter profile is preoperatively selected and/or designed to substantially match the perimeter profile of the patient's resected tibial surface.

FIGS. 163A and 163B show an approach for identifying the patient's tibial implant perimeter profile based on the depth and angle of the proximal tibial resection, which can applied in the selection and/or design of the tibial tray perimeter profile and/or the tibial insert perimeter profile. As shown in the bottom image, the lines inside the perimeter of the cut surface represent the perimeters of the various cuts in the top image taken at various depths from the patient's tibial surface. FIGS. 164A and 164B show the same approach as described for FIGS. 163A and 163B, but applied to a different patient having a smaller tibia (e.g., smaller diameter and perimeter length).

Similarly, FIGS. 165A to 165D show four different exemplary tibial implant profiles, for example, having different medial and lateral condyle perimeter shapes that generally match various different relative medial and lateral condyle perimeter dimensions. In certain embodiments, a tibial tray and/or insert can be selected (e.g., preoperatively or intraoperatively) from a collection or library of implants for a particular patient (i.e., to best-match the perimeter of the patient's cut tibial surface) and implanted without further alteration to the perimeter profile. However, in certain embodiments, these different tibial tray and/or insert perimeter profiles can serve as blanks. For example, one of these tibial tray and/or insert profiles can be selected preoperatively from a library (e.g., an actual or virtual library) for a particular patient to best-match the perimeter of the patient's cut tibial surface. Then, the selected implant perimeter can be designed or further altered based on patient-specific data, for example, to substantially match the perimeter of the patient's cut tibial surface.

As described in this example, various features of a tibial implant component can be designed or altered based on patient-specific data. For example, the tibial implant component design or alterations can be made to maximize coverage and extend to cortical margins; maximize medial compartment coverage; minimize overhang from the medial compartment; avoid internal rotation of tibial components to avoid patellar dislocation; and avoid excessive external rotation to avoid overhang laterally and impingement on the popliteus tendon.

Example 14

Bone Cuts Using a Femur-First Jig Set

This example describes methods and devices for performing a series of bone cuts to receive a patient-specific implant. Specifically, a set of jigs is designed in connection with the design of a patient-specific implant component. The designed jigs guide the surgeon in performing one or more patient-specific cuts to the bone so that those cut bone surface(s) negatively-match the patient-specific bone cuts of the implant component. The set of jigs described in this example are designed for a femur-first cut technique.

In a first step, shown in FIGS. 166A and 166B, a first femur jig is used to establish peg holes and pin placements for a subsequent jig used for a distal cut. In this example, the first jig is designed to circumvent 3 mm of cartilage thickness. In a second step, shown in FIGS. 167A and 167B, the distal cut is performed with a second femur jig. In this example, the second jig is patient-specific. However, in certain embodiments that apply a traditional distal cut, a standard jig can be used. In a third step, as shown in FIG. 168A, the anterior cut, the posterior cut, and the chamfer cuts are performed with a third femur jig. In this example, the jig includes slots that are 1.5 mm wide to allow for a saw blade thickness (i.e., no metal guides). As shown in FIG. 168B, in certain embodiments, for implant component designs having six or more inner, bone-facing surfaces, for example, having one or two additional chamfer cuts, the additional cuts can be performed using one or more additional jigs. In this example, the additional jig is designed to accommodate two steep additional chamfer cuts.

Next, the tibia is cut using one or more jigs designed to make patient-specific cuts to the tibia. An exemplary tibial jig is depicted in FIGS. 169A and 169B. A tibial alignment pin 16900 is used to help properly orient the jig. The portion 16910 of the jig inserted between the femur and tibia can have a variable thickness. In certain embodiments, the tibial jig can be designed to accommodate for composite thickness from the distal cut femur 16920. Alternatively or additionally, a balancing chip can be used to address differences in the distance between the tibia and femur surfaces. For example, in certain embodiments a tibia jig may be designed to rest on 2 mm of cartilage, while a balancing chip is designed to rest on the distal cut femur.

A balancing chip is shown in FIG. 170. If a varus deformity of the knee is observed, virtual realignment can be addressed by including added thickness to the balancing chip in the area that would produce a leg in neutral alignment 17010. For a grossly mal-aligned contra-lateral leg, correction can be per a surgeon's order. The balancing chip can include a feature 17020 to attach it to the tibia jig, and thereby allow for accurate distal placement of the tibial cut while at the same time accommodating for composite thickness. An exemplary balancing chip attached to a tibia jig is shown in FIGS. 171A and 171B. To facilitate attachment, the balancing chip handle 18000 matches the tibial slope designed into the tibial cut and tibial implant. Preferably, the balancing chip is designed to enter into the joint easily.

Example 15

Bone Cuts Using a Tibial-First Jig Set

This example describes methods and devices for performing a series of bone cuts to receive a patient-specific implant. Specifically, a set of jigs is designed in connection with the design of a patient-specific implant component. The designed jigs guide the surgeon in performing one or more patient-specific cuts to the bone so that those cut bone surface(s) negatively-match the patient-specific bone cuts of the implant component. The set of jigs described in this example are designed for cuts to a femoral implant component in a tibia-first cut technique.

In a first step, shown in FIG. 172, a first jig is used to establish placement and alignment of femoral implant peg holes. In the example, the placement is flexed 5 degrees with respect to the sagittal femoral axis. In a second step, shown in FIG. 173, a second jig is used to establish placement pins for the distal cut jig. The second jig can have different thicknesses 17300 to accommodate composite thickness from the cut tibial surface. In a third step, as shown in FIG. 174, a distal cut jig is positioned based on the placement established by the previous jig. The distal cut jig can be patient-specific or standard. Lastly, as shown in FIG. 175, remaining cuts are performed with a chamfer cut jig. In the example, the anterior cut is not oblique.

INCORPORATION BY REFERENCE

The entire disclosure of each of the publications, patent documents, and other references referred to herein is incorporated herein by reference in its entirety for all purposes to the same extent as if each individual source were individually denoted as being incorporated by reference.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A knee replacement system for implantation in a knee joint of a patient, comprising:
    a knee replacement implant including a femoral implant for implantation on a femur of the patient and a tibial implant for implantation on a tibia of the patient,
    the femoral implant including a lateral condyle portion having a curved condylar shape and having a lateral bearing surface configured to articulate with the tibial implant when the tibial and femoral implants are implanted in the knee joint of the patient and an inner surface configured to abut one or more bone cut surfaces of a femur when the femoral implant is implanted in the knee joint of the patient, and
    the tibial implant including a bearing surface configured to articulate with the lateral bearing surface of the femoral implant when the tibial and femoral implants are implanted in the knee joint of the patient, and a bone-facing surface configured to abut a surface of a tibia of the patient when the tibial implant is implanted in the knee joint of the patient,
    wherein the lateral condyle portion has a narrowed posterior portion relative to a lateral distal portion of the lateral condyle portion, such that the width of the lateral condyle portion measured in substantially the mediolateral direction narrows in a posterior part of the lateral condylar portion, wherein the narrowed posterior portion of the lateral condyle portion is configured to avoid soft tissue impingement.

2. The knee implant system of claim 1, wherein the narrowed posterior portion of the lateral condyle portion corresponds to the location of a popliteus tendon of the patient when the femoral implant is implanted in the patient.

3. The knee implant system of claim 1, wherein the narrowed posterior portion is a divot or concavity or relief.

4. The knee implant system of claim 1, wherein the femoral implant includes an anterior flange and wherein the anterior flange of the lateral condylar portion of the femoral implant corresponds to and avoids a soft tissue of the patient when the implant is implanted in the patient.

5. The knee implant system of claim 1, wherein the lateral condyle portion has a patient specific curvature in a substantially coronal plane.

6. The knee implant system of claim 1, wherein the lateral condyle portion has a constant curvature in a substantially coronal plane.

7. The knee implant system of claim 1, wherein the lateral condyle portion has a patient specific curvature in a substantially sagittal plane.

8. The knee implant system of claim 1, wherein the lateral condyle portion has a constant curvature in a substantially sagittal plane.

9. The knee implant system of claim 1, wherein the femoral implant further comprises a medial condyle portion having a first curved condylar shape and wherein the lateral condyle portion includes a second curved condylar shape; and wherein the curved condylar shape of the medial condylar portion is larger than the second curved condylar shape of the lateral condyle portion.

10. The knee implant system of claim 1, wherein the femoral implant further comprises a medial condyle portion, wherein the femoral implant further comprises a cam extending between the medial condyle portion and the lateral condyle portion, wherein the cam is asymmetrical relative to a sagittal plane of the implant.

11. The knee implant system of claim 1, wherein the tibial implant includes one or more features for avoiding impingement of soft tissue when the tibial implant is implanted in the patient.

12. A knee replacement implant system for implantation in a knee joint of a patient, comprising:
    a knee replacement implant including a femoral implant for implantation on a femur of the patient and a tibial implant for implantation on a tibia of the patient,
    the femoral implant including a lateral condyle portion having a curved condylar shape and having a lateral bearing surface configured to articulate with the tibial implant when the tibial and femoral implants are implanted in the knee joint of the patient and an inner surface configured to abut one or more bone cut surfaces of a lateral condyle of a femur when the femoral implant is implanted in the knee joint of the patient and further including a medial condyle portion having a second curved condylar shape and having a medial bearing surface configured to articulate with the tibial implant when the tibial and femoral implants are implanted in the knee joint of the patient and a second inner surface configured to abut one or more bone cut surfaces of a medial condyle of the femur when the femoral implant is implanted in the knee joint of the patient; and
    wherein a lateral periphery of the lateral condyle portion is configured to avoid or accommodate a popliteus tendon associated with a knee joint of a patient.

13. A knee replacement implant system for implantation in a knee joint of a patient, comprising:
    a total knee replacement implant including a femoral implant for implantation on a femur of the patient and a tibial implant for implantation on a tibia of the patient,
    the femoral implant including a lateral condyle portion having a curved condylar shape and having an lateral bearing surface configured to articulate with the tibial implant when the tibial and femoral implants are implanted in the knee joint of the patient and an inner surface configured to abut one or more bone cut surfaces of a lateral condyle of a femur when the femoral implant is implanted in the knee joint of the patient and further including a medial condyle portion having a second curved condylar shape and having a medial bearing surface configured to articulate with the tibial implant when the tibial and femoral implants are implanted in the knee joint of the patient and a second inner surface configured to abut one or more bone cut surfaces of a medial condyle of the femur when the femoral implant is implanted in the knee joint of the patient; and
    wherein the lateral condyle portion has a narrowed posterior lateral portion relative to a lateral distal portion of the lateral condyle portion, such that the width of the lateral condyle portion measured in substantially the mediolateral direction narrows in a posterior part of the lateral condylar portion to avoid a soft tissue of the patient when the femoral implant is implanted in the patient.

14. The knee replacement implant system of claim 13, wherein the medial condyle portion further includes a medial posterior portion and a medial distal portion, the medial distal portion and the lateral distal portion each having substantially the same width measured in substantially the mediolateral direction and the posterior medial portion being wider than the lateral posterior portion measured in substantially the mediolateral direction.

15. The knee replacement implant system of claim 13, further comprising a cam extending between the medial condyle portion and the lateral condyle portion, wherein the cam has an increasing thickness in a substantially mediolateral direction.

16. The femoral implant system of claim 13, wherein the posterior medial portion has a greater thickness than the posterior lateral portion.

17. The knee replacement system of claim 13, wherein the total knee replacement system is a cruciate retaining total knee implant, retaining the posterior cruciate ligament.

\* \* \* \* \*